US012448371B2

(12) United States Patent
Flynn et al.

(10) Patent No.: US 12,448,371 B2
(45) Date of Patent: Oct. 21, 2025

(54) INHIBITOR COMPOUNDS

(71) Applicant: Cincera Therapeutics Pty Ltd, Melbourne (AU)

(72) Inventors: Bernard Luke Flynn, Donvale (AU); Giang Le, Templestowe Lower (AU); Shuxin Yang, Brunswick (AU)

(73) Assignee: Cincera Therapeutics Pty Ltd, Melbourne (AU)

( * ) Notice: Subject to any disclaimer, the term of this patent is extended or adjusted under 35 U.S.C. 154(b) by 917 days.

(21) Appl. No.: 17/629,218

(22) PCT Filed: Jul. 24, 2020

(86) PCT No.: PCT/AU2020/050763

§ 371 (c)(1),
(2) Date: Jan. 21, 2022

(87) PCT Pub. No.: WO2021/012018

PCT Pub. Date: Jan. 28, 2021

(65) Prior Publication Data

US 2022/0274970 A1 Sep. 1, 2022

(30) Foreign Application Priority Data

Jul. 24, 2019 (AU) ................................ 2019 902614

(51) Int. Cl.

| | |
|---|---|
| ***C07D 413/12*** | (2006.01) |
| ***A61P 11/00*** | (2006.01) |
| ***C07D 401/12*** | (2006.01) |
| ***C07D 401/14*** | (2006.01) |
| ***C07D 413/14*** | (2006.01) |
| ***C07D 417/12*** | (2006.01) |

(52) U.S. Cl.

CPC ............ *C07D 413/12* (2013.01); *A61P 11/00* (2018.01); *C07D 401/12* (2013.01); *C07D 401/14* (2013.01); *C07D 413/14* (2013.01); *C07D 417/12* (2013.01)

(58) Field of Classification Search

CPC .. C07D 401/12; C07D 401/14; C07D 413/12; C07D 413/14; C07D 417/12

See application file for complete search history.

(56) References Cited

FOREIGN PATENT DOCUMENTS

| | | |
|---|---|---|
| CN | 108079303 A | 5/2018 |
| WO | WO 2008/142073 | 11/2008 |
| WO | WO 2012/164103 | 12/2012 |
| WO | WO 2015/155738 | 10/2015 |
| WO | WO 2015/196258 | 12/2015 |
| WO | WO 2018/112077 | 6/2018 |

OTHER PUBLICATIONS

PCT International Search Report and Written Opinion issued in International Application No. PCT/AU2020/050763, mailed Aug. 14, 2020.

Rajak et al., "2,5-Disubstituted-1,3,4-oxadiazoles/thiadiazole as surface recognition moiety: design and synthesis of novel hydroxamic acid based histone deacetylase inhibitors," *Bioorganic & Medicinal Chemistry Letters*, 21(19):5735-5738, 2011.

Aurelio, Luigi et al, From Sphingosine Kinase to Dihydroceramide Desaturase: A Structure-Activity Relationship (SAR) Study of the Enzyme Inhibitory and Anticancer Activity of 4-((4-(4-Chlorophenyl)thiazol-2-yl)amino)phenol) (SKI-II), *J. Med. Chem.*, 2016, 59,965-984.

Kretschmer, Simon B.M., et al., Development of novel aminothiazole-comprising 5-LO inhibitors, Future Medicinal Chemistry, 2016, 8(2), pp. 149-164.

Nozaki, Masakatsu et al., Medicinal Chemistry, first edition, Kagaku-Dojin Publishing Company, Inc., 1995, pp. 98-99 (no English counterpart—see Thornber as the original source of Table 5.2 in Nozaki).

Park, Sang Won et al., Synthesis and evaluation of 6-heteroarylamino-2,4,5-triemthylpyridin-3-ols as inhibitors of TNF-a induced cell adhesion and inflammatory bowel disease, MedChemComm., 2018, 9(8), 1305-1310.

Thornber, C.W, Isosterism and Molecular Modification in Drug Design, *Chem. Soc. Rev.*, 8, 563-580, 1979.

*Primary Examiner* — James D. Anderson

(74) *Attorney, Agent, or Firm* — pH IP Law

(57) ABSTRACT

The disclosure relates to heterocyclic compounds and methods for their preparation. The disclosure provides compounds that may have beneficial therapeutic activity in the treatment of a disease or condition mediated by excessive or otherwise undesirable Des1 and/or fibrotic activity.

23 Claims, 2 Drawing Sheets

INHIBITOR COMPOUNDS

Figure 1:
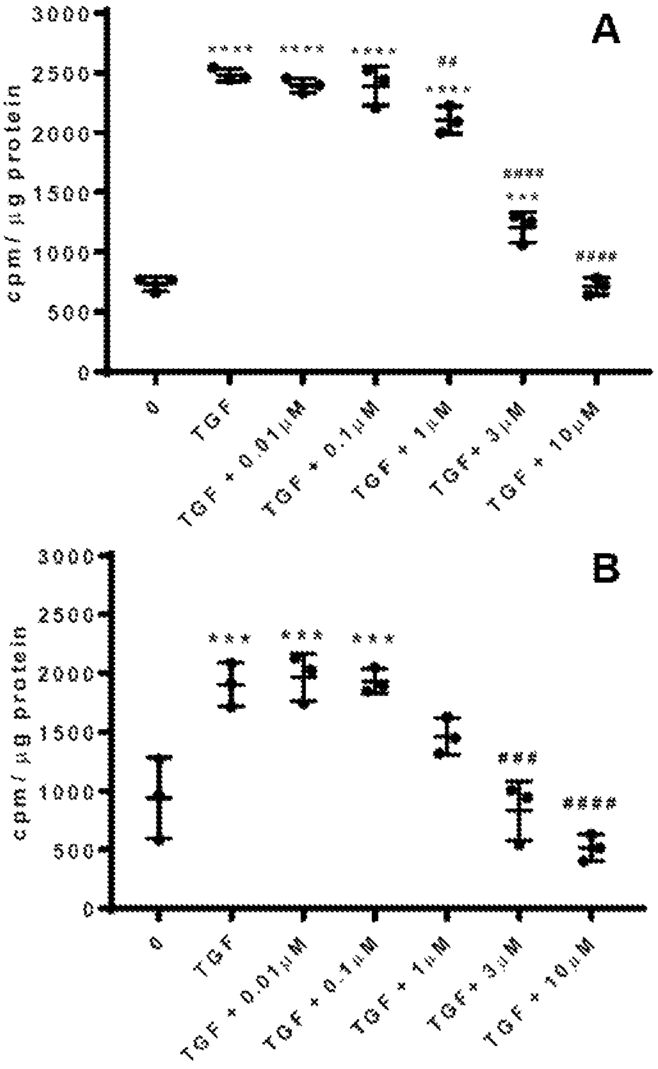

The present application is a national phase application under 35 U.S.C. § 371 of International Application No. PCT/AU2020/050763, filed Jul. 24, 2020, which claims the priority benefit of Australian Application No. 2019902614, filed Jul. 24, 2019, the entire contents of each of which are hereby incorporated by reference.

FIELD

The present disclosure relates generally, but not exclusively, to compounds and their use in therapy, for example as enzyme interacting agents which interact with one or more enzymes in the sphingolipid biosynthesis pathway, e.g. dihydroceramide desaturase. The disclosure further relates to the use of such compounds as research tools, their use in therapy, to compositions and agents comprising said compounds, their manufacture, and to methods of treatment using said compounds.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Sphingolipids, a class of compounds defined by their common 18 carbon amino alcohol backbones, mediate cell-cell and cell-substratum interactions, modulate the behavior of cellular proteins and receptors, and participate in signal transduction. The sphingolipids are synthesised de novo from palmitoyl-CoA and serine via a pathway whereby the carbon backbone, alcohol and amino groups are modified to form the various bioactive compounds, such as dihydroceramide, ceramide, sphingosine and sphingosine-1-phosphate (Scheme 1). Perturbations in the sphingolipid biosynthetic pathway are implicated in many physiological and pathophysiological processes, including cancer, diabetes, fibrosis, inflammation, viral infection and Alzheimer's disease.

Scheme 1

Palmitoyl-CoA + Serine

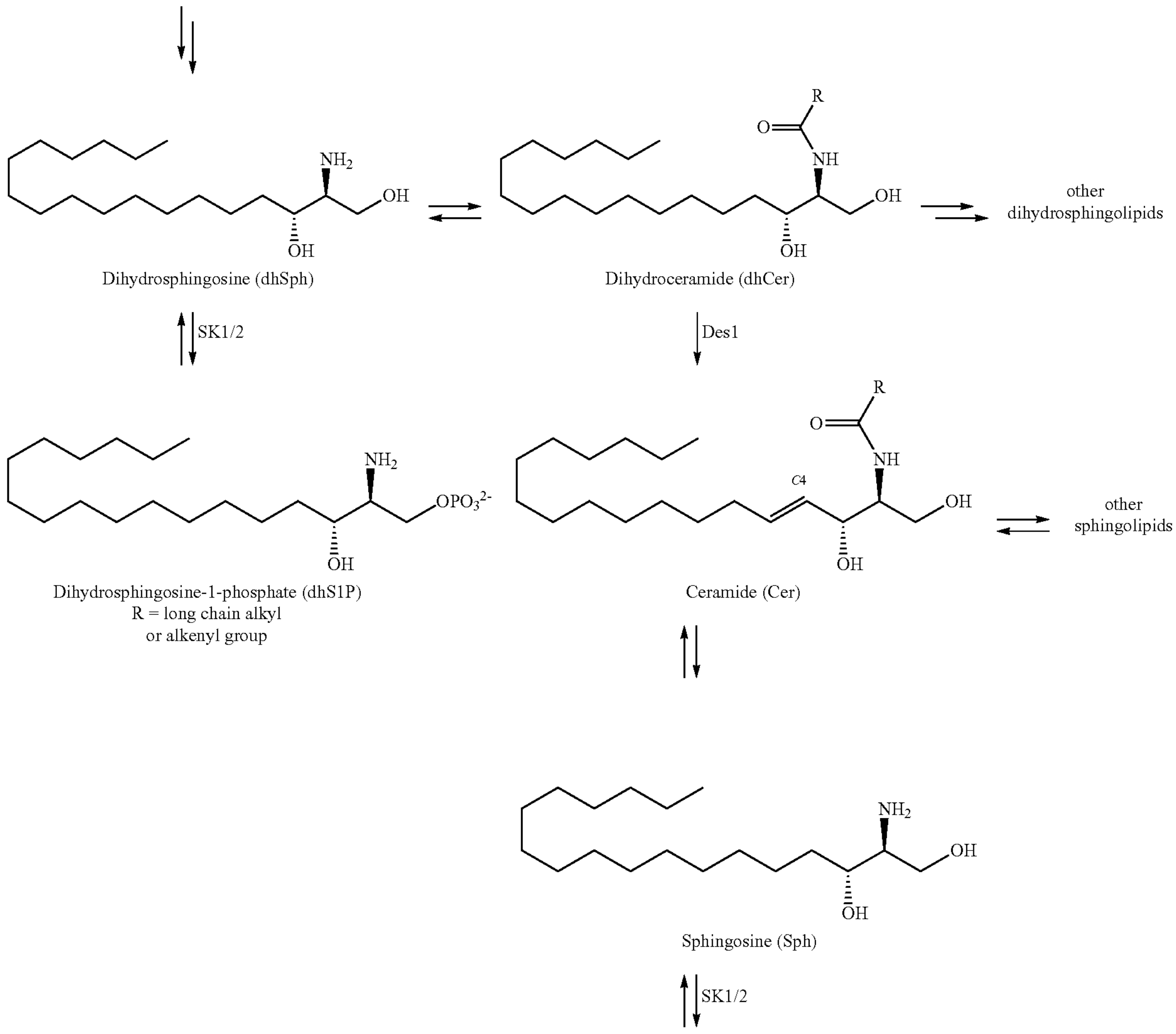

Dihydrosphingosine (dhSph)

Dihydroceramide (dhCer)

Dihydrosphingosine-1-phosphate (dhS1P)

R = long chain alkyl or alkenyl group

Ceramide (Cer)

Sphingosine (Sph)

-continued

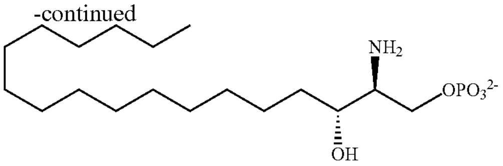

Sphingosine-1-phosphate (S1P)

Dihydroceramide desaturase (Des), introduces a double-bond at C4 of the C18 back-bone, converting dihydroceramides (dhCer) to ceramides (Cer). There are two isoforms of Des, Des1 and Des2. Des1 accounts for a major component of the Cer production in most tissues, whereas Des2 acts mostly as a C4-hydoxylase, converting Cer to phytoceramides. Whilst Des1 is found in most tissues, Des2 expression is confined mostly to the skin, intestines and kidneys. Since both dhCer and Cer are able undergo reversible conversion into other sphingolipids, including sphingosine (Sph) and sphingosine-1-phosphate (S1P), Des1 effectively controls the C4-saturation status of all sphingolipids. The activation status of Des1 controls the ratio of dihydro- and C4-unsaturated sphingolipids, which have different, and sometimes opposing, effects on cells function. Increased Des1 expression and/or activity increases the level of bioactive C4-unsaturated sphingolipids and has been linked to disease progression in a number of diseases, such as cancer, inflammation, fibrosis and metabolic disease. Accordingly, the use of Des1 inhibitors in drug therapy for the treatment of different diseases has been proposed, including cancer, inflammatory bowel disease (IBD), diabetes, non-alcoholic steatohepatitis (NASH), cystic fibrosis, heart failure, chronic kidney disease and viral and bacterial infection, amongst others (Gagliostro V et al. *Prog. Lipid Res.* 2012, 51. 82-94; Siddique, M. M. et al. *J. Biol. Chem.* 2015, 290, 15371-15379; Magaye, R., R. et al. *Cell. Mol. Life Sci.* 2019, 76, 1107-1134; Vieira, C. R. et al., *Chem. Biol.* 2010, 17, 766-775).

SUMMARY

In one or more embodiments the disclosure provides compounds that have Des1 inhibitory activity. In one or more embodiments, the disclosure provides compounds that may have beneficial therapeutic activity in the treatment of a disease or condition mediated by excessive or otherwise undesirable Des1 and/or fibrotic activity.

In one aspect, the disclosure provides a compound of formula (I'):

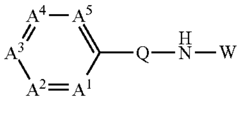

wherein:

$A^1$-$A^5$ are independently selected from C—$R^a$ and N, wherein any 0, 1, 2, 3 or 4 of $A^1$-$A^5$ may be N;

each $R^a$ is independently H or $R^{aa}$, wherein $R^{aa}$ is selected from halo, alkyl, haloalkyl, cycloalkyl, halocycloalkyl, alkoxy, haloalkoxy, cycloalkoxy, cycloamino, halocycloamino, alkoxylalkyl, and alkoxyalkoxy;

Q is a 5-membered heteroaromatic ring having 2, 3 or 4 ring heteroatoms, at least one of which must be N, and the remaining are independently selected from N, O and S, and wherein a ring carbon atom bearing a hydrogen atom, or a ring nitrogen atom bearing a hydrogen atom, if present, may be optionally substituted with $Q^a$, which is selected from halo, haloalkyl and alkyl;

W is a 6-membered N-containing heterocycle selected from:

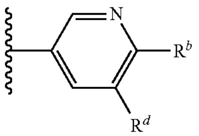

(A)

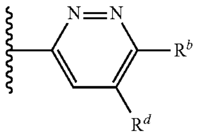

(B)

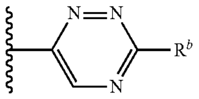

(C)

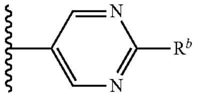

(D)

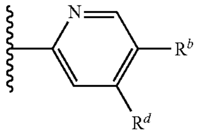

(E)

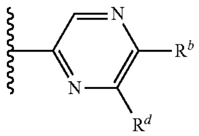

(F)

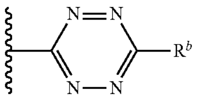

(G)

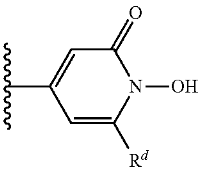

(H)

-continued (I)

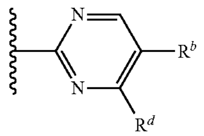

(J)

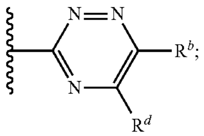

wherein $R^b$ is selected from:

—OH, provided that when $R^b$ is OH, W is (E) or (I);

—K—$NR^c$—Y, or a tautomer thereof,

—$(CH_2)_p$—NH—OH, and

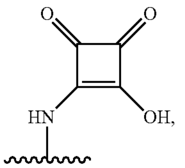

wherein

K is SO, $SO_2$, C(═X') or NHC(═X'), where X' is O or NH;

$R^c$ is H, $C_{1-6}$alkyl; or hydroxy$C_{1-6}$alkyl;

Y is OH, $NHR^e$ (wherein $R^e$ is H, $C_{1-6}$alkyl, —(C═O)H or —(C═O)$C_{1-6}$alkyl, hydroxy$C_{1-6}$alkyl or ($SC_{1-6}$alkyl)$C_{1-6}$alkyl; and p is 0 or 1;

and $R^d$ is selected from H, OH, halo, $C_{1-6}$alkyl and $C_{1-6}$ alkoxy;

provided that the compound does not have the formula

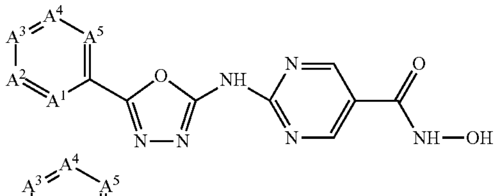

or

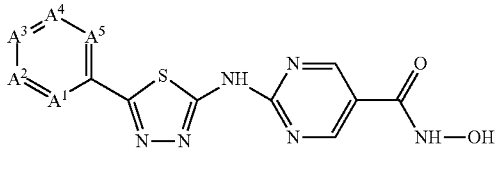

where any four of $A^1$-$A^5$ are C—H, and the other is C—$R^a$ where $R^a$ is H, halo, $CH_3$ or $OCH_3$;

or a pharmaceutically acceptable salt or solvate thereof.

In another aspect, there is provided a compound of Formula (I"), wherein $R^b$ and $R^d$ of Formula (I') are transposed, or a pharmaceutically acceptable salt or solvate thereof.

In some embodiments, the 5-membered heteroaromatic ring has 2 or 3 ring heteroatoms. In some embodiments Q is selected from

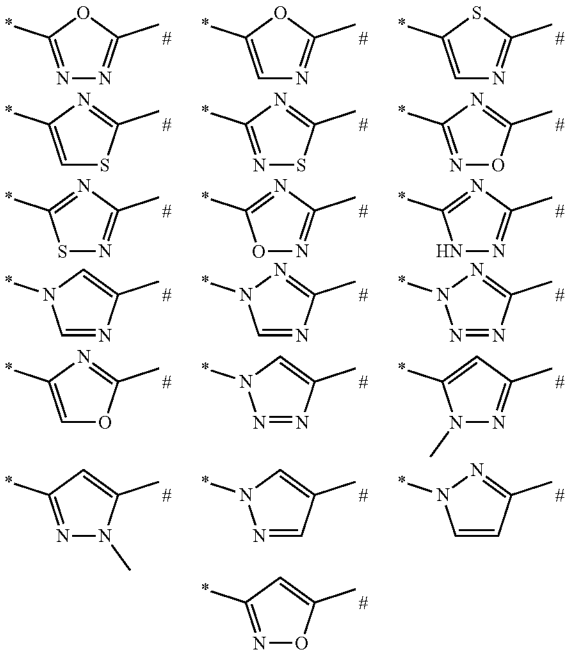

wherein # denotes the bond attached to NH and * denotes the bond attached to the aryl or heteroaryl ring defined by $A^1$-$A^5$.

In some embodiments $Q^a$ is selected from halo, $C_{1-6}$alkyl (i.e. $C_1$ alkyl, $C_2$ alkyl, $C_3$ alkyl, $C_4$ alkyl, $C_5$ alkyl or $C_6$ alkyl), and halo$C_{1-6}$alkyl (i.e. halo$C_1$ alkyl, halo$C_2$ alkyl, halo$C_3$ alkyl, halo$C_4$ alkyl, halo$C_5$ alkyl or halo$C_6$ alkyl).

In some embodiments, Each of $A^1$-$A^5$ is C—$R^a$. In some further embodiments thereof one or two of C—$R^a$ is C—$R^{aa}$, and the remainder C—H. In some further embodiments, at least $A^3$ is C—$R^{aa}$.

In some embodiments, 0, 1, 2, 3 or 4 of $A^1$, $A^2$, $A^4$ and $A^5$ are N. In some embodiments thereof $A^3$ is C—$R^{aa}$.

In some embodiments, at least $A^3$ is C—$R^{aa}$. In some further embodiments $A^3$ is C—$R^{aa}$ and $A^1$, $A^2$, $A^4$ and $A^5$ are each C—H. In some embodiments $A^3$ is C—$R^{aa}$ and one of $A^4$ or $A^2$ is the same or different C—$R^{aa}$. In some embodiments, any one or two of $A^1$, $A^2$, $A^3$, $A^4$ or $A^5$ may be N. In some embodiments $A^3$ is C—$R^{aa}$ and $A^1$ or $A^5$ is N. In further embodiments thereof, $A^3$ is C—$R^{aa}$, $A^1$ or $A^5$ is N and the remaining A are C—H.

In some embodiments, $A^5$ or $A^1$ is N; or $A^2$ or $A^4$ is N; or $A^1$ and $A^5$ are both N; or $A^2$ and $A^4$ are both N; or $A^1$ and $A^4$, or $A^2$ and $A^5$ are both N; or $A^1$ and $A^2$ or $A^4$ and $A^5$ are both N. In some of these embodiments $A^3$ is C—$R^{aa}$.

In some embodiments, W contains 1 or 2 ring nitrogen atoms i.e. (A), (B), (D), (E), (F), (H) and (I). In some embodiments, where $R^b$ is not OH, W is not a group of formula (E). In some embodiments, where $R^b$ is not OH, W is not a group of formula (I). In some embodiments, where $R^b$ is not OH, W is not a group of formula (I) or (E). In some embodiments, where $R^b$ is not OH, W is a group having at least one N ring atom adjacent, or ortho- to the ring carbon atom bearing $R^b$.

In some embodiments, Rb is OH and W is (E) or (I).

In some embodiments, $R^b$ is K—$NR^c$—Y, or a tautomer thereof, or —$(CH_2)_p$—NH—OH. In further embodiments, $NHR^e$ is $NH_2$, $NHC_{1-3}$alkyl, NHC(═O)H, NH(C(═O)$C_{1-3}$ alkyl.

In some embodiments, $R^b$ is K—$NR^c$—Y, or a tautomer thereof, or —$(CH_2)_p$—NH—OH, and W is one of (A), (B), (C), (D), (F), (G), (H), (J). In further embodiments, $NHR^e$ is $NH_2$, $NHC_{1-3}$alkyl, NHC(═O)H, NH(C(═O)$C_{1-3}$alkyl.

$R^d$ may be selected from H, OH, F, Cl, Br, I, $C_1$alkyl, $C_2$alkyl, $C_3$alkyl, $C_4$alkyl, $C_5$alkyl, $C_6$alkyl, $C_1$alkoxy, $C_2$alkoxy, $C_3$alkoxy, $C_4$alkoxy $C_5$alkoxy, $C_6$alkoxy. In some further embodiments, $R^d$ is H, OH, F, Cl, Br, I, $CH_3$ or $OCH_3$.

In another aspect, the disclosure provides a composition comprising a compound of Formula (I') and/or (I"), or a pharmaceutically acceptable salt or solvate thereof, and a pharmaceutically acceptable additive.

The disclosure also provides a compound of Formula (I') and/or (I"), or a pharmaceutically acceptable salt or solvate thereof, or a composition comprising said compound or a pharmaceutically acceptable salt or solvate thereof, for use as an agent for inhibiting or otherwise interacting with Des1.

The disclosure also provides a compound of Formula (I') and/or (I"), or a pharmaceutically acceptable salt or solvate thereof, or a composition comprising said compound or a pharmaceutically acceptable salt or solvate thereof, for use in therapy, such as treating a disease or condition in which Des1 inhibition is beneficial, and/or for treating fibrosis or a fibrotic disease.

A further aspect disclosed herein provides a method of treating a disease or condition in which Des1 inhibition is beneficial, in a subject in need thereof, comprising administering to said subject, a compound of Formula (I') and/or (I"), or a pharmaceutically acceptable salt or solvate thereof.

In some embodiments, the disease or condition is a proliferative, inflammatory or fibrotic disease Yet another aspect disclosed herein provides use of a compound of Formula (I') and/or (I"), or a pharmaceutically acceptable salt or solvate thereof, in the manufacture of a medicament for treating a disease in which Des1 inhibition is beneficial.

Yet another aspect disclosed herein provides use of a compound of Formula (I') and/or (I"), or a pharmaceutically acceptable salt or solvate thereof, in the manufacture of a medicament for treating a fibrosis or a fibrotic disease.

Yet another aspect disclosed herein provides a method of treating fibrosis or a fibrotic disease in a subject in need thereof, comprising administering to said subject, a compound of Formula (I') and/or (I"), or a pharmaceutically acceptable salt or solvate thereof.

In some embodiments, the compounds disclosed herein may also be useful as research tools, for example in the investigation of the role and activity of Des1, and/or as candidate, comparison or control molecules in an assay or model for Des1 activity or its inhibition, and/or as candidate, comparison or control molecules in an assay or model for one or more potential therapeutic applications, such anti-fibrotic activity for the prevention or treatment of fibrosis.

FIGURES

FIG. 1 graphically depicts proline incorporation in renal mesangial cells stimulated with TGF-β1 (5 ng/ml) in the presence or absence of Compound 8 (FIG. 1A) and Compound 46 (FIG. 1B) at 0.01, 0.1, 3 and 10 μM. Data is represented as mean+/−standard deviation of raw $^3$H-proline counts per minute normalised to micrograms of protein. Data is from 3 independent experiments. One way ANOVA with Tukeys pos hoc analysis to correct for multiple differences. *, **=$p<0.001$ & 0.0001 compared to zero control. ##, ###, ####=$p<0.01$, 0.001 & 0.0001 compared to TGF-β1 alone.

Figure 2:
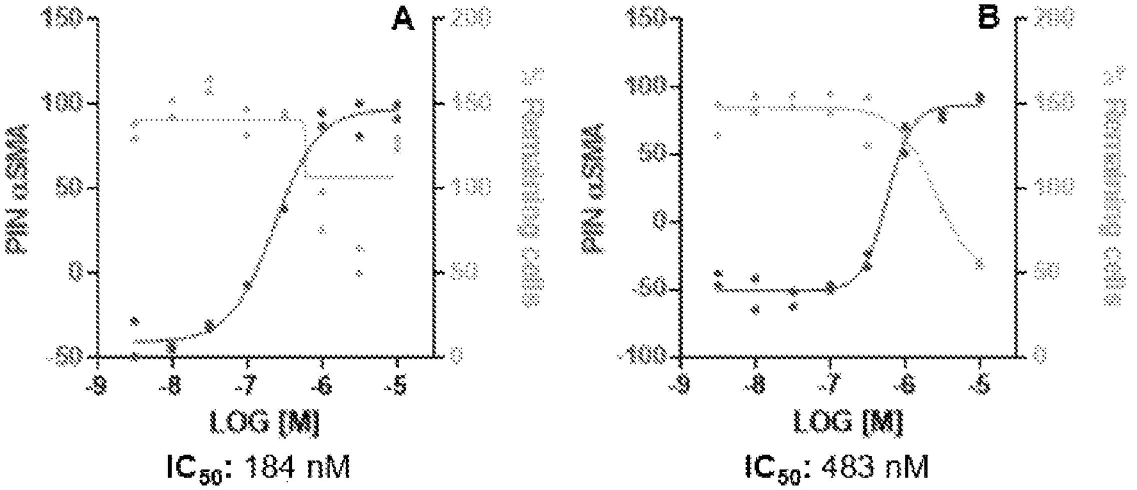

FIG. 2 represents the concentration-dependent inhibition of TGF-β1-mediated αSMA expression in IPF donors in the presence of Compound 8 (FIG. 2A) and Compound 46 (FIG. 2B). The graphs display normalised data for percentage of inhibition (PIN) and remaining cells (%).

DESCRIPTION

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers or steps.

Throughout this specification and the claims which follow, unless the context requires otherwise, the phrase "consisting essentially of", and variations such as "consists essentially of" will be understood to indicate that the recited element(s) is/are essential i.e. necessary, elements of the invention. The phrase allows for the presence of other non-recited elements which do not materially affect the characteristics of the invention but excludes additional unspecified elements which would affect the basic and novel characteristics of the method defined.

All aspects, embodiments and examples described herein are encompassed and contemplated by the term "invention".

The singular forms "a", "an" and "the" as used throughout are intended to include plural aspects where appropriate unless the context clearly dictates otherwise.

Unless the context indicates otherwise, features described below may apply independently to any aspect or embodiment of the invention As used herein, the term "halo" (or "halogen") denotes fluoro (fluorine), chloro (chlorine), bromo (bromine) or iodo (iodine).

As used herein, the term "alkyl" (or "alk"), as used alone or in a composite term such as alkoxy, haloalkyl etc) denotes saturated straight chain, or branched alkyl, preferably $C_{1-20}$ alkyl, e.g. $C_{1-10}$ or $C_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl and 1,1,3,3-tetramethylbutyl. Where an alkyl group is referred to generally as "propyl", butyl" etc, it will be understood that this can refer to any of straight or branched isomers where appropriate. An alkyl group, either alone or as part of an alkoxy, haloalkyl or haloalkoxy etc group as defined for $R^a$ may be unsubstituted or substituted by one or more (e.g. 1, 2, 3, 4, 5 etc, as permitted), same or different, optional substituents.

The term "cycloalkyl" includes any of non-aromatic monocyclic, bicyclic and polycyclic, (including fused or bridged) hydrocarbon residues, e.g. $C_{3-20}$ (such as $C_{3-10}$ or $C_{3-8}$ or $C_{3-6}$) monocyclic 5-6-membered or bicyclic 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl and decalinyl. A cycloalkyl group may be optionally substituted by one or more optional substituents as herein defined. In some embodiments, a monocycloalkyl group may be substituted by a bridging group to form a bicyclic bridged group.

"Halocycloalkyl" refers to a cycloalkyl group, as herein defined, independently substituted one or more times with one or more, same or different halogen atoms. One or more carbon atoms (e.g. 1, 2, or more) are independently substituted with one or more halogen atoms. In some embodiments, two hydrogen atoms attached to any one carbon ring atom are replaced by the same or different halogen atom. In some embodiments one hydrogen atom attached to any one carbon ring atom is replaced by a halogen atom. Some non-limiting examples include chloro-, iodo-, fluoro or bromo-cyclopropyl, cyclobutyl, cyclopentyl and cyclohexyl, and dichloro-, diiodo-, difluoro or dibromo-cyclopropyl, cyclobutyl, cyclopentyl and cyclohexyl.

"Cycloalkoxy" when used alone or in a composite term denotes cycloalkyl, as herein defined, when linked by an oxygen atom. Some non-limiting examples include: $OC_{3-6}$ cycloalkyl (e.g. cyclopropyloxy, cyclobutyloxy, cyclopentyloxy and cyclohexyloxy).

The term "cycloamino" refers to a cycloalkyl group as herein defined wherein a carbon atom is replaced by a nitrogen atom. The cycloamino group may be connected via a carbon ring atom or a nitrogen ring atom. In some embodiments, the carbon atom connecting the group is replaced by nitrogen, i.e. the cycloamino group is connected through the nitrogen atom. Some exemplary groups include, 3, 4, 5, and 6-membered rings, e.g. aziridinyl, azetidinyl, pyrrolidinyl, and piperidinyl. In embodiments where the cycloamino group is attached via a carbon atom, the ring nitrogen may be unsubstituted or may be i substituted with one or two, same or different, $C_{1-6}$alkyl groups, e.g., $C_1$alkyl, $C_2$alkyl, $C_3$alkyl, $C_4$alkyl, $C_5$alkyl, $C_6$alkyl.

The term "halocycloamino" refers to a cycloamino group independently substituted one or more times with one or more, same or different halogen atoms. One or more carbon atoms (e.g. 1, 2, or more) are independently substituted with one or more halogen atoms. In some embodiments, all hydrogen atoms attached to any one carbon atom are replaced by the same or different halogen atom. In some embodiments, two hydrogen atoms attached to any one carbon atom are replaced by the same or different halogen atom. In some embodiments one hydrogen atom attached to any one carbon atom is replaced by a halogen atom. Some non-limiting examples include chloro-, iodo-, fluoro or bromo-aziridinyl, azetidinyl, pyrrolidinyl, and piperidinyl, and dichloro-, diiodo-, difluoro or dibromo-aziridinyl, azetidinyl, pyrrolidinyl, and piperidinyl.

"Alkoxy" when used alone or in a composite term denotes alkyl, as herein defined, when linked by an oxygen atom. Some non-limiting examples include: $OC_{1-6}$ alkyl (e.g. OMe, OEt, On-Pr, Oi-Pr, On-Bu, Oi-Bu, Ot-Bu).

"Haloalkyl" refers to an alkyl group, as herein defined, independently substituted one or more times with one or more, same or different halogen atoms. Where "alkyl" comprises more than one carbon atom, some (e.g. 1, 2, or more) or all of the carbon atoms are independently substituted with one or more halogen atoms. In some embodiments, all hydrogen atoms attached to any one carbon atom are replaced by the same or different halogen atom. In some embodiments, two hydrogen atoms attached to any one carbon atom are replaced by the same or different halogen atom. In some embodiments one hydrogen atom attached to any one carbon atom is replaced by a halogen atom. The alkyl group may be straight chained or branched. Some non-limiting examples of "haloalkyl" include halo$C_{1-6}$alkyl, such as: $—(CH_2)_qCF_3$, $—(CH_2)_qCCl_3$, $—(CH_2)_qCBr_3$, $—(CH_2)_qCHF_2$, $—(CH_2)_qCHCl_2$, $—(CH_2)_qCHBr_2$, $—(CH_2)_qCH_2F$, $—(CH_2)_qCH_2Cl$, and $—(CH_2)_qCH_2Br$, where q is 0, 1, 2, 3, 4 or 5).

"Haloalkoxy" refers to a haloalkyl group, as defined above, when linked by an oxygen atom. Some non-limiting examples include O(halo$C_{1-6}$ alkyl) such as: $—O(CH_2)_qCF_3$, $—O(CH_2)_qCCl_3$, $—O(CH_2)_qCBr_3$, $—O(CH_2)_qCHF_2$, $—O(CH_2)_qCHCl_2$, and $—O(CH_2)_qCHBr_2$, $—O(CH_2)_qCH_2F$, $—O(CH_2)_qCH_2Cl$, and $—O(CH_2)_qCH_2Br$, where q is 0, 1, 2, 3, 4 or 5).

"Alkoxyalkyl" refers to an alkyl group, as herein defined, independently substituted one or more times with an alkoxy group. Where "alkyl" comprises more than one carbon atom, some (e.g. 1, 2, or more) or all of the carbon atoms may be independently substituted with one or more same or different alkoxy groups. The alkyl group may be straight chained or branched and the alkoxy group may be straight chained or branched. Some non-limiting examples of "alkoxyalkyl" include $C_{1-6}$alkoxy$C_{1-6}$alkyl, including $C_{1-3}$alkoxy$C_{1-6}$alkyl, $C_{1-6}$alkoxy$C_{1-3}$alkyl, and $C_{1-3}$alkoxy$C_{1-3}$alkyl. Some further non-limiting examples include: $—(CH_2)_qO(CH_2)_tH$ (where q is 1, 2, 3, 4 5 or 6 and for any value of q, t is 1, 2, 3, 4, 5, or 6).

"Alkoxyalkoxy" refers to an alkoxy group, as herein defined, independently substituted one or more times with an alkoxy group. Some non-limiting examples include $C_{1-6}$ alkoxy (e.g. $C_{1-3}$alkoxy) independently substituted one or more times with the same or different $C_{1-6}$ alkoxy group (e.g. $C_{1-3}$alkoxy). Some non-limiting examples include: $—OCH_2OCH_3$, $—O(CH_2)_2OCH_3$, $—O(CH_2)_3OCH_3$, $—OCH_2OCH_2CH_3$, $—O(CH_2)_2OCH_2CH_3$, $—O(CH_2)_3OCH_2CH_3$, $—OCH_2O(CH_2)_2CH_3$, $—O(CH_2)_2O(CH_2)_2CH_3$, $—O(CH_2)_3O(CH_2)_2CH_3$.

"Hydroxyalkyl" refers to an alkyl group, as herein defined, independently substituted one or more times (e.g. 1, 2 or 3 times) with a hydroxy group. Some non-limiting examples include hydroxy$C_{1-6}$alkyl, i.e. $C_{1-6}$alkyl substituted one or more times (e.g. 1, 2 or 3 times) with a hydroxyl group. The alkyl group may be straight chained or branched. In further examples hydroxyalkyl refers to hydroxy$C_{1-3}$alkyl, i.e. $C_{1-3}$alkyl substituted one or more times (e.g. 1, 2 or 3 times) with a hydroxy group. Some non-limiting examples include: $—(CH_2)OH$, $—(CH_2)_2OH$, $—CH(OH)CH_2OH$, $CH(OH)CH_3$, $—(CH_2)_3OH$, $—CH(OH)(CH_2)_2OH$, $—CH_2CH(OH)CH_2OH$, $—(CH(OH))_2CH_3$ and $—(CH(OH))_2CH_2OH$.

"($SC_{1-6}$alkyl)$C_{1-6}$alkyl" refers to $C_{1-6}$alkyl group, as herein defined, independently substituted one or more times (e.g. 1, 2 or 3 times) with a $—SC_{1-6}$alkyl group. Some non-limiting examples include $C_{1-3}$alkyl substituted one or more times (e.g. 1, 2 or 3 times) with a $—SC_{1-6}$alkyl group. The alkyl group may be straight chained or branched. In further examples—Some non-limiting examples include: $—(CH_2)SCH_3$, $—(CH_2)_2SCH_3$, $—CH(SCH_3)CH_2SCH_3$, $CH(SCH_3)CH_3$, $—(CH_2)_3SCH_3$, $—CH(SCH_3)(CH_2)_2SCH_3$, $—CH_2CH(SCH_3)CH_2SCH_3$, $—(CH(SCH_3))_2CH_3$ and $—(CH(SCH_3))_2CH_2SCH_3$.

As defined herein, a group may be optionally substituted, ie it may be unsubstituted or further substituted by one or more, same or different optional substituents. Optional substituents (which may be further substituted where indicated below) for "alkyl" or "alk", either used alone or in a composite term, or by reference to in the definition of a term, for example cycloalkyl or cycloamino, include:

alkyl, (e.g. $C_{1-6}$alkyl such as methyl, ethyl, propyl, butyl),
cycloalkyl (e.g. $C_{3-6}$cycloalkyl, such as cyclopropyl, cyclobutyl, cyclopentyl or cyclohexyl), hydroxyalkyl (e.g. hydroxy$C_{1-6}$alkyl, such as hydroxymethyl, hydroxyethyl, hydroxypropyl),
alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl),
alkoxy (e.g. $C_{1-6}$alkoxy, such as methoxy, ethoxy, propoxy, butoxy),
alkoxyalkoxy (e.g. $C_{1-6}$alkoxy$C_{1-6}$alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy),
cycloalkoxy (e.g. cyclopropoxy, cyclobutoxy, cyclopentoxyl, cyclohexyloxy),
halo,
haloalkyl (which includes, mono-, di-, and trihalo, e.g. halo$C_{1-6}$alkyl, such as trifluoromethyl, trichloromethyl, tribromomethyl),
haloalkoxy (which includes, mono-, di-, and trihalo, e.g. halo$C_{1-6}$alkoxy, such as trifluoromethoxy, trichloromethoxy, tribromomethoxy),
hydroxy,
thiol (—SH),
alkylthio (e.g. —$SC_{1-6}$alkyl),
phenyl (which itself may be further substituted e.g., by one or more of $C_{1-6}$alkyl, halo, hydroxy, hydroxy$C_{1-6}$ alkyl, $C_{1-6}$alkoxy, $C_{1-6}$alkoxy$C_{1-6}$alkyl, $C_{1-6}$alkoxy$C_{1-6}$ alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
phenoxy (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
benzyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
—$NH_2$,
alkylamino (e.g. —$NHC_{1-6}$alkyl, such as methylamino, ethylamino, propylamino etc),
dialkylamino (e.g. —NH($C_{1-6}$alkyl)$_2$, such as dimethylamino, diethylamino, dipropylamino),
acylamino (e.g. —NHC(O)$C_{1-6}$alkyl, such as —NHC(O)$CH_3$),
phenylamino (i.e. —NHphenyl, wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$ alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)$C_{1-6}$alkyl),
nitro,
cyano,
formyl,
acyl, including —C(O)-alkyl (e.g. —C(O)$C_{1-6}$alkyl, such as acetyl),
—O—C(O)-alkyl (e.g. —$OC(O)C_{1-6}$alkyl, such as acetyloxy),
benzoyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
benzoyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
$CO_2H$,
$CO_2$alkyl (e.g. $CO_2C_{1-6}$alkyl such as methyl ester, ethyl ester, propyl ester, butyl ester),
$CO_2$phenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
$CO_2$benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
—$CONH_2$,
—C(O)NHphenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$ alkyl, $C_{1-6}$alkoxy$C_{1-6}$alkoxy, halo$C_{1-6}$ alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
—C(O)NHbenzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$ alkyl, $C_{1-6}$alkoxy$C_{1-6}$alkoxy, halo$C_{1-6}$ alkyl, halo$C_{1-6}$alkoxy, cyano, nitro, —$OC(O)C_{1-6}$alkyl, —$NH_2$, —$NHC_{1-6}$alkyl, —NHC(O)$C_{1-6}$alkyl and —N($C_{1-6}$alkyl)($C_{1-6}$alkyl)),
—C(O)NHalkyl (e.g. C(O)$NHC_{1-6}$ alkyl such as methyl ester, ethyl ester, propyl ester, butyl amide),
—C(O)NHdialkyl (e.g. C(O)NH($C_{1-6}$alkyl)$_2$),
aminoalkyl (e.g., $HNC_{1-6}$alkyl-, $C_{1-6}$alkylHN—$C_{1-6}$alkyl- and ($C_{1-6}$alkyl)$_2$N—$C_{1-6}$alkyl-),
thioalkyl (e.g., $HSC_{1-6}$alkyl-),
carboxyalkyl (e.g., $HO_2CC_{1-6}$alkyl-),
carboxyesteralkyl (e.g., $C_{1-6}$alkyl$O_2CC_{1-6}$alkyl-),
amidoalkyl (e.g., $H_2N(O)CC_{1-6}$alkyl-, H($C_{1-6}$alkyl)N(O)$CC_{1-6}$alkyl-), formylalkyl (e.g., $H(O)CC_{1-6}alkyl$-),
acylalkyl (e.g., $C_{1-6}alkyl(O)CC_{1-6}alkyl$-),
nitroalkyl (e.g., $O_2NC_{1-6}alkyl$-),
replacement of $CH_2$ with C═O, and
where 2 carbon atoms (1,2 or 1,3) are substituted by one end each of a —O—$(CH_2)_n$—O— or —NH—$(CH_2)_n$—NH— group, wherein n is 1 or 2.

In some embodiments, each $R^a$ is independently selected from H, chloro, fluoro, bromo, iodo, halo$C_{1-6}$alkyl, (e.g. fluoro$C_{1-6}$alkyl, such as —$CHF_2$ and —$CF_3$), $C_{1-6}$alkyl, $C_{1-6}$alkoxy $C_{3-6}$cycloalkyl, aziridinyl, azetidinyl, pyrrolidinyl, piperidinlyl, haloaziridinyl, haloazetidinyl, halopyrrolidinyl, halopiperidinlyl and halo$C_{1-6}$alkoxy (e.g. fluoro$C_{1-6}$ alkoxy, such as —$OCHF_2$ and —$OCF_3$). In further embodiments, each $R^a$ is independently selected from H, chloro, fluoro, bromo, iodo, halo$C_{1-3}$alkyl, $C_{1-3}$alkyl, $C_{1-3}$alkoxy, $C_{3-6}$cycloalkyl and halo$C_{1-3}$alkoxy.

In some embodiments, Each of $A^1$-$A^5$ is C—$R^a$. In still further embodiments, $A^3$ is not C—H. In some further embodiments thereof one or two of C—$R^a$ is C—$R^{aa}$, wherein $R^{aa}$ is not H, with the remainder C—H. In still further embodiments, $R^{aa}$ is selected from F, Cl, I, Me, cyclopropyl, difluoroazetidinyl, OMe, $CHF_2$, $CF_3$ $OCHF_2$ and $OCF_3$ In some embodiments, at least $A^3$ is C—$R^{aa}$, and in a further embodiments thereof, $A^3$ is not C—H. In some further embodiments $A^3$ is C—$R^{aa}$ and $A^1$, $A^2$, $A^4$ and $A^5$ are each C—H. In some embodiments $A^3$ is C—$R^{aa}$ and one of $A^4$ or $A^2$ is the same or different C—$R^{aa}$. In still further embodiments, each $R^{aa}$ is independently selected from F, Cl, I, Me, cyclopropyl, difluoroazetidinyl, OMe, $CHF_2$, $CF_3$ $OCHF_2$ and $OCF_3$.

In some embodiments, any one or two of $A^1$, $A^2$, $A^3$, $A^4$ or $A^5$ may be N. In some embodiments, $A^5$ or $A^1$ is N; or $A^2$ or $A^4$ is N; or $A^1$ and $A^5$ are both N; or $A^2$ and $A^4$ are both N; or $A^1$ and $A^4$, or $A^2$ and $A^5$ are both N; or $A^1$ and $A^2$ or $A^4$ and $A^5$ are both N. In some of these embodiments $A^3$ is C—$R^{aa}$. In still further embodiments, $R^{aa}$ is selected from F, Cl, I, Me, cyclopropyl, difluoroazetidinyl, OMe, $CHF_2$, $CF_3$ $OCHF_2$ and $OCF_3$ In some embodiments Q is a 5-membered heteroaromatic ring having 2, 3 or 4 ring heteroatoms, at least one of which must be N and the remaining heteroatoms independently selected from N, O and S, and is selected from heterocyclic formulas (a)-(kk), which may optionally substituted with a group $Q^a$ where permissible (where the bonds labelled # are attached to NH and the bonds labelled * are attached to the aryl ring defined by $A^1$-$A^5$):

(a)

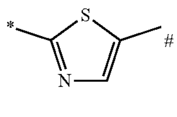

(b)

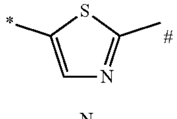

(c)

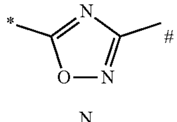

(d)

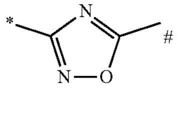

-continued (e)

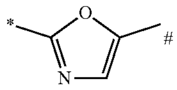

(f)

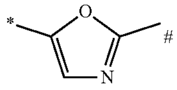

(g)

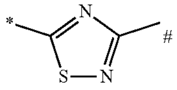

(h)

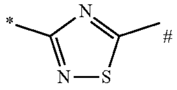

(i)

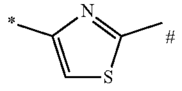

(j)

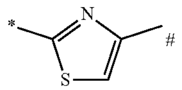

(k)

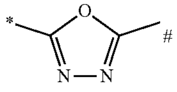

(l)

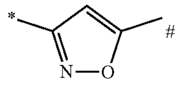

(m)

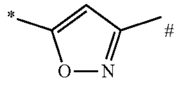

(n)

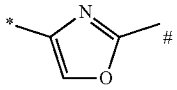

(o)

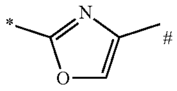

(p)

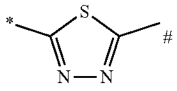

(q)

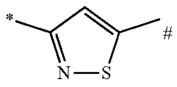

(r)

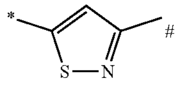

(s)

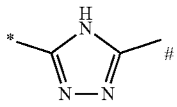

-continued (t)

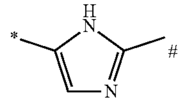

(u)

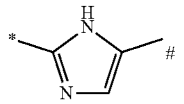

(v)

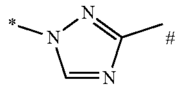

(w)

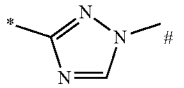

(x)

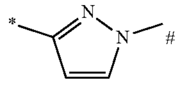

(y)

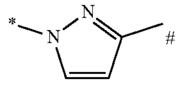

(z)

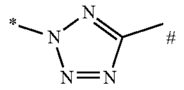

(aa)

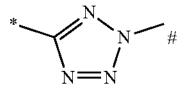

(bb)

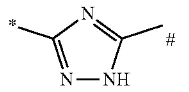

(cc)

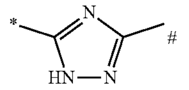

(dd)

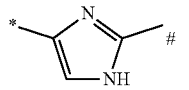

(ee)

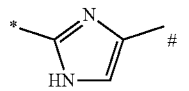

(ff)

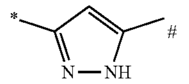

(gg)

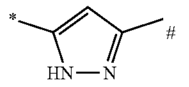

(hh)

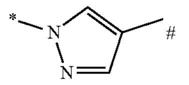

(ii)

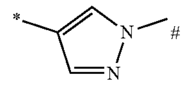

-continued (jj)

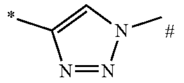

(kk)

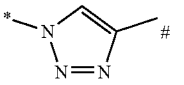

Where Q contains a carbon or nitrogen ring atom bearing a hydrogen atom (e.g. (a), (b), (e), (f), (i), (j), (l), (m), (n), (o), (q), (r), (t), (u), (v), (w), x), (y), (bb), (cc), (dd), (ee), (ff), (gg), (hh) and (ii)), that carbon or nitrogen atom may be optionally substituted (i.e. the hydrogen atom replaced) with a group $Q^a$, selected from halo, haloalkyl and alkyl. For example, $Q^a$ may be selected from, Cl, F, Br, I, $C_{1-6}$alkyl (e.g. methyl, ethyl, n- and i-propyl, n-, sec- and t-butyl, pentyl, hexyl), and halo$C_{1-6}$alkyl (e.g. $(CH_2)_qCF_3$, $(CH_2)_qCCl_3$, $(CH_2)_qCBr_3$, $(CH_2)_qCHF_2$, $(CH_2)_qCHCl_2$, and $(CH_2)_qCHBr_2$, $(CH_2)_qCH_2F$, $(CH_2)_qCH_2Cl$, and $(CH_2)_qCH_2Br$, where q is 0, 1, 2, 3, 4 or 5). In further embodiments, $Q^a$ is selected from Cl, F, Br, I, $CH_3$, $CF_3$, $CBr_3$, and $CCl_3$. In some embodiments said carbon or nitrogen ring atom is unsubstituted. In other embodiments said carbon or nitrogen ring atom is substituted with $Q^a$.

Some further non-limiting examples of Q having a carbon or nitrogen ring atom substituted with $Q^a$ include:

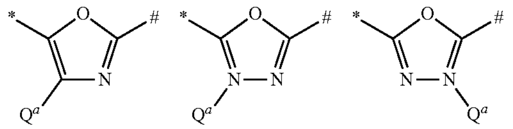

Further embodiments include where $Q^a$, is for example Cl, F, Br, I, $C_{1-6}$alkyl (e.g. methyl, ethyl, n- and i-propyl). In some further embodiments $Q^a$ is methyl.

In some embodiments, Q is a 5-membered heteroaromatic ring having 2 or 3 ring heteroatoms, at least one of which must be N and the remaining independently selected from N, O and S, where a carbon or nitrogen ring atom may be optionally substituted as described above.

In some embodiments, Q is selected from one or more of $Q_1$, $Q_2$, $Q_3$, $Q_4$ or $Q_5$:

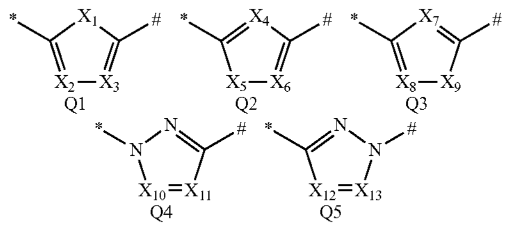

Q1 Q2 Q3 Q4 Q5 wherein $X_1$ is O, S or NH and $X_2$ and $X_3$ are independently CH or N, provided both are not CH (formulae (a), (b), (e), (f), (k), (p), (s), (t) and (u));

$X_5$ is O, S or NH and $X_4$ and $X_6$ are independently CH or N, provided both are not CH (formulae (c), (g), (j), (f), (m), (o), (r), (cc), (ee) and (gg));

$X_9$ is O, S or NH and $X_7$ and $X_8$ are independently CH or N, provided both are not CH (formulae (d), (h), (i), (l), (n), (q), (bb), (dd) and (ff)); and $X_{10}$—$X_{13}$ are in dependently CH or N (formulae (v), (w), (x) and (y)):

and wherein Q may be unsubsituted, or substituted with $Q^a$.

In some embodiments, Q has 3 ring heteroatoms (formulae (c), (d), (g), (h), (k) (p), (s), (v), w), (jj) and (kk)). In some examples thereof, Q has two ring nitrogen atoms and one ring oxygen atom. In other examples thereof, Q has two ring nitrogen atoms and one ring sulfur atom. In other examples thereof, Q has three ring nitrogen atoms.

In other embodiments Q has 2 ring heteroatoms (formulae (a), (b), (e), (f), (i) (j) (l), (m), (n), (o), (q), (r), (t), (u), (x), (y), (hh) and (ii)). In some examples thereof, Q has one ring nitrogen atom and one ring oxygen atom. In other examples thereof, Q has one ring nitrogen atom and one ring sulfur atom. In other examples thereof, Q has two ring nitrogen atoms.

In other embodiments, Q has one or two nitrogen ring atoms and one ring oxygen atom (formulae (c), (d), (e), (f), (k) (l) (m), (n) and (o)).

In other embodiments Q has one or two nitrogen ring atoms and one ring sulfur atom (formulae (a), (b), (g), (h), (i) (j) (p), (q) and (r)).

In other embodiments, Q has two or three or 4 nitrogen ring atoms and no O or S ring atoms (formulae (s), (t), (u), (v), (w), (x), (y), (z), (aa), (bb), (cc), (dd), (ee), (ff), (gg) (hh), (ii), (jj) and (kk).

In some embodiments, Q is selected from (c), (d), (f), (g), (h), (i), (j), (k) and (p).

In some embodiments, Q is selected from (c), (d), (f), (h), (i), (j), (k) and (p).

In some embodiments, Q is selected from (c), (d), (f), (i), (j), (k) and (p).

In some embodiments, Q is an oxadiazolyl group (formulae (c), (d) and (k)).

In some embodiments, Q is selected from (d), (f), (i), (k), (l), (n), (v), (y), (ee), (ff) (hh) and (kk). In some further embodiments, Q is selected from (f) and (k).

In some embodiments, including any one embodiment of Q as described above, such as where Q is selected from (f), (i), (k) (n) and (v), and including where a ring carbon or nitrogen atom may be optionally substituted with $Q^a$, W contains 1 or 2 nitrogen ring atoms. In some embodiments, W contains at least 1 nitrogen ring atom at a position ortho-to C—$R^b$, i.e. having the formula (A), (B), (C), (D), (F), (G), or (J). In further examples of any one such embodiments, $R^d$ is H, OH, C, Br, F, I, $CH_3$ or $OCH_3$. In some further embodiments, W is selected from:

(A)

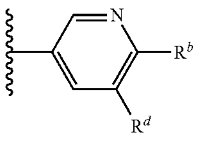

(B)

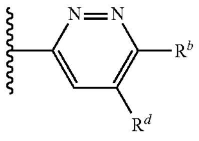

(D)

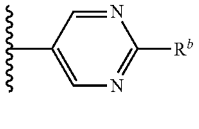

-continued (E)

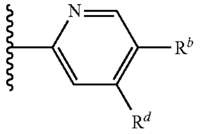

(F)

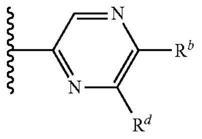

(H)

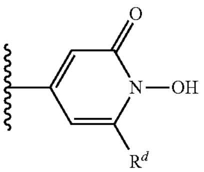

and $R^d$ is H, OH, F, I, Cl, Br, $CH_3$ or $OCH_3$. $R^b$ may K—$NR^C$—Y, or a tautomer thereof.

In some embodiments, including any one embodiment of Q as described above, such as where Q is selected from (f), (i), (k) (n) and (v), and including where a ring carbon or nitrogen atom is optionally substituted with $Q^a$, W is a 6-membered N-containing heterocycle (aromatic or non-aromatic) selected from:

(A)

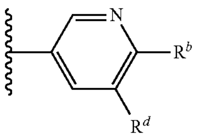

(B)

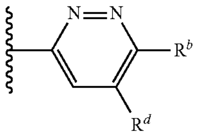

(C)

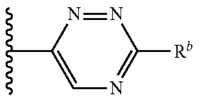

(D)

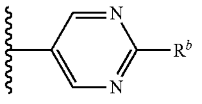

(E)

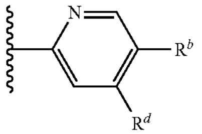

(F)

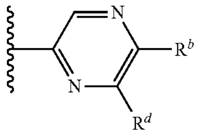

-continued (G)

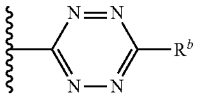

(H)

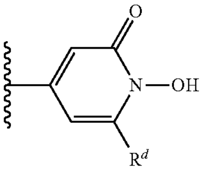

(I)

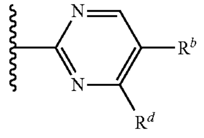

(J)

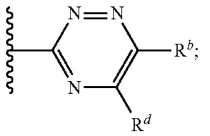

wherein $R^d$ is H, OH, F, CL, I, Br, $CH_3$ or $OCH_3$, and $R^b$ is —K—$NR^c$—Y, or a tautomer thereof.

In some embodiments, including any one of the embodiments described above, $R^b$ is —K—$NR^c$—Y, or tautomer thereof, where:

K is $SO_2$, C(═O), C(═NH), or NHC(═O), $R^c$ is H, $C_{1-6}$alkyl (e.g. $C_{1-3}$alkyl, such as $CH_3$, $CH_2CH_3$ or $(CH_2)_2CH_3$); or hydroxy$C_{1-6}$alkyl (e.g. hydroxy$C_{1-3}$ alkyl; such as —$(CH_2)$OH, —$(CH_2)_2$OH, —CH(OH)$CH_2$OH, CH(OH)$CH_3$, —$(CH_2)_3$OH, —CH(OH)$(CH_2)_2$OH, —$CH_2$CH(OH)$CH_2$OH, —$(CH(OH))_2$$CH_3$ and —$(CH(OH))_2$$CH_2$OH); and Y is OH, $NH_2$, NH$C_{1-6}$alkyl, NHC(═O)H, NH(C(═O)$C_{1-6}$alkyl, hydroxy$C_{1-6}$alkyl (e.g. hydroxy$C_{1-3}$alkyl; such as —$(CH_2)$OH, —$(CH_2)_2$OH, —CH(OH)$CH_2$OH, CH(OH)$CH_3$, —$(CH_2)_3$OH, —CH(OH)$(CH_2)_2$OH, —$CH_2$CH(OH)$CH_2$OH, —$(CH(OH))_2$$CH_3$ and —$(CH(OH))_2$$CH_2$OH); or (S$C_{1-6}$alkyl)$C_{1-6}$alkyl (e.g. (S$C_{1-3}$alkyl)$C_{1-3}$alkyl, such as —$(CH_2)$S$CH_3$, —$(CH_2)_2$S$CH_3$, —CH(S$CH_3$)$CH_2$S$CH_3$, CH(S$CH_3$)$CH_3$, —$(CH_2)_3$S$CH_3$, —CH(S$CH_3$)$(CH_2)_2$S$CH_3$, —$CH_2$CH(S$CH_3$)$CH_2$S$CH_3$, —$(CH(SCH_3))_2$$CH_3$ and —$(CH(SCH_3))_2$$CH_2$S$CH_3$).

In some embodiments $R^b$ is

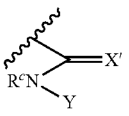

wherein

X' is O or NH, $R^c$ is H or $C_{1-6}$alkyl; or hydroxy$C_{1-6}$alkyl; and

Y is OH or $NH_2$.

or W is of formula (H).

In still further embodiments, $R^b$ is selected from:

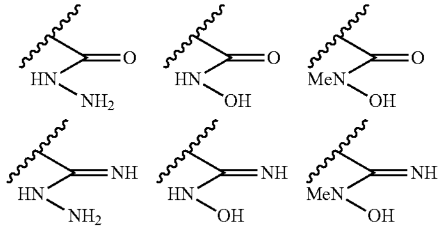

or a tautomer thereof. By way of example, in some further embodiments, $R^b$ may be either

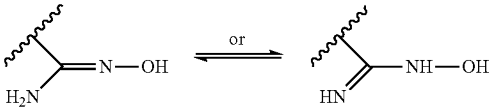

or

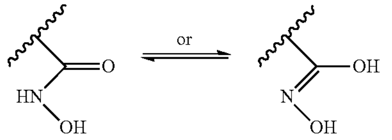

The amidine group may be present as a substantially pure (e.g. >90%, or 95% or 99%) E- or Z-isomer, or may be a mixture of E- and Z-isomers.

In some further embodiments, Q is of formula (f) or (k), and $R^b$ is —C(═X')—$NR^c$—Y, wherein X' is O or NH, $R^c$ is H or Me, and Y is OH or $NH_2$.

In some embodiments, W comprises the moiety C(═O)—N—OH, e.g. W has the formula (H) or where $R^b$ is C(═O)—NR'—OH, or NHC(═O)—NR'—OH (where R' is H, $C_{1-6}$alkyl or hydroxy$C_{1-6}$alkyl). In still further embodiments, $R^d$ is H, OH, F, CL, I, Br, $CH_3$ or $OCH_3$.

In some embodiments, $R^b$ is OH and W is (E) or (I). $R^d$ may be selected from H, OH, F, Cl, Br, I, $C_1$alkyl, $C_2$alkyl, $C_3$alkyl, $C_4$alkyl, $C_5$alkyl, $C_6$alkyl, $C_1$alkoxy, $C_2$alkoxy, $C_3$alkoxy, $C_4$alkoxy $C_5$alkoxy, $C_6$alkoxy. In some further embodiments, $R^d$ is H, OH, F, Cl, Br, I, $CH_3$ or $OCH_3$.

In some embodiments, $R^b$ is K—$NR^c$—Y, or a tautomer thereof, or —$(CH_2)_p$—NH—OH. In further embodiments, $NHR^e$ is $NH_2$, NH$C_{1-3}$alkyl, NHC(═O)H, NH(C(═O)$C_{1-3}$ alkyl. $R^d$ may be selected from H, OH, F, Cl, Br, I, $C_1$alkyl, $C_2$alkyl, $C_3$alkyl, $C_4$alkyl, $C_5$alkyl, $C_6$alkyl, $C_1$alkoxy, $C_2$alkoxy, $C_3$alkoxy, $C_4$alkoxy $C_5$alkoxy, $C_6$alkoxy. In some further embodiments, $R^d$ is H, OH, F, Cl, Br, I, $CH_3$ or $OCH_3$.

In some embodiments, $R^b$ is K—$NR^c$—Y, or a tautomer thereof, or —$(CH_2)_p$—NH—OH, and W is one of (A), (B), (C), (D), (F), (G), (H), (J). In further embodiments, $NHR^e$ is $NH_2$, NH$C_{1-3}$alkyl, NHC(═O)H, NH(C(═O)$C_{1-3}$alkyl. $R^d$ may be selected from H, OH, F, Cl, Br, I, $C_1$alkyl, $C_2$alkyl, $C_3$alkyl, $C_4$alkyl, $C_5$alkyl, $C_6$alkyl, $C_1$alkoxy, $C_2$alkoxy, $C_3$alkoxy, $C_4$alkoxy $C_5$alkoxy, $C_6$alkoxy. In some further embodiments, $R^d$ is H, OH, F, Cl, Br, I, $CH_3$ or $OCH_3$.

In some embodiments, including any embodiment of Q as described above, and including where a ring carbon or nitrogen atom is optionally substituted with $Q^a$, W is (E) or (I) and Rb is OH. In still further embodiments thereof, $R^d$ is H, OH, F, Cl, I, Br, $CH_3$ or $OCH_3$.

In some embodiments, when W is of formula (I), then $R^b$ is not —(C═O)—NH—OH.

The disclosure also provides compounds of Formula (I"), wherein $R^b$ and $R^d$ of Formula (I') are transposed, and pharmaceutically acceptable salts and solvates thereof.

In another aspect, there is provided compounds of Formula (IA), comprising compounds of Formula (I'), and pharmaceutically acceptable salts and solvates thereof and compounds of Formula (I"), wherein $R^b$ and $R^d$ of Formula (I') are transposed, and pharmaceutically acceptable salts and solvates thereof. Any one of the embodiments described for (I') apply to (II'). In some embodiments W does not contain a N ring atom adjacent, or ortho-, to a ring carbon bearing a OH group.

For compounds that are capable of tautomerism, under certain conditions, e.g., solvents, salt forms, pH, etc, one tautomer may be a preferred form over another, but changes in conditions may result in formation of the other tautomer. It will be understood that, where appropriate, tautomers of Formula (I'), for example certain $R^b$ groups, may exist, and are also encompassed by the disclosure herein. Unless otherwise specified, a compound depicted in one tautomeric form is also a disclosure of the other tautomeric form. Some exemplary tautomeric $R^b$ groups include:

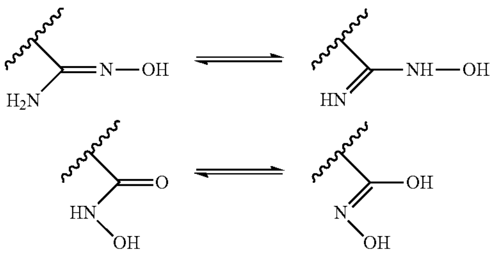

It will be appreciated that tautomers can exists in E- and Z-forms where appropriate, either as substantially pure (e.g. >90%, or 95% or 99%) E- or Z-isomers or a mixture of isomers.

In some embodiments, compounds disclosed herein have any one or more of any of $A^1$-$A^5$, $R^a$, $R^{aa}$, Q, W, $R^b$ $R^c$, $R^d$ and $R^e$ as depicted in the compounds disclosed or described in the Examples 1-120. Thus, also expressly disclosed herein are compounds having any combination of, for example, $A^1$-$A^5$ and Q, $A^1$-$A^5$ and W, Q and W, $R^b$ and W, as depicted in any one of compounds 1-120.

It will also be recognised that certain compounds of the disclosure may possess asymmetric centres and are therefore capable of existing in more than one stereoisomeric form, such as enantiomers and diastereomers. The invention thus also relates to optically active compounds and compounds in substantially pure isomeric form at one or more asymmetric centres, e.g., enantiomers having greater than about 90% ee, such as about 95% or 97% ee or greater than 99% ee, as well as mixtures, including racemic mixtures, thereof. Such isomers may be prepared by asymmetric synthesis, for example using chiral intermediates or reagents, enzymes, or mixtures may be resolved by conventional methods, e.g., chromatography, recrystallization, or use of a resolving agent.

In some embodiments, at least one of $R^a$, $R^b$, $R^cR^d$ and $R^e$ possess at least one chiral centre. In further such embodiments, at one of $R^a$, $R^b$ and $R^c$, $R^d$ and $R^e$ possess a chiral centre. In some embodiments, one of $R^a$, $R^b$, $R^c$, $R^d$ or $R^e$ has one chiral centre and the compound exists as a mixture of enantiomers, e.g. a racemic mixture, or the compound may be substantially enantiomerically pure, i.e. substantially the R- or S-form. One example is $R^b$=—$CH_2C^*H(OH)CH_2OH$, where C* is the chiral centre. Compounds bearing $R^b$=—$CH_2C^*H(OH)CH_2OH$, may exist as a mixture of enantiomers (e.g. a racemic mixture) or may be in the substantially enantiomerically pure R- or S-form.

Compounds of the disclosure may be prepared using any suitable methodology. The Examples section sets out numerous methodologies that can be further extrapolated to the preparation the compounds of the disclosure, using routine skill and knowledge, such as by varying starting materials and reagents, solvents, etc. and methods for the preparation of heterocycles as known in the art (see for example, Aurelio, L., et al, *J. Med. Chem.,* 2016, 59, 965-984; Sharma, S., *Sulfur Reports,* 1989, 8, 327-469). In some non-limiting embodiments, compounds can be prepared by coupling a precursor comprising the $R^a$-substituted phenyl and Q moieties (or their precursor(s)) with an appropriate W moiety or precursor thereof. In other non-limiting embodiments compounds may be prepared by internal cyclization (to produce a Q' moiety), of a precursor compound comprising the $R^a$-substituted phenyl and W moieties, (or precursor(s) thereof). As used herein, a "precursor" includes a chemical entity or moiety that may be converted to the desired compound or moiety by one or more chemical transformations and/or couplings. Some illustrative generalized schemes for preparation of various compounds of formula (I') and/or precursors therefor, are set out in Schemes A-V below.

Scheme A

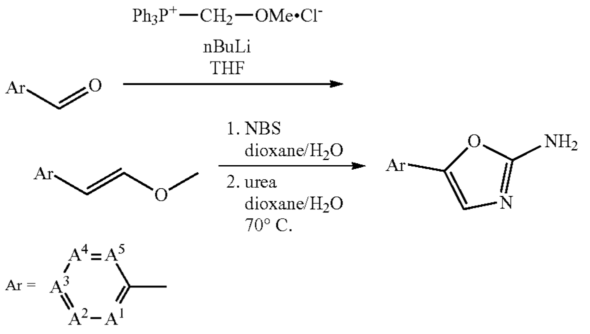

Scheme B

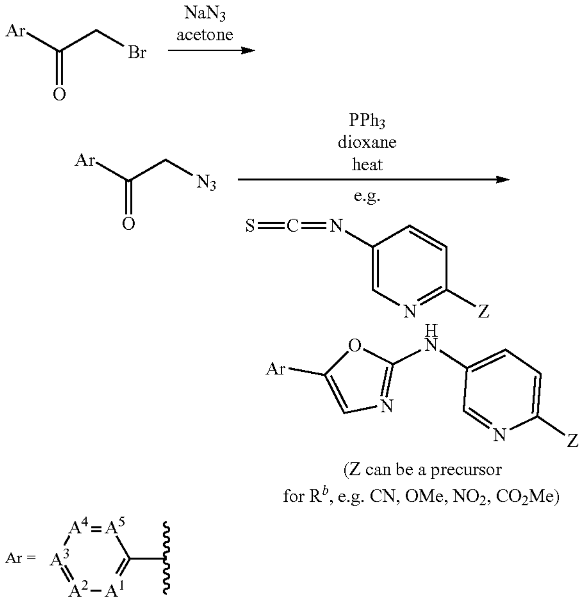

Scheme C
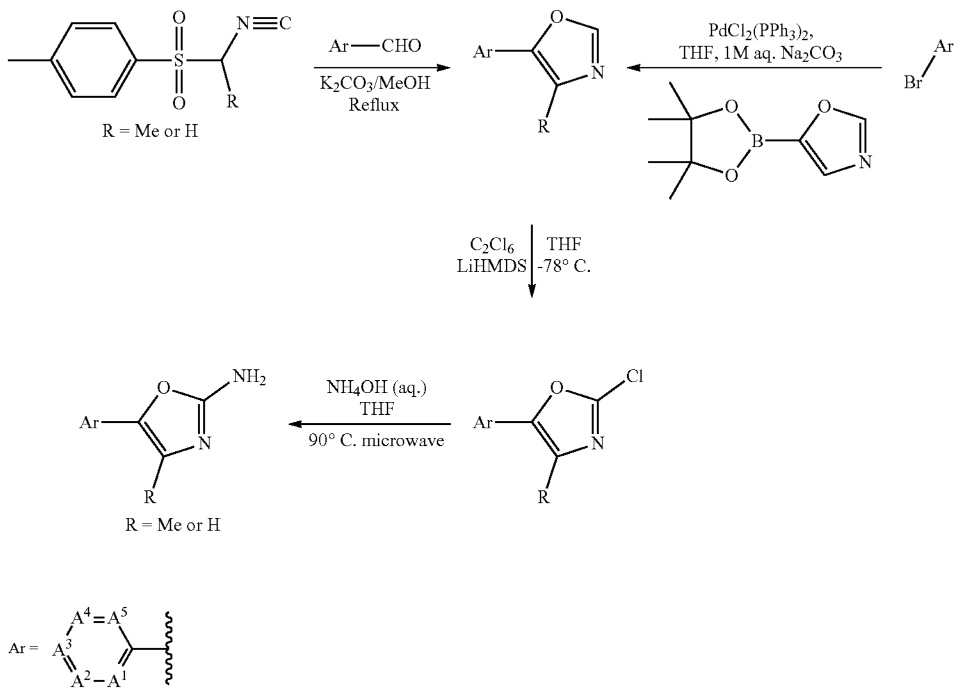
Scheme D
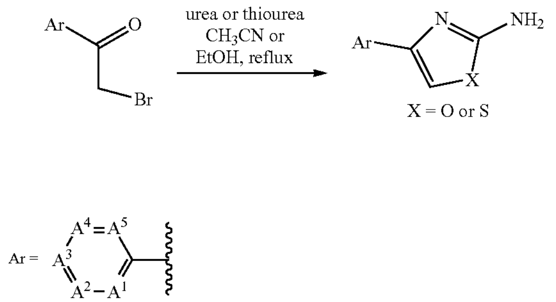
Scheme E
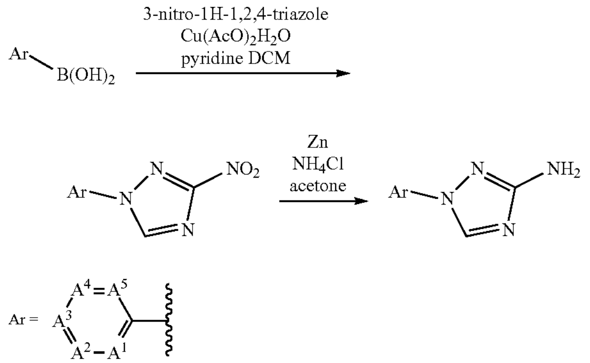
Scheme F
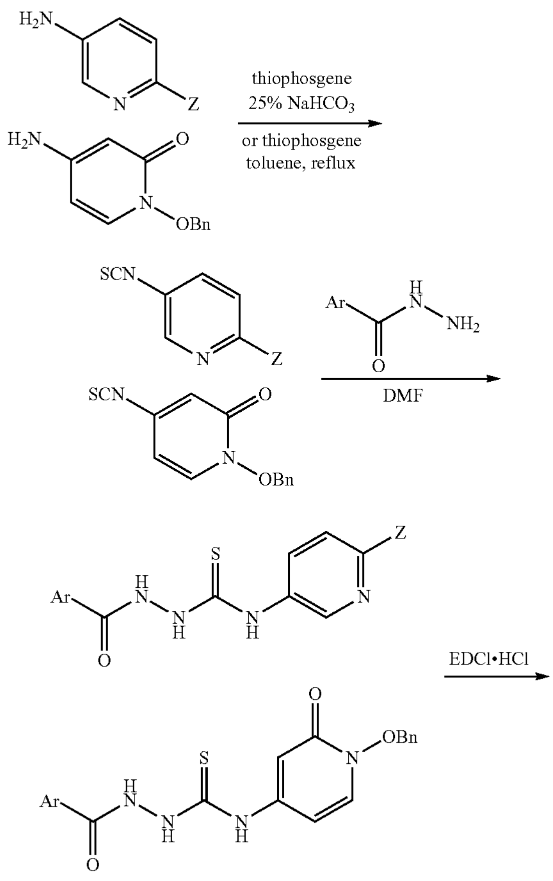

-continued
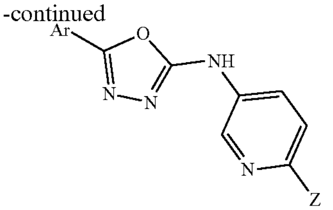
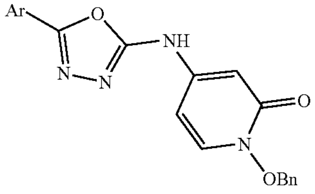
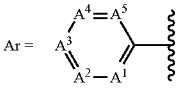
(Z can be a precursor for $R^b$, e.g. CN, $CO_2Me$, OMe, $NO_2$)
Scheme G
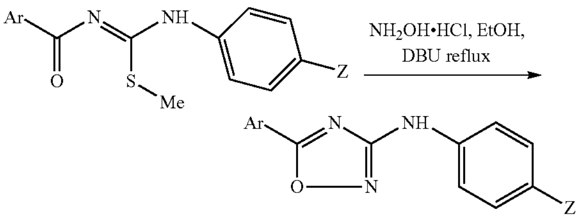
(Z can be a precursor for $R^b$, e.g. CN, $CO_2Me$, OMe, $NO_2$)
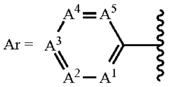
Scheme H
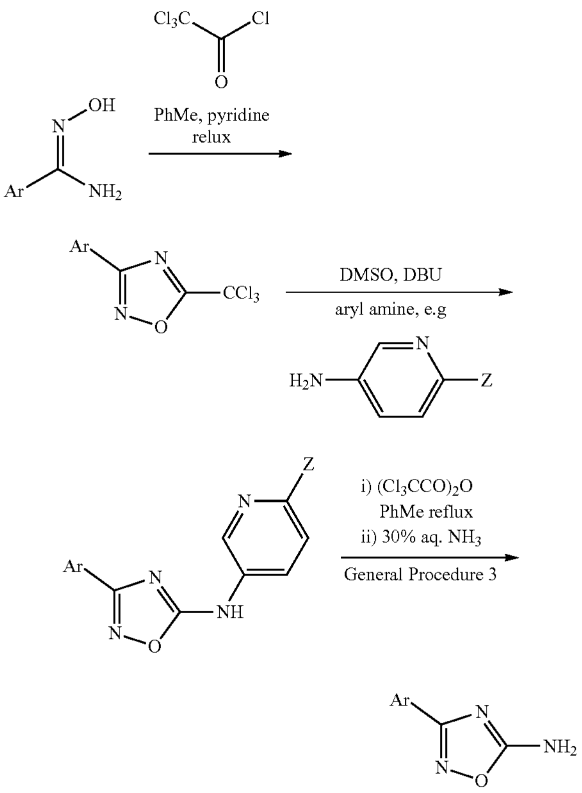
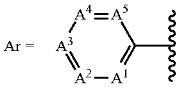
(Z can be a precursor for $R^b$, e.g. CN, $CO_2Me$, OMe, $NO_2$)
Scheme I
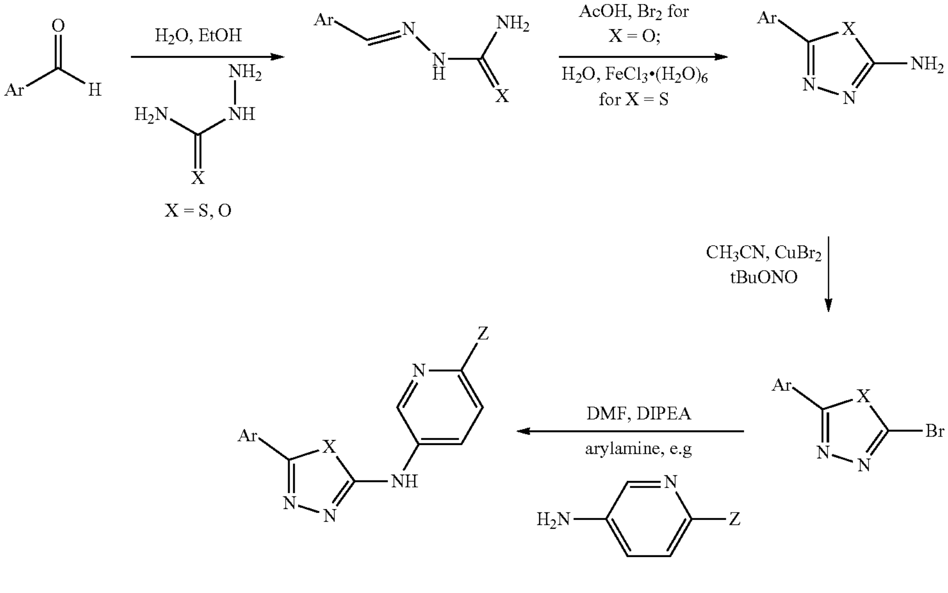

-continued
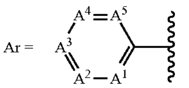
(Z can be a precursor for $R^b$, e.g. CN, $CO_2Me$, OMe, $NO_2$)
Scheme J
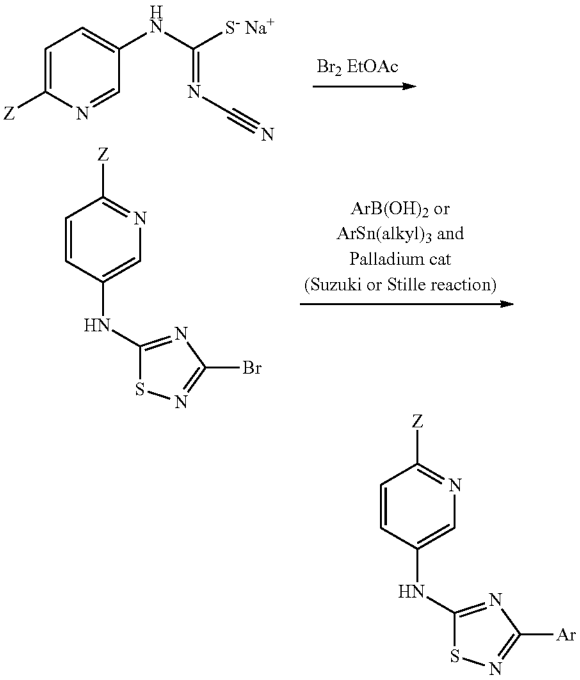
(Z can be a precursor for $R^b$ e.g. CN, $CO_2Me$, OMe, $NO_2$)
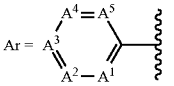
Scheme K
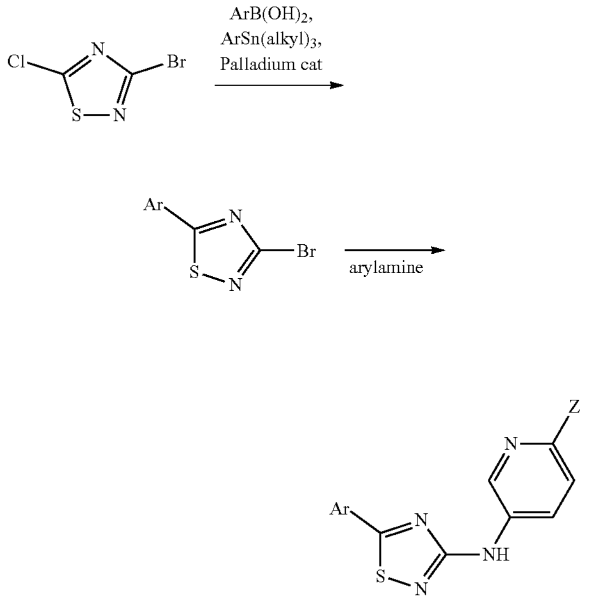
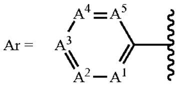
(Z can be a precursor for $R^b$, e.g. CN, $CO_2Me$, OMe, $NO_2$)
Scheme L
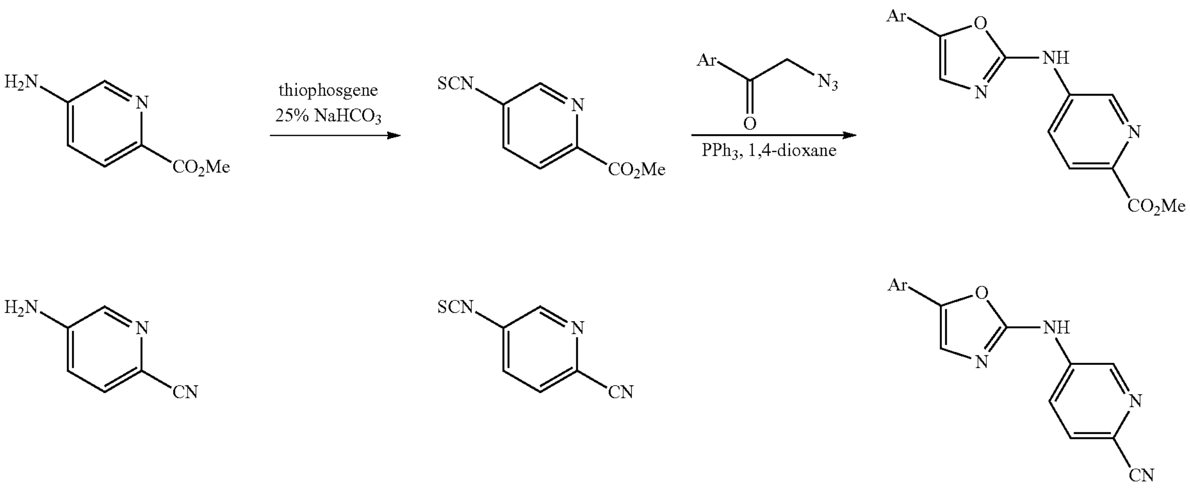

-continued
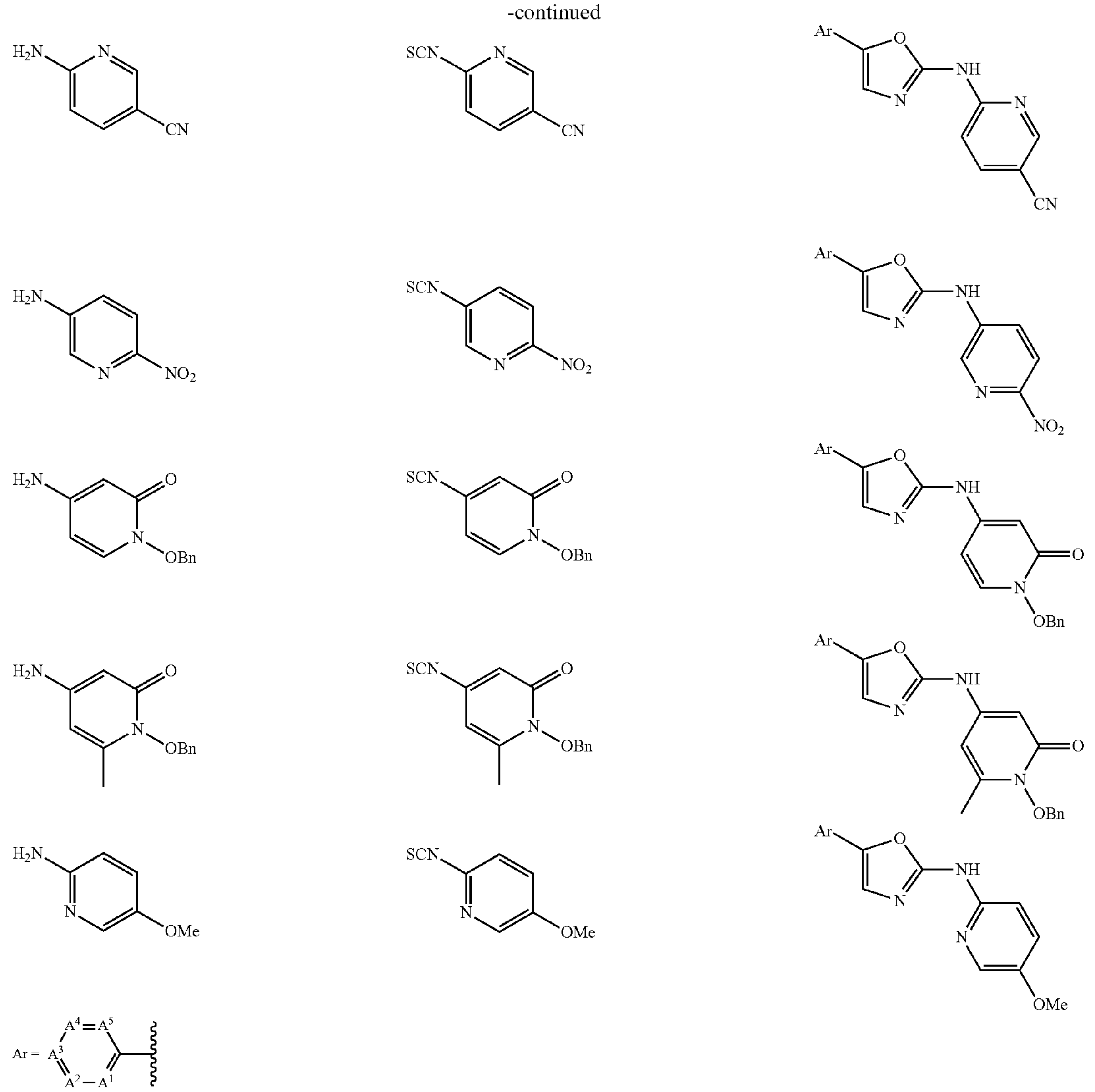
Scheme M
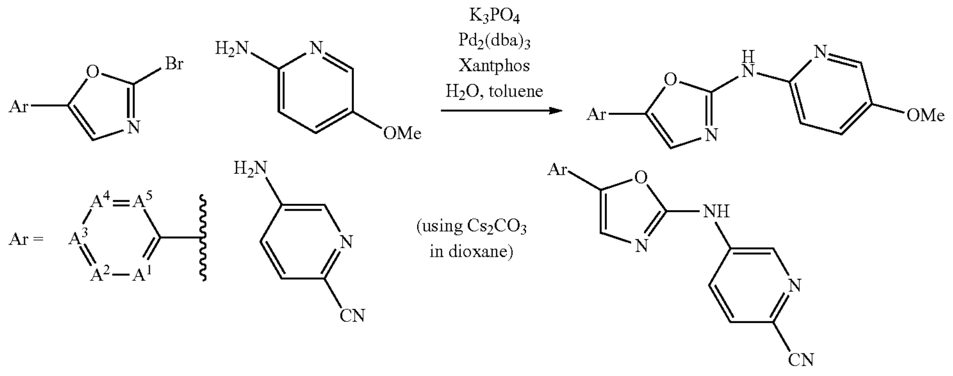

-continued
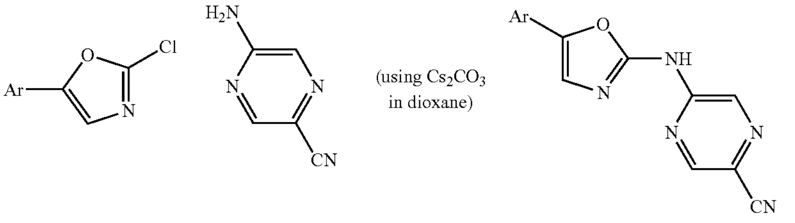
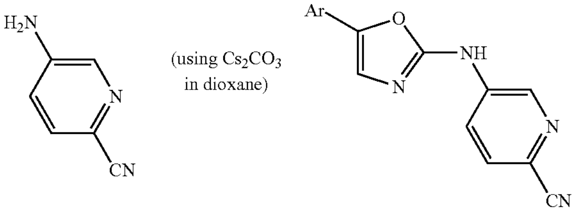
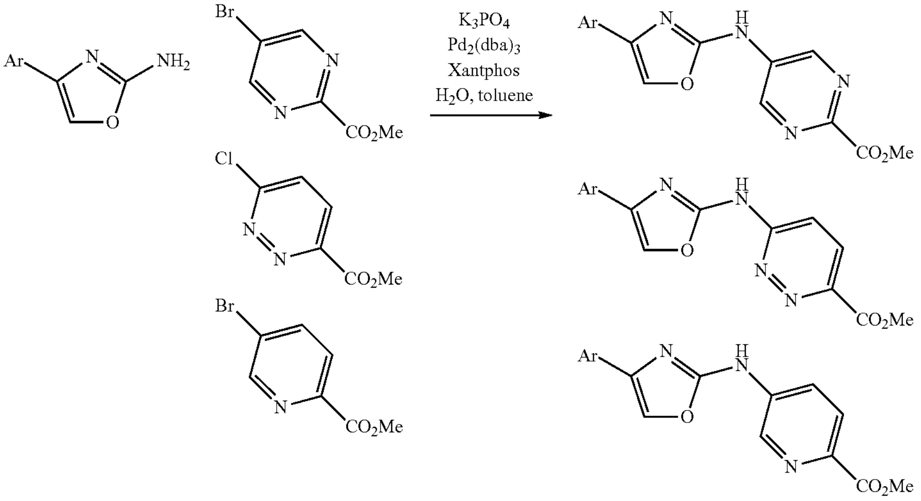
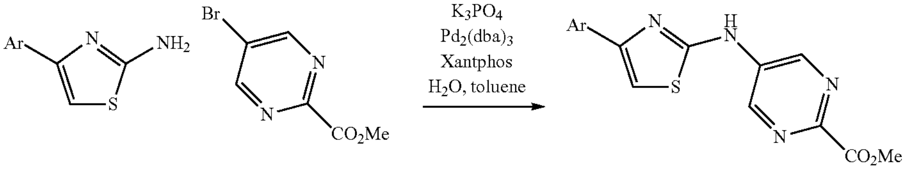
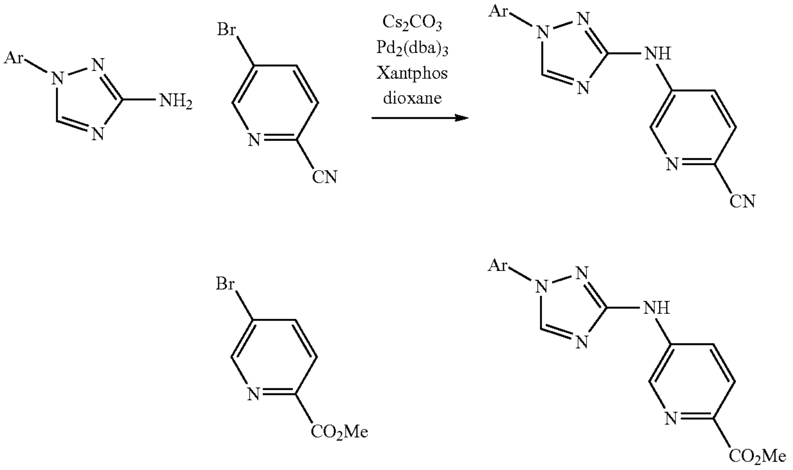

-continued
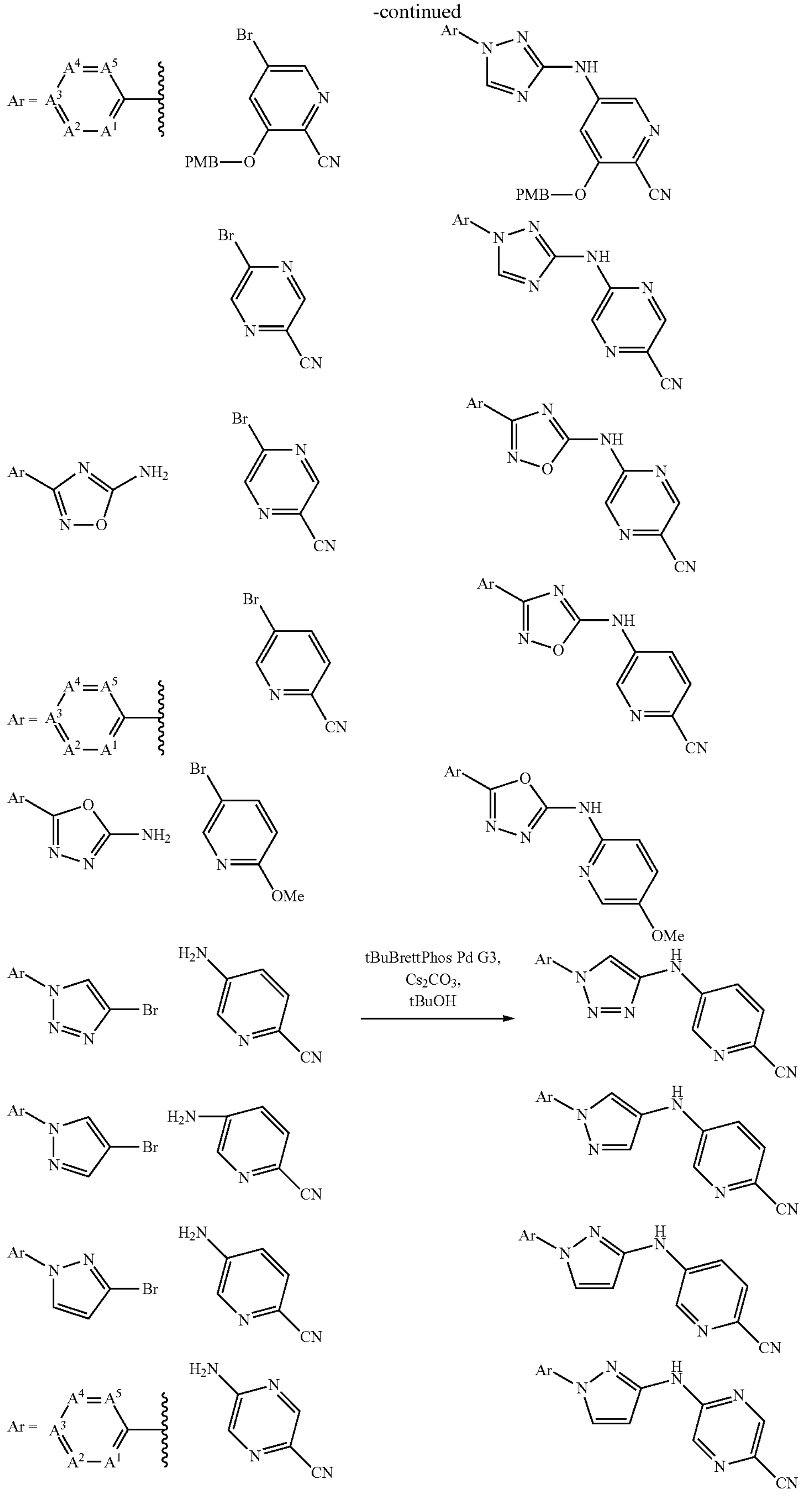

Scheme N
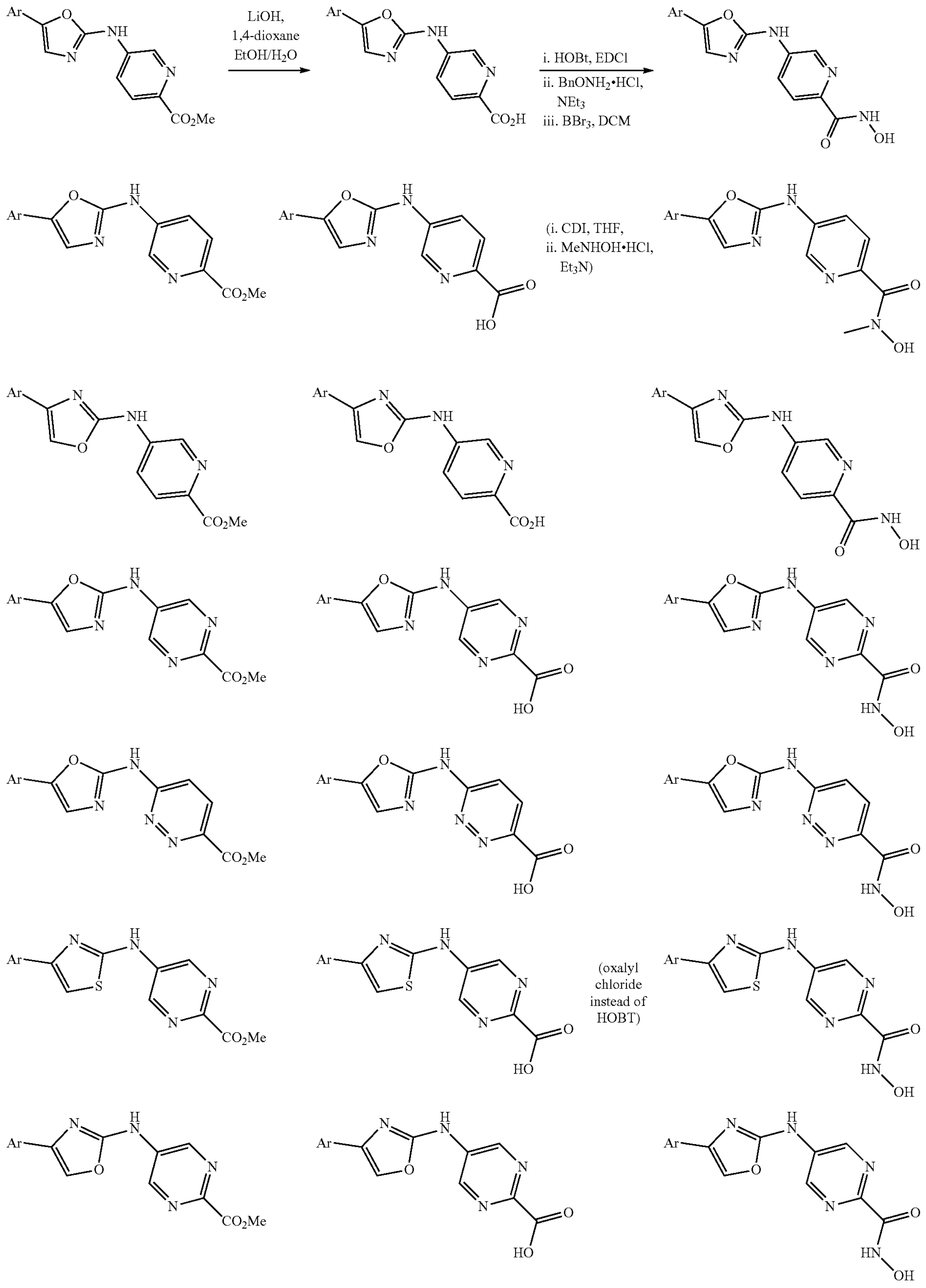

-continued
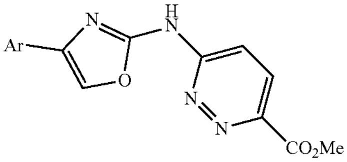 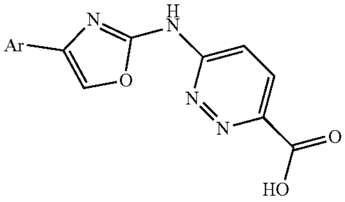 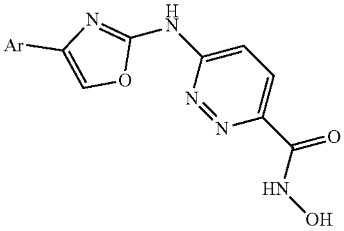
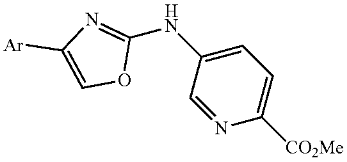 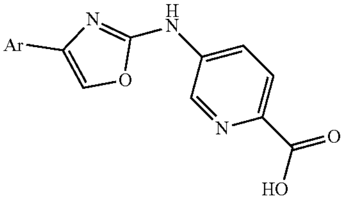 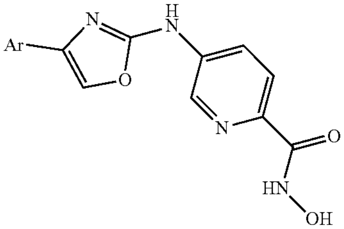
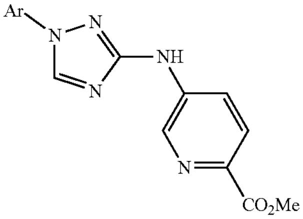 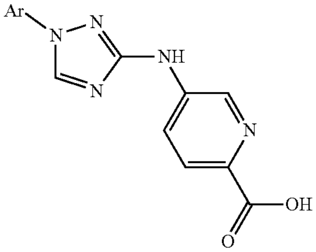
(replace
$BnONH_2$•HCl
with
PMPO—NHMe
and $BBr_3$
with TFA)
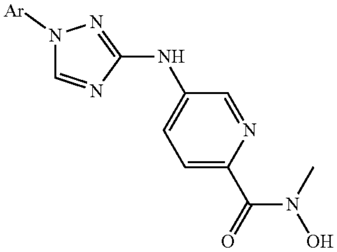
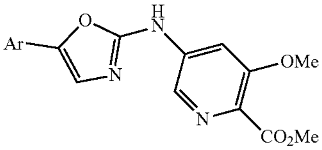 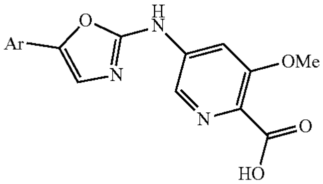
(replace
$BnONH_2$•HCl
with
PMPO—NHMe)
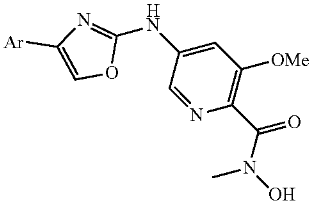
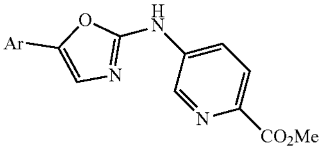 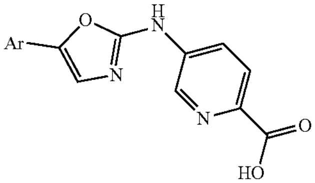
(replace
$BnONH_2$•HCl
with
PMPO—NHEt
and $BBr_3$
with TFA)
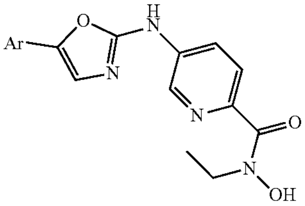
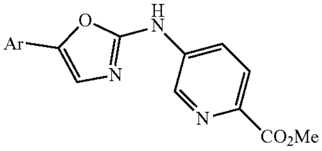 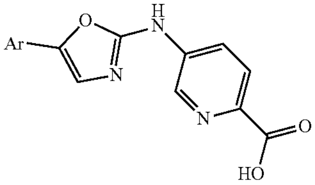
(replace
$BnONH_2$•HCl
with
PMPO—NHPr
and $BBr_3$
with TFA)
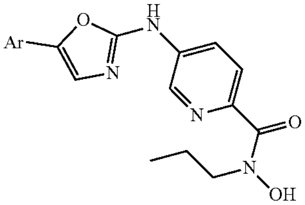
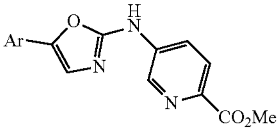 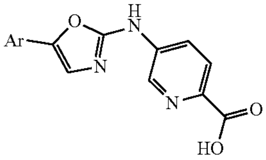
(replace $BnONH_2$•HCl
with
TBDMSO—$CH_2CH_2$—(OBn)NH)
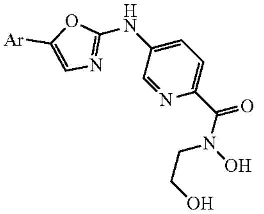
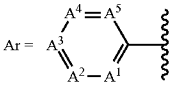

Scheme O
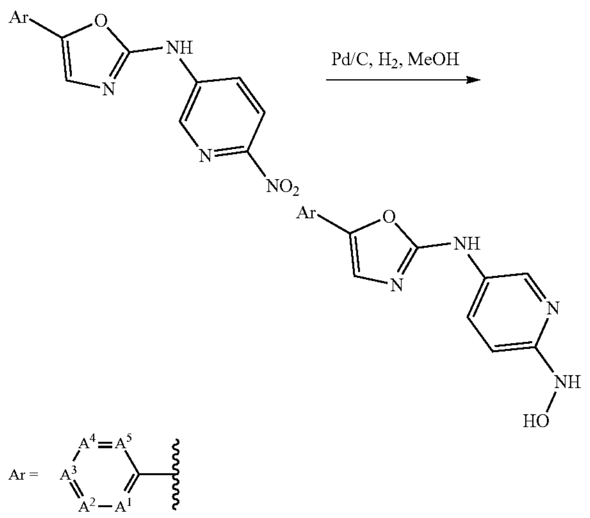
Scheme P
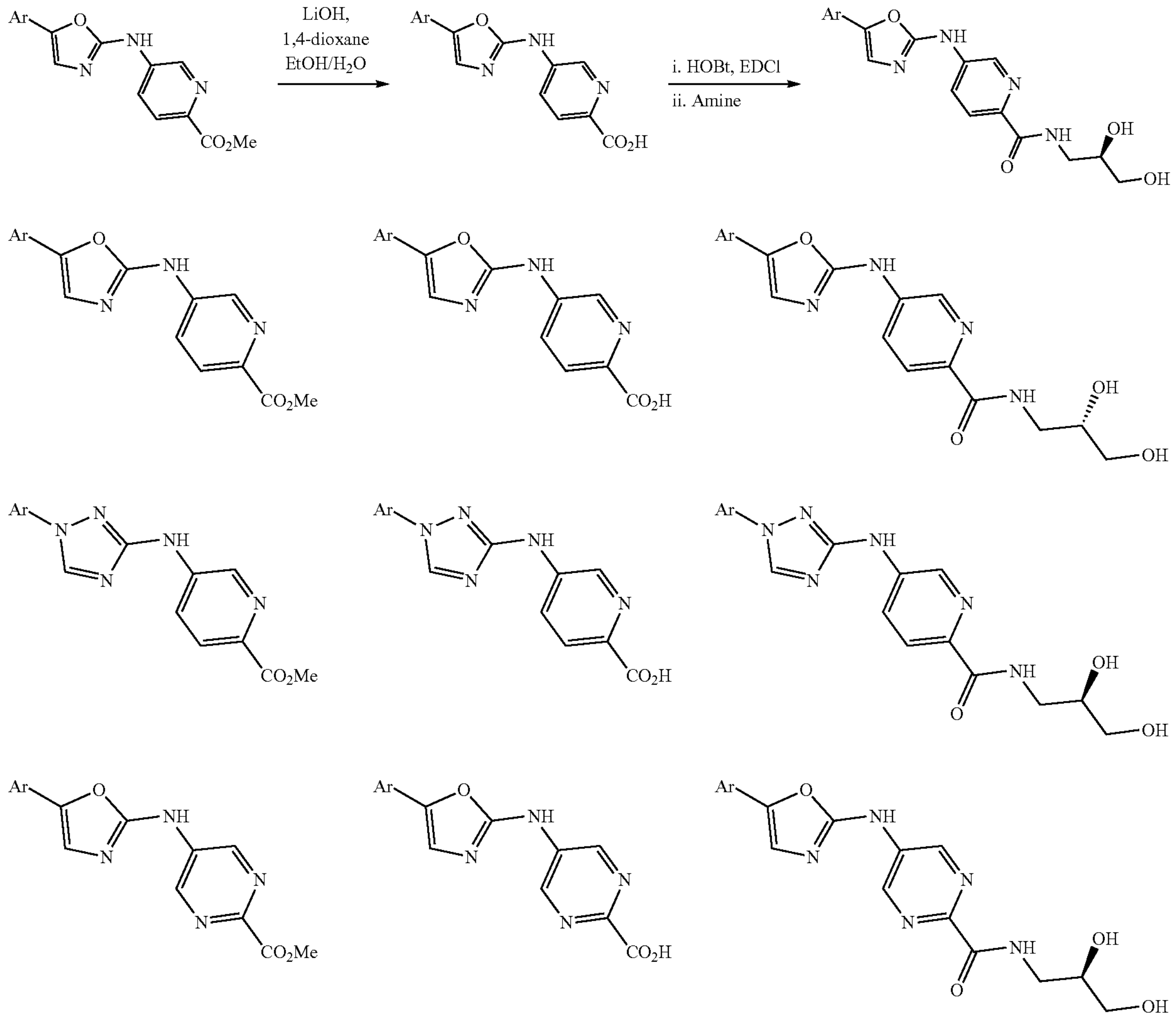

-continued
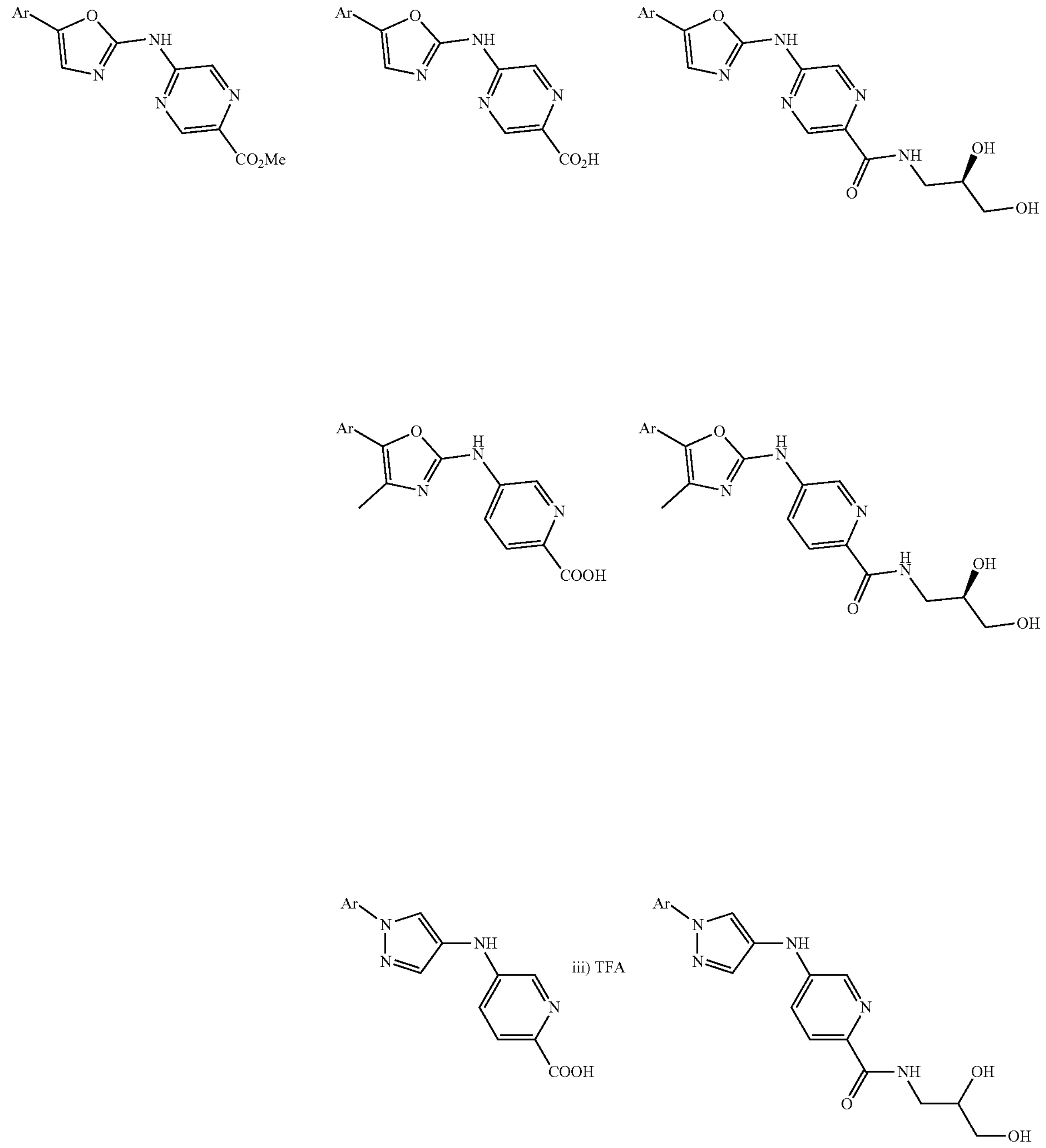
Ar = 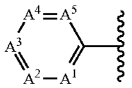

Scheme Q
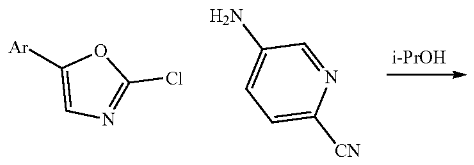
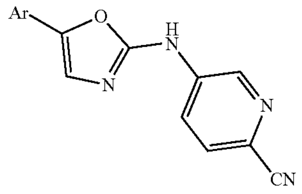
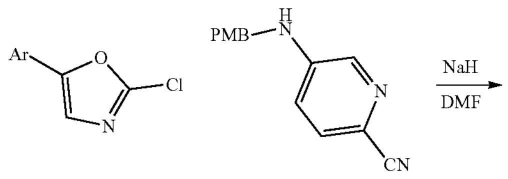
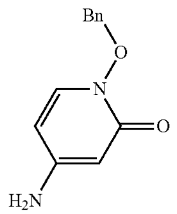
-continued
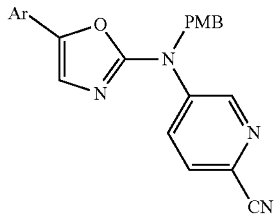
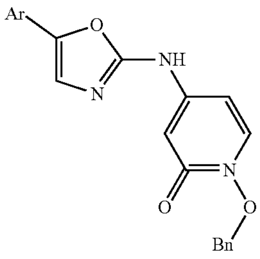
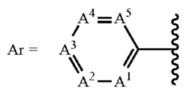
Scheme R
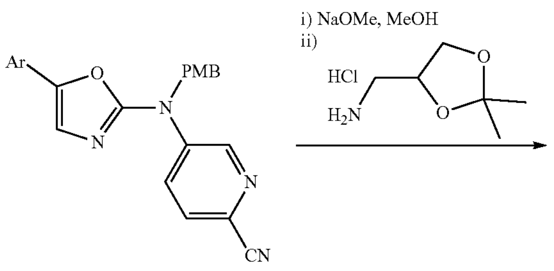
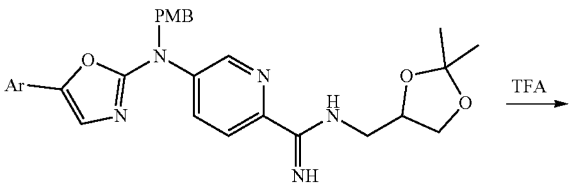
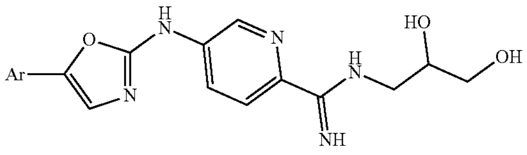

Scheme S

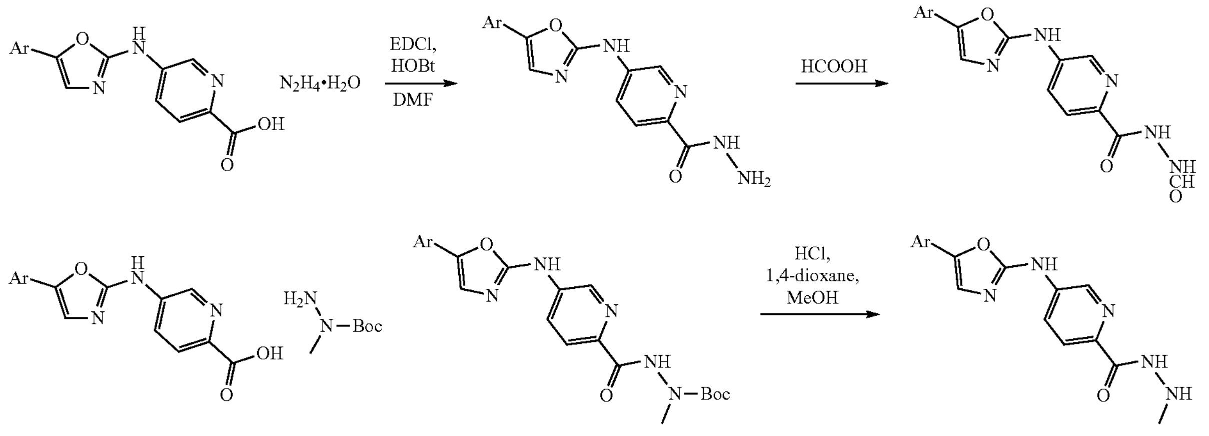

Scheme T

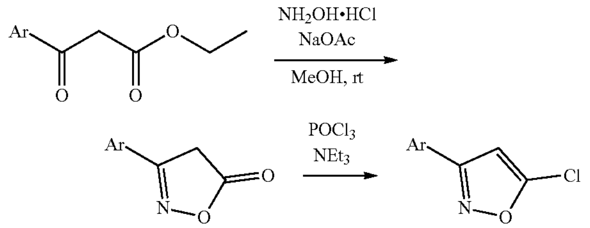

Scheme U

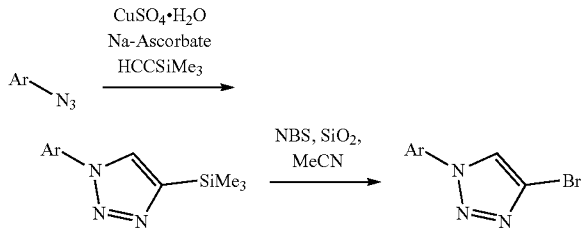

Scheme V

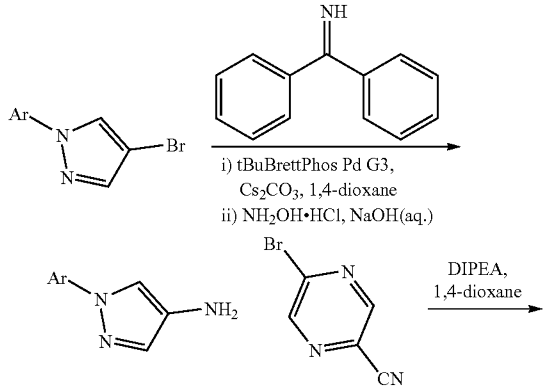

-continued

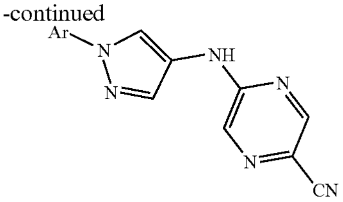

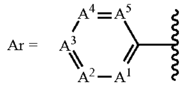

Scheme W

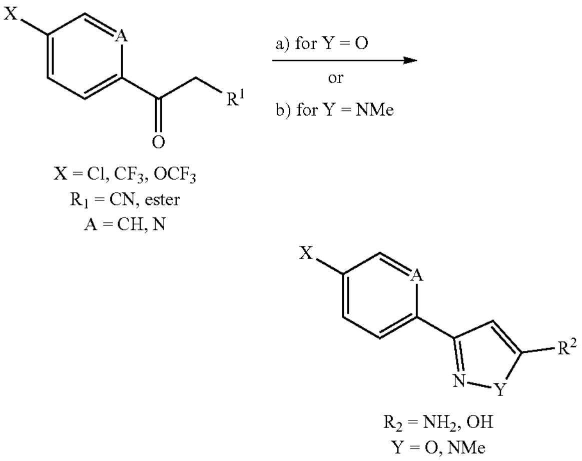

a) $NH_2OH \cdot HCl$, NaOAc, MeOH, rt, 2 h to overnight b) $MeNHNH_2 \cdot HCl$, $Et_3N$, EtOH, reflux 18 h It will be recognised that during the processes for the preparation of compounds of the disclosure, it may be necessary or desirable to protect certain functional groups which may be reactive or sensitive to the reaction or transformation conditions undertaken. Examples of such groups include: OH (including diols), $NH_2$, $CO_2H$, SH and C═O. Suitable protecting groups for such functional groups are known in the art and may be used in accordance with standard practice. As used herein, the term “protecting group", refers to an introduced functionality which temporarily renders a particular functional group inactive under certain conditions. Such protecting groups and methods for their installation and subsequent removal at an appropriate stage are described in *Protective Groups in Organic Chemistry,* 3rd Edition, T. W. Greene and P. G. Wutz, John Wiley and Sons, 1999, the entire contents of which are incorporated herein by reference. Exemplary forms of protected groups include: for amino ($NH_2$)-carbamates (such as Cbz, Boc, Fmoc), benzylamines, acetamides (e.g. acetamide, trifluoroacetamide);

for carbonyl—acetals, ketals, dioxanes, dithianes, and hydrazones;

for hydroxy—ethers (e.g. alkyl ethers, alkoxylalkyl ethers, allyl ethers, silyl ethers, benzyl ethers, such as p-methoxybenzyl, tetrahydropyranyl ethers), carboxylic acid esters, acetals (e.g. acetonide and benzylidene acetal);

for thio (SH)—ethers (e.g. alkyl ethers, benzyl ethers), esters; and for $CO_2H$—esters (e.g. alkyl esters, benzyl esters).

Further General Procedures for the preparation of compounds of the disclosure and/or precursors therefor, are set out below General Procedure 1: General Procedure for Amidoxime (Scheme GP 1)

Scheme GP 1

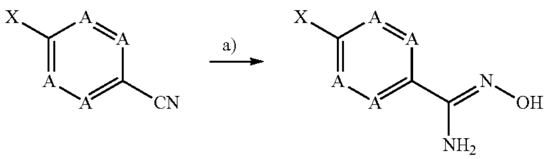

X = Cl, $CF_3$, $OCF_3$, $R_1R_2$—N—, etc.
A = CH, N a) Method 1) aq. $NH_2OH$ (50%), EtOH, rt-reflux, 1-8 h; Method 2) $NH_2OH$•HCl, $Et_3N$, dry MeOH or EtOH, reflux, 1-16 h; Method 3) $NH_2OH$•HCl, $Et_3N$, dry MeOH, reflux, 1-3 h. (Alternative work up)

Method 1: $NH_2OH$ (aq. 50%, 1.05 equiv.) was added dropwise to a solution of nitrile (1.0 equiv.) in EtOH at rt and the mixture was stirred at this temperature for 1 h or refluxed for 8 h. The solvent was removed in vacuo thus giving the titled amidoxime as a white solid with quantitative yield.

Method 2: $NH_2OH{\cdot}HCl$ (3-8 eq.) and $Et_3N$ (3-8 eq.) were added to a suspension of nitrile in dry MeOH or EtOH. The mixture was stirred at reflux for 1-16 h. LCMS indicated that the reaction was complete. The volatiles were removed and the precipitated solids were suspended in water, collected by filtration then washed well with $H_2O$. The solids were washed with $Et_2O$ and DCM and dried to provide the title compound. If required, compounds can be further purified via preparative HPLC.

Method 3: $NH_2OH{\cdot}HCl$ (3-8 eq.) and $Et_3N$ (3-8 eq.) were added to a suspension of nitrile in dry MeOH. The mixture was stirred at reflux for 1-3h. LCMS or TLC indicated that the reaction was complete. The reaction was cooled to room temperature and the precipitated solids were collected by filtration then washed well with $H_2O$. If no solid formed at rt, the reaction was diluted with water (at least 3 fold, MeOH volume) prior to filtration to induce precipitation. The solids were washed with $Et_2O$, and as indicated with $CH_2Cl_2$, then dried to provide the title compound. If required, compounds can be further purified via preparative HPLC.

General Procedure 2: Nucleophillic Substitution (Scheme GP 2)

Scheme GP 2

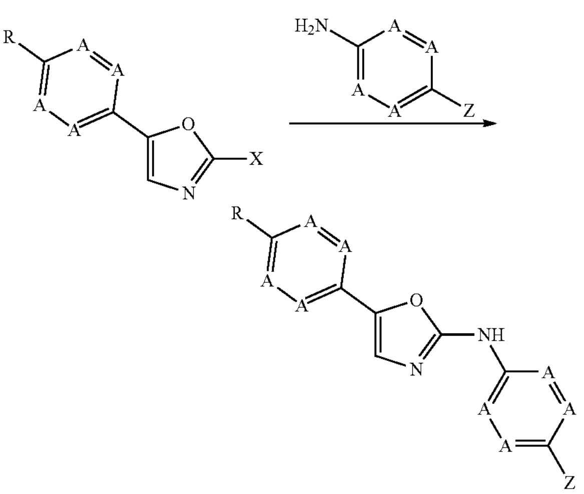

A = CH, N
R = $CF_3$, Cl, $OCF_3$, etc.
X = Br, Cl (Z can be a precursor for $R^b$, e.g. CN, OMe, $NO_2$, $CO_2Me$)

Method 1) arylamine, 2-propanol, reflux, 16 h; Method 2) amine, NaH (60% dispersion in mineral oil), rt, 16 h.

Method 1: A mixture of oxazole chloride or bromide (1.0 eq.) and aromatic amine or heteroaromatic amine (1.5-2.0 eq.) in anhydrous 2-propanol was stirred at reflux for 16 h. Upon cooling, the reaction mixture was concentrated in vacuo. The resultant crude was suspended in $H_2O$, filtered and washed with $Et_2O$. If required, the filtered solids were purified through reverse-phase chromatography ($H_2O$, MeCN 10-100%) to yield the desired product.

Method 2: NaH (1.5-3.0 equiv., 60% dispersion in mineral oil) was added to a solution of aromatic amine or heteroaromatic amine (1.5-2.0 equiv.) in DMF at 0° C. under an atmosphere of nitrogen. The mixture was stirred for 0.5 h at this temperature. A solution of chloride (1.0 equiv.) in DMF was added dropwise to the mixture. After a further 16 h, at rt, the solid was collected by filtration, washed with water, DCM, $Et_2O$ and dried under vacuum. If required, the filtered solids were purified through reverse-phase chromatography ($H_2O$, MeCN 10-100%) to yield the desired product.

General Procedure 3: General Procedure for Amino-Oxadiazole (Scheme GP 3)

Scheme GP 3

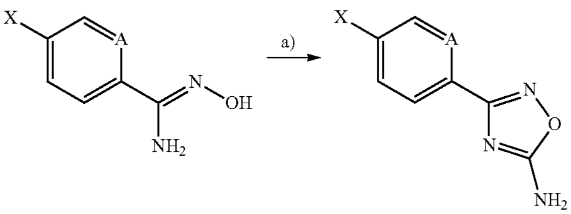

X = Cl, $CF_3$, $OCF_3$
A = CH, N a) i. trichloroacetic anhydride, toluene, reflux, 5-8 h; ii. aq. $NH_3$ (28 ~ 30%), rt, overnight.

Trichloroacetic anhydride (1.1 equiv.) was added dropwise to a suspension of amidoxime (1.0 equiv.) in toluene at rt and the mixture was refluxed for 5 to 8 h. The volatiles were removed in vacuo thus giving the trichloromethyloxadiazole intermediate (used without further purification), which was then added dropwise to an aqueous solution of $NH_3$ (28~30%). The mixture was stirred at rt overnight. The solid was filtered and washed with water (3×20 mL) then PE/DCM (1:1, 3×20 mL) thus giving the titled compound.

General Procedure 4: General Procedure for Buchwald-Hartwig Coupling (Scheme GP 4)

Scheme GP 4

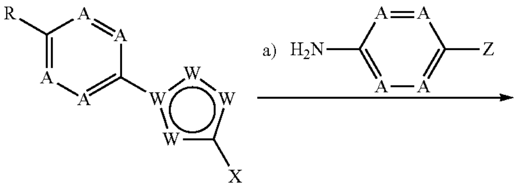

R = Cl, $CF_3$, $OCF_3$, etc.
A = CH, N
W = CH, O, N, N—Me, etc.
X = Cl or Br

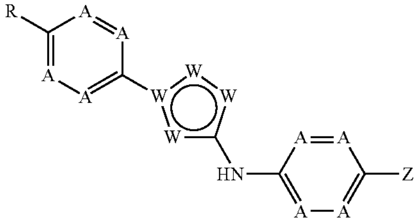
or (Z can be a precursor for $R^b$, e.g. CN, OMe, $NO_2$, $CO_2Me$)

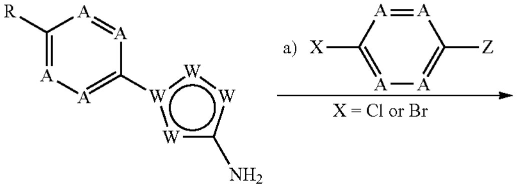

R = Cl, $CF_3$, $OCF_3$, etc.
A = CH, N
W = CH, O, N, N—Me, etc.

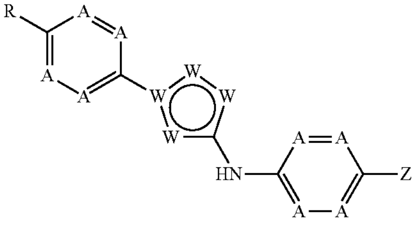

(Z can be a precursor for $R^b$, e.g. CN, OMe, $NO_2$, $CO_2Me$)

a) Method 1) $Pd_2(dba)_3$, Xantphos, $Cs_2CO_3$, 1,4-dioxane, 95-110° C., 5-16 h; Method 2) tBuBrettphos Pd G3, $Cs_2CO_3$, tBuOH, 80-100° C., 5-16 h.

Method 1: A re-sealable Schlenk tube was charged with amine (1.0 eq.), $Pd_2(dba)_3$ (0.02-0.20 eq., typically 5 mol %), Xantphos (0.04-0.40 eq., typically 10 mol %), (hetero) arylhalide (typically 0.5-5.0 eq., typically 1.0-1.5 eq.), $Cs_2CO_3$ (1.5-3.0 eq.), and 1,4-dioxane. After the mixture was degassed and carefully subjected to three cycles of evacuation and backfilling with $N_2$, the reaction was stirred at 95-110° C. for 5-16 h. The volatiles were evaporated. The mixture was then suspended in $H_2O$, filtered and washed with $H_2O$, aq. potassium ethyl xanthate solution (10%) and DCM to give the titled compound. If required, the compound was purified via column chromatography with mixtures of petroleum spirit, DCM, EtOAc and/or MeOH as eluents, or via reverse-phase chromatography.

Method 2: The nitrogen nucleophile, (hetero)arylhalide, $Cs_2CO_3$ (1.5-3 eq.) and tBuBrettphos Pd G3 (0.02-0.20 eq., typically 5 mol %) precatalyst were placed in a sealable vessel under a $N_2$ atmosphere, $N_2$ sparged tBuOH was added and the vessel was sealed and heated to the indicated temperature for the indicated time. Unless otherwise indicated, the reaction was then concentrated, diluted with water and EtOAc, brine was added as required to aid phase separation, the phases were separated, the organic layer was washed with brine, dried with $MgSO_4$, filtered and concentrated onto silica before purification with silica gel flash chromatography using the indicated solvents, typically mixtures of petroleum spirit, DCM, EtOAc and/or MeOH.

General Procedure 5: Oxazole Formation from Azido Ketone (Scheme GP 5)

Scheme GP 5

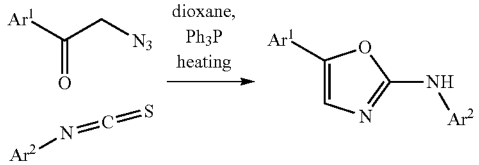

$Ar^1$ and $Ar^2$ = aromatics or heteroaromatics
$Ph_3P$, 1,4-dioxane, reflux, 1-8 h.

A solution of the appropriate 2-azido-ketone (1 eq.), and isothiocyanate (1 eq.) and $PPh_3$ (1 eq.) in dry 1,4-dioxane (0.15 M) was heated to 90° C. for the indicated time, typically from 1 to 8 h. On cooling, the mixture was concentrated to a solid and triturated with organic solvents, e.g. DCM, EtOAc or $Et_2O$. The product was collected by filtering and further washing with the same organic solvent. If required, the product can be purified on silica gel or reversed phase (C18).

General Procedure 6: Isothiocyanate Formation (Scheme GP 6)

Scheme GP 6

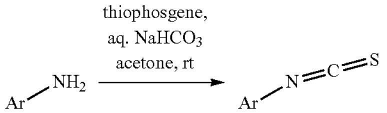

Thiophosgene, aq. 25% $NaHCO_3$, acetone, rt

To a suspension of the appropriate aromatic amine (1 eq.) in a 3:2 mixture of acetone:25% $NaHCO_3$ (aq.) (0.25 M in substrate) was added a solution of thiophosgene (1.2 eq.) in acetone (1.5 M) at 0° C. and the mixture was stirred at rt for the indicated time, typically from 1 to 24 h. Reaction progress was monitored by $^1H$ NMR, LCMS, or TLC. Once the starting amine has been completely consumed, the mixture was diluted with EtOAc and washed with $H_2O$. The organic layer was dried over $MgSO_4$ and concentrated to give the crude product, which in most instances can be used without purification. If required, the crude isothiocyanate can be further purified on silica gel using a mixture of petroleum spirits and EtOAc or DCM and EtOAc to furnish the pure product.

General Procedure 7: Oxadiazole Formation (Scheme GP 7)

Scheme GP 7

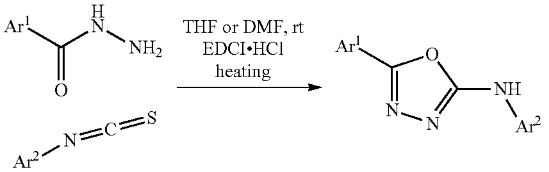

$Ar^1$ and $Ar^2$ = aromatics and heteroaromatics
i) THF of DMF, rt; ii) EDCI•HCl, 60° C., 2 h.

A DMF or THF solution of the appropriate aromatic isothiocyanate (1 eq., 0.2 to 0.5 M concentration) and hydrazide (1 eq.) were stirred at rt for the indicated time, typically from 2 to 18 h. EDCI·HCl (1.2 equiv.) was then added and the mixture heated at 60° C. for 2 h. On cooling, water (1-2 folds volume of organic solvents) was added and the mixture stirred at rt for 0.5 h. The resulting precipitate was filtered and washed with water and occasionally with organic solvents, e.g. DCM or $Et_2O$, solubility permitting, to provide the desired oxadiazole.

General Procedure 8: Alkyl Deprotection with $BBr_3$ (Scheme GP 8)

Scheme GP 8

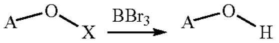

A = $CR_3$, $NH_2$, aromatics, heteroaromatics, etc
X = Me, Bn, etc
$BBr_3$, DCM, rt.

$BBr_3$ (3-20 equivalents as a commercially available solution in organic solvent or neat) was added dropwise to a solution of the protected substrate in dry DCM (0.2 to 0.5 M concentrations) under $N_2$ at 0° C. The resultant reaction was stirred at rt for the indicated time, typically from 2 to 18 h, sat. aq. $NaHCO_3$ solution was then poured into the flask to quench $BBr_3$ and the mixture was stirred for 2 h. Occasionally most of the organic solvents were removed in vacuo prior to quenching with sat. $NaHCO_3$ solution. After removing the volatile solvents, products were isolated with filtering and washing with water. In some instances, the product was purified using preparative HPLC.

General Procedure 9: Isoxazole Formation (Scheme GP 9)

Scheme GP 9

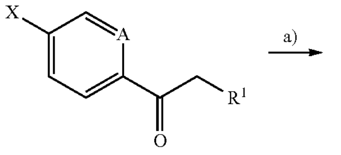

-continued

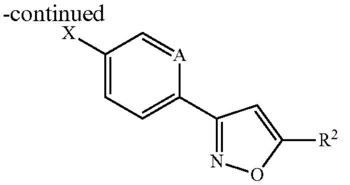

X = Cl, $CF_3$, $OCF_3$
$R^1$ = CN, $CO_2Me$, $CO_2Et$
A = CH, N
$R^2$ = $NH_2$, OH
a) $NH_2OH$•HCl, NaOAc, MeOH, rt, 2 h-16 h.

$NH_2OH$·HCl (3.0 equiv.) and NaOAc (3.0 equiv.) were stirred in $CH_3OH$ at room temperature for 1 h, and then β-ketonitrile/-ester (1.0 equiv.) was added to the mixture. The reaction mixture was left to react until the starting material was consumed completely as judged by TLC detection. Water was added to the reaction which was extracted with ethyl acetate, and the organic layer was washed with brine and dried with anhydrous $Na_2SO_4$. The crude reaction mixture was purified by column chromatography on silica gel with mixtures of petroleum spirit, DCM, EtOAc and/or MeOH.

General Procedure 10: Chloro-Isoxazole Formation (Scheme GP 10)

Scheme GP 10

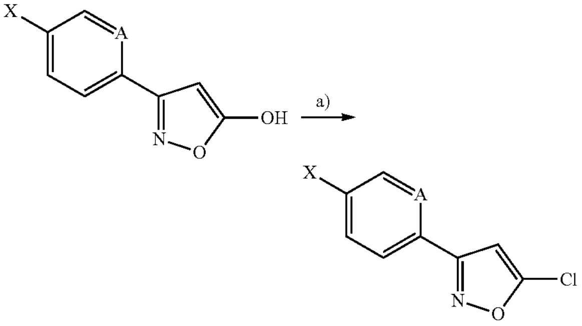

X = Cl, $CF_3$, $OCF_3$
A = CH, N
a) $POCl_3$, $Et_3N$, 0-60° C., 36-50 h.

Triethylamine (0.6 equiv.) was added dropwise at 0° C. to a stirring suspension of the isoxazol-5(4H)-one (1.0 equiv.) in $POCl_3$ (10 equiv.). The mixture was stirred at 60° C. for the indicated time, typically from 36 to 50 h, poured into ice, carefully basified to a pH of 6-7 by addition of 10% aq. KOH, and extracted with DCM. The organic layer was dried over $Na_2SO_4$ and filtered. The solvent was evaporated, and the product was purified by column chromatography (petroleum spirits: EtOAc, 10:1) to give the desired chloroisoxazole.

General Procedure 11: PMB Deprotection with TFA (Scheme GP 11)

Scheme GP 11

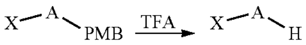

A = O or NR
X = $CR_3$, $NH_2$, Ar, etc
TFA, $Et_3SiH$, 1-18 h.

The protected substrate was stirred in a mixture of TFA (0.2-0.5 M concentration) and $Et_3SiH$ (5% volume) at the indicated temperature, typically at rt, but occasionally at reflux. In some instances, anisole was used instead of $Et_3SiH$. The reaction progress was monitored by LCMS. Upon complete consumption of the starting material, typically after 1 to 18 h, the volatile solvents were evaporated in vacuo to dryness the residue was purified on preparative HPLC to provide the desired deprotected product. Alternatively, when the reaction results in a suspension, the product may be isolated filtering, then washing with water, and organic solvents, solubility permitting.

General Procedure 12: Suzuki Coupling (Scheme GP 12)

Scheme GP 12.

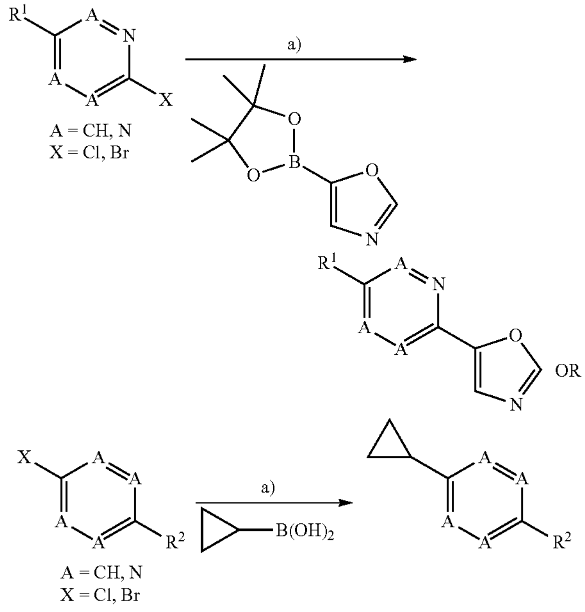

$R^1 = CF_3, OCF_3$ $R^2$ = aromatics or heteroaromatics a) Method 1) $PdCl_2(PPh_3)_2$, THF: 1M aq. $Na_2CO_3$ (3.5:1.5), reflux, 16 h; Method 2) $Pd(OAc)_2$, $K_3PO_4$, tricyclohexylphosphine, toluene/$H_2O$, 100° C., 16 h.

Method 1: To a degassed biphasic solution of THF (3.5 mL) and 1 M aq. $Na_2CO_3$ (1.5 mL), the (hetero)arylhalide (1.0 eq.), 5-(4,4,5,5-tetramethyl-1,3,2-dioxaborolan-2-yl)oxazole (1.0 M in THF, 1.1 eq.) and $PdCl_2(PPh_3)_2$ (0.1 eq.) and the mixture heated to 100° C. and stirred for 16 h. Upon completion, the reaction mixture was diluted with EtOAc and the organic layer filtered through cotton wool, and washed with sat. $NaHCO_3$. The organic layer was dried over anhydrous $MgSO_4$ and concentrated in vacuo to yield the crude product. The crude product subjected to purification via flash column chromatography (PhMe, 0-20% EtOAc) to give the desired product.

Method 2: To a solution of (hetero)arylhalide (1.0 equiv.), boronic acid (1.3 equiv.), potassium phosphate (3.0 equiv.) and tricyclohexylphosphine (0.01 equiv.) in toluene/water (10:1, 0.1-0.2 M) under a nitrogen atmosphere was added $Pd(OAc)_2$ (0.005 equiv.). The mixture was heated to 100° C. overnight and then cooled to room temperature. Water was added and the mixture extracted with EtOAc, the combined organics were washed with brine, dried over $MgSO_4$ and concentrated in vacuo. Purification by column chromatography afforded the desired compound.

General Procedure 13: Synthesis of Aldehyde (Scheme GP 13)

Scheme GP 13

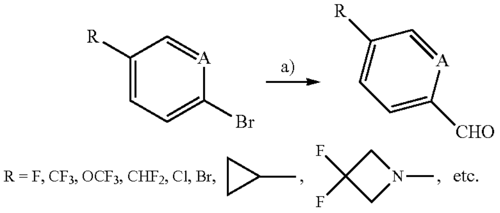

A = CH, N a) Method 1) n-BuLi, THF, -78° C., DMF; Method 2) i-PrMgCl, DMF, DCM, -20-6° C.

Method 1: n-BuLi (1.6 M in hexane, 1.1 equiv.) was added to a solution of bromide (1.0 equiv.) in dry THF (0.5 M) over 10 min at −78° C. under nitrogen atmosphere. After a further 0.5 h, DMF (3.0-6.0 equiv.) was added and the mixture was stirred for 1 h at −78° C. then brought to 0° C. over 2 h. Saturated aq. $NH_4Cl$ solution was added and the aqueous phase was extracted with EtOAc. The combined organic phases was dried over $MgSO_4$, filtered, concentrated and subjected to flash chromatography on silica gel (2%-10%, EtOAc/petroleum spirits).

Method 2: i-PrMgCl (2M in $Et_2O$, 1.15 equiv.) was added to the bromide (1.0 equiv.) in DCM (0.3-0.5 M) at −2° C. over 3 min. After stirring at 0-6° C. for 40 min, the mixture was cooled to −20° C. and DMF (2.0 equiv.) was added in one portion. The mixture was warmed to 0° C. over 20 minutes then quenched by addition of saturated aq. $NaHCO_3$ in one portion then filtered through a celite pad, extracted with EtOAc, dried over $Na_2SO_4$, concentrated under reduced pressure to give the desired product. If required, the compound was purified via column chromatography with mixtures of petroleum spirit, DCM, EtOAc and/or MeOH.

General Procedure 14: Synthesis of Oxazole (Scheme GP 14)

Scheme GP 14

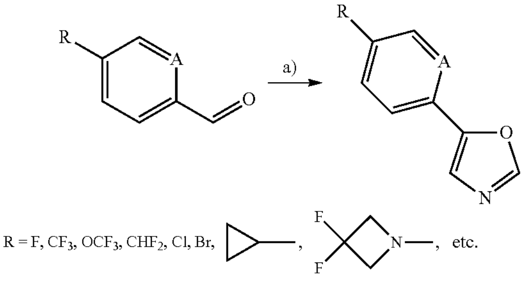

A = CH, N a) TosMIC, $K_2CO_3$, MeOH, reflux, 5 h.

A suspension of aryl aldehyde (1.0 equiv.), $K_2CO_3$ (1.2 equiv.), TosMIC (1.1 equiv.) in MeOH was heated to reflux for the indicated time. Volatiles were removed in vacuo, then $H_2O$ was added, followed by an extraction with $Et_2O$. The combined organic layer was dried over $MgSO_4$ and concentrated under reduced pressure. The resultant crude residue was subjected to flash chromatography on silica gel (3%-20%, EtOAc/petroleum spirits) to give the indicated oxazole.

General Procedure 15: Halogenation of Oxazole (Scheme GP 15)

Scheme GP 15

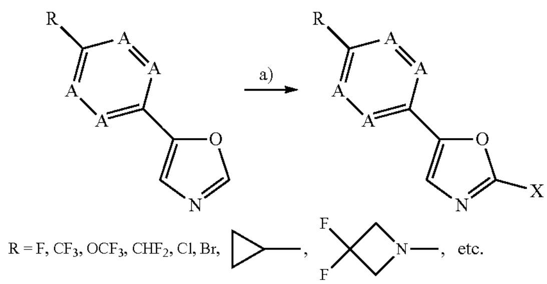

A = CH, N
X = Cl, Br
a) Method 1) LiHMDS, $C_2Cl_6$, THF, -78° C.-rt; Method 2) t-BuOLi, $BrCF_2CF_2Br$, DMF/m-xylene, rt-60° C.;

Method 1: LiHMDS (1.0 M in THF, 1.05-1.2 equiv.) was added to a solution of oxazole (1.0 equiv.) in dry THF (0.1-0.2 M) at −78° C. under $N_2$ atmosphere. After a further 0.5 h, a solution of $C_2Cl_6$ (1.5 equiv.) in THF (2M) was added. The resulting reaction mixture was stirred at −78° C. for another 2 h and allowed to warm to rt over 14 h. The reaction was quenched with saturated aq. $NaHCO_3$ solution. The aqueous phase was extracted with EtOAc. The combined organic phases were dried over $Na_2SO_4$, filtered, concentrated and subjected to flash chromatography on silica gel (2%-10%, EtOAc/petroleum spirits).

Method 2: $BrCF_2CF_2Br$ (2.0 equiv.) and t-BuOLi (2.0 equiv.) were added to a solution of oxazole (1.0 equiv.) in DMF/m-xylene (1:1 ratio, 0.3-0.5 M). The resulting mixture was stirred at 60° C. for 3 h and quenched with saturated aq. $NaHCO_3$ solution. The aqueous phase was extracted with EtOAc. The combined organic phases were dried over $Na_2SO_4$, filtered, concentrated and subjected to flash chromatography on silica gel (3%-10%, EtOAc/petroleum spirits).

$^1H$ NMR spectra were recorded at 400 MHz. $^{13}C$ NMR spectra were recorded at 101 MHz. All chemical shifts were calibrated using residual non-deuterated solvent (e.g. chloroform) as an internal reference and are reported in parts per million (δ) relative to trimethylsilane (δ=0). Thin layer chromatography (TLC) was performed using 0.25 mm thick plates pre-coated with Merck Kieselgel 60 F254 silica gel, and visualised using UV light (254 nm and 365 nm). Liquid chromatography mass spectrometry (LCMS) was performed using either APCI or ESI LCMS. Each method used 254 nm and 214 nm detectors and a reverse phase C8(2) 5μ50×4.6 mm 100A column. The column temperature was 30° C. The eluent system used was solvent A ($H_2O$ with 0.1% formic acid) and solvent B (MeCN with 0.1% formic acid). LCMS (ESI) method: the gradient starts from [95% solvent A/5% solvent B] for 1 minute, reaches [100% solvent B] over 1.5 min, maintained for 1.3 min, and then changed to [95% solvent A/5% solvent B] over 1.2 min. High resolution mass spectra (HRMS) were recorded on both a time-of-flight mass spectrometer fitted with either an electrospray (ESI) ion or atmospheric pressure chemical ionisation (APCI) source, the capillary voltage was 4000 V or on an exactive mass spectrometer fitted with an ASAP ion source.

Without limiting the disclosure by theory, in some embodiments the compounds described herein may interact with Des1 and be useful in treating a disease or condition mediated by Des1 activity. As used herein, the term "interact" when used at least in the context of the compounds of the disclosure, includes an association of the compound with the enzyme so as to partially or fully inhibit, retard or prevent biochemical activity of the enzyme, (e.g. introduction of the Δ4 double bond into dihydroceramide to generate ceramide). This may occur through any means such as chemically or associatively binding at one or more sites of the enzyme, promoting reaction with other endogenous molecules or associating in such a manner so as to cause degradation or a conformational change in the enzyme. Determination of the interaction of the compounds with one or more enzymes may be determined in accordance with any suitable methods of the art, including methods which measure enzyme activity inhibition, such as the procedures described in the Examples. In some embodiments, a compound may be considered to interact with an enzyme if, in accordance with the procedure used, it demonstrates at least a measurable or otherwise determinable level of enzyme activity inhibition. Selective interaction, e.g. selective inhibition, refers to the interaction of a compound with an enzyme and/or binding site thereof in complete or partial preference over another enzyme and/or binding site.

In some embodiments, the compounds may selectively inhibit one Des isoform over the other. For example, one or more compounds may be selective Des1 inhibitors. In other embodiments, one or more compounds may be selective Des2 inhibitors.

In further embodiments, one or more compounds may exhibit an $IC_{50}$ with respect to Des (e.g. Des1 and/or Des2) activity of less than about 100 μM. In further embodiments, one or more compounds may exhibit an $IC_{50}$ with respect to Des (e.g. Des1 and/or Des2) activity of less than about 50 μM. In further embodiments, one or more compounds may exhibit an $IC_{50}$ with respect to Des (e.g. Des1 and/or Des2) activity in the range of less than about 10-5 μM. In further embodiments, one or more compounds may exhibit an $IC_{50}$ with respect to Des (e.g. Des1 and/or Des2) activity of less than about 1 μM. In further embodiments, one or more compounds may exhibit an $IC_{50}$ with respect to Des (e.g. Des1 and/or Des2) activity of less than about 1 μM. In still further embodiments, one or more compounds may exhibit an $IC_{50}$ with respect to Des (e.g. Des1 and/or Des2) activity of less than about 0.1 μM. In still further embodiments, one or more compounds may exhibit an $IC_{50}$ with respect to Des (e.g. Des1 and/or Des2) activity of less than about 0.01 μM. In still further embodiments, one or more compounds may exhibit an $IC_{50}$ with respect to Des (e.g. Des1 and/or Des2) activity of less than about 0.001 μM. In still further embodiments, one or more compounds may exhibit an $IC_{50}$ with respect to Des (e.g. Des1 and/or Des2) activity of less than about 0.0001 μM. In still further embodiments, one or more compounds may exhibit an $IC_{50}$ with respect to Des (e.g. Des1 and/or Des2) activity in the range of about 1.0-10 μM, or 0.1-1.0 μM., or 0.01-0.1 μM, or 0.001-0.01 μM, or 0.0001-0.001 μM.

In some embodiments, one or more compounds of Formula (I') and/or (II") demonstrate inhibitory activity of Des (e.g. Des1 and/or Des2) that makes them useful in the treatment and/or prevention of diseases mediated by undesirable or excessive Des activity and/or where the inhibition of Des enzyme activity is therapeutically beneficial. In some embodiments, compounds of Formula (I') and/or (II") demonstrate inhibitory activity of Des1. In some embodiments Des activity, such as Des1 activity, may be linked to fibrosis or proliferative diseases. Thus, without limiting the present disclosure by theory, in some embodiments Des inhibition, such as Des1 inhibition, may be useful in treating fibrosis or a proliferative disease. In some embodiments, compounds of the disclosure demonstrate antiproliferative activity and/or demonstrate anti-fibrotic activity.

Some compounds with Des1 inhibitory have also been shown to have anti-proliferative activity (see Aurelio, L. et al, supra). In some embodiments, one or more compounds of Formulae (I') and/or (II") demonstrate antiproliferative activity. In still further example, the antiproliferative activity may be observed against a single cell line or type, or may be observed in two or more different cell lines or cancer types. Thus, one or more compounds of the disclosure may be useful in therapy against a single cancer type or two or more cancer types.

In some embodiments, the compounds of the disclosure, may be useful in treating a disease or condition mediated by Des1, for example in which excessive or undesirable Des1 activity is implicated, such as where undesirable cell proliferation is involved, including the treatment or inhibition of cancer and/or metastases, or the treatment of fibrotic diseases, and may be administered to a subject in a treatment or inhibiting effective amount. A treatment or inhibiting effective amount is intended to include an amount which, when administered according to the desired dosing regimen, at least partially attains the desired therapeutic treatment or inhibiting effect, and may include one or more of: alleviating, eliminating or reducing the frequency of occurrence of one or more symptoms of, preventing or delaying the onset of, inhibiting the progression of, or halting or reversing (partially or altogether) the onset or progression of the particular disorder or condition, or pathology thereof, being treated. As used herein, "inhibiting undesirable cell proliferation", includes preventing, arresting, retarding the rate or extent of, or otherwise delaying or reversing excessive, uncontrolled, detrimental or otherwise undesirable cell proliferation, such as may occur in cancer growth or metastasis.

In some embodiments, compounds of the disclosure and/or their salts or solvates may therefore be useful as anti-proliferative agents e.g. in treating undesirable cell proliferation as, such as found in cancerous conditions, including hormone-related cancers, such as breast cancer and prostate cancer, and their metastasis. Other cancerous conditions which may be amenable to treatment by the compounds described herein include lung, colon, pancreatic and brain cancer as well as lymphoma. The compounds described herein may have utility in treating primary cancers and/or treating or inhibiting metastases (i.e. secondary cancers).

In some embodiments, compounds of the disclosure, including their pharmaceutically acceptable salts and solvates, may be useful in the treatment of fibrosis and/or fibrotic diseases. As used herein, fibrosis and fibrotic disease includes the formation of excess fibrous connective tissue in an organ or tissue, such as a reactive or reparative response to an injury, such as organ transplant, or pathological state, such as inflammation, which can interfere with normal organ or tissue function. Fibrosis may be found in vascular, heart, lung, liver, skin or kidney tissue, and may include pulmonary fibrosis, liver cirrhosis, systemic sclerosis, progressive kidney disease and cardiac fibrosis associated with various cardiovascular diseases.

Some examples of fibrotic diseases or conditions that may be treated by one or more embodiments of the disclosure include: pulmonary (lung) fibrosis, including idiopathic pulmonary fibrosis and cystic fibrosis; liver fibrosis, (cirrhosis), for example, resulting from chronic liver disease, or hepatitis B, C or D virus infection; cardiac (heart) fibrosis, including endomyocardial fibrosis, atrial fibrosis, and fibrosis resulting from myocardial infarction (heart attack); kidney fibrosis, such as resulting from diabetic nephropathy; primary biliary cirrhosis, gall bladder fibrosis, skin or dermal fibrosis, such as scleroderma, hypertrophic scarring and keloids; bone marrow fibrosis, and intestinal fibrosis, such as Crohn's disease.

In some embodiments, one or more compounds of the disclosure, for example, which inhibit or otherwise interact with Des1, including their pharmaceutically acceptable salts and solvates, may be useful in the treatment of metabolic disease, in particular non-alcoholic fatty liver disease and non-alcoholic steatohepatitis (NASH) (NAFLD/NASH) (see for example B. Chaurasia et al., *Science,* 2019, 365 (6451), 386-392). Further examples of diseases which may be treated by one or more compounds of the disclosure may include cardiovascular disease, hypertension, type-2 diabetes, cystic fibrosis, chromic kidney disease, diabetic nephropathy, scleroderma, cancer (including, but not limited, prostate cancer, breast cancer, brain cancer, hepatocellular carcinoma, multiple myeloma, acute lymphoid myeloma and colon cancer), neurodegenerative disease, iodiopathic pulmonary fibrosis, chronic obstructive pulmonary disease, and viral disease (Magaye, R., R. et al. *Cell. Mol. Life Sci.* 2019, 76, 1107-1134; Vieira, C. R. et al., *Chem. Biol.* 2010, 17, 766-775).

Subjects to be treated include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention.

Suitable dosage amounts and dosing regimens can be determined by the attending physician and may depend on the particular condition being treated, the severity of the condition as well as the general age, health and weight of the subject. Suitable dosage amounts may lie in the range of from 1 μg to 1 g of compound, salt or solvate, for example, 1 μg-1 mg (such as 100 μg, 250 μg, 500 μg, 750 μg), 1 mg-10 mg (such as 2, 5 or 7 mg), 10 mg-50 mg (such as 15, 20, 25, 30, or 40 mg), 50 mg-100 mg (such as 60, 70, 80, 90 mg) or 100 mg-500 mg (such as 200, 250, 300, 400 mg). Dosages may be administered once, or multiple times daily (e.g. 2, 3, or 4 times), or one or more times weekly, fortnightly or monthly. Administration may be over a limited period of time to treat an acute disorder or condition, for example 1, 2, 3, or 4 weeks, or 2 or 3 months, or may occur over extended periods to treat a chronic disorder or condition, for example greater than 3 months, e.g. 6 or 12 months, 1-2 years or longer.

The active ingredient may be administered in a single dose or a series of doses. While it is possible for the active ingredient to be administered alone, it is preferable to present it as a composition, preferably as a pharmaceutical composition, with one or more pharmaceutically acceptable additives. The compounds may also be packaged or presented as a combination with one or more other therapeutic agents and/or anti-proliferative or anti-cancer agents. The components of the combinations may be administered in conjunction with each other, either contemporaneously or at separate times, as a single composition or separate compositions, as appropriate. Thus, the compositions contemplated herein may contain the compounds of the disclosure, or a pharmaceutically acceptable salt or solvate thereof, as the only therapeutic agent or anti-proliferative/anti-cancer or anti-fibrotic agent, or may further contain one or more additional therapeutic or anti-proliferative/anti-cancer or anti-fibrotic agents. Thus, the present disclosure also relates to the use of a compound of Formula (I') or (I") or a pharmaceutically acceptable salt or solvate thereof in the manufacture of a medicament for treating a disease or condition in which excessive or undesirable sphingosine kinase activity is implicated, or inhibiting undesirable cell proliferation, e.g. in treating cancer or inhibiting or preventing metastasis, or treating fibrotic diseases.

The formulation of such compositions is well known to those skilled in the art, see for example, *Remington's Pharmaceutical Sciences,* 21$^{st}$ Edition, Mack Publishing, 2005. The composition may contain any suitable additives, carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The additive must be pharmaceutically acceptable in the sense of being compatible with the other ingredients of the composition and not injurious to the subject. Compositions include those suitable for oral, rectal, nasal, topical (including dermal, buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the additive which constitutes one or more accessory ingredients. In general, the compositions are prepared by uniformly and intimately bringing into association the active ingredient with liquid additive or finely divided solid additive or both, and then if necessary shaping the product.

Compositions comprising a compound of the disclosure may be administered to a subject via any suitable method, including, orally, parenterally, topically, rectally, vaginally, or by inhalation.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Devices for transdermal delivery, such as patches, may also be used to administer the compounds of the invention.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this disclosure may include other additives or agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The present disclosure also relates to prodrugs of Formula (I') and (I"). Any compound that is a prodrug of a compound of Formula (I') or (I") is within the scope and spirit of the invention. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as phosphonate, sulphonate and carboxy esters, such as an acetate, or thioester or where a free amino group is converted into an amide such as a carboxy, phosphonate or sulphonate amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.,* 1979, 20, 369, Kyncl, J. et al), enamines (see, for example, *J. Pharm. Sci.,* 1971, 60, 1810, Caldwell, H. et al), Schiff bases (see, for example, U.S. Pat. No. 2,923,661 and *Antimicrob. Agents Chemother.,* 1981, 19, 1004, Smyth, R. et al), oxazolidines (see, for example, *J. Pharm. Sci,* 1983, 72, 1294, Johansen, M. et al), Mannich bases (see, for example, *J. Pharm. Sci.* 1980, 69, 44, Bundgaard, H. et al and *J. Am. Chem. Soc.,* 1959, 81, 1198, Gottstein, W. et al), hydroxymethyl derivatives (see, for example, *J. Pharm. Sci,* 1981, 70, 855, Bansal, P. et al) and N-(acyloxy)alkyl derivatives and carbamates (see, for example, *J. Med. Chem.,* 1980, 23, 469, Bodor, N. et al, *J. Med. Chem.,* 1984, 27, 1037, Firestone, R. et al, *J. Med. Chem.,* 1967, 10, 960, Kreiger, M. et al, U.S. Pat. No. 5,684,018 and *J. Med. Chem.,* 1988, 31, 318-322, Alexander, J. et al). Other conventional procedures for the selection and preparation of suitable prodrugs are known in the art and are described, for example, in WO 00/23419; Design of Prodrugs, H. Bundgaard, Ed., Elsevier Science Publishers, 1985; *Methods in Enzymology,* 42: 309-396, K. Widder, Ed, Academic Press, 1985; *A Textbook of Drug Design and Development*, Krogsgaard-Larsen and H. Bundgaard, Eds, Chapter 5, p 113-191 (1991); *Advanced Drug Delivery Reviews,* 8; 1-38 (1992); *Journal of Pharmaceutical Sciences,* 77; 285 (1988), H. Bundgaard, et al; *Chem Pharm Bull,* 32692 (1984), N. Kakeya et al and *The Organic Chemistry of Drug Design and Drug Action*, Chapter 8, pp 352-401, Academic press, Inc., 1992.

Suitable pharmaceutically acceptable salts of compounds of the disclosure may include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, o-(p-hydroxybenzoyl)benzoic, 4'-4"-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides or dialkyl sulfates such as dimethyl and diethyl sulfate.

An example of a pharmaceutically acceptable salt of any of the compounds described herein in any of the aspects, embodiments or examples is the hydrochloride salt.

The compounds of the disclosure may be in crystalline form either as the free compounds or salts, or as solvates and it is intended that both forms are within the scope of the present disclosure. The term "solvate" refers to a complex or aggregate formed by one or more molecules of a solute, i.e. compounds of the disclosure, and one or more molecules of a solvent. Suitable solvents are well understood in the art and include for example, of water, i.e. to form hydrates, and common organic solvents such as alcohols (MeOH, ethanol, isopropanol) and acetic acid. Methods of solvation are generally known within the art, for example, recrystallization from an appropriate solvent.

It will also be recognised that certain compounds of formula (I') may possess asymmetric centres and are therefore capable of existing in more than one stereoisomeric form, such as enantiomers and diastereomers. The invention thus also relates to optically active compounds and compounds in substantially pure isomeric form at one or more asymmetric centres, e.g., enantiomers having greater than about 90% ee, such as about 95% or 97% ee or greater than 99% ee, as well as mixtures of isomers, including racemic mixtures, thereof. Such isomers may be prepared by asymmetric synthesis, for example using chiral intermediates, enzymes, or mixtures may be resolved by conventional methods, e.g., chromatography, recrystallization, or use of a resolving agent.

The compounds of the disclosure may also be presented for use in veterinary compositions. These may be prepared by any suitable means known in the art. Examples of such compositions include those adapted for:

oral administration, external application (e.g. drenches including aqueous and non-aqueous solutions or suspensions), tablets, boluses, powders, granules, pellets for admixture with feedstuffs, pastes for application to the tongue;

parenteral administration, e.g. subcutaneous, intramuscular or intravenous injection as a sterile solution or suspension;

topical application e.g. creams, ointments, gels, lotions etc.

The following examples are provided for the purpose of illustrating some embodiments of the disclosure but are not to be construed as limiting the generality hereinbefore described.

EXAMPLES

Example 1

1. 5-((5-(4-Chlorophenyl)oxazol-2-yl)amino)-N-hydroxypicolinamide (Scheme 1)

Scheme 1

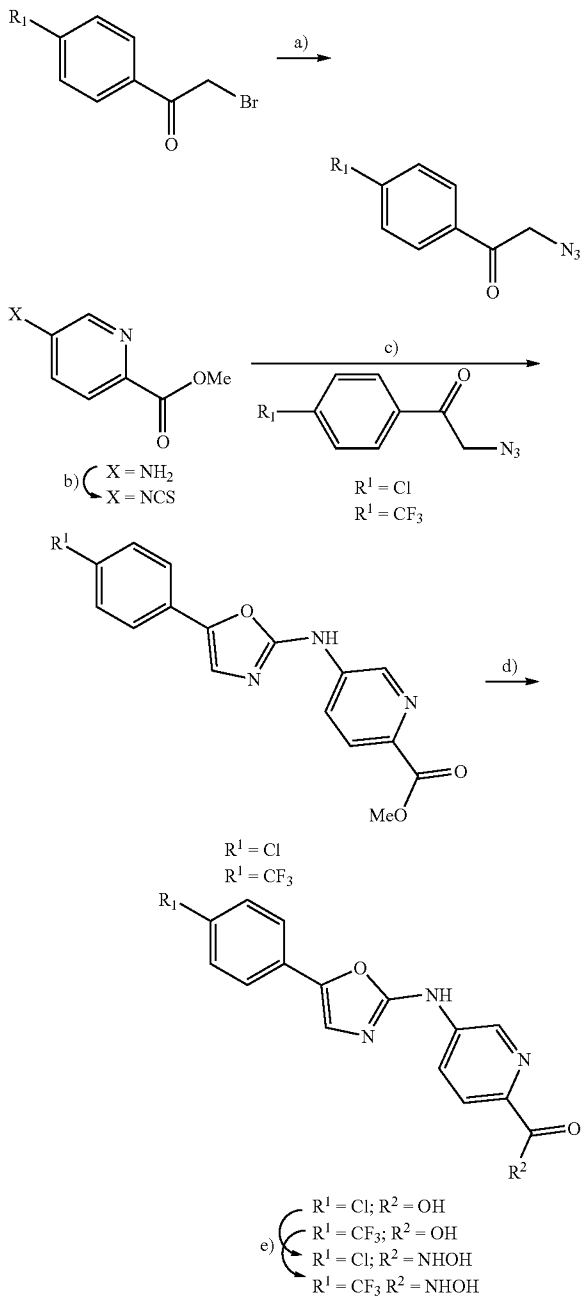

a) $NaN_3$, acetone, rt, 1 h; b) Thiophosgene, 25% $NaHCO_3$, acetone rt 1 h; c) $PPh_3$, 1,4-dioxane, 90° C. 1.5 h; d) LiOH•$H_2O$, 1,4-dioxane:EtOH:$H_2O$ (2:2:1), 100° C. 3.5 h; e) i. HOBt, EDCI, DMF rt 2 h ii. O-benzylhydroxylamine•HCl, $Et_3N$; iii) $BBr_3$, DCM rt 2-3 h.

To a suspension of methyl 5-aminopicolinate (0.380 g, 2.50 mmol) in acetone (6 mL) and 25% $NaHCO_3$ (aq.) (4 mL) was added a solution of thiophosgene (0.230 mL, 3.00 mmol) in acetone (2 mL) at 0° C. and the mixture stirred at rt for 1 h. The mixture was diluted with EtOAc (30 mL) and washed with $H_2O$ (2×15 mL). The organic layer was dried over $MgSO_4$ and concentrated to give methyl 5-isothiocyanatopicolinate as a cream semi-solid (0.387 g, 80% yield). $^1H$ NMR (401 MHz, $CDCl_3$) δ 8.66-8.55 (m, 1H), 8.15 (dd, J=8.4, 0.6 Hz, 1H), 7.64 (dd, J=8.4, 2.4 Hz, 1H), 4.02 (s, 3H). $^{13}C$ NMR (101 MHz, $CDCl_3$) δ 164.7 (C═O), 147.0 (CH), 145.3 (C), 141.5 (C), 133.2 (CH), 132.8 (C), 126.0 (CH), 53.3 ($CH_3$). LCMS $R_f$ (min)=5.52, MS m/z=195.1 $[M+H]^+$.

A solution of 2-bromo-4'-chloroacetophenone (0.20 g, 0.75 mmol) and $NaN_3$ (0.097 g, 1.5 mmol) in acetone (10 mL) was stirred at rt for 16 h. The reaction mixture was then concentrated in vacuo and the residue redissolved in DCM (30 mL) and washed with $H_2O$ (2×15 mL). The organic layer was dried over $MgSO_4$ and concentrated to an orange semi-solid (0.14 g). 2-Azido-1-(4-chlorophenyl)ethan-1-one (0.094 g, 0.41 mmol) was then dissolved in dry 1,4-dioxane (4 mL) and methyl 5-isothiocyanatopicolinate (0.080 g, 0.41 mmol) and $PPh_3$ (0.11 g, 0.41 mmol) added and the mixture heated to 90° C. for 1.5 h. The mixture was then concentrated to a solid and triturated with DCM, providing methyl 5-((5-(4-chlorophenyl)oxazol-2-yl)amino)picolinate as a cream solid (0.089 g, 73% yield). $^1H$ NMR (401 MHz, DMSO-$d_6$) δ 11.14 (s, 1H, NH), 8.82 (d, J=2.2 Hz, 1H), 8.30 (dd, J=8.7, 2.7 Hz, 1H), 8.11-8.05 (m, 1H), 7.63 (d, J=8.8 Hz, 2H), 7.62 (s, 1H), 7.52 (d, J=8.7 Hz, 2H), 3.85 (s, 3H). $^{13}C$ NMR (101 MHz, DMSO-$d_6$) δ 164.9 (C═O), 155.5 (C), 143.8 (C), 139.5 (C), 138.9 (C), 138.5 (CH), 131.7 (C), 129.2 (CH), 126.6 (C), 126.0 (CH), 124.5 (CH), 123.4 (CH), 122.5 (CH), 52.0 ($CH_3$).

LiOH·$H_2O$ (0.031 g, 0.74 mmol)) in $H_2O$ (0.75 mL) was added to a solution of methyl 5-((5-(4-chlorophenyl)oxazol-2-yl)amino)picolinate (0.081 g, 0.25 mmol) in 1,4-dioxane (1.5 mL) and EtOH (1.5 mL) and the mixture heated at reflux for 3.5 h. Volatiles were removed in vacuo and to the suspension was added NaCl (0.5 g), followed by 1.0 M HCl (aq.) dropwise at 0° C. The resulting precipitate was filtered and washed with $H_2O$ (3 mL), providing 5-((5-(4-chlorophenyl)oxazol-2-yl)amino)picolinic acid as a yellow solid that was recrystallised from $H_2O$ (0.67 g, 86% yield). $^1H$ NMR (401 MHz, DMSO-$d_6$) δ 10.87 (s, 1H, NH), 8.73 (d, J=2.4 Hz, 1H), 8.15 (dd, J=8.6, 2.5 Hz, 1H), 7.96 (d, J=8.6 Hz, 1H), 7.62 (d, J=8.7 Hz, 2H), 7.59 (s, 1H), 7.51 (d, J=8.7 Hz, 2H). $^{13}C$ NMR (101 MHz, DMSO-$d_6$) δ 166.7 (C═O), 155.9 (C), 143.5* (C), 137.4 (CH), 131.6 (C), 129.1 (CH), 126.7* (C), 124.8 (CH), 124.4 (CH), 123.4 (CH), 123.0 (CH).

* Overlapping quaternary carbon resonances

A solution of 5-((5-(4-chlorophenyl)oxazol-2-yl)amino) picolinic acid (0.040 g, 0.13 mmol), HOBt·$H_2O$ (0.021 g, 0.15 mmol) and EDCI·HCl (0.032 g, 0.17 mmol) in dry DMF (1.5 mL) was stirred at rt for 2 h. After this time, O-benzylhydroxylamine hydrochloride (0.10 g, 0.64 mmol) and $Et_3N$ (0.090 mL, 0.64 mmol) were added and the mixture stirred at rt for a further 16 h. DMF was removed in vacuo, washing with toluene (2 mL×3) to aid this process. $H_2O$ (2 mL) was then added and the mixture left to stir at rt for 10 min. The resulting precipitate was filtered and washed with $H_2O$ (1 mL), providing a grey solid (0.035 g) that was chromatographed on silica gel eluting with 25% EtOAc in DCM to afford N-(benzyloxy)-5-((5-(4-chlorophenyl)oxazol-2-yl)amino)picolinamide as a white solid (0.017 g, 32% yield). $^1H$ NMR (401 MHz, DMSO-$d_6$) δ 11.83 (s, 1H, NH), 11.02 (s, 1H, NH), 8.76 (d, J=2.6 Hz, 1H), 8.28 (dd, J=8.7, 2.6 Hz, 1H), 7.99 (d, J=8.8 Hz, 1H), 7.63 (d, J=8.7 Hz, 2H), 7.61 (s, 1H), 7.52 (d, J=8.7 Hz, 2H), 7.46 (s, 2H), 7.42-7.32 (m, 3H), 4.93 (s, 2H). $^{13}$C NMR (101 MHz, DMSO-$d_6$) δ 161.6 (C═O), 155.7 (C), 143.7 (C), 142.1 (C), 138.5 (C), 137.2 (CH), 136.0 (C), 131.8 (C), 129.2 (CH), 128.8 (CH), 128.3 (CH), 128.3 (CH), 126.6 (C), 124.5 (CH), 123.4 (CH), 123.4 (CH), 123.0 (CH), 77.1 ($CH_2$). LCMS $R_f$ (min)=3.58, MS m/z=420.8 [M+H]$^+$.

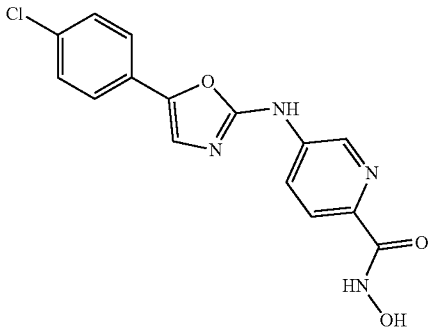 [SMILES: O=C(NO)c1ccc(Nc2ncc(-c3ccc(Cl)cc3)o2)cn1]

$BBr_3$ 1.0 M in heptane (0.22 mL, 0.22 mmol) was added dropwise to a solution of N-(benzyloxy)-5-((5-(4-chlorophenyl)oxazol-2-yl)amino)picolinamide (0.047 g, 0.11 mmol) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The precipitate was filtered and washed with $H_2O$ (10 mL) and $Et_2O$ (2 mL), providing the title compound as a brown solid (0.030 g, 81% yield). Mp 264-269° C. dec. $^1$H NMR (401 MHz, DMSO-$d_6$) δ 11.20 (s, 1H, NH), 10.97 (s, 1H, OH), 8.96 (s, 1H, NH), 8.75 (d, J=2.4 Hz, 1H), 8.26 (dd, J=8.6, 2.6 Hz, 1H), 7.96 (d, J=8.7 Hz, 1H), 7.63 (d, J=8.6 Hz, 2H), 7.61 (s, 1H), 7.52 (d, J=8.7 Hz, 2H). $^{13}$C NMR (101 MHz, DMSO-$d_6$) δ 161.4 (C═O), 155.7 (C), 143.6 (C), 142.7 (C), 138.0 (C), 137.1 (CH), 131.6 (C), 129.1 (CH), 126.6 (C), 124.4 (CH), 123.4 (CH), 123.3 (CH), 122.6 (CH). LCMS $R_f$ (min)=5.73, MS m/z=329.0 [M−H]$^-$. HRMS (ESI) calcd for $C_{15}H_{12}ClN_4O_3^+$ [M+H]$^+$ 331.0592, found 331.0593.

2. N-Hydroxy-5-((5-(4-(trifluoromethyl)phenyl)oxazol-2-yl)amino)picolinamide (Scheme 1)

(Intermediate A—2-azido-1-(4-(trifluoromethyl)phenyl)ethan-1-one) Sodium azide (2 equiv.) was added to a solution of 2-bromo-1-(4-(trifluoromethyl)phenyl)ethan-1-one (0.400 g, 1.498 mmol) in acetone (10 mL) and the mixture stirred at rt for 1 h. On formation of the azide intermediate, the mixture was concentrated to a residue before being partitioned between DCM (30 mL) and $H_2O$ (10 mL). The organic layer was collected and the aq. layer back extracted with DCM (3×20 mL). The combined organic layers were dried over $MgSO_4$ and concentrated to give 2-azido-1-(4-(trifluoromethyl)phenyl)ethan-1-one as an orange semi-solid (0.327 g, 95.3% yield).

A solution of 2-azido-1-(4-(trifluoromethyl)phenyl)ethan-1-one (0.279 g, 1.22 mmol), methyl 5-isothiocyanatopicolinate (0.250 g, 1.22 mmol) and $PPh_3$ (0.320 g, 1.22 mmol) in dry 1,4-dioxane (8 mL) was heated to 90° C. for 1.5 h. On cooling, the mixture was concentrated to a solid and triturated with DCM (5 mL), providing methyl 5-((5-(4-(trifluoromethyl)phenyl)oxazol-2-yl)amino)picolinate as an off-white solid (0.256 g, 58% yield). $^1$H NMR (401 MHz, DMSO-$d_6$) δ 11.25 (s, 1H, NH), 8.83 (d, J=2.3 Hz, 1H), 8.31 (dd, J=8.7, 2.7 Hz, 1H), 8.09 (d, J=8.7 Hz, 1H), 7.82 (s, 4H), 7.80 (s, 1H), 3.85 (s, 3H). $^{13}$C NMR (101 MHz, DMSO-$d_6$) δ 164.9 (C═O), 156.1 (C), 143.5 (C), 139.7 (C), 138.9 (C), 138.6 (CH), 131.4 (C), 127.1 (C), 126.2 (q, J=3.9 Hz, $CF_3$), 126.1 (CH), 125.3 (CH), 123.2* (CH), 122.8 (CH), 52.1 ($CH_3$). LCMS $R_f$ (min)=5.98, MS m/z=364.1 [M+H]$^+$.

* Overlapping CH resonances (CH from pyridine ring and CH from oxazole)

(Intermediate B—5-((5-(4-(trifluoromethyl)phenyl)oxazol-2-yl)amino)picolinic acid) LiOH·$H_2O$ (0.052 g, 1.2 mmol)) in $H_2O$ (1 mL) was added to a solution of methyl 5-((5-(4-(trifluoromethyl)phenyl)oxazol-2-yl)amino)picolinate (0.15 g, 0.41 mmol) in 1,4-dioxane (2 mL) and EtOH (2 mL) and the mixture heated at reflux for 3 h. Volatiles were removed in vacuo and to the suspension was added NaCl (0.5 g), followed by 1.0 M HCl (aq.) dropwise at 0° C. The resulting precipitate was filtered and washed with $H_2O$ (3 mL), providing 5-((5-(4-(trifluoromethyl)phenyl)oxazol-2-yl)amino)picolinic acid as a yellow solid that was recrystallised from $H_2O$ (0.12 g, 84% yield). $^1$H NMR (401 MHz, DMSO-$d_6$) δ 11.07 (s, 2H, OH, NH), 8.78 (s, 1H), 8.21 (d, J=8.2 Hz, 1H), 8.00 (d, J=8.1 Hz, 1H), 7.81 (s, 4H), 7.77 (s, 1H). $^{13}$C NMR (101 MHz, DMSO-$d_6$) δ 166.3 (C═O), 156.4 (C), 143.6 (C), 138.5 (C), 138.3 (CH), 131.6 (C), 127.6 (C), 127.3 (C), 126.3 (q, J=3.7 Hz, $CF_3$), 125.8 (CH), 125.4 (CH), 123.4* (CH), 123.2 (CH).

* Overlapping CH resonances (CH from pyridine ring and CH from oxazole)

A solution of 5-((5-(4-(trifluoromethyl)phenyl)oxazol-2-yl)amino)picolinic acid (0.050 g, 0.14 mmol), HOBt·$H_2O$ (0.022 g, 0.17 mmol) and EDCI·HCl (0.034 g, 0.18 mmol) in dry DMF (2 mL) was stirred at rt for 2 h. After this time, O-benzylhydroxylamine hydrochloride (0.11 g, 0.69 mmol) and $Et_3N$ (0.10 mL, 0.69 mmol) were added and the mixture stirred at rt for a further 16 h. The mixture was then diluted with EtOAc (20 mL) and washed with $H_2O$ (3×10 mL). The combined organic layers were dried over $MgSO_4$ and concentrated to a grey solid (0.092 g) that was triturated with petroleum spirit (4 mL), providing N-(benzyloxy)-5-((5-(4-(trifluoromethyl)phenyl)oxazol-2-yl)amino)picolinamide as a white solid (0.024 g, 39% yield). $^1$H NMR (401 MHz, DMSO-$d_6$) δ 11.84 (s, 1H, NH), 11.12 (s, 1H, NH), 8.77 (s, 1H), 8.34-8.25 (m, 1H), 8.00 (d, J=8.7 Hz, 1H), 7.82 (s, 4H), 7.79 (s, 1H), 7.47 (d, J=6.7 Hz, 2H), 7.43-7.31 (m, 3H), 4.93 (s, 2H). $^{13}$C NMR (101 MHz, DMSO-$d_6$) δ 161.5 (C═O), 156.2 (C), 143.3 (C), 142.2 (C), 138.4 (C), 137.2 (CH), 136.0 (C), 131.5 (C), 128.7 (CH), 128.3 (CH), 128.2 (CH), 127.0 (C), 126.1 (q, J=3.8 Hz, $CF_3$), 125.3 (CH), 123.5 (CH), 123.1* (CH), 123.0 (CH), 77.1 ($CH_2$). LCMS $R_f$ (min)=3.58, MS m/z=454.8 [M+H]$^+$.

* Overlapping CH resonances (CH from pyridine ring and CH from oxazole)

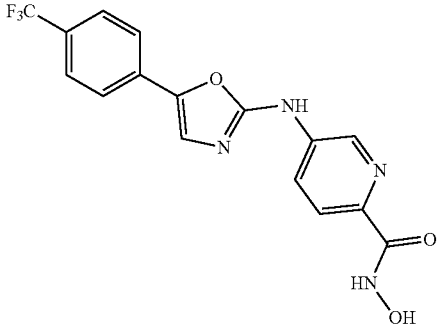 [SMILES: O=C(NO)c1ccc(Nc2ncc(-c3ccc(C(F)(F)F)cc3)o2)cn1]

$BBr_3$ 1.0 M in heptane (0.33 mL, 0.33 mmol) was added to a solution of N-(benzyloxy)-5-((5-(4-(trifluoromethyl)phenyl)oxazol-2-yl)amino)picolinamide (0.050 g, 0.11 mmol)

in dry DCM (1.5 mL) at 0° C. and the mixture stirred at rt for 3 h. Volatiles were removed in vacuo and the residue suspended in sat. $NaHCO_3$ (aq.) (3 mL) and stirred at rt for 20 min. The precipitate was filtered and washed with $H_2O$ (10 mL) and $Et_2O$ (2 mL), providing the title compound as a yellow solid (0.021 g, 53% yield). Mp 184-188° C. $^1H$ NMR (401 MHz, DMSO-$d_6$) δ 11.22 (d, J=1.9 Hz, 1H, NH), 11.07 (s, 1H, OH), 8.97 (d, J=2.0 Hz, 1H, NH), 8.76 (d, J=2.3 Hz, 1H), 8.31-8.24 (m, 1H), 7.97 (d, J=8.7 Hz, 1H), 7.81 (s, 4H), 7.78 (s, 1H). $^{13}C$ NMR (101 MHz, DMSO-$d_6$) δ 161.4 (C═O), 156.3 (C), 143.2 (C), 142.8 (C), 137.9 (C), 137.2 (CH), 131.5 (C), 127.3 (C), 126.1 (q, J=3.9 Hz, $CF_3$), 125.3 (CH), 123.5 (CH), 123.1* (CH), 122.6 (CH). LCMS $R_f$ (min)=3.66, MS m/z=364.8 $[M+H]^+$. HRMS (ESI) calcd for $C_{16}H_{11}F_3N_4O_3{}^+$ $[M+H]^+$ 365.0856, found 365.0856.

* Overlapping CH resonances (CH from pyridine ring and CH from oxazole)

3. N'-Hydroxy-6-((5-(4-(trifluoromethyl)phenyl)oxazol-2-yl)amino)nicotinimidamide hydrochloride (Scheme 2)

Scheme 2

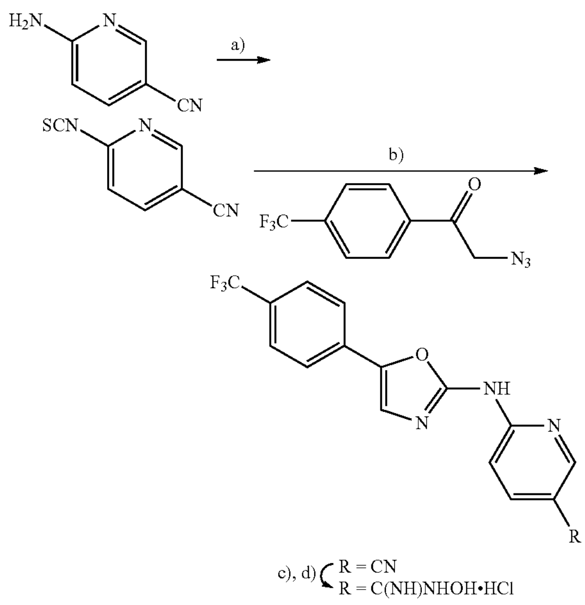

a) Thiophosgene, 25% $NaHCO_3$, THF rt 0.5 h; b) $PPh_3$, 1,4-dixoane, 90° C. 1.5 h: c) $HONH_2$•HCl, $Et_3N$, EtOH, 80° C. 6 h; d) HCl 4.0M in 1,4-dioxane, EtOAc, rt 16 h.

To a suspension of 6-amino-3-pyridinecarbonitrile (0.300 g, 2.52 mmol) in THF (4 mL) and 25% $NaHCO_3$ (aq.) (5 mL) was added a solution of thiophosgene (0.210 mL, 2.77 mmol) in THF (1 mL) at 0° C. and the mixture stirred at rt for 0.5 h. The mixture was then diluted with DCM (20 mL) and washed with $H_2O$ (2×10 mL). The combined organic layers were dried over $MgSO_4$ and concentrated to a dark brown oil that was chromatographed on silica gel eluting with 100% DCM, providing 6-isothiocyanatonicotinonitrile as a light brown semi-solid (0.117 g, 29% yield). $^1H$ NMR (401 MHz, $CDCl_3$) δ 8.71 (s, 1H), 7.97 (dd, J=8.3, 2.3 Hz, 1H), 7.16 (d, J=8.3 Hz, 1H). $^{13}C$ NMR (101 MHz, $CDCl_3$) δ 153.3 (CH), 149.9 (C), 145.9 (C), 142.0 (CH), 119.5 (CH), 116.0 (C), 107.9 (C). LCMS $R_f$ (min)=3.11, MS m/z=161.9 $[M+H]^+$.

A solution of 2-azido-1-(4-(trifluoromethyl)phenyl)ethan-1-one (Intermediate A) (0.074 g, 0.33 mmol), 6-isothiocyanatopicolinonitrile (0.052 g, 0.32 mmol) and $PPh_3$ (0.085 g, 0.32 mmol) in dry 1,4-dioxane (3 mL) was heated to 90° C. for 1.5 h. On cooling, the mixture was concentrated to a brown solid that was triturated with DCM (4 mL), providing 6-((5-(4-(trifluoromethyl)phenyl)oxazol-2-yl)amino)nicotinonitrile as a white solid (0.11 g, 100% yield). $^1H$ NMR (401 MHz, DMSO-$d_6$) δ 11.77 (s, 1H, NH), 8.74 (d, J=1.6 Hz, 1H), 8.24 (dd, J=8.9, 2.2 Hz, 1H), 8.16 (d, J=9.1 Hz, 1H), 7.83 (s, 4H), 7.82 (s, 1H). $^{13}C$ NMR (101 MHz, DMSO-$d_6$) δ 155.2 (C), 154.3 (C), 152.3 (CH), 143.9 (C), 141.9 (CH), 131.3 (C), 126.1 (q, J=3.9 Hz, $CF_3$), 125.1 (CH), 123.3* (CH), 122.8 (C), 117.7 (C), 110.3 (CH), 101.2 (C). LCMS $R_f$ (min)=3.24, MS m/z=129.0 $[M-H]^-$.

* Two overlapping CH resonances (CH from pyridine ring and CH from oxazole ring)

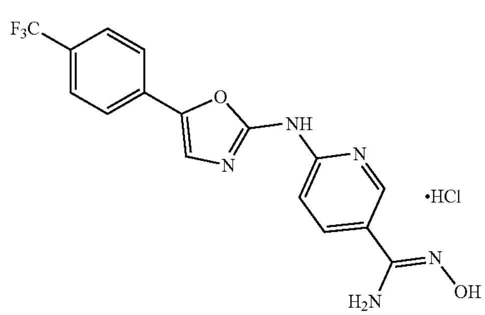 [SMILES: N/C(=N\O)c1ccc(Nc2ncc(-c3ccc(C(F)(F)F)cc3)o2)nc1 ; Cl]

A solution of 6-((5-(4-(trifluoromethyl)phenyl)oxazol-2-yl)amino)nicotinonitrile (0.050 g, 0.15 mmol), $HONH_2$·HCl (0.042 g, 0.60 mmol) and $Et_3N$ (0.085 mL, 0.60 mmol) in EtOH (3 mL) was heated at reflux for 16 h. On cooling, the mixture was diluted with $H_2O$ (5 mL) and the resulting precipitate filtered and washed with $H_2O$ (3 mL), providing a cream solid (0.045 g). This material was then salted by diluting in EtOAc (1 mL) and adding 4.0 M HCl in 1,4-dioxane (0.030 mL, 0.12 mmol) and stirring at rt for 16 h. The resulting precipitate was filtered and washed with EtOAc (3 mL), affording a yellow solid (0.027 g) that was further purified using RP-HPLC in an AA 30-100B solvent system to give the title compound as a pale yellow solid (0.012 g, 22% yield). Mp 257-261° C. $^1H$ NMR (401 MHz, DMSO-$d_6$) δ 11.24 (s, 1H, NH), 9.77 (s, 1H, OH), 8.58 (s, 1H), 8.05 (s, 2H), 7.81 (s, 4H), 7.77 (s, 1H), 6.04 (s, 2H, $NH_2$). $^{13}C$ NMR (101 MHz, DMSO-$d_6$) δ 155.7 (C), 154.3 (C), 146.0* (CH), 143.7 (C), 137.4 (CH), 131.4† (C), 126.1 (q, J=3.7 Hz, $CF_3$), 125.6 (C), 125.1 (CH), 123.3‡ (CH), 122.9 (C). LCMS $R_f$ (min)=4.91, MS m/z=362.0 $[M-H]^-$. HRMS (ESI) calcd for $C_{16}H_{13}F_3N_5O_2{}^+$ $[M+H]^+$ 364.1016, found 364.1012.

* Missing resonance: CH signal is below the signal to noise ratio by $^{13}C$ NMR, found using HSQC † Overlapping quaternary carbon resonances ‡ Overlapping CH resonances (—$CF_3$ substituted ring)

4. N-(6-(Hydroxyamino)pyridin-3-yl)-5-(4-(trifluoromethyl)phenyl)oxazol-2-amine (Scheme 3)

Scheme 3

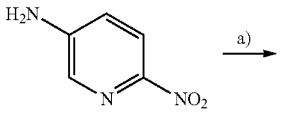

-continued

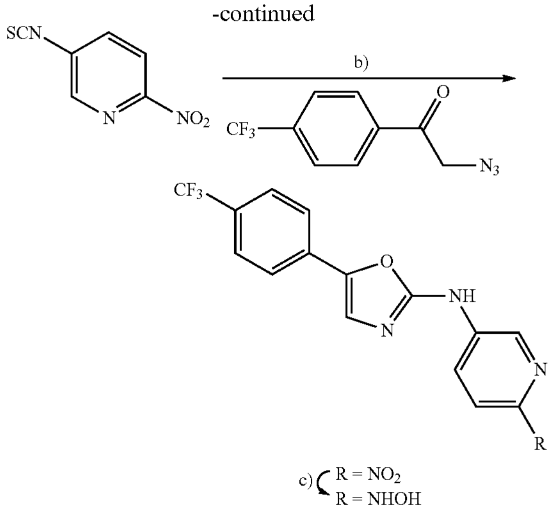

a) Thiophosgene, 25% $NaHCO_3$, DCM rt 16 h; b) $PPh_3$, 1,4-dioxane, 90° C. 1.5 h: c) Pd/C, $H_2$, MeOH rt 16 h.

To a suspension of 6-nitropyridin-3-amine (0.050 g, 0.36 mmol) in DCM (1.5 mL) and 25% $NaHCO_3$ (aq.) (1.5 mL) was added neat thiophosgene (0.030 mL, 0.40 mmol) at 0° C. and the mixture stirred at rt for 16 h. After this time, the mixture was diluted with DCM (30 mL) and washed with $H_2O$ (2×15 mL). The organic layer was dried over $MgSO_4$ and concentrated to give 5-isothiocyanato-2-nitropyridine as a cream solid (0.051 g, 79% yield). $^1$H NMR (401 MHz, $CDCl_3$) δ 3.73 (d, J=2.4 Hz, 1H), 3.54 (dd, J=8.6, 0.5 Hz, 1H), 3.03 (dd, J=8.6, 2.5 Hz, 1H). $^{13}$C NMR (101 MHz, $CDCl_3$) δ 153.4 (C), 145.8 (CH), 143.4 (C), 135.6 (CH), 135.5 (C), 119.3 (CH). LCMS $R_f$ (min)=5.43, MS m/z=180.1 $[M+H]^+$.

A solution of 2-azido-1-(4-(trifluoromethyl)phenyl)ethan-1-one (Intermediate A) (0.425 g, 1.86 mmol), 5-isothiocyanato-2-nitropyridine (0.336 g, 1.86 mmol) and $PPh_3$ (0.486 g, 1.86 mmol) in 1,4-dioxane was heated to 90° C. for 1.5 h. On cooling, the mixture was concentrated to a dark brown solid that was triturated with DCM (5 mL), affording N-(6-nitropyridin-3-yl)-5-(4-(trifluoromethyl)phenyl)oxazol-2-amine as a brown solid (0.432 g, 67% yield). Mp 319-324° C. $^1$H NMR (401 MHz, DMSO-$d_6$) δ 11.62 (s, 1H, NH), 8.74 (d, J=2.5 Hz, 1H), 8.47 (dd, J=9.0, 2.7 Hz, 1H), 8.39 (d, J=8.9 Hz, 1H), 7.84 (s, 1H), 7.83 (s, 4H). $^{13}$C NMR (101 MHz, DMSO-$d_6$) δ 155.7 (C), 149.9 (C), 143.9 (C), 141.1 (C), 136.7 (CH), 131.3 (C), 127.7 (C), 126.2 (q, J=3.8 Hz, $CF_3$), 125.2 (CH), 124.9 (CH), 123.4* (CH), 120.0 (CH). LCMS $R_f$ (min)=3.96, MS m/z=350.8 $[M+H]^+$. HRMS (ESI) calcd for $C_{15}H_{10}F_3N_4O_3^+$ $[M+H]^+$ 351.0700, found 351.0703.

*Overlapping resonances (—$CF_3$ substituted ring)

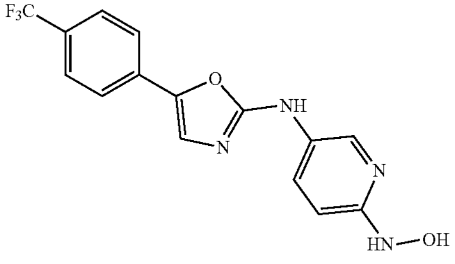 [SMILES: ONc1ccc(Nc2ncc(-c3ccc(C(F)(F)F)cc3)o2)cn1]

Pd/C 10% (0.025 g) was added to a solution of N-(6-nitropyridin-3-yl)-5-(4-(trifluoromethyl)phenyl)oxazol-2-amine (0.040 g, 0.11 mmol) in MeOH (1.5 mL) and the mixture placed under vacuum and flushed with $H_2$×3 to remove any oxygen. The reaction mixture was then stirred at rt under $H_2$ gas for 16 h. After this time, the solution was filtered through celite to remove Pd/C and concentrated to a light brown solid (0.028 g) that was triturated with EtOAc (4 mL), providing the title compound as a cream solid (0.011 g, 29% yield). Mp 212-215° C. $^1$H NMR (401 MHz, DMSO-$d_6$) δ 10.26 (s, 1H, NH), 8.51 (d, J=2.0 Hz, 1H, NH), 8.42 (d, J=1.8 Hz, 1H, OH), 8.34 (d, J=2.3 Hz, 1H), 7.92 (dd, J=8.9, 2.7 Hz, 1H), 7.76 (ABq, J=8.7 Hz, 4H), 7.66 (s, 1H), 6.90 (d, J=8.9 Hz, 1H). $^{13}$C NMR (101 MHz, DMSO-$d_6$) δ 158.9 (C), 157.7 (C), 142.4 (C), 136.8 (CH), 131.8 (C), 128.9 (C), 127.6 (CH), 126.0 (q, J=3.9 Hz, $CF_3$), 125.6 (CH), 122.9 (C), 122.6* (CH), 107.4 (CH). LCMS $R_f$ (min)=4.89, MS m/z=336.8 $[M+H]^+$. HRMS (ESI) calcd for $C_{15}H_{12}F_3N_4O_2^+$ $[M+H]^+$ 337.0907, found 337.0905.

* Overlapping resonances (—$CF_3$ substituted ring)

5. 5-((5-[4-(Trifluoromethyl)phenyl]-1,3,4-oxadiazol-2-yl)amino)-N-hydroxy-pyridine-2-carboximidamide (Scheme 4, X=H)

Scheme 4

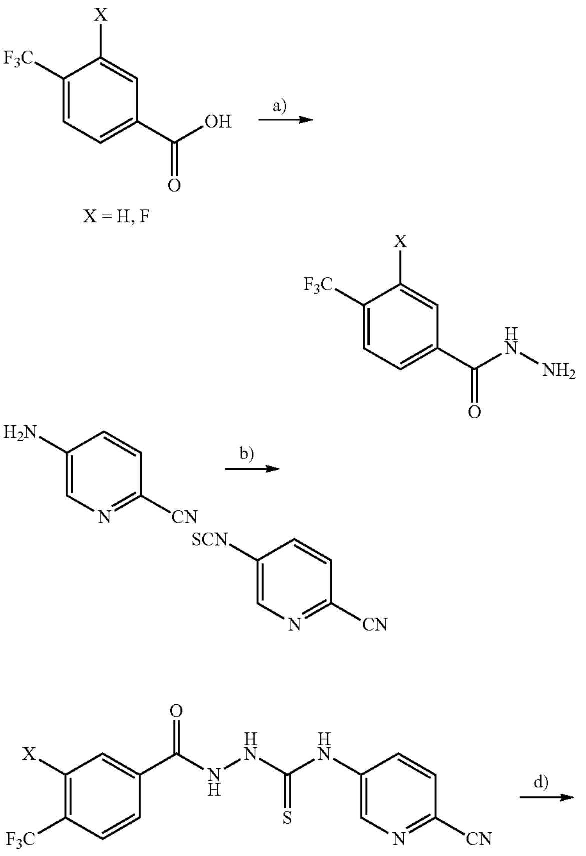

-continued

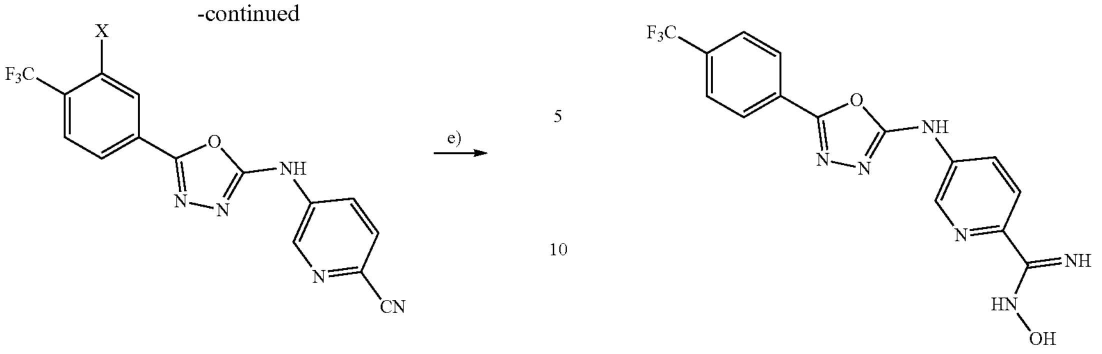

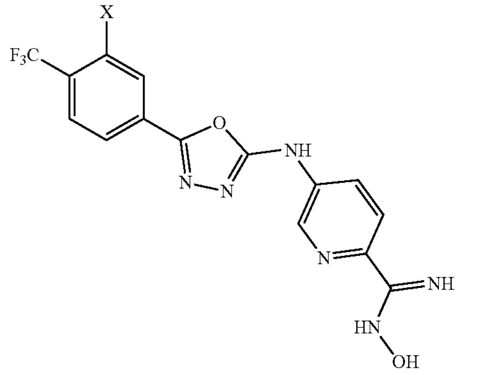

a) i. $H_2SO_4$, MeOH, 0° C. to reflux, 16 h; ii. $H_2NNH_2•H_2O$, MeOH, 0° C. to rt, 1 h; b) thiophosgene, toluene, 16 h; c) aroyl hydrazide, DMF, rt, 16 h; d) EDCI•HCl, DMF, 60° C., 2 h; e) $NH_2OH•HCl$, $Et_3N$, EtOH, reflux, 3 h.

$H_2SO_4$ (3 mL) was added dropwise to 4-(trifluoromethyl) benzoic acid (10.000 g, 52.598 mmol) in MeOH (250 mL) at 0° C. and the mixture refluxed for 16 h. On cooling, hydrazine monohydrate (73.700 mL) was added and the mixture stirred at rt for 1 h. The solution was then concentrated under reduced pressure. Ice water was added and the resulting precipitate was filtered and washed with $H_2O$ (10 mL) and $Et_2O$ (3 mL), giving 4-(trifluoromethyl)benzohydrazide as a white crystalline solid (0.847 g, 78.9% yield). $^1$H NMR (400 MHz, DMSO-$d_6$) δ 9.90 (s, 1H), 7.94 (d, J=8.3 Hz, 2H), 7.45 (d, J=8.2 Hz, 2H), 4.68 (s, 2H). $^{13}$C NMR (101 MHz, DMSO-$d_6$) δ 164.6, 150.1, 132.4, 129.2, 121.2, 120.6. LCMS $R_f$ (min)=5.29, MS m/z=220.1 $[M+H]^+$.

Thiophosgene (1.1 equiv.) was added to a suspension of 5-aminopicolinonitrile (1.000 g, 8.394 mmol) in toluene (40 mL) and the mixture was heated at reflux for 2 h. Volatiles were then removed in vacuo and the residue redissolved in dry DMF (6 mL). To the solution was then added 4-(trifluoromethyl)benzohydrazide (1 equiv.) and the mixture stirred at rt for 16 h. EDCI·HCl (1.2 equiv.) was then added and the mixture heated at 60° C. for 2 h. On cooling, $H_2O$ (5 mL) was added and the mixture stirred at rt for 0.5 h. The resulting precipitate was filtered and washed with $H_2O$ (5 mL) and DCM (2 mL), providing 5-((5-(4-(trifluoromethyl) phenyl)-1,3,4-oxadiazol-2-yl)amino)picolinonitrile as a yellow solid (1.165 g, 86.1% yield). $^1$H NMR (400 MHz, DMSO-$d_6$) δ 11.75 (s, 1H), 8.85 (d, J=2.2 Hz, 1H), 8.29 (dd, J=8.6, 2.4 Hz, 1H), 8.12 (d, J=8.1 Hz, 2H), 8.06 (d, J=8.6 Hz, 1H), 7.97 (d, J=8.2 Hz, 2H). $^{13}$C NMR (101 MHz, DMSO-$d_6$) δ 159.93, 158.24, 140.94, 139.00, 130.40, 127.70, 127.07, 126.93, 125.08, 124.09, 118.32. LCMS $R_f$ (min)=3.381, MS m/z=331.8 $[M+H]^+$.

A solution of 5-((5-(4-(trifluoromethyl)phenyl)-1,3,4-oxadiazol-2-yl)amino)picolinonitrile (0.076 g, 0.229 mmol), $NH_2OH$ (2.5 equiv.) and $Et_3N$ (2.5 equiv.) in EtOH (2 mL) was heated to reflux for 4 h. On reaction completion, the crude material was purified using preparative HPLC in a 95% A:5% B to 100% B solvent system. The TFA and ACN were removed through rotary evaporation and $H_2O$ through the use of the freeze dryer, providing the title compound as a white solid (0.036 g, 43.1% yield). $^1$H NMR (400 MHz, DMSO-$d_6$) δ 10.88 (s, 1H), 10.20 (s, 1H), 8.62 (s, 2H), 8.16 (d, J=9.1 Hz, 1H), 8.12 (d, J=8.1 Hz, 2H), 7.99 (d, J=8.4 Hz, 2H), 7.63 (d, J=7.5 Hz, 2H. $^{13}$C NMR (101 MHz, DMSO-$d_6$) δ 165.77, 164.00, 159.82, 159.69, 157.60, 143.84, 138.49, 137.54, 137.44, 127.29, 126.67, 126.52, 126.45, 125.17, 125.17, 124.22, 122.80, 122.46. LCMS $R_f$ (min)=4.926, MS m/z=364.8 $[M+H]^+$. HRMS (ESI) calcd for $C_{15}H_{12}F_3N_6O_2^+$ $[M+H]^+$ 365.097, found 365.0968.

6. 5-((5-[3-Fluoro-4-(trifluoromethyl)phenyl]-1,3,4-oxadiazol-2-yl)amino)-N-hydroxypyridine-2-carboximidamide (Scheme 4, X═F)

$H_2SO_4$ (0.270 mL) was added dropwise to 3-fluoro-4-(trifluoromethyl)benzoic acid (1.000 g, 4.805 mmol) in MeOH (25 mL) at 0° C. and the mixture was refluxed for 16 h. On cooling, hydrazine monohydrate (6.730 mL) was added and the mixture stirred at rt for 1 h. The solution was then concentrated under reduced pressure. Ice water was added and the resulting precipitate was filtered and washed with $H_2O$ (10 mL) and $Et_2O$ (3 mL), giving 3-fluoro-4-(trifluoromethyl)benzohydrazide as a white crystalline solid (0.869 g, 81.4% yield). $^1$H NMR (400 MHz, $CDCl_3$) δ 7.74 (t, J=7.4 Hz, 1H), 7.63 (t, J=10.1 Hz, 2H), 7.40 (s, 1H), 4.15 (s, 2H). $^{13}$C NMR (101 MHz, DMSO-$d_6$) δ 164.6, 150.1, 132.4, 129.2, 121.2, 120.6. LCMS $R_f$ (min)=3.003, MS m/z=222.9 $[M+H]^+$.

Thiophosgene (1.1 equiv.) was added to a suspension of 5-amino-2-pyridinecarbonitrile (0.134 g, 1.125 mmol) in toluene (8 mL) and the mixture was heated to reflux for 2 h. Volatiles were then removed in vacuo and the residue redissolved in dry DMF (6 mL). To the solution was then added 3-fluoro-4-(trifluoromethyl)benzohydrazide (1 equiv.) and the mixture stirred at rt for 16 h. EDCI·HCl (1.2 equiv.) was then added and the mixture heated at 60° C. for 2 h. On cooling, $H_2O$ (5 mL) was added and the mixture stirred at rt for 0.5 h. The resulting precipitate was filtered and washed with $H_2O$ (5 mL) and DCM (1 mL), providing 5-((5-(3-fluoro-4-(trifluoromethyl)phenyl)-1,3,4-oxadiazol-2-yl) amino)picolinonitrile as a yellow solid (0.277 g, 70.5% yield). $^1$H NMR (400 MHz, DMSO-$d_6$) δ 8.86 (s, 1H), 8.30 (d, J=8.4 Hz, 1H), 8.05 (dd, J=15.0, 8.0 Hz, 2H), 7.96 (dd, J=15.6, 9.9 Hz, 2H). $^{13}$C NMR (101 MHz, DMSO-$d_6$) δ

174.82, 160.05, 140.90, 138.76, 130.27, 130.06, 129.35, 125.17, 124.06, 122.69, 118.22, 114.62, 114.40. LCMS $R_f$ (min)=3.523, MS m/z=349.8 $[M+H]^+$.

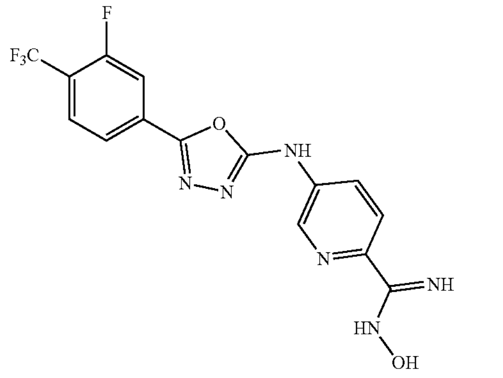 [SMILES: N=C(NO)c1ccc(Nc2nnc(-c3ccc(C(F)(F)F)c(F)c3)o2)cn1]

A solution of 5-((5-(3-fluoro-4-(trifluoromethyl)phenyl)-1,3,4-oxadiazol-2-yl)amino)picolinonitrile (0.100 g, 0.286 mmol), $NH_2OH{\cdot}HCl$ (2.5 equiv.) and $Et_3N$ (2.5 equiv.) in EtOH (2 mL) was heated to reflux for 4 h. Upon reaction completion, $H_2O$ (50 mL) was added and the solution was extracted with EtOAc (3x15 mL). The combined organic layers were dried over $MgSO_4$ and concentrated to give the title compound as a white solid (0.028 g, 26.9% yield). $^1H$ NMR (400 MHz, DMSO-$d_6$) δ 11.30 (s, 1H), 9.80 (s, 1H), 8.80 (d, J=2.5 Hz, 1H), 8.10 (dd, J=8.8, 2.6 Hz, 1H), 8.04 (t, J=7.7 Hz, 1H), 7.93 (m, 3H), 5.80 (s, 2H). $^{13}C$ NMR (101 MHz, DMSO-$d_6$) δ 160.19, 157.77, 156.38, 149.26, 143.85, 137.19, 135.44, 129.84, 128.86, 124.62, 123.62, 122.11, 120.92, 119.84, 114.10, 113.87. LCMS $R_f$ (min)=5.319. HRMS (ESI) calcd for $C_{15}H_{11}F_4N_6O_2^+$ $[M+H]^+$ 383.0874, found 383.0875.

7. 1-Hydroxy-4-((5-[4-(trifluoromethyl)phenyl]-1,3,4-oxadiazol-2-yl)amino)-1,2-dihydropyridin-2-one (Scheme 5)

Scheme 5

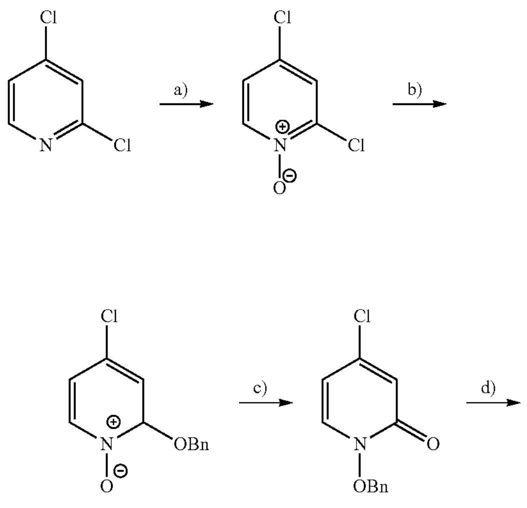

-continued

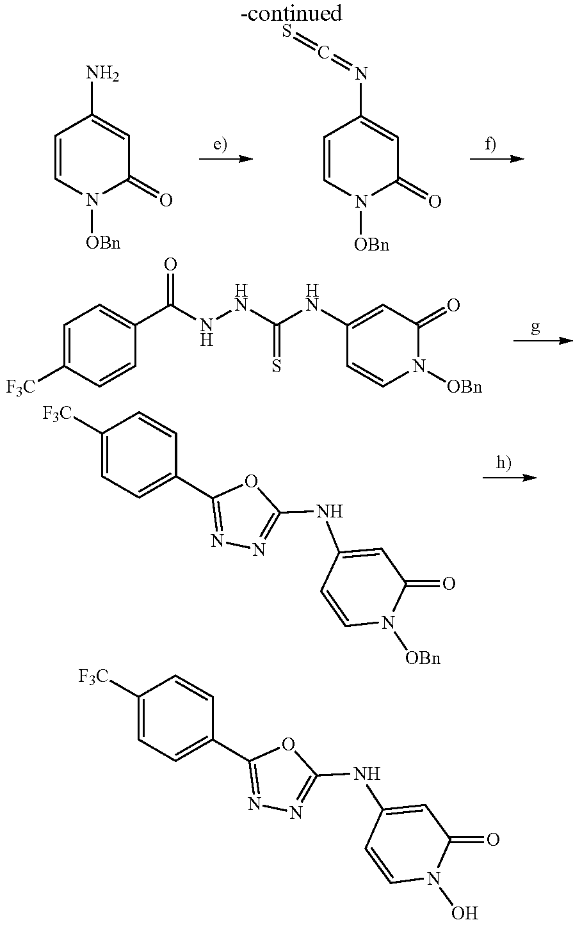

a) $H_2O_2$•Urea, TFAA, DCM, rt, 5 h; b) Benzyl alcohol, n-BuLi, THF, 0° C., 10 min; c) toluene, reflux, 1 h; d) $NaN_3$, DMSO, 80° C., 8 h; e) Thiophosgene, toluene, reflux, 2h; f) 4-trifluoromethylbenzohydrazide, DMF, rt, 16 h; g) EDCI•HCl, THF, 60° C., 2 h; h) $BBr_3$, DCM, 0° C.~rt, 30 h.

$H_2O_2$·urea (2 equiv.) was added to a solution of 2,4-dichloropyridine (2.000 g, 13.514 mmol) in dry DCM (60 mL). On cooling to 0° C., a solution of TFAA (2 equiv.) in dry DCM was added dropwise and the mixture was stirred at rt for 5 h. The reaction mixture was diluted with sat. $NaS_2O_3$ (15 mL) and stirred at rt for 0.5 h then poured into $H_2O$ (10 mL) and extracted with DCM (3x10 mL). The combined organic layers were washed with 1 M NaOH (15 mL), dried over $MgSO_4$ and concentrated to a cream semi-solid. The solid was then chromatographed on silica gel eluting with 5% EtOH in DCM, providing a yellow crystalline solid (2.068 g, 93.3% yield). $^1H$ NMR (400 MHz, DMSO-$d_6$) δ 8.29-8.23 (m, 1H), 7.51 (d, J=2.9 Hz, 1H), 7.20 (dd, J=7.1, 2.9 Hz, 1H). $^{13}C$ NMR (101 MHz, DMSO-$d_6$) δ 142.9, 140.9, 131.4, 127.0, 124.5. LCMS $R_f$(min)=1.88. MS m/z 164.0 $[M+H]^+$.

n-BuLi 2.37 M in cyclohexane (1.1 equiv.) was added dropwise to a solution of benzyl alcohol (1.5 equiv.) in dry THF (10 mL) at 0° C. under $N_2$ and the mixture was stirred at this temperature for 10 min. The mixture was transferred dropwise into a solution of 2,4-dichloropyridine-1-oxide (0.448 g, 2.732 mmol) in dry THF (10 mL) and the mixture stirred at 0° C. for 15 min. The reaction mixture was quenched with $H_2O$ (10 mL) and extracted with EtOAc (2x20 mL). The combined organic layers were washed with $H_2O$ (2x10 mL), dried over $MgSO_4$ and concentrated to an orange cream semi-solid. The solid was chromatographed on silica gel eluting with 20% EtOAc in DCM, providing a white crystalline solid (1.282 g, 88.4% yield), which should be stored at −20° C. $^1$H NMR (400 MHz, $CDCl_3$) δ 8.15 (d, J=6.9 Hz, 1H), 7.43 (dd, J=7.9, 1.5 Hz, 2H), 7.40-7.30 (m, 3H), 6.88 (dd, J=6.9, 2.7 Hz, 1H), 6.85 (d, J=2.7 Hz, 1H), 5.39 (s, 2H). $^{13}$C NMR (101 MHz, DMSO-$d_6$) δ 157.87, 140.34, 134.09, 132.80, 128.99, 128.96, 127.75, 118.71, 112.02, 72.82. LCMS $R_f$ (min)=2.975, MS m/z=235.9 $[M+H]^+$.

The solution of 2-(benzyloxy)-4-chloropyridine-1-oxide (1.282 g, 5.440 mmol) in toluene (10 mL) was heated at 100° C. for 3 h. The solvent was then removed through rotary evaporation. The residual solid was chromatographed on silica gel eluting with 10% EtOAc in DCM, providing 1-(benzyloxy)-4-chloropyridin-2(1H)-one as a yellow crystalline solid (0.620 g, 48.3% yield). $^1$H NMR (400 MHz, $CDCl_3$) δ 7.38 (m, 5H), 7.01 (d, J=7.5 Hz, 1H), 6.70 (d, J=2.6 Hz, 1H), 5.92 (dd, J=7.6, 2.7 Hz, 1H), 5.25 (s, 2H). $^{13}$C NMR (101 MHz, DMSO) δ 157.66, 145.80, 136.66, 133.36, 130.16, 129.61, 128.90, 121.10, 106.10, 78.65. LCMS $R_f$ (min)=3.222, MS m/z=257.8 $[M+Na]^+$.

$NaN_3$ (3 equiv.) was added to a solution of 1-(benzyloxy)-4-chloropyridin-2-one (0.500 g, 2.122 mmol) in DMSO (10 mL). The solution was then heated at 80° C. for 28 h. The reaction mixture was cooled to rt and diluted with 1N HCl (2 mL). The resulting mixture was poured into distilled water (20 mL) and the aq. layer was washed with EtOAc (2×20 mL). The aq. layer was slowly neutralized with sat. aq. $NaHCO_3$ solution and extracted with EtOAc (2×20 mL). The combined organic layers were collected, dried over $MgSO_4$ and concentrated to a cream semi-solid. The solid was chromatographed on silica gel eluting with 1% $Et_3N$ in EtOAc, providing 4-amino-1-(benzyloxy)pyridin-2(1H)-one as a yellow crystalline solid (0.220 g, 42.8% yield). $^1$H NMR (400 MHz, $CDCl_3$) δ 7.42-7.30 (m, 5H), 6.83 (d, J=7.6 Hz, 1H), 5.69 (d, J=2.3 Hz, 1H), 5.41 (dd, J=7.6, 2.5 Hz, 1H), 5.17 (s, 2H), 4.52 (s, 2H). $^{13}$C NMR (101 MHz, $CDCl_3$) δ 159.97, 155.23, 136.24, 134.18, 130.09, 129.16, 128.69, 97.51, 97.00, 78.58, 40.96. LCMS $R_f$ (min)=2.920, MS m/z=216.9 $[M+H]^+$.

Thiophosgene (1.2 equiv.) was added dropwise to a solution of 1-benzyloxy-4-amino-2-pyridin-2-one (0.200 mg, 0.925 mmol) in dry toluene (5 mL) at rt. The solution was then heated at reflux for 2 h. Reaction progress was monitored by $^1$H NMR. After 2 h the starting material had completely disappeared and a new product was formed as confirmed by $^1$H NMR. Toluene and thiophosgene were removed in vacuo and the residue redissolved in dry DMF (5 mL). To the solution was then added 4-(trifluoromethyl) benzohydrazide (1 equiv.) and the mixture stirred at rt for 16 h. EDCI·HCl (1.2 equiv.) was then added and the mixture heated to 60° C. for 2 h. On cooling, $H_2O$ (5 mL) was added and the mixture stirred at rt for 0.5 h. The resulting precipitate was filtered and washed with $H_2O$ (5 mL), providing 1-((benzyloxy)-4-((5-(4-(trifluoromethyl)phenyl)-1,3,4-oxadiazol-2-yl)amino)pyridin-2(1H)-one as a brown solid (0.176 g, 42.9% yield). $^1$H NMR (400 MHz, DMSO-$d_6$) δ 11.24 (s, 1H), 8.11 (d, J=8.1 Hz, 2H), 7.97 (d, J=8.3 Hz, 2H), 7.72 (d, J=7.8 Hz, 1H), 7.49 (dd, J=6.6, 3.1 Hz, 2H), 7.44-7.40 (m, 3H), 6.91 (d, J=2.9 Hz, 1H), 6.23 (dd, J=7.8, 2.9 Hz, 1H), 5.19 (s, 2H). LCMS $R_f$ (min)=3.359, MS m/z=428.8 $[M+H]^+$.

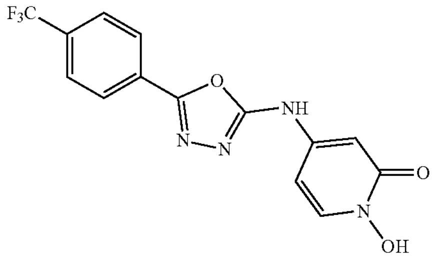 [SMILES: O=c1cc(Nc2nnc(-c3ccc(C(F)(F)F)cc3)o2)ccn1O]

$BBr_3$ (10 equiv.) was added dropwise to a solution of 1-(benzyloxy)-4-((5-(4-(trifluoromethyl)phenyl)-1,3,4-oxadiazol-2-yl)amino)pyridin-2(1H)-one (0.080 mg, 0.411 mmol) in dry DCM (4 mL) under $N_2$ at 0° C. The reaction was stirred at rt for 30 h. Sat. $NaHCO_3$ solution was then poured into the flask to quench $BBr_3$ and the mixture was stirred for 2 h. The crude material was purified using preparative HPLC in a 95% A: 5% B to 100% B solvent system. The TFA and ACN were removed through rotary evaporation and $H_2O$ through freeze-drying, providing the title compound as a white solid (0.015 g, 29.0% yield). $^1$H NMR (400 MHz, DMSO-$d_6$) δ 11.17 (s, 1H), 8.11 (d, J=8.1 Hz, 2H), 7.97 (d, J=8.3 Hz, 2H), 7.85 (d, J=7.7 Hz, 1H), 6.87 (d, J=2.8 Hz, 1H), 6.33 (dd, J=7.7, 2.9 Hz, 1H). LCMS $R_f$ (min)=6.009. HRMS (ESI) calcd for $C_{14}H_{10}F_3N_4O_3^+$ $[M+H]^+$ 339.0700, found 339.0697.

8. 5-((5-[4-(Trifluoromethyl)phenyl]-1,3-oxazol-2-yl)amino)-N-hydroxy-pyridine-2-carboximidamide (Scheme 6)

Scheme 6

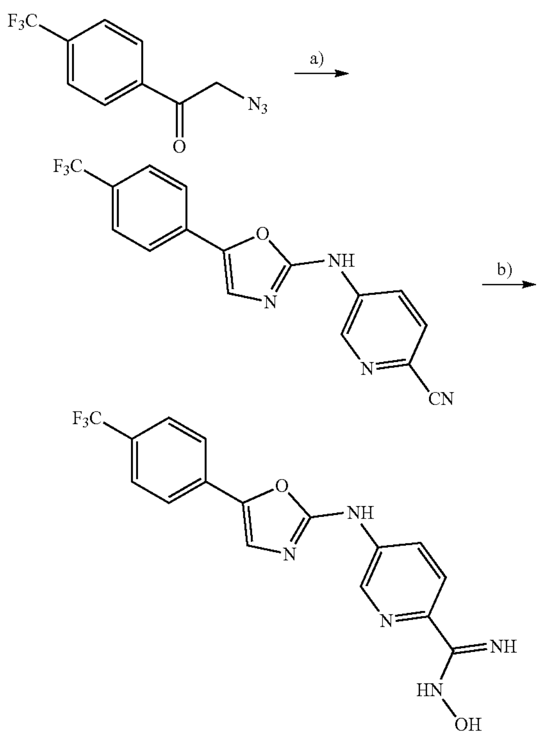

a) $PPh_3$, 5-isothiocyanatopicolinonitrile, 1,4-dioxane, 95° C., 20 min; b) $HONH_2$•HCl, $Et_3N$, EtOH, reflux, 4 h.

(Intermediate C—5-((5-(4-(trifluoromethyl)phenyl)oxazol-2-yl)amino)picolinonitrile) To the solution of 2-azido-1-(4-(trifluoromethyl)phenyl)ethan-1-one in dry 1,4-dioxane (Intermediate A) (10 mL) was added 5-isothiocyanatopicolinonitrile (1.15 equiv.) and $PPh_3$ (1.15 equiv.) and the mixture heated at 95° C. for 20 min. Upon completion, the reaction mixture was concentrated under reduced pressure. The crude residue was chromatographed on silica gel eluting with 30% EtOAc in toluene to give 5-((5(4-(trifluoromethyl)phenyl)oxazol-2-yl)amino)picolinonitrile as a yellow crystalline solid (0.380 g, 66.9% yield). $^1H$ NMR (400 MHz, DMSO-$d_6$) δ 11.42 (s, 1H), 8.86 (d, J=2.2 Hz, 1H), 8.34 (dd, J=8.7, 2.7 Hz, 1H), 8.01 (d, J=8.6 Hz, 1H), 7.83 (br s, 4H), 7.82 (s, 1H). $^{13}C$ NMR (101 MHz, DMSO-$d_6$) δ 164.6, 150.1, 132.4, 129.2, 121.2, 120.6. LCMS $R_f$ (min)=6.079, MS m/z=329.1 $[M-H]^-$.

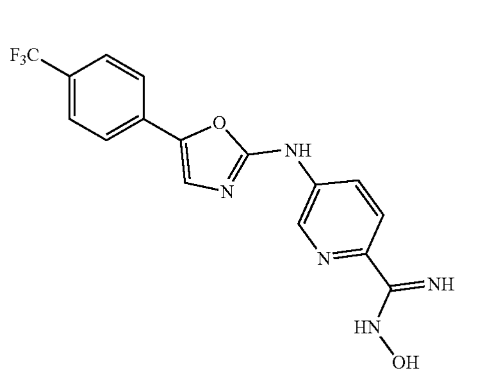 [SMILES: N=C(NO)c1ccc(Nc2ncc(-c3ccc(C(F)(F)F)cc3)o2)cn1]

$Et_3N$ (2.5 equiv.) was added to a solution of 5-((5-(4-(trifluoromethyl)phenyl)oxazol-2-yl)amino)picolinonitrile (0.080 g, 0.242 mmol) and $NH_2OH{\cdot}HCl$ (2.5 equiv.) in EtOH (10 mL) and the mixture heated at reflux for 4 h. On reaction completion, the solution was diluted with EtOAc (30 mL) and washed with $H_2O$ (3×15 mL). The aq. layers were then collected and back extracted with EtOAc (3×15 mL). The combined organic layers were dried over $MgSO_4$ and concentrated to a yellow solid. The crude product was then redissolved and recrystallized in EtOH, providing the title compound as a yellow crystalline solid (0.036 g, 40.9% yield). $^1H$ NMR (400 MHz, DMSO-$d_6$) δ 10.89 (s, 1H), 9.74 (s, 1H), 8.78 (d, J=2.2 Hz, 1H), 8.13 (dd, J=8.8, 2.6 Hz, 1H), 7.84 (d, J=8.7 Hz, 1H), 7.80 (s, 4H), 7.76 (s, 1H), 5.76 (s, 2H). LCMS $R_f$ (min)=5.935. HRMS (ESI) calcd for $C_{16}H_{13}F_3N_5O_2^+$ $[M+H]^+$ 364.1025, found 364.1016.

9. 5-([4-(4-Chlorophenyl)-1,3-thiazol-2-yl]amino)-N-hydroxypyrimidine-2-carboxamide (Scheme 7)

Scheme 7

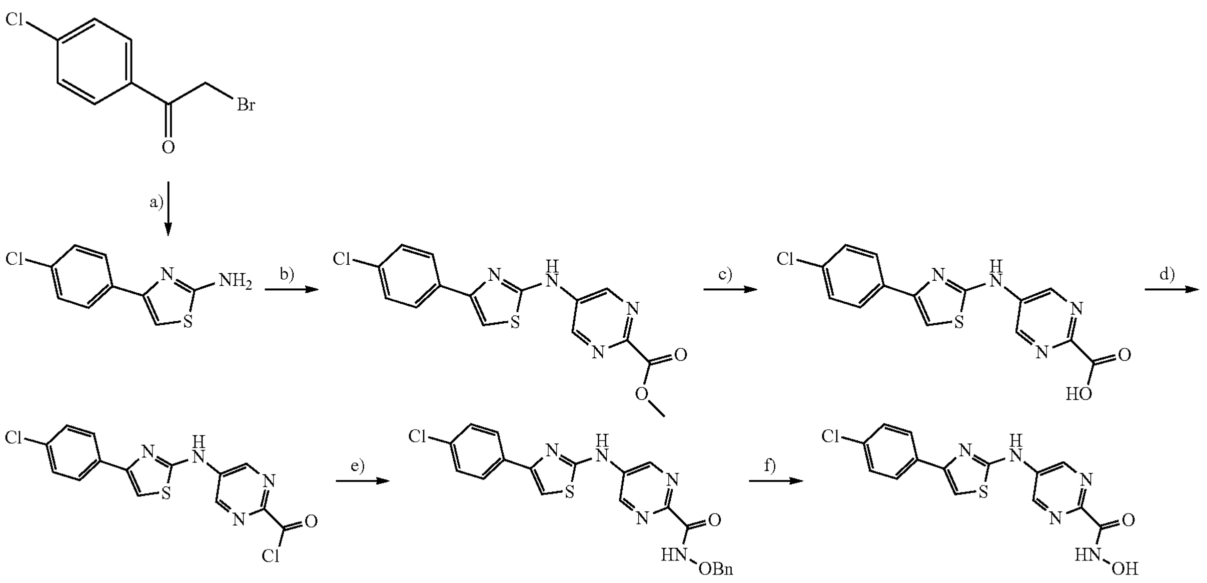

a) Thiourea, acetonitrile, reflux overnight; b) methyl 5-bromopyrimidine-2-carboxylate, $K_3PO_4$, $Pd_2(dba)_3$, Xantphos, $H_2O$, 1,4-dioxane, 140° C., 16 h; c) $LiOH{\cdot}H_2O$, 1,4-dioxane: EtOH: $H_2O$ (2:2:1.5), reflux, 3 h; d) Oxayl chloride, DCM: DMF, 0° C. to rt, 3 h; e) O-benzyl hydroxylamine•HCl, DIPEA, DCM, rt, 16 h; f) $BBr_3$ 1.0M in heptane, DCM, 0° C.

Thiourea (6.841 g, 89.871 mmol) was added to solution of 2-bromo-1-(4-chlorophenyl)ethan-1-one (2.000 g, 7.489 mmol) in acetonitrile (50 mL) and the mixture heated to reflux for 16 h. On cooling, the mixture was concentrated under vacuum. The mixture was then washed with $H_2O$ (10 mL) and DCM (5 mL) to afford 4-(4-chlorophenyl)thiazol-2-amine as a pale yellow solid. $^1H$ NMR (401 MHz, DMSO-$d_6$) δ 7.83-7.77 (m, 2H), 7.45-7.36 (m, 2H), 7.08 (s, 2H), 7.03 (s, 1H). $^{13}C$ NMR (101 MHz, DMSO-$d_6$) δ 168.44, 148.65, 133.78, 131.62, 128.53, 127.28, 102.38. LCMS $R_f$ (min)=3.112, MS m/z=210.9 $[M+H]^+$.

A re-sealable Schlenk tube was charged with $Pd_2(dba)_3$ (0.02 equiv.), Xantphos (0.06 equiv.), 5-(4-chlorophenyl)thiazol-2-amine (1.2 equiv.), $K_3PO_4$ (fine powder, 1.4 equiv.), methyl 5-bromopyrimidine-2-carboxylate (0.150 g, 0.691 mmol) and 1,4-dioxane (4 mL). After the mixture was degassed and carefully subjected to three cycles of evacuation and backfilling with $N_2$, $H_2O$ (1.0 mmol) was added dropwise. This was then sealed and immersed in a 140° C. oil bath. After 15 h, the mixture was cooled and filtered. The precipitate was washed with $H_2O$ (5 mL) and DCM (2 mL), providing methyl 5-((4-(4-chlorophenyl)thiazol-2-yl)amino) pyrimidine-2-carboxylate as a grey solid (0.13 g, 54.2% yield). $^1H$ NMR (401 MHz, DMSO) δ 9.32 (s, 2H), 8.18-7.91 (m, 2H), 7.61 (s, 1H), 7.53-7.43 (m, 2H), 3.88 (s, 3H). $^{13}C$ NMR (101 MHz, DMSO-$d_6$) δ 163.19, 155.43, 148.43, 144.37, 144.35, 137.93, 135.93, 134.84, 128.11, 127.79, 125.72, 125.57, 122.90, 52.49. LCMS $R_f$ (min)=3.646, MS m/z=344.8 $[M-H]^-$.

LiOH·$H_2O$ (3 equiv.) in $H_2O$ (1.5 mL) was added to a solution of methyl 5-((4-(4-chlorophenyl)thiazol-2-yl) amino)pyrimidine-2-carboxylate (0.200 g, 0.577 mmol) in 1,4-dioxane (2 mL) and EtOH (2 mL) and the mixture refluxed for 3 h. Volatiles were removed in vacuo and to the suspension was added brine (3 mL), followed by 6M HCl (2 mL) dropwise at 0° C. The resulting precipitate was filtered and washed with $H_2O$ (3 mL), providing 5-((4-(4-chlorophenyl)thiazol-2-yl)amino)pyrimidine-2-carboxylic acid as a yellow solid (0.180 g, 93% yield). $^1H$ NMR (400 MHz, DMSO-$d_6$) δ 11.14 (s, 1H), 9.32 (s, 2H), 7.99 (d, J=8.4 Hz, 2H), 7.63 (s, 1H), 7.52 (d, J=8.4 Hz, 2H). $^{13}C$ NMR (101 MHz, DMSO-$d_6$) δ 164.70, 162.20, 149.48, 144.77, 137.53, 133.34, 132.79, 129.29, 127.95, 106.81.

Oxalyl chloride (2.5 equiv.) was added dropwise to a solution of 5-((4-(4-chlorophenyl)thiazol-2-yl)amino)pyrimidine-2-carboxylic acid (0.100 g, 0.301 mmol) in dry DCM (2 mL) and dry DMF (1 drop) at 0° C. and the mixture stirred at rt for 3 h. The solvent was removed in vacuo and the residue redissolved in dry DCM. O-benzylhydroxylamine hydrochloride (5 equiv.) and DIPEA (5 equiv.) were added and the mixture stirred at rt for a further 16 h. Upon completion, all the volatiles were removed under reduced pressure. $H_2O$ (2 mL) was then added. The resulting precipitate was filtered and washed with DCM (2 mL), $H_2O$ (1 mL) and $Et_{20}$ (1 mL) to give N-(benzyloxy)-5-((4-(4-chlorophenyl)thiazol-2-yl)amino)pyrimidine-2-carboxamide as a pale yellow solid (0.062 g, 90.4% yield). $^1H$ NMR (401 MHz, DMSO) δ 12.06 (s, 1H), 11.11 (s, 1H), 9.31 (s, 2H), 7.98 (d, J=8.6 Hz, 2H), 7.64 (s, 1H), 7.54 (d, J=8.6 Hz, 2H), 7.49 (d, J=6.9 Hz, 2H), 7.43-7.36 (m, 3H), 4.95 (s, 2H). LCMS $R_f$ (min)=3.646, MS m/z=435.8 $[M-H]^-$. The crude material was used in the next step without further purification.

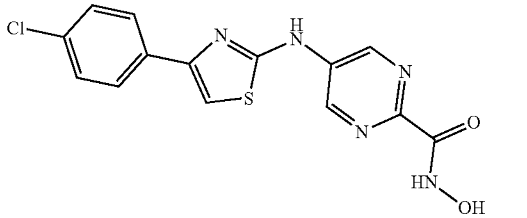 [SMILES: O=C(NO)c1ncc(Nc2nc(-c3ccc(Cl)cc3)cs2)cn1]

$BBr_3$ 1.0 M in heptane (3 equiv.) was added dropwise to a solution of N-(benzyloxy)-5-([4-(4-chlorophenyl)-1,3-thiazol-2-yl]amino)pyrimidine-2-carboxamide (0.060 g, 0.132 mmol) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The crude material was purified using preparative HPLC in 95% A:5% B to 100% B solvent system. The TFA and ACN were removed through rotary evaporation and $H_2O$ through freeze-drying, providing the title compound as a white solid (0.015 g, 31.2% yield). $^1H$ NMR (400 MHz, DMSO-$d_6$) δ 11.04 (s, 1H), 9.28 (s, 2H), 9.12 (s, 1H), 7.97 (d, J=8.6 Hz, 2H), 7.61 (s, 1H), 7.52 (d, J=8.6 Hz, 2H). LCMS $R_f$ (min)=3.236. HRMS (ESI) calcd for $C_{14}H_{11}ClN_5O_2S^+$ $[M+H]^+$ 348.0311, found 348.0366.

10. N-Hydroxy-6-((5-[4-(trifluoromethyl)phenyl]-1,3-oxazol-2-yl)amino)pyrimidine-3-carboxamide (Scheme 8)

Scheme 8

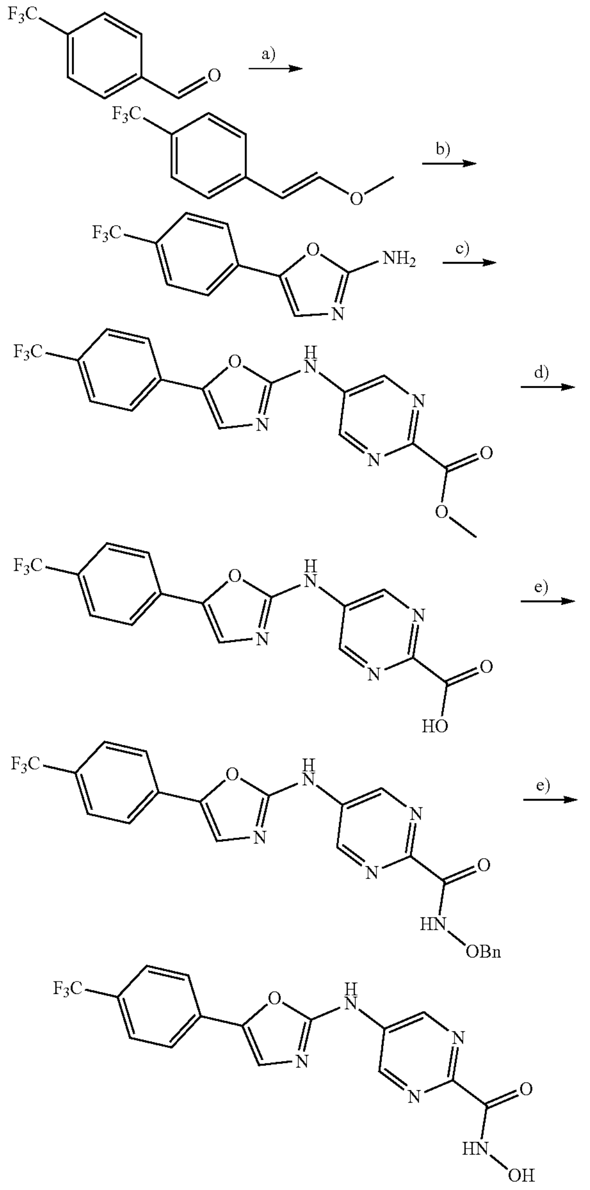

a) i. (methoxymethyl)triphenylphosphonium chloride, n-BuLi, THF, 0° C., 1 h; ii. THF, rt, 16 h; b) i. NBS, 1,4-dioxane:$H_2O$ (1:1), rt, 1 h, ii. urea, 1,4-dioxane: $H_2O$ (1:1), 70° C., 16 h; c) methyl 5-bromopyrimidine-2-carboxylate, $K_2PO_4$, $Pd_2(dba)_3$, Xantphos, $H_2O$, 1,4-dioxane, 140° C., 16 h; d) LiOH•$H_2O$, 1,4-dioxane: EtOH:$H_2O$ (2:2:1), reflux, 3 h; e) O-benzyl hydroxyamine•HCl, HOBt, EDCI•HCl, DMF, rt, 16 h; f) $BBr_3$ 1.0M in heptane, DCM, 0° C.~rt, 2 h.

n-BuLi (2.17 M in cyclohexane) (1.2 equiv.) was added dropwise to a solution of (methoxymethyl)triphenylphosphonium chloride (1.2 equiv.) in dry THF (15 mL) at 0° C.

and the mixture stirred at this temperature for 1 h. 4-(trifluoromethyl)benzaldehyde (3.930 mL, 28.716 mmol) was then added and the mixture stirred at rt for 16 h. The mixture was quenched with $H_2O$ (3 mL) and extracted with EtOAc (2×20 mL). The combined organic layers were then dried over $MgSO_4$ and concentrated to yellow liquid. Crude material was chromatographed on silica gel eluting with 100% hexanes providing (E)-1-(2-methoxyvinyl)-4-(trifluoromethyl)benzene as a colourless liquid (5.430 g, 77.9% yield). $^1H$ NMR (400 MHz, $CDCl_3$) δ 7.65 (d, J=8.2 Hz, 2H), 7.51 (d, J=8.3 Hz, 2H), 6.24 (d, J=7.0 Hz, 1H), 5.25 (d, J=7.0 Hz, 1H), 3.82 (s, 3H).

(Intermediate D synthesis—5-(4-(trifluoromethyl)phenyl)oxazol-2-amine) NBS (1.1 equiv.) was added to solution of (E)-1-trifluoromethyl-4-(2-methoxyvinyl)benzene (5.000 g, 24.730 mmol) in $H_2O$ (25 mL) and 1,4-dioxane (25 mL) at 0° C. and the mixture stirred at rt for 1 h. Urea (1 equiv.) was then added and the mixture heated at 70° C. for 16 h. On cooling, volatiles were removed under reduced pressure and the mixture was quenched with sat. $NaHCO_3$ (aq.). The precipitate was then filtered and washed with $H_2O$ (20 mL) and DCM (10 mL) to afford 5-(4-(trifluoromethyl)phenyl)oxazol-2-amine as a white solid (3.200 g, 56.7% yield). $^1H$ NMR (401 MHz, $CDCl_3$) δ 7.71 (d, J=8.4 Hz, 2H), 7.63 (d, J=8.2 Hz, 2H), 7.42 (s, 1H), 7.06 (s, 2H). LCMS $R_f$ (min)=3.331, MS m/z=228.9 $[M+H]^+$.

A re-sealable Schlenk tube was charged with $Pd_2(dba)_3$ (0.02 equiv.), Xantphos (0.06 equiv.), 5-(4-(trifluoromethyl)phenyl)oxazol-2-amine (Intermediate D) (1.2 equiv.), $K_3PO_4$ (fine powder, 1.4 equiv.), methyl 5-bromopyrimidine-2-carboxylate (0.250 g, 1.152 mmol) and 1,4-dioxane (4 mL). After the mixture was degassed and carefully subjected to three cycles of evacuation and backfilling with $N_2$, $H_2O$ (0.021 g, 1.0 mmol) was added dropwise. This was then sealed and immersed in a 140° C. oil bath. After 15 h, the mixture was cooled, diluted with EtOAc (20 mL) and washed with $H_2O$ (15 mL). The aq. layers were then back extracted with EtOAc (2×15 mL). The crude product was concentrated under reduced pressure and chromatographed on a $SiO_2$ column (EtOAc:toluene=1:1) to give methyl 5-((5-(4-(trifluoromethyl)phenyl)oxazol-2-yl)amino)pyrimidine-2-carboxylate as a white solid (0.21 g, 50.0% yield). $^1H$ NMR (400 MHz, DMSO-$d_6$) δ 9.05 (s, 2H), 7.77 (s, 4H), 7.75 (s, 1H), 3.85 (s, 3H). $^{13}C$ NMR (101 MHz, DMSO-$d_6$) δ 163.29, 147.65, 144.76, 143.29, 131.51, 126.06, 126.03, 125.43, 123.02, 52.37. LCMS $R_f$ (min)=3.523, MS m/z=364.8 $[M+H]^+$.

LiOH·$H_2O$ (3 equiv.) in $H_2O$ (1 mL) was added to a solution of methyl 5-((5-(4-(trifluoromethyl)phenyl)oxazol-2-yl)amino)pyrimidine-2-carboxylate (0.125 g, 0.343 mmol) in 1,4-dioxane (1.5 mL) and EtOH (1.5 mL) and the mixture refluxed for 3 h. Volatiles were removed in vacuo and to the suspension was added brine (2 mL), followed by 6M HCl (2 mL) dropwise at 0° C. The resulting precipitate was filtered and washed with $H_2O$ (2 mL), providing 5-((5-(4-(trifluoromethyl)phenyl)oxazol-2-yl)amino)pyrimidine-2-carboxylic acid as a yellow solid (0.120 g, 99.8% yield). $^1H$ NMR (400 MHz, DMSO-$d_6$) δ 11.37 (s, 1H), 9.16 (s, 2H), 7.83 (s, 5H). LCMS $R_f$ (min)=3.660. $^{13}C$ NMR (101 MHz, DMSO-$d_6$) δ 164.21, 155.68, 149.71, 144.45, 143.78, 135.52, 131.30, 127.48, 127.16, 126.11, 126.07, 125.52, 125.21, 123.21, 122.82. MS m/z=350.8 $[M+H]^+$.

A solution of 5-((5-(4-(trifluoromethyl)phenyl)oxazol-2-yl)amino)pyrimidine-2-carboxylic acid (0.100 g, 0.286 mmol), anhydrous HOBt (1.2 equiv.) and EDCI·HCl (1.3 equiv.) in dry DMF (2 mL) was stirred at rt for 2 h. O-Benzylhydroxylamine hydrochloride (5 equiv.) and $Et_3N$ (5 equiv.) were then added and the mixture stirred at rt for a further 16 h. DMF was removed in vacuo, washing with toluene (3×2 mL) to aid this process. $H_2O$ (2 mL) was then added and the mixture left to stir at rt for 10 min. The resulting precipitate was filtered and washed with $H_2O$ (1 mL) and hexanes (2 mL), providing N-(benzyloxy)-5-((5-(4-(trifluoromethyl)phenyl)oxazol-2-yl)amino)pyrimidine-2-carboxamide as a brown solid (0.080 g, 61.7% yield). $^1H$ NMR (401 MHz, DMSO-$d_6$) δ 12.05 (s, 1H), 9.15 (s, 2H), 7.83 (s, 5H), 7.62-7.20 (m, 5H), 4.94 (s, 2H). LCMS $R_f$ (min)=3.551, MS m/z=455.8 $[M+H]^+$.

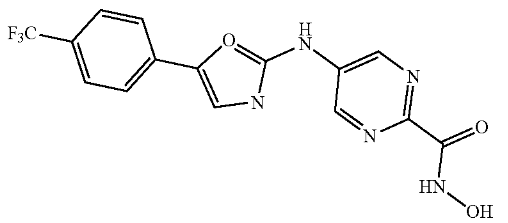

$BBr_3$ 1.0 M in heptane (3 equiv.) was added dropwise to a solution of N-(benzyloxy)-5-((5-(4-(trifluoromethyl)phenyl)oxazol-2-yl)amino)pyrimidine-2-carboxamide (0.060 g, 0.132 mmol) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The crude material was purified using preparative HPLC in a 95% A:5% B to 100% B solvent system. The TFA and ACN were removed through rotary evaporation and $H_2O$ through freeze-drying, providing the title compound as a white solid (0.023 g, 47.9% yield). $^1H$ NMR (400 MHz, DMSO-$d_6$) δ 11.42 (s, 1H), 9.13 (s, 1H), 9.13 (s, 2H), 7.83 (s, 4H), 7.82 (s, 1H). $^{13}C$ NMR (101 MHz, DMSO-$d_6$) δ 160.40, 156.27, 151.38, 144.86, 144.15, 135.68, 131.80, 127.60, 126.61, 126.01, 125.76, 123.65, 123.31, 40.63, 40.42. LCMS $R_f$ (min)=5.513 HRMS (ESI) calcd for $C_{15}H_{11}F_3N_5O_3^+$ $[M+H]^+$ 366.0809, found 366.0807.

11. N-Hydroxy-6-((5-[4-(trifluoromethyl)phenyl]-1,3-oxazol-2-yl)amino)pyridazine-3-carboxamide (Scheme 9)

Scheme 9

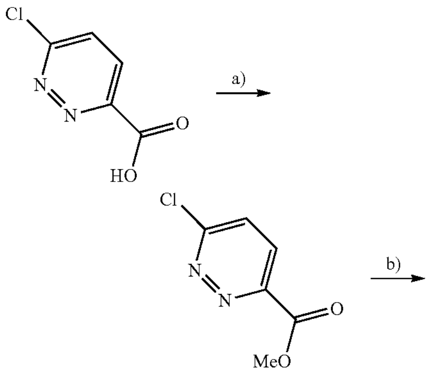

-continued

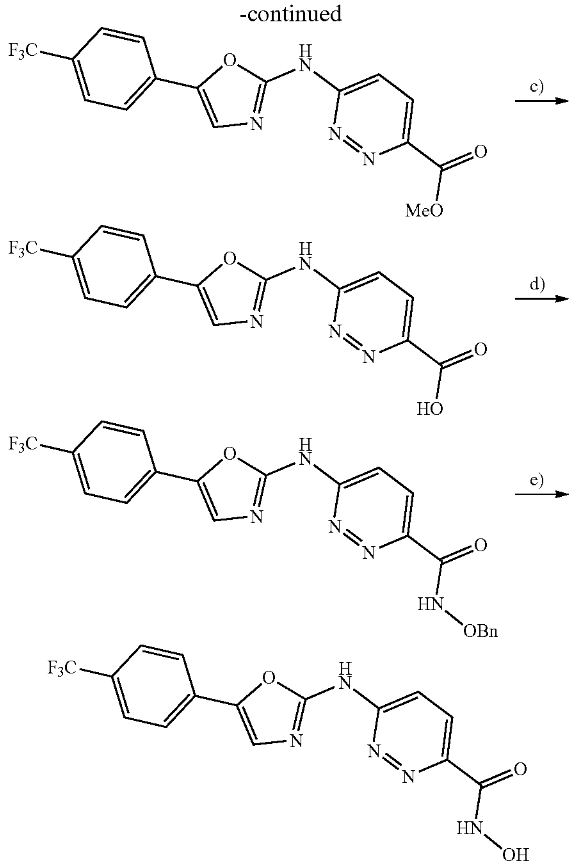

a) i. oxalyl chloride, DMF, DCM, 0° C. to rt, 1 h; ii. MeOH, DCM, rt, 1 h; b) 5-(4-(trifluoromethyl)phenyl)oxazol-2-amine, $K_3PO_4$, $Pd_2(dba)_3$, Xantphos, $H_2O$, 1,4-dioxane, 140° C., 15 h; c) $LiOH•H_2O$, 1,4-dioxane: EtOH: $H_2O$ (2:2:1.5), reflux, 3 h; d) O-benzyl hydroxylamine•HCl, HOBt, EDCI•HCl, $Et_3N$, DMF, rt, 16 h; e) $BBr_3$ 1.0M in heptane, DCMm 0° C.~rt, 2 h.

Oxalyl chloride (1 equiv.) was added dropwise to a solution of 6-chloro-3-pyridazinecarboxylic acid (1.000 g, 6.308 mmol) in dry DCM (30 mL) and dry DMF (1 drop) at 0° C. and the mixture stirred at this temperature for 1 h. The solvent was removed in vacuo and the residue redissolved in dry DCM. MeOH (1 equiv.) were added and the mixture stirred at rt for a further 1 h. The mixture was quenched with $H_2O$ (20 mL) and extracted with DCM (2x20 mL). The combined organic layers were then dried over $MgSO_4$ and concentrated to give methyl 6-chloropyridazine-3-carboxylate as a white solid. (0.960 g, 88.2% yield). $^1H$ NMR (400 MHz, $CDCl_3$) δ 8.17 (d, J=8.8 Hz, 1H), 7.68 (d, J=8.8 Hz, 1H), 4.09 (s, 3H).

A re-sealable Schlenk tube was charged with $Pd_2(dba)_3$ (0.1 equiv.), Xantphos (0.3 equiv.), 5-(4-(trifluoromethyl)phenyl)oxazol-2-amine (Intermediate D) (1.2 equiv.), $K_3PO_4$ (fine powder, 1.4 equiv.), methyl 6-chloropyridazine-3-carboxylate (0.200 g, 1.159 mmol) and 1,4-dioxane (4 mL). After the mixture was degassed and carefully subjected to three cycles of evacuation and backfilling with $N_2$, $H_2O$ (1.0 mmol) was added dropwise. This was then sealed and immersed in a 140° C. oil bath. After 15 h, the mixture was cooled, diluted with EtOAc (20 mL) and washed with $H_2O$ (15 mL). The aq. layers were then back extracted with EtOAc (2x15 mL). The crude product was concentrated under reduced pressure and chromatographed on a $SiO_2$ column (EtOAc:toluene=1:1) to give methyl 6-((5-(4-(trifluoromethyl)phenyl)oxazol-2-yl)amino)pyridazine-3-carboxylate as a white solid (0.28 g, 66.3% yield). $^1H$ NMR (400 MHz, DMSO-$d_6$) δ 8.33 (d, J=9.5 Hz, 1H), 8.05 (d, J=9.4 Hz, 1H), 7.79 (s, 4H), 7.75 (s, 1H), 3.90 (s, 3H). LCMS $R_f$ (min)=3.907, MS m/z=364.8 $[M+H]^+$.

$LiOH·H_2O$ (3 equiv.) in $H_2O$ (1.5 mL) was added to a solution of methyl 6-((5-[4-(trifluoromethyl)phenyl]-1,3-oxazol-2-yl)amino)pyridazine-3-carboxylate (0.140 g, 0.384 mmol) in 1,4-dioxane (2 mL) and EtOH (2 mL) and the mixture refluxed for 3 h. Volatiles were removed in vacuo and to the suspension was added brine (2 mL), followed by 6M HCl (2 mL) dropwise at 0° C. The resulting precipitate was filtered and washed with $H_2O$ (2 mL), providing 6-((5-(4-(trifluoromethyl)phenyl)oxazol-2-yl)amino)pyridazine-3-carboxylic acid as a yellow solid (0.130 g, 96.6% yield). $^1H$ NMR (400 MHz, DMSO-$d_6$) δ 8.44 (s, 1H), 8.20 (s, 1H), 7.84 (s, 5H). LCMS $R_f$ (min)=3.797, MS m/z=350.8 $[M-H]^-$.

A solution of 6-((5-[4-(trifluoromethyl)phenyl]-1,3-oxazol-2-yl)amino)pyridazine-3-carboxylic acid (0.080 g, 0.228 mmol), anhydrous HOBt (1.1 equiv.) and EDCI·HCl (1.3 equiv.) in dry DMF (2 mL) was stirred at rt for 2 h. After this time, O-benzylhydroxylamine hydrochloride (5 equiv.) and $Et_3N$ (5 equiv.) were added and the mixture stirred at rt for a further 16 h. DMF was removed in vacuo, washing with toluene (2 mLx3) to aid this process. $H_2O$ (2 mL) was then added and the mixture left to stir at rt for 10 min. The resulting precipitate was filtered and washed with $H_2O$ (1 mL) and hexanes (2 mL), providing N-(benzyloxy)-6-((5-(4-(trifluoromethyl)phenyl)oxazol-2-yl)amino)pyridazine-3-carboxamide as a brown solid (0.090 g, 86.5% yield). $^1H$ NMR (400 MHz, DMSO-$d_6$) δ 12.35 (s, 1H), 8.49 (s, 1H), 8.18 (s, 2H), 7.85 (s, 4H), 7.60-7.14 (m, 5H), 4.98 (s, 2H). $^{13}C$ NMR (101 MHz, DMSO-$d_6$) δ 160.71, 144.42, 136.27, 131.78, 129.27, 128.75, 128.29, 128.03, 126.58, 125.99, 125.40, 123.76, 123.29, 77.61. LCMS $R_f$ (min)=3.879, MS m/z=455.8 $[M+H]^+$.

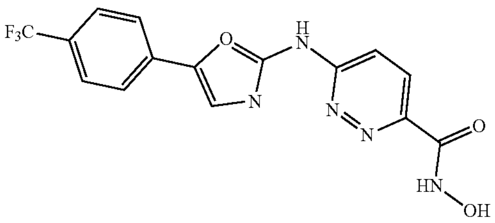

$BBr_3$ 1.0 M in heptane (3 equiv.) was added dropwise to a solution of N-(benzyloxy)-6-((5-[4-(trifluoromethyl)phenyl]-1,3-oxazol-2-yl)amino)pyridazine-3-carboxamide (0.090 g, 0.198 mmol) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The crude material was purified using preparative HPLC in a 95% A:5% B to 100% B solvent system. The TFA and ACN were removed through rotary evaporation and $H_2O$ through freeze-drying, providing the title compound as a white solid (0.031 g, 42.9% yield). $^1H$ NMR (400 MHz, DMSO-$d_6$) δ 12.09 (s, 1H), 11.69 (s, 1H), 8.48 (s, 1H), 8.14 (d, J=9.0 Hz, 1H), 7.84 (m, 4H), 7.84 (s, 1H). $^{13}C$ NMR (101 MHz, DMSO-$d_6$) δ 160.59, 156.64, 144.35, 131.79, 128.16, 128.01, 127.69, 126.55, 126.00, 125.34, 123.76, 123.30. LCMS $R_f$ (min)=5.501. HRMS (ESI) calcd for $C_{15}H_{11}F_3N_5O_3^+$ $[M+H]^+$ 366.0811, found 366.0809.

12. N-Hydroxy-5-((4-[4-(trifluoromethyl)phenyl]-1,3-oxazol-2-yl)amino)pyrimidine-2-carboxamide (Scheme 10)

Scheme 10

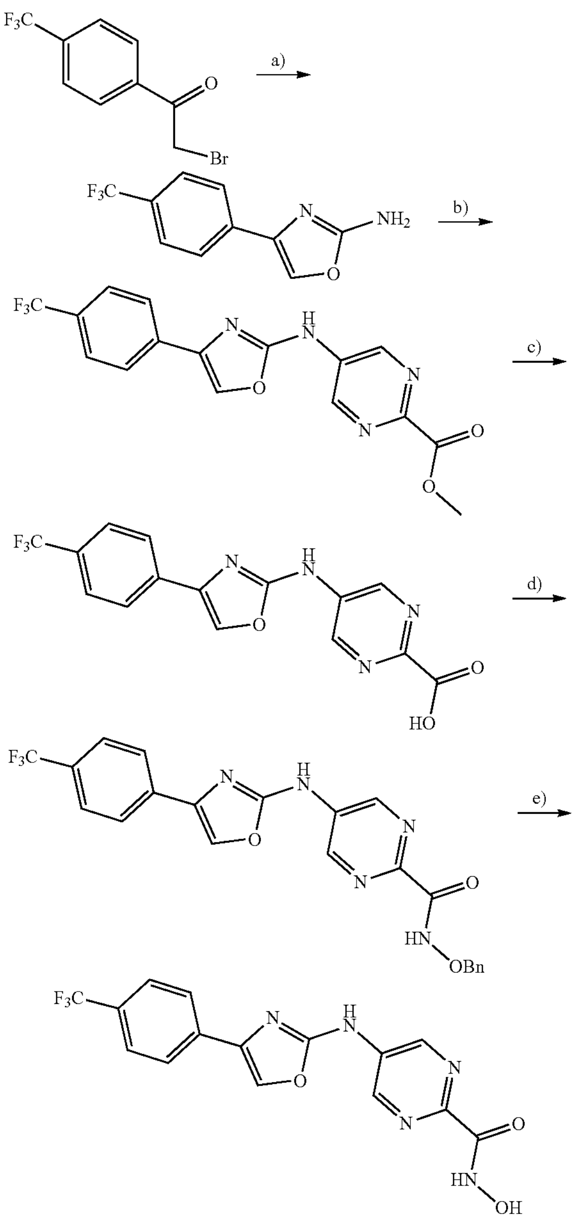

a) Urea, ACN, reflux, 16 h: b) methyl 5-bromopyrimidine-2-carboxylate, $K_3PO_4$, $Pd(dba)_3$, Xantphos, $H_2O$, 1,4-dioxane, 140° C., 16 h; c) $LiOH•H_2O$, 1,4-dioxane: EtOH: $H_2O$ (2:2:1.5), 100° C., 5 h; d) O-benzyl hydroxylamine•HCl, HOBt, EDCI•HCl, $Et_3N$, DMF, rt, 16 h; e) $BBr_3$ 1.0M in heptane, DCM,0° C.~rt, 2 h.

(Intermediate E synthesis—4-(4-(trifluoromethyl)phenyl) oxazol-2-amine) Urea (12 equiv.) was added to solution of 2-bromo-1-(4-(trifluoromethyl)phenyl)ethan-1-one (3.000 g, 11.234 mmol) in ACN (30 mL) and the mixture heated to reflux for 16 h. On cooling, the mixture was concentrated under vacuum. The mixture was then filtered with $H_2O$ (10 mL) and washed with DCM (5 mL) to afford 4-(4-(trifluoromethyl)phenyl)oxazol-2-amine as a pale yellow solid (2.200 g, 85.8% yield). $^1H$ NMR (400 MHz, $CDCl_3$) δ 7.73 (d, J=8.2 Hz, 2H), 7.63 (d, J=8.3 Hz, 2H), 7.53 (s, 1H), 5.09 (s, 2H). LCMS $R_f$ (min)=3.359, MS m/z=228.9 $[M+H]^+$.

A re-sealable Schlenk tube was charged with $Pd_2(dba)_3$ (0.02 equiv.), Xantphos (0.06 equiv.), (4-[4-(trifluoromethyl)phenyl]-1,3-oxazol-2-yl)amine (1.2 equiv.), $K_3PO_4$ (fine powder, 1.4 equiv.), methyl 5-bromopyrimidine-2-carboxylate (0.150 g, 0.691 mmol) and 1,4-dioxane (4 mL). After the mixture was degassed and carefully subjected to three cycles of evacuation and backfilling with $N_2$, $H_2O$ (1.0 mmol) was added dropwise. This was then sealed and immersed in a 140° C. oil bath. After 15 h, the mixture was cooled, diluted with EtOAc (20 mL) and washed with $H_2O$ (15 mL). The aq. layers were then back extracted with EtOAc (2×15 mL). The crude product was concentrated under reduced pressure and chromatographed on a $SiO_2$ column (EtOAc:toluene=1:1) to give methyl 5-((4-(4-(trifluoromethyl)phenyl)oxazol-2-yl)amino)pyrimidine-2-carboxylate as a white solid (0.18 g, 71.5% yield). $^1H$ NMR (400 MHz, DMSO-$d_6$) δ 11.29 (s, 1H), 9.26 (s, 2H), 8.49 (s, 1H), 8.04 (d, J=8.1 Hz, 2H), 7.81 (d, J=8.2 Hz, 2H), 3.89 (s, 3H). $^{13}C$ NMR (101 MHz, DMSO-$d_6$) δ 163.19, 155.43, 148.43, 144.37, 144.35, 137.93, 135.93, 134.84, 128.11, 127.79, 125.72, 125.57, 122.90, 52.49. LCMS $R_f$ (min) =3.517, MS m/z=364.8 $[M+H]^+$.

$LiOH·H_2O$ (3 equiv.) in $H_2O$ (1 mL) was added to a solution of methyl 5-((4-(4-(trifluoromethyl)phenyl)oxazol-2-yl)amino)pyrimidine-2-carboxylate (0.160 g, 0.439 mmol) in 1,4-dioxane (1.5 mL) and EtOH (1.5 mL) and the mixture refluxed for 3 h. Volatiles were removed in vacuo and to the suspension was added brine (2 mL), followed by 6M HCl (2 mL) dropwise at 0° C. The resulting precipitate was filtered and washed with $H_2O$ (2 mL), providing 5-((4-(4-(trifluoromethyl)phenyl)oxazol-2-yl)amino)pyrimidine-2-carboxylic acid as a yellow solid (0.150 g, 97.0% yield). $^1H$ NMR (400 MHz, DMSO-$d_6$) δ 11.26 (s, 1H), 9.27 (s, 2H), 8.50 (s, 2H), 8.04 (d, J=8.1 Hz, 2H), 7.81 (d, J=8.2 Hz, 2H). $^{13}C$ NMR (101 MHz, DMSO-$d_6$) δ 164.87, 155.92, 139.61, 138.92, 138.45, 137.90, 135.03, 125.93, 125.67, 125.53, 122.50, 64.11, 52.06, 52.04. LCMS $R_f$ (min)=3.811, MS m/z=348.9 $[M-H]^-$.

A solution of 5-((4-(4-(trifluoromethyl)phenyl)oxazol-2-yl)amino)pyrimidine-2-carboxylic acid (0.100 g, 0.286 mmol), anhydrous HOBt (1.2 equiv.) and EDCI·HCl (1.3 equiv.) in dry DMF (2 mL) was stirred at rt for 2 h. After this time, O-benzylhydroxylamine hydrochloride (5 equiv.) and $Et_3N$ (5 equiv.) were added and the mixture stirred at rt for a further 16 h. DMF was removed in vacuo, washing with toluene (2 mL×3) to aid this process. $H_2O$ (2 mL) was then added and the mixture left to stir at rt for 10 min. The resulting precipitate was filtered and washed with $H_2O$ (1 mL) and hexanes (2 mL), providing N-(benzyloxy)-5-((4-(4-(trifluoromethyl)phenyl)oxazol-2-yl)amino)pyrimidine-2-carboxamide as a brown solid (0.11 g, 84.6% yield). $^1H$ NMR (400 MHz, DMSO-$d_6$) δ 12.05 (s, 1H), 11.19 (s, 1H), 9.25 (s, 2H), 8.50 (s, 1H), 8.02 (d, J=8.1 Hz, 2H), 7.83 (d, J=8.3 Hz, 2H), 7.57-7.30 (m, 5H), 4.95-4.86 (m, 2H). $^{13}C$ NMR (101 MHz, DMSO-$d_6$) δ 159.82, 155.60, 150.06, 144.24, 137.88, 135.84, 135.64, 134.87, 131.15, 128.73, 128.27, 128.24, 128.08, 127.76, 125.71, 125.48, 122.90, 77.02, 45.64, 8.61. LCMS $R_f$ (min)=3.879, MS m/z=455.8 $[M+H]^+$.

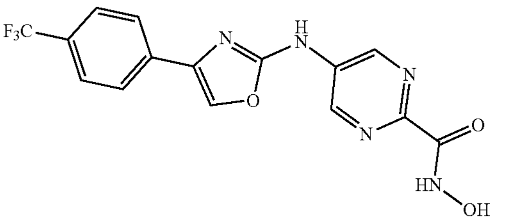

$BBr_3$ 1.0 M in heptane (3 equiv.) was added dropwise to a solution of N-(benzyloxy)-5-((4-(4-(trifluoromethyl)phenyl)oxazol-2-yl)amino)pyrimidine-2-carboxamide (0.110 g, 0.242 mmol) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The crude material was purified using preparative HPLC in a 95% A:5% B to 100% B solvent system. The TFA and ACN were removed through rotary evaporation and $H_2O$ through freeze-drying, providing the title compound as a white solid (0.035 g, 39.7% yield). $^1H$ NMR (400 MHz, DMSO-$d_6$) δ 11.43 (s, 1H), 11.13 (s, 1H), 9.23 (s, 2H), 9.15 (s, 1H), 8.50 (s, 1H), 8.02 (d, J=8.0 Hz, 2H), 7.83 (d, J=8.2 Hz, 2H). $^{13}C$ NMR (101 MHz, DMSO-$d_6$) δ 160.44, 156.18, 151.31, 145.71, 144.76, 138.39, 135.81, 135.41, 131.59, 128.58, 128.26, 126.26, 126.22, 125.99, 123.39. LCMS $R_f$ (min)=5.571. HRMS (ESI) calcd for $C_{15}H_{11}F_3N_5O_3^+$ [M+H]$^+$ 366.0809, found 366.0803.

13. N-Hydroxy-6-((4-(4-(trifluoromethyl)phenyl)oxazol-2-yl)amino)pyridazine-3-carboxamide (Scheme 11)

Scheme 11

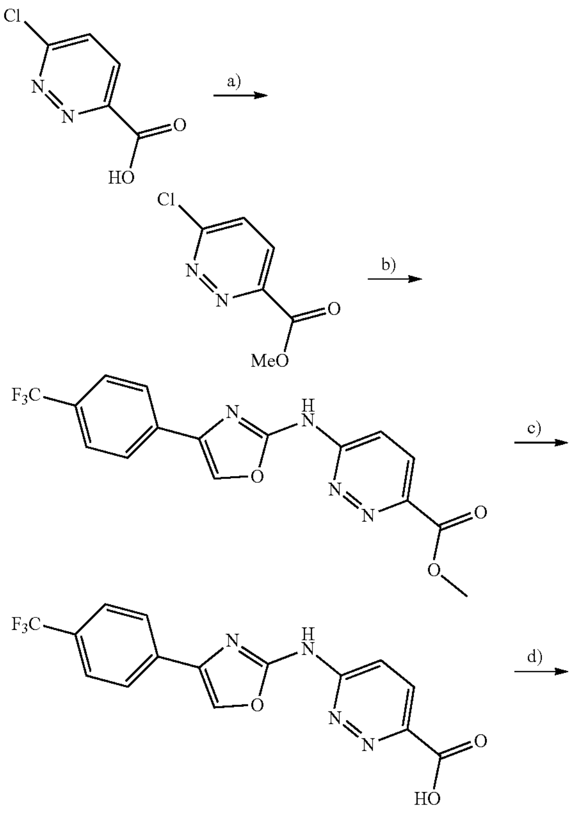

-continued

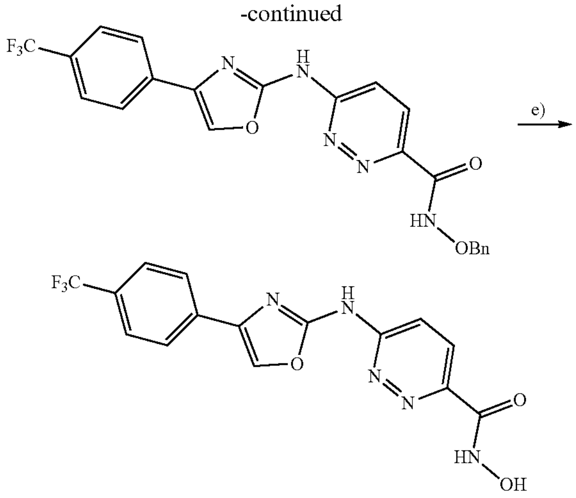

a) oxalyl chloride, DMF, DCM, 0° C. to rt, 1 h; MeOH, DCM, rt, 1 h; b) 4-(4-(trifluoromethyl)phneyl)oxazol-2-amine, $K_3PO_4$, Pd(dba)$_3$, Xantphos, $H_2O$, 1,4-dioxane, 140° C., 16 h; c) LiOH•$H_2O$, 1,4-dioxane: EtOH: $H_2O$ (2:2:1.5), reflux, 3 h; d) O-benzyl hydroxyamine•HCl, HOBt, EDCI•HCl, $Et_3N$, DMF, rt, 16 h; e) $BBr_3$ 1.0M in heptane, DCM, 0° C.~rt, 2 h.

Oxalyl chloride (1 equiv.) was added dropwise to a solution of 6-chloro-3-pyridazinecarboxylic acid (1.000 g, 6.308 mmol) in dry DCM (30 mL) and dry DMF (1 drop) at 0° C. and the mixture stirred at this temperature for 1 h. The solvent was removed in vacuo and the residue redissolved in dry DCM. MeOH (1 equiv.) were added and the mixture stirred at rt for a further 1 h. The mixture was quenched with $H_2O$ (20 mL) and extracted with DCM (2×20 mL). The combined organic layers were then dried over $MgSO_4$ and concentrated to give methyl 6-chloropyridazine-3-carboxylate as a white solid. (0.960 g, 88.2% yield). $^1H$ NMR (400 MHz, $CDCl_3$) δ 8.17 (d, J=8.8 Hz, 1H), 7.68 (d, J=8.8 Hz, 1H), 4.09 (s, 3H).

A re-sealable Schlenk tube was charged with $Pd_2(dba)_3$ (0.02 equiv.), Xantphos (0.06 equiv.), 4-(4-(trifluoromethyl)phenyl)oxazol-2-amine (Intermediate E) (1.2 equiv.), $K_3PO_4$ (fine powder, 1.4 equiv.), methyl 6-chloropyridazine-3-carboxylate (0.250 g, 1.152 mmol) and 1,4-dioxane (4 mL). After the mixture was degassed and carefully subjected to three cycles of evacuation and backfilling with $N_2$, $H_2O$ (1.0 mmol) was added dropwise. This was then sealed and immersed in a 140° C. oil bath. After 15 h, the mixture was cooled, diluted with EtOAc (20 mL) and washed with $H_2O$ (15 mL). The aq. layers were then back extracted with EtOAc (2×15 mL). The crude product was concentrated under reduced pressure and chromatographed on a $SiO_2$ column (EtOAc:toluene=1:1) to give methyl 6-((4-(4-(trifluoromethyl)phenyl)oxazol-2-yl)amino)pyridazine-3-carboxylate as a white solid (0.27 g, 51.2% yield). $^1H$ NMR (400 MHz, DMSO-$d_6$) δ 8.63 (d, J=8.8 Hz, 1H), 8.53 (s, 1H), 8.25 (d, J=9.1 Hz, 1H), 8.03 (d, J=7.9 Hz, 2H), 7.81 (d, J=8.3 Hz, 3H), 3.94 (s, 3H). $^{13}C$ NMR (101 MHz, DMSO-$d_6$) δ 137.86, 134.86, 131.60, 130.00, 128.14, 127.82, 125.69, 125.58, 122.90, 52.57, 39.52. LCMS $R_f$ (min)=3.496, MS m/z=364.8 [M+H]$^+$.

LiOH·$H_2O$ (3 equiv.) in $H_2O$ (2 mL) was added to a solution of methyl 6-((4(4-(trifluoromethyl)phenyl)oxazol-2-yl)amino)pyridazine-3-carboxylate (0.250 g, 0.686 mmol) in 1,4-dioxane (2 mL) and EtOH (2 mL) and the mixture refluxed for 3 h. Volatiles were removed in vacuo and to the suspension was added brine (2 mL), followed by 6M HCl (2 mL) dropwise at 0° C. The resulting precipitate was filtered and washed with $H_2O$ (2 mL), providing 6-((4-(4-(trifluoromethyl)phenyl)oxazol-2-yl)amino)pyridazine-3-carboxylic acid as a yellow solid (0.240 g, 99.8% yield). $^1H$ NMR (400 MHz, DMSO-$d_6$) δ 8.60 (s, 1H), 8.52 (s, 1H), 8.21 (s, 1H), 8.03 (d, J=8.1 Hz, 2H), 7.81 (d, J=8.3 Hz, 2H). $^{13}C$ NMR (101 MHz, DMSO-$d_6$) δ 138.33, 135.38, 131.97, 130.56, 130.40, 128.77, 128.60, 128.28, 127.97, 126.15, 126.12, 126.05, 123.36. LCMS $R_f$ (min)=3.742, MS m/z=350.8 [M+H]$^+$.

A solution of 6-((4-(4-(trifluoromethyl)phenyl)oxazol-2-yl)amino)pyridazine-3-carboxylic acid (0.220 g, 0.628 mmol), anhydrous HOBt (1.2 equiv.) and EDCI·HCl (1.3 equiv.) in dry DMF (3 mL) was stirred at rt for 2 h. After this time, O-benzylhydroxylamine hydrochloride (5 equiv.) and $Et_3N$ (5 equiv.) were added and the mixture stirred at rt for a further 16 h. DMF was removed in vacuo, washing with toluene (2 mL×3) to aid this process. $H_2O$ (2 mL) was then added and the mixture left to stir at rt for 10 min. The resulting precipitate was filtered and washed with $H_2O$ (1 mL) and hexanes (2 mL), providing N-(benzyloxy)-6-((4-(4-(trifluoromethyl)phenyl)oxazol-2-yl)amino)pyridazine-3-carboxamide as a brown solid (0.20 g, 69.9% yield).). $^1H$ NMR (400 MHz, DMSO-$d_6$) δ 12.36 (s, 1H), 8.65 (d, J=8.8 Hz, 1H), 8.54 (s, 1H), 8.19 (d, J=9.4 Hz, 1H), 8.04 (d, J=8.1 Hz, 2H), 7.82 (d, J=8.3 Hz, 2H), 7.54-7.46 (m, 2H), 7.45-7.33 (m, 3H), 4.98 (s, 2H). $^{13}C$ NMR (101 MHz, DMSO-$d_6$) δ 160.71, 144.42, 136.27, 131.78, 129.27, 128.75, 128.29, 128.03, 126.58, 125.99, 125.40, 123.76, 123.29, 77.61. LCMS $R_f$ (min)=3.852, MS m/z=455.8 [M+H]$^+$.

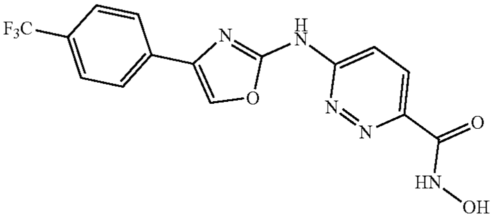 [SMILES: O=C(NO)c1ccc(Nc2nc(-c3ccc(C(F)(F)F)cc3)co2)nn1]

$BBr_3$ 1.0 M in heptane (3 equiv.) was added dropwise to a solution of N-(benzyloxy)-6-((4-(4-(trifluoromethyl)phenyl)oxazol-2-yl)amino)pyridazine-3-carboxamide (0.180 g, 0.395 mmol) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The crude material was purified using preparative HPLC in a 95% A:5% B to 100% B solvent system. The TFA and ACN were removed through rotary evaporation and $H_2O$ through freeze-drying, providing the title compound as a white solid (0.050 g, 34.6% yield). $^1H$ NMR (400 MHz, DMSO-$d_6$) δ 11.43 (s, 1H), 11.13 (s, 1H), 9.23 (s, 2H), 9.15 (s, 1H), 8.50 (s, 1H), 8.02 (d, J=8.0 Hz, 2H), 7.83 (d, J=8.2 Hz, 2H). LCMS $R_f$(min)=3.386. HRMS (ESI) calcd for $C_{15}H_{11}F_3N_5O_3^+$ [M+H]$^+$ 366.0809, found 366.0826.

14. N-Hydroxy-5-((4-[4-(trifluoromethyl)phenyl]-1,3-oxazol-2-yl)amino)picolinamide (Scheme 12)

Scheme 12

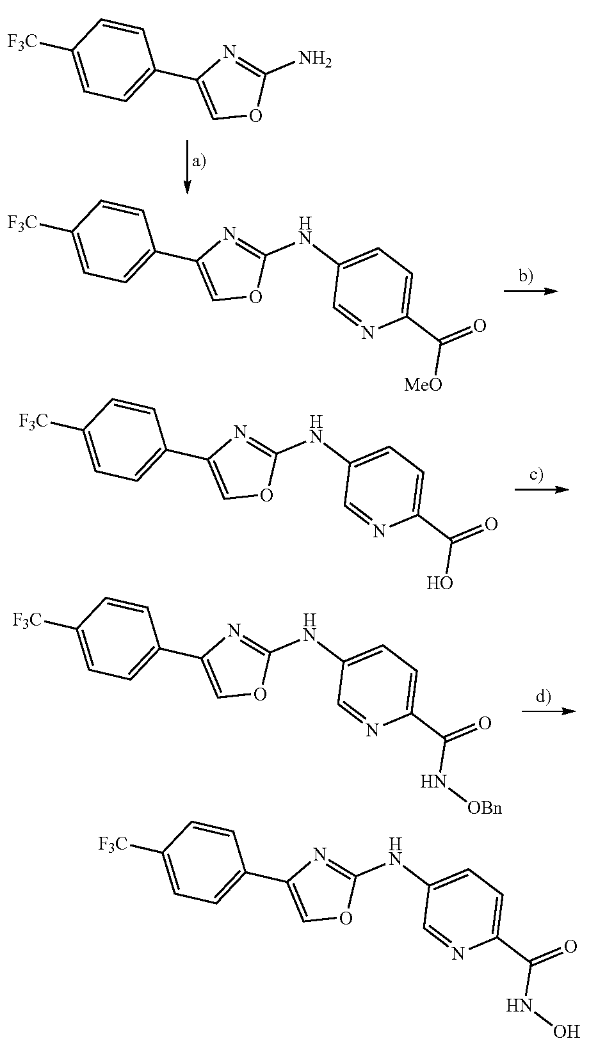

a) methyl 5-bromopicolinate, $K_3PO_4$, $Pd_2(dba)_3$, Xantphos, $H_2O$, 1,4-dioxane, 140° C., 16 h; b) $LiOH•H_2O$, 1,4-dioxane:EtOH:$H_2O$ (1:1:1), 100° C., 5 h; c) O-benzylhydroxylamine•HCl, HOBt, EDCI•HCl, $Et_3N$, DMF, rt, 16 h; d) $BBr_3$ 1.0M in heptane, DCM, 0° C.~rt, 2 h.

A re-sealable Schlenk tube was charged with $Pd_2(dba)_3$ (0.02 equiv.), Xantphos (0.06 equiv.), 4-(4-(trifluoromethyl)phenyl)oxazol-2-amine (Intermediate E) (1.2 equiv.), $K_3PO_4$ (fine powder, 1.4 equiv.), methyl 5-bromopicolinate (0.250 g, 1.152 mmol) and 1,4-dioxane (4 mL). After the mixture was degassed and carefully subjected to three cycles of evacuation and backfilling with $N_2$, $H_2O$ (1.0 mmol) was added dropwise. This was then sealed and immersed in a 140° C. oil bath. After 15 h, the mixture was cooled, diluted with EtOAc (20 mL) and washed with $H_2O$ (15 mL). The aq. layers were then back extracted with EtOAc (2×15 mL). The crude product was concentrated under reduced pressure and chromatographed on a $SiO_2$ column (EtOAc:toluene=1:1) to give methyl 5-((4-(4-(trifluoromethyl)phenyl)oxazol-2-yl)amino)picolinate as a white solid (0.21 g, 49.8% yield). $^1H$ NMR (400 MHz, DMSO-$d_6$) δ 11.04 (s, 1H), 8.90 (d, J=2.5

Hz, 1H), 8.44 (s, 1H), 8.36 (dd, J=8.7, 2.6 Hz, 1H), 8.08 (d, J=8.6 Hz, 1H), 8.00 (d, J=8.1 Hz, 2H), 7.78 (d, J=8.4 Hz, 2H), 3.85 (s, 3H). $^{13}C$ NMR (101 MHz, DMSO-$d_6$) δ 164.22, 155.55, 149.46, 144.33, 137.96, 135.69, 135.68, 134.91, 131.18, 125.74, 125.57, 125.55. LCMS $R_f$ (min)=3.907, MS m/z=363.8 $[M+H]^+$.

LiOH·$H_2O$ (3 equiv.) in $H_2O$ (2 mL) was added to a solution of methyl 5-((4-(4-(trifluoromethyl)phenyl)oxazol-2-yl)amino)picolinate (0.180 g, 0.495 mmol) in 1,4-dioxane (2 mL) and EtOH (2 mL) and the mixture refluxed for 3 h. Volatiles were removed in vacuo and to the suspension was added brine (2 mL), followed by 6M HCl (2 mL) dropwise at 0° C. The resulting precipitate was filtered and washed with $H_2O$ (2 mL), providing 5-((4-(4-(trifluoromethyl)phenyl)oxazol-2-yl)amino)picolinic acid as a yellow solid (0.240 g, 99.8% yield). $^1H$ NMR (400 MHz, DMSO-$d_6$) δ 11.01 (s, 1H), 8.90 (d, J=2.4 Hz, 1H), 8.46 (s, 1H), 8.34 (dd, J=8.6, 2.6 Hz, 1H), 8.07 (d, J=8.6 Hz, 1H), 8.02 (d, J=8.0 Hz, 2H), 7.81 (d, J=8.2 Hz, 2H). $^{13}C$ NMR (101 MHz, DMSO-$d_6$) δ 166.27, 156.47, 146.55, 140.97, 139.20, 138.93, 138.75, 138.55, 138.36, 135.52, 131.28, 130.57, 128.94, 128.51, 128.19, 127.61, 127.05, 126.17, 125.99, 123.77, 123.39, 123.16. LCMS $R_f$ (min)=3.578, MS m/z=349.8 $[M+H]^+$.

A solution of 5-((4-(4-(trifluoromethyl)phenyl)oxazol-2-yl)amino)picolinic acid (0.110 g, 0.315 mmol), anhydrous HOBt (1.2 equiv.) and EDCI·HCl (1.3 equiv.) in dry DMF (3 mL) was stirred at rt for 2 h. After this time, O-benzylhydroxylamine hydrochloride (5 equiv.) and $Et_3N$ (5 equiv.) were added and the mixture stirred at rt for a further 16 h. DMF was removed in vacuo, washing with toluene (2 mL×3) to aid this process. $H_2O$ (2 mL) was then added and the mixture left to stir at rt for 10 min. The resulting precipitate was filtered and washed with $H_2O$ (1 mL) and hexanes (2 mL), providing N-(benzyloxy)-5-((4-(4-(trifluoromethyl)phenyl)oxazol-2-yl)amino)picolinamide as a brown solid (0.14 g, 97.8% yield). $^1H$ NMR (400 MHz, DMSO-$d_6$) δ 11.86 (s, 1H), 10.97 (s, 1H), 8.91 (d, J=2.4 Hz, 1H), 8.45 (s, 1H), 8.32 (dd, J=8.7, 2.5 Hz, 1H), 8.01 (dd, J=8.4, 3.3 Hz, 2H), 7.82 (d, J=8.5 Hz, 2H), 7.51-7.24 (m, 5H), 4.94 (d, J=3.0 Hz, 2H). $^{13}C$ NMR (101 MHz, DMSO-$d_6$) δ 162.01, 156.54, 142.58, 138.98, 138.35, 137.52, 136.46, 129.20, 128.75, 126.20, 125.97, 123.85, 123.39, 77.56, 77.51. LCMS $R_f$ (min)=4.043, MS m/z=454.8 $[M+H]^+$.

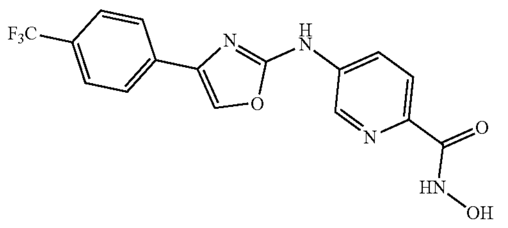 [SMILES: O=C(NO)c1ccc(Nc2nc(-c3ccc(C(F)(F)F)cc3)co2)cn1]

$BBr_3$ 1.0 M in heptane (3 equiv.) was added dropwise to a solution of N-(benzyloxy)-5-((4-(4-(trifluoromethyl)phenyl)oxazol-2-yl)amino)picolinamide (0.120 g, 0.264 mmol) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The crude material was purified using preparative HPLC in a 95% A:5% B to 100% B solvent system. TFA and ACN were removed through rotary evaporation and $H_2O$ through freeze-drying, providing the title compound as a white solid (0.029 g, 30.1% yield). $^1H$ NMR (400 MHz, DMSO-$d_6$) δ 11.23 (s, 1H), 10.91 (s, 1H), 8.89 (d, J=2.2 Hz, 1H), 8.45 (s, 1H), 8.29 (dd, J=8.6, 2.6 Hz, 1H), 8.02-7.97 (m, 3H), 7.82 (d, J=8.2 Hz, 2H), 5.76 (s, 1H). $^{13}C$ NMR (101 MHz, DMSO-$d_6$) δ 161.41, 156.15, 142.74, 140.13, 138.08, 137.86, 137.02, 135.10, 130.66, 130.09, 129.27, 128.02, 127.70, 125.73, 125.69, 125.47, 123.37, 122.92, 122.50, 39.52. LCMS $R_f$ (min)=5.908. HRMS (ESI) calcd for $C_{16}H_{12}F_3N_4O_3^+$ $[M+H]^+$ 365.0856, found 365.0861.

15. N-Hydroxy-N-methyl-5-((5-[4-(trifluoromethyl)phenyl]-1,3-oxazol-2-yl)amino) pyridine-2-sulfonamide (Scheme 13)

Scheme 13

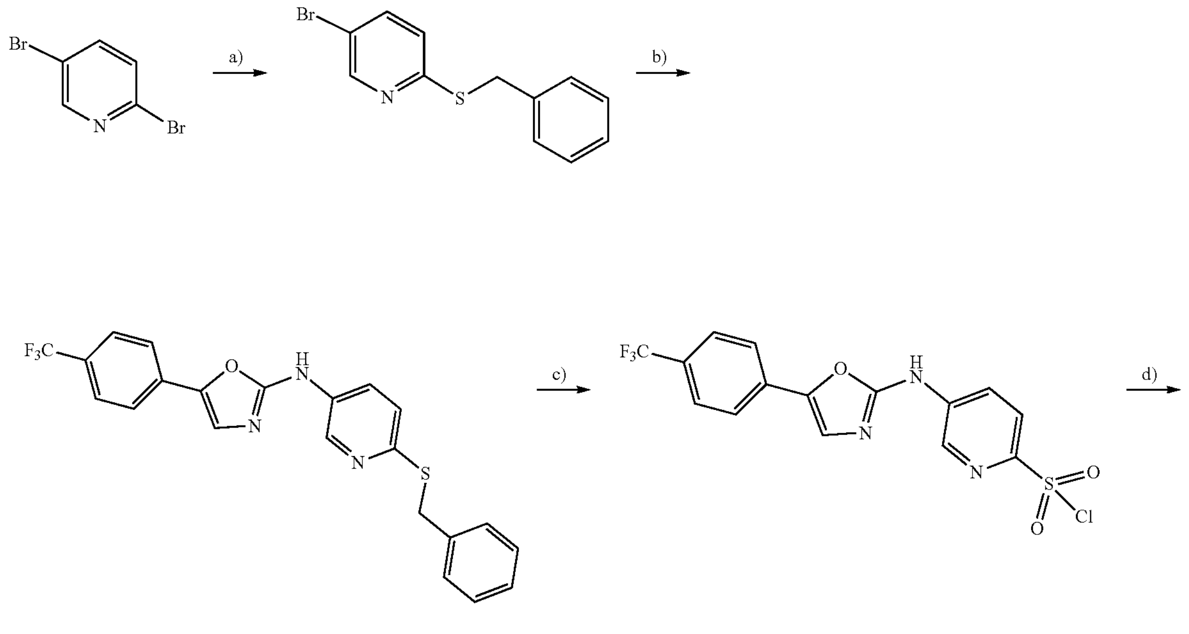

-continued

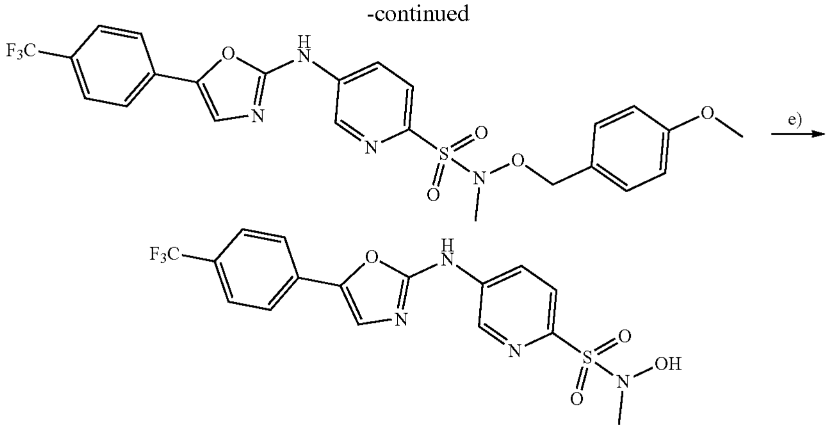

a) $Cs_2CO_3$, benzyl mercaptan, DMF, 30 min; b) 5-(4-(trifluoromethyl)phenyl)oxazol-2-amine, $K_3PO_4$, $Pd_2(dba)_3$, Xantphos, $H_2O$, 1,4-dioxane, 140° C., 16 h; c) sulfuryl chloride, DCM: $H_2O$ (5:1), 0° C. to rtm 20 min; d) O-(4-methoxybenzyl)-N-methylhydroxylamine, DIPEA, DCM, 2 d; e) triethylsilane, trifluoroacetic acid, 2 h.

A solution of $Cs_2CO_3$ (29.227 g, 89.704 mmol) and benzyl mercaptan (10.511 mL, 89.704 mmol) in DMF (70 mL) stirred for 15 min. 2,5-dibromopyridine (5.000 g, 25.107 mmol) in DMF (30 mL) was added and the resulting solution stirred for 30 min at rt. The reaction mixture was diluted with water and extracted with EtOAc (3x20 mL). The combined organic layers were washed with brine and dried over anhydrous $Na_2SO_4$, filtered and concentrated under reduced pressure to yield crude 2-(benzylthio)-5-bromopyridine that was used without further purification. $^1H$ NMR (400 MHz, $CDCl_3$) δ 8.50 (dd, J=2.5, 0.7 Hz, 1H), 7.57 (dd, J=8.5, 2.4 Hz, 1H), 7.45-7.21 (m, 5H), 7.05 (dd, J=8.5, 0.7 Hz, 1H), 4.40 (s, 2H). LCMS $R_f$(min)=3.956. MS m/z 323.9 $[M+H]^+$.

A re-sealable Schlenk tube was charged with $Pd_2(dba)_3$ (0.327 g, 0.357 mmol), Xantphos (0.620 g, 1.071 mmol), 5-(4-(trifluoromethyl)phenyl)oxazol-2-amine (Intermediate D) (0.977 g, 4.283 mmol), $K_3PO_4$ (fine powder, 1.061 g, 4.997 mmol), 2-(benzylthio)-5-bromopyridine (1.000 g, 3.569 mmol) and 1,4-dioxane (20 mL). After the mixture was degassed and carefully subjected to three cycles of evacuation and backfilling with $N_2$, $H_2O$ (0.018 mL, 1.0 mmol) was added dropwise. This was then sealed and immersed in a 140° C. sand bath. After 15 h the volatiles were evaporated. The mixture was then filtered and washed with $H_2O$ (10 mL), 10% potassium ethyl xanthate solution (10 mL) and ether (10 mL) to give N-(6-(benzylthio)pyridin-3-yl)-5-(4-(trifluoromethyl)phenyl)oxazol-2-amine as a grey solid (0.56 g, 43.1% yield). $^1H$ NMR (400 MHz, DMSO-$d_6$) δ 10.68 (s, 1H), 8.73 (d, J=2.3 Hz, 1H), 7.99 (dd, J=8.7, 2.6 Hz, 1H), 7.78 (s, 4H), 7.71 (s, 1H), 7.42-7.20 (m, 5H), 4.38 (s, 2H). $^{13}C$ NMR (101 MHz, DMSO-$d_6$) δ 156.79, 149.31, 142.84, 138.50, 138.23, 133.20, 131.60, 128.81, 128.36, 128.27, 127.04, 126.94, 126.72, 126.04, 126.01, 125.57, 125.38, 125.06, 122.10, 33.97. LCMS $R_f$(min)=3.907, MS m/z=427.9 $[M+H]^+$.

Sulfuryl chloride (0.185 g, 2.293 mmol) was added to a solution of N-(6-(benzylthio)pyridin-3-yl)-5-(4-(trifluoromethyl)phenyl)oxazol-2-amine (0.140 g, 0.328 mmol) in DCM (2 mL) and $H_2O$ (0.5 mL) at 0° C. The reaction mixture slowly warmed to rt and stirred for 30 min under $N_2$. The grey suspension became yellow as $SO_2Cl_2$ was added gradually until it returned to grey suspension again. After the sulfonyl chloride was formed, the solvent was evaporated completely. The mixture was then redissolved in DCM (2 mL). DIPEA (0.285 mL, 0.742 mmol) and O-(4-methoxybenzyl)-N-methylhydroxylamine (0.066 mg, 0.393 mmol) was added into the suspension and the mixture was stirred at rt for 2 d. On completion, the mixture was extracted with EtOAc (3x20 mL). The organic layers were collected and washed with brine. The crude material (N-((4-methoxybenzyl)oxy)-N-methyl-5-((5-(4-(trifluoromethyl)phenyl)oxazol-2-yl)amino)pyridine-2-sulfonamide) was used in the next step without further purification (0.062 g, 35.4% yield). $^1H$ NMR (401 MHz, DMSO-$d_6$) δ 8.86 (d, J=2.5 Hz, 1H), 8.43 (dd, J=8.8, 2.6 Hz, 1H), 8.05 (d, J=8.7 Hz, 1H), 7.82 (s, 4H), 7.80 (s, 1H), 7.37-7.19 (m, 2H), 7.01-6.83 (m, 2H), 4.85 (s, 2H), 3.74 (s, 3H), 2.90 (s, 3H). LCMS $R_f$ (min)=3.660, MS m/z=534.9 $[M+H]^+$.

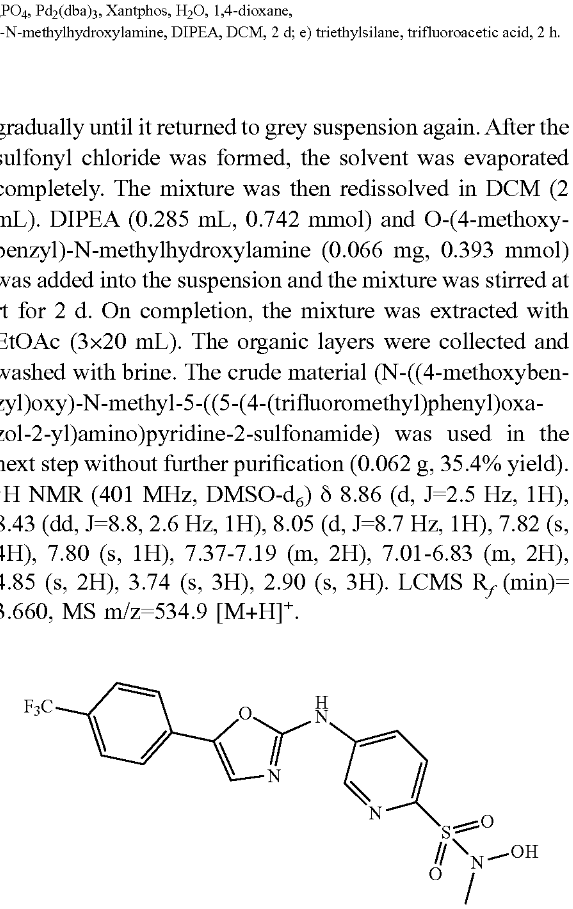

N-[(4-Methoxybenzyl)oxy]-N-methyl-5-((5-[4-(trifluoromethyl)phenyl]-1,3-oxazol-2-yl)amino) pyridine-2-sulfonamide was dissolved in 10% triethylsilane in trifluoroacetic acid (2 mL). The mixture was stirred at rt for 4 h. On completion, the mixture was filtered and washed with $Et_2O$ (2 mL), providing a pale yellow solid. The crude material was purified using preparative HPLC. The TFA and ACN were removed through rotary evaporation and $H_2O$ through the use of the freeze dryer, providing the title compound as a white solid (0.040 g, 83.2% yield). $^1H$ NMR (401 MHz, DMSO-$d_6$) 11.39 (s, 1H), 10.27 (s, 1H), 8.90 (d, J=2.5 Hz, 1H), 8.43 (dd, J=8.7, 2.5 Hz, 1H), 8.00 (d, J=8.7 Hz, 1H), 7.83 (s, 4H), 7.82 (s, 1H), 2.95 (s, 3H). LCMS $R_f$ (min)=6.114. HRMS (ESI) calcd for $C_{16}H_{14}F_3N_4O_4S^+$ $[M+H]^+$ 415.0682, found 415.0687.

16. rac-N-(2,3-Dihydroxypropyl)-5-((5-[4-(trifluoromethyl)phenyl]-1,3-oxazol-2-yl)amino)pyridine-2-sulfonamide (Scheme 14)

Scheme 14

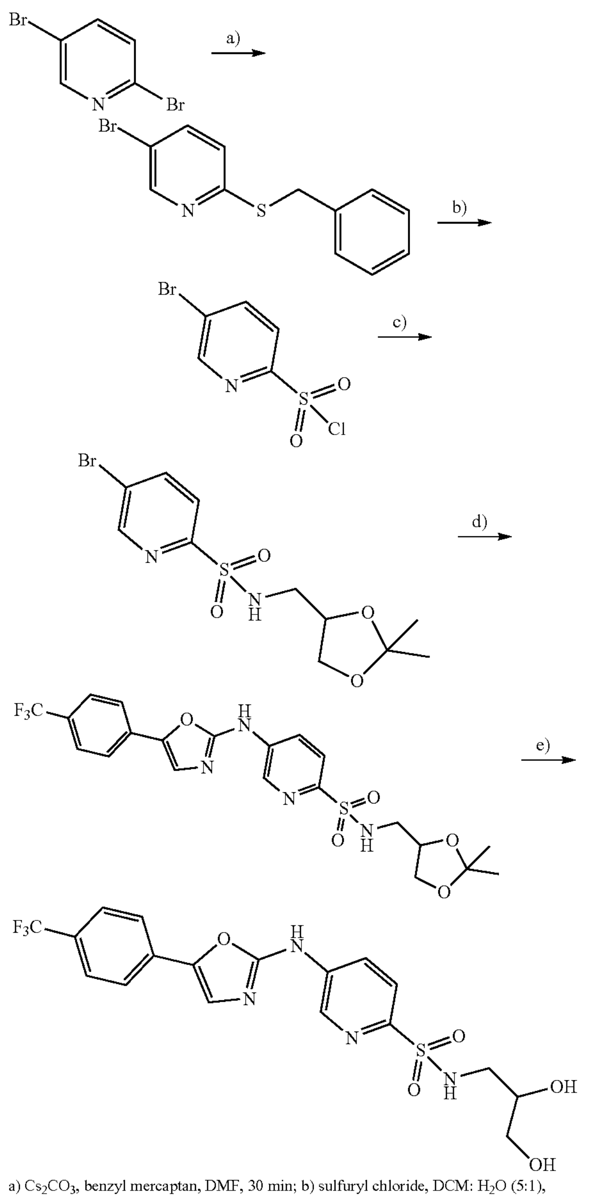

a) $Cs_2CO_3$, benzyl mercaptan, DMF, 30 min; b) sulfuryl chloride, DCM: $H_2O$ (5:1), 0° C to rt, 30 min; c) 2,2-dimethyl-1,3-dioxolan-4-yl)methanamine, triethylamine, DCM, 2 d; d) 5-(4-(trifluoromethyl)phenyl)oxazol-2-amine, $K_3PO_4$, $Pd_2(dba)_3$, Xantphos,
$H_2O$, 1,4-dioxane, 140° C., 16 h; e) triethylsilane, frifluoroacetic acid, 2 h.

A solution of $Cs_2CO_3$ (29.227 g, 89.704 mmol) and benzyl mercaptan (10.511 mL, 89.704 mmol) in DMF (70 mL) was stirred for 15 min. 2,5-Dibromopyridine (5.000 g, 25.107 mmol) in DMF (30 mL) was added and the resulting solution stirred for 30 min at rt. The reaction mixture was diluted with water and extracted with EtOAc (3×20 mL). The combined organic layers were washed with brine and dried over anhydrous $Na_2SO_4$, filtered and concentrated under reduced pressure to yield crude 2-(benzylthio)-5-bromopyridine that was used without further purification. $^1H$ NMR (400 MHz, $CHCl_3$) δ 8.50 (dd, J=2.5, 0.7 Hz, 1H), 7.57 (dd, J=8.5, 2.4 Hz, 1H), 7.45-7.21 (m, 5H), 7.05 (dd, J=8.5, 0.7 Hz, 1H), 4.40 (s, 2H). LCMS $R_f$ (min)=3.956, MS m/z=323.9 $[M+H]^+$.

Sulfuryl chloride (1.010 mL, 12.492 mmol) was added to a solution of 2-(benzylthio)-5-bromopyridine (0.500 g, 1.785 mmol) in DCM (10 mL) and $H_2O$ (2 mL) at 0° C. The reaction mixture was slowly warmed to rt and stirred for 30 min. The mixture was then extracted with DCM (10 mL×3). The organic layers were combined and evaporated completely to give a grey solid. The solid was then redissolved with DCM (10 mL). A solution of rac-2,2-dimethyl-1,3-dioxolan-4-yl)methanamine and $Et_3N$ in DCM (2 mL) was added dropwise at 0° C. The mixture was then stirred at rt for 2 h. On completion, the suspension was extracted with EtOAc (3×20 mL). The organic layers were collected and washed with brine. The crude product was further purified by silica column, eluting with 30% DCM in petroleum spirit to afford rac-5-bromo-N-((2,2-dimethyl-1,3-dioxolan-4-yl)methyl)pyridine-2-sulfonamide as a yellow solid (0.482 g, 69.98% yield). $^1H$ NMR (401 MHz, $CHCl_3$) δ 8.75 (dd, J=2.2, 0.6 Hz, 1H), 8.04 (dd, J=8.3, 2.3 Hz, 1H), 7.88 (dd, J=8.3, 0.7 Hz, 1H), 7.43-7.36 (m, 1H), 4.24 (qd, J=6.3, 4.0 Hz, 1H), 4.03 (dd, J=8.5, 6.4 Hz, 1H), 3.74 (dd, J=8.5, 5.9 Hz, 1H), 3.32 (dd, J=13.1, 4.0 Hz, 1H), 3.14 (dd, J=13.1, 6.4 Hz, 1H), 1.39 (s, 3H), 1.32 (s, 3H). $^{13}C$ NMR (101 MHz, $CDCl_3$) δ 156.06, 151.32, 140.71, 130.78, 128.93, 124.43, 123.47, 109.82, 74.76, 74.36, 66.58, 59.19, 46.04, 26.88, 25.27. LCMS $R_f$ (min)=3.770, MS m/z=292.8 $[M+H]^+$.

A re-sealable Schlenk tube was charged with $Pd_2(dba)_3$ (0.033 g, 0.057 mmol), Xantphos (0.099 g, 0.171 mmol), 5-(4-(trifluoromethyl)phenyl)oxazol-2-amine (Intermediate D) (0.156 g, 0.683 mmol), $K_3PO_4$ (fine powder, 0.169 g, 0.797 mmol), rac-5-bromo-N-((2,2-dimethyl-1,3-dioxolan-4-yl)methyl)pyridine-2-sulfonamide (0.200 g, 0.569 mmol) and 1,4-dioxane (5 mL). After the mixture was degassed and carefully subjected to three cycles of evacuation and backfilling with $N_2$, $H_2O$ (0.010 mL, 1.0 mmol) was added dropwise. This was then sealed and immersed in a 140° C. sand bath. After 15 h, the volatiles were evaporated. The mixture was then filtered and washed with $H_2O$ (10 mL), 10% potassium ethyl xanthate solution (10 mL) and ether (10 mL) to give rac-N-((2,2-dimethyl-1,3-dioxolan-4-yl)methyl)-5-((5-(4-(trifluoromethyl)phenyl)oxazol-2-yl)amino)pyridine-2-sulfonamide as a yellow solid (0.164 g, 57.7% yield). $^1H$ NMR (401 MHz, DMSO-$d_6$) δ 11.26 (s, 1H), 8.85 (d, J=2.5 Hz, 1H), 8.35 (dd, J=8.7, 2.6 Hz, 1H), 7.94 (d, J=8.7 Hz, 1H), 7.89 (t, J=6.2 Hz, 1H), 7.81 (s, 4H), 7.79 (s, 1H), 4.12-4.00 (m, 1H), 3.93 (dd, J=8.4, 6.2 Hz, 1H), 3.66 (dd, J=8.4, 5.5 Hz, 1H), 3.14-2.89 (m, 2H), 1.27 (s, 3H), 1.21 (s, 3H). $^{13}C$ NMR (101 MHz, DMSO-$d_6$) δ 154.23, 147.95, 141.66, 136.65, 136.50, 129.58, 125.94, 125.62, 125.30, 124.99, 124.28, 124.25, 123.73, 123.39, 121.79, 121.35, 120.95, 106.78, 72.51, 64.72, 43.79, 27.73, 24.97, 23.43.

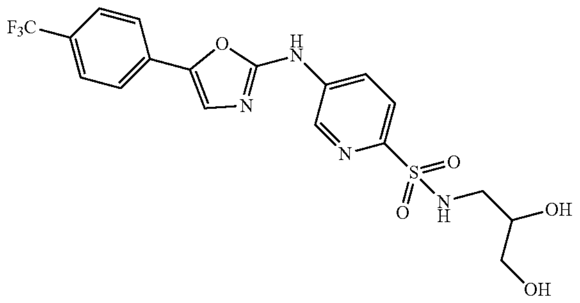 [SMILES: O=S(=O)(NCC(O)CO)c1ccc(Nc2ncc(-c3ccc(C(F)(F)F)cc3)o2)cn1]

rac-N-[(2,2-Dimethyl-1,3-dioxolan-4-yl)methyl]-5-((5-[4-(trifluoromethyl)phenyl]-1,3-oxazol-2-yl)amino) pyridine-2-sulfonamide was dissolved in 10% triethylsilane in trifluoroacetic acid (2 mL). The mixture was stirred at rt for 4 h. On completion, the mixture was filtered and washed with $Et_2O$ (2 mL), providing the title compound as a pale yellow solid (0.102 g, 67.6% yield). $^1H$ NMR (401 MHz, DMSO-$d_6$) δ 11.27 (s, 1H), 8.85 (d, J=2.4 Hz, 1H), 8.35 (dd, J=8.7, 2.6 Hz, 1H), 7.93 (d, J=8.7 Hz, 1H), 7.81 (s, 3H), 7.79 (s, 1H), 7.50 (t, J=6.1 Hz, 1H), 3.62-3.38 (m, 10H), 3.32-3.20 (m, 3H), 3.10-2.95 (m, 1H), 2.85-2.74 (m, 1H). $^{13}C$ NMR (101 MHz, DMSO-$d_6$) δ 156.53, 150.22, 143.91, 138.87, 138.68, 131.85, 127.86, 127.54, 126.54, 126.01, 125.68, 124.06, 123.63, 123.29, 70.99, 63.96, 46.84. LCMS $R_f$(min)=3.572, MS m/z=458.9 $[M+H]^+$. HRMS (ESI) calcd for $C_{18}H_{18}F_3N_4O_5S$ $[M+H]^+$ 459.0945, found 459.0951.

17. rac-N-(2,3-Dihydroxypropyl)-5-((5-[4-(trifluoromethyl)phenyl]-1,3-oxazol-2-yl)amino) picolinamide (Scheme 15)

Scheme 15

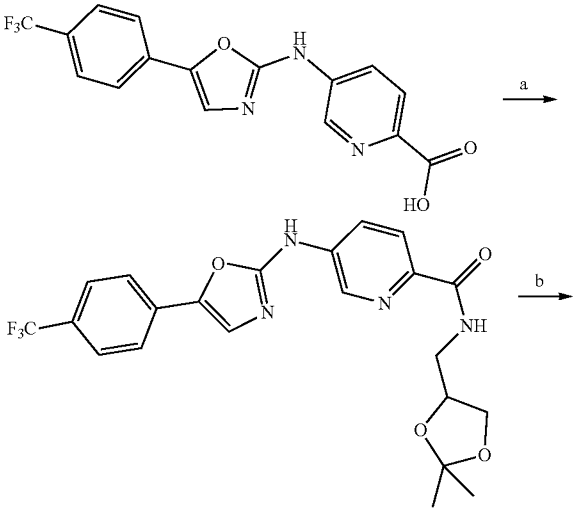

-continued

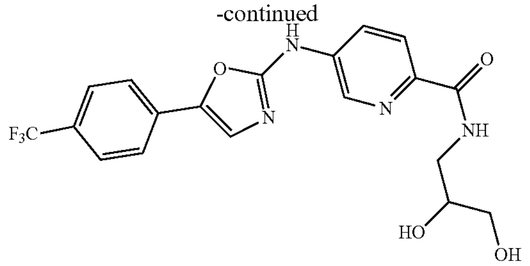

a) HBTU, DIPEA, N-((2,2-dimethyl-1,3-dioxolan-4-yl) methyl)hydroxylamine, DMF, 60° C., 3 h; (b) HCl in $Et_2O$, MeOH, $H_2O$, 4 h.

HBTU (0.261 g, 0.687 mmol) and DIPEA (0.499 mL, 2.863 mmol) were added to a stirred solution of 5-((5-(4-(trifluoromethyl)phenyl)oxazol-2-yl)amino)picolinic acid (Intermediate B) (0.200 g, 0.573 mmol) in DMF (5 mL). The reaction mixture was stirred for 10 min at rt. An excess of rac-N-((2,2-dimethyl-1,3-dioxolan-4-yl)methyl)hydroxylamine (0.090 g, 0.687 mmol) was added and the resulting suspension was stirred for 3 h at 60° C. The reaction mixture was partition in $H_2O$ and EtOA. The organic phase was separated, and washed aq. $NaHCO_3$, 10% w/v aq. citric acid and brine. The organic layer was dried with $MgSO_4$ and the solvent was removed under reduced pressure to afford the crude residue, which was subjected to column chromatography to give rac-N-((2,2-dimethyl-1,3-dioxolan-4-yl) methyl)-5-((5-(4-(trifluoromethyl)phenyl)oxazol-2-yl) amino)picolinamide (0.260 g, 98.3% yield). $^1H$ NMR (401 MHz, DMSO-$d_6$) δ 11.09 (s, 1H), 8.80 (d, J=2.2 Hz, 1H), 8.59 (t, J=6.2 Hz, 1H), 8.30 (dd, J=8.6, 2.6 Hz, 1H), 8.04 (d, J=8.6 Hz, 1H), 7.81 (s, 4H), 7.78 (s, 1H), 4.24 (p, J=5.8 Hz, 1H), 3.98 (dd, J=8.3, 6.3 Hz, 1H), 3.72 (dd, J=8.3, 5.6 Hz, 1H), 3.42 (t, J=6.1 Hz, 2H), 1.36 (s, 3H), 1.26 (s, 3H). $^{13}C$ NMR (101 MHz, DMSO-$d_6$) δ 164.33, 156.70, 143.73, 143.04, 138.70, 137.61, 131.90, 127.74, 127.42, 126.53, 126.49, 126.02, 125.74, 123.99, 123.53, 123.15, 108.90, 74.64, 67.15, 42.06, 27.27, 25.73. LCMS $R_f$ (min)=3.633, MS m/z=462.8 $[M+H]^+$.

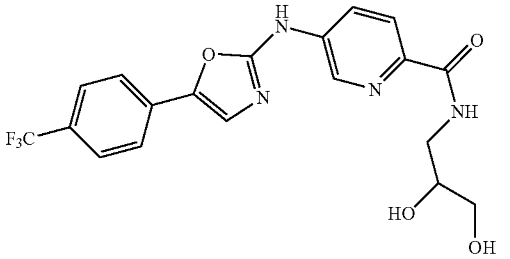 [SMILES: O=C(NCC(O)CO)c1ccc(Nc2ncc(-c3ccc(C(F)(F)F)cc3)o2)cn1]

HCl in $Et_{2O}$ (0.054 mL, 0.216 mmol) was added dropwise to a solution of rac-N-((2,2-dimethyl-1,3-dioxolan-4-yl) methyl)-5-((5-[4-(trifluoromethyl)phenyl]-1,3-oxazol-2-yl) amino) picolinamide (0.050 g, 0.108 mmol) in MeOH (2 mL) and $H_2O$ (0.5 mL). The mixture was stirred at rt for 4 h. On completion, the mixture was filtered and washed with $Et_2O$ (2 mL), providing the title compound as a bright yellow solid (0.040 g, 87.6% yield). $^1H$ NMR (401 MHz, DMSO-$d_6$) δ 11.18 (s, 1H), 8.81 (s, 1H), 8.47 (s, 1H), 8.31 (d, J=8.6 Hz, 1H), 8.05 (d, J=8.6 Hz, 1H), 7.81 (s, 4H), 7.78 (s, 1H), 3.62 (dq, J=10.8, 5.5 Hz, 1H), 3.56-3.45 (m, 1H), 3.35 (ddd, J=26.5, 11.0, 5.6 Hz, 2H), 3.27-3.18 (m, 1H). $^{13}C$ NMR (101 MHz, DMSO-$d_6$) δ 163.68, 156.26, 143.31, 142.65, 138.23, 137.12, 131.46, 128.28, 127.64, 127.32, 127.00, 126.68, 126.10, 126.06, 125.58, 125.27, 123.67, 123.10, 122.88, 122.62, 120.18, 70.26, 63.98, 42.40. LCMS $R_f$(min)=3.235, MS m/z=422.8 $[M+H]^+$. HRMS (ESI) calcd for $C_{19}H_{18}F_3N_4O_4$ $[M+H]^+$ 423.1275, found 423.1285.

18. 6-((5-(4-(Trifluoromethyl)phenyl)oxazol-2-yl) amino)pyridin-3-ol (Scheme 16)

Scheme 16

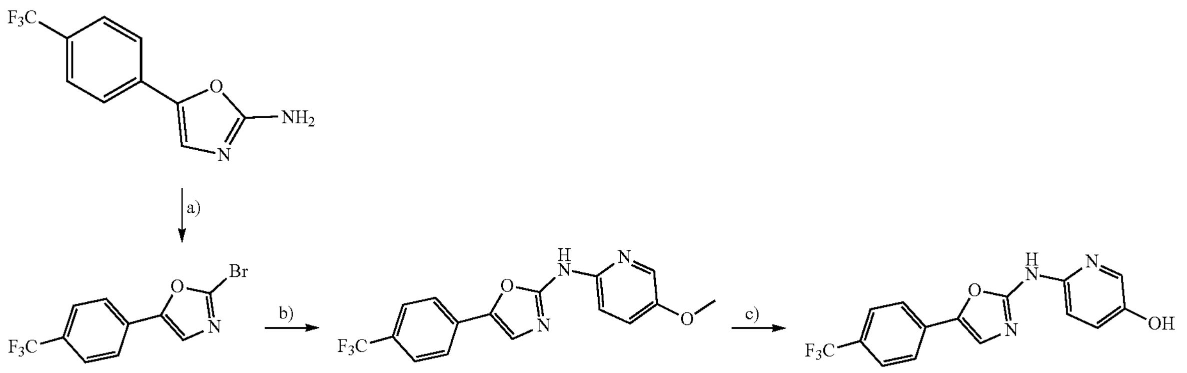

a) $CuBr_2$, t-butyl nitrite, ACN 0° C.-rt 2 h; b) 5-methoxy-2-aminopyridine, $K_3PO_4$, $Pd(dba)_3$, Xantphos, $H_2O$, toluene, 100° C., 16 h; c) $BBr_3$, DCM, 0° C. to rt, overnight To a suspension of 5-(4-(trifluoromethyl)phenyl)oxazol-2-amine (Intermediate D) (0.51 g, 2.235 mmol) in ACN (4 mL) was added $CuBr_2$ (0.603 g, 2.839 mmol) at 0° C. The solution became dark green and tert-butyl nitrite (0.705 mL, 5.879 mmol) was added at 0° C. dropwise, whereupon the mixture was stirred at rt for 2 h. The reaction mixture was poured into water (5 mL) and DCM (5 mL) and the phases were separated. The aq. phase was extracted with DCM (3×5 mL), dried with $Na_2SO_4$ and evaporated to afford the crude product. Purification by column chromatography afforded 2-bromo-5-(4-(trifluoromethyl)phenyl)oxazole (0.153 g, 23.4% yield). $^1H$ NMR (401 MHz, DMSO-$d_6$) δ 7.93 (s, 1H), 7.88 (d, J=8.2 Hz, 2H), 7.81 (d, J=8.3 Hz, 2H). $^{13}C$ NMR (101 MHz, DMSO-$d_6$) δ 153.25, 134.45, 130.11, 129.38, 129.06, 128.74, 128.42, 128.04, 126.98, 126.20, 126.16, 126.12, 126.09, 125.34, 124.48, 122.63. LCMS $R_f$ (min)=3.633, MS m/z=291.7 $[M+H]^+$.

A re-sealable Schlenk tube was charged with $Pd_2(dba)_3$ (0.047 g, 0.051 mmol), Xantphos (0.089 g, 0.154 mmol), 2-bromo-5-[4-(trifluoromethyl)phenyl]oxazole (0.150 g, 0.514 mmol), $K_3PO_4$ (fine powder, 0.153 g, 0.719 mmol), 5-methoxypyridin-2-amine (0.077 g, 0.616 mmol) and 1,4-dioxane (5 mL). After the mixture was degassed and carefully subjected to three cycles of evacuation and backfilling with $N_2$, $H_2O$ (0.009 mL, 1.0 mmol) was added dropwise. The reaction was then sealed and immersed in a 140° C. sand bath. After 15 h, the volatiles were evaporated. The mixture was then filtered and washed with $H_2O$ (10 mL), 10% potassium ethyl xanthate solution (10 mL) and ether (10 mL) to give a bright yellow solid (0.092 g). The crude product (N-(5-methoxypyridin-2-yl)-5-(4-(trifluoromethyl) phenyl)oxazol-2-amine) was used in the next step without further purification. $^1H$ NMR (401 MHz, DMSO) δ 10.84 (s, 1H), 8.03 (d, J=2.8 Hz, 1H), 8.00 (d, J=9.1 Hz, 1H), 7.83-7.76 (m, 4H), 7.71 (s, 1H), 7.48 (dd, J=9.1, 3.1 Hz, 1H), 3.82 (s, 3H). $^{13}C$ NMR (101 MHz, DMSO) δ 157.28, 151.57, 146.12, 143.16, 134.83, 132.17, 127.43, 127.12, 126.54, 126.51, 126.47, 126.47, 126.43, 126.07, 125.72, 124.36, 123.31, 111.87, 56.32. LCMS $R_f$ (min)=3.907, MS m/z=336.0 $[M+H]^+$.

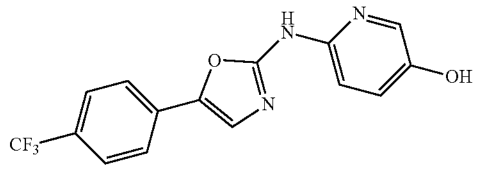 [SMILES: Oc1ccc(Nc2ncc(-c3ccc(C(F)(F)F)cc3)o2)nc1]

$BBr_3$ 1.0 M in heptane (0.079 mL, 0.823 mmol) was added dropwise to the crude N-(5-methoxypyridin-2-yl)-5-(4-(trifluoromethyl)phenyl)oxazol-2-amine (0.092 g) in dry DCM (1 mL) at 0° C. and the mixture stirred at rt for 2 h. Volatiles were removed in vacuo and the residue suspended in sat. $NaHCO_3$ (aq.) (3 mL) and stirred at rt for 20 min. The crude material was purified using preparative HPLC in 95% A:5% B to 100% B solvent system. The TFA and ACN were removed through rotary evaporation and $H_2O$ through freeze-drying, providing the title compound as a white solid (0.017 g, 19.3% yield). $^1H$ NMR (401 MHz, DMSO-$d_6$) δ 11.42 (s, 1H), 8.87 (d, J=2.2 Hz, 1H), 8.35 (dd, J=8.7, 2.7 Hz, 1H), 8.01 (d, J=8.6 Hz, 1H), 7.83 (s, 4H), 7.83 (s, 1H). LCMS $R_f$ (min)=5.275. HRMS (ESI) calcd for $C_{15}H_{11}F_3N_3O_2^+$ $[M+H]^+$ 322.0798, found 322.0802.

19. N-(2-Hydroxyethyl)-5-((5-(4-(trifluoromethyl) phenyl)oxazol-2-yl)amino)picolinamide (Scheme 17)

Scheme 17

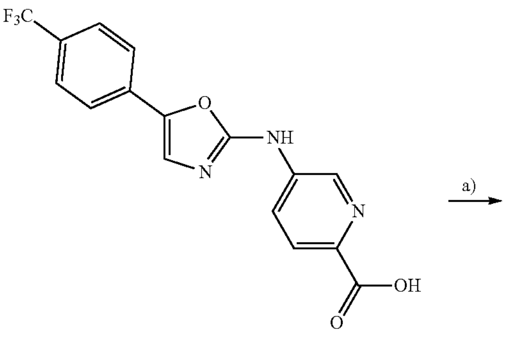

-continued

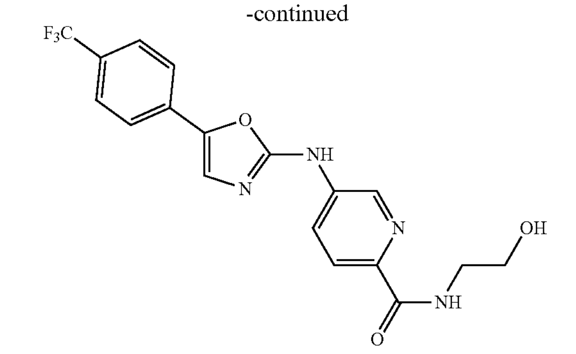

a) i. CDI, THF, 55° C., 48 h; ii. ethanolamine, rt, 16 h.

5-((5-(4-(Trifluoromethyl)phenyl)oxazol-2-yl)amino)picolinic acid (Intermediate B) (105 mg, 0.30 mmol) was suspended in dry THF, CDI (1.5 equiv.) was added and the resulting mixture was stirred at 55° C. for 24 h. More CDI (1 equiv.) was added and the stirring continued for an additional 24 h. Ethanolamine (10 equiv.) was added and the stirring continued overnight at rt. LCMS indicated that the reaction was complete. The volatiles were removed and the residue triturated with 1N HCl, the solid was collected via filtering and washing with $H_2O$ (3×). The solid product was freeze-dried from DMSO/dioxane to provide the title product (containing ~molar 20% DMSO); 103 mg, 87.32%; $^1H$ NMR (401 MHz, DMSO-$d_6$) δ 11.10 (s, 1H), 8.80 (d, J=2.4 Hz, 1H), 8.50 (t, J=5.8 Hz, 1H), 8.29 (dd, J=8.6, 2.5 Hz, 1H), 8.03 (d, J=8.6 Hz, 1H), 7.81 (s, 4H), 7.78 (s, 1H), 4.80 (t, J=5.4 Hz, 1H), 3.52 (m, 2H), 3.37 (m, 2H). LCMS $R_f$ (min)=4.081, MS m/z=393.0 $[M+H]^+$. HRMS (ESI) calcd for $C_{18}H_{16}F_3N_4O_3^+$ $[M+H]^+$ 393.1169 found 393.1177

20. N-Nydroxy-N-methyl-5-((5-(4-(trifluoromethyl)phenyl)oxazol-2-yl)amino)picolinamide (Scheme 18)

Scheme 18

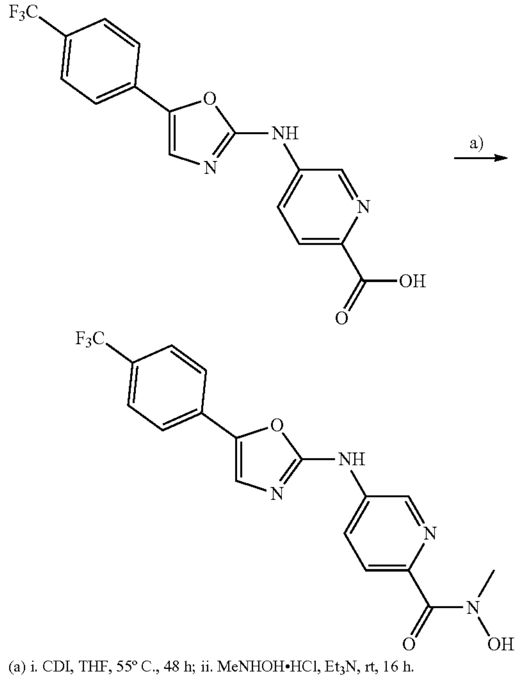

(a) i. CDI, THF, 55° C., 48 h; ii. MeNHOH•HCl, $Et_3N$, rt, 16 h.

5-((5-(4-(Trifluoromethyl)phenyl)oxazol-2-yl)amino)picolinic acid (Intermediate B) (92 mg, 0.263 mmol) was suspended in dry THF, CDI (1.5 equiv.) added and the resulting mixture was stirred at 55° C. for 24 h. More CDI (1 equiv.) was added and the stirring continued for an additional 24 h. MeNHOH·HCl and $Et_3N$ (10 equiv. each) were added and the stirring continued overnight at rt. The volatiles were removed, the solid was collected via filtering and washing with $H_2O$ (3×). The residual solid product was purified on basic ion exchange resin (Dowex@66) eluting with MeOH, then MeOH containing 0.1% $Et_3N$. The fractions containing products were pooled, evaporated to dryness and then purified on prep HPLC to provide the title compound (69 mg, 69.24% yield). $^1H$ NMR (401 MHz, DMSO-$d_6$) δ 11.06 (s, 1H), 8.80 (s, 1H), 8.24 (d, J=8.5 Hz, 1H), 7.81 (s, 4H), 7.77 (s, 1H), 7.72 (br, 1H), 5.85 (br, 1H), 3.33 (s, 3H). LCMS $R_f$ (min)=4.130, MS m/z=378.9 $[M+H]^+$. HRMS (ESI) calcd for $C_{17}H_{14}F_3N_4O_3^+$ $[M+H]^+$ 379.1013, found 379.1018.

21. N-Hydroxy-N,3-dimethyl-5-((5-(4-(trifluoromethyl)phenyl)oxazol-2-yl)amino)picolinamide (Scheme 19)

Scheme 19

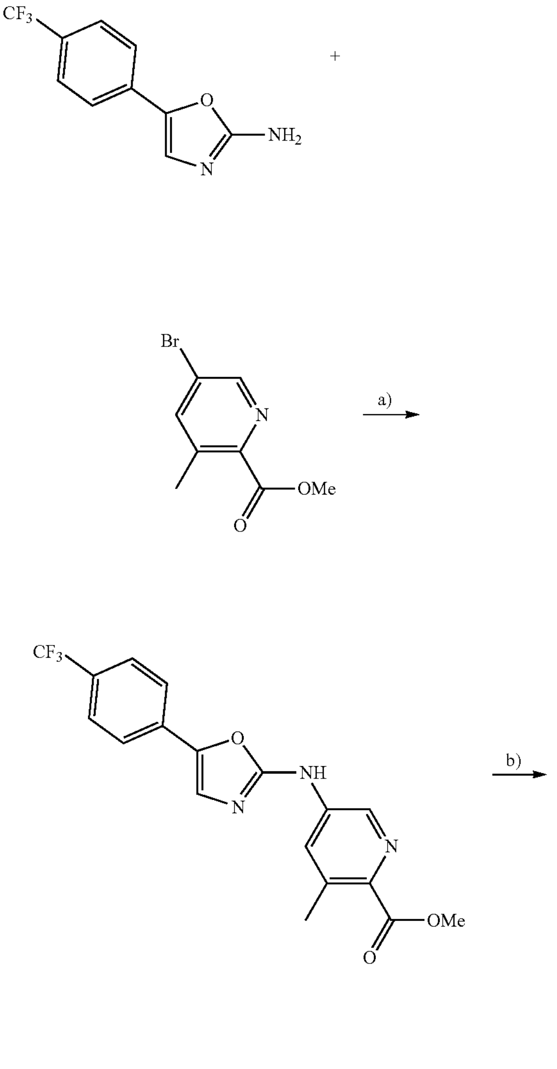

-continued

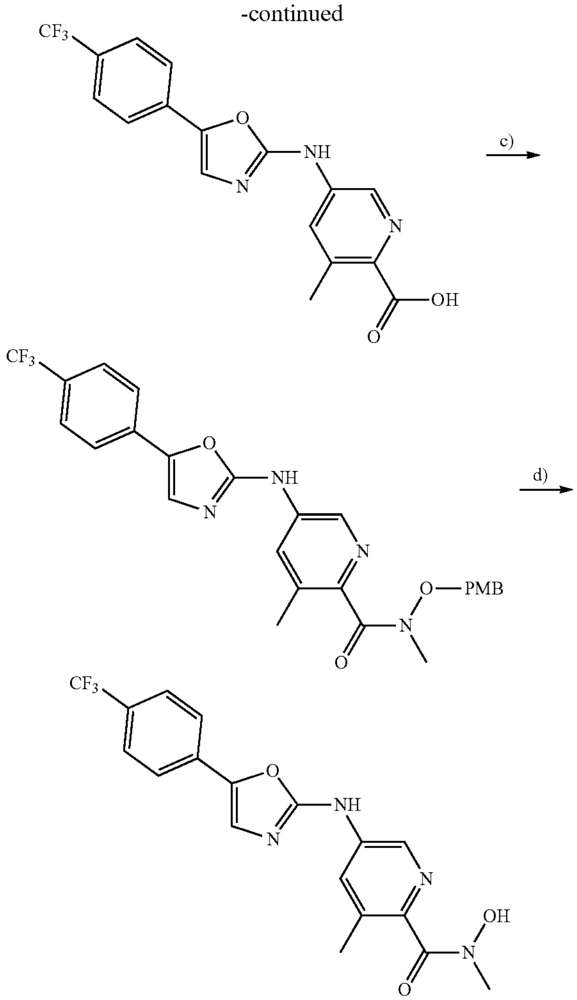

a) $Cs_2CO_3$, $Pd(dba)_3$, 1,4-dioxane, 110° C., 5 h; b) $LiOH{\bullet}H_2O$, dioxane, $H_2O$, EtOH, 100° C., 3 h; c) EDCI•HCl, HOBt, DMF, rt; d) TFA, $Et_3SiH$, rt.

Intermediate D (5-(4-(trifluoromethyl)phenyl)oxazol-2-amine) (0.8 g, 3.506 mmol) was reacted with methyl 5-bromo-3-methylpicolinate (1.0 g, 4.382 mmol) as General Procedure 4 Method 1. Upon completion, the volatile solvents were removed in vacuo, and the residue treated with water and 1N HCl to adjust pH to 4-5. The solid precipitates were collected via filtering, washed with 5% potassium xanthate (2×), water (5×), diethyl ether (5×) to provide methyl 3-methyl-5-((5-(4-(trifluoromethyl)phenyl)oxazol-2-yl)amino)picolinate in 83.75% yield (1.108 g). $^1$H NMR (401 MHz, DMSO-$d_6$) δ 11.07 (s, 1H), 8.64 (s, 1H), 8.07 (s, 1H), 7.78 (s, 4H), 7.76-7.74 (m, 1H), 3.81 (s, 3H), 2.50 (s, 3H). $^{13}$C NMR (101 MHz, DMSO-$d_6$) δ 166.42, 156.59, 143.74, 139.76, 138.24, 136.28, 136.19, 131.88, 127.74, 127.42, 126.53, 126.50, 126.01, 125.73, 125.53, 123.52, 123.31, 52.20, 20.40. LCMS $R_f$ (min)=3.807. HRMS (ESI) calcd for $C_{18}H_{15}F_3N_3O_3^+$ [M+H]$^+$ 378.1060, found 378.1065.

Methyl 3-methyl-5-((5-(4-(trifluoromethyl)phenyl)oxazol-2-yl)amino)picolinate (0.297 g, 0.787 mmol) was hydrolysed as per step b, Scheme 12 to provide 3-methyl-5-((5-(4-(trifluoromethyl)phenyl)oxazol-2-yl)amino)picolinic in 93.71% yield (0.268 g). $^1$H NMR (401 MHz, DMSO-$d_6$) δ 11.07 (s, 1H), 8.67 (s, 1H), 8.07 (s, 1H), 7.79 (s, 5H), 2.54 (s, 3H). $^{13}$C NMR (101 MHz, DMSO-$d_6$) δ 167.08, 156.62, 143.74, 140.05, 138.29, 136.25, 135.69, 131.88, 127.74, 127.43, 126.53, 126.50, 126.01, 125.91, 125.74, 123.52, 123.31, 20.52. HRMS (ESI) calcd for $C_{17}H_{13}F_3N_3O_3^+$ [M+H]$^+$ 364.0904, found 364.0912. LCMS $R_f$ (min)=3.695, MS m/z=363.9 [M+H]$^+$.

3-Methyl-5-((5-(4-(trifluoromethyl)phenyl)oxazol-2-yl)amino)picolinic acid (0.248 g, 0.682 mmol) was coupled with O-(4-methoxybenzyl)-N-methylhydroxylamine hydrochloride as per step c, Scheme 12 to provide N-((4-methoxybenzyl)oxy)-N,3-dimethyl-5-((5-(4-(trifluoromethyl)phenyl)oxazol-2-yl)amino)picolinamide in 60.88% yield (0.213 g). $^1$H NMR (401 MHz, $CDCl_3$) δ 9.10 (brs, 1H), 8.55 (s, 1H), 7.98 (d, J=1.8 Hz, 1H), 7.60 (s, 4H), 7.29 (s, 1H), 6.89 (s, 2H), 6.76 (s, 2H), 4.73 (s, 2H), 3.72 (s, 3H), 3.38 (s, 3H), 2.32 (s, 3H). $^{13}$C NMR (101 MHz, $CDCl_3$) δ 160.05, 156.50, 144.45, 135.87, 131.08, 129.28, 128.95, 125.95, 125.92, 125.77, 125.35, 123.43, 122.99, 122.65, 113.93, 55.23, 18.05. LCMS $R_f$ (min)=3.479. HRMS (ESI) calcd for $C_{26}H_{24}F_3N_4O_4^+$ [M+H]$^+$ 513.1744, found 513.1726.

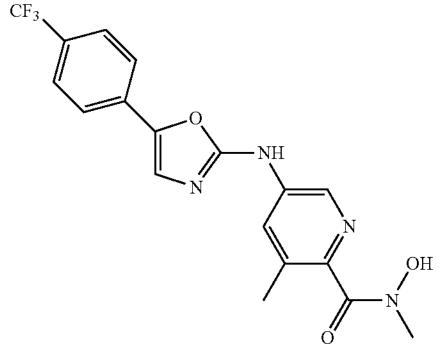 [SMILES: Cc1cc(Nc2ncc(-c3ccc(C(F)(F)F)cc3)o2)cnc1C(=O)N(C)O]

N-((4-Methoxybenzyl)oxy)-N,3-dimethyl-5-((5-(4-(trifluoromethyl)phenyl)oxazol-2-yl)amino)picolinamide (0.193 g, 0.376 mmol) was subjected to deprotection as per General procedure 11 in TFA and $Et_3SiH$ to provide N-hydroxy-N,3-dimethyl-5-((5-(4-(trifluoromethyl)phenyl)oxazol-2-yl)amino)picolinamide in 79.18% yield (0.117 g). $^1$H NMR (401 MHz, DMSO) δ 10.78 (s, 1H: 2 peaks due to isomers), 9.98 (brs, 1H), 8.60 (s, 2H), 7.98 (s, 1H: 2 peaks due to isomers), 7.78 (s, 4H), 7.73 (s, 1H), 3.28 (s, 2H: of major isomer), 3.05 (m, 1H: of minor isomer), 2.25 (s, 3H: 2 peaks due to isomers). $^{13}$C NMR (101 MHz, DMSO) δ 167.88, 157.10, 147.75, 143.41, 136.04, 135.72, 135.19, 131.98, 130.52, 128.71, 127.60, 127.28, 126.96, 126.50, 126.46, 126.02, 125.75, 125.22, 123.39, 123.32, 120.62, 36.07, 17.82. LCMS $R_f$ (min)=3.234, MS m/z=392.9 [M+H]$^+$. HRMS (ESI) calcd for $C_{18}H_{16}F_3N_4O_3^+$ [M+H]$^+$ 393.1169, found 393.1178.

22. N-Hydroxy-N-(2-hydroxyethyl)-5-((5-(4-(trifluoromethyl)phenyl)oxazol-2-yl)amino)picolinamide (Scheme 20)

Scheme 20

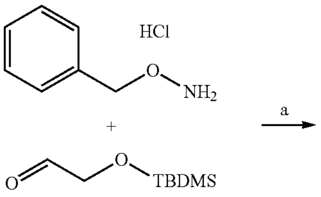

-continued

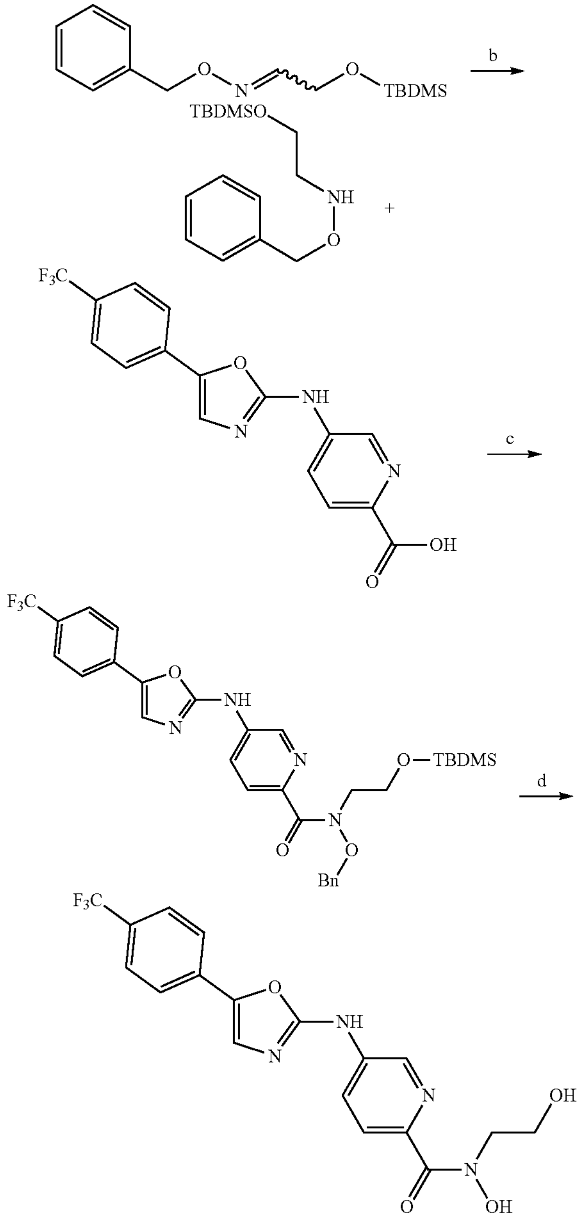

a) Pyridine, rt, overnight; b) $NaBH_3CN$, EtOH, AcOH, rt; c) EDCI•HCl, HOBt, DMF, rt, 3 h; d) $BBr_3$, DCM, rt.

2-((tert-Butyldimethylsilyl)oxy)acetaldehyde (0.8 g, 4.59 mmol) was stirred with O-benzylhydroxylamine hydrochloride salt (1.1 g, 6.88 mmol) in pyridine (9 mL) overnight at rt. The reaction was deemed complete by LCMS. Volatile pyridine was removed on the rotavap and the residue was taken up in DCM and sat. $NaHCO_3$ solution. The phases were separated and the aq. phase was extracted with additional DCM (3×). The combined organic phases were dried over $MgSO_4$ and evaporated to dryness. The residue was purified on silica gel with neat DCM to provide the product 2-((tert-butyldimethylsilyl)oxy)acetaldehyde O-benzyl oxime as a ~1:1 mixture of E and Z isomers (1.20 g, 93.5% yield). $^1$H NMR (401 MHz, $CDCl_3$; chemical shifts of both are assigned) δ 7.48 (t, J=5.6 Hz, 1H), 7.38-7.28 (m, 10H), 6.83 (t, J=3.4 Hz, 1H), 5.09 (s, 2H), 5.07 (s, 2H), 4.48 (d, J=3.4 Hz, 2H), 4.25 (d, J=5.6 Hz, 2H), 0.91-0.90 (m, 9H), 0.88 (d, J=2.9 Hz, 9H), 0.07 (s, 6H), 0.06 (s, 6H). LCMS $R_f$ (min)=3.95, MS m/z=280.0 $[M+H]^+$.

2-((tert-Butyldimethylsilyl)oxy)acetaldehyde O-benzyl oxime (1.14 g, 4.08 mmol) was dissolved in a mixture of EtOH (20 mL) and acetic acid (4 mL); $NaBH_3CN$ (5 equiv.) was added portion-wise and the resulting reaction mixture was stirred overnight at rt. The reaction was deemed complete by LCMS. The reaction mixture was cooled down to 0° C. and neutralized with 2N NaOH then diluted further with sat. $NaHCO_3$ solution. The product was extracted with DCM (3×), which was dried over $MgSO_4$ and evaporated to dryness. The residue was purified on silica gel with petroleum spirits/DCM to provide O-benzyl-N-(2-((tert-butyldimethylsilyl)oxy)ethyl)hydroxylamine (1.01 g, 87.96% yield). $^1$H NMR (401 MHz, $CDCl_3$) δ 7.38-7.27 (m, 5H), 6.5-5.5 (brs, 1H), 4.72 (s, 2H), 3.74 (t, J=5.3 Hz, 2H), 3.02 (t, J=5.3 Hz, 2H), 0.88 (s, 9H), 0.05 (s, 6H). LCMS $R_f$ (min)=4.426, MS m/z=282.1 $[M+H]^+$.

5-((5-(4-(Trifluoromethyl)phenyl)oxazol-2-yl)amino)picolinic acid (Intermediate B) (200 mg, 0.572 mmol) was suspended in DMF (11 mL), EDCI·HCl (1.3 equiv.) and HOBt (1.4 equiv.) added and the resulting mixture was stirred at rt for 3 h. O-Benzyl-N-(2-((tert-butyldimethylsilyl)oxy)ethyl)hydroxylamine (2 equiv.) was added and the stirring continued overnight. The reaction mixture was diluted with sat. $NaHCO_3$ solution and EtOAc. After separation, the aq. phase was extracted with further EtOAc (3×). The combined organic phases were dried over $MgSO_4$ and evaporated to dryness. The residue was purified on silica gel using toluene and EtOAc mixtures as eluents to give the product N-(benzyloxy)-N-(2-((tert-butyldimethylsilyl)oxy)ethyl)-5-((5-(4-(trifluoromethyl)phenyl)oxazol-2-yl)amino)picolinamide (263 mg, 74.95% yield). $^1$H NMR (401 MHz, $CDCl_3$) δ 8.69 (d, J=2.3 Hz, 1H), 8.14 (dd, J=8.6, 2.6 Hz, 1H), 7.80 (s, 1H), 7.60 (m, 4H), 7.28 (m, 5H), 5.02 (s, 2H), 3.99 (t, J=5.7 Hz, 2H), 3.85 (m, 2H), 0.82 (s, 9H), −0.00 (s, 6H). LCMS $R_f$ (min)=4.001, MS m/z=613.0 $[M+H]^+$.

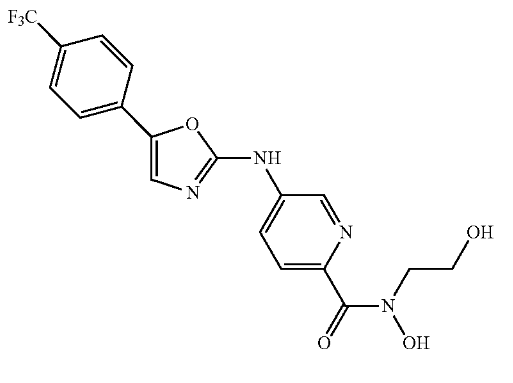 [SMILES: O=C(c1ccc(Nc2ncc(-c3ccc(C(F)(F)F)cc3)o2)cn1)N(O)CCO]

N-(Benzyloxy)-N-(2-((tert-butyldimethylsilyl)oxy)ethyl)-5-((5-(4-(trifluoromethyl)phenyl)oxazol-2-yl)amino)picolinamide (320 mg, 0.522 mmol) was suspended in DCM (2.6 mL) and of $BBr_3$ (2.5 equiv. of 0.5M DCM solution) was added at 0° C. The reaction mixture was stirred at rt. After 1 h more $BBr_3$ (1.2 equiv.) added and the stirring continued. LCMS indicated that after 1 h there was still some benzyl-protected intermediate (~15%). More $BBr_3$ (1.2 equiv., total=4.8 equiv.) added. After an additional 1 h of stirring the volatiles were removed in vacuo and the residue treated with MeOH containing 1% DIPEA until pH ~9. MeOH was removed and the residue stirred in $H_2O$/DMSO (1/1) for 0.5 h then run through a C18 silica gel plug.

The crude product was purified by preparative HPLC. The fractions containing the desired product were combined, diluted with dioxane and freeze-dried to provide the title compound (83 mg, 31.88% yield), with the product still containing a trace of dioxane. $^1$H NMR (401 MHz, DMSO-$d_6$) δ 11.32 (s, 1H), 8.86 (d, J=2.5 Hz, 1H), 8.31 (dd, J=8.7, 2.6 Hz, 1H), 8.20 (d, J=8.7 Hz, 1H), 7.80 (s, 4H), 7.79 (s, 1H), 4.58-4.54 (m, 2H), 3.61-3.57 (m, 2H). LCMS $R_f$ (min)=3.060, MS m/z=408.9[M+H]$^+$. HRMS (ESI) calcd for $C_{18}H_{16}F_3N_4O_4^+$ [M+H]$^+$ 409.1118 found 409.1129.

23. 1-(Hydroxy)-4-((5-(4-(trifluoromethyl)phenyl) oxazol-2-yl)amino)pyridin-2(1H)-one (Scheme 21)

Scheme 21

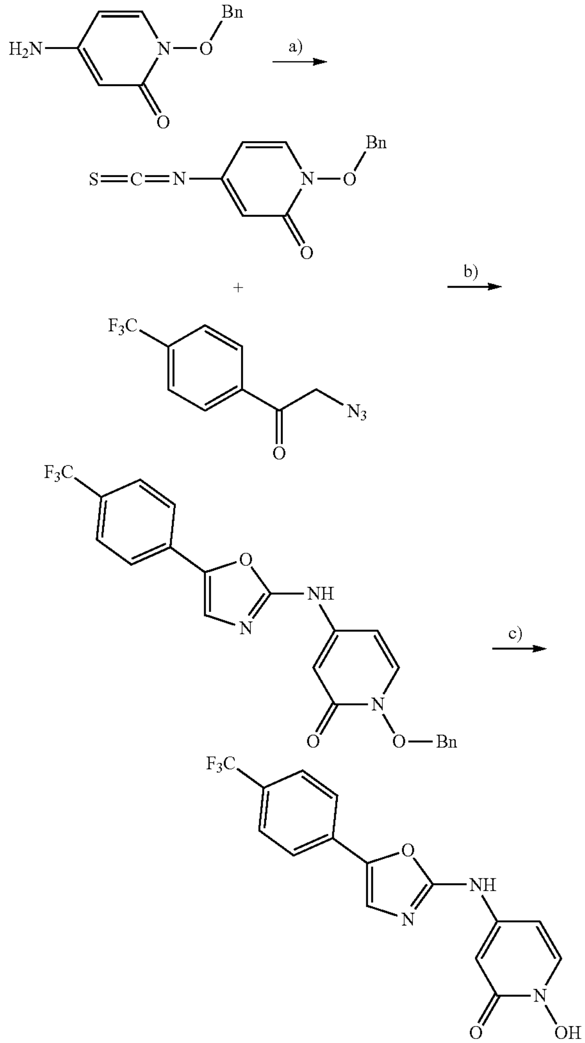

a) Thiophosgene, acetone, rt, 1 h; b) $Ph_3P$, dioxane, 100° C., 2 h; c) $BBr_3$, DCM, rt, 4 h.

4-Amino-1-(benzyloxy)pyridin-2(1H)-one (240 mg, 1.11 mmol) was suspended in a mixture of acetone (11 mL) and sat. $NaHCO_3$ solution (11 mL) and cooled to 0° C. Thiophosgene (1.2 equiv.) was added dropwise and the resultant mixture was stirred at rt for 1 h. The reaction was deemed complete by TLC (neat EtOAc). The reaction mixture was poured into sat. $NaHCO_3$ solution and the product extracted with DCM (5×). The combined organic phases were dried over $MgSO_4$ and evaporated to dryness. The residue was dissolved in dioxane (5.5 mL), 2-azido-1-(4-(trifluoromethyl)phenyl)ethan-1-one (Intermediate A) and $Ph_3P$ (1.25 equiv. each) were added. The resulting mixture was stirred at reflux for 2 h. All volatile solvents were removed and the residue triturated with DCM. The solids were filtered with DCM and washed with $Et_2O$ to provide the product 1-(benzyloxy)-4-((5-(4-(trifluoromethyl)phenyl)oxazol-2-yl)amino)pyridin-2(1H)-one as a creamy solid (206 mg, 43.53% yield). $^1$H NMR (401 MHz, DMSO-$d_6$) δ 10.90 (s, 1H), 7.81 (m, 4H), 7.78 (s, 1H), 7.66 (d, J=7.8 Hz, 1H), 7.51-7.44 (m, 2H), 7.44-7.38 (m, 3H), 6.99 (d, J=2.8 Hz, 1H), 6.21 (dd, J=7.8, 2.8 Hz, 1H), 5.17 (s, 2H). LCMS $R_f$ (min)=3.406, MS m/z=428.0 [M+H]$^+$.

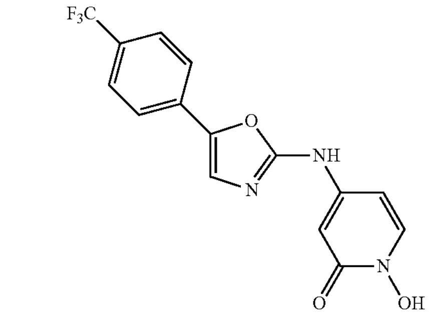 [SMILES: O=c1cc(Nc2ncc(-c3ccc(C(F)(F)F)cc3)o2)ccn1O]

1-(Benzyloxy)-4-((5-(4-(trifluoromethyl)phenyl)oxazol-2-yl)amino)pyridin-2(1H)-one (100 mg, 0.233 mmol) was suspended in DCM then cooled to 0° C. $BBr_3$ (0.089 mL; 0.935 mmol) was added dropwise. After 4 h of stirring at rt, LCMS indicated that all of the starting material had been consumed. The volatile solvents were removed and the residue quenched with sat. $NaHCO_3$ solution and MeOH for 1 h. The volatiles were removed and the residue purified by preparative HPLC to provide the title compound (32 mg, 40.5% yield). $^1$H NMR (401 MHz, DMSO-$d_6$) δ 10.84 (s, 1H), 7.80 (s, 5H), 7.76 (s, 1H), 6.94 (s, 1H), 6.32 (d, J=5.6 Hz, 1H). $^{13}$C NMR (101 MHz, DMSO-$d_6$) δ 158.49, 155.85, 146.34, 143.30, 135.71, 131.39, 127.40, 127.09, 126.11, 126.07, 125.54, 125.21, 123.18, 122.84, 100.42, 96.73. LCMS $R_f$ (min)=3.199. HRMS (ESI) calcd for $C_{15}H_{11}F_3N_3O_3^+$ [M+H]$^+$ 338.0747, found 338.0743

24. N'-Hydroxy-5-((1-(4-(trifluoromethyl)phenyl)-1H-1,2,4-triazol-3yl)amino)picolinimidamide (Scheme 22)

Scheme 22

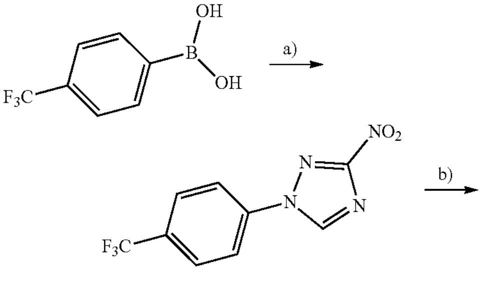

-continued

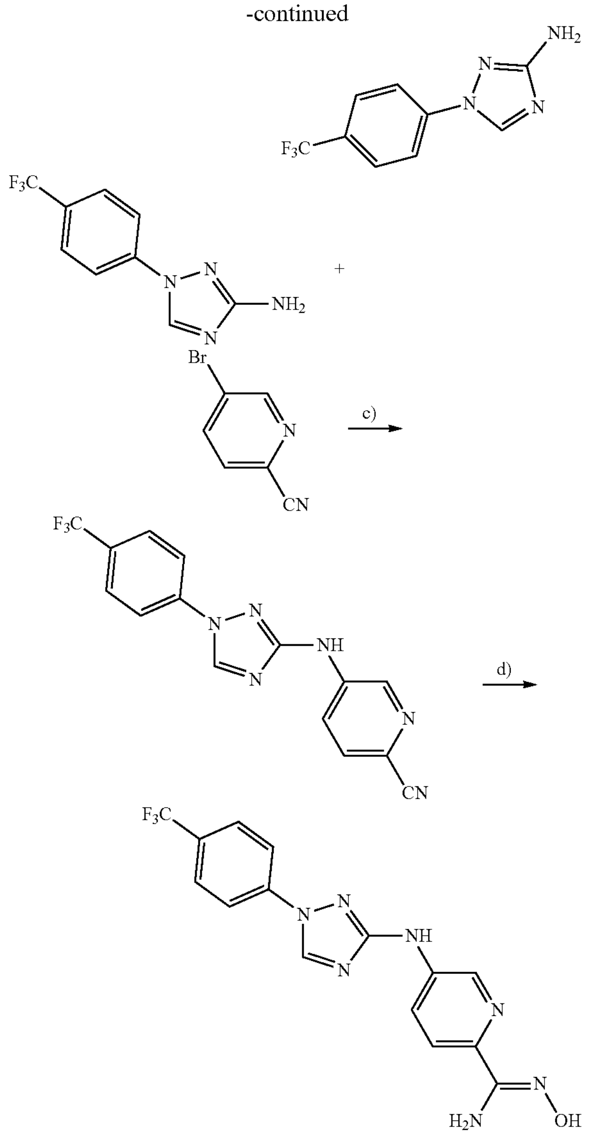

a) 3-nitro-1H-1,2,4-triazole, $Cu(Ac)_2•H_2O$, pyridine, DCM, 25° C., 5 d; b) Zn dust, aq. sat. $NH_4Cl$, acetone, rt, 1 h; c) $Cs_2CO_3$, $Pd_2(dba)_3$, Xantphos, 1,4-dioxane, 110° C., 5 h; d) $NH_2OH•HCl$, $Et_3N$, EtOH, reflux, 16 h.

4-(Trifluoromethyl)phenylboronic acid (6.661 g, 35.05 mmol), $Cu(OAc)_2{\cdot}H_2O$ (5.251 g, 26.32 mmol) and pyridine (2.825 mL, 35.06 mmol) were added to a solution of 3-nitro-1H-1,2,4-triazole (2.0 g, 17.54 mmol) in DCM (100 mL). The resulting solution was stirred for 5 d at 25° C. The solvent was removed under reduced pressure to obtain the crude product. The crude product was purified over a $SiO_2$ column using a Reveleris X2 flash chromatography system (EtOAc:petroleum spirit=2-2.5:10) to obtain 3-nitro-1-(4-(trifluoromethyl)phenyl)-1H-1,2,4-triazole as a white solid (2.55 g, 56.3% yield). $^1$H NMR (401 MHz, $CDCl_3$) δ 8.71 (s, 1H), 7.93 (d, J=8.6 Hz, 2H), 7.88 (d, J=8.6 Hz, 2H).

Intermediate F synthesis—1-(4-(trifluoromethyl)phenyl)-1H-1,2,4-triazol-3-amine) Zinc dust (3.039 g) was added slowly to the stirring suspension of 3-nitro-1-(4-(trifluoromethyl)phenyl)-1H-1,2,4-triazole (2.4 g) in aq. sat. $NH_4Cl$ (25 mL) and acetone (100 mL) at 0° C. After the complete addition, the ice bath was removed and the mixture was stirred for 1 h while warming up to rt. The mixture was filtered and the filtrate was concentrated under reduced pressure, then diluted with EtOAc (200 mL). The EtOAc layer was separated, washed with aq. sat. $NaHCO_3$ (30 mL) and brine (2×50 mL) and again separated, dried over $MgSO_4$, filtered and concentrated in vacuo to give 1-(4-(trifluoromethyl)phenyl)-1H-1,2,4-triazol-3-amine (2.0 g, 94.3% yield). The obtained compound was used without any purification. $^1$H NMR (401 MHz, DMSO-$d_6$) δ 8.98 (s, 1H), 7.93 (d, J=8.6 Hz, 2H), 7.85 (d, J=8.7 Hz, 2H), 5.85 (s, 2H).

An oven-dried RBF was charged with $Pd_2(dba)_3$ (0.05 equiv.), Xantphos (0.1 equiv.), 1-(4-(trifluoromethyl)phenyl)-1H-1,2,4-triazol-3-amine (Intermediate F) (0.680 g, 2.98 mmol), $Cs_2CO_3$ (1.5 equiv.), 5-bromopicolinonitrile (0.818 g, 1.5 mmol) and 1,4-dioxane (15 mL). Vacuum was applied briefly to the reaction flask followed by backfilling with $N_2$ and the procedure was repeated 5 times. The mixture was then heated to 100° C. and stirred for 5 h. LCMS showed that no amine was left. The volatiles were removed in vacuo and the residue was treated with $H_2O$ and 1N HCl to adjust pH to 4-5. The solid precipitates were collected via filtration and washed with 5% potassium xanthate (2×), $H_2O$ (5×), diethyl ether (5×) to provide 5-((1-(4-(trifluoromethyl)phenyl)-1H-1,2,4-triazol-3-yl)amino)picolinonitrile (0.655 g, 66.54% yield). $^1$H NMR (401 MHz, DMSO-$d_6$) δ 10.56 (s, 1H), 9.34 (s, 1H), 8.84 (d, J=2.2 Hz, 1H), 8.26 (dd, J=8.6, 2.4 Hz, 1H), 8.09 (d, J=8.4 Hz, 2H), 7.92 (d, J=8.4 Hz, 3H). $^{13}$C NMR (101 MHz, DMSO-$d_6$) δ 160.18, 142.89, 141.32, 140.36, 139.88, 130.22, 127.69, 127.53, 127.49, 127.37, 125.80, 123.10, 122.68, 122.12, 119.20, 118.80. LCMS $R_f$ (min)=3.337. HRMS (ESI) calcd for $C_{15}H_{10}F_3N_6^+$ $[M+H]^+$ 331.093, found 331.0914

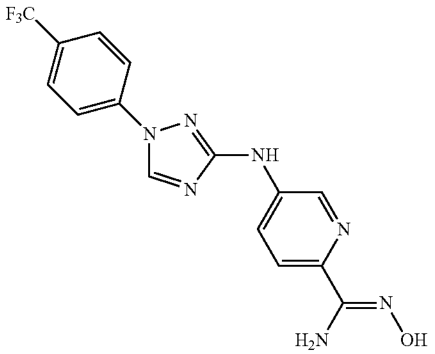 [SMILES: N/C(=N\O)c1ccc(Nc2ncn(-c3ccc(C(F)(F)F)cc3)n2)cn1]

5-((1-(4-(Trifluoromethyl)phenyl)-1H-1,2,4-triazol-3-yl)amino)picolinonitrile (0.18 g, 0.545 mmol) was suspended in EtOH (25 mL) and $NH_2OH{\cdot}HCl$ (0.303 g, 4.36 mmol) added. Approximately half of the EtOH was then removed in vacuo. $Et_3N$ (0.595 mL, 4.36 mol) was then added and the resulting reaction mixture was stirred at reflux overnight. LCMS indicated that the reaction was complete. The volatiles were removed and the resulting solids were suspended in water, collected by filtration then washing well with $H_2O$. The solids were washed with $Et_2O$ and dried to provide the title compound (0.143 g, 72.2% yield). $^1$H NMR (401 MHz, DMSO-$d_6$) δ 10.01 (s, 1H), 9.68 (s, 1H), 9.29 (s, 1H), 8.86 (s, 1H), 8.09-7.82 (m, 6H), 5.75 (s, 2H). $^{13}$C NMR (101 MHz, DMSO-$d_6$) δ 160.94, 150.03, 142.65, 142.07, 140.06, 138.68, 136.73, 127.52, 127.48, 127.38, 127.06, 125.85, 123.62, 123.16, 120.06, 118.98. LCMS $R_f$ (min)=2.924. HRMS (ESI) calcd for $C_{15}H_{13}F_3N_7O^+$ $[M+H]^+$ 364.1128, found 364.1140.

25. N-Hydroxy-N-methyl-5-((1-(4-(trifluoromethyl)phenyl)-1H-1,2,4-triazol-3-yl)amino)picolinamide (Scheme 23)

Scheme 23

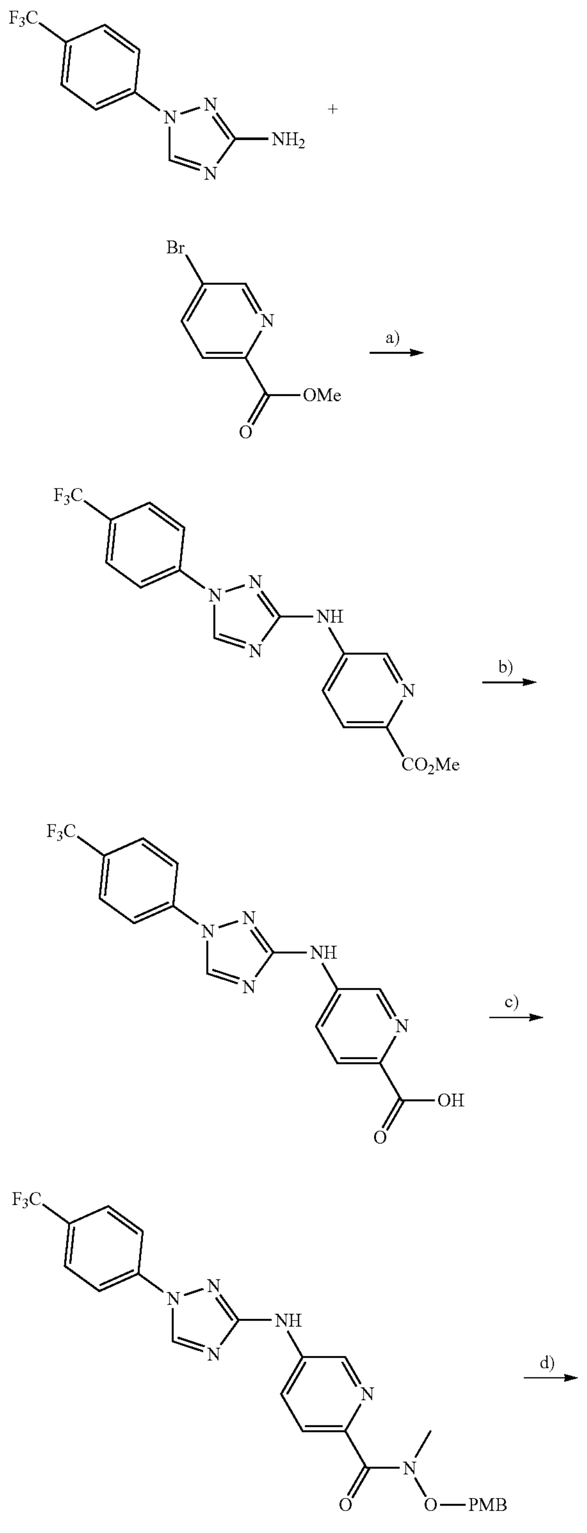

-continued

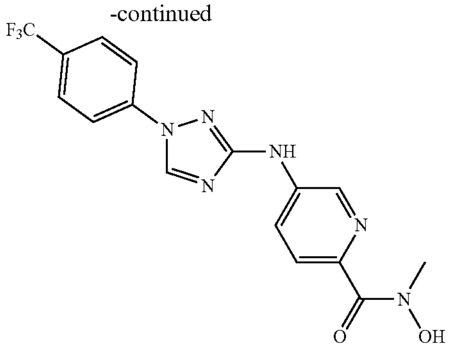

a) $Cs_2CO_3$, $Pd_2(dba)_3$, Xantphos, 1,4-dioxane, 110° C., 5 h; b) LiOH•$H_2O$, dioxane, $H_2O$, EtOH, 100° C., 3 h; c) EDCI•HCl, HOBt, DMF, rt, 16 h; d) TFA, $Et_3NSiH$, rt, 4 h.

An oven-dried RBF was charged with $Pd_2(dba)_3$ (0.130 g, 0.05 equiv.), Xantphos (0.165 g, 0.1 equiv.), 1-(4-(trifluoromethyl)phenyl)-1H-1,2,4-triazol-3-amine (Intermediate F) (0.650 g, 2.848 mmol), $Cs_2CO_3$ (1.392 g, 1.5 equiv.), methyl 5-bromopicolinate (0.823 g, 1.5 mmol) and 1,4-dioxane (15 mL). Vacuum was applied briefly to the reaction flask followed by backfilling with $N_2$ and the procedure was repeated 5 times. The mixture was then heated to 110° C. and stirred for 5 h. LCMS showed that no amine was left. The reaction was poured into $H_2O$, acidified with 1N HCl (pH 4-5) then extracted with chloroform (5×). The combined organic phases were dried over $MgSO_4$ and evaporated to dryness. The residue was chromatographed on silica gel using mixtures of DCM/EtOAc as eluents to provide methyl 5-((1-(4-(trifluoromethyl)phenyl)-1H-1,2,4-triazol-3-yl)amino)picolinate (0.42 g, 40.6% yield). $^1H$ NMR (401 MHz, DMSO-$d_6$) δ 10.39 (s, 1H), 9.34 (s, 1H), 8.88 (d, J=2.3 Hz, 1H), 8.23 (dd, J=8.7, 2.7 Hz, 1H), 8.10 (d, J=9.0 Hz, 2H), 8.04 (d, J=8.7 Hz, 1H), 7.93 (d, J=8.6 Hz, 2H), 3.84 (s, 3H). LCMS $R_f$ (min)=3.352. HRMS (ESI) calcd for $C_{16}H_{13}F_3N_5O_2^+$ $[M+H]^+$ 364.1016, found 364.1028.

Methyl 5-((1-(4-(trifluoromethyl)phenyl)-1H-1,2,4-triazol-3-yl)amino)picolinate (0.4 g, 1.10 mmol) was mixed with LiOH·$H_2O$ (0.138 g, 3.30 mmol), dioxane (1.8 mL), $H_2O$ (1.1 mL) and EtOH (2.8 mL). The resulting mixture was heated to 100° C. and stirred for 3 h. All volatiles were removed in vacuo and the residue acidified with 1N HCl (pH~4). The solid was filtered, washed with $H_2O$ (3×) and dried under high vacuum to provide 5-((1-(4-(trifluoromethyl)phenyl)-1H-1,2,4-triazol-3-yl)amino)picolinic acid (0.355 g, 92.3% yield). $^1H$ NMR (401 MHz, DMSO-$d_6$) δ 10.06 (s, 1H), 9.30 (s, 1H), 8.68 (s, 1H), 8.17 (d, J=8.2 Hz, 1H), 8.07 (d, J=8.0 Hz, 2H), 7.94 (m, 3H). LCMS $R_f$ (min)=3.379, MS m/z=349.9 $[M+H]^+$.

5-((1-(4-(Trifluoromethyl)phenyl)-1H-1,2,4-triazol-3-yl)amino)picolinic acid (0.3 g, 0.858 mmol) was suspended in DMF (17 mL), EDCI·HCl (0.214 g, 1.116 mmol) and HOBt (0.141 g, 1.1202 mmol) added. The resulting mixture was stirred at rt for 3 h. O-(4-methoxybenzyl)-N-methylhydroxylamine (0.287 g, 1.717 mmol) was added and the stirring continued overnight. The reaction mixture was diluted with sat. $NaHCO_3$ solution and EtOAc. After separation, the aq. phase was extracted with further EtOAc (3×). The combined organic phases were dried over $MgSO_4$ and evaporated to dryness. The residue was purified on silica gel using a mixture of petroleum spirit and EtOAc as eluents. The fractions containing the desired product were combined and evaporated to dryness. The solid residue was filtered and washed well with $Et_2O$ to provide the product N-((4-methoxybenzyl)oxy)-N-methyl-5-((1-(4-(trifluoromethyl)

phenyl)-1H-1,2,4-triazol-3-yl)amino)picolinamide (224 mg, 52.31% yield). $^1$H NMR (401 MHz, DMSO-$d_6$) δ 10.18 (s, 1H), 9.33 (s, 1H), 8.85 (d, J=2.5 Hz, 1H), 8.19 (d6, J=8.6, 2.6 Hz, 1H), 8.12 (d, J=8.5 Hz, 2H), 7.94 (d, J=8.7 Hz, 2H), 7.64 (d, J=8.6 Hz, 1H), 7.22 (d, J=7.7 Hz, 2H), 6.87 (d, J=8.5 Hz, 2H), 4.95 (s, 2H), 3.71 (s, 3H), 3.33 (s, 3H). LCMS $R_f$ (min)=3.517. HRMS (ESI) calcd for $C_{25}H_{22}F_3N_4O_4^+$ $[M+H]^+$ 499.1588, found 499.1578.

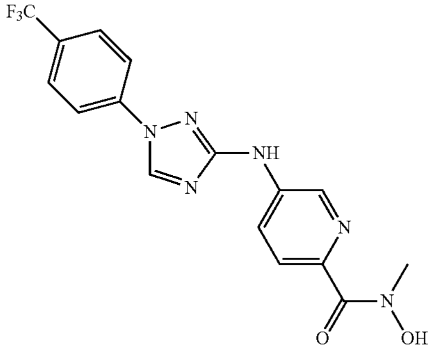 [SMILES: CN(O)C(=O)c1ccc(Nc2ncn(-c3ccc(C(F)(F)F)cc3)n2)cn1]

N-((4-Methoxybenzyl)oxy)-N-methyl-5-((1-(4-(trifluoromethyl)phenyl)-1H-1,2,4-triazol-3-yl)amino)picolinamide (0.105 g, 0.21 mmol) was stirred in a mixture of TFA (2 mL) and $Et_3SiH$ (0.105 mL) at rt for 4 h. All volatiles were removed on rotavap and the residue filtered with toluene then washed with DCM and $Et_2O$. The solid was freeze-dried from dioxane then filtered with MeOH and washed with a small amount of MeOH and $Et_2O$ to provide the title compound (0.051 g, 64.1% yield). $^1$H NMR (401 MHz, DMSO-$d_6$) δ 10.18 (s, 1H), 9.32 (s, 1H), 8.83 (s, 1H), 8.16 (m, 1H), 8.10 (m, 2H), 7.94 (m, 2H), 7.71 (s, 1H) (the resonance of N-Me overlapped with $H_2O$, and not assigned). $^{13}$C NMR (101 MHz, DMSO-$d_6$) δ 142.80, 140.00, 139.66, 127.50, 127.23, 125.83, 125.25, 123.13, 120.43, 119.11, 31.14. LCMS $R_f$ (min)=3.337. HRMS (ESI) calcd for $C_{16}H_{14}F_3N_6O_2^+$ $[M+H]^+$ 379.1125, found 379.1138.

26. N',3-Dihydroxy-5-((5-(4-(trifluoromethyl)phenyl)oxazol-2-yl)amino)picolinimidamide (Scheme 24)

Scheme 24

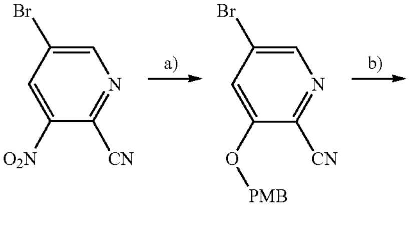

-continued

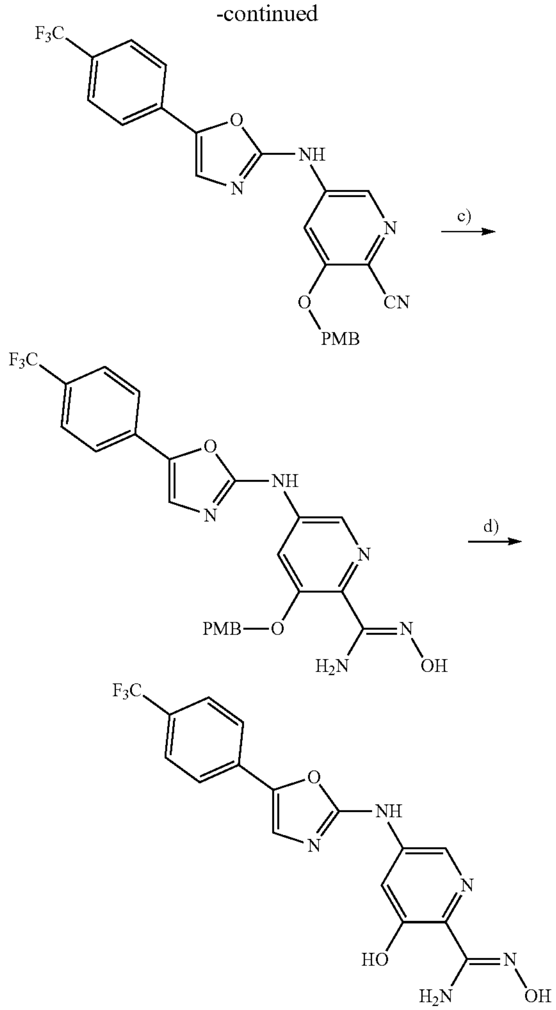

a) PMB-OH, NaH (60% dispersion in mineral oil), THF, rt, 24 h; b) $Cs_2CO_3$, $Pd_2(dba)_3$, Xantphos, 1,4-dioxane, 110° C., 5 h; c) $NH_2OH•HCl$, $Et_3N$, EtOH, reflux, 16 h; d) TFA, $Et_3SiH$, rt, 1 h.

(Intermediate G—5-bromo-3-((4-methoxybenzyl)oxy)picolinonitrile) p-Methoxybenzyl alcohol (1.57 g, 11.4 mmol, 1.3 equiv.) was dissolved in anhydrous THF (30 mL), cooled to 0° C. and NaH (60%, 0.273 g, 11.4 mmol, 1.3 equiv.) added. The mixture was stirred at 0° C. for 30 min then 5-bromo-3-nitropicolinonitrile (2 g, 8.77 mmol) was added. The resultant reaction mixture turned black and was stirred at rt for 24 h. LCMS indicated that there was still some starting material, so more NaH (60%, 0.5 equiv.) was added and the stirring continued for another 24 h. The reaction mixture was poured into sat. $NaHCO_3$ solution (300 mL) and extracted with EtOAc (3×100 mL). The combined organic layers were dried over $MgSO_4$ and concentrated to dryness. The solid residue was purified on silica gel eluting with neat toluene to provide 5-bromo-3-((4-methoxybenzyl)oxy)picolinonitrile (Intermediate G) (1.02 g, 36.43% yield). $^1$H NMR (401 MHz, $CDCl_3$) δ 8.32 (d, J=1.8 Hz, 1H), 7.55 (d, J=1.8 Hz, 1H), 7.35 (d, J=8.7 Hz, 2H), 6.93 (d, J=8.7 Hz, 2H), 5.16 (s, 2H), 3.82 (s, 3H). $^{13}$C NMR (101 MHz, $CDCl_3$) δ 160.09, 157.63, 144.06, 144.04, 129.16, 128.24, 125.99, 125.09, 123.92, 122.59, 114.58, 114.41, 71.43, 55.37. LCMS $R_f$ (min)=3.337. HRMS (ESI) calcd for $C_{14}H_{12}BrN_2O_2^+$ $[M+H]^+$ 319.0077, found 319.0068.

An oven-dried RBF was charged with $Pd_2(dba)_3$ (0.064 g, 0.05 equiv.), Xantphos (0.081 g, 0.1 equiv.), 5-bromo-3-((4-methoxybenzyl)oxy)picolinonitrile (Intermediate G) (0.447 g, 1.402 mmol), $Cs_2CO_3$ (0.685 g, 1.5 equiv.), 5-(4-(trifluoromethyl)phenyl)oxazol-2-amine (Intermediate D) (0.32 g, 1.402 mmol) and 1,4-dioxane (7 mL). Vacuum was applied briefly to the reaction flask followed by backfilling with $N_2$ and the procedure was repeated 5 times. The mixture was then heated to 110° C. and stirred for 5 h. LCMS showed that starting materials had been consumed. The volatiles were removed in vacuo and the residue treated with $H_2O$ and 1N HCl to adjust the pH to 4-5. The solid precipitates were collected via filtering and washed with 5% aqueous solution of potassium ethyl xanthate (2×), $H_2O$ (5×), $Et_2O$ (5×) to provide 3-((4-methoxybenzyl)oxy)-5-((5-(4-(trifluoromethyl)phenyl)oxazol-2-yl)amino)picolinonitrile (0.502 g, 76.74% yield). $^1H$ NMR (401 MHz, DMSO-$d_6$) δ 11.43 (br, 1H), 8.36 (s, 1H), 8.28 (s, 1H), 7.84 (s, 1H), 7.82 (s, 4H), 7.48 (d, J=8.4 Hz, 2H), 7.00 (d, J=8.4 Hz, 2H), 5.25 (s, 2H), 3.78 (s, 3H). $^{13}C$ NMR (101 MHz, DMSO-$d_6$) δ 159.90, 159.02, 156.25, 144.08, 140.98, 133.28, 131.75, 130.44, 127.95, 127.60, 126.58, 126.00, 125.70, 123.71, 123.30, 116.55, 114.47, 113.84, 107.50, 70.65, 55.61. LCMS $R_f$ (min)=3.642, MS m/z=466.9 $[M+H]^+$.

3-((4-Methoxybenzyl)oxy)-5-((5-(4-(trifluoromethyl)phenyl)oxazol-2-yl)amino)picolinonitrile (0.208 g, 0.445 mmol) was suspended in EtOH (25 mL), $NH_2OH{\cdot}HCl$ (0.248 g, 3.567 mmol) added and approximately half of the EtOH was removed in vacuo. $Et_3N$ (0.487 mL, 3.567 mol) was added and the resulting reaction mixture was stirred at reflux overnight. LCMS indicated that the reaction was complete. The volatiles were removed and the resulting solids were suspended in water, collected by filtration then washing well with $H_2O$. The solids were washed with $Et_2O$, dried in high vacuum to provide N'-hydroxy-3-((4-methoxybenzyl)oxy)-5-((5-(4-(trifluoromethyl)phenyl)oxazol-2-yl)amino)picolinimidamide (0.176 g, 79% yield). $^1H$ NMR (401 MHz, DMSO-$d_6$) δ 10.91 (s, 1H), 9.66 (s, 1H), 8.36 (s, 1H), 8.02 (s, 1H), 7.80 (s, 4H), 7.78 (s, 1H), 7.47 (d, J=8.5 Hz, 2H), 6.94 (d, J=8.6 Hz, 2H), 5.73 (s, 2H), 5.12 (s, 2H), 3.75 (s, 4H). LCMS $R_f$ (min)=3.202. HRMS (ESI) calcd for $C_{24}H_{21}F_3N_5O_4^+$ $(M)^+$ 499.1574, found 499.1549.

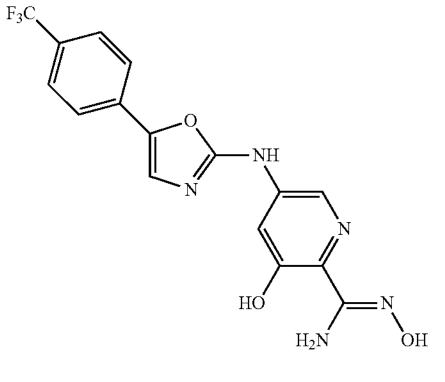 [SMILES: N/C(=N\O)c1ncc(Nc2ncc(-c3ccc(C(F)(F)F)cc3)o2)cc1O]

N'-Hydroxy-3-((4-methoxybenzyl)oxy)-5-((5-(4-(trifluoromethyl)phenyl)oxazol-2-yl)amino)picolinimidamide (0.163 g, 0.326 mmol) was stirred in a mixture of TFA (3.26 mL) and $Et_3SiH$ (0.163 mL) at rt. LCMS indicated that the reaction was complete after 1 h. The reaction mixture was filtered to remove black precipitates, washed with more TFA (3×). The combined TFA phases were evaporated to dryness, filtered with $Et_2O$ and then washed with toluene, DCM and $Et_2O$. The residue was purified on preparative HPLC to provide the title compound (0.072 g, 58.16% yield). $^1H$ NMR (401 MHz, DMSO-$d_6$) δ 11.15 (s, 1H), 10.62-10.55 (brs, 1H), 8.30 (d, J=2.1 Hz, 2H), 7.97 (s, 1H), 7.81 (s, 4H), 7.79 (s, 1H), 3.56 (s, 1H). LCMS $R_f$ (min)=3.243, MS m/z=379.9 $[M+H]^+$. HRMS (ESI) calcd for $C_{16}H_{13}F_3N_5O_3^+$ $[M+H]^+$ 380.0965, found 380.0977.

27. 1-Hydroxy-6-methyl-4-((5-(4-(trifluoromethyl)phenyl)oxazol-2-yl)amino)pyridin-2(1H)-one (Scheme 25)

Scheme 25

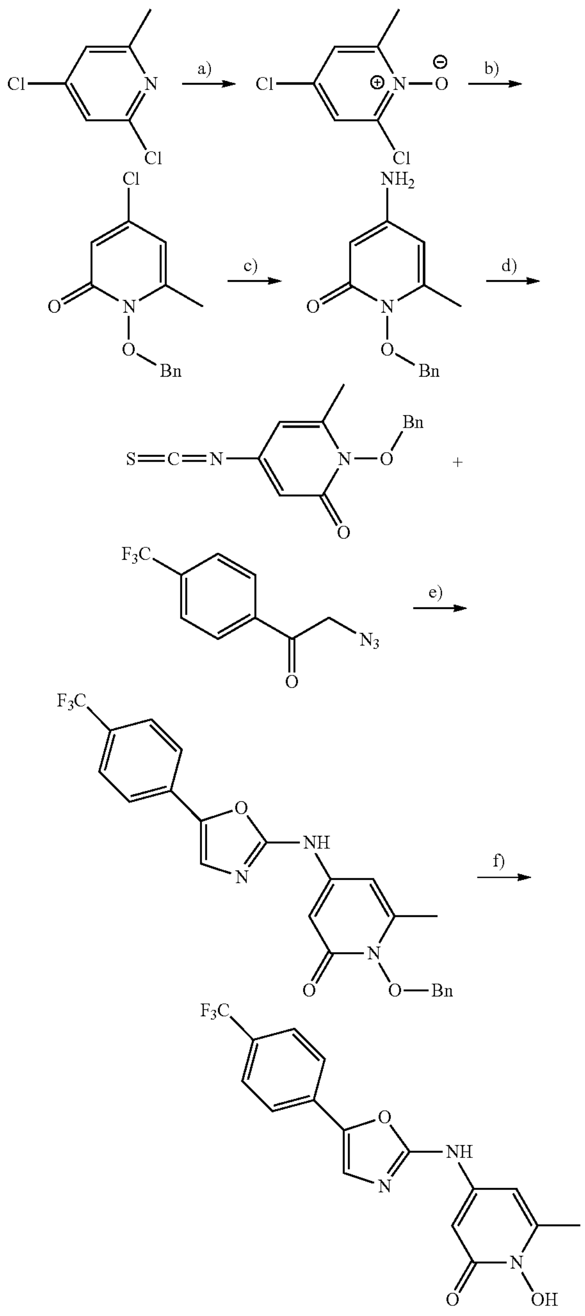

a) $H_2O_2$•Urea, TFAA, DCM, rt, 16 h; b) i. benzyl alcohol, LiBu$^t$O, THF, 0° C., 3 h, ii. BnCl, toluene, reflux, 28 h; c) $NaN_3$, DMSO, 80° C., 28 h; d) Thiophosgene, aq. $NaHCO_3$, acetone, rt, 1 h; e) $Ph_3P$, dioxane, reflux, 2 h; f) $BBr_3$, DCM, rt, 4 h.

To a solution of 2,4-dichloro-6-methylpyridine (2.50 g, 15.43 mmol) in dry DCM (60 mL) was added $H_2O_2$·urea (2 equiv.). On cooling to 0° C., a solution of TFAA (2 equiv.) in dry DCM was added dropwise and the mixture stirred at rt overnight. The reaction mixture was diluted with sat. $NaS_2O_3$ (15 mL) and stirred at rt for 0.5 h then poured into $H_2O$ (20 mL) and extracted with DCM (7×20 mL). The combined organic layers were washed with 1 M NaOH (15 mL), dried over $MgSO_4$ and concentrated to a creamy semi-solid. The solid was chromatographed on silica gel eluting with 5% EtOH in DCM, providing 2,4-dichloro-6-methylpyridine 1-oxide as a yellow crystalline solid (2.4 g, 87.4% yield). $^1$H NMR (401 MHz, $CDCl_3$) δ 7.42 (dd, J=2.9, 0.5 Hz, 1H), 7.22 (dd, J=2.9, 0.5 Hz, 1H), 2.55 (s, 3H). LCMS $R_f$ (min)=1.734, MS m/z=177.9/179.9 $[M+H]^+$.

Benzyl alcohol (4.186 g, 38.76 mmol) was dissolved in anhydrous THF (40 mL), cooled to 0° C. and then $LiBu^tO$ (1.55 g, 19.38 mmol) added. The mixture was stirred at 0° C. for 30 min and 2,4-dichloro-6-methylpyridine 1-oxide (2.3 g, 12.92 mmol) added. The resultant reaction mixture was stirred at rt for 3 h. The reaction was deemed complete by TLC (DCM/EtOAc 9/1). The reaction mixture was poured into sat. $NaHCO_3$ and extracted with EtOAc (7×) until no more product was detected in the extracting EtOAc phase. The combined organic phases were dried over $MgSO_4$ and evaporated to dryness. The residue was dissolved in toluene (800 mL), BnCl (4 mL) added and the solution heated at reflux for 28 h. A small amount of N-oxide remained unreacted. The toluene was removed and the residue was freeze-dried from $H_2O$/dioxane to remove excess BnOH and BnCl. The remainder was purified on silica gel with a mixture of DCM and EtOAc to afford the product, 1-(benzyloxy)-4-chloro-6-methylpyridin-2(1H)-one (1.37 g, 42.46% yield). $^1$H NMR (401 MHz, $CDCl_3$) δ 7.49-7.42 (m, 2H), 7.42-7.34 (m, 3H), 6.61-6.55 (m, 1H), 5.96-5.85 (m, 1H), 5.25 (s, 2H), 2.15 (s, 3H). $^{13}$C NMR (101 MHz, $CDCl_3$) δ 158.54, 146.84, 145.31, 133.56, 130.03, 129.51, 128.78, 117.91, 106.37, 17.56. LCMS $R_f$ (min)= 3.528. HRMS (ESI) calcd for $C_{13}H_{13}ClNO_2^+$ $[M+H]^+$ 250.0629, found 250.0636.

1-(Benzyloxy)-4-chloro-6-methylpyridin-2(1H)-one (1.25 g, 5.0 mmol) was stirred with $NaN_3$ (1.50 g, 25.0 mmol, 5 equiv.) in DMSO at 80° C. for 28 h. There was still some starting material left. Both azide and amine along with other impurities were formed. The solvents were removed by freeze-drying and the solid filtered and washed with DCM. The combined filtrates were evaporated to dryness. The residue was dissolved in MeOH, dithiothreitol (DTT, 3.09 g, 20 mmol, 4 equiv.) and $LiOH·H_2O$ (0.84 g, 20 mmol, 4 equiv.) added. The reaction mixture was stirred at rt for 2 h then poured into sat. $NaHCO_3$ solution and DCM. The aq. phase was extracted with more DCM and the combined organic solutions were dried over $MgSO_4$, evaporated to dryness. The residue was purified on silica gel using a mixture of DCM and EtOAc then DCM and MeOH to provide 4-amino-1-(benzyloxy)-6-methylpyridin-2(1H)-one (0.176 g, 15.2% yield). $^1$H NMR (401 MHz, MeOH-$d_4$) δ 7.50-7.41 (m, 2H), 7.40-7.33 (m, 3H), 5.64 (s, 1H), 5.56 (d, J=2.6 Hz, 1H), 5.13 (s, 2H), 2.10 (s, 3H). $^{13}$C NMR (101 MHz, MeOH-$d_4$) δ 161.73, 157.20, 145.65, 134.11, 129.69, 128.88, 128.27, 98.67, 92.21, 77.67, 16.23. HRMS (ESI) calcd for $C_{13}H_{15}N_2O_2^+$ $[M+H]^+$ 231.1128, found 231.1132.

4-Amino-1-(benzyloxy)-6-methylpyridin-2(1H)-one (0.157 g, 0.681 mmol) was dissolved in acetone (7 mL) and sat. $NaHCO_3$ solution (7 mL) and cooled to 0° C. Thiophosgene (1.2 equiv.) was added dropwise and the resultant mixture was stirred at rt for 1 h. The reaction was deemed complete by TLC (neat EtOAc). The reaction mixture was poured into sat. $NaHCO_3$ solution and the product extracted with DCM (5×). The combined organic phases were dried over $MgSO_4$ and evaporated to dryness. The residue was dissolved in dioxane (4 mL), 2-azido-1-(4-(trifluoromethyl) phenyl)ethan-1-one (Intermediate A) and $Ph_3P$ (1.25 equiv. each) were added. The resulting mixture was stirred at reflux for 2 h. All volatiles were removed and the residue triturated with DCM. The solids were filtered with DCM and washed with $Et_2O$ to provide 1-(benzyloxy)-6-methyl-4-((5-(4-(trifluoromethyl)phenyl)oxazol-2-yl)amino)pyridin-2(1H)-one as a creamy solid (182 mg 60.47%). $^1$H NMR (401 MHz, DMSO-$d_6$) δ 10.81-10.65 (br, 1H), 7.81 (s, 4H), 7.77 (s, 1H), 7.52 (m, J=3.5 Hz, 2H), 7.43 (m, J=3.2 Hz, 3H), 6.88 (d, J=2.5 Hz, 1H), 6.15 (s, 1H), 5.19 (s, 2H), 2.26 (s, 3H). $^{13}$C NMR (101 MHz, DMSO-$d_6$) δ 159.41, 156.22, 147.02, 146.50, 143.84, 134.75, 131.81, 130.18, 129.51, 129.00, 127.90, 127.58, 126.56, 126.00, 125.69, 123.69, 99.75, 97.51, 77.15, 17.74. LCMS $R_f$ (min)=3.499, MS m/z=441.9 $[M+H]^+$.

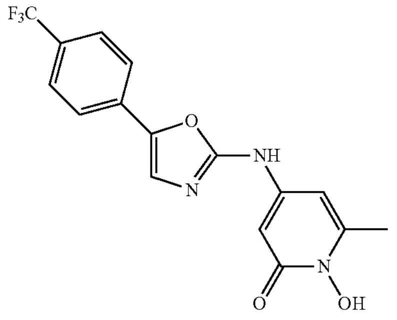 [SMILES: Cc1cc(Nc2ncc(-c3ccc(C(F)(F)F)cc3)o2)cc(=O)n1O]

1-(Benzyloxy)-6-methyl-4-((5-(4-(trifluoromethyl)phenyl)oxazol-2-yl)amino)pyridin-2(1H)-one (165 mg, 0.373 mmol) was suspended in DCM then cooled to 0° C. $BBr_3$ (0.142 mL; 1.495 mmol, 4 equiv.) was added dropwise. After 4 h of stirring at rt, LCMS indicated that all of SM had been consumed. Ice (5 g) added then $NaHCO_3$ added slowly until no gas evolved. The reaction mixture was stirred at rt for 3 h and DCM was removed in vacuo. The residue was acidified with TFA and chromatographed on preparative HPLC to provide the title compound) 52 mg, 39.60%). $^1$H NMR (401 MHz, DMSO-$d_6$) δ 10.74 (s, 1H), 7.82-7.75 (m, 4H), 7.74 (s, 1H), 6.82 (d, J=2.7 Hz, 1H), 6.24 (d, J=2.2 Hz, 1H), 2.29 (s, 3H). $^{13}$C NMR (101 MHz, DMSO-$d_6$) δ 159.13, 156.40, 146.05, 144.64, 143.68, 131.87, 127.81, 127.49, 126.56, 126.52, 126.01, 125.68, 123.60, 123.31, 98.03, 96.69, 66.82, 17.87. LCMS $R_f$ (min)=3.325, MS m/z=351.9 $[M+H]^+$. HRMS (ESI) calcd for $C_{16}H_{13}F_3N_3O_3^+$ $[M+H]^+$ 352.0904, found 352.0910.

28. N,3-Dihydroxy-N-methyl-5-((5-(4-(trifluoromethyl)phenyl)oxazol-2-yl)amino)picolinamide (Scheme 26)

Scheme 26

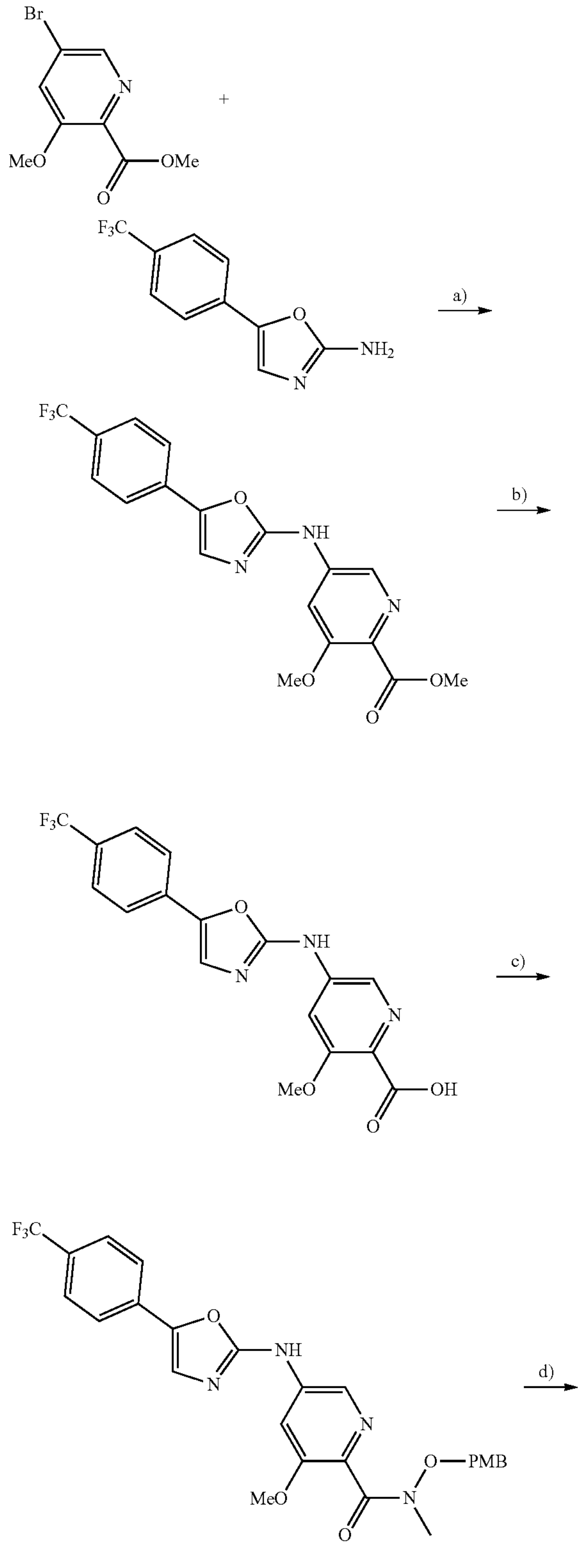

-continued

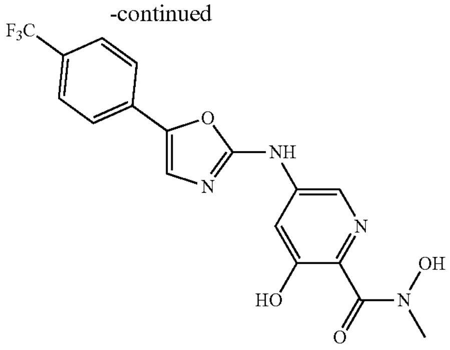

a) $Cs_2CO_3$, $Pd_2(dba)_3$, Xantphos, 1,4-dioxane, 110° C., 5 h; b) $LiOH{\bullet}H_2O$, dioxane, water, EtOH, 100° C., 3 h; c) EDCI•HCl, HOBt, DMF, rt, 16 h; d) $BBr_3$, DCM rt 4 h.

5-(4-(Trifluoromethyl)phenyl)oxazol-2-amine (Intermediate D) (0.88 g, 3.576 mmol) was reacted with methyl 5-bromo-3-methoxypicolinate as per Scheme 23 (step a) to provide methyl 3-methoxy-5-((5-(4-(trifluoromethyl)phenyl)oxazol-2-yl)amino)picolinate in 82.46% yield (1.15 g). $^1$H NMR (401 MHz, DMSO-$d_6$) δ 11.18 (s, 1H), 8.31 (s, 1H), 8.08 (s, 1H), 7.78 (s, J=5.4 Hz, 4H), 3.87 (s, 3H), 3.78 (s, 3H). $^{13}$C NMR (101 MHz, DMSO-$d_6$) δ 165.14, 156.60, 156.29, 143.79, 139.83, 131.86, 130.98, 130.14, 127.81, 127.50, 126.58, 126.01, 125.73, 123.58, 123.32, 107.23, 66.82, 56.14, 52.20. HRMS (ESI) calcd for $C_{18}H_{15}F_3N_3O_4^+$ $[M+H]^+$ 394.1009, found 394.1016. LCMS $R_f$ (min)=3.555, MS m/z=393.9 $[M+H]^+$.

Methyl 3-methoxy-5-((5-(4 (trifluoromethyl)phenyl)oxazol-2-yl)amino)picolinate (1.13 g, 2.872 mmol) was hydrolysed as per Scheme 23 (step b) to afford 3-methoxy-5-((5-(4-(trifluoromethyl)phenyl)oxazol-2-yl)amino)picolinic acid in 94.5% yield (1.03 g). $^1$H NMR (401 MHz, DMSO-$d_6$) δ 12.44 (br, 1H), 11.12 (s, 1H), 8.32 (s, 1H), 8.06 (s, 1H), 7.80 (s, 5H), 3.87 (s, 3H). $^{13}$C NMR (101 MHz, DMSO-$d_6$) δ 165.87, 156.66, 156.10, 143.75, 139.62, 131.99, 131.87, 129.74, 127.79, 127.48, 126.57, 126.53, 126.01, 125.72, 123.56, 123.31, 107.39, 56.08. LCMS $R_f$ (min)=4.057, MS m/z=379.9 $[M+H]^+$.

3-Methoxy-5-((5-(4-(trifluoromethyl)phenyl)oxazol-2-yl)amino)picolinic acid (0.5 g, 1.318 mmol) was couple with O-(4-methoxybenzyl)-N-methylhydroxylamine hydrochloride as per Scheme 23 (step c) to provide the product (3-methoxy-N-((4-methoxybenzyl)oxy)-N-methyl-5-((5-(4-(trifluoromethyl)phenyl)oxazol-2-yl)amino)picolinamide) in 85.1% yield (0.593 g). $^1$H NMR (401 MHz, DMSO-$d_6$) δ 10.96 (s, 1H), 8.34 (t, J=7.2 Hz, 1H), 8.00 (s, 1H), 7.81 (s, 4H), 7.77 (d, J=8.5 Hz, 1H), 6.93-6.83 (m, 2H), 6.79 (br, 2H), 4.71 (s, 2H), 3.81 (s, 3H), 3.67 (s, 3H), 3.32 (d, J=9.8 Hz, 3H). $^{13}$C NMR (101 MHz, DMSO-$d_6$) δ 159.92, 157.02, 152.95, 143.55, 137.83, 131.97, 131.07, 127.69, 127.37, 126.58, 126.54, 126.03, 125.80, 123.48, 123.34, 114.16, 107.28, 56.04, 55.51. LCMS $R_f$ (min)=3.650. HRMS (ESI) calcd for $C_{26}H_{24}F_3N_4O_5^+$ $[M+H]^+$ 529.1693, found 529.1699.

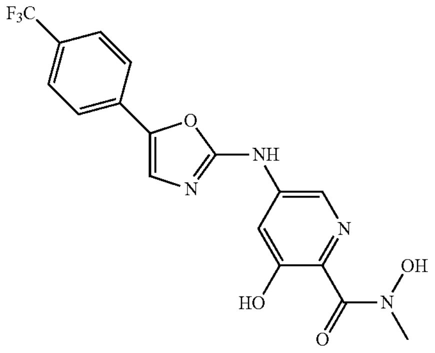 [SMILES: CN(O)C(=O)c1ncc(Nc2ncc(-c3ccc(C(F)(F)F)cc3)o2)cc1O]

3-Methoxy-N-((4-methoxybenzyl)oxy)-N-methyl-5-((5-(4-(trifluoromethyl)phenyl)-oxazol-2-yl)amino)picolinamide (193 mg, 0.365 mmol) was suspended in DCM then cooled to 0° C. $BBr_3$ (0.173 mL; 1.825 mmol, 5 equiv.) was added and the resultant mixture stirred at rt for 4 h. Reaction was deemed complete by LCMS. The reaction was quenched with 1.5 mL of sat. $NaHCO_3$ solution and solid $NaHCO_3$ added until gas evolution ceased. The mixture was stirred for 2 h at rt then DCM was removed in vacuo. The residual suspension was acidified with TFA and purified on prep HPLC. After evaporation to dryness, the title compound was collected by filtered with $H_2O$ and washed with $H_2O$ and $Et_{20}$ (73 mg, 50.69% yield). $^1H$ NMR (401 MHz, DMSO-$d_6$) δ 11.56 (s, 1H), 11.02 (s, 1H), 8.20 (d, J=1.9 Hz, 1H), 7.87 (d, J=1.8 Hz, 1H), 7.79 (s, 4H), 7.75 (d, J=7.8 Hz, 1H), 3.34 (s, 3H). $^{13}C$ NMR (101 MHz, DMSO-$d_6$) δ 163.95, 156.71, 155.16, 143.67, 138.78, 131.91, 127.72, 127.41, 126.55, 126.51, 126.02, 125.76, 123.51, 123.32, 110.94. LCMS $R_f$ (min)=3.904. HRMS (ESI) calcd for $C_{17}H_{14}F_3N_4O_4^+$ $[M+H]^+$ 395.0962, found 395.0969.

29. 6-((5-(4-(Trifluoromethyl)phenyl)oxazol-2-yl)amino)pyridine-3,4-diol (Scheme 27)

Scheme 27

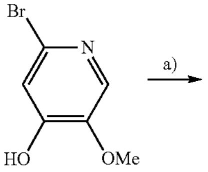

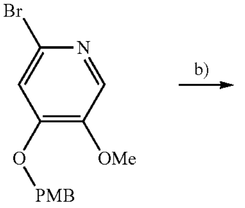

-continued

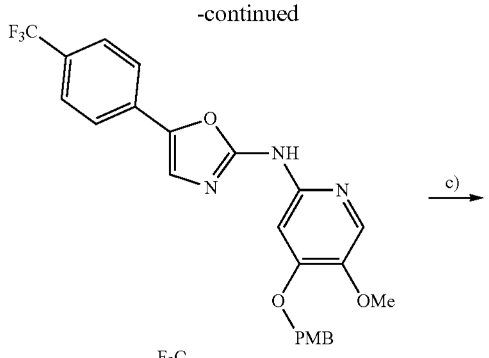

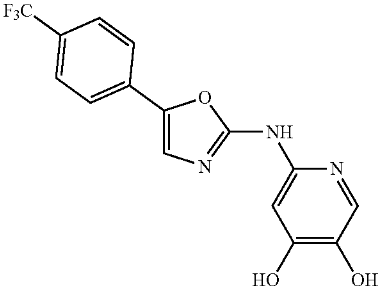

a) PMBCl, $K_2CO_3$, DMF, rt, 16 h; b) $Cs_2CO_3$, $Pd_2(dba)_3$, Xantphos, 1,4-dioxane, 110° C., 18 h; c) $BBr_3$, DCM, rt, 4 h.

2-Bromo-5-methoxypyridin-4-ol (0.35 g, 1.715 mmol) and $K_2CO_3$ (0.711 g, 5.15 mmol) were suspended in DMF then PMB-Cl (0.403 g, 2.57 mmol) added. The resultant mixture was stirred at rt overnight. The reaction was deemed complete by TLC (DCM/EtOAc 9:1). The reaction mixture was poured into sat. $NaHCO_3$ solution and the product extracted with EtOAc (5×). The combined organic phases were dried over $MgSO_4$ and evaporated to dryness. The residue was purified on silica gel using a mixture of DCM and EtOAc as eluents to provide 2-bromo-5-methoxy-4-((4-methoxybenzyl)oxy)pyridine (0.356 g, 64.01% yield). $^1H$ NMR (401 MHz, $CDCl_3$) δ 7.85 (s, 1H), 7.34 (d, J=8.7 Hz, 2H), 6.97 (s, 1H), 6.92 (d, J=8.7 Hz, 2H), 5.06 (s, 2H), 3.88 (s, 3H), 3.81 (s, 3H). $^{13}C$ NMR (101 MHz, $CDCl_3$) δ 159.92, 155.84, 146.23, 133.58, 133.07, 129.39, 126.89, 114.25, 111.79, 70.80, 56.76, 55.34. LCMS $R_f$ (min)=3.775, MS m/z=345.9/347.9 $[M+Na]^+$.

An oven-dried RBF was charged with $Pd_2(dba)_3$ (0.090 g, 0.10 equiv.), Xantphos (0.114 g, 0.2 equiv.), 5-(4-(trifluoromethyl)phenyl)oxazol-2-amine (Intermediate D) (0.281 g, 1.233 mmol, 1.25 equiv.), $Cs_2CO_3$ (0.482 g, 1.5 equiv.), 2-bromo-5-methoxy-4-((4-methoxybenzyl)oxy)pyridine (0.32 g, 0.987 mmol) and 1,4-dioxane (5 mL). Vacuum was applied briefly to the reaction flask followed by backfilling with $N_2$ and the procedure was repeated 5 times. The mixture was then heated to 110° C. and stirred for 18 h. The reaction mixture was poured into $H_2O$, acidify with 1N HCl (pH 4-5), extracted with EtOAc (5×). The combined organic phases were dried over $MgSO_4$, evaporated to dryness. The residue was chromatographed on silica gel using mixtures of DCM/EtOAc as eluents to provide N-(5-methoxy-4-((4-methoxybenzyl)oxy)pyridin-2-yl)-5-(4-(trifluoromethyl)phenyl)oxazol-2-amine (0.083 g, 17.83% yield). $^1H$ NMR (401 MHz, DMSO-$d_6$) δ 10.83 (s, 1H), 7.95-7.85 (br, 2H), 7.82-7.76 (m, 4H), 7.75 (s, 1H), 7.45 (d, J=8.7 Hz, 2H), 6.97 (d, J=8.7 Hz, 2H), 5.11 (s, 2H), 3.78 (s, 3H), 3.76 (s, 3H). LCMS $R_f$ (min)=3.619. HRMS (ESI) calcd for $C_{24}H_{21}F_3N_3O_4^+$ $[M+H]^+$ 472.1479, found 472.1473.

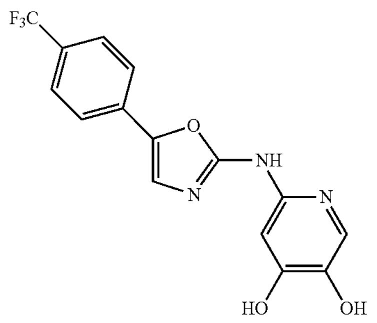 [SMILES: Oc1cnc(Nc2ncc(-c3ccc(C(F)(F)F)cc3)o2)cc1O]

N-(5-Methoxy-4-((4-methoxybenzyl)oxy)pyridin-2-yl)-5-(4-(trifluoromethyl)phenyl)oxazol-2-amine (0.077 g, 0.163 mmol) was suspended in DCM and cooled to 0° C. $BBr_3$ (4 equiv.) was added dropwise. After 4 h of stirring at rt, LCMS indicated that all starting material had been consumed. The volatiles were removed and the residue quenched with sat. $NaHCO_3$ solution and MeOH for 1 h. The volatiles were removed and the residue chromatographed on preparative HPLC to provide the title compound (0.042 g, 76.24% yield). $^1H$ NMR (401 MHz, DMSO-$d_6$) δ 7.87 (s, 1H), 7.82 (s, 5H), 7.73 (s, 1H), 7.15 (s, 1H). $^{13}C$ NMR (101 MHz, DMSO-$d_6$) δ 155.76, 143.66, 140.34, 131.60, 128.06, 127.74, 126.56, 126.52, 125.98, 123.71, 123.28, 99.42. LCMS $R_f$ (min)=3.333. HRMS (ESI) calcd for $C_{15}H_{11}F_3N_3O_3^+$ $[M+H]^+$ 338.0747, found 338.0751.

30. 3-Hydroxy-4-((5-((5-(4-(trifluoromethyl)phenyl)oxazol-2-yl)amino)pyridin-2-yl)amino)cyclobut-3-ene-1,2-dione (Scheme 28)

Scheme 28

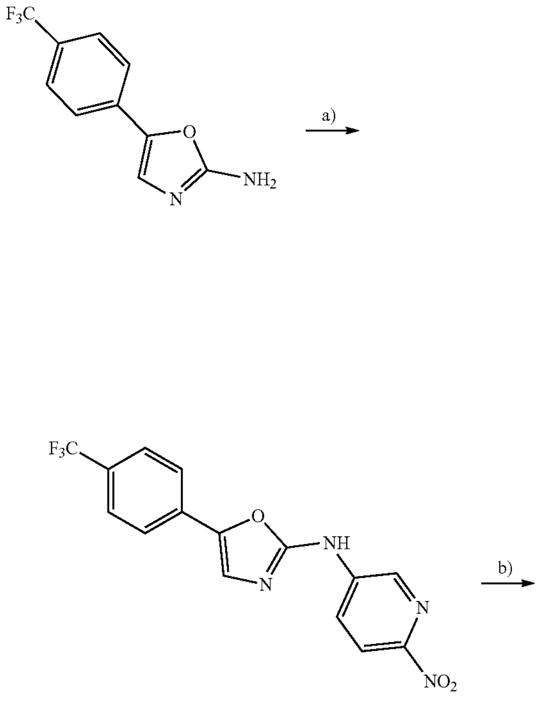

-continued

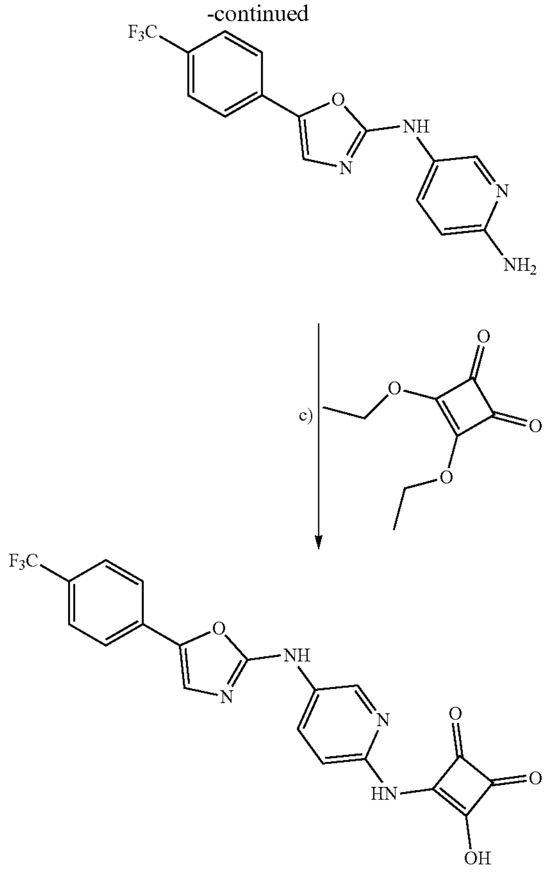

a) 5-bromo-2-nitropyridine, $Pd_2(dba)_3$, Xantphos, $K_3PO_4$, 1,4-dioxane, 100° C., 16 h; b) 10% Pd/C, $H_2$ (balloon), MeOH, rt, 16 h; c) $Et_3N$, reflux, 16 h.

A re-sealable Schlenk tube was charged with $Pd_2(dba)_3$ (0.05 equiv.), Xantphos (0.1 equiv.), 5-(4-(trifluoromethyl)phenyl)oxazol-2-amine (Intermediate D) (1.2 equiv.), $K_3PO_4$ (1.4 equiv.), 5-bromo-2-nitropyridine (0.102 g) and 1,4-dioxane (3.0 mL). After the mixture was degassed and carefully subjected to three cycles of evacuation and back-filling with $N_2$, reaction mixture was heated at 100° C. overnight under $N_2$ atmosphere. The mixture was cooled, diluted with EtOAc (50 mL) and washed with brine (20 mL). The organic layer was separated, dried ($MgSO_4$), filtered and concentrated under reduced pressure to obtain the crude product, which was purified on a $SiO_2$ column using a Reveleris X2 flash chromatography system (EtOAc:petroleum spirit=1:1) to obtain N-(6-nitropyridin-3-yl)-5-(4-(trifluoromethyl)phenyl)oxazol-2-amine as a brown solid (130 mg, 74% yield). $^1H$ NMR (401 MHz, DMSO-$d_6$) δ 11.63 (s, 1H), 8.75 (d, J=2.5 Hz, 1H), 8.48 (dd, J=9.0, 2.6 Hz, 1H), 8.40 (d, J=9.0 Hz, 1H), 7.97-7.74 (m, 5H).

(Intermediate H—$N_5$-(5-(4-(trifluoromethyl)phenyl)oxazol-2-yl)pyridine-2,5-diamine) To a solution of N-(6-nitropyridin-3-yl)-5-(4-(trifluoromethyl)phenyl)oxazol-2-amine (0.11 g) in MeOH (5.0 mL) was added 10% Pd/C (0.15 g). The mixture was stirred under a hydrogen atmosphere (balloon) overnight. After completion, the reaction mixture was filtered through a pad of celite and the filtrate was concentrated under reduced pressure to obtain the crude product, which was purified on a $SiO_2$ column (MeOH:DCM=0.05-1:10) to obtain $N_5$-(5-(4-(trifluoromethyl)phenyl)oxazol-2-yl)pyridine-2,5-diamine as a light brown solid (70 mg, 70% yield). $^1H$ NMR (401 MHz, DMSO-$d_6$) δ 9.97

(s, 1H), 8.15 (d, J=2.4 Hz, 1H), 7.78-7.72 (m, 4H), 7.66 (dd, J=8.8, 2.8 Hz, 1H), 7.63 (s, 1H), 6.48 (d, J=8.8 Hz, 1H), 5.67 (s, 2H). $^{13}$C NMR (101 MHz, DMSO-$d_6$) δ 158.2, 155.7, 142.2, 137.8, 131.9, 128.6, 126.6, 126.3, 126.03, 126.0, 125.7, 125.6, 122.9, 122.5, 107.9. LCMS $R_f$ (min)=3.04. HRMS (ESI) calcd for $C_{15}H_{12}F_3N_4O^+$ [M+H]$^+$ 321.0958, found 321.0966.

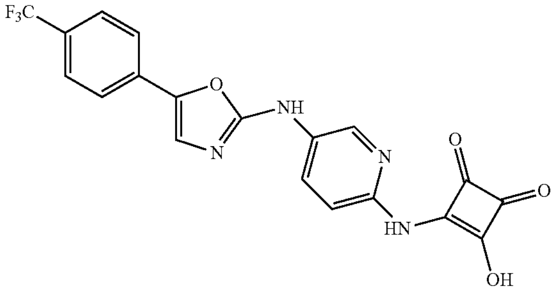 [SMILES: O=c1c(O)c(Nc2ccc(Nc3ncc(-c4ccc(C(F)(F)F)cc4)o3)cn2)c1=O]

N$^5$-(5-(4-(Trifluoromethyl)phenyl)oxazol-2-yl)pyridine-2,5-diamine (0.080 g, 0.249 mmol) was stirred with 3,4-diethoxycyclobut-3-ene-1,2-dione (0.064 g, 0.374 mmol) in EtOH (3 mL) and $Et_3N$ (0.041 mL, 0.299 mmol) at reflux overnight. The solvents were removed in vacuo and the residual mixture was purified using preparative HPLC to provide the title compound (0.073 g, 70.2% yield). $^1$H NMR (401 MHz, DMSO-$d_6$) δ 11.50 (s, 1H), 10.94 (s, 1H), 8.72 (s, 1H), 8.17 (d, J=7.3 Hz, 1H), 7.78 (s, 4H), 7.74 (s, 1H), 7.39 (d, J=7.3 Hz, 1H). LCMS $R_f$(min)=3.672. HRMS (ESI) calcd for $C_{19}H_{12}F_3N_4O_4^+$ [M+H]$^+$ 417.0805, found 417.0805.

31. N',3-Dihydroxy-5-((1-(4-(trifluoromethyl)phenyl)-1H-1,2,4-triazol-3-yl)amino)picolinimidamide (Scheme 29)

Scheme 29

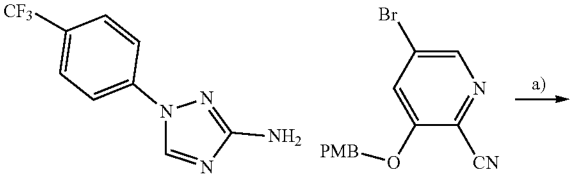

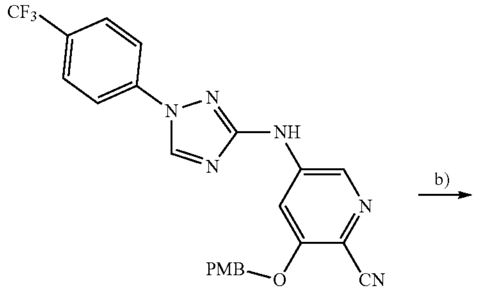

-continued

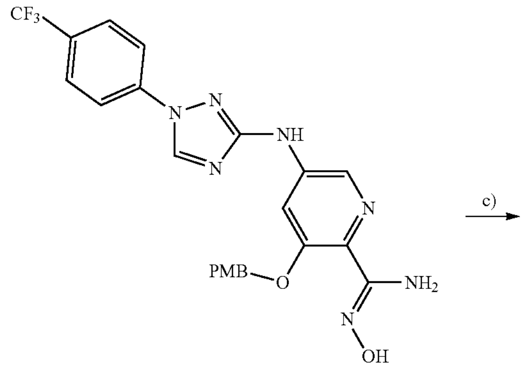

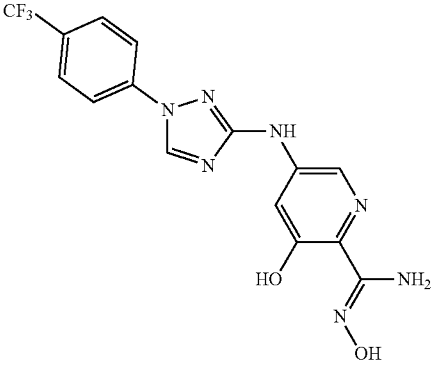

a) $Cs_2CO_3$, $Pd_2(dba)_3$, Xantphos, 1,4-dioxane, 110° C., 5 h; b) $NH_2OH$•HCl, $Et_3N$, EtOH, relfux, 16 h; c) TFA, $Et_3SiH$, rt, 1 h.

1-(4-(Trifluoromethyl)phenyl)-1H-1,2,4-triazol-3-amine (Intermediate F) (0.3 g, 1.314 mmol) was reacted with 5-bromo-3-((4-methoxybenzyl)oxy)picolinonitrile (Intermediate G) (0.419 g, 1.314 mmol) as per Scheme 24 (step b) to provide the product, 3-((4-methoxybenzyl)oxy)-5-((1-(4-(trifluoromethyl)phenyl)-1H-1,2,4-triazol-3-yl)amino)picolinonitrile in 80.4% yield (0.493 g). $^1$H NMR (401 MHz, DMSO-$d_6$) δ 10.60 (s, 1H), 9.35 (s, 1H), 8.37 (s, 1H), 8.11 (s, 1H), 8.06 (d, J=7.5 Hz, 2H), 7.93 (d, J=7.7 Hz, 2H), 7.44 (d, J=7.6 Hz, 2H), 6.95 (d, J=7.7 Hz, 2H), 5.27 (s, 2H), 3.74 (s, 3H). $^{13}$C NMR (101 MHz, DMSO-$d_6$) δ 160.20, 159.77, 159.11, 142.79, 139.85, 133.15, 130.05, 127.83, 127.73, 127.54, 127.50, 125.79, 123.09, 119.24, 116.87, 114.44, 112.35, 106.44, 70.39, 66.82, 55.55. LCMS $R_f$(min)=3.484, MS m/z=467.0 [M+H]$^+$.

3-((4-Methoxybenzyl)oxy)-5-((1-(4-(trifluoromethyl)phenyl)-1H-1,2,4-triazol-3-yl)amino)picolinonitrile (0.471 g, 1.01 mmol) was reacted as per Scheme 24 (step c) to provide N'-hydroxy-3-((4-methoxybenzyl)oxy)-5-((1-(4-(trifluoromethyl)phenyl)-1H-1,2,4-triazol-3-yl)amino)picolinimidamide in 93% yield (0.469 g). $^1$H NMR (401 MHz, DMSO-$d_6$) δ 10.00 (s, 1H), 9.59 (s, 1H), 9.29 (s, 1H), 8.42 (s, 1H), 8.04 (s, 2H), 7.92 (s, 3H), 7.45 (s, 2H), 6.92 (s, 2H), 5.59 (s, 2H), 5.17 (s, 2H), 3.72 (s, 3H). $^{13}$C NMR (101 MHz, DMSO-$d_6$) δ 160.90, 159.27, 153.65, 150.45, 142.67, 140.02, 139.28, 132.66, 129.58, 129.29, 129.08, 127.53, 127.50, 127.41, 127.09, 125.85, 123.15, 118.97, 114.23, 108.94, 69.87, 55.48. LCMS $R_f$(min)=3.067. HRMS (ESI) calcd for $C_{23}H_{21}F_3N_7O_3^+$ [M+H]$^+$, 500.1652 found 500.163.

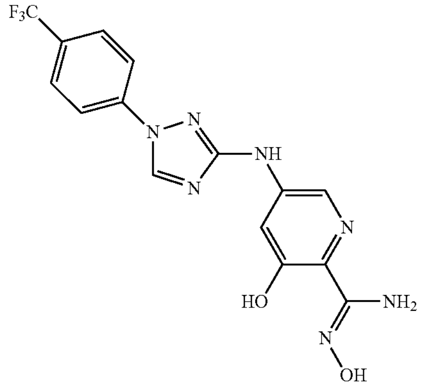 [SMILES: N/C(=N\O)c1ncc(Nc2ncn(-c3ccc(C(F)(F)F)cc3)n2)cc1O]

N'-hydroxy-3-((4-methoxybenzyl)oxy)-5-((1-(4-(trifluoromethyl)phenyl)-1H-1,2,4-triazol-3-yl)amino)picolinimidamide (0.45 g, 0.90 mmol) was deprotected as per Scheme 24 (step d) to provide the title compound in 38.33% yield (0.131 g). $^1$H NMR (401 MHz, DMSO-$d_6$) δ 10.43 (brs, 1H), 10.22 (s, 1H), 9.33 (s, 1H), 8.34 (s, 1H), 8.10 (d, J=7.8 Hz, 2H), 7.94 (d, J=7.5 Hz, 2H), 7.88 (s, 1H), 7.19 (brs, 2H). $^{13}$C NMR (101 MHz, DMSO-$d_6$) δ 160.65, 155.36, 154.95, 142.72, 141.06, 140.01, 130.26, 127.55, 127.18, 125.83, 123.13, 118.99, 109.80. LCMS $R_f$ (min)=3.072. HRMS (ESI) calcd for $C_{15}H_{13}F_3N_7O_2^+$ [M+H]$^+$, 380.1077 found 380.1085.

32. N-Ethyl-N-hydroxy-5-((5-(4-(trifluoromethyl)phenyl)oxazol-2-yl)amino)picolinamide (Scheme 30)

Scheme 30

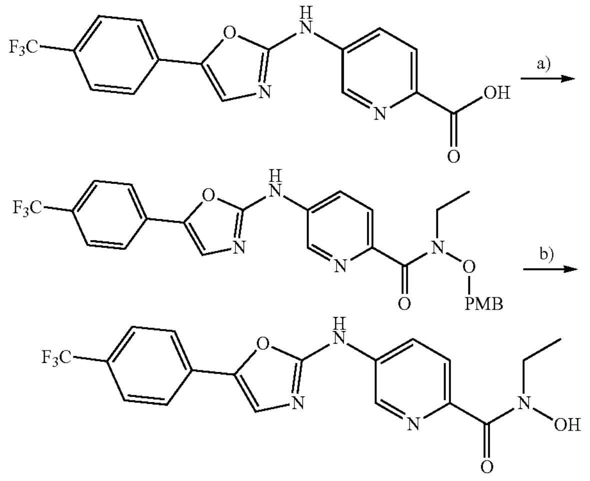

a) EDCI•HCl, HOBt, DMF, rt, 16 h; b) TFA, $Et_3SiH$, rt, 5 h.

5-((5-(4-(Trifluoromethyl)phenyl)oxazol-2-yl)amino)picolinic acid (Intermediate B) (0.31 g, 0.89 mmol) was added to a solution of HOBt (0.12 g, 1.07 mmol) and EDCI·HCl (0.19 g, 0.98 mmol) in anhydrous DMF (15 mL). The resulting mixture was stirred at rt for 3 h under $N_2$. N-Ethyl-O-(4-methoxybenzyl)hydroxylamine (0.19 g, 1.07 mmol) was then added to the mixture and allowed to stir for a further 16 h. The reaction mixture was quenched with aq. $NaHCO_3$ solution (20 mL) and diluted with EtOAc (20 mL). The organic layer was extracted with EtOAc (3×25 mL). The combined organic fractions were dried over $MgSO_4$, filtered and concentrated under reduced pressure. The residue was chromatographed on silica gel eluting with 50% EtOAc in DCM to afford N-ethyl-N-((4-methoxybenzyl)oxy)-5-((5-(4-(trifluoromethyl)phenyl)oxazol-2-yl)amino)picolinamide as an off-white solid (0.243 g, 53% yield). $^1$H NMR (400 MHz, DMSO-$d_6$) δ 11.04 (s, 1H), 8.81 (d, J=2.4 Hz, 1H), 8.24 (dd, J=8.6, 2.6 Hz, 1H), 7.80 (s, 4H), 7.77 (s, 1H), 7.66 (d, J=8.1 Hz, 1H), 7.20 (d, J=8.3 Hz, 2H), 6.88 (d, J=8.5 Hz, 2H), 4.92 (s, 2H), 3.77 (q, J=7.0 Hz, 2H), 3.72 (s, 3H), 1.18 (t, J=7.0 Hz, 3H). $^{13}$C NMR (100 MHz, DMSO-$d_6$) δ 159.90, 156.87, 146.18, 143.66, 137.55, 137.39, 131.96, 131.28, 127.70, 127.39, 126.03, 125.79, 123.77, 123.50, 123.33, 114.16, 75.62, 67.86, 55.58, 55.54, 40.00. LCMS $R_f$ (min)=3.65, MS m/z 513.0 [M+H]$^+$.

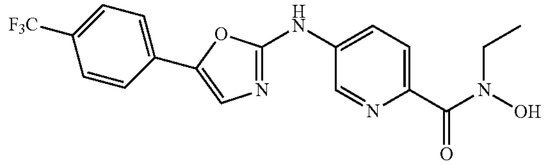 [SMILES: CCN(O)C(=O)c1ccc(Nc2ncc(-c3ccc(C(F)(F)F)cc3)o2)cn1]

N-Ethyl-N-((4-methoxybenzyl)oxy)-5-((5-(4-(trifluoromethyl)phenyl)oxazol-2-yl)amino)picolinamide (0.20 g, 0.39 mmol) was dissolved in TFA (4.0 mL) and $Et_3SiH$ (0.4 mL) and the mixture was stirred at rt for 5 h. The volatiles were then removed under reduced pressure and the residue was directly subjected to preparative HPLC using 0.1% TFA in $H_2O$ and 0.1% TFA in ACN as eluents to yield the title compound as bright yellow solid (0.14 g, 92%). $^1$H NMR (400 MHz, DMSO-$d_6$) δ 11.04 (s, 1H), 8.79 (s, 1H), 8.24 (dd, J=8.6, 2.4 Hz, 1H), 7.80 (s, 4H), 7.76 (s, 1H), 7.71 (d, J=7.8 Hz, 1H), 3.71 (dd, J=13.6, 6.7 Hz, 2H), 1.19 (t, J=7.0 Hz, 3H). $^{13}$C NMR (100 MHz, DMSO-$d_6$) δ 156.84, 143.66, 137.19, 131.94, 128.82, 128.72, 127.71, 127.39, 126.02, 125.77, 124.01, 123.51, 69.00, 40.89. LCMS $R_f$(min)=3.68, MS m/z 393.9 [M+H]$^+$. HRMS (ESI) calcd for $C_{18}H_{16}F_3N_4O_3^+$ [M+H]$^+$ 393.1169, found 393.1172.

33. N-Hydroxy-N-propyl-5-((5-(4-(trifluoromethyl)phenyl)oxazol-2-yl)amino)picolinamide (Scheme 31)

Scheme 31

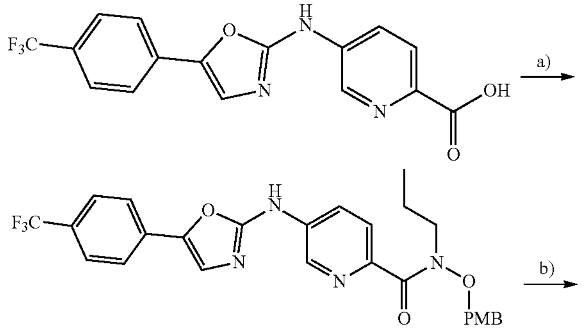

-continued

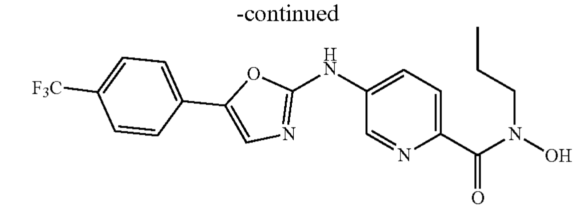

a) EDCI•HCl, HOBt, DMF, rt, 16 h; b) TFA, $Et_3SiH$, rt, 6 h.

5-((5-(4-(Trifluoromethyl)phenyl)oxazol-2-yl)amino)picolinic acid (Intermediate B) (0.132 g, 0.38 mmol) HOBt (0.053 g, 0.45 mmol) and EDCl·HCl (0.080 g, 0.42 mmol) were added into a dry RBF and stirred with anhydrous DMF (6.5 mL) for 3 h with continuous flow of $N_2$. N-Propyl-O-(4-methoxybenzyl)hydroxylamine (0.089 g, 0.45 mmol) was then added to the reaction mixture and stirring was continued for 16 h. After this period of time the reaction was quenched with aq. $NaHCO_3$ solution (10 mL) and diluted with EtOAc (10 mL). The organic layer was extracted with EtOAc (3×10 mL) and the combined organics were dried over $MgSO_4$. The mixture was filtered, concentrated under reduced pressure and the crude material (0.112 g) was used in the next step without further purification. LCMS $R_f$ (min)=3.69, MS m/z 527.0 $[M+H]^+$.

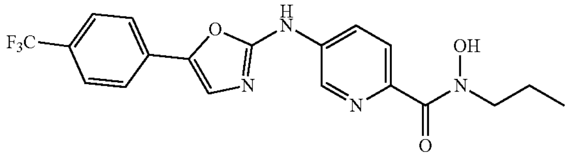 [SMILES: CCCN(O)C(=O)c1ccc(Nc2ncc(-c3ccc(C(F)(F)F)cc3)o2)cn1]

TFA (2.5 mL) and $Et_3SiH$ (0.3 mL) were combined with crude N-((4-methoxybenzyl)oxy)-N-propyl-5-((5-(4-(trifluoromethyl)phenyl)oxazol-2-yl)amino)picolinamide (0.112 g) and the resulting mixture was stirred at rt for 6 h. The volatiles were removed under reduced pressure and the residue was directly subjected to preparative HPLC using 0.1% TFA in $H_2O$ and 0.1% TFA in ACN as eluents to yield the title compound as bright yellow solid (0.082 g, 54% over two steps). $^1H$ NMR (400 MHz, DMSO-$d_6$) δ 11.01 (s, 1H), 8.78 (d, J=2.4 Hz, 1H), 8.23 (dd, J=8.6, 2.3 Hz, 1H), 7.80 (s, 4H), 7.77 (s, 1H), 7.68 (d, J=7.5 Hz, 1H), 3.66 (t, J=6.0 Hz, 2H), 1.73-1.54 (m, 2H), 0.86 (t, J=8.0 Hz, 3H). $^{13}C$ NMR (100 MHz, DMSO-$d_6$) δ 156.88, 143.63, 137.28, 137.10, 132.15, 131.95, 127.70, 127.38, 126.03, 125.79, 123.50, 66.82, 11.44. LCMS $R_f$(min)=3.39, MS m/z 407.0 $[M+H]^+$. HRMS (ESI) calcd for $C_{19}H_{18}F_3N_4O_3^+$ $[M+H]^+$ 407.1326, found 407.1336.

34. N-Hydroxy-N-isopropyl-5-((5-(4-(trifluoromethyl)phenyl)oxazol-2-yl)amino)picolinamide (Scheme 32)

Scheme 32

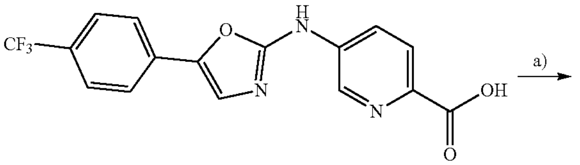

-continued

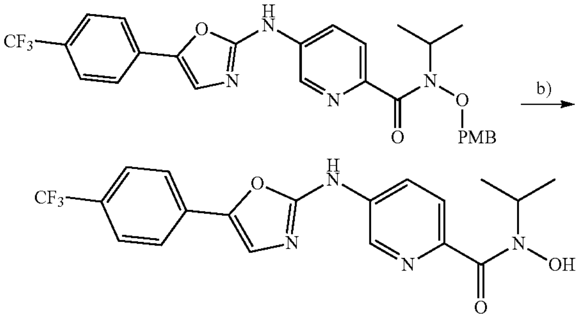

a) EDCI•HCl, HOBt, DMF, rt, 16 h; b) TFA, $Et_3SiH$, rt, 6 h.

5-((5-(4-(Trifluoromethyl)phenyl)oxazol-2-yl)amino)picolinic acid (0.086 g) was converted to N-isopropyl-N-((4-methoxybenzyl)oxy)-5-((5-(4-(trifluoromethyl)phenyl)oxazol-2-yl)amino)picolinamide as per Scheme 31 (step a). The crude product used in the next step without further purification. LCMS $R_f$(min)=3.51, MS m/z=527.0 $(M+H)^+$.

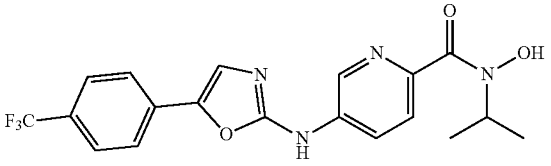 [SMILES: CC(C)N(O)C(=O)c1ccc(Nc2ncc(-c3ccc(C(F)(F)F)cc3)o2)cn1]

TFA (2.0 mL) and $Et_3SiH$ (0.2 mL) were added into a RBF with the crude N-isopropyl-N-((4-methoxybenzyl)oxy)-5-((5-(4-(trifluoromethyl)phenyl)oxazol-2-yl)amino)picolinamide and the resulting mixture was stirred at rt for 6 h. The volatiles were removed under reduced pressure and the residue was directly subjected to preparative HPLC using 0.1% TFA in $H_2O$ and 0.1% TFA in ACN as eluents to yield N-hydroxy-N-isopropyl-5-((5-(4-(trifluoromethyl)phenyl)oxazol-2-yl)amino)picolinamide as bright yellow solid (0.064 g, 37% over two steps). $^1H$ NMR (400 MHz, DMSO-$d_6$) δ 11.02 (s, 1H), 8.79 (s, 1H), 8.23 (dd, J=8.6, 2.4 Hz, 1H), 7.80 (s, 4H), 7.76 (s, 1H), 7.67 (d, J=8.5 Hz, 1H), 4.58 (s, 1H), 1.17 (d, J=6.6 Hz, 6H). $^{13}C$ NMR (100 MHz, DMSO) δ 156.70, 143.45, 131.78, 127.52, 127.20, 126.39, 126.35, 125.85, 125.61, 123.32, 123.15, 40.72, 39.52. LCMS $R_f$(min)=3.37, MS m/z 407.0 $(M+H)^+$. HRMS (ESI) calcd for $C_{19}H_{18}F_3N_4O_3^+$ $(M+H)^+$ 407.1326, found 407.1338.

35. 1-Hydroxy-1-methyl-3-(5-((5-(4-(trifluoromethyl)phenyl)oxazol-2-yl)amino)pyridin-2-yl)urea (Scheme 33)

Scheme 33

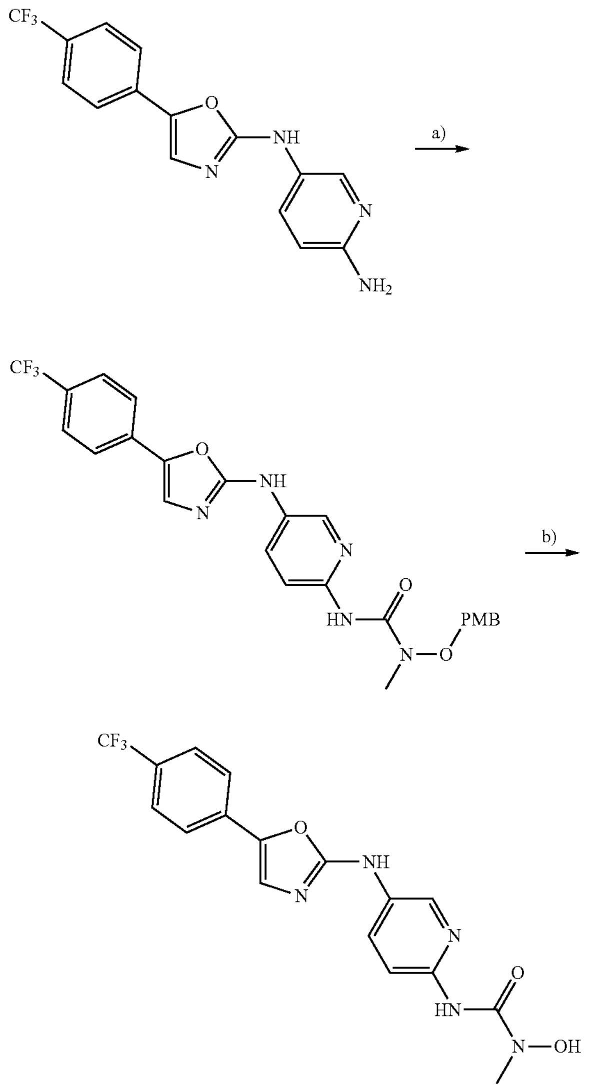

a) i. triphosgene, DIPEA, DCM, rt, 16 h; ii. O-PMB-N-methylhydroxylamine, DIPEA, 16 h; (b) TFA, $Et_3SiH$, rt, 5 h.

$N^5$-(5-(4-(Trifluoromethyl)phenyl)oxazol-2-yl)pyridine-2,5-diamine (Intermediate H) (0.1 g, 0.312 mmol) was suspended in dry DCM (6 mL), and triphosgene (0.037 g, 0.124 mmol) and DIPEA (0.080 g, 0.624 mmol) were added. The resulting mixture was stirred overnight at rt. O-(4-Methoxybenzyl)-N-methylhydroxylamine and DIPEA (2 equiv. each) were added and the reaction was stirred at rt overnight. The reaction mixture was quenched with sat. $NaHCO_3$ (aq.) and was extracted with EtOAc (3×). The organic solutions were combined, dried over $MgSO_4$ and evaporated to dryness. The residue was chromatographed on silica gel with neat EtOAc to provide 1-((4-methoxybenzyl)oxy)-1-methyl-3-(5-((5-(4-(trifluoromethyl)phenyl)oxazol-2-yl)amino)pyridin-2-yl)urea (34 mg, 21.2% yield). $^1H$ NMR (400 MHz, $CDCl_3$) δ 8.65 (s, 1H), 8.12 (d, J=8.9 Hz, 1H), 7.56 (s, 1H), 7.49 (s, 4H), 7.33-7.29 (m, 2H), 7.23 (d, J=8.7 Hz, 1H), 6.75 (d, J=8.2 Hz, 2H), 4.83 (s, 2H), 3.65 (s, 3H), 2.97 (s, 3H). $^{13}C$ NMR (100 MHz, DMSO-$d_6$) δ 159.42, 156.39, 145.71, 143.18, 137.07, 136.92, 131.48, 130.80, 128.65, 128.25, 127.23, 126.91, 125.55, 125.31, 123.30, 123.03, 122.85, 113.69, 75.15, 55.06, 39.52, 33.23. LCMS $R_f$ (min)=4.09, MS m/z 514.1 $[M+H]^+$. HRMS (ESI) calcd for $C_{25}H_{23}F_3N_5O_4^+$ $[M+H]^+$ 514.1697, found 514.1683.

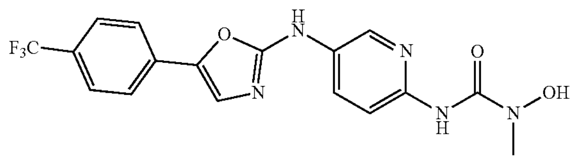 [SMILES: CN(O)C(=O)Nc1ccc(Nc2ncc(-c3ccc(C(F)(F)F)cc3)o2)cn1]

1-((4-Methoxybenzyl)oxy)-1-methyl-3-(5-((5-(4-(trifluoromethyl)phenyl)oxazol-2-yl)amino)pyridin-2-yl)urea (0.034 g, 0.066 mmol) was dissolved in TFA (1.0 mL) and $Et_3SiH$ (0.1 mL) and the mixture was stirred at rt for 5 h. The volatiles were then removed under reduced pressure and the residue was directly subjected to preparative HPLC using 0.1% TFA in $H_2O$ and 0.1% TFA in ACN as eluents to yield the title product as bright yellow solid (24.14 mg, 93% yield). $^1H$ NMR (400 MHz, DMSO-$d_6$) δ 10.70 (s, 1H), 10.13 (s, 1H), 9.20 (s, 1H), 8.57 ((d, J=1.4 Hz, 1H), 8.07 (dd, J=9.1, 2.5 Hz, 1H), 7.85 (d, J=9.2 Hz, 1H), 7.72 (s, 4H), 7.66 (s, 1H), 3.07 (s, 3H). $^{13}C$ NMR (100 MHz, DMSO-$d_6$) δ 156.80, 156.51, 145.47, 142.89, 131.65, 131.58, 127.06, 126.74, 126.06, 126.02, 125.57, 125.35, 122.87, 113.50, 66.35, 39.52, 37.38. LCMS $R_f$ (min)=3.62, MS m/z 393.9 $[M+H]^+$. HRMS (ESI) calcd for $C_{17}H_{15}F_3N_5O_3^+$ $[M+H]^+$ 394.1122, found 394.1141.

36. (R)—N-(2,3-Dihydroxypropyl)-5-((5-(4-(trifluoromethyl)phenyl)oxazol-2-yl)amino)picolinamide (Scheme 34)

Scheme 34

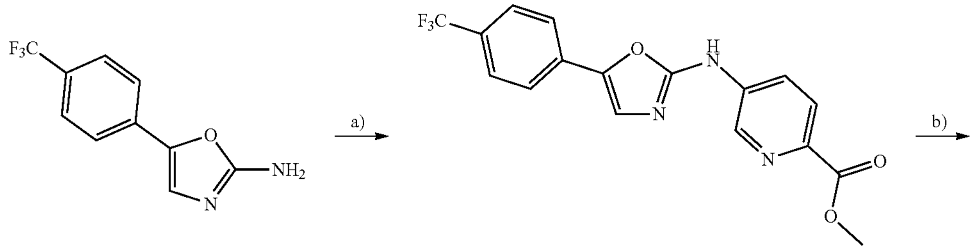

-continued

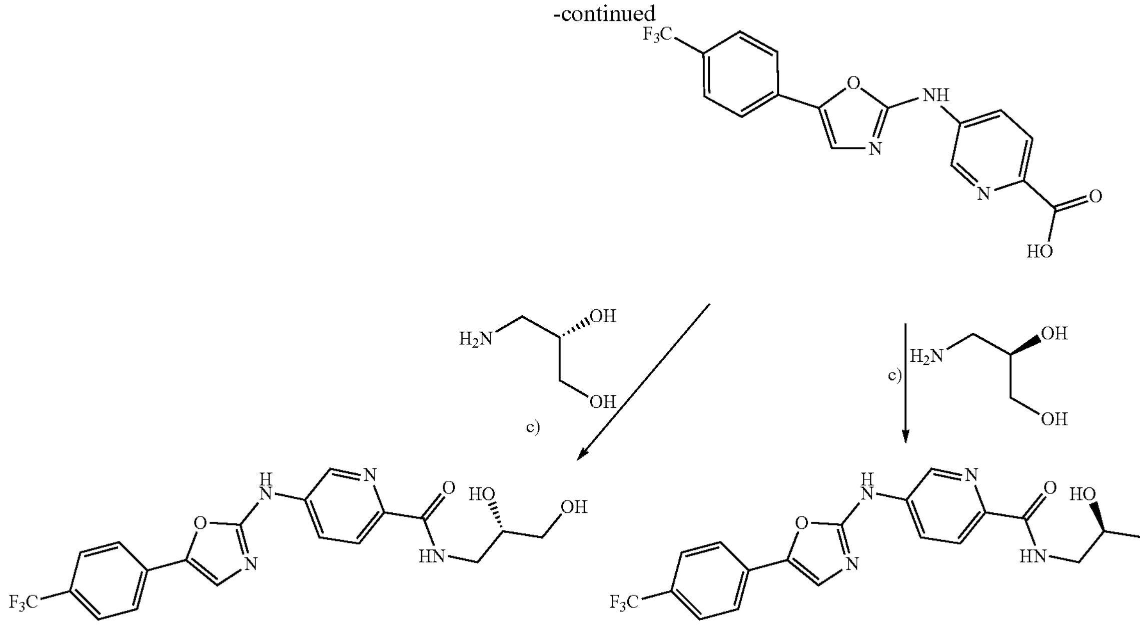

a) methyl 5-bromopicolinate, $Pd_2(dba)_3$, Xantphos, $K_3PO_5$, 1,4-dioxane, 140° C., 15 h; b) LiOH•HCl, 1,4-dioxane:EtOH:$H_2O$ (1:1:1), reflux, 3 h; c) DMF, EDCl, HOBt, rt, 15 h.

A re-sealable Schlenk tube was charged with $Pd_2(dba)_3$ (0.02 equiv.), Xantphos (0.06 equiv.), 5-(4-(trifluoromethyl) phenyl)oxazol-2-amine (Intermediate D) (1.2 equiv.), $K_3PO_4$ (fine powder, 1.4 equiv.), methyl 5-bromopicolinate (0.250 g, 1.152 mmol) and 1,4-dioxane (4 mL). After the mixture was degas sed and carefully subjected to three cycles of evacuation and backfilling with $N_2$, the reaction mixture was heated at 140° C. for 15 h under a $N_2$ atmosphere. The reaction mixture was cooled, diluted with EtOAc (30 mL) and washed with $H_2O$ (20 mL). The aq. layer was then back-extracted with EtOAc (2×15 mL). The combined organics were concentrated in vacuo to obtain the crude product. This was purified on a $SiO_2$ column (EtOAc: toluene=1:1) to give methyl 5-((5-(4-(trifluoromethyl)phenyl)oxazol-2-yl)amino)picolinate as a white solid (0.21 g, 49.8% yield). $^1$H NMR (400 MHz, DMSO-$d_6$) δ 11.04 (s, 1H), 8.90 (d, J=2.5 Hz, 1H), 8.44 (s, 1H), 8.36 (dd, J=8.7, 2.6 Hz, 1H), 8.08 (d, J=8.6 Hz, 1H), 8.00 (d, J=8.1 Hz, 2H), 7.78 (d, J=8.4 Hz, 2H), 3.85 (s, 3H). $^{13}$C NMR (101 MHz, DMSO-$d_6$) δ 164.2, 155.5, 149.5, 144.3, 138.0, 135.7, 135.68, 134.91, 131.2, 125.7, 125.6, 125.5. LCMS $R_f$(min)=3.907, MS m/z 363.8 $[M+H]^+$.

LiOH·$H_2O$ (3 equiv.) in $H_2O$ (2 mL) was added to a solution of methyl 5-((5-(4-(trifluoromethyl)phenyl)oxazol-2-yl)amino)picolinate (0.180 g, 0.495 mmol) in 1,4-dioxane (2 mL) and EtOH (2 mL) and the reaction mixture was refluxed for 3 h. The volatile solvents were removed in vacuo and to the obtained suspension was added brine (2 mL), followed by 6M HCl (2 mL) dropwise at 0° C. The resulting precipitate was filtered and washed with $H_2O$ (2×2 mL), providing 5-((5-(4-(trifluoromethyl)phenyl)oxazol-2-yl)amino)picolinic acid as a yellow solid (0.240 g, 99.8% yield). $^1$H NMR (400 MHz, DMSO-$d_6$) δ 11.01 (s, 1H), 8.90 (d, J=2.4 Hz, 1H), 8.46 (s, 1H), 8.34 (dd, J=8.6, 2.6 Hz, 1H), 8.07 (d, J=8.6 Hz, 1H), 8.02 (d, J=8.0 Hz, 2H), 7.81 (d, J=8.2 Hz, 2H). LCMS $R_f$ (min)=3.578, MS m/z 349.8 $[M+H]^+$.

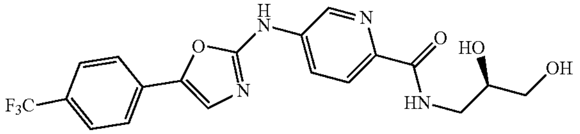 [SMILES: O=C(NC[C@@H](O)CO)c1ccc(Nc2ncc(-c3ccc(C(F)(F)F)cc3)o2)cn1]

5-((5-[4-(Trifluoromethyl)phenyl]-1,3-oxazol-2-yl) amino)picolic acid (0.15 g) was suspended in DMF (3.0 mL), and EDCI (1.3 equiv.) and HOBt (1.4 equiv.) were added. The resulting mixture was stirred at rt for 1 h. (R)-3-Aminopropane-1,2-diol (2.0 equiv.) was then added to the reaction mixture and stirring was continued overnight. The reaction mixture was concentrated under reduced pressure to obtain a gummy solid, which was washed with DCM (2×2 mL) followed by MeOH (2×1 mL) to obtain the title compound as a beige solid (0.095 g, 52% yield). $^1$H NMR (400 MHz, DMSO-$d_6$) δ 11.1 (brs, 1H), 8.80 (d, J=2.3 Hz, 1H), 8.45 (t, J=5.8 Hz, 1H), 8.31 (dd, J=8.6, 2.5 Hz, 1H), 8.05 (d, J=8.6 Hz, 1H), 7.87-7.74 (m, 5H), 4.94 (brs, 1H), 4.65 (brs, 1H), 3.66-3.57 (m, 1H), 3.54-3.45 (m, 1H), (the resonance of 2 protons overlapped with $H_2O$, and not assigned), 3.26-3.17 (m, 1H). $^{13}$C NMR (101 MHz, DMSO-$d_6$) δ 163.7, 156.2, 143.3, 142.7, 138.2, 137.1, 131.4, 127.3, 127.0, 126.0, 125.5, 125.3, 123.5, 123.1, 122.8, 122.6, 70.2, 64.0, 42.4. LCMS $R_f$ (min)=3.30. HRMS (ESI) calcd for $C_{19}H_{18}F_3N_4O_4^+$ $[M+H]^+$ 423.1275, found 423.1289.

37. (S)—N-(2,3-Dihydroxypropyl)-5-((5-(4-(trifluoromethyl)phenyl)oxazol-2-yl)amino)picolinamide (Scheme 34)

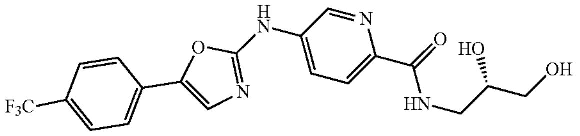 [SMILES: O=C(NC[C@H](O)CO)c1ccc(Nc2ncc(-c3ccc(C(F)(F)F)cc3)o2)cn1]

5-((5-[4-(Trifluoromethyl)phenyl]-1,3-oxazol-2-yl) amino)picolic acid (0.15 g) was suspended in DMF (3.0 mL), and EDCI (1.3 equiv.) and HOBt (1.4 equiv.) were added. The resulting mixture was stirred at rt for 1 h. (S)-3-Aminopropane-1,2-diol (2.0 equiv.) was then added to the reaction mixture and stirring was continued overnight. LCMS indicated the completion of reaction. The reaction mixture was concentrated under reduced pressure to obtain a gummy solid. This was washed with DCM (2×2 mL) followed by MeOH (2×1 mL) to obtain the title compound as a beige solid (0.094 g, 52% yield). $^1$H NMR (401 MHz, DMSO-$d_6$) δ 11.07 (brs, 1H), 8.80 (d, J=2.2 Hz, 1H), 8.45 (t, J=5.7 Hz, 1H), 8.30 (dd, J=8.6, 2.3 Hz, 1H), 8.04 (d, J=8.6 Hz, 1H), 7.94-7.64 (m, 5H), 4.94 (d, J=4.2 Hz, 1H), 4.65 (brs, 1H), 3.61 (m, 1H), 3.56-3.44 (m, 1H), (the resonance of 2 protons overlapped with $H_2O$, and not assigned), 3.27-3.12 (m, 1H). $^{13}$C NMR (101 MHz, DMSO-$d_6$) δ 163.7, 156.2, 143.3, 142.7, 138.2, 137.1, 131.4, 127.3, 126.9, 126.0, 125.5, 125.3, 123.5, 123.0, 122.8, 122.5, 70.3, 64.0, 42.4. LCMS $R_f$ (min)=3.306. HRMS (ESI) calcd for $C_{19}H_{18}F_3N_4O_4^+$ [M+H]$^+$ 423.1275, found 423.1287.

38. (R)—N-(2,3-Dihydroxypropyl)-5-((1-(4-(trifluoromethyl)phenyl)-1H-1,2,4-triazol-3-yl)amino)picolinamide (Scheme 35)

Scheme 35

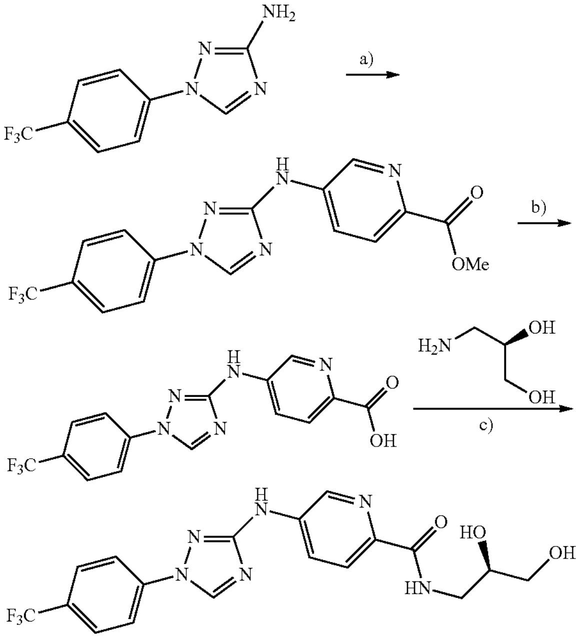

a) methyl 5-bromopicolinate, $Pd_2(dba)_3$, Xantphos, $Cs_2CO_3$, 1,4-dioxane, 100° C., 16 h; b) LiOH•$H_2O$, 1,4-dioxane: EtOH: $H_2O$ (2:2:1), 100° C., 3 h; c) DMF, EDCI, HOBt, rt, 15 h.

A re-sealable Schlenk tube was charged with $Pd_2(dba)_3$ (0.05 equiv.), Xantphos (0.1 equiv.), 1-(4-(trifluoromethyl) phenyl)-1H-1,2,4-triazol-3-amine (Intermediate F) (0.3 g), $Cs_2CO_3$ (1.5 equiv.), methyl 5-bromopicolinate (1.2 equiv.) in 1,4-dioxane (20 mL). The mixture was degassed and carefully subjected to three cycles of evacuation and back-filling with $N_2$ and heated at 100° C. overnight under $N_2$ atmosphere. After completion, the mixture was cooled, diluted (100 mL of EtOAc) and washed with $H_2O$ (2×30 mL). The organic layer was separated, dried ($MgSO_4$), filtered and concentrated under reduced pressure to obtain the crude product. The crude product was washed with $Et_2O$ (3×2.0 mL) to obtain methyl 5-((1-(4-(trifluoromethyl)phenyl)-1H-1,2,4-triazol-3-yl)amino)picolinate as a beige solid (0.262 g, 55.5% yield). $^1$H NMR (401 MHz, δ 10.40 (s, 1H), 9.34 (s, 1H), 8.88 (d, J=2.4 Hz, 1H), 8.24 (dd, J=8.7, 2.4 Hz, 1H), 8.12 (d, J=8.4 Hz, 2H), 8.04 (d, J=8.7 Hz, 1H), 7.94 (d, J=8.6 Hz, 2H), 3.84 (s, 3H).

LiOH·$H_2O$ (0.087 g) in $H_2O$ (2.0 mL) was added to a solution of methyl 5-((1-(4-(trifluoromethyl)phenyl)-1H-1,2,4-triazol-3-yl)amino)picolinate in 1,4-dioxane (4 mL) and EtOH (4 mL). The resulting mixture was heated to 100° C. for 3 h. Volatiles were removed in vacuo and the remaining suspension was acidified with 1N HCl (pH~4). The resulting precipitate was filtered and washed with $H_2O$ (3×2 mL), providing 5-((1-(4-(trifluoromethyl)phenyl)-1H-1,2,4-triazol-3-yl)amino)picolinic acid as a yellow solid (0.180 g, 93% yield). $^1$H NMR (401 MHz, DMSO-$d_6$) δ 10.37 (s, 1H), 9.34 (s, 1H), 8.89 (d, J=2.0 Hz, 1H), 8.24 (dd, J=8.6, 2.2 Hz, 1H), 8.12 (d, J=8.3 Hz, 2H), 8.04 (d, J=8.6 Hz, 1H), 7.94 (d, J=8.4 Hz, 2H).

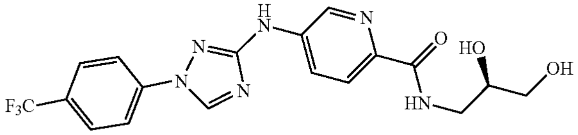 [SMILES: O=C(NC[C@@H](O)CO)c1ccc(Nc2ncn(-c3ccc(C(F)(F)F)cc3)n2)cn1]

EDCI (1.3 equiv.) and HOBt (1.4 equiv.) were added to a suspension of 5-((1-(4-(trifluoromethyl)phenyl)-1H-1,2,4-triazol-3-yl)amino)picolinic acid (0.08 g) in DMF (5.0 mL). The reaction mixture was stirred at rt for 1 h. (R)-3-Aminopropane-1,2-diol (1.5 equiv.) was then added to the reaction mixture and stirring continued overnight. LCMS indicated that the reaction was completed. The reaction mixture was concentrated under reduced pressure to obtain the crude material, which was washed with DCM (2×2 mL) followed by MeOH (2×1 mL) to obtain the title compound as a beige solid (0.055 g, 56.9% yield). $^1$H NMR (401 MHz, DMSO-$d_6$) δ 10.27 (s, 1H), 9.34 (s, 1H), 8.89 (d, J=2.4 Hz, 1H), 8.42 (t, J=5.8 Hz, 1H), 8.22 (dd, J=8.6, 2.5 Hz, 1H), 8.12 (d, J=8.4 Hz, 2H), 8.00 (d, J=8.6 Hz, 1H), 7.95 (d, J=8.6 Hz, 2H), 4.94 (d, J=5.0 Hz, 1H), 4.65 (t, J=5.8 Hz, 1H), 3.64-3.58 (m, 1H), 3.53-3.47 (m, 1H), 3.42-3.27 (m, 2H), 3.25-3.16 (m, 1H). $^{13}$C NMR (101 MHz, DMSO-$d_6$) δ 163.9, 160.2, 142.3, 141.3, 140.1, 139.5, 136.7, 127.1, 126.7, 125.4, 122.7, 122.5, 118.6, 70.3, 64.0, 42.3. LCMS $R_f$ (min)=3.135. HRMS (ESI) calcd for $C_{18}H_{18}F_3N_6O_3^+$ [M+H]$^+$ 423.1387, found 423.1395.

39. N',3-Dihydroxy-5-((4-methyl-5-(4-(trifluoromethyl)phenyl)oxazol-2-yl)amino)picolinimidamide (Scheme 36)

Scheme 36

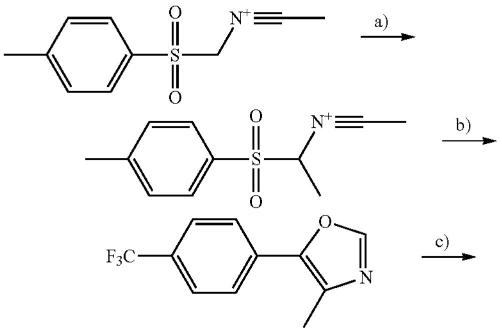

-continued

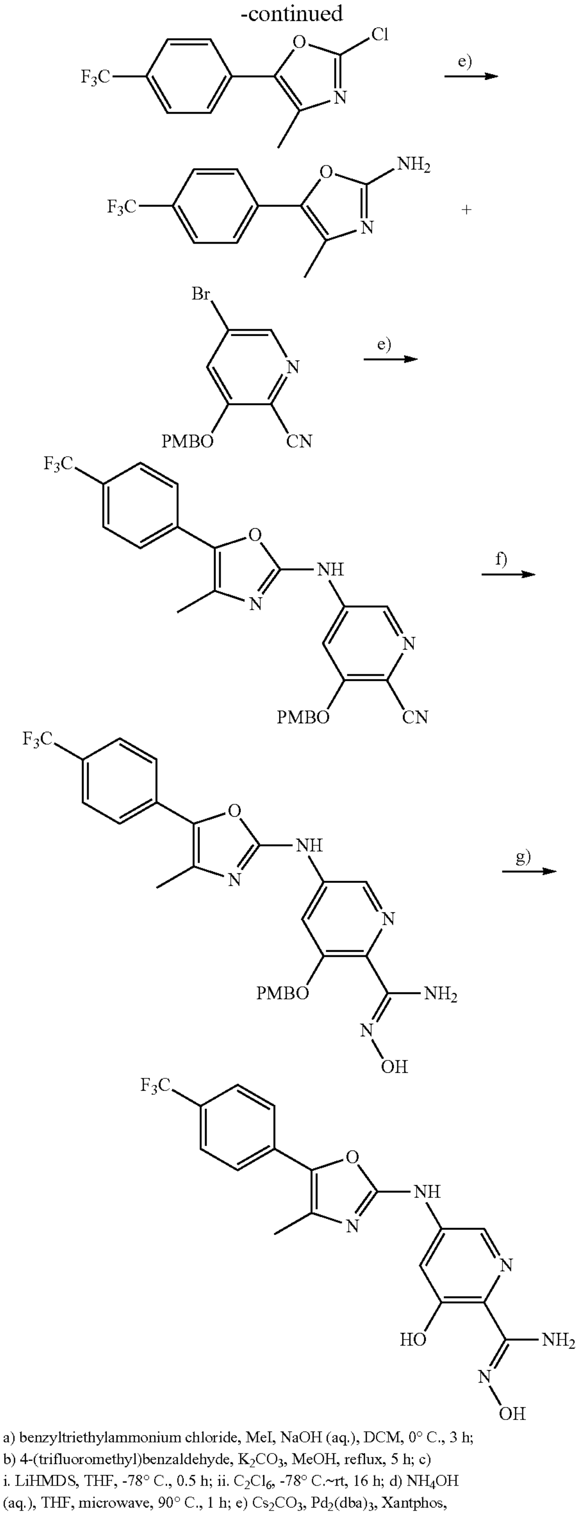

a) benzyltriethylammonium chloride, MeI, NaOH (aq.), DCM, 0° C., 3 h; b) 4-(trifluoromethyl)benzaldehyde, $K_2CO_3$, MeOH, reflux, 5 h; c) i. LiHMDS, THF, -78° C., 0.5 h; ii. $C_2Cl_6$, -78° C.~rt, 16 h; d) $NH_4OH$ (aq.), THF, microwave, 90° C., 1 h; e) $Cs_2CO_3$, $Pd_2(dba)_3$, Xantphos, 1,4-dioxane, 100° C., 5 h; f)$NH_2OH$•HCl, $Et_3N$, EtOH, reflux, 16 h; g) TFA, $Et_3SiH$, rt, 1 h.

Benzyltriethylammonium chloride (0.12 g, 0.51 mmol), iodomethane (0.72 g, 5.1 mmol) and NaOH (30% aqueous solution, 6 mL) were added to a solution of TosMIC (0.5 g, 2.55 mmol) in DCM (6 mL) at 0° C. The resulting mixture was stirred at 0° C. for 3 h then diluted with DCM (10 mL), washed with water (10 mL×2), dried over $MgSO_4$, filtered and concentrated to give a brown oil that was subjected to flash chromatography on silica gel (20% EtOAc/hexane), providing 1-[(1-isocyanoethyl)sulfonyl]-4-methylbenzene as a light yellow oil (0.43 g, 80% yield). $^1H$ NMR (400 MHz, $CDCl_3$) δ 7.79 (d, J=8.0 Hz, 2H), 7.37 (d, J=8.0 Hz, 2H), 4.63 (q, J=6.8 Hz, 1H), 2.42 (s, 3H), 1.64 (d, J=6.8 Hz, 3H), MS m/z=207.9 $[M-H]^-$.

4-(Trifluoromethyl)benzaldehyde (1.25 g, 7.17 mmol) and $K_2CO_3$ (1.24 g, 8.96 mmol) were added to a solution of 1-((1-isocyanoethyl)sulfonyl)-4-methylbenzene (1.5 g, 7.17 mmol) in MeOH (35 mL) at rt. The resulting mixture was then refluxed for 5 h under nitrogen before being concentrated under reduced pressure. The residue was partitioned between $Et_2O$ and $H_2O$. The aqueous phase was extracted with $Et_2O$ (20 mL×2), and the combined organic phases were dried over $MgSO_4$, filtered and concentrated to give a light yellow oil that was subjected to flash chromatography on silica gel (10% EtOAc/hexane), providing 4-methyl-5-[4-(trifluoromethyl)phenyl]oxazole as a white solid (1.4 g, 86% yield). $^1H$ NMR (400 MHz, $CDCl_3$) δ 7.87 (s, 1H), 7.68-7.74 (m, 4H), 2.48 (s, 3H), MS m/z=228.0 $[M+H]^+$.

LiHMDS (1.0 M in THF, 0.53 mL, 0.53 mmol) was added to a solution of 4-methyl-5-[4-(trifluoromethyl)phenyl]oxazole (0.1 g, 0.44 mmol) in dry THF (3 mL) at −78° C. under nitrogen atmosphere. After a further 0.5 h, a solution of $C_2Cl_6$ (0.16 g, 0.66 mmol) in THF (1 mL) was treated. The resulting reaction mixture was stirred at −78° C. for another 2 h and allowed to warm to rt over 14 h. The reaction was partitioned with saturated $NaHCO_3$ (3 mL) and EtOAc (10 mL). The aqueous phase was extracted with EtOAc (8 mL×2). The combined organic phases were dried over $Na_2SO_4$, filtered, and concentrated to give a brown oil that was subjected to flash chromatography on silica gel (5% EtOAc/hexane), providing 2-chloro-4-methyl-5-[4-(trifluoromethyl)phenyl]oxazole as a white solid (0.11 g, 92% yield). $^1H$ NMR (400 MHz, $CDCl_3$) δ 7.65-7.71 (m, 4H), 2.44 (s, 3H), MS m/z=261.9 $[M+H]^+$.

Ammonium hydroxide (28-30% aq., 2 mL) was added to a solution of 2-chloro-4-methyl-5-[4-(trifluoromethyl)phenyl]oxazole (0.11 g, 0.43 mmol) in THF (0.5 mL) at rt. The resulting reaction mixture was irradiated under microwave conditions for 1 h at 90° C. The solid was filtered and washed with DCM (2 mL×2), providing 4-methyl-5-[4-(trifluoromethyl)phenyl]oxazol-2-amine as a white solid (0.1 g, 95% yield). $^1H$ NMR (400 MHz, $CDCl_3$) δ 7.61 (d, J=8.0 Hz, 2H), 7.54 (d, J=8.0 Hz, 2H), 2.33 (s, 3H). MS m/z 243.0 $[M+H]^+$.

An oven-dried RBF was charged with $Pd_2(dba)_3$ (0.028 g, 0.05 equiv.), Xantphos (0.036 g, 0.1 equiv.), 5-bromo-3-((4-methoxybenzyl)oxy)picolinonitrile (0.217 g, 0.681 mmol, 1.1 equiv.), $Cs_2CO_3$ (0.303 g, 1.5 equiv.), 4-methyl-5-(4-(trifluoromethyl)phenyl)oxazol-2-amine (0.15 g, 0.619 mmol) and 1,4-dioxane (7 mL). Vacuum was applied briefly to the reaction flask followed by backfilling with $N_2$ and the procedure was repeated five times. The mixture was then heated to 100° C. and stirred for 5 h. LCMS indicated that the starting materials had been completely consumed. The reaction mixture was then poured into water and extracted with EtOAc (5×). The combined organic solvents were dried over $MgSO_4$ and evaporated to dryness. The residue was purified on silica gel using mixtures of DCM and EtOAc to provide 3-((4-methoxybenzyl)oxy)-5-((4-methyl-5-(4-(trifluoromethyl)phenyl)oxazol-2-yl)amino)picolinonitrile (0.15 g, 50.4% yield). $^1H$ NMR (401 MHz, DMSO-$d_6$) δ 11.34 (s, 1H), 8.33 (d, J=2.0 Hz, 1H), 8.27 (d, J=1.9 Hz, 1H), 7.82 (d, J=8.4 Hz, 2H), 7.73 (d, J=8.3 Hz, 2H), 7.48 (d, J=8.7 Hz, 2H), 6.98 (d, J=8.7 Hz, 2H), 5.26 (s, 2H), 3.76 (s, 3H), 2.45 (s, 3H). $^{13}C$ NMR (101 MHz, DMSO-$d_6$) δ 159.88, 158.95, 154.46, 140.72, 138.31, 134.92, 133.08, 132.59, 130.35, 127.60, 127.25, 126.94, 126.45, 126.03, 124.75, 123.33, 116.53, 114.48, 113.88, 107.52, 55.59, 14.10. LCMS $R_f$ (min)=4.20, MS m/z=480.9 $[M+H]^+$.

3-((4-Methoxybenzyl)oxy)-5-((4-methyl-5-(4-(trifluoromethyl)phenyl)oxazol-2-yl)amino)picolinonitrile (0.15 g, 0.312 mmol) was suspended in EtOH (20 mL), then $NH_2OH{\cdot}HCl$ (0.109 g, 1.561 mmol) was added and approximately half of the EtOH was removed in vacuo. $Et_3N$ (0.213 mL, 1.561 mol) was added and the resulting reaction mixture was stirred at reflux overnight. LCMS indicated that the reaction was complete. The volatile solvents were removed and the resulting solids were suspended in water, collected by filtering then washing well with water. The solids were washed with $Et_2O$ then dried under high vacuum to provide N-hydroxy-3-((4-methoxybenzyl)oxy)-5-((4-methyl-5-(4-(trifluoromethyl)phenyl)oxazol-2-yl)amino)picolinimidamide (0.081 g, 50.5% yield). $^1H$ NMR (401 MHz, DMSO-$d_6$) δ 10.77 (s, 1H), 9.62 (s, 1H), 8.34 (d, J=2.0 Hz, 1H), 8.01 (d, J=2.0 Hz, 1H), 7.81 (d, J=8.4 Hz, 2H), 7.71 (d, J=8.3 Hz, 2H), 7.46 (d, J=8.7 Hz, 2H), 6.94 (d, J=8.7 Hz, 2H), 5.59 (s, 2H), 5.13 (s, 2H), 3.75 (d, J=5.6 Hz, 3H), 2.08 (s, 3H). $^{13}C$ NMR (101 MHz, DMSO-$d_6$) δ 159.39, 155.36, 153.54, 150.27, 137.64, 137.18, 135.11, 134.15, 132.89, 129.69, 129.57, 128.87, 126.88, 126.57, 126.47, 126.09, 124.46, 123.39, 114.26, 109.64, 55.54, 14.18. LCMS $R_f$ (min)=3.236. HRMS (ESI) calcd for $C_{25}H_{23}F_3N_5O_4^+$ [M+H]$^+$ 514.1697, found 514.1687.

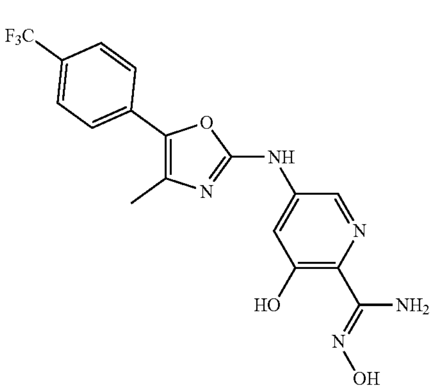 [SMILES: Cc1nc(Nc2cnc(/C(N)=N/O)c(O)c2)oc1-c1ccc(C(F)(F)F)cc1]

N'-hydroxy-3-((4-methoxybenzyl)oxy)-5-((4-methyl-5-(4-(trifluoromethyl)phenyl)oxazol-2-yl)amino)picolinimidamide (71.9 mg, 0.140 mmol) was stirred in a mixture of TFA (1.4 mL) and $Et_3SiH$ (0.07 mL) at rt for 1 h. The reaction mixture was evaporated to dryness. The residue was purified on preparative HPLC to provide the title compound (40.9 mg, 74.26%) as a pale yellow solid. 1H NMR (401 MHz, DMSO-$d_6$) δ 11.00 (s, 1H), 10.79-10.21 (brs, 1H), 8.29 (d, J=2.2 Hz, 1H), 7.93 (d, J=2.0 Hz, 1H), 7.82 (d, J=8.4 Hz, 2H), 7.73 (d, J=8.3 Hz, 2H), 7.70-7.76 (brs, 1H), 2.41 (s, 3H). $^{13}C$ NMR (101 MHz, DMSO-$d_6$) δ 154.8 (C), 154.6 (C), 137.5 (C), 134.6 (C), 132.3 (C), 129.9 (CH), 126.6 (C), 126.3 (C), 126.0 (CH), 125.6 (C), 124.2 (CH), 122.9 (C), 110.1 (CH), 13.7 (C), 13.6 ($CH_3$). LCMS: $R_f$ (min)=3.688, MS m/z=393.9 [M+H]$^+$. HRMS (ESI) calcd for $C_{17}H_{15}F_3N_5O_3^+$ [M+H]$^+$ 394.1122, found 394.1140.

40. N',3-Dihydroxy-5-((5-(5-(trifluoromethyl)pyridin-2-yl)oxazol-2-yl)amino)picolinimidamide hydrochloride (Scheme 37)

Scheme 37

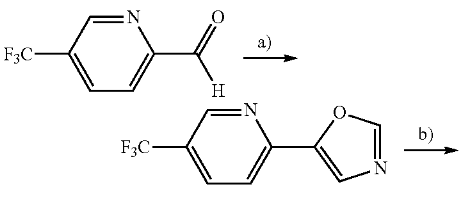

-continued

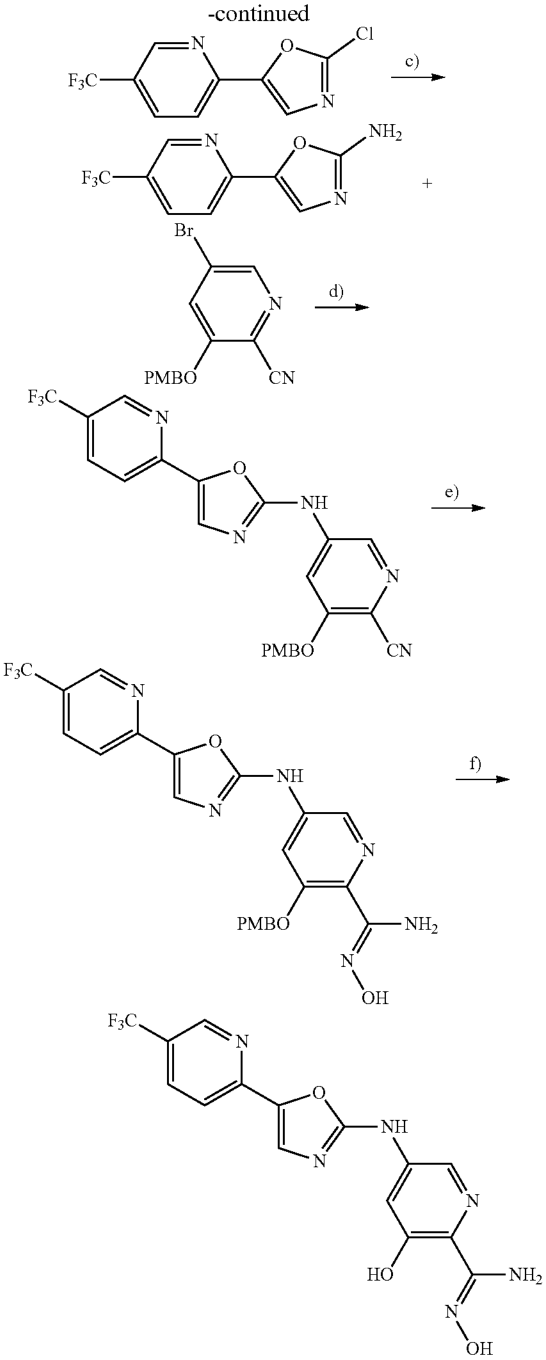

a) $K_2CO_3$, MeOH, reflux, 5 h; b) i. LiHMDS, THF, -78° C., 0.5 h; ii. $C_2Cl_6$ -78° C.~rt, overnight; c) $NH_4OH$ (aq.), THF, microwave 90° C., 1 h; d) $Cs_2CO_3$, $Pd_2(dba)_3$, Xantphos, 1,4-dioxane 110° C., overnight; e) $NH_2OH{\cdot}HCl$, $Et_3N$, EtOH, reflux, overnight; f) TFA, $Et_3SiH$, rt, 1 h.

i-PrMgCl (2M in THF, 10.0 mL, 20.0 mmol) was added to a solution of 2-bromo-5-(trifluoromethyl)pyridine (4.0 g, 17.7 mmol) in DCM (550 mL) at 0° C. over 5 minutes. After stirring at 0-6° C. for 40 minutes, the mixture was cooled to −20° C. and DMF (2.8 mL, 35.4 mmol) was added in one portion. The mixture was warmed to rt over 2 h, then quenched by addition of sat. $NaHCO_3$ aqueous solution (15 mL). After stirring for 10 minutes, the suspension was filtered through a celite pad. The filtrate layers were separated. The celite pad was further washed with 20 mL DCM and the organic liquid was then used to re-extract the aqueous layer. The combined organic phases were dried over $MgSO_4$, filtered, and concentrated under reduced pressure. The resultant crude (~3.6 g) was used in the next step without further characterisations.

5-(Trifluoromethyl)picolinaldehyde (0.65 g, 3.71 mmol) and $K_2CO_3$ (0.62 g, 4.45 mmol) were added to a solution of 1-((isocyanomethyl)sulfonyl)-4-methylbenzene (0.80 g, 4.08 mmol) in MeOH (10 mL) at rt. The resulting mixture was refluxed for 5 h under nitrogen before being concentrated under reduced pressure. The residue was partitioned between $Et_2O$ and $H_2O$. The aqueous phase was extracted with $Et_2O$ (20 mL×2), and the combined organic phases were dried over $MgSO_4$, filtered and concentrated to give a light yellow oil that was subjected to flash chromatography on silica gel (3% to 20%, EtOAc/hexane). Collection of the appropriate fractions provided 5-(5-(trifluoromethyl)pyridin-2-yl)oxazole as a white solid. (0.65 g, 82% yield). $^1$H NMR (400 MHz, $CDCl_3$) δ 8.87 (m, 1H), 8.02 (s, 1H), 8.00 (m, 1H), 7.82 (s, 1H), 7.77 (d, J=8.3 Hz, 1H). MS m/z=215.0 $[M+H]^+$.

Intermediate J—2-chloro-5-(5-(trifluoromethyl)pyridin-2-yl)oxazole LiHMDS (1.0 M in THF, 5.88 mL, 5.88 mmol) was added to a solution of 5-(5-(trifluoromethyl)pyridin-2-yl)oxazole (1.05 g, 4.90 mmol) in dry THF (10 mL) at −78° C. under nitrogen atmosphere. After a further 0.5 h, a solution of $C_2Cl_6$ (1.74 g, 7.35 mmol) in THF (5 mL) was treated. The resulting reaction mixture was stirred at −78° C. for another 2 h and allowed to warm to rt over 14 h. The reaction was quenched with saturated $NaHCO_3$ (10 mL). The aqueous phase was extracted with EtOAc (30 mL×2). The combined organic phases were dried over $Na_2SO_4$, filtered, and concentrated to give a brown oil that was subjected to flash chromatography on silica gel (2%~10%, EtOAc/hexane). Collection of the appropriate fractions provided 2-chloro-5-(5-(trifluoromethyl)pyridin-2-yl)oxazole (Intermediate J) as a white solid (1.04 g, 85% yield). $^1$H NMR (400 MHz, $CDCl_3$) δ 8.86 (m, 1H), 8.00 (m, 1H), 7.75 (s, 1H), 7.71 (d, J=8.0 Hz, 1H). MS m/z=248.9 $[M+H]^+$.

Intermediate K—5-(5-(trifluoromethyl)pyridin-2-yl)oxazol-2-amine

Ammonium hydroxide (28-30% aqueous solution, 10 mL) was added to a solution of 2-chloro-5-(5-(trifluoromethyl)pyridin-2-yl)oxazole (0.60 g, 2.41 mmol) in THF (1.5 mL) at rt. The resulting reaction mixture was irradiated under microwave at 90° C. for 1 h. The solid was filtered and washed with DCM (5 mL×2), providing 5-(5-(trifluoromethyl)pyridin-2-yl)oxazol-2-amine as a white solid (0.52 g, 95% yield). $^1$H NMR (400 MHz, DMSO-$d_6$) δ 8.81 (t, J=1.5 Hz, 1H), 8.13 (dd, J=8.4, 1.5 Hz, 1H), 7.60 (s, 1H), 7.57 (d, J=8.4 Hz, 1H), 7.33 (s, 2H). MS m/z=230.0 $[M+H]^+$.

An oven-dried RBF was charged with $Pd_2(dba)_3$ (0.030 g, 0.05 equiv.), Xantphos (0.038 g, 0.1 equiv.), 5-bromo-3-((4-methoxybenzyl)oxy)picolinonitrile (0.209 g, 0.681 mmol, 1.0 equiv.), $Cs_2CO_3$ (0.320 g, 1.5 equiv.), 5-(5-(trifluoromethyl)pyridin-2-yl)oxazol-2-amine (0.15 g, 0.654 mmol) and 1,4-dioxane (7 mL). Vacuum was applied briefly to the reaction flask followed by backfilling with $N_2$ and the procedure was repeated five times. The mixture was then heated to 110° C. and stirred for 18 h. LCMS indicated that the starting materials had been completely consumed. The reaction mixture was poured into water and extracted with EtOAc (5×). The combined organic solvents were dried over $MgSO_4$ and evaporated to dryness. The residue was purified on silica gel using mixtures of DCM and EtOAc to provide 3-((4-methoxybenzyl)oxy)-5-((5-(5-(trifluoromethyl)pyridin-2-yl)oxazol-2-yl)amino)picolinonitrile (0.215 g, 70.3% yield). $^1$H NMR (401 MHz, DMSO-$d_6$) δ 11.65 (s, 1H), 8.95 (s, 1H), 8.36 (d, J=1.9 Hz, 1H), 8.28 (m, 2H), 7.98 (s, 1H), 7.81 (d, J=8.4 Hz, 1H), 7.52-7.43 (d, J=8.7 Hz, 2H), 6.99 (d, J=8.7 Hz, 2H), 5.22 (s, 2H), 3.79 (s, 3H). $^{13}$C NMR (101 MHz, DMSO-$d_6$) δ 159.91, 158.99, 156.98, 150.22, 144.34, 140.59, 135.26, 133.21, 130.48, 129.28, 127.54, 118.43, 116.45, 114.48, 114.27, 107.77, 70.71, 55.61. LCMS $R_f$ (min)=3.626, MS m/z=467.9 $[M+H]^+$.

3-((4-Methoxybenzyl)oxy)-5-((5-(5-(trifluoromethyl)pyridin-2-yl)oxazol-2-yl)amino)picolinonitrile (0.20 g, 0.427 mmol) was suspended in EtOH (30 mL), then $NH_2OH·HCl$ (0.238 g, 3.423 mmol) was added and approximately half of the EtOH was removed in vacuo. $Et_3N$ (0.467 mL, 3.423 mol) was added and the resulting reaction mixture was stirred at reflux overnight. LCMS indicated that the reaction was complete. The volatile solvents were removed and the resulting solids were suspended in water, collected by filtering and washing well with water. The solids were washed with $Et_2O$ and dried under high vacuum to provide N'-hydroxy-3-((4-methoxybenzyl)oxy)-5-((5-(5-(trifluoromethyl)pyridin-2-yl)oxazol-2-yl)amino)picolinimidamide (0.183 g, 85.75% yield). $^1$H NMR (401 MHz, DMSO-$d_6$) δ 11.09 (s, 1H), 9.61 (s, 1H), 8.93 (s, 1H), 8.36 (s, 1H), 8.26 (d, J=7.7 Hz, 1H), 8.01 (s, 1H), 7.92 (s, 1H), 7.77 (d, J=8.2 Hz, 1H), 7.47 (d, J=7.7 Hz, 2H), 6.94 (d, J=7.8 Hz, 2H), 5.60 (s, 2H), 5.12 (s, 2H), 3.75 (s, 3H). $^{13}$C NMR (101 MHz, DMSO-$d_6$) δ 159.41, 157.87, 153.61, 150.43, 150.23, 147.04, 143.79, 136.96, 135.21, 134.62, 129.87, 129.72, 129.57, 128.79, 125.62, 123.17, 122.85, 118.08, 114.25, 109.80, 70.07, 55.54. LCMS $R_f$ (min)=3.082, MS m/z=500.9 $[M+H]^+$.

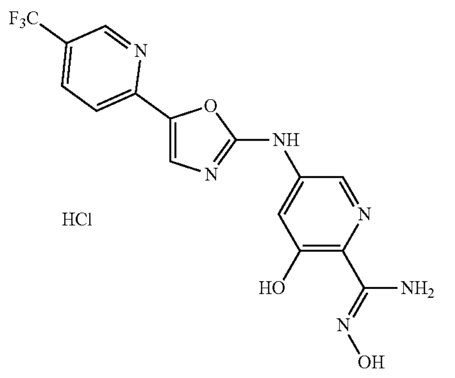 [SMILES: N/C(=N\O)c1ncc(Nc2ncc(-c3ccc(C(F)(F)F)cn3)o2)cc1O ; Cl]

N'-Hydroxy-3-((4-methoxybenzyl)oxy)-5-((5-(5-(trifluoromethyl)pyridin-2-yl)oxazol-2-yl)amino)-picolinimidamide (170 mg, 0.339 mmol) was stirred in a mixture of TFA (3 mL) and $Et_3SiH$ (0.15 mL) at rt for 4 h. The reaction mixture was evaporated to dryness. The residue was purified on preparative HPLC, then freeze-dried from 4N HCl dioxane solution to provide N',3-dihydroxy-5-((5-(5-(trifluoromethyl)pyridin-2-yl)oxazol-2-yl)amino)picolinimidamide hydrogen chloride (104 mg, 66.43% yield, corrected for presence of HCL salt and 0.5 molar equivalent of dioxane). $^1$H NMR (401 MHz, DMSO-$d_6$) δ 12.30-12.03 (br, 1H), 11.54 (s, 1H), 10.90 (brs, 1H), 8.94 (d, J=0.9 Hz, 1H), 8.50 (br, 1H), 8.37 (d, J=2.1 Hz, 1H), 8.28 (dd, J=8.5, 2.0 Hz, 1H), 8.12 (s, 1H), 7.95 (s, 1H), 7.85 (d, J=8.4 Hz, 1H). $^{13}$C NMR (101 MHz, DMSO-$d_6$) δ 157.32, 155.51, 150.30, 147.06, 144.20, 140.12, 135.26, 131.19, 129.37, 125.58, 123.39, 118.32, 110.89. LCMS $R_f$ (min)=3.682, MS m/z=380.9 $[M+H]^+$. HRMS (ESI) calcd for $C_{15}H_{12}F_3N_6O_3^+$ $[M+H]^+$ 381.0917, found 381.0928.

41. (R)—N-(2,3-Dihydroxypropyl)-6-((5-(4-(trifluoromethyl)phenyl)oxazol-2-yl)amino)-pyridazine-3-carboxamide (Scheme 38)

Scheme 38

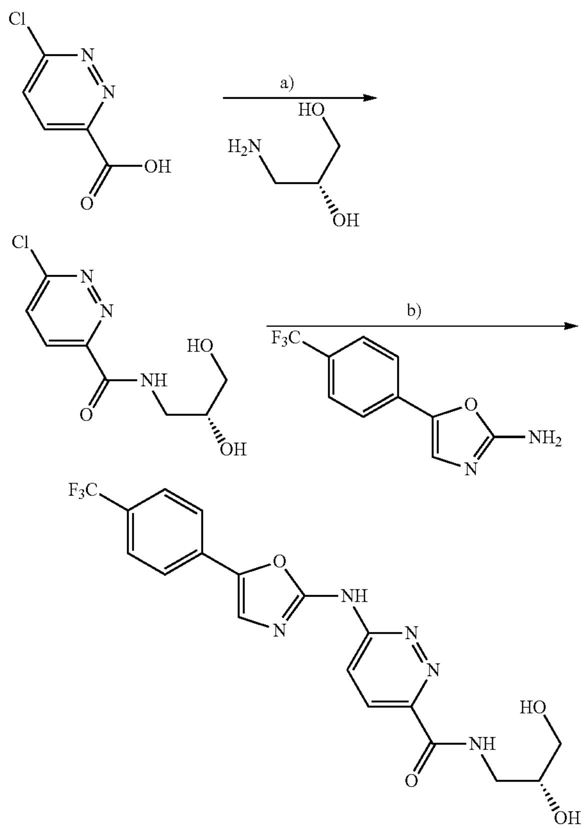

a) Oxalylchloride, DCM, then $Et_3N$, amine, EtOH, i-PrOH; b) $Pd_2(dba)_3$, Xantphos, $Cs_2CO_3$, 1,4-dioxane, 110° C., 18 h.

6-Chloropyridazine-3-carboxylic acid (0.57 g, 3.595 mmol) was dissolved in DCM (18 mL) with a catalytic amount of DMF. Oxalylchloride (0.617 mL, 4.19 mmol, 2 equivalents) was added dropwise, and the resulting solution was stirred at rt on. The volatile solvents were removed in vacuo, and the residue was dried under high vacuum. (R)-3-Aminopropane-1,2-diol (0.982 g, 10.78 mmol, 3 equiv.), and $Et_3N$ (1.45 mL, 10.78 mmol, 3 equiv.) were dissolved in a mixture of $^{i}$PrOH (5 mL) and EtOH (5 mL). The amine solution was added slowly to the solid residue of the crude acid chloride, and the resultant reaction mixture was stirred at rt on. All volatile solvents were removed in vacuo and the residue freeze-dried from water. The crude product was dissolved in MeOH, and treated with IR120 ion exchange resins to remove excess amines and $Et_3N$. The resins were washed well with MeOH, and the combined MeOH washing solutions were evaporated to dryness. The solid residue was purified on silica gel using DCM and MeOH mixtures as eluents to provide (R)-6-chloro-N-(2,3-dihydroxypropyl)pyridazine-3-carboxamide (0.477 g, 57.27%). $^1$H NMR (401 MHz, DMSO-$d_6$) δ 8.98 (s, 1H), 8.24 (d, J=8.7 Hz, 1H), 8.10 (d, J=8.7 Hz, 1H), 4.92 (br, 1H), 4.65 (br, 1H), 3.68 (br, 1H), 3.55-3.46 (m, 1H), 3.29 (m, 3H). $^{13}$C NMR (101 MHz, DMSO-$d_6$) δ 162.12, 158.66, 152.91, 130.75, 129.27, 70.38, 64.43, 43.28. LCMS $R_f$(min)=1.393, MS m/z=231.9 $[M+H]^+$.

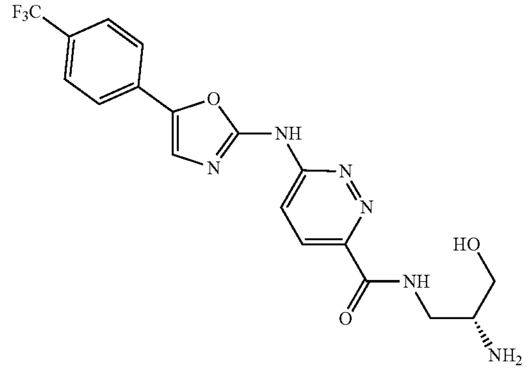 [SMILES: N[C@@H](CO)CNC(=O)c1ccc(Nc2ncc(-c3ccc(C(F)(F)F)cc3)o2)nn1]

An oven-dried RBF was charged with $Pd_2(dba)_3$ (0.020 g, 0.05 equiv.), Xantphos (0.025 g, 0.1 equiv.), (R)-6-chloro-N-(2,3-dihydroxypropyl)pyridazine-3-carboxamide (0.101 g, 0.438 mmol, 1.0 equiv.), $Cs_2CO_3$ (0.214 g, 1.5 equiv.), 5-(4-(trifluoromethyl)-phenyl)oxazol-2-amine (0.1 g, 0.438 mmol) and 1,4-dioxane (8 mL). Vacuum was applied briefly to the reaction flask followed by backfilling with $N_2$ and the procedure was repeated five times. The mixture was then heated to 110° C. and stirred for 18 h. LCMS indicated that the starting materials had been completely consumed. The volatile solvents were removed in vacuo, and the residue triturated with water. The solid precipitates were collected via filtering, washed with 5% potassium xanthate (2×) aqueous solutions, 10% citric acid aqueous solutions, water. The residual solids was purified on preparative HPLC to provide (R)—N-(2,3-dihydroxypropyl)-6-((5-(4-(trifluoromethyl)-phenyl)oxazol-2-yl)amino)pyridazine-3-carboxamide (0.072 g, 38.8% yield). $^1$H NMR (401 MHz, DMSO-$d_6$) δ 12.13 (s, 1H), 8.74 (s, 1H), 8.46 (s, 1H), 8.20 (d, J=9.2 Hz, 1H), 7.82 (s, 4H), 7.815 (s, 1H), 4.94 (d, J=5.0 Hz, 1H), 4.65 (t, J=5.6 Hz, 1H), 3.66 (m, 1H), 3.52 (m, 1H), 3.38 (m, 2H), 3.27 (m, 1H). $^{13}$C NMR (101 MHz, DMSO-$d_6$) δ 162.90, 144.38, 131.79, 128.16, 128.01, 127.69, 126.58, 126.54, 126.00, 123.76, 123.30, 70.56, 64.44, 43.02. LCMS $R_f$ (min)=4.032. HRMS (ESI) calcd for $C_{18}H_{17}F_3N_5O_4^+$ $[M+H]^+$ 424.1227, found 424.1225.

42. N',4-Dihydroxy-6-((5-(4-(trifluoromethyl)phenyl)oxazol-2-yl)amino)pyridazine-3-carboximidamide (Scheme 39)

Scheme 39

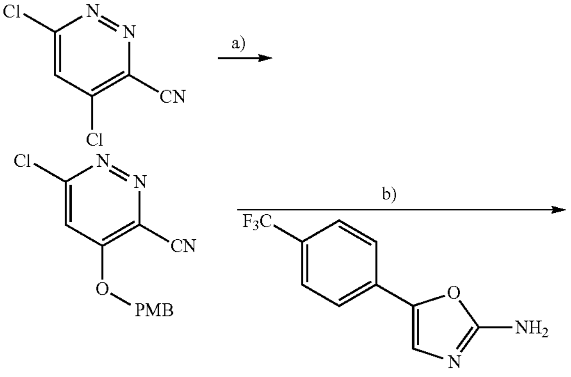

-continued

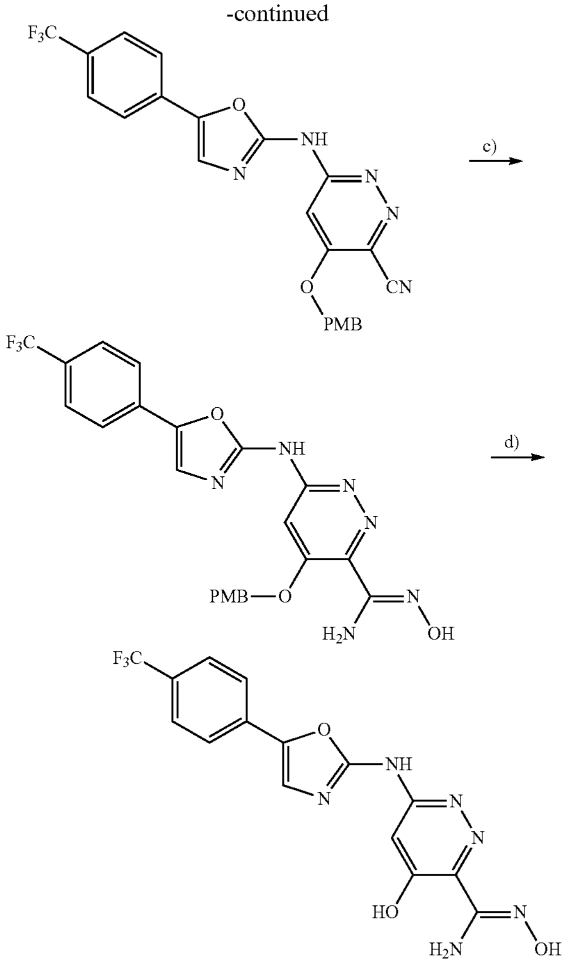

a) PMB-OH, NaH (60% dispersion in mineral oil), THF; b) $Cs_2CO_3$, $Pd_2(dba)_3$, Xantphos, 1,4-dioxane, 110° C., 18 h; c) $NH_2OH$•HCl, $Et_3N$, EtOH, reflux 18 h; d) TFA, $Et_3SiH$, rt.

p-Methoxybenzyl alcohol (0.121 g, 0.879 mmol, 1.0 equiv.) was dissolved in dry THF (5 mL), and NaH (60%, 0.021 g, 0.879 mmol, 1.0 equiv.) added under $N_2$. After 10 minutes of stirring, the solution was transferred to a flask containing 4,6-dichloropyridazine-3-carbonitrile (0.153 g, 0.879 mmol) in dry THF (5 mL). The resultant reaction mixture was stirred at rt for 1 h. LCMS indicated that all starting material had been consumed. The reaction mixture was poured into sat. aq. $NaHCO_3$ solution and the product extracted with DCM (5×). The combined organic solutions were dried over $MgSO_4$, and evaporated to dryness. The residue was purified on silica gel using petroleum spirit and EtOAc mixtures as eluents to provide 6-chloro-4-((4-methoxybenzyl)oxy)pyridazine-3-carbonitrile (0.127 g, 52.38%). $^1H$ NMR (401 MHz, $CDCl_3$) δ 7.35 (d, J=8.6 Hz, 2H), 7.16 (s, 1H), 6.95 (d, J=8.6 Hz, 2H), 5.24 (s, 2H), 3.82 (s, 3H). $^{13}C$ NMR (101 MHz, $CDCl_3$) δ 160.55, 159.42, 158.49, 132.41, 129.59, 124.34, 114.64, 112.29, 110.58, 72.15, 55.41. LCMS $R_f$ (min)=3.298, MS m/z=297.9 $[M+Na]^+$.

An oven-dried RBF was charged with $Pd_2(dba)_3$ (0.021 g, 0.05 equiv.), Xantphos (0.026 g, 0.1 equiv.), 5-(4-(trifluoromethyl)phenyl)oxazol-2-amine (0.119 g, 0.544 mmol, 1.2 equiv.), $Cs_2CO_3$ (0.221 g, 1.5 equiv.), 6-chloro-4-((4-methoxybenzyl)oxy)pyridazine-3-carbonitrile (0.125 g, 0.453 mmol) and 1,4-dioxane (8 mL). Vacuum was applied briefly to the reaction flask followed by backfilling with $N_2$ and the procedure was repeated five times. The mixture was then heated to 110° C. and stirred for 18 h. LCMS indicated that the starting materials had been completely consumed. The reaction mixture was then poured into water and extracted with EtOAc (5×). The combined organic solvents were dried over $MgSO_4$ and evaporated to dryness. The residue was purified on silica gel using mixtures of DCM, EtOAc, and MeOH to provide 4-((4-methoxybenzyl)oxy)-6-((5-(4-(trifluoromethyl)phenyl)oxazol-2-yl)amino)-pyridazine-3-carbonitrile (0.046 g, 21.7% yield). The purity was ~80%, and the product was used in the next step without further purification. LCMS $R_f$ (min)=4.47, MS m/z=467.9 $[M+H]^+$.

4-((4-Methoxybenzyl)oxy)-6-((5-(4-(trifluoromethyl) phenyl)oxazol-2-yl)amino)pyridazine-3-carbonitrile (0.046 g, 0.098 mmol) was suspended in EtOH (10 mL), then $NH_2OH$·HCl (0.055 g, 0.787 mmol) was added and approximately half of the EtOH was removed in vacuo. $Et_3N$ (0.107 mL, 0.787 mmol) was added and the resulting reaction mixture was stirred at reflux overnight. LCMS indicated that the reaction was complete. The volatile solvents were removed and the resulting solids were suspended in water, collected by filtering then washing well with water. The solids were washed with $Et_2O$ then dried under high vacuum to provide N'-hydroxy-4-((4-methoxybenzyl)oxy)-6-((5-(4-(trifluoromethyl)phenyl)oxazol-2-yl)amino)pyridazine-3-carboximidamide (0.037 g, 75.12% yield). The product was used in the next step without further purification LCMS $R_f$ (min)=3.717, MS m/z=500.9 $[M+H]^+$.

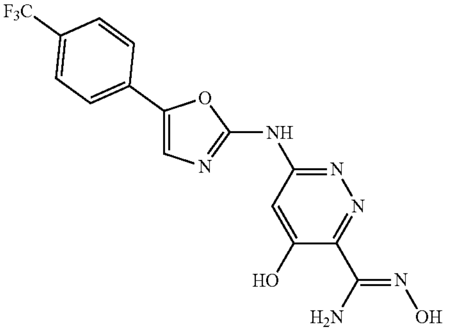 [SMILES: N/C(=N\O)c1nnc(Nc2ncc(-c3ccc(C(F)(F)F)cc3)o2)cc1O]

N'-Hydroxy-4-((4-methoxybenzyl)oxy)-6-((5-(4-(trifluoromethyl)phenyl)oxazol-2-yl)amino)pyridazine-3-carboximidamide (37 mg, 0.069 mmol) was stirred in a mixture of TFA (2 mL) and $Et_3SiH$ (0.1 mL) at rt for 4 h. The reaction mixture was evaporated to dryness. The residue was purified on preparative HPLC to provide N',4-dihydroxy-6-((5-(4-(trifluoromethyl)phenyl)oxazol-2-yl)amino)pyridazine-3-carboximidamide (5.3 mg, 19.96% yield). $^1H$ NMR (401 MHz, DMSO-$d_6$) δ 10.79 (s, 1H), 7.87 (s, 1H), 7.81 (m, 4H), 7.59 (br, 3H). LCMS $R_f$ (min)=3.615, MS m/z=380.9 $[M+H]^+$. HRMS (ESI) calcd for $C_{15}H_{12}F_3N_6O_3^+$ $[M+H]^+$ 381.0917, found 381.0912.

43. 5-((5-(3-Fluoro-4-(trifluoromethyl)phenyl)oxazol-2-yl)amino)-N',3-dihydroxypicolinimidamide (Scheme 40)

Scheme 40

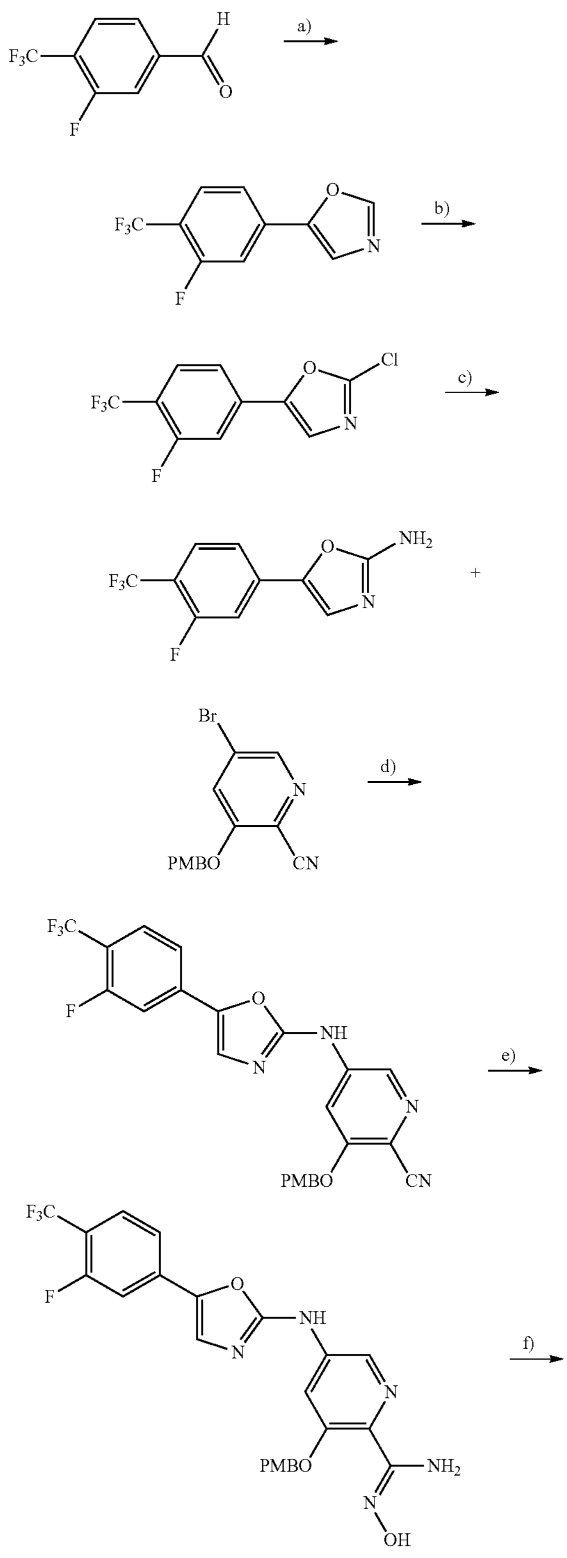

-continued

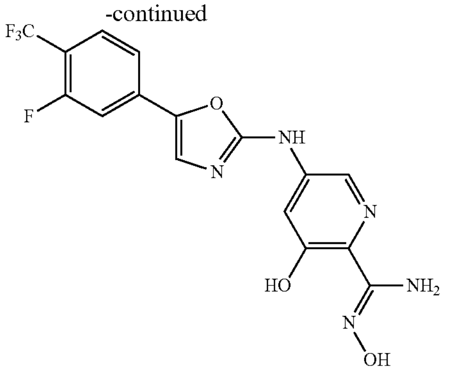

a) TosMIC, $K_2CO_3$, MeOH, reflux 2.5 h; b) i. LiHMDS, THF, -78° C. 0.5 h; ii. $C_2Cl_6$ rt overnight; c) $NH_4OH$ (aq.), THF, microwave 1 h 90° C.; d) $Cs_2CO_3$, $Pd_2(dba)_3$, Xantphos, 1,4-dioxane reflux, 8 h; e) $NH_2OH$•HCl, $Et_3N$, EtOH, reflux overnight; f) TFA, $Et_3SiH$ rt 4 h.

3-Fluoro-4-(trifluoromethyl)benzaldehyde (2.5 g, 13.01 mmol), p-toluenesulfonylmethyl isocyanide (2.723 g, 13.01 mmol), $K_2CO_3$ (2.158 g, 15.61 mmol) were added into a dry RBF and refluxed with MeOH (7 mL) for 2.5 h. After this period of time the solvent was evaporated and aq. $NaHCO_3$ solution (20 mL) was added. The suspension was extracted with DCM (3×25 mL). The combined organic fractions were washed with brine, dried over $MgSO_4$, filtered and concentrated under reduced pressure. The residue was chromatographed on silica gel eluting with 50% EtOAc in hexane to afford 5-(3-fluoro-4-(trifluoromethyl)phenyl)oxazole as white solid (2.808 g, 94%). $^1$H NMR (400 MHz, DMSO-$d_6$) δ 8.54 (s, 1H), 7.93 (s, 1H), 7.78 (dd, J=10.0, 5.4 Hz, 2H), 7.65 (d, J=8.3 Hz, 1H). $^{13}$C NMR (101 MHz, DMSO-$d_6$) δ 160.51, 157.99, 153.09, 148.09, 133.70, 128.21, 125.42, 120.01, 112.33, 112.10. LCMS $R_f$ (min)=3.461, MS m/z=232.0 $[M+H]^+$.

LiHMDS (1.00 M in THF, 14.75 mL, 14.02 mmol) was added to a solution of 5-(3-fluoro-4-(trifluoromethyl)phenyl)oxazole (2.70 g, 11.68 mmol) in THF (90 mL) at −78° C. The mixture was stirred at −78° C. for 1 h. After this period of time a solution of $C_2Cl_6$ (4.15 g, 17.52 mmol) in THF (6 mL) was added at −78° C., and the resultant mixture was allowed to stir at −78° C. for 2 h. Then the mixture was allowed to warm to rt and stirred further for 14 h. The reaction was quenched $H_2O$ (15 mL), and diluted with EtOAc (20 mL). The organic layer was extracted with EtOAc (3×20 mL). The combined organics were washed with brine (20 mL), dried over $MgSO_4$, filtered and evaporated to dryness. The resultant white crytalline solid was used in next step without further purification (2.825 g, 94%). $^1$H NMR (400 MHz, $CDCl_3$) δ 7.65 (t, J=7.7 Hz, 1H), 7.49-7.37 (m, 3H). $^{13}$C NMR (101 MHz, DMSO-$d_6$) δ 160.53, 158.02, 153.09, 148.12, 133.70, 128.21, 128.15, 125.42, 120.05, 112.10. LCMS $R_f$ (min)=3.745, MS m/z=265.8 $[M+H]^+$.

$NH_4OH_{(aq)}$ solution (28-30% $NH_3$ basis, 35 mL) was added in to a microwave vial containing 2-chloro-5-(3-fluoro-4-(trifluoromethyl)phenyl)oxazole (0.577 g, 2.173 mmol) in THF (4 mL) and the mixture was subjected to microwave irradiation for 1 h at 90° C. The resulting suspension was filtered, washed with $Et_2O$ and dried under vacuum to yield 5-(3-fluoro-4-(trifluoromethyl)phenyl)oxazol-2-amine as yellow solid (0.494 g, 92%). $^1$H NMR (400 MHz, MeOH-$d_4$) δ 7.61 (t, J=7.8 Hz, 1H), 7.41 (t, J=10.5 Hz, 2H), 7.31 (s, 1H). $^{13}$C NMR (101 MHz, DMSO-$d_6$) δ 162.21, 158.42, 140.69, 134.82, 134.72, 128.21, 127.14, 117.59, 109.58, 109.35. $^{13}C$ NMR (101 MHz, DMSO-$d_6$) δ 162.66, 161.14, 158.85, 141.14, 135.16, 128.65, 127.58, 121.86, 118.02, 110.02. LCMS $R_f$ (min)=3.273, MS m/z=246.9 $[M+H]^+$.

5-(3-Fluoro-4-(trifluoromethyl)phenyl)oxazol-2-amine (0.300 g, 1.219 mmol), 5-bromo-3-((4-methoxybenzyl)oxy)picolinonitrile (0.466 g, 1.462 mmol), $Cs_2CO_3$ (0.596 g, 1.828 mmol), $Pd_2(dba)_3$ (0.056 g, 0.0609 mmol), 4,5-bis(diphenylphosphino)-9,9-dimethylxanthene (0.0705 g, 0.122 mmol) and anhydrous 1,4-dioxane (16 mL) were added into a dry RBF. The mixture was degassed, refilled with $N_{2(g)}$ (×5) and was refluxed for 8 h under $N_{2(g)}$. The reaction mixture was quenched with aq. $NaHCO_3$ solution (10 mL) and diluted with EtOAc (15 mL). The organic layer was extracted with EtOAc (4×15 mL). The combined organic fractions were dried over $MgSO_4$, filtered and evaporated to dryness. The residue (0.426 g) was subjected to next step without further purification. LCMS $R_f$ (min)=3.732, MS m/z=484.9 $[M+H]^+$.

5-((5-(3-Fluoro-4-(trifluoromethyl)phenyl)oxazol-2-yl)amino)-3-((4-methoxybenzyl)oxy)picolinonitrile (0.426 g) was suspended in EtOH (12 mL) and $NH_2OH \cdot HCl$ (0.148 g, 2.132 mmol) was added to the mixture while stirring at rt. Then, EtOH volume was halved (~6 mL) under vacuum, $Et_3N$ (0.30 mL, 2.132 mmol) was added and the mixture was allowed to stir at reflux for 24 h. After this period of time the volatiles were evaporated to dryness. The residue was washed with $H_2O$ (15 mL) and $Et_2O$ (20 mL) to yield 5-((5-(3-fluoro-4-(trifluoromethyl)phenyl)oxazol-2-yl)amino)-N'-hydroxy-3-((4-methoxybenzyl)oxy)picolinimidamide as bright orange solid (0.325 g, 76%). $^1H$ NMR (400 MHz, DMSO-$d_6$) δ 10.61 (s, 1H), 8.11-8.06 (m, 1H), 7.83 (q, J=5.3, 3.4 Hz, 3H), 7.67 (d, J=11.8 Hz, 1H), 7.54 (d, J=8.0 Hz, 1H), 7.48 (d, J=8.5 Hz, 2H), 7.35 (s, 1H), 6.97 (d, J=8.5 Hz, 2H), 5.14 (s, 2H), 3.76 (s, 3H). $^{13}C$ NMR (101 MHz, DMSO-$d_6$) δ 159.79, 157.89, 155.06, 142.14, 141.84, 140.88, 140.59, 138.85, 138.79, 138.68, 133.23, 131.03, 130.47, 130.00, 128.11, 127.65, 125.91, 118.71, 114.38, 114.30, 110.33, 70.35, 55.58. LCMS $R_f$ (min)=3.350, MS m/z=517.9 $[M+H]^+$.

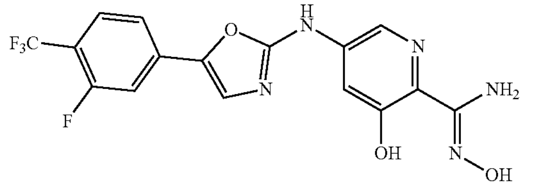 [SMILES: N/C(=N\O)c1ncc(Nc2ncc(-c3ccc(C(F)(F)F)c(F)c3)o2)cc1O]

TFA (2.0 mL) and $Et_3SiH$ (0.2 mL) were added into a RBF with 5-((5-(3-fluoro-4-(trifluoromethyl)phenyl)oxazol-2-yl)amino)-N'-hydroxy-3-((4-methoxybenzyl)oxy)picolinimidamide (0.1124 g, 0.217 mmol) and the resulting mixture was stirred at RT for 4 h. The volatiles were removed under reduced pressure and the residue was directly subjected to preparative HPLC to provide 5-((5-(3-fluoro-4-(trifluoromethyl)phenyl)oxazol-2-yl)amino)-N',3-dihydroxypicolinimidamide as orange solid (0.069 g, 80%, 100% purity). $^1H$ NMR (400 MHz, DMSO-$d_6$) δ 11.15 (s, 1H), 10.5 (brs, 1H), 8.30 (d, J=2.1 Hz, 1H), 7.96-7.88 (m, 3H), 7.73 (d, J=12.0 Hz, 1H), 7.59 (d, J=8.3 Hz, 1H). $^{13}C$ NMR (101 MHz, DMSO-$d_6$) δ 158.25, 158.10, 156.55, 154.67, 142.26, 134.11, 129.86, 128.49, 128.47, 126.98, 123.99, 118.58, 118.55, 110.72, 110.38. LCMS $R_f$ (min)=3.341, MS m/z=397.9 $[M+H]^+$. HRMS (ESI) calcd for $C_{16}H_{12}F_4N_5O_3^+$ $[M+H]^+$ 398.0871, found 398.0877.

44. (R)—N-(2,3-Dihydroxypropyl)-5-((5-(3-fluoro-4-(trifluoromethyl)phenyl)oxazol-2-yl)amino)picolinamide (Scheme 41)

Scheme 41

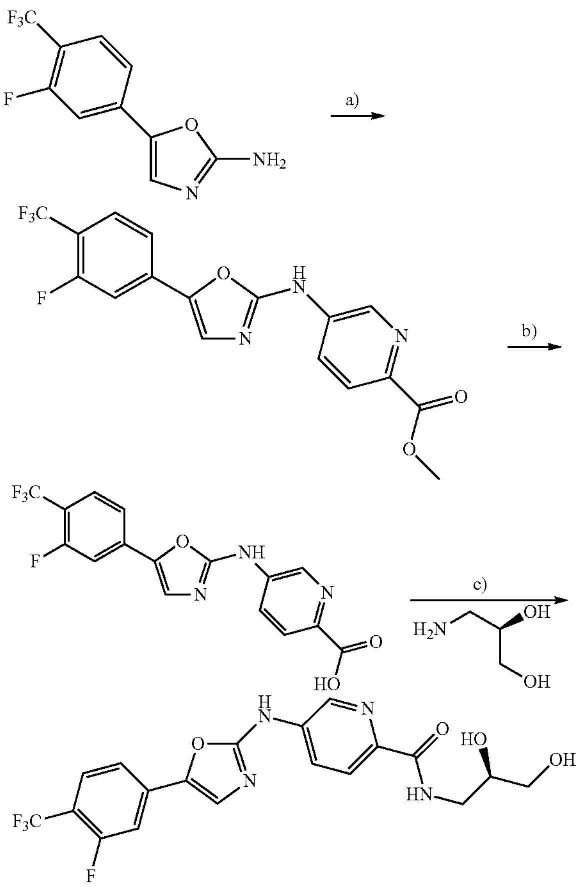

a) methyl 5-bromopicolinate, $Pd_2(dba)_3$, Xantphos, $Cs_2CO_3$, 1,4-dioxane, reflux, 24 h; b) $LiOH \cdot H_2O$, 1,4-dioxane: EtOH: $H_2O$ (2:2:1), reflux, 1 h; c) DMF, EDCI, HOBt, rt, 15 h.

5-(3-Fluoro-4-(trifluoromethyl)phenyl)oxazol-2-amine (0.198 g, 0.804 mmol), methyl 5-bromopicolinate (0.208 g, 0.964 mmol), $Cs_2CO_3$ (0.393 g, 1.205 mmol), $Pd_2(dba)_3$ (0.037 g, 0.0402 mmol), Xantphos (0.0465 g, 0.0803 mmol) and anhydrous 1,4-dioxane (10 mL) were added into a dry RBF. The mixture was degassed, filled up with $N_{2(g)}$ (×5) and was refluxed for 24 h under $N_{2(g)}$. The reaction mixture was quenched with aq. $NaHCO_3$ solution (8 mL) and diluted with EtOAc (10 mL). The organic layer was extracted with EtOAc (3×10 mL). The combined organic fractions were dried over $MgSO_4$, filtered and concentrated under reduced pressure. The residue was chromatographed on silica gel eluting with 50% EtOAc in DCM to afford methyl 5-((5-(3-fluoro-4-(trifluoromethyl)phenyl)oxazol-2-yl)amino)picolinate as light brown solid (0.227 g, 74%). $^1H$ NMR (400 MHz, DMSO-$d_6$) δ 11.30 (s, 1H), 8.83 (d, J=2.6 Hz, 1H), 8.31 (dd, J=8.7, 2.6 Hz, 1H), 8.09 (d, J=8.7 Hz, 1H), 7.89 (s, 1H), 7.86 (t, J=8.1 Hz, 1H), 7.60 (d, J=8.2 Hz, 1H), 3.85 (s, 3H). $^{13}C$ NMR (101 MHz, DMSO-$d_6$) δ 166.97, 164.82, 156.41, 139.87, 138.60, 136.99, 132.37, 131.71, 131.59, 128.66, 126.94, 125.97, 122.85, 118.66, 52.07. LCMS $R_f$ (min)=3.794, MS m/z=381.9 $[M+H]^+$.

A solution of LiOH·$H_2O$ (0.0387 g, 0.922 mmol) in $H_2O$ (1 mL) was added dropwise to a solution of methyl 5-((5-(3-fluoro-4-(trifluoromethyl)phenyl)oxazol-2-yl)amino)picolinate (0.352 g, 0.922 mmol) in 1,4-dioxane (2 mL) and EtOH (2 mL). The mixture was stirred at 80° C. for 1 h. After this period of time the contents were evaporated to dryness. The residue was washed with $Et_2O$ (15 mL), filtered off and dried under vaccum to afford the title compound as white solid (0.258 g, 76%) which was used in next step without further purification. $^1$H NMR (400 MHz, DMSO-$d_6$) δ 8.58 (d, J=2.5 Hz, 1H), 8.14 (dd, J=8.5, 2.6 Hz, 1H), 7.88 (d, J=8.6 Hz, 1H), 7.81-7.74 (m, 2H), 7.60 (d, J=12.2 Hz, 1H), 7.50 (d, J=8.1 Hz, 1H). $^{13}$C NMR (101 MHz, DMSO-$d_6$) δ 168.60, 156.61, 142.90, 142.22, 137.98, 137.23, 134.11, 128.40, 126.97, 123.99, 123.72, 122.56, 121.29, 118.56, 110.47. LCMS $R_f$ (min)=4.702, MS m/z=367.9 $[M+H]^+$.

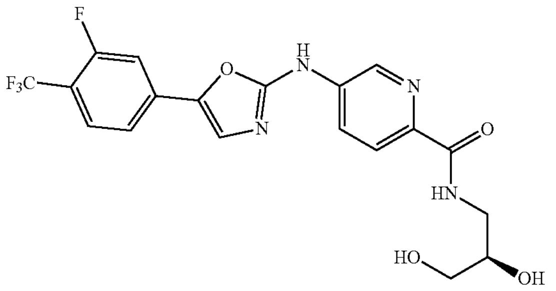 [SMILES: O=C(NC[C@@H](O)CO)c1ccc(Nc2ncc(-c3ccc(C(F)(F)F)c(F)c3)o2)cn1]

5-((5-(3-Fluoro-4-(trifluoromethyl)phenyl)oxazol-2-yl)amino)picolinic acid (0.12 g, 0.327 mmol), HOBt (0.046 g, 0.392 mmol), EDCI·HCl (0.069 g, 0.360 mmol) were added into a dry RBF and stirred with anhydrous DMF (6.5 mL) for 3 hours with continuous flow of $N_{2(g)}$. Then, (R)-3-amino-propane-1,2-diol (0.036 g, 0.392 mmol) was added and stirring was continued for 16 h. After this period of time the reaction was quenched with aq. $NaHCO_3$ solution (8 mL) and diluted with EtOAc (10 mL). The organic layer was extracted with EtOAc (3×10 mL) and the combined organics were dried over $MgSO_4$. The volatiles were removed under reduced pressure and the residue was subjected to preparative HPLC using 0.1% TFA in $H_2O$ and 0.1% TFA in ACN as eluents to yield (R)—N-(2,3-dihydroxypropyl)-5-((5-(3-fluoro-4-(trifluoromethyl)phenyl)oxazol-2-yl)amino)picolinamide as white solid (0.086 g, 60%, 100% purity). $^1$H NMR (400 MHz, DMSO-$d_6$) δ 11.18 (s, 1H), 8.80 (d, J=2.6 Hz, 1H), 8.46 (t, J=5.9 Hz, 1H), 8.30 (dd, J=8.6, 2.6 Hz, 1H), 8.05 (d, J=8.6 Hz, 1H), 7.88 (s, 1H), 7.85 (d, J=8.0 Hz, 1H), 7.73 (d, J=12.0 Hz, 1H), 7.59 (d, J=8.3 Hz, 1H), 4.95 (d, J=4.9 Hz, 1H), 4.66 (t, J=5.8 Hz, 1H), 3.63 (m, 1H), 3.50 (m, 1H), (the resonance of 2 protons overlapped with $H_2O$, and not assigned), 3.23 (m, 1H). $^{13}$C NMR (101 MHz, DMSO-$d_6$) δ 163.60, 156.61, 142.90, 142.22, 137.98, 137.23, 134.11, 128.40, 126.97, 123.99, 123.72, 122.56, 121.29, 118.56, 110.71, 110.47, 70.20, 63.94, 42.34. LCMS $R_f$ (min)=3.266, MS m/z=440.9 $[M+H]^+$. HRMS (ESI) calcd for $C_{19}H_{17}F_4N_4O_4^+$ $[M+H]^+$ 441.118, found 441.1197.

45. 5-((5-(3-Fluoro-4-(trifluoromethyl)phenyl)oxazol-2-yl)amino)-N'-hydroxypicolinimidamide (Scheme 42)

Scheme 42

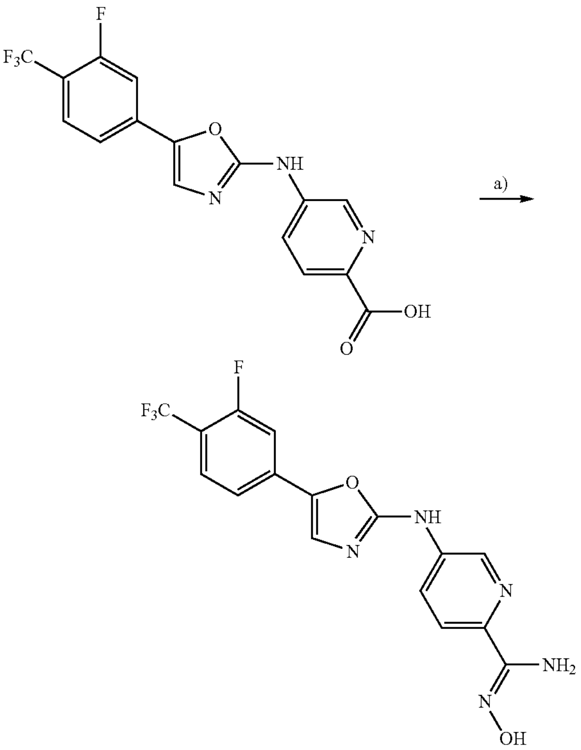

a) i. DMF, EDCI, HOBt, aq. $NH_4OH$, rt, 15 h., ii. TFAA, $Et_3N$, rt, 2 h; iii. $NH_2OH$•HCl, $Et_3N$, EtOH, reflux overnight;

5-((5-(3-Fluoro-4-(trifluoromethyl)phenyl)oxazol-2-yl)amino)picolinic acid (0.093 g, 0.253 mmol) was suspended in DMF (3.0 mL), then EDCI (1.3 equiv.) and HOBt (1.4 equiv.) were added. The resulting mixture was stirred at rt for 3 h. Concentrated aqueous ammonia solution (1 mL) was added and stirring was continued overnight. The reaction mixture was concentrated under reduced pressure, and the residue was purified on preparative HPLC to provide (5-((5-(3-fluoro-4-(trifluoromethyl)phenyl)oxazol-2-yl)amino)picolinamide (LCMS $R_f$ (min)=3.723, MS m/z=366.9 $[M+H]^+$), which was suspended in anhydrous THF. $Et_3N$ (3 equiv.) was added followed by TFAA (1.5 equiv.). The resulting solution was stirred at rt for 2 h, and the volatile solvents were removed in vacuo. The crude 5-((5-(3-fluoro-4-(trifluoromethyl)phenyl)oxazol-2-yl)amino)picolinonitrile was dried under high vacuum, then redissolved in absolute EtOH. $NH_2OH$·HCl (5 equivalents), and $Et_3N$ (5 equivalents) were added, and the resultant reaction mixture was stirred at reflux overnight. All volatile solvents were removed and the residue purified on preparative HPLC to provide 5-((5-(3-fluoro-4-(trifluoromethyl)-phenyl)oxazol-2-yl)amino)-N'-hydroxypicolinimidamide (0.023 g; 21.35% yield over three steps, corrected for 0.5 molar equivalent of dioxane present). $^1$H NMR (401 MHz, DMSO-$d_6$) δ 11.36 (s, 1H), 10.92-10.88 (br, 1H), 8.87 (s, 1H), 8.30 (d, J=8.7 Hz, 1H), 8.03 (d, J=8.6 Hz, 1H), 7.87 (s, 1H), 7.84 (t, J=8.0 Hz, 1H), 7.70 (d, J=12.0 Hz, 1H), 7.58 (d, J=8.4 Hz, 1H). $^{13}$C NMR (101 MHz, DMSO-$d_6$) δ 161.09, 158.56, 156.88, 142.85, 138.85, 138.75, 134.51, 134.41, 128.85, 127.37, 127.14, 124.44, 123.88, 123.16, 121.75, 119.08, 119.04, 115.15, 115.03, 114.83, 114.71, 111.22, 110.99. LCMS $R_f$ (min)=3.782, MS m/z=381.9 $[M+H]^+$. HRMS (ESI) calcd for $C_{16}H_{12}F_4N_5O_2^+$ $[M+H]^+$ 382.0922, found 382.0907.

46. N'-hydroxy-5-((5-(5-(trifluoromethyl)pyridin-2-yl)oxazol-2-yl)amino)-picolinimidamide (Scheme 43)

Scheme 43

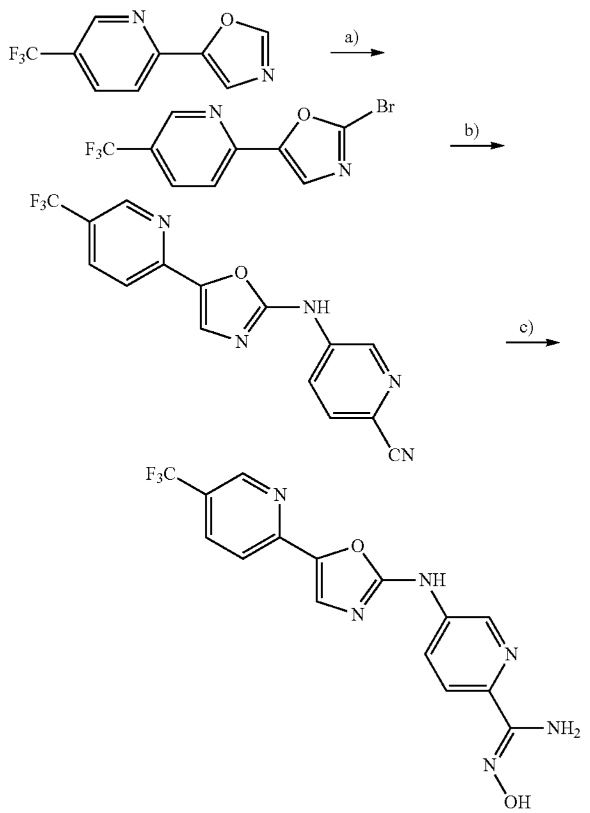

a) $BrCF_2CF_2Br$, ${}^tBuOLi$, DMF/m-xylene, 60° C. 3 h; b) 5-aminopicolinonitrile, $Cs_2CO_3$, $Pd_2(dba)_3$, Xantphos, 1,4-dioxane 110° C., 18 h; b) $NH_2OH{\bullet}HCl$, $Et_3N$, EtOH, reflux, 16 h.

Intermediate L—2-bromo-5-(5-(trifluoromethyl)pyridin-2-yl)oxazole $BrCF_2CF_2Br$ (1.71 g, 6.6 mmol) and ${}^tBuOLi$ (0.53 g, 6.6 mmol) were added to a solution of 5-(5-(trifluoromethyl) pyridin-2-yl)oxazole (0.70 g, 3.3 mmol) in DMF/m-xylene (5/5 mL). The resulting mixture was stirred at 60° C. for 3 h and quenched with saturated $NaHCO_3$ (10 mL). The aqueous phase was extracted with EtOAc (20 mL×2). The combined organic phases were dried over $Na_2SO_4$, filtered, and concentrated to give a brown oil that was subjected to flash chromatography on silica gel (3%~10%, EtOAc/hexane). Collection of the appropriate fractions provided 2-bromo-5-(5-(trifluoromethyl)pyridin-2-yl)oxazole as a white solid (0.68 g, 70% yield). ${}^1H$ NMR (400 MHz, $CDCl_3$) δ 8.86 (m, 1H), 8.00 (dd, J=8.3, 1.7 Hz, 1H), 7.75 (s, 1H), 7.72 (d, J=8.3 Hz, 1H). MS m/z=292.9 $[M+H]^+$.

An oven-dried RBF was charged with $Pd_2(dba)_3$ (0.025 g, 0.04 equiv.), Xantphos (0.031 g, 0.08 equiv.), 2-bromo-5-

(5-(trifluoromethyl)pyridin-2-yl)oxazole (Intermediate L) (0.2 g, 0.68 mmol), $Cs_2CO_3$ (0.332 g, 1.5 equiv.), 5-aminopicolinonitrile (0.405 g, 3.4 mmol, 5 equiv.) and 1,4-dioxane (10 mL). Vacuum was applied briefly to the reaction flask followed by backfilling with $N_2$ and the procedure was repeated five times. The mixture was then heated to 110° C. and stirred for 18 h. The reaction mixture was poured into water and extracted with EtOAc (5×). The combined organic solvents were dried over $MgSO_4$ and evaporated to dryness. The residue was purified on silica gel using mixtures of DCM and EtOAc to provide 5-((5-(5-(trifluoromethyl)pyridin-2-yl)oxazol-2-yl)amino)picolinonitrile (0.127 g, 56.36% yield). ${}^1H$ NMR (401 MHz, DMSO-$d_6$) δ 11.59 (s, 1H), 8.93 (d, J=1.0 Hz, 1H), 8.85 (d, J=2.4 Hz, 1H), 8.32 (dd, J=8.7, 2.6 Hz, 1H), 8.26 (dd, J=8.6, 2.1 Hz, 1H), 7.99 (d, J=8.7 Hz, 1H), 7.93 (s, 1H), 7.81 (d, J=8.4 Hz, 1H). ${}^{13}C$ NMR (101 MHz, DMSO-$d_6$) δ 157.07, 150.25, 147.07, 144.32, 140.75, 139.28, 135.28, 130.30, 129.31, 125.56, 124.60, 123.47, 123.14, 118.42, 118.38. LCMS $R_f$ (min)=2.978, MS m/z=332.1 $[M+H]^+$.

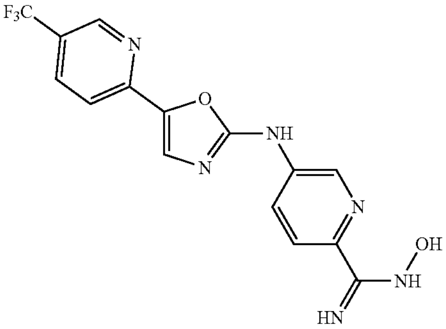 [SMILES: N=C(NO)c1ccc(Nc2ncc(-c3ccc(C(F)(F)F)cn3)o2)cn1]

5-((5-(5-(Trifluoromethyl)pyridin-2-yl)oxazol-2-yl) amino)picolinonitrile (0.127 g, 0.383 mmol) was suspended in EtOH (10 mL), then $NH_2OH{\cdot}HCl$ (0.213 g, 3.067, mmol, 8 equiv.) was added and approximately half of the EtOH was removed in vacuo. $Et_3N$ (0.42 mL, 3.067, mmol, 8 equiv.) was added and the resulting reaction mixture was stirred at reflux overnight. The volatile solvents were removed and the resulting solids were suspended in water, were collected by filtering then washing well with water. The crude solid was purified on preparative HPLC to provide N-hydroxy-5-((5-(5-(trifluoromethyl)pyridin-2-yl)oxazol-2-yl)amino)picolinimidamide (0.106 g; 75.9%). ${}^1H$ NMR (401 MHz, DMSO-$d_6$) δ 11.50 (s, 1H), 10.97-10.88 (brs, 1H), 8.95-8.93 (m, 1H), 8.89 (d, J=2.5 Hz, 1H), 8.6-8.2 (br, 1H), 8.32 (dd, J=8.8, 2.6 Hz, 1H), 8.27 (dd, J=8.7, 2.1 Hz, 1H), 8.04 (d, J=8.8 Hz, 1H), 7.94 (s, 1H), 7.81 (d, J=8.4 Hz, 1H). ${}^{13}C$ NMR (101 MHz, DMSO-$d_6$) δ 158.42, 157.39, 154.87, 150.31, 147.06, 144.17, 138.92, 138.84, 135.26, 129.41, 125.57, 123.96, 123.38, 123.33, 123.06, 122.87, 118.28. LCMS $R_f$ (min)=2.865, MS m/z=365.1 $[M+H]^+$. HRMS (ESI) calcd for $C_{15}H_{12}F_3N_6O_2^+$ $[M+H]^+$ 365.0968, found 365.0974.

47. 6-((5-(4-Fluorophenyl)oxazol-2-yl)amino)-N'-hydroxypyridazine-3-carboximidamide (Scheme 44)

Scheme 44

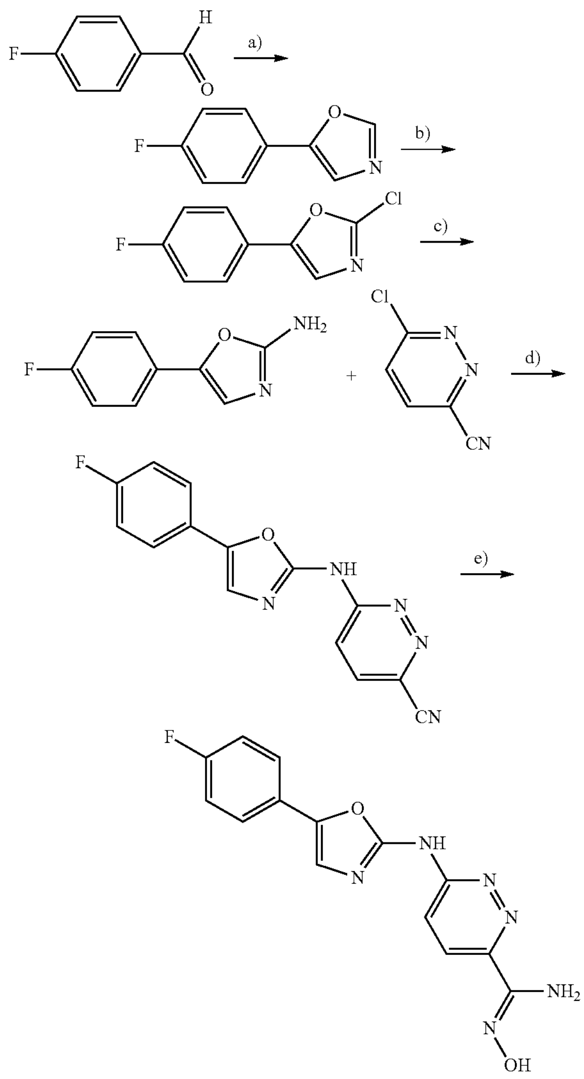

a) TosMIC, $K_2CO_3$, MeOH, reflux, 5 h; b) i. LiHMDS, THF, -78° C., 0.5 h; ii. $C_2Cl_6$, -78° C.~rt, overnight; c) $NH_4OH$ (aq.), THF, microwave, 90° C., 1 h; d) $Cs_2CO_3$, $Pd_2(dba)_3$, Xantphos, 1,4-dioxane, 110° C., 18 h; e) $NH_2OH$•HCl, $Et_3N$, EtOH, reflux overnight; f) TFA, $Et_3SiH$ rt 4 h.

4-Fluorobenzaldehyde (2.00 g, 16.11 mmol) and $K_2CO_3$ (2.67 g, 19.33 mmol) were added to a solution of p-toluenesulfonylmethyl isocyanide (3.46 g, 17.73 mmol) in MeOH (30 mL) at rt. The resulting mixture was then refluxed for 5 h under nitrogen before being concentrated under reduced pressure. The residue was partitioned between $Et_2O$ and $H_2O$. The aqueous phase was extracted with $Et_2O$ (50 mL×2), and the combined organic phases were dried over $MgSO_4$, filtered and concentrated to give a light yellow oil that was subjected to flash chromatography on silica gel (3%×20%, EtOAc/hexane). Collection of the appropriate fractions provided 5-(4-fluorophenyl)oxazole as a white solid. (2.16 g, 82% yield). $^1$H NMR (400 MHz, $CDCl_3$) δ) δ 7.90 (s, 1H), 7.58-7.63 (m, 2H), 7.28 (s, 1H), 7.07-7.13 (m, 2H). MS m/z=164.1 $[M+H]^+$.

LiHMDS (1.0 M in THF, 6.58 mL, 6.58 mmol) was added to a solution of 5-(4-fluorophenyl)oxazole (0.98 g, 5.98 mmol) in dry THF (6 mL) at −78° C. under nitrogen atmosphere. After a further 0.5 h, a solution of $C_2Cl_6$ (2.12 g, 8.97 mmol) in THF (5 mL) was treated. The resulting reaction mixture was stirred at −78° C. for another 2 h and allowed to warm to rt over 14 h. The reaction was quenched with saturated $NaHCO_3$ (10 mL). The aqueous phase was extracted with EtOAc (30 mL×2). The combined organic phases were dried over $Na_2SO_4$, filtered, and concentrated to give a brown oil that was subjected to flash chromatography on silica gel (2% ~10%, EtOAc/hexane). Collection of the appropriate fractions provided 2-chloro-5-(4-fluorophenyl) oxazole as a white solid (1.06 g, 90% yield). $^1$H NMR (400 MHz, $CDCl_3$) δ 7.55-7.60 (m, 2H), 7.23 (s, 1H), 7.10-7.15 (m, 2H). MS m/z=198.0 $[M+H]^+$.

$NH_4OH$ (28~30% $NH_3$ basis aqueous solution, 8 mL) was added to a solution of 2-chloro-5-(4-fluorophenyl)oxazole (0.60 g, 3.04 mmol) in THF (1.5 mL) at rt. The resulting reaction mixture was irradiated under microwave for 1 h at 90° C. The solid was filtered and washed with DCM (5 mL×2), providing 5-(4-fluorophenyl)oxazol-2-amine as a white solid (0.52 g, 96% yield). $^1$H NMR (400 MHz, DMSO-$d_6$) δ 7.47-7.50 (m, 2H), 7.18-7.23 (m, 2H), 7.15 (s, 1H), 6.82 (s, 2H). MS m/z=179.0 $[M+H]^+$.

An oven-dried RBF was charged with $Pd_2(dba)_3$ (0.044 g, 0.05 equiv.), Xantphos (0.055 g, 0.10 equiv.), 5-(4-fluorophenyl)oxazol-2-amine (0.17 g, 0.954 mmol), $Cs_2CO_3$ (0.466 g, 1.5 equiv.), 6-chloropyridazine-3-carbonitrile (0.146 g, 1.05 mmol, 1.1 equiv.) and 1,4-dioxane (5 mL). Vacuum was applied briefly to the reaction flask followed by backfilling with $N_2$ and the procedure was repeated five times. The mixture was then heated to 110° C. and stirred for 18 h. The reaction mixture was poured into water and extracted with EtOAc (5×). The combined organic solvents were dried over $MgSO_4$ and evaporated to dryness. The residue was purified on silica gel using mixtures of DCM and EtOAc to provide 6-((5-(4-fluorophenyl)oxazol-2-yl)amino)pyridazine-3-carbonitrile (0.181 g, 67.44% yield). $^1$H NMR (401 MHz, DMSO-$d_6$) δ 12.37 (br, 1H), 8.41 (s, 1H), 8.22 (d, J=9.4 Hz, 1H), 7.67 (dd, J=8.7, 5.4 Hz, 2H), 7.59 (s, 1H), 7.32 (t, J=8.9 Hz, 2H). $^{13}$C NMR (101 MHz, DMSO-$d_6$) δ 163.26, 160.82, 133.39, 125.81, 125.73, 124.53, 124.50, 117.07, 116.75, 116.53. LCMS $R_f$ (min)=3.185. MS m/z=282.1 $[M+H]^+$.

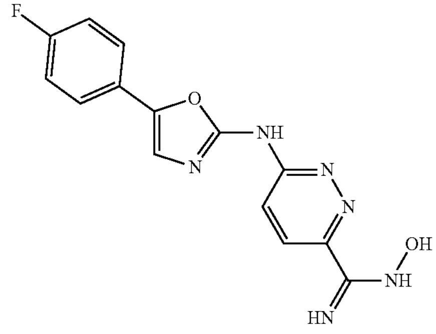

6-((5-(4-Fluorophenyl)oxazol-2-yl)amino)pyridazine-3-carbonitrile (0.152 g, 0.54 mmol) was suspended in EtOH (12 mL), then $NH_2OH$·HCl (0.301 g, 4.323 mmol, 8 equiv.) was added and approximately half of the EtOH was removed in vacuo. $Et_3N$ (0.59 mL, 4.323 mmol, 8 equiv.) was added and the resulting reaction mixture was stirred at reflux overnight. The volatile solvents were removed and the resulting solids were suspended in water, collected by filtering then washing well with water. The crude solid was purified on preparative HPLC to provide 6-((5-(4-fluorophenyl)oxazol-2-yl)amino)-N-hydroxypyridazine-3-carboximidamide (0.075 g; 43.4%). $^1H$ NMR (401 MHz, DMSO-$d_6$) δ 10.59 (s, 1H), 8.28 (d, J=8.9 Hz, 1H), 8.08 (d, J=9.5 Hz, 1H), 7.68 (dd, J=8.7, 5.4 Hz, 2H), 7.59 (s, 1H), 7.32 (t, J=8.9 Hz, 2H), $^{13}C$ NMR (101 MHz, DMSO-$d_6$) δ 163.19, 160.75, 158.51, 156.23, 144.92, 127.54, 125.71, 125.63, 124.69, 121.95, 116.73, 116.51. LCMS $R_f$ (min)=2.935, MS m/z=315.1 $[M+H]^+$. HRMS (ESI) calcd for $C_{14}H_{12}FN_6O_2^+$ $[M+H]^+$ 315.1, found 315.0991.

48. 6-((5-(3,4-Difluorophenyl)oxazol-2-yl)amino)-N'-hydroxypyridazine-3-carboximidamide (Scheme 45)

Scheme 45

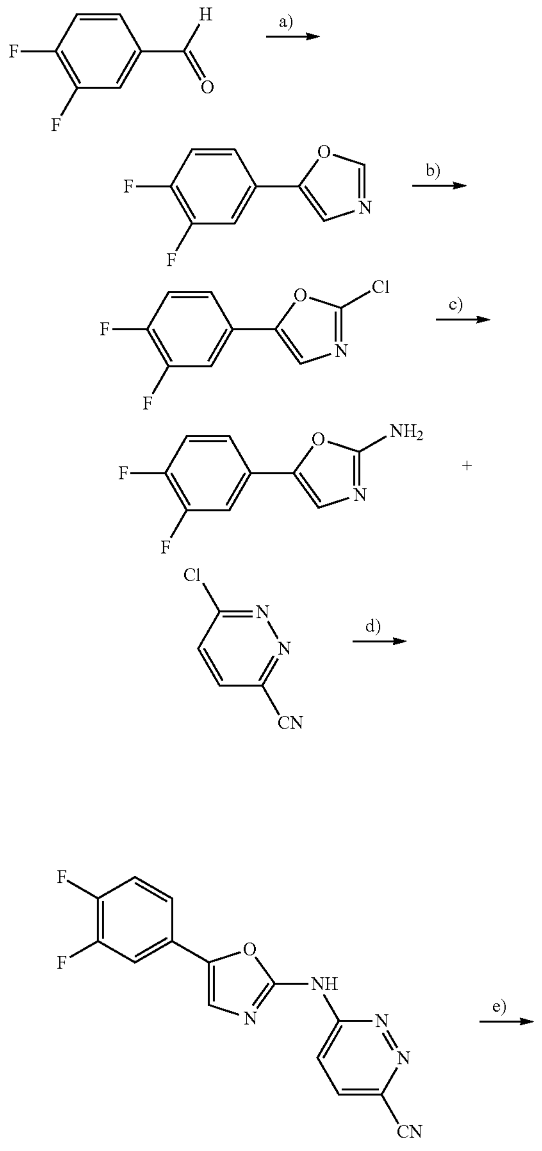

-continued

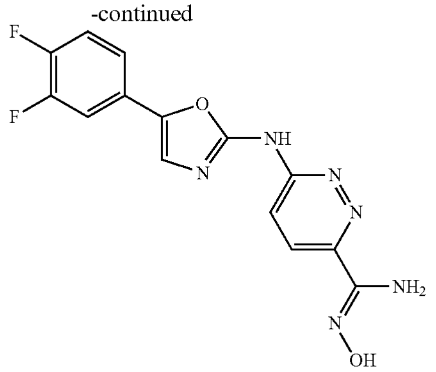

a) TosMIC, $K_2CO_3$, MeOH, reflux 5 h; b) i. LiHMDS, THF, -78° C. 0.5 h; ii. $C_2Cl_6$, -78° C.~rt, overnight; c) $NH_4OH$ (aq.), THF, microwave, 90° C., 1 h; d) $Cs_2CO_3$, $Pd_2(dba)_3$, Xantphos, 1,4-dioxane, 110° C., 18 h; e) $NH_2OH$•HCl, $Et_3N$, EtOH, reflux, overnight; f) TFA, $Et_3SiH$, rt, 4 h.

3,4-Difluorobenzaldehyde (2.00 g, 14.1 mmol) and $K_2CO_3$ (2.33 g, 16.9 mmol) were added to a solution of TosMIC (3.02 g, 15.5 mmol) in MeOH (30 mL) at rt. The resulting mixture was then refluxed for 5 h under nitrogen before being concentrated under reduced pressure. The residue was partitioned between $Et_2O$ and $H_2O$. The aqueous phase was extracted with $Et_2O$ (50 mL×2), and the combined organic phases were dried over $MgSO_4$, filtered and concentrated to give a light yellow oil that was subjected to flash chromatography on silica gel (3%~20%, EtOAc/hexane). Collection of the appropriate fractions provided 5-(3,4-difluorophenyl)oxazole) as a white solid. (2.25 g, 88% yield). $^1H$ NMR (400 MHz, $CDCl_3$) δ) δ 7.55-7.60 (m, 2H), 7.23 (s, 1H), 7.09-7.15 (m, 2H), MS m/z=182.0 $[M+H]^+$.

LiHMDS (1.0 M in THF, 8.46 mL, 8.46 mmol) was added to a solution of 5-(3,4-difluorophenyl)oxazole (1.40 g, 7.69 mmol) in dry THF (10 mL) at −78° C. under nitrogen atmosphere. After a further 0.5 h, a solution of $C_2Cl_6$ (2.73 g, 11.5 mmol) in THF (5 mL) was treated. The resulting reaction mixture was stirred at −78° C. for another 2 h and allowed to warm to rt over 14 h. The reaction was quenched with saturated $NaHCO_3$ (10 mL). The aqueous phase was extracted with EtOAc (40 mL×2). The combined organic phases were dried over $Na_2SO_4$, filtered, and concentrated to give a brown oil that was subjected to flash chromatography on silica gel (2% ~10%, EtOAc/hexane). Collection of the appropriate fractions provided 2-chloro-5-(3,4-difluorophenyl)oxazole as a white solid (1.41 g, 85% yield). $^1H$ NMR (400 MHz, $CDCl_3$) δ 7.47 (m, 1H), 7.39 (m, 1H), 7.32 (s, 1H), 7.31 (m, 1H). MS m/z=216.0 $[M+H]^+$.

$NH_4OH$ (28-30% $NH_3$ basis aqueous solution, 12 mL) was added to a solution of 2-chloro-5-(3,4-difluorophenyl) oxazole (1.10 g, 4.42 mmol) in THF (2.0 mL) at rt. The resulting reaction mixture was irradiated under microwave for 1 h at 90° C. The solid was filtered and washed with DCM (5 mL×2), providing 5-(3,4-difluorophenyl)oxazol-2-amine as a white solid (0.82 g, 95% yield). $^1H$ NMR (400 MHz, DMSO-$d_6$) δ 7.38-7.49 (m, 2H), 7.25 (s, 2H), 6.93 (s, 2H). MS m/z=197.0 $[M+H]^+$.

An oven-dried RBF was charged with $Pd_2(dba)_3$ (0.058 g, 0.05 equiv.), Xantphos (0.074 g, 0.10 equiv.), 5-(3,4-difluorophenyl)oxazol-2-amine (0.25 g, 1.274 mmol), $Cs_2CO_3$ (0.622 g, 1.5 equiv.), 6-chloropyridazine-3-carbonitrile (0.196 g, 1.40 mmol, 1.1 equiv.) and 1,4-dioxane (7 mL). Vacuum was applied briefly to the reaction flask followed by backfilling with $N_2$ and the procedure was repeated five times. The mixture was then heated to 110° C. and stirred for 18 h. The reaction mixture was poured into water and extracted with EtOAc (5×). The combined organic solvents were dried over $MgSO_4$ and evaporated to dryness. The residue was purified on silica gel using mixtures of DCM and EtOAc to provide 6-((5-(3,4-difluorophenyl)oxazol-2-yl)amino)pyridazine-3-carbonitrile (0.194 g, 50.9% yield). $^{1}H$ NMR (401 MHz, DMSO-$d_6$) δ 12.44-12.38 (br s, 1H), 8.41 (d, J=8.9 Hz, 1H), 8.23 (d, J=9.4 Hz, 1H), 7.74-7.69 (m, 1H), 7.68 (s, 1H), 7.56 (dt, J=10.5, 8.5 Hz, 1H), 7.48-7.43 (m, 1H). $^{13}C$ NMR (101 MHz, DMSO-$d_6$) δ 156.61, 154.90, 151.62, 151.49, 150.43, 149.18, 149.05, 148.10, 133.42, 125.44, 120.44, 119.13, 118.95, 117.04, 112.84, 112.65. LCMS $R_f$ (min)=3.061, MS m/z=300.0 $[M+H]^+$.

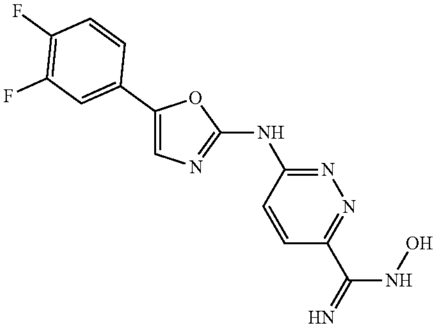

6-((5-(3,4-Difluorophenyl)oxazol-2-yl)amino)pyridazine-3-carbonitrile (0.095 g, 0.317 mmol) was suspended in EtOH (12 mL), then $NH_2OH \cdot HCl$ (0.177 g, 2.54 mmol, 8 equiv.) was added and approximately half of the EtOH was removed in vacuo. $Et_3N$ (0.347 mL, 2.54 mmol, 8 equiv.) was added and the resulting reaction mixture was stirred at reflux overnight. The volatile solvents were removed and the resulting solids were suspended in water, collected by filtering then washing well with water. The crude solid was purified on preparative HPLC to provide 6-((5-(3,4-difluorophenyl)oxazol-2-yl)amino)-N-hydroxypyridazine-3-carboximidamide (0.083 g; 78.67%). $^{1}H$ NMR (401 MHz, DMSO-$d_6$) δ 11.85 (brs, 1H), 10.16 (brs, 1H), 8.31-7.47 (m, 6H), 5.97 (s, 2H). LCMS $R_f$(min)=2.848, MS m/z=333.1 $[M+H]^+$. HRMS (ESI) calcd for $C_{14}H_{11}F_2N_6O_2^+$ $[M+H]^+$ 333.0906, found 333.0908.

49. 6-((5-(5-Fluoropyridin-2-yl)oxazol-2-yl)amino)-N'-hydroxypyridazine-3-carboximidamide (Scheme 46)

Scheme 46

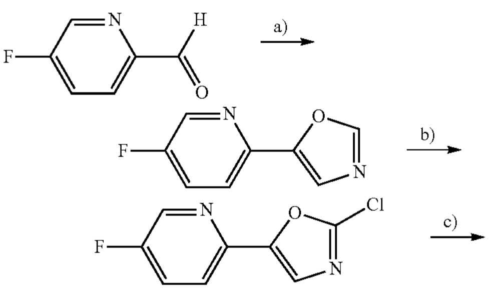

-continued

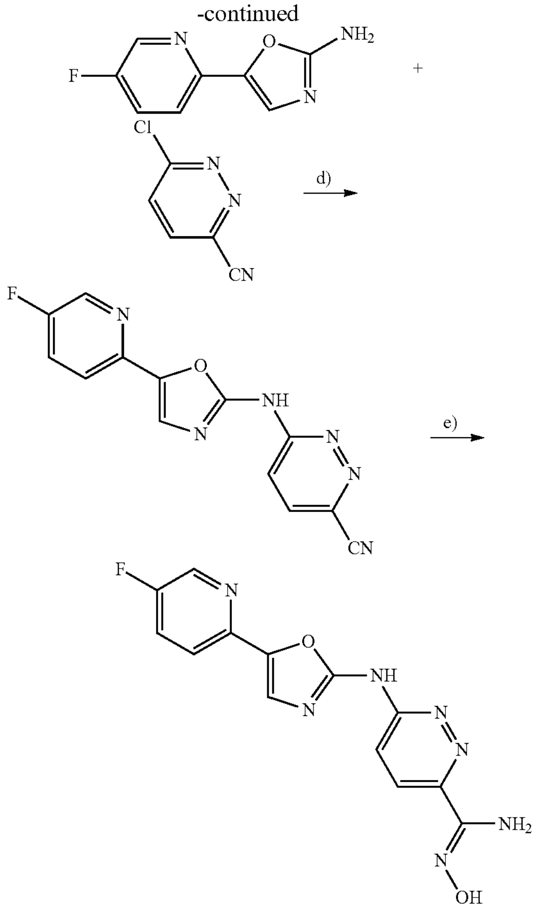

a) TosMIC, $K_2CO_3$, MeOH, reflux 5 h; b) i. LiHMDS, THF, -78° C. 0.5 h; ii. $C_2Cl_6$, -78° C.~rt, overnight; c) $NH_4OH$ (aq.), THF, microwave, 90° C., 1 h; d) $Cs_2CO_3$, $Pd_2(dba)_3$, Xantphos, 1,4-dioxane, 110° C., 18 h; e) $NH_2OH \cdot HCl$, $Et_3N$, EtOH, reflux, overnight; f) TFA, $Et_3SiH$, rt, 4 h.

5-Fluoropicolinaldehyde (1.20 g, 9.60 mmol) and $K_2CO_3$ (1.60 g, 11.5 mmol) were added to a solution of p-toluenesulfonylmethyl isocyanide (2.06 g, 10.6 mmol) in MeOH (20 mL) at rt. The resulting mixture was then refluxed for 5 h under nitrogen before being concentrated under reduced pressure. The residue was partitioned between $Et_2O$ and $H_2O$. The aqueous phase was extracted with $Et_2O$ (20 mL×2), and the combined organic phases were dried over $MgSO_4$, filtered and concentrated to give a light yellow oil that was subjected to flash chromatography on silica gel (3%~20%, EtOAc/hexane). Collection of the appropriate fractions provided 5-(5-fluoropyridin-2-yl)oxazole as a white solid. (1.39 g, 88% yield). $^{1}H$ NMR (400 MHz, $CDCl_3$) δ) δ 8.49 (d, J=2.8 Hz, 1H, split by F), 7.95 (s, 1H), 7.66-7.69 (m, 1H), 7.64 (s, 1H), 7.48 (td, J=8.3, 2.8 Hz, 1H). MS m/z=165.1 $[M+H]^+$.

LiHMDS (1.0 M in THF, 5.18 mL, 5.18 mmol) was added to a solution of 5-(5-fluoropyridin-2-yl)oxazole (0.80 g, 4.93 mmol) in dry THF (5 mL) at −78° C. under nitrogen atmosphere. After a further 0.5 h, a solution of $C_2Cl_6$ (1.52 g, 6.41 mmol) in THF (5 mL) was treated. The resulting reaction mixture was stirred at −78° C. for another 2 h and allowed to warm to rt over 14 h. The reaction was quenched with saturated $NaHCO_3$ (10 mL). The aqueous phase was extracted with EtOAc (30 mL×2). The combined organic phases were dried over $Na_2SO_4$, filtered, and concentrated to give a brown oil that was subjected to flash chromatography on silica gel (2% ~10%, EtOAc/hexane). Collection of the appropriate fractions provided 2-chloro-5-(5-fluoropyridin-2-yl)oxazole as a white solid (0.82 g, 84% yield). $^1$H NMR (400 MHz, $CDCl_3$) δ 7.47 (d, J=2.8 Hz, 1H, split by F), 7.59-7.63 (m, 1H), 7.56 (s, 1H), 7.48 (td, J=8.0 and 2.8 Hz, 1H). MS m/z=198.9 $[M+H]^+$.

$NH_4OH$ (28-30% $NH_3$ basis aqueous solution, 4 mL) was added to a solution 2-chloro-5-(5-fluoropyridin-2-yl)oxazole (0.20 g, 1.02 mmol) in THF (0.5 mL) at rt. The resulting reaction mixture was irradiated under microwave for 1 h at 90° C. The solid was filtered and washed with DCM (3 mL×2), providing 5-(5-fluoropyridin-2-yl)oxazol-2-amine as a white solid (0.18 g, 97% yield). $^1$H NMR (400 MHz, DMSO-$d_6$) δ 8.48 (s, 1H), 7.72 (m, 1H), 7.47 (m, 1H), 7.30 (s 1H), 7.05 (s, 2H). MS m/z=180.1 $[M+H]^+$.

An oven-dried RBF was charged with $Pd_2(dba)_3$ (0.044 g, 0.05 equiv.), Xantphos (0.055 g, 0.10 equiv.), 5-(5-fluoropyridin-2-yl)oxazol-2-amine (0.17 g, 0.948 mmol), $Cs_2CO_3$ (0.464 g, 1.5 equiv.), 6-chloropyridazine-3-carbonitrile (0.146 g, 1.04 mmol, 1.1 equiv.) and 1,4-dioxane (5 mL). Vacuum was applied briefly to the reaction flask followed by backfilling with $N_2$ and the procedure was repeated five times. The mixture was then heated to 110° C. and stirred for 18 h. The reaction mixture was poured into water and extracted with EtOAc (5×). The combined organic solvents were dried over $MgSO_4$ and evaporated to dryness. The residue was purified on silica gel using mixtures of DCM and EtOAc to provide 6-((5-(5-fluoropyridin-2-yl)oxazol-2-yl)amino)pyridazine-3-carbonitrile (0.053 g, 19.78% yield). $^1$H NMR (401 MHz, DMSO-$d_6$) δ 12.51 (s, 1H), 8.61 (d, J=2.8 Hz, 1H), 8.46 (d, J=9.0 Hz, 1H), 8.25 (d, J=9.4 Hz, 1H), 7.86 (td, J=8.7, 2.9 Hz, 1H), 7.72 (m, J=4.1 Hz, 2H). $^{13}$C NMR (101 MHz, DMSO-$d_6$) δ 159.74, 157.21, 156.60, 145.29, 143.53, 138.57, 138.33, 133.46, 125.05, 124.86, 120.38, 120.34, 117.04. LCMS $R_f$ (min)=2.892, MS m/z=283.1 $[M+H]^+$.

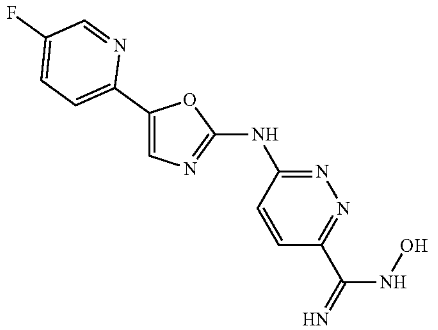

6-((5-(5-Fluoropyridin-2-yl)oxazol-2-yl)amino)pyridazine-3-carbonitrile (0.05 g, 0.177 mmol) was suspended in EtOH (7 mL), then $NH_2OH·HCl$ (0.099 g, 1.417 mmol, 8 equiv.) was added and approximately half of the EtOH was removed in vacuo. $Et_3N$ (0.193 mL, 1.417 mmol, 8 equiv.) was added and the resulting reaction mixture was stirred at reflux overnight. The volatile solvents were removed and the resulting solids were suspended in water, collected by filtering then washing well with water, EtOH, and $Et_2O$ to provide 6-((5-(5-fluoropyridin-2-yl)oxazol-2-yl)amino)-N'-hydroxypyridazine-3-carboximidamide (0.041 g; 73.4%). $^1$H NMR (401 MHz, DMSO-$d_6$) δ 11.97-11.87 (br, 1H), 10.17 (s, 1H), 8.60 (d, J=2.7 Hz, 1H), 8.29 (br, 1H), 8.02 (d, J=8.9 Hz, 1H), 7.85 (td, J=8.7, 2.8 Hz, 1H), 7.72-7.69 (m, 1H), 7.67 (s, 1H), 5.98 (s, 2H). $^{13}$C NMR (101 MHz, DMSO-$d_6$) δ 159.58, 157.07, 144.72, 143.85, 138.50, 138.26, 124.99, 124.79, 120.06, 120.02. LCMS $R_f$ (min)=

2.439, MS m/z=316.1 $[M+H]^+$. HRMS (ESI) calcd for $C_{13}H_{11}FN_7O_2^+$ $[M+H]^+$ 316.0953, found 316.0954.

50. N,5-Dihydroxy-2-((5-(4-(trifluoromethyl)phenyl)oxazol-2-yl)amino)isonicotinimid-amide (Scheme 47)

Scheme 47

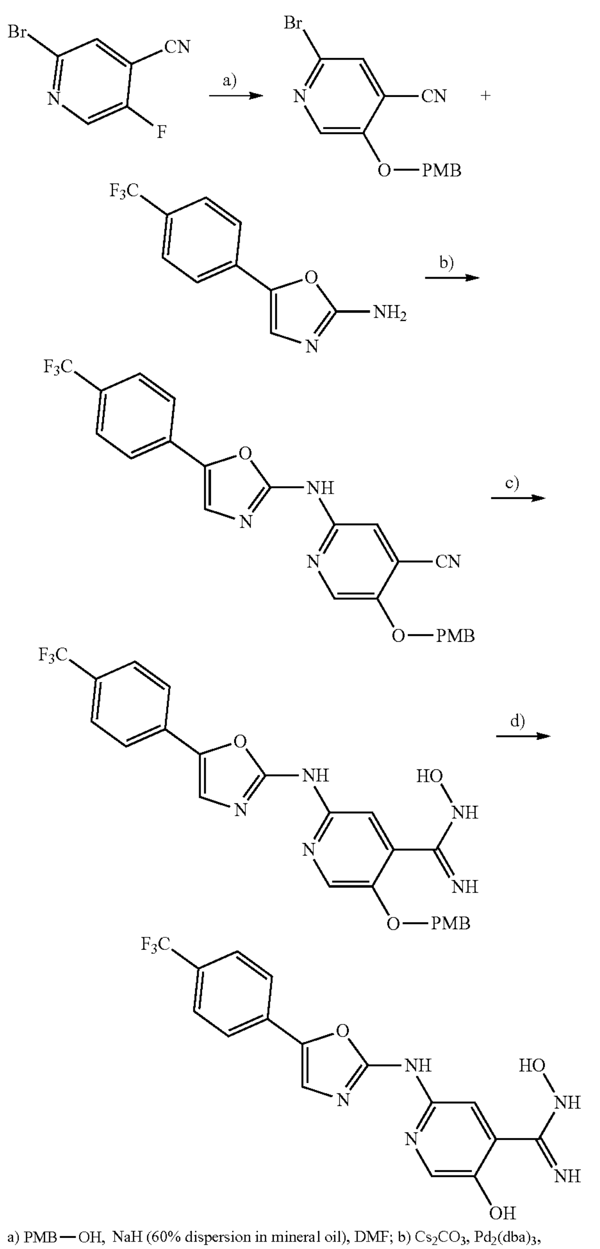

a) PMB—OH, NaH (60% dispersion in mineral oil), DMF; b) $Cs_2CO_3$, $Pd_2(dba)_3$, Xantphos, 1,4-dioxane, 110° C., 18 h; c) $NH_2OH$•HCl, $Et_3N$, EtOH, reflux 18 h; d) TFA, $Et_3SiH$, rt.

4-Methoxybenzyl alcohol (0.687 g, 4.975 mmol, 1.0 equivalent) was dissolved in dry DMF (12 mL), then NaH (60%, 0.119 g, 4.975 mmol, 1.0 equivalent)) added under nitrogen atmosphere at 0° C. After 15 minutes of stirring, the solution was transferred to a flask containing 2-bromo-5-fluoroisonicotinonitrile (1.0 g, 0.495 mmol) in dry DMF (12 mL) at 0° C. The resultant reaction mixture was stirred at rt for 1 h. LCMS indicated that all starting material had been consumed. The reaction mixture was poured into sat. aq. $NaHCO_3$ solution and the product extracted with DCM (5×). The combined organic solutions were dried over $MgSO_4$, and evaporated to dryness. The residue was purified on silica gel using neat toluene as eluents to provide 2-bromo-5-((4-methoxybenzyl)oxy)isonicotinonitrile (1.37 g, 86.27%). $^1H$ NMR (401 MHz, $CDCl_3$) δ 8.25 (s, 1H), 7.59 (d, J=0.4 Hz, 1H), 7.36-7.33 (m, 2H), 6.94-6.89 (m, 2H), 5.23 (s, 2H), 3.81 (d, J=3.3 Hz, 3H). $^{13}C$ NMR (101 MHz, $CDCl_3$) δ 160.10, 154.31, 136.57, 131.84, 130.35, 129.26, 126.22, 114.38, 112.86, 112.73, 71.87, 55.36. LCMS $R_f$ (min)=3.691, MS m/z=316.9/318.9 $(M-H)^-$.

An oven-dried RBF was charged with $Pd_2(dba)_3$ (0.108 g, 0.15 equiv.), Xantphos (0.09 g, 0.2 equiv.), 5-(4-(trifluoromethyl)phenyl)oxazol-2-amine (Intermediate D) (0.215 g, 0.939 mmol, 1.2 equiv.), $Cs_2CO_3$ (0.383 g, 1.5 equiv.), 2-bromo-5-((4-methoxybenzyl)oxy)isonicotinonitrile (0.25 g, 0.783 mmol) and 1,4-dioxane (15 mL). Vacuum was applied briefly to the reaction flask followed by backfilling with $N_2$ and the procedure was repeated five times. The mixture was then heated to 110° C. and stirred for 18 h. LCMS indicated that the starting materials had been completely consumed. The reaction mixture was then poured into water and extracted with EtOAc (5×). The combined organic solvents were dried over $MgSO_4$ and evaporated to dryness. The residue was purified on silica gel using mixtures of DCM and EtOAc to provide 5-((4-methoxybenzyl)oxy)-2-((5-(4-(trifluoromethyl)phenyl)oxazol-2-yl)amino)isonicotinonitrile (0.051 g, 13.95% yield). $^1H$ NMR (401 MHz, DMSO-$d_6$) δ 11.33 (s, 1H), 8.63-8.42 (s, 1H), 8.31 (s, 1H), 7.80 (s, 4H), 7.74 (s, 1H), 7.43 (d, J=8.4 Hz, 2H), 6.95 (d, J=8.5 Hz, 2H), 5.28 (s, 2H), 3.77 (s, 3H). LCMS $R_f$ (min)=3.93, MS m/z=467.1 $[M+H]^+$.

5-((4-Methoxybenzyl)oxy)-2-((5-(4-(trifluoromethyl)phenyl)oxazol-2-yl)amino)isonicotinonitrile (0.043 g, 0.092 mmol) was suspended in EtOH (10 mL), then $NH_2OH·HCl$ (0.051 g, 0.737 mmol) was added and approximately half of the EtOH was removed in vacuo. $Et_3N$ (0.101 mL, 0.737 mmol) was added and the resulting reaction mixture was stirred at reflux overnight. LCMS indicated that the reaction was complete. The volatile solvents were removed and the resulting solids were suspended in water, collected by filtering then washing well with water. The solids were washed with $Et_2O$ then dried under high vacuum to provide N-hydroxy-5-((4-methoxybenzyl)oxy)-2-((5-(4-(trifluoromethyl)phenyl)oxazol-2-yl)amino)isonicotinimidamide (0.033 g, 71.66% yield). The product was used in the next step without further purification LCMS $R_f$ (min)=4.733, MS m/z=499.9 $[M+H]^+$.

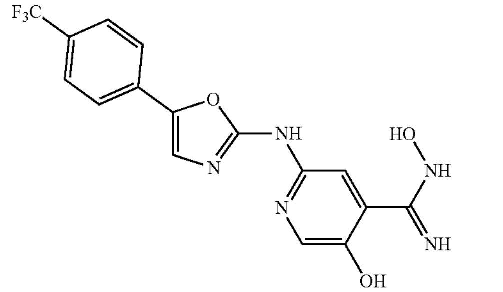 [SMILES: N=C(NO)c1cc(Nc2ncc(-c3ccc(C(F)(F)F)cc3)o2)ncc1O]

(N-hydroxy-5-((4-methoxybenzyl)oxy)-2-((5-(4-(trifluoromethyl)phenyl)oxazol-2-yl)amino)isonicotinimidamide (33 mg, 0.066 mmol) was stirred in a mixture of TFA (2 mL) and $Et_3SiH$ (0.1 mL) at rt for 4 h. The reaction mixture was evaporated to dryness. The residue was purified on preparative HPLC to provide N,5-dihydroxy-2-((5-(4-(trifluoromethyl)phenyl)oxazol-2-yl)amino)isonicotinimidamide (5.0 mg, 19.95% yield). $^1H$ NMR (401 MHz, DMSO-$d_6$) δ 10.68 (s, 1H), 10.48 (s, 1H), 8.42 (s, 1H), 8.12 (s, 1H), 7.99 (s, 1H), 7.77 (s, 4H), 7.71 (s, 1H), 6.43 (s, 2H). $^{13}C$ NMR (101 MHz, DMSO) δ 158.83, 158.52, 157.53, 152.33, 148.30, 144.76, 143.21, 136.99, 132.23, 128.77, 127.69, 127.37, 127.06, 126.74, 126.48, 126.44, 126.07, 125.77, 124.37, 123.26, 108.41. LCMS $R_f$ (min)=3.62, MS m/z=380.1 $[M+H]^+$. HRMS (ESI) calcd for $C_{16}H_{13}F_3N_5O_3^+$ $[M+H]^+$ 380.0965, found 380.0967.

51. 5-((5-(4-(Difluoromethoxy)phenyl)oxazol-2-yl)amino)-N'-hydroxy picolinimidamide (Scheme 48)

Scheme 48

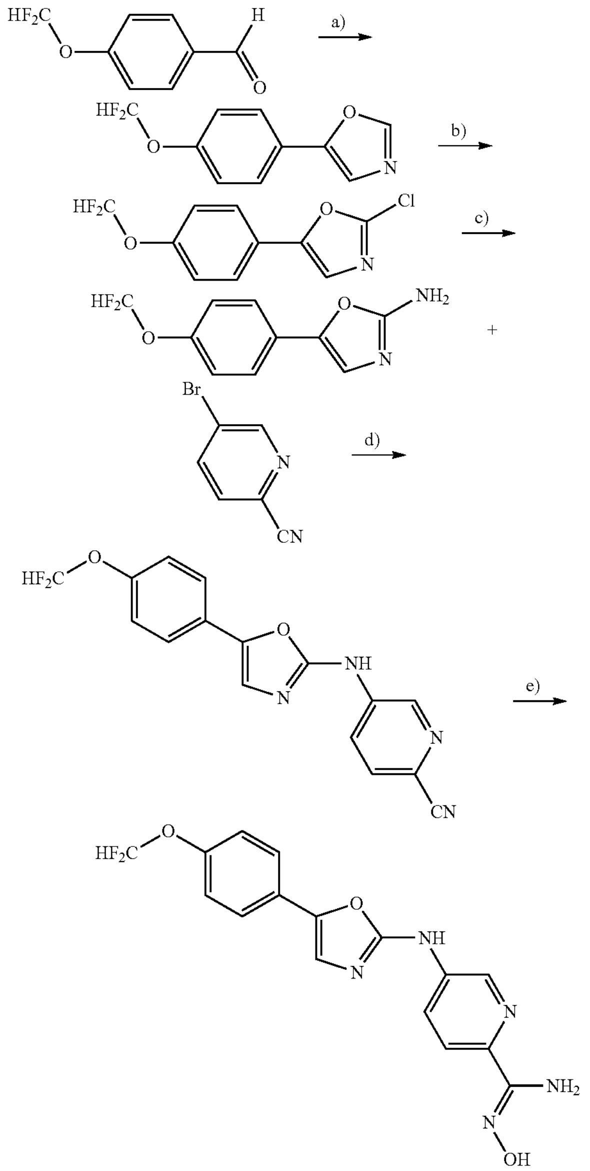

a) TosMIC, $K_2CO_3$, MeOH, reflux 5 h; b) i. LiHMDS, THF, -78° C., 0.5 h; ii. $C_2Cl_6$, -78° C.~rt, overnight; c) $NH_4OH$ (aq.), THF, microwave, 90° C., 1 h; d) $Cs_2CO_3$, $Pd_2(dba)_3$, Xantphos, 1,4-dioxane, 110° C., 5 h; e) $NH_2OH$•HCl, $Et_3N$, EtOH, reflux, overnight; f) TFA, $Et_3SiH$, rt, 4 h.

4-(Difluoromethoxy)benzaldehyde (3.0 g, 17.4 mmol) and $K_2CO_3$ (2.89 g, 20.9 mmol) were added to a solution of TosMIC (3.74 g, 19.2 mmol) in MeOH (40 mL) at rt. The resulting mixture was refluxed for 5 h under nitrogen before being concentrated under reduced pressure. The residue was partitioned between $Et_2O$ and $H_2O$. The aqueous phase was extracted with $Et_2O$ (40 mL×2), and the combined organic phases were dried over $MgSO_4$, filtered and concentrated to give a light yellow oil that was subjected to flash chromatography on silica gel (3%~10%, EtOAc/hexane). Collection of the appropriated fractions provided 5-(4-(difluoromethoxy)phenyl)oxazole as a white solid (3.23 g, 88% yield). $^1H$ NMR (400 MHz, $CDCl_3$) δ 7.91 (s, 1H), 7.63 (d, J=8.0 Hz, 2H), 7.31 (s, 1H), 7.17 (d, J=8.0 Hz, 2H), 6.54 (t, J=72 Hz, 1H, split by F). MS m/z=212.1 $[M+H]^+$.

LiHMDS (1.0 M in THF, 8.86 mL, 8.86 mmol) was added to a solution of 5-(4-(difluoromethoxy)phenyl)oxazole (1.70 g, 8.05 mmol) in dry THF (15 mL) at −78° C. under nitrogen atmosphere. After a further 0.5 h, a solution of $C_2Cl_6$ (2.86 g, 12.1 mmol) in THF (5 mL) was treated. The resulting reaction mixture was stirred at −78° C. for another 2 h and allowed to warm to rt over 14 h then quenched with saturated $NaHCO_3$ (10 mL). The aqueous phase was extracted with EtOAc (30 mL×3). The combined organic phases were dried over $Na_2SO_4$, filtered, and concentrated to give a brown oil that was subjected to flash chromatography on silica gel (5%, EtOAc/hexane), Collection of the appropriated fractions provided 2-chloro-5-(4-(difluoromethoxy)phenyl)oxazole as a white solid (1.78 g, 90% yield). $^1H$ NMR (400 MHz, $CDCl_3$) δ 7.58 (d, J=8.0 Hz, 2H), 7.25 (s, 1H), 7.17 (d, J=8.0 Hz, 2H), 6.55 (t, J=72 Hz, 1H, split by F). MS m/z=246.0 $[M+H]^+$.

$NH_4OH$ (28~30% $NH_3$ basis aqueous solution, 10 mL) was added to a solution of 2-chloro-5-(4-(difluoromethoxy)phenyl)oxazole (1.2 g, 4.89 mmol) in THF (1.5 mL) at rt. The resulting reaction mixture was irradiated under microwave for 1 h at 90° C. The solid was filtered and washed with DCM (5 mL×2), providing 5-(4-(difluoromethoxy)phenyl)oxazol-2-amine as a white solid (1.05 g, 95% yield). $^1H$ NMR (400 MHz, DMSO-$d_6$) δ 7.50 (d, J=8.0 Hz, 2H), 7.20 (d, J=8.0 Hz, 2H), 7.20 (t, J=72 Hz, 1H, split by F), 6.86 (s, 2H). MS m/z=227.1 $[M+H]^+$.

A degassed solution of 5-(4-(difluoromethoxy)phenyl)oxazol-2-amine (200 mg, 0.88 mmol), 5-bromopicolinonitrile (178 mg, 0.97 mmol), $Cs_2CO_3$ (430 mg, 1.32 mmol), $Pd_2(dba)_3$ (40 mg, 0.044 mmol), and Xantphos (51 mg, 0.088 mmol) in 1,4-dioxane (10 mL) was stirred for 5 h at 110° C. The volatile solvents were removed in vacuo. The residue was partitioned between EtOAc and $H_2O$. The aqueous phase was extracted with EtOAc (20 mL×3). The combined organic phases were dried over $MgSO_4$, filtered, and concentrated to give a yellow residue that was subjected to flash chromatography on silica gel (5%~50%, EtOAc/DCM). Collection of the appropriate fractions provided 5-((5-(4-(difluoromethoxy)phenyl) oxazol-2-yl)amino)picolinonitrile as a white solid (0.26 g, 89% yield). $^1H$ NMR (400 MHz, DMSO-$d_6$) δ 11.29 (s, 1H), 8.83 (d, J=2.5 Hz, 1H), 8.32 (dd, J=8.6, 2.5 Hz, 1H), 7.97 (d, J=8.6 Hz, 1H), 7.66 (d, J=8.8 Hz, 1H), 7.27 (d, J=8.8 Hz, 1H), 7.20 (t, J=74 Hz, 1H, split by F). MS m/z=329.1 $[M+H]^+$.

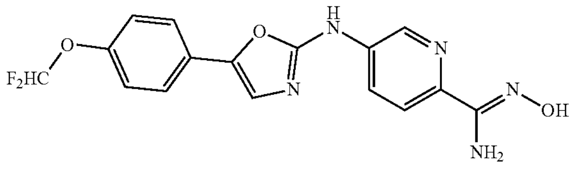 [SMILES: N/C(=N\O)c1ccc(Nc2ncc(-c3ccc(OC(F)F)cc3)o2)cn1]

$Et_3N$ (0.81 mL, 5.85 mmol) and $NH_2OH·HCl$ (406 mg, 5.85 mmol) was added to a suspension of 5-((5-(4-(difluoromethoxy)phenyl) oxazol-2-yl)amino)picolinonitrile (240 mg, 0.73 mmol) in EtOH (10 mL) at rt. The reaction mixture was stirred at reflux overnight. The volatile solvents were removed and the crude material was purified using preparative HPLC to provide 5-((5-(4-(difluoromethoxy)phenyl) oxazol-2-yl)amino)-N'-hydroxy picolinimidamide as a light yellow solid (0.022 g, 8.3% yield). $^1H$ NMR (400 MHz, DMSO-$d_6$) δ 11.15 (s, 1H), 10.79 (brs, 1H), 8.87 (d, J=2.5 Hz, 1H), 8.30 (dd, J=8.8, 2.5 Hz, 1H), 8.01 (d, J=8.8 Hz, 1H), 7.67 (d, J=8.8 Hz, 1H), 7.28 (d, J=8.8 Hz, 1H), 7.28 (t, J=74 Hz, 1H, split by F). $^{13}C$ NMR (101 MHz, DMSO-$d_6$) δ 150.0, 143.8, 138.8, 138.0, 124.8, 124.6, 123.0, 122.5, 119.5, 116.3. LCMS $R_f$(min)=2.54, MS m/z=362.1 $[M+H]^+$. HRMS (ESI) calcd for $C_{16}H_{14}F_2N_5O_3^+$ $[M+H]^+$ 362.1065, found 362.1045.

52. 5-((5-(4-(Difluoromethyl)phenyl)oxazol-2-yl) amino)-N'-hydroxypicolinimidamide (Scheme 49)

Scheme 49

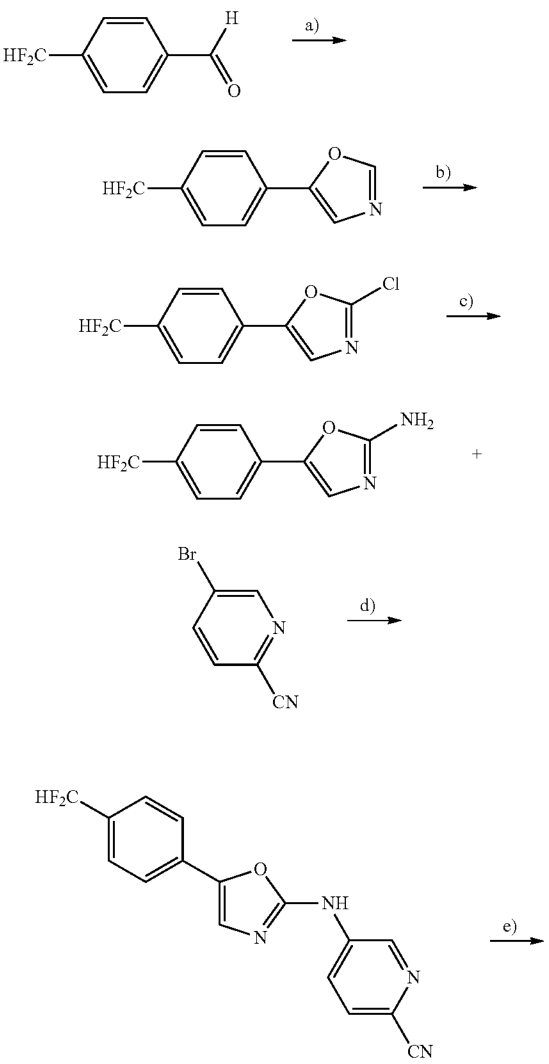

-continued

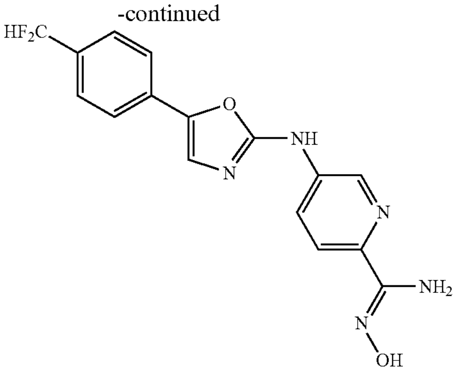

a) TosMIC, $K_2CO_3$, MeOH, reflux 5 h; b) i. LiHMDS, THF, -78° C. 0.5 h; ii. $C_2Cl_6$, -78° C.~rt, overnight; c) $NH_4OH$ (aq.), THF, microwave, 90° C., 1 h; d) $Cs_2CO_3$, $Pd_2(dba)_3$, Xantphos, 1,4-dioxane, 110° C., 5 h; e) $NH_2OH$•HCl, $Et_3N$, EtOH, reflux, overnight; f) TFA, $Et_3SiH$, rt, 4 h.

4-(Difluoromethyl)benzaldehyde (1.38 g, 8.84 mmol) and $K_2CO_3$ (1.47 g, 10.6 mmol) were added to a solution of TosMIC (1.90 g, 9.72 mmol) in MeOH (20 mL) at rt. The resulting mixture was then refluxed for 5 h under nitrogen before being concentrated under reduced pressure. The residue was partitioned between $Et_2O$ and $H_2O$. The aqueous phase was extracted with $Et_2O$ (30 mL×2), and the combined organic phases were dried over $MgSO_4$, filtered and concentrated to give a light yellow oil that was subjected to flash chromatography on silica gel (3%~20%, EtOAc/hexane). Collection of the appropriate fractions provided 5-(4-(difluoromethyl)phenyl)oxazole as a white solid. (1.40 g, 81% yield). $^1H$ NMR (400 MHz, $CDCl_3$) δ) δ 7.94 (s, 1H), 7.72 (d, J=8.2 Hz, 2H), 7.55 (d, J=8.2 Hz, 2H), 7.42 (s, 1H), 6.66 (t, J=56 Hz, 1H, split by F). MS m/z=196.0 $[M+H]^+$.

LiHMDS (1.0 M in THF, 4.22 mL, 4.22 mmol) was added to a solution of 5-(4-(difluoromethyl)phenyl)oxazole (0.75 g, 3.84 mmol) in dry THF (10 mL) at −78° C. under nitrogen atmosphere. After a further 0.5 h, a solution of $C_2Cl_6$ (1.36 g, 5.76 mmol) in THF (5 mL) was treated. The resulting reaction mixture was stirred at −78° C. for another 2 h and allowed to warm to rt over 14 h. The reaction was quenched with saturated $NaHCO_3$ (10 mL). The aqueous phase was extracted with EtOAc (30 mL×2). The combined organic phases were dried over $Na_2SO_4$, filtered, and concentrated to give a brown oil that was subjected to flash chromatography on silica gel (2%~10%, EtOAc/hexane). Collection of the appropriate fractions provided 2-chloro-5-(4-(difluoromethyl)phenyl)oxazole as a white solid (0.73 g, 83% yield). $^1H$ NMR (400 MHz, $CDCl_3$) δ 7.77 (d, J=8.4 Hz, 2H), 7.56 (d, J=8.4 Hz, 2H), 7.35 (s, 1H), 6.66 (t, J=56 Hz, 1H, split by F). MS m/z=230.0 $[M+H]^+$.

$NH_4OH$ (28~30% $NH_3$ basis aqueous solution, 10 mL) was added to a solution of 2-chloro-5-(4-(difluoromethyl)phenyl)oxazole) (0.75 g, 3.27 mmol) in THF (1.5 mL) at rt. The resulting reaction mixture was radiated under microwave for 1 h at 90° C. The solid was filtered and washed with DCM (5 mL×2), providing 5-(4-(difluoromethyl)phenyl)oxazol-2-amine as a yellow solid (0.66 g, 96% yield). $^1H$ NMR (400 MHz, DMSO) δ 7.52-7.61 (m, 4H), 7.33 (s, 1H), 7.14-6.86 (m, 3H). MS m/z=211.0 $[M+H]^+$.

A degassed solution of 5-(4-(difluoromethyl)phenyl)oxazol-2-amine (152 mg, 0.72 mmol), 5-bromopicolinonitrile (199 mg, 1.08 mmol), $Cs_2CO_3$ (469 mg, 1.44 mmol), $Pd_2(dba)_3$ (53 mg, 0.058 mmol), and Xantphos (42 mg, 0.072 mmol) in 1,4-dioxane (10 mL) was stirred for 5 h at 110° C. The volatile solvents were removed in vacuo. The residue was partitioned between EtOAc and $H_2O$. The aqueous phase was extracted with EtOAc (20 mL×3). The combined organic phases were dried over $MgSO_4$, filtered, and concentrated to give a grey residue that was subjected to flash chromatography with EtOAc/DCM (5% to 50%). Collection of the appropriate fractions provided 5-((5-(4-(difluoromethyl)phenyl)oxazol-2-yl)amino)picolinonitrile as a white solid (0.20 g, 90% yield). $^1H$ NMR (400 MHz, DMSO-$d_6$) δ 11.36 (s, 1H), 8.85 (d, J=2.5 Hz, 1H), 8.32 (dd, J=8.6, 2.5 Hz, 1H), 7.98 (d, J=8.6 Hz, 1H), 7.75 (d, J=8.2 Hz, 1H), 7.71 (s, 1H), 7.65 (d, J=8.2 Hz, 1H), 7.05 (t, J=56 Hz, 1H, split by F). MS m/z=313.1 $[M+H]^+$.

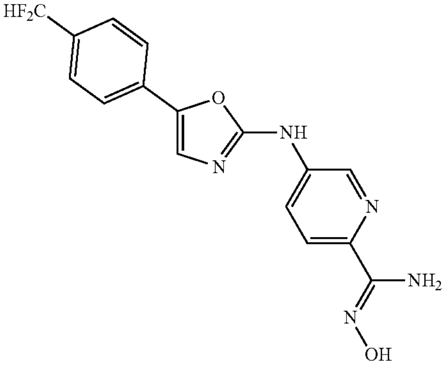

$Et_3N$ (0.57 mL, 4.10 mmol) and $NH_2OH$·HCl (284 mg, 4.10 mmol) was added to a suspension of 5-((5-(4-(difluoromethyl)phenyl)oxazol-2-yl)amino)picolinonitrile (160 mg, 0.51 mmol) in EtOH (8 mL) at rt. The reaction mixture was stirred at reflux overnight. The volatile solvents were removed and the crude material was purified using preparative HPLC to provide 5-((5-(4-(difluoromethyl)phenyl)oxazol-2-yl)amino)-N'-hydroxypicolinimidamide as a brown solid (0.016 g, 9.1% yield). $^1H$ NMR (400 MHz, DMSO-$d_6$) δ 11.19 (s, 1H), 10.70 (brs, 1H), 8.87 (d, J=2.3 Hz, 1H), 8.29 (dd, J=8.7, 2.3 Hz, 1H), 8.00 (d, J=8.7 Hz, 1H), 7.75 (d, J=8.2 Hz, 2H), 7.70 (s, 1H), 7.65 (d, J=8.2 Hz, 2H), 7.05 (t, J=56 Hz, 1H, split by F). $^{13}C$ NMR (101 MHz, DMSO-$d_6$) δ 155.8, 143.9, 138.0, 132.9, 132.7, 132.5, 130.0, 126.6(4), 126.5(8), 126.5(2), 124.2, 123.3, 123.0, 122.4, 117.1, 114.8, 112.4. LCMS $R_f$ (min)=2.65, MS m/z=346.1 $[M+H]^+$. HRMS (ESI) calcd for $C_{16}H_{14}F_2N_5O_2^+$ $[M+H]^+$ 346.1116, found 346.1107.

53. N'-Hydroxy-6-((5-(4-(trifluoromethyl)phenyl)oxazol-2-yl)amino)pyridazine-3-carboximidamide (Scheme 50)

Scheme 50

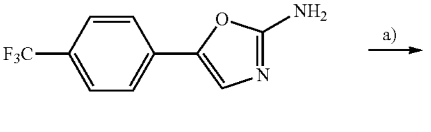

-continued

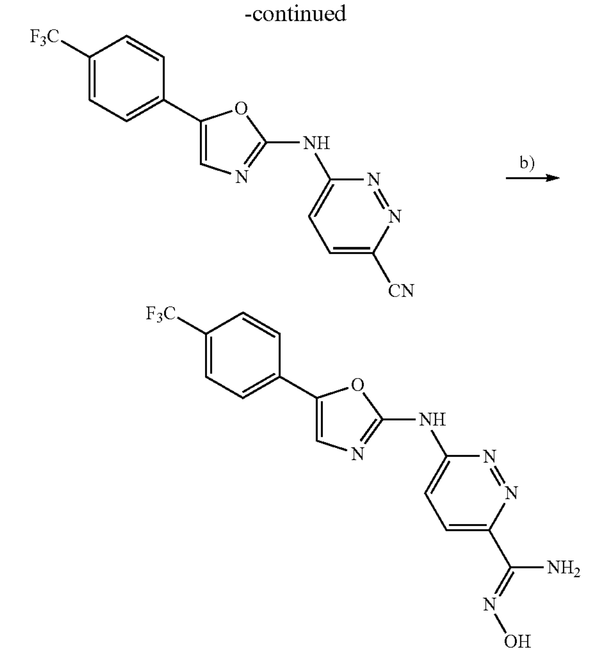

a) 6-Chloropyridazine-3-carbonitrile, $Pd_2(dba)_3$, Xantphos, $Cs_2CO_3$, 1,4-dioxane, 100° C., overnight; b) $NH_2OH$•HCl, $Et_3N$, EtOH, reflux, overnight.

A re-sealable Schlenk tube was charged with $Pd_2(dba)_3$ (0.05 equiv) Xantphos (0.1 equiv), 6-chloropyridazine-3-carbonitrile (1.1 equiv), $Cs_2CO_3$ (1.3 equiv) and 5-(4-(trifluoromethyl)phenyl)oxazol-2-amine (Intermediate D) (0.2 g, 0.88 mmoL) in 1,4-dioxane (8 mL). The mixture was degassed and carefully subjected to three cycles of evacuation-backfilling with $N_2$ and heated at 100° C. overnight. After completion, the mixture was cooled and solvent evaporated to obtain crude, which was stirred with 5% aqueous solution of potassium xanthogenate (10 mL) for 5 min, filtered, washed with water (2x10 mL), MeOH (3x5 mL) and $Et_2O$ (3x5 mL) to obtain pure product as yellow solid (210 mg, 72.3%). $^1H$ NMR (401 MHz, DMSO-$d_6$) δ 8.44 (d, J=7.9 Hz, 1H), 8.24 (d, J=9.3 Hz, 1H), 7.82 (s, 5H). LCMS $R_f$ (min)=3.604. MS m/z=332.1 $[M+H]^+$.

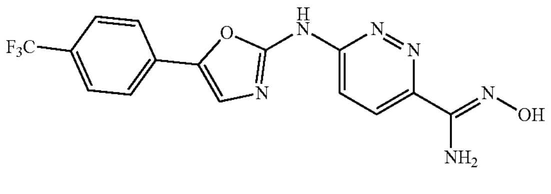 [SMILES: N/C(=N\O)c1ccc(Nc2ncc(-c3ccc(C(F)(F)F)cc3)o2)nn1]

6-((5-(4-(Trifluoromethyl)phenyl)oxazol-2-yl)amino)pyridazine-3-carbonitrile (0.15 g) was suspended in EtOH (15 mL) followed by the addition of $NH_2OH{\cdot}HCl$ (8.0 equiv) and $Et_3N$ (8 equiv). The resulting mixture was refluxed overnight. After completion, mixture was cooled and solid filtered, washed with water (2x10 mL), MeOH (3x5 mL) and $Et_2O$ (2x5 mL) to obtain pure product as beige solid (90 mg, 54.6%). $^1H$ NMR (401 MHz, DMSO-$d_6$) δ 11.98 (s, 1H), 10.16 (s, 1H), 8.25 (s, 1H), 8.02 (s, 1H), 7.82 (s, 5H), 5.97 (s, 2H). LCMS $R_f$ (min)=3.463. HRMS (ESI) calcd for $C_{15}H_{12}F_3N_6O_2^+$ $[M+H]^+$ 365.0968, found 365.0975.

54. N'-Hydroxy-5-((5-(4-(trifluoromethyl)phenyl)oxazol-2-yl)amino)pyrazine-2-carboximidamide (Scheme 51)

Scheme 51

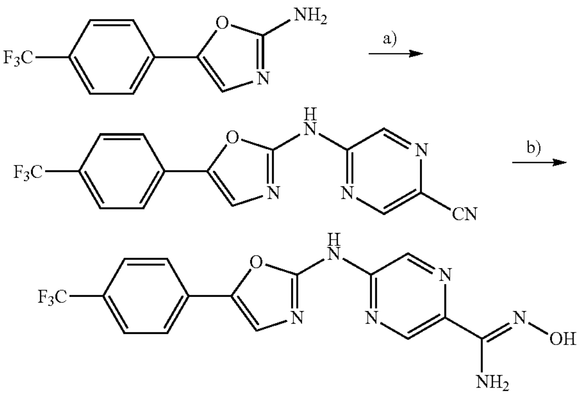

a) 5-Bromopyridazine-2-carbonitrile, $Pd_2(dba)_3$, Xantphos, $Cs_2CO_3$, 1,4-dioxane, 100° C., overnight; b) $HONH_2$•HCl, $Et_3N$, EtOH, reflux, overnight.

A re-sealable Schlenk tube was charged with $Pd_2(dba)_3$ (0.05 equiv), Xantphos (0.1 equiv), 5-bromopyrazine-2-carbonitrile (1.1 equiv), $Cs_2CO_3$ (1.3 equiv) and 5-(4-(trifluoromethyl)phenyl)oxazol-2-amine (Intermediate D) (0.2 g, 0.877 mmoL) in 1,4-dioxane. The mixture was carefully subjected to three cycles of evacuation-backfilling with $N_2$ and heated at 100° C. overnight. After completion, the mixture was cooled and solvent evaporated to obtain crude, which was stirred with 5% aqueous solution of potassium xanthogenate (10 mL) for 5 min, filtered, washed with water (3x10 mL), MeOH (3x5 mL) and $Et_2O$ (2x5 mL) to obtain pure product as yellow solid (200 mg, 69%). $^1H$ NMR (401 MHz, DMSO-$d_6$) δ 12.24 (s, 1H), 9.25 (s, 1H), 8.87 (s, 1H), 7.86 (s, 1H), 7.83 (m, 4H). LCMS $R_f$ (min)=3.551, MS m/z=332.0 $[M+H]^+$.

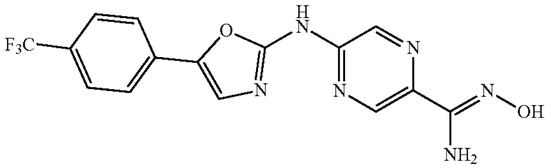 [SMILES: N/C(=N\O)c1cnc(Nc2ncc(-c3ccc(C(F)(F)F)cc3)o2)cn1]

5-((5-(4-(Trifluoromethyl)phenyl)oxazol-2-yl)amino)pyrazine-2-carbonitrile (0.15 g) was suspended in EtOH (15 mL) followed by the addition of $NH_2OH{\cdot}HCl$ (8.0 equiv) and $Et_3N$ (8.0 equiv). The resulting mixture was refluxed overnight. After completion, the mixture was cooled and solid filtered, washed with water (2x10 mL), MeOH (3x5 mL), 1,4-dioxane: $Et_2O$ (1:1, 3x5 mL), and $Et_2O$ (2x5 mL) to provide N'-hydroxy-5-((5-(4-(trifluoromethyl)phenyl)oxazol-2-yl)amino)pyrazine-2-carboximidamide as beige solid (70 mg, 42%). $^1H$ NMR (401 MHz, DMSO-$d_6$) δ 11.59 (s, 1H), 9.94 (s, 1H), 9.23 (s, 1H), 8.75 (s, 1H), 7.82 (br s, 5H), 5.85 (s, 2H). LCMS $R_f$ (min)=3.697. HRMS (ESI) calcd for $C_{15}H_{12}F_3N_6O_2^+$ $[M+H]^+$ 365.0968, found 365.0984.

55. N'-Hydroxy-5-((5-(4-(trifluoromethyl)phenyl) oxazol-2-yl)amino)pyrimidine-2-carboximidamide (Scheme 52)

Scheme 52

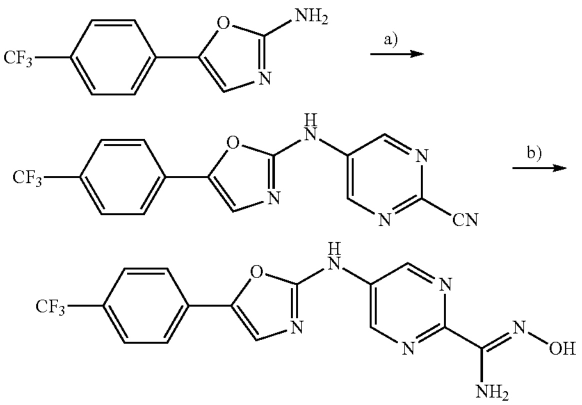

a) 5-Bromopyridazine-2-carbonitrile, $Pd_2(dba)_3$, Xantphos, $Cs_2CO_3$, 1,4-dioxane, 100° C., overnight; b) $HONH_2$•HCl, $Et_3N$, EtOH, reflux, overnight.

A re-sealable Schlenk tube was charged with $Pd_2(dba)_3$ (0.05 equiv), Xantphos (0.1 equiv), 5-bromopyrimidine-2-carbonitrile (1.1 equiv), $Cs_2CO_3$ (1.3 equiv) and 5-(4-(trifluoromethyl)phenyl)oxazol-2-amine (Intermediate D) (0.2 g, 0.877 mmoL) in 1,4-dioxane (8 mL). The mixture was degassed and carefully subjected to three cycles of evacuation-backfilling with $N_2$ and heated at 100° C. overnight. After completion, the mixture was cooled and solvent evaporated to obtain crude, which was stirred with 5% aqueous solution of potassium xanthogenate (10 mL) for 5 min, filtered, washed with water (3x10 mL), MeOH (3x5 mL) and $Et_2O$ (2x5 mL) to provide 5-((5-(4-(trifluoromethyl)phenyl)oxazol-2-yl)amino)pyrimidine-2-carbonitrile as beige solid (200 mg, 69%). The compound was used as such without any further purification.

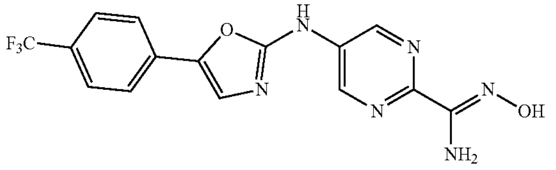 [SMILES: N/C(=N\O)c1ncc(Nc2ncc(-c3ccc(C(F)(F)F)cc3)o2)cn1]

5-((5-(4-(Trifluoromethyl)phenyl)oxazol-2-yl)amino)pyrimidine-2-carbonitrile (0.11 g) was suspended in EtOH (10 mL) followed by the addition of $NH_2OH{\cdot}HCl$ (8.0 equiv) and $Et_3N$ (8.0 equiv). The resulting mixture was refluxed overnight. After completion, the mixture was cooled and solid filtered, washed with water (2x10 mL), MeOH (2x5 mL), 1,4-dioxane:$Et_2O$ (1:1, 3x5 mL) and $Et_2O$ (2x5 mL) to provide N'-hydroxy-5-((5-(4-(trifluoromethyl)phenyl)oxazol-2-yl)amino)pyrimidine-2-carboximidamide as beige solid (50 mg, 41.3%). $^1H$ NMR (401 MHz, DMSO-$d_6$) δ 11.28 (s, 1H), 9.79 (s, 1H), 8.80 (s, 2H), 7.82 (m, 5H), 6.01 (s, 2H). LCMS $R_f$ (min)=3.597. HRMS (ESI) calcd for $C_{15}H_{12}F_3N_6O_2^+$ $[M+H]^+$ 365.0968, found 365.0982.

56. 3-Fluoro-N'-hydroxy-5-((5-(5-(trifluoromethyl) pyridin-2-yl)oxazol-2-yl)amino)picolinimidamide (Scheme 53)

Scheme 53

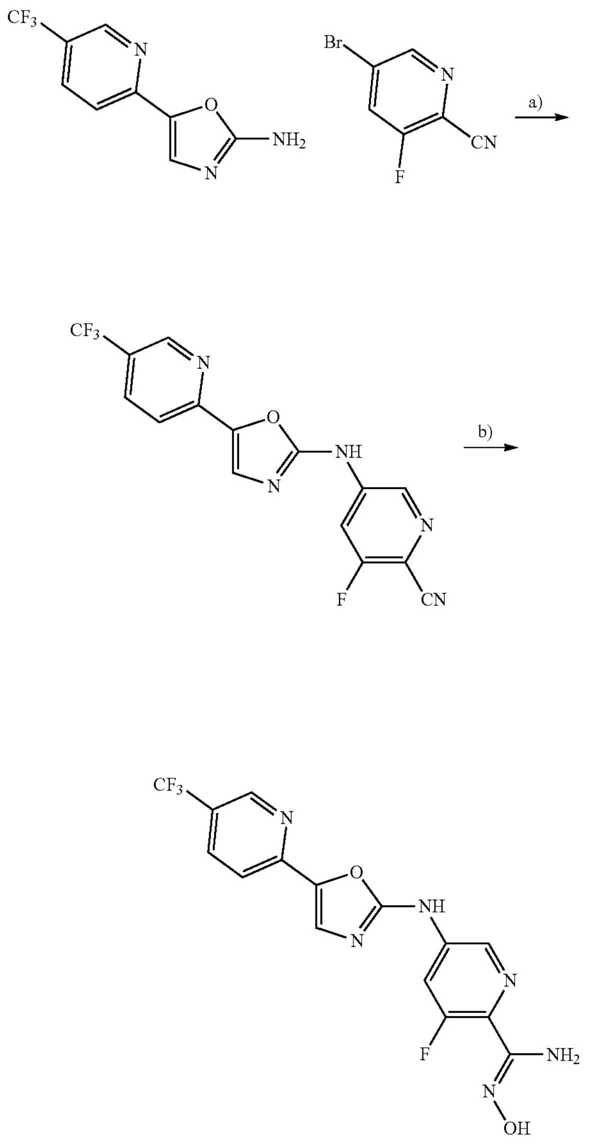

a) $Pd_2(dba)_3$, Xantphos, $Cs_2CO_3$, 1,4-dioxane, 110° C., 18 h; b) $NH_2OH$•HCl, $Et_3N$, EtOH, reflux, 18 h.

Intermediate K (5-(5-(trifluoromethyl)pyridin-2-yl)oxazol-2-amine) (0.2 g, 0.872 mmol) was reacted with 5-bromo-3-fluoropicolinonitrile (0.175 g, 0.872 mmol) following General Procedure 4 Method 1. The crude product was purified on silica gel using mixtures of DCM and EtOAc (0 to 30%) as eluents to provide the desired 3-fluoro-5-((5-(5-(trifluoromethyl)pyridin-2-yl)oxazol-2-yl)amino)picolinonitrile in 73.16% yield (0.223 g). $^1H$ NMR (401 MHz, DMSO-$d_6$) δ 11.99 (br s, 1H), 8.95 (s, 1H), 8.60 (s, 1H), 8.35 (d, J=11.5 Hz, 1H), 8.29 (d, J=8.3 Hz, 1H), 7.97 (s, 1H), 7.83 (d, J=8.3 Hz, 1H). LCMS $R_f$(min)=3.351, MS m/z=350.1 $[M+H]^+$.

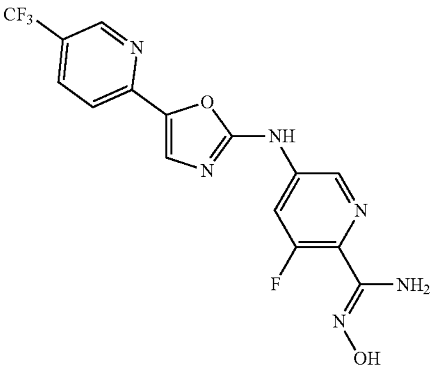 [SMILES: N/C(=N\O)c1ncc(Nc2ncc(-c3ccc(C(F)(F)F)cn3)o2)cc1F]

3-Fluoro-5-((5-(5-(trifluoromethyl)pyridin-2-yl)oxazol-2-yl)amino)picolinonitrile (0.21 g, 0.6 mmol) was subjected to amidoxime formation in EtOH as per General Procedure 1 Method 2 to furnish 3-fluoro-N'-hydroxy-5-((5-(5-(trifluoromethyl)pyridin-2-yl)oxazol-2-yl)amino)picolinimidamide (91.8%, 211 mg) after filtering with water, then washing with water, EtOH, and $Et_2O$. $^1H$ NMR (401 MHz, DMSO-$d_6$) δ 9.95 (s, 1H), 8.94 (s, 1H), 8.58 (s, 1H), 8.27 (d, J=6.7 Hz, 1H), 8.14 (dd, J=13.1, 1.8 Hz, 1H), 7.92 (s, 1H), 7.80 (d, J=8.4 Hz, 1H), 5.76 (s, 2H). LCMS $R_f$ (min)=3.027, MS m/z=383.1 $[M+H]^+$. HRMS (ESI) calcd for $C_{15}H_{11}F_4N_6O_2^+$ $[M+H]^+$ 383.0874, found 383.0871.

57. N'-Hydroxy-5-((5-(5-(trifluoromethyl)pyridin-2-yl)oxazol-2-yl)amino)pyrazine-2-carboximidamide (Scheme 54)

Scheme 54

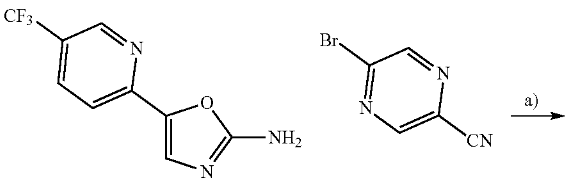

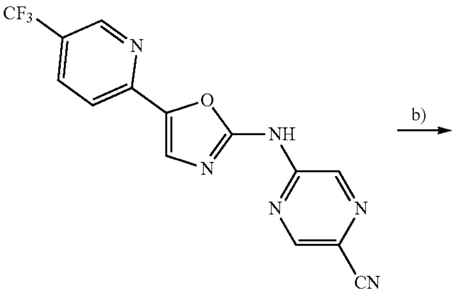

-continued

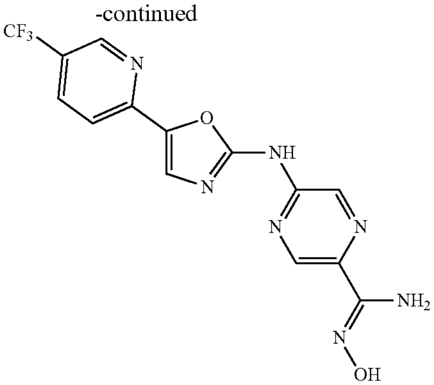

a) $Pd_2(dba)_3$, Xantphos, $Cs_2CO_3$, 1,4-dioxane, 110° C., 18 h; b) $NH_2OH{\bullet}HCl$, $Et_3N$, EtOH, reflux, 18 h.

Intermediate K (5-(5-(trifluoromethyl)pyridin-2-yl)oxazol-2-amine) (0.156 g, 0.68 mmol) was reacted with 5-bromopyrazine-2-carbonitrile (0.125 g, 0.68 mmol) following General Procedure 4 Method 1. The crude product was purified on silica gel using mixtures of DCM and EtOAc (0 to 70%) as eluents to provide the desired 5-((5-(5-(trifluoromethyl)pyridin-2-yl)oxazol-2-yl)amino)pyrazine-2-carbonitrile in 32.34% yield (0.073 g). $^1H$ NMR (401 MHz, DMSO-$d_6$) δ 12.36 (br s, 1H), 9.29 (s, 1H), 8.94 (s, 1H), 8.88 (d, J=0.9 Hz, 1H), 8.28 (dd, J=8.4, 1.9 Hz, 1H), 7.95 (s, 1H), 7.81 (d, J=8.4 Hz, 1H). LCMS $R_f$ (min)=2.961, MS m/z=333.0 $[M+H]^+$.

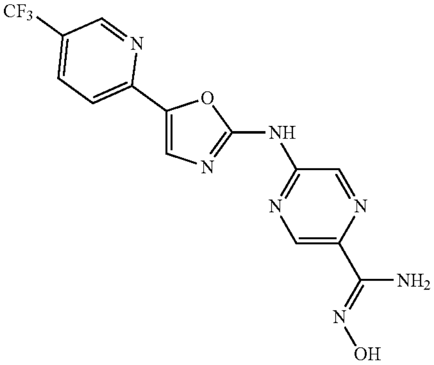 [SMILES: N/C(=N\O)c1cnc(Nc2ncc(-c3ccc(C(F)(F)F)cn3)o2)cn1]

5-((5-(5-(Trifluoromethyl)pyridin-2-yl)oxazol-2-yl)amino)pyrazine-2-carbonitrile (0.06 g, 0.180 mmol) was subjected to amidoxime formation in EtOH as per General Procedure 1 Method 2 to furnish N'-hydroxy-5-((5-(5-(trifluoromethyl)pyridin-2-yl)oxazol-2-yl)amino)pyrazine-2-carboximidamide (77.3%, 51 mg) after filtering with water, then washing with water, EtOH, and $Et_2O$. $^1H$ NMR (401 MHz, DMSO-$d_6$) δ 11.75 (s, 1H), 9.96 (s, 1H), 9.26 (s, 1H), 8.95 (s, 1H), 8.76 (s, 1H), 8.29 (d, J=7.4 Hz, 1H), 7.95 (s, 1H), 7.81 (d, J=8.2 Hz, 1H), 5.86 (s, 2H). LCMS $R_f$ (min)=2.936, MS m/z=366.1 $[M+H]^+$. HRMS (ESI) calcd for $C_{14}H_{11}F_3N_7O_2^+$ $[M+H]^+$ 366.0921, found 366.0932.

58. N'-Hydroxy-5-((5-(5-(trifluoromethyl)pyridin-2-yl)oxazol-2-yl)amino)pyrimidine-2-carboximidamide (Scheme 55)

Scheme 55

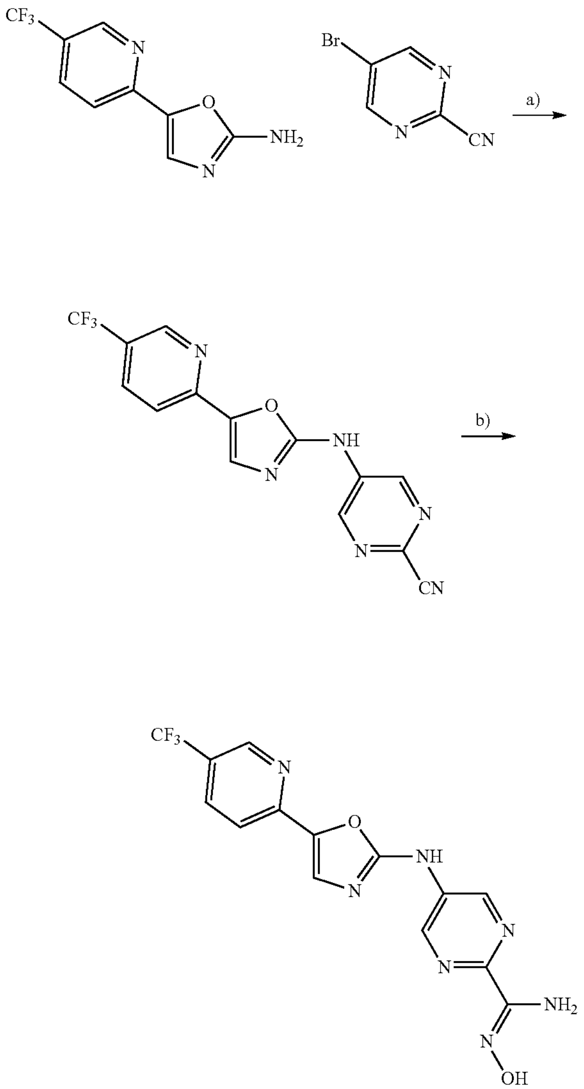

a) $Pd_2(dba)_3$, Xantphos, $Cs_2CO_3$, 1,4-dioxane, 110° C., 18 h; b) $NH_2OH•HCl$, $Et_3N$, EtOH, reflux, 18 h.

Intermediate K (5-(5-(trifluoromethyl)pyridin-2-yl)oxazol-2-amine) (0.156 g, 0.68 mmol) was reacted with 5-bromopyrimidine-2-carbonitrile (0.125 g, 0.68 mmol) following General Procedure 4 Method 1. The crude product was purified on silica gel using mixtures of DCM and EtOAc (0 to 30%) as eluents to provide the desired 5-((5-(5-(trifluoromethyl)pyridin-2-yl)oxazol-2-yl)amino)pyrimidine-2-carbonitrile in 25.25% yield (0.057 g). $^1H$ NMR (401 MHz, DMSO-$d_6$) δ 9.17 (s, 2H), 8.96 (d, J=0.9 Hz, 1H), 8.28 (dd, J=8.5, 2.1 Hz, 1H), 7.97 (s, 1H), 7.84 (d, J=8.4 Hz, 1H). LCMS $R_f$ (min)=3.072, MS m/z=333.1 $[M+H]^+$.

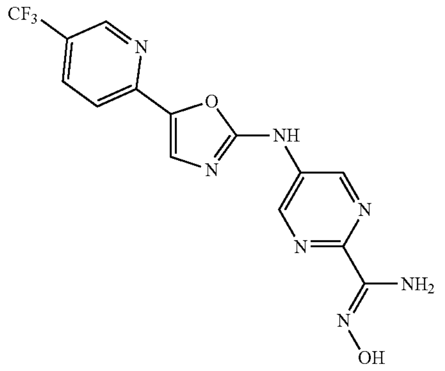 [SMILES: N/C(=N\O)c1ncc(Nc2ncc(-c3ccc(C(F)(F)F)cn3)o2)cn1]

5-((5-(5-(Trifluoromethyl)pyridin-2-yl)oxazol-2-yl)amino)pyrimidine-2-carbonitrile (0.051 g, 0.153 mmol) was subjected to amidoxime formation in EtOH as per General Procedure 1 Method 2 to furnish N'-hydroxy-5-((5-(5-(trifluoromethyl)pyridin-2-yl)oxazol-2-yl)amino)pyrimidine-2-carboximidamide (85.1%, 47.7 mg) after purification via preparative HPLC. $^1H$ NMR (401 MHz, DMSO-$d_6$) δ 11.70 (br s, 1H), 11.04-10.92 (br s, 1H), 9.20 (s, 2H), 8.97-8.94 (m, 1H), 8.29 (dd, J=8.7, 2.1 Hz, 1H), 8.24-8.18 (br s, 1H), 7.97 (s, 1H), 7.83 (d, J=8.4 Hz, 1H). LCMS $R_f$ (min)=2.779, MS m/z=366.1 $[M+H]^+$. HRMS (ESI) calcd for $C_{14}H_{11}F_3N_7O_2^+$ $[M+H]^+$ 366.0921, found 366.0921.

59. N'-Hydroxy-5-((5-(6-(trifluoromethyl)pyridin-3-yl)oxazol-2-yl)amino)picolinimidamide (Scheme 56)

Scheme 56

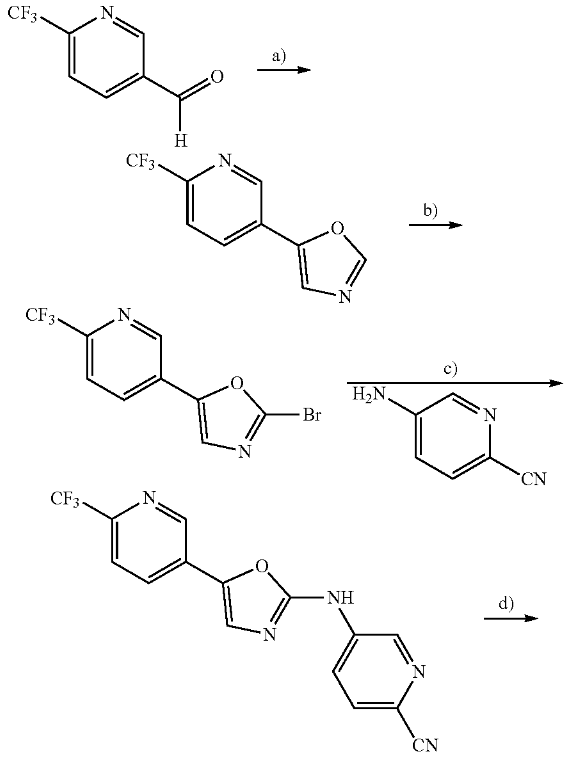

-continued

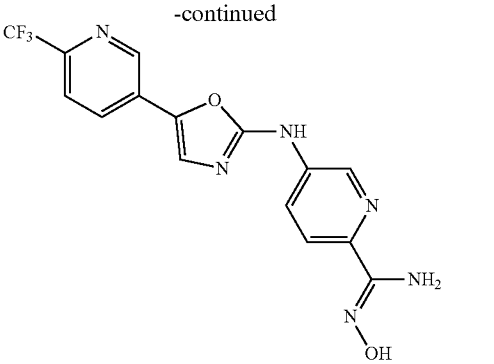

a) TosMIC, $K_2CO_3$, MeOH, reflux, 5 h; b) $BrCF_2CF_2Br$, t-BuOLi, DMF/m-xylene, 60° C., 3 h; c) a) $Pd_2(Dba)_3$, Xantphos, $Cs_2CO_3$, 1,4-dioxane, 110° C., 18 h; b) $NH_2$-OH.HCl, $Et_3N$, EtOH, reflux, 18 h.

6-(Trifluoromethyl)nicotinaldehyde (1.2 g, 6.85 mmol) was reacted with TosMIC (1.54 g, 7.88 mmol) and $K_2CO_3$ (1.14 g, 8.22 mmol) in MeOH (20 mL) as per General Procedure 14 to provide 5-(6-(trifluoromethyl)pyridin-3-yl)oxazole in 89% yield (1.31 g) as a white solid. $^1H$ NMR (401 MHz, $CDCl_3$) δ 9.01 (d, J=1.9 Hz, 1H), 8.10 (dd, J=8.2, 1.6 Hz, 1H), 8.03 (s, 1H), 7.72 (m, 1H), 7.57 (s, 1H). LCMS $R_f$ (min)=2.622, MS m/z=215.1 $[M+H]^+$.

5-(6-(Trifluoromethyl)pyridin-3-yl)oxazole (1.04 g, 4.86 mmol) was reacted with $BrCF_2CF_2Br$ (0.93 mL, 7.77 mmol) and t-BuOLi (0.622 g, 7.77 mmol) in DMF/m-xylene (5/5 mL) at 60° C. for 3 h as per General Procedure 15 Method 2 to provide 2-bromo-5-(6-(trifluoromethyl)pyridin-3-yl)oxazole (0.678 g, 48%) as a yellow solid. $^1H$ NMR (401 MHz, $CDCl_3$) δ 8.95 (s, 1H), 8.06 (d, J=7.6 Hz, 1H), 7.75 (d, J=8.0 Hz, 1H), 7.52 (s, 1H). LCMS $R_f$ (min)=3.338, MS m/z=295.0 $[M+H]^+$.

2-Bromo-5-(6-(trifluoromethyl)pyridin-3-yl)oxazol (0.12 g, 0.68 mmol) was reacted with 5-aminopicolinonitrile (0.405 g, 3.4 mmol) following General Procedure 4 Method 1. The crude product was purified preparative HPLC to provide 5-((5-(6-(trifluoromethyl)pyridin-3-yl)oxazol-2-yl)amino)picolinonitrile in 50.1% yield (0.113 g). $^1H$ NMR (401 MHz, DMSO-$d_6$) δ 11.67-11.30 (br s, 1H), 9.01 (s, 1H), 8.83 (d, J=2.4 Hz, 1H), 8.32 (dd, J=8.7, 2.6 Hz, 1H), 8.20 (m, 1H), 7.97 (m, 2H), 7.93 (s, 1H). LCMS $R_f$ (min)=3.449, MS m/z=332.1 $[M+H]^+$.

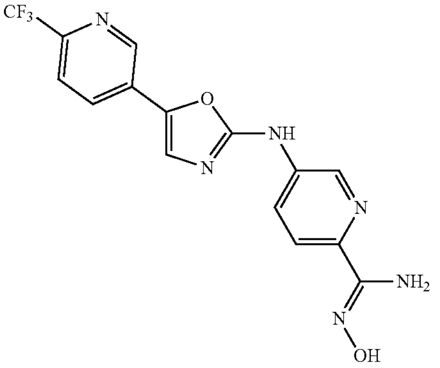 [SMILES: N/C(=N\O)c1ccc(Nc2ncc(-c3ccc(C(F)(F)F)nc3)o2)cn1]

5-((5-(6-(trifluoromethyl)pyridin-3-yl)oxazol-2-yl)amino)picolinonitrile (0.1 g, 0.301 mmol) was subjected to amidoxime formation as per General Procedure 1 Method 2 to furnish N'-hydroxy-5-((5-(6-(trifluoromethyl)pyridin-3-yl)oxazol-2-yl)amino)picolinimidamide (85.24%, 123 mg, treated as TFA salt) after purification via preparative HPLC. $^1H$ NMR (401 MHz, DMSO-$d_6$) δ 11.40 (s, 1H), 10.89 (br s, 1H), 9.02 (d, J=2.0 Hz, 1H), 8.89 (d, J=2.2 Hz, 1H), 8.32 (dd, J=8.8, 2.5 Hz, 1H), 8.21 (dd, J=8.2, 1.8 Hz, 1H), 8.03 (d, J=8.8 Hz, 1H), 7.98 (d, J=8.1 Hz, 1H), 7.93 (s, 1H). $^{13}C$ NMR (101 MHz, DMSO) δ 158.79, 158.46, 157.06, 154.68, 144.84, 144.66, 144.50, 141.46, 138.88, 138.78, 131.66, 127.47, 127.42, 126.19, 123.90, 123.47, 123.21, 121.67, 120.76. LCMS $R_f$ (min)=2.849, MS m/z=365.1 $[M+H]^+$. HRMS (ESI) calcd for $C_{15}H_{12}F_3N_6O_2^+$ $[M+H]^+$ 365.0968, found 365.0973.

60. N'-Hydroxy-5-((4-(4-(trifluoromethyl)phenyl)oxazol-2-yl)amino)picolinimidamide (Scheme 57)

Scheme 57

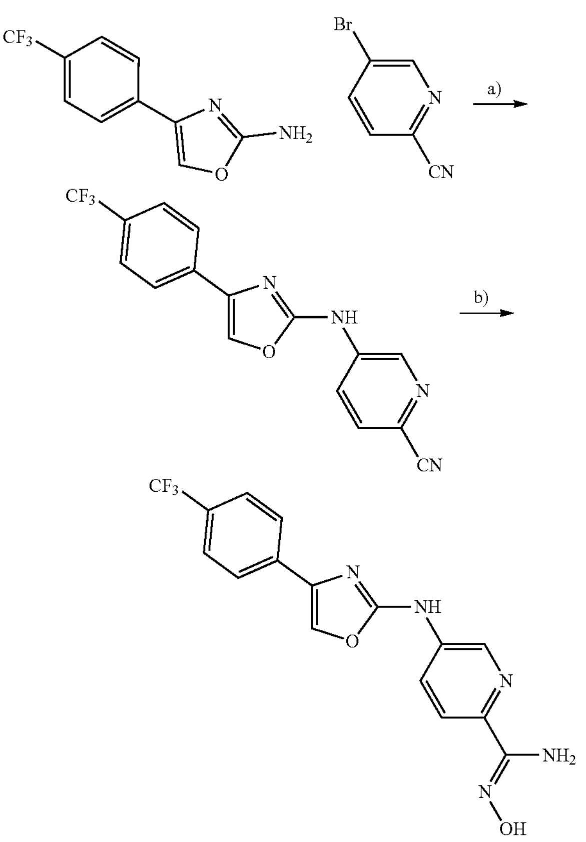

a) $Pd_2(dba)_3$, Xantphos, $Cs_2CO_3$, 1,4-dioxane, 110° C., 18 h; b) $NH_2OH$•HCl, $Et_3N$, MeOH, reflux, 18 h.

Intermediate E (4-(4-(trifluoromethyl)phenyl)oxazol-2-amine) (0.935 g, 4.1 mmol) was reacted with 5-bromopicolinonitrile (0.75 g, 4.1 mmol) following General Procedure 4 Method 1. The crude product was purified on silica gel using mixtures of DCM and EtOAc (0 to 20%) as eluents to provide the desired 5-((4-(4-(trifluoromethyl)phenyl)oxazol-2-yl)amino)picolinonitrile in 13.2% yield (0.179 g). $^1H$ NMR (401 MHz, DMSO-$d_6$) δ 11.22 (s, 1H), 8.87 (d, J=2.3 Hz, 1H), 8.47 (s, 1H), 8.42 (dd, J=8.7, 2.6 Hz, 1H), 8.04-7.94 (m, 3H), 7.79 (d, J=8.3 Hz, 2H). LCMS $R_f$ (min)=3.542, MS m/z=331.0 $[M+H]^+$.

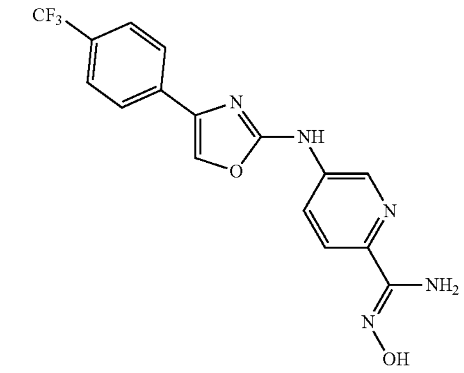 [SMILES: N/C(=N\O)c1ccc(Nc2nc(-c3ccc(C(F)(F)F)cc3)co2)cn1]

5-((4-(4-(Trifluoromethyl)phenyl)oxazol-2-yl)amino)picolinonitrile (0.153 g, 0.463 mmol) was subjected to amidoxime formation in MeOH as per General procedure 1 Method 2 to furnish N'-hydroxy-5-((4-(4-(trifluoromethyl)phenyl)oxazol-2-yl)amino)picolinimidamide (77.96%, corrected for 0.5 molar equivalent of dioxane, 147 mg) after isolation via filtering with water, and washing with water and $Et_2O$. $^1H$ NMR (401 MHz, DMSO-$d_6$) δ 10.73 (s, 1H), 9.81 (s, 1H), 8.91 (d, J=2.2 Hz, 1H), 8.42 (s, 1H), 8.17 (dd, J=8.8, 2.6 Hz, 1H), 8.01 (d, J=8.0 Hz, 2H), 7.87 (d, J=8.8 Hz, 1H), 7.80 (d, J=8.2 Hz, 2H), 5.91 (s, 2H). $^{13}C$ NMR (101 MHz, DMSO-$d_6$) δ 156.86, 150.14, 143.13, 138.33, 137.14, 136.94, 135.66, 130.95, 128.43, 128.11, 126.18, 126.14, 126.10, 125.96, 124.20, 123.42, 120.32. LCMS $R_f$ (min)=3.163, MS m/z=364.1 $[M+H]^+$. HRMS (ESI) calcd for $C_{16}H_{13}F_3N_5O_2^+$ $[M+H]^+$ 364.1016, found 364.1019.

61. 6-((5-(5-(Trifluoromethyl)pyridin-2-yl)oxazol-2-yl)amino)pyridazine-3-carbonitrile (Scheme 58)

Scheme 58

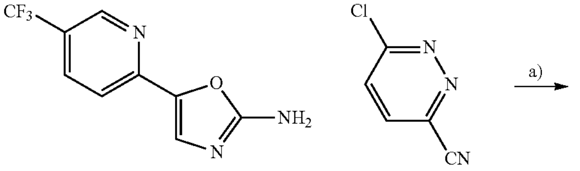

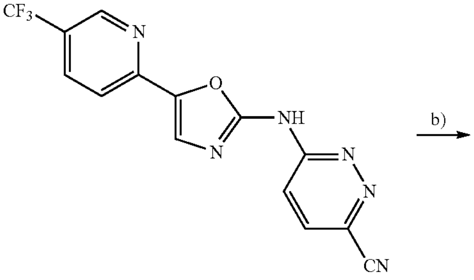

-continued

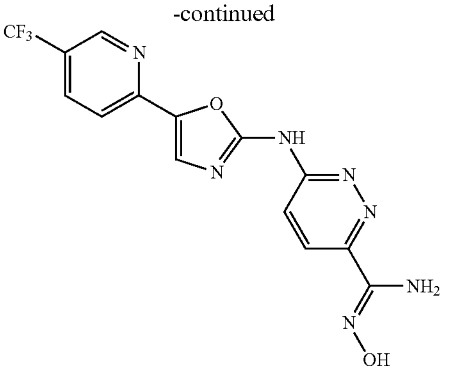

a) $Pd_2(dba)_3$, Xantphos, $Cs_2CO_3$, 1,4-dioxane, 110° C., 18 h; b) $NH_2OH.HCl$, $Et_3N$, MeOH, reflux, 18 h.

Intermediate K (5-(5-(trifluoromethyl)pyridin-2-yl)oxazol-2-amine) (0.197 g, 0.86 mmol) was reacted with 6-chloropyridazine-3-carbonitrile (0.12 g, 0.86 mmol) following General Procedure 4 Method 1. Upon completion, the volatile solvents were removed in vacuo, and the solid residue, triturated with water, filtered and washed well with water. The resultant crude product was washed with $Et_2O$ and DCM until all catalysts and ligands were removed, providing the desired 6-((5-(5-(trifluoromethyl)pyridin-2-yl)oxazol-2-yl)amino)pyridazine-3-carbonitrile in 79.4% yield (0.227 g). $^1H$ NMR (401 MHz, DMSO-$d_6$) δ 8.96 (s, 1H), 8.47 (m, 1H), 8.29 (m, 2H), 7.97 (s, 1H), 7.83 (d, J=8.4 Hz, 1H), 7.42 (m, 1H). LCMS $R_f$ (min)=3.361, MS m/z=333.1 $[M+H]^+$.

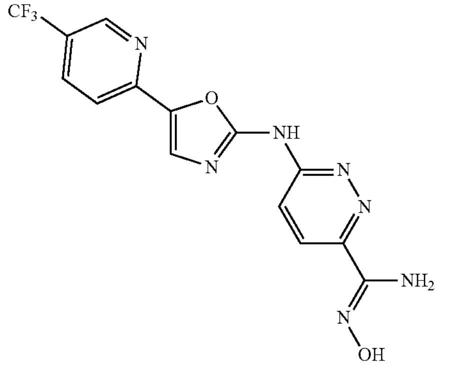 [SMILES: N/C(=N\O)c1ccc(Nc2ncc(-c3ccc(C(F)(F)F)cn3)o2)nn1]

6-((5-(5-(Trifluoromethyl)pyridin-2-yl)oxazol-2-yl)amino)pyridazine-3-carbonitrile (0.207 g, 0.623 mmol) was subjected to amidoxime formation in MeOH as per General Procedure 1 Method 2 to furnish N'-hydroxy-6-((5-(5-(trifluoromethyl)pyridin-2-yl)oxazol-2-yl)amino)pyridazine-3-carboximidamide (87%, 198 mg) after isolation via filtering with water, and washing with water and $Et_2O$. $^1H$ NMR (401 MHz, DMSO-$d_6$) δ 12.20-11.90 (br s, 1H), 10.18 (s, 1H), 8.95 (s, 1H), 8.28 (s, 2H), 8.06-7.71 (m, 3H), 6.00 (s, 2H). LCMS $R_f$ (min)=3.248, MS m/z=366.0 $[M+H]^+$. HRMS (ESI) calcd for $C_{14}H_{11}F_3N_7O_2^+$ $[M+H]^+$ 366.0921, found 366.091.

62. 5-((5-(5-Cyclopropylpyridin-2-yl)oxazol-2-yl)amino)-N'-hydroxypicolinimidamide (Scheme 59)

Scheme 59

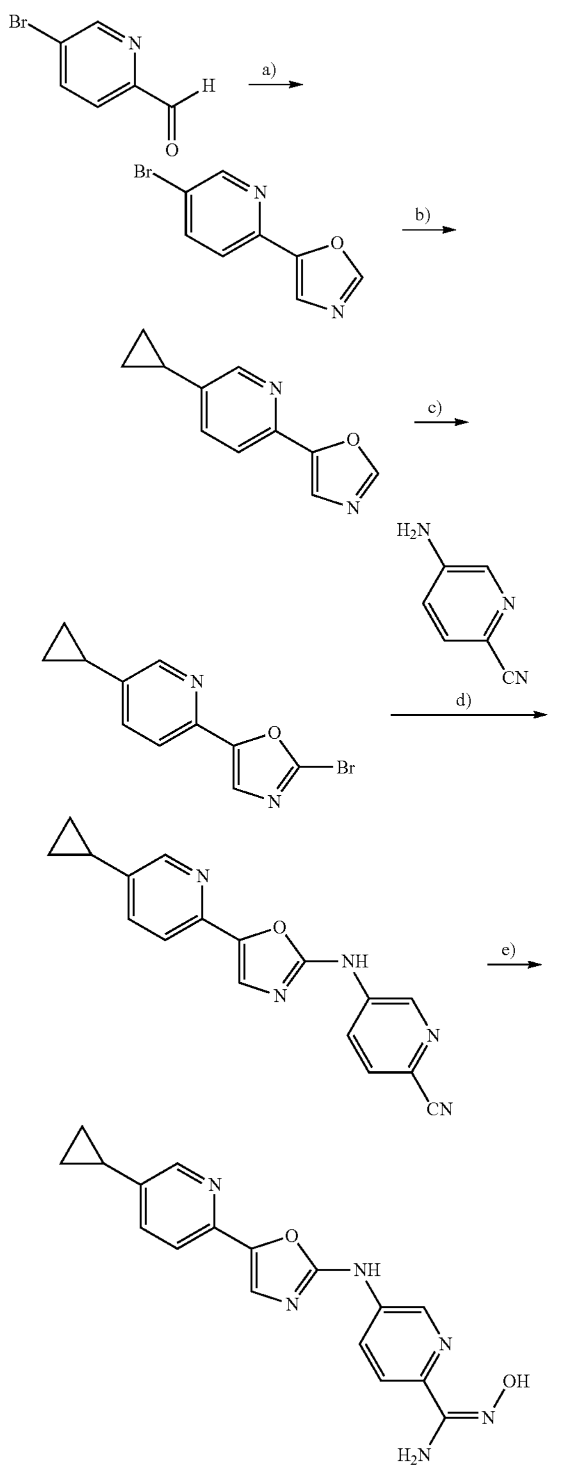

a) TosMIC, $K_2CO_3$, MeOH, reflux, 5 h; b) cyclopropylboronic acid, $Pd(OAc)_2$, $K_3PO_4$, $Pd(OAC)_2$, toluene/$H_2O$, 100° C., 16 h; c) $BrCF_2CF_2Br$, t-BuOLi, DMF/m-xylene, 60° C., 3 h; d) $Pd_2(Dba)_3$, Xantphos, $Cs_2CO_3$, 1,4-dioxane, 110° C., 18 h; e) $NH_2OH.HCl$, $Et_3N$, MeOH, reflux, 18 h.

5-Bromopicolinaldehyde (3.53 g, 18.89 mmol) was reacted with TosMIC (4.26 g, 21.82 mmol) and $K_2CO_3$ (3.15 g, 22.78 mmol) as per General Procedure 14 in MeOH (40 mL) to provide 5-(5-bromopyridin-2-yl)oxazole (3.84 g, 90%) as a pale yellow solid.

5-(5-Bromopyridin-2-yl)oxazole (2.0 g, 8.89 mmol) was coupled with cyclopropylboronic acid (0.99, 11.56 mmol) as per General Procedure 12 Method 1 in toluene/$H_2O$ (50/5 mL) to provide 5-(5-cyclopropylpyridin-2-yl)oxazole (1.42 g, 86%) as a white solid. $^1H$ NMR (401 MHz, $CDCl_3$) δ 8.39 (d, J=2.2 Hz, 1H), 7.90 (d, J=1.6 Hz, 1H), 7.59 (d, J=1.9 Hz, 1H), 7.49 (d, J=8.2 Hz, 1H), 7.30 (dd, J=8.2, 2.3 Hz, 1H), 1.88 (tt, J=8.4, 5.0 Hz, 1H), 1.27-0.84 (m, 2H), 0.71 (dt, J=6.6, 4.9 Hz, 2H). LCMS $R_f$ (min)=3.329, MS m/z=187.1 $[M+H]^+$.

5-(5-Cyclopropylpyridin-2-yl)oxazole (0.35 g, 1.88 mmol) was converted to 2-bromo-5-(5-cyclopropylpyridin-2-yl)oxazole as per General Procedure 15 Method 2 (0.26 g, 52%). $^1H$ NMR (401 MHz, $CDCl_3$) δ 8.38 (d, J=2.1 Hz, 1H), 7.53 (s, 1H), 7.45 (d, J=8.2 Hz, 1H), 7.31 (dd, J=8.2, 2.3 Hz, 1H), 1.89 (tt, J=8.5, 5.1 Hz, 1H), 1.04 (ddd, J=8.4, 6.5, 4.8 Hz, 2H), 0.73 (dt, J=6.6, 4.9 Hz, 2H). LCMS $R_f$ (min)= 3.354, MS m/z=265.0 $[M+H]^+$.

2-Bromo-5-(5-cyclopropylpyridin-2-yl)oxazole (0.35 g, 1.32 mmol) was reacted with 5-aminopicolinonitrile (0.79 g, 6.6 mmol) following General Procedure 4 Method 1. The crude product was purified on silica gel using mixtures of DCM and EtOAc (0 to 40%) as eluents to provide the desired 5-((5-(5-cyclopropylpyridin-2-yl)oxazol-2-yl)amino)picolinonitrile in 29.2% yield (0.117 g). $^1H$ NMR (401 MHz, DMSO-$d_6$) δ 11.41 (s, 1H), 8.84 (d, J=2.6 Hz, 1H), 8.42 (d, J=1.5 Hz, 1H), 8.33 (dd, J=8.7, 2.6 Hz, 1H), 7.99 (d, J=8.7 Hz, 1H), 7.63 (s, 1H), 7.51 (s, 2H), 2.02-1.94 (m, 1H), 1.07-0.99 (m, 2H), 0.80-0.74 (m, 2H). LCMS $R_f$ (min)=3.373, MS m/z=304.1 $[M+H]^+$.

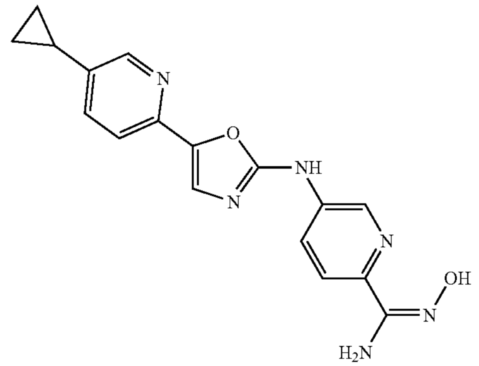 [SMILES: N/C(=N/O)c1ccc(Nc2ncc(-c3ccc(C4CC4)cn3)o2)cn1]

5-((5-(5-Cyclopropylpyridin-2-yl)oxazol-2-yl)amino)picolinonitrile (0.105 g, 0.346 mmol) was subjected to amidoxime formation in MeOH as per General Procedure 1 Method 2 to furnish 5-((5-(5-cyclopropylpyridin-2-yl)oxazol-2-yl)amino)-N'-hydroxypicolinimidamide (91.0%, 106 mg) after isolation via filtering with water, and washing with water and $Et_2O$. $^1H$ NMR (401 MHz, DMSO-$d_6$) δ 10.88 (s, 1H), 9.77 (s, 1H), 8.77 (s, 1H), 8.43 (s, 1H), 8.13 (d, J=7.2 Hz, 1H), 7.83 (d, J=8.7 Hz, 1H), 7.57 (s, 1H), 7.50 (s, 2H), 5.78 (s, 2H), 1.97 (m, 1H), 1.01 (m, 2H), 0.76 (m, 2H). $^{13}C$ NMR (101 MHz, DMSO) δ 156.67, 149.86, 148.24, 144.94, 144.51, 143.39, 138.27, 137.14, 136.75, 133.51, 125.28, 124.19, 120.18, 117.99, 13.11, 9.89. LCMS $R_f$ (min)=2.238, MS m/z=337.1 $[M+H]^+$. HRMS (ESI) calcd for $C_{17}H_{17}N_6O_2^+$ $[M+H]^+$ 337.1408, found 337.1404.

63. N'-Hydroxy-2-((5-(4-(trifluoromethyl)phenyl)oxazol-2-yl)amino)pyrimidine-5-carboximidamide (Scheme 60)

Scheme 60

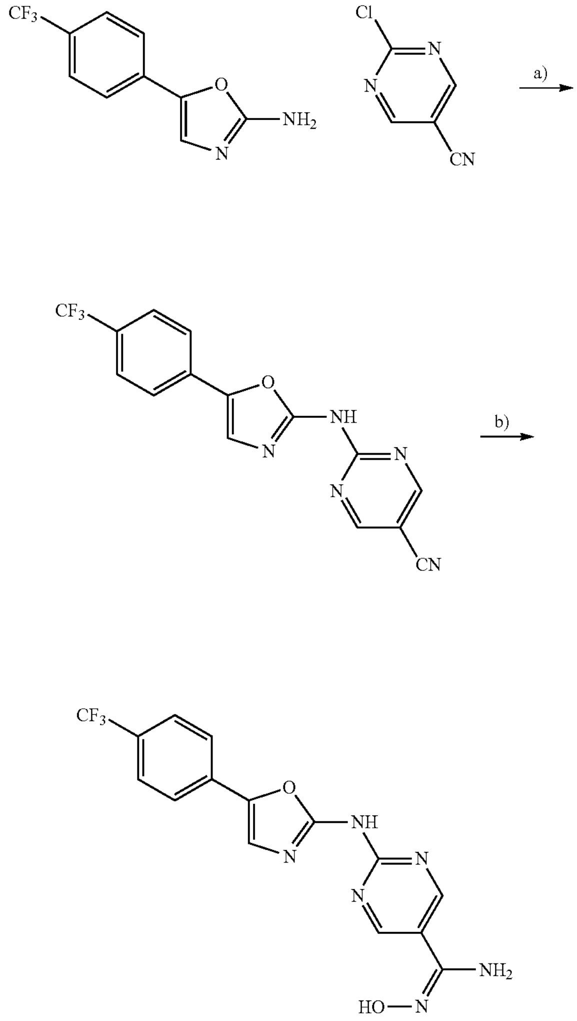

a) $Pd_2(dba)_3$, Xantphos, $Cs_2CO_3$, 1,4-dioxane, 110° C., 18 h; b) $NH_2OH.HCl$, $Et_3N$, MeOH, reflux, 18 h.

Intermediate D (5-(4-(trifluoromethyl)phenyl)oxazol-2-amine) (0.229 g, 1 mmol) was reacted with 2-chloropyrimidine-5-carbonitrile (0.14 g, 1 mmol) following General Procedure 4 Method 1. Upon completion, the volatile solvents were removed in vacuo, and the solid residue, triturated with water, filtered and washed well with water. The resultant crude product was washed with $Et_2O$ and DCM until all catalysts and ligands were removed, providing the 2-((5-(4-(trifluoromethyl)phenyl)oxazol-2-yl)amino)pyrimidine-5-carbonitrile in 65.6% yield (0.218 g). $^1H$ NMR (401 MHz, DMSO) δ 12.07-11.63 (br s, 1H), 8.93 (s, 2H), 7.82 (m, 4H), 7.79 (s, 1H). LCMS $R_f$ (min)=2.842, MS m/z=332.1 $[M+H]^+$.

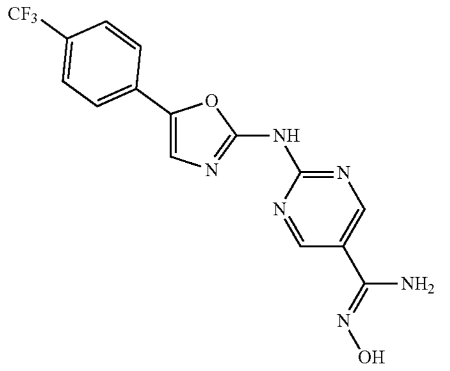 [SMILES: N/C(=N\O)c1cnc(Nc2ncc(-c3ccc(C(F)(F)F)cc3)o2)nc1]

2-((5-(4-(Trifluoromethyl)phenyl)oxazol-2-yl)amino)pyrimidine-5-carbonitrile (0.20 g, 0.603 mmol) was subjected to amidoxime formation in MeOH as per General Procedure 1 Method 2 to furnish N'-hydroxy-2-((5-(4-(trifluoromethyl)phenyl)oxazol-2-yl)amino)pyrimidine-5-carboximidamide (80.5%, 177 mg) after isolation via filtering with water, and washing with water and $Et_2O$. $^1H$ NMR (401 MHz, DMSO-$d_6$) δ 11.28 (s, 1H), 9.81 (s, 1H), 8.81 (s, 2H), 7.82 (s, 5H), 6.02 (s, 2H). $^{13}C$ NMR (101 MHz, DMSO-$d_6$) δ 158.85, 155.84, 155.28, 147.61, 131.97, 128.04, 127.72, 126.55, 126.51, 126.00, 125.67, 123.88, 123.30, 120.98. LCMS $R_f$ (min)=3.415, MS m/z=365.1 $[M+H]^+$. HRMS (ESI) calcd for $C_{15}H_{12}F_3N_6O_2^+$ $[M+H]^+$ 365.0968, found 365.0967.

64. 5-((5-(4-(3,3-Difluoroazetidin-1-yl)phenyl)oxazol-2-yl)amino)-N'-hydroxypicolinimidamide (Scheme 61)

Scheme 61

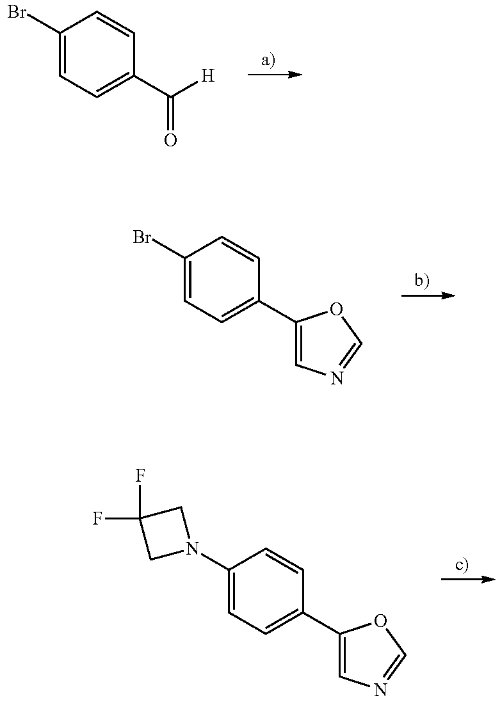

-continued

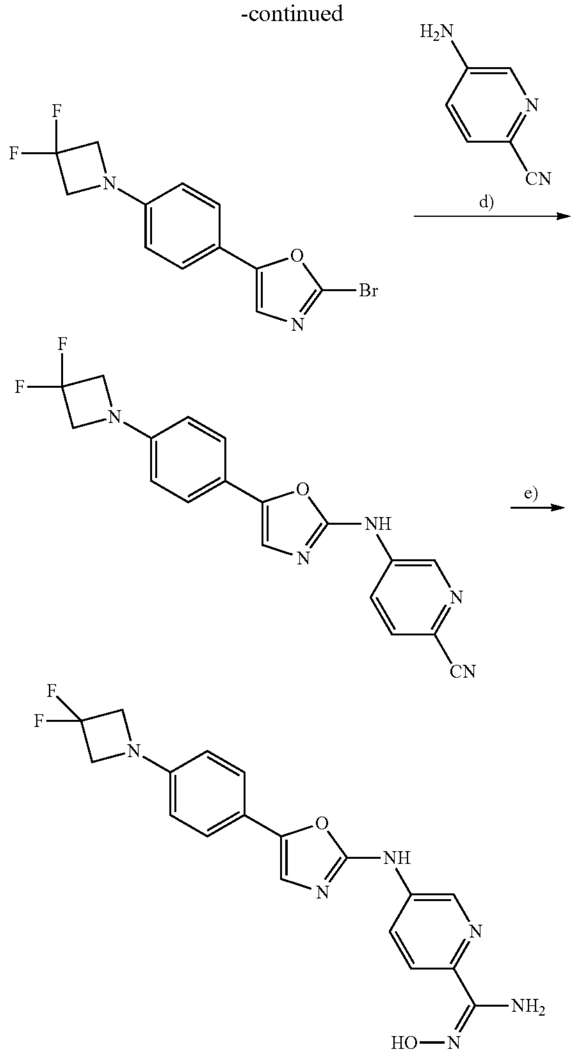

TosMIC, $K_2CO_3$, MeOH, reflux, 5 h; b) 3,3-difluoroazetidine•HCl, $Pd_2(dba)_3$, Xantphos, $Cs_2CO_3$, 1,4-dioxane, 100° C., 16 h; c) $BrCF_2CF_2Br$, t-BuOLi, DMF/m-xylene, 60° C., 3 h; d) $Pd_2(Dba)_3$, Xantphos, $Cs_2CO_3$, 1,4-dioxane, 110° C., 18 h; e) $NH_2OH.HCl$, $Et_3N$, MeOH, reflux, 18 h.

4-Bromobenzaldehyde (5.0 g, 27.02 mmol) was reacted with TosMIC (5.80 g, 29.73 mmol) and $K_2CO_3$ (4.48 g, 32.4 mmol) in MeOH (80 mL) as per General Procedure 14 to provide 5-(4-bromophenyl)oxazole (5.26 g, 87%) as a white solid.

5-(4-Bromophenyl)oxazole (1.0 g, 4.46 mmol) was reacted with 3,3-difluoroazetidine·HCl (0.694 g, 5.36 mmol), in the presence of $Pd_2(dba)_3$ (0.327 g, 0.36 mmol), Xantphos (0.232 g, 0.40 mmol) and $Cs_2CO_3$ (4.36 g, 13.38 mmol) in 1,4-dioxane (10 mL) at 100° C. for 16 h as per General Procedure 4 Method 1 to provide 5-(4-(3,3-difluoroazetidin-1-yl)phenyl)oxazole (0.875 g, 83%). $^1H$ NMR (401 MHz, $CDCl_3$) δ 7.85 (s, 1H), 7.55 (d, J=8.8 Hz, 2H), 7.20 (s, 1H), 6.53 (d, J=8.8 Hz, 2H), 4.27 (t, J=11.7 Hz, 4H). LCMS $R_f$ (min)=2.824, MS m/z=237.1 $[M+H]^+$.

5-(4-(3,3-Difluoroazetidin-1-yl)phenyl)oxazole (0.80 g, 3.37 mmol) reacted with $BrCF_2CF_2Br$ (0.64 mL, 5.39 mmol) and t-BuOLi (0.405 g, 5.06 mmol) in DMF/m-xylene (10/10 mL) at 60° C. for 3 h as per General Procedure 15 Method 2 to provide 2-bromo-5-(4-(3,3-difluoroazetidin-1-yl)phenyl)oxazole (0.50 g, 47%) as a yellow solid. $^1H$ NMR (401 MHz, $CDCl_3$) δ 7.49 (d, J=8.8 Hz, 2H), 7.14 (s, 1H), 6.52 (d, J=8.8 Hz, 2H), 4.27 (t, J=11.7 Hz, 4H). LCMS $R_f$ (min)=3.587. MS m/z=314.9 $[M+H]^+$.

2-Bromo-5-(4-(3,3-difluoroazetidin-1-yl)phenyl)oxazole) (0.28 g, 0.888 mmol) was reacted with 5-aminopicolinonitrile (0.53 g, 4.44 mmol) following General Procedure 4 Method 1. The crude product was purified on silica gel using mixtures of DCM and EtOAc (0 to 30%) and then preparative HPLC to provide the 5-((5-(4-(3,3-difluoroazetidin-1-yl)phenyl)oxazol-2-yl)amino)picolinonitrile in 18.15% yield (0.057 g). $^1H$ NMR (401 MHz, DMSO) δ 11.16 (s, 1H), 8.80 (s, 1H), 8.30 (d, J=6.3 Hz, 1H), 7.94 (d, J=7.4 Hz, 1H), 7.48 (d, J=6.3 Hz, 2H), 7.33 (s, 1H), 6.63 (d, J=6.3 Hz, 2H), 4.30 (t, J=11.2 Hz, 4H). LCMS $R_f$ (min)=2.986, MS m/z=354.1 $[M+H]^+$.

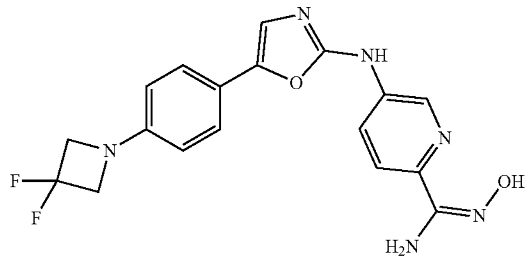 [SMILES: N/C(=N/O)c1ccc(Nc2ncc(-c3ccc(N4CC(F)(F)C4)cc3)o2)cn1]

5-((5-(4-(3,3-Difluoroazetidin-1-yl)phenyl)oxazol-2-yl)amino)picolinonitrile (0.055 g, 0.155 mmol) was subjected to amidoxime formation in MeOH as per General Procedure 1 Method 2 to furnish 5-((5-(4-(3,3-difluoroazetidin-1-yl)phenyl)oxazol-2-yl)amino)-N'-hydroxypicolinimidamide (76.5%, 46 mg) after isolation via filtering with water, and washing with water and $Et_2O$. $^1H$ NMR (401 MHz, DMSO-$d_6$) δ 10.63 (s, 1H), 9.71 (s, 1H), 8.76 (s, 1H), 8.11 (d, J=8.5 Hz, 1H), 7.82 (d, J=8.4 Hz, 1H), 7.48 (d, J=7.5 Hz, 2H), 7.29 (s, 1H), 6.65 (d, J=7.7 Hz, 2H), 5.75 (s, 2H), 4.30 (t, J=12.0 Hz, 4H). $^{13}C$ NMR (101 MHz, DMSO-$d_6$) δ 155.45, 149.88, 149.49, 145.29, 143.06, 137.02, 136.93, 124.36, 123.88, 120.33, 120.13, 119.85, 119.04, 117.13, 114.42, 113.60, 63.59, 63.34, 63.09. LCMS $R_f$ (min)=2.45, MS m/z=387.1 $[M+H]^+$. HRMS (ESI) calcd for $C_{18}H_{17}F_2N_6O_2^+$ $[M+H]^+$ 387.1376, found 387.1373.

65. N'-Hydroxy-5-((5-(5-(trifluoromethyl)pyrimidin-2-yl)oxazol-2-yl)amino)picolinimidamide (Scheme 62)

Scheme 62

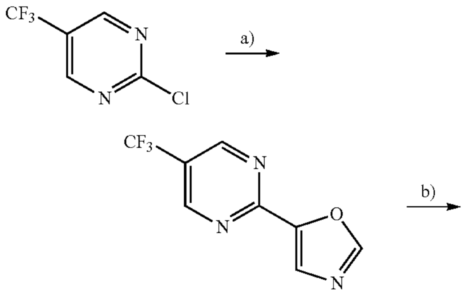

-continued

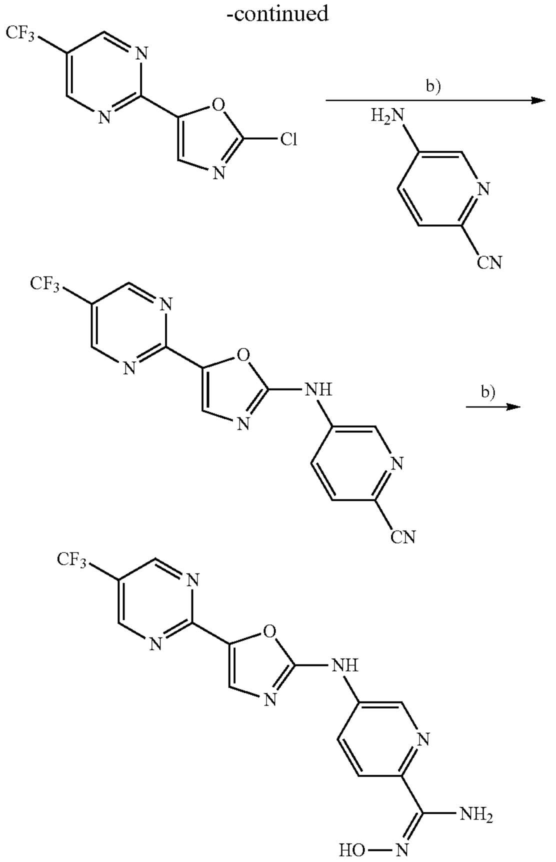

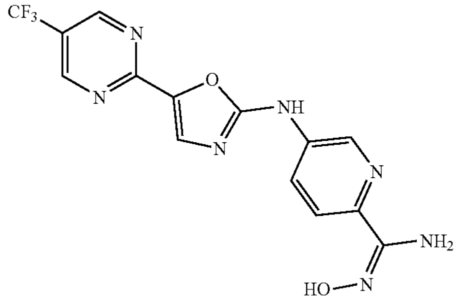 [SMILES: N/C(=N/O)c1ccc(Nc2ncc(-c3ncc(C(F)(F)F)cn3)o2)cn1]

a) $PdCl_2(PPh_3)_2$, THF:1M $Na_2CO_3$ (3.5:1.5), reflux, 16 h; b) 1. LiHMDS, THF, -78° C., 0.5 h, ii. $C_2Cl_6$, -78° C.~rt, 5 h; c) $Pd_2(dba)_3$, Xantphos, $Cs_2CO_3$, 1,4-dioxane, 110° C., 18 h; b) $NH_2OH.HCl$, $Et_3N$, MeOH, reflux, 18 h.

To a degassed biphasic solution of THF (3.5 mL) and 1 M $Na_2CO_3$ (1.5 mL), was added 2-chloro-5-(trifluoromethyl) pyrimidine (876 mg, 4.80 mmol, 1.0 eq.), 5-(4,4,5,5-tetramethyl-1,3,2-dioxaborolan-2-yl)oxazole (1.0 M in THF, 7.20 mL, 7.20 mmol, 1.5 eq.) and $PdCl_2(PPh_3)_2$ (835 mg, 0.720 mmol, 0.15 eq.). The mixture was reacted according to General Procedure 12 Method 1 to afford 5-(5-(trifluoromethyl)pyrimidin-2-yl)oxazole as a brown solid (53 mg, 5.1%). $^1H$ NMR (401 MHz, $CDCl_3$) δ 9.02 (s, 2H), 8.12 (s, 1H), 8.07 (s, 1H); 13C NMR (101 MHz, $CDCl_3$) δ 155.1, 153.5, 149.0, 132.0, 132.0, 126.8, 124.1, 123.3, 122.9, 121.4, 118.6 ppm. LCMS $R_f$ (min)=3.344, MS m/z=216.1 $[M+H]^+$.

5-(5-(Trifluoromethyl)pyrimidin-2-yl)oxazole (0.205 g, 0.95 mmol) was reacted with LiHMDS (1.05 mL, 1.05 mmol, 1 M in hexane) and $C_2Cl_6$ (0.339 g, 1.43 mmol) in THF (10 mL) as per General Procedure 15 Method 1 to provide 2-chloro-5-(5-(trifluoromethyl)pyrimidin-2-yl)oxazole (0.206 g, 87%) as a white solid. $^1H$ NMR (401 MHz, $CDCl_3$) δ 9.01 (d, J=0.6 Hz, 2H), 7.98 (s, 1H). LCMS $R_f$ (min)=2.871, MS m/z=250.0 $[M+H]^+$.

2-Chloro-5-(5-(trifluoromethyl)pyrimidin-2-yl)oxazole (0.3 g, 1.2 mmol) was reacted with 5-aminopicolinonitrile (0.43 g, 3.6 mmol) following General Procedure 4 Method 1. The crude product was purified on preparative HPLC to provide the 5-((5-(5-(trifluoromethyl)pyrimidin-2-yl)oxazol-2-yl)amino)picolinonitrile in 9.3% yield (0.037 g). $^1H$ NMR (401 MHz, DMSO-$d_6$) δ 11.81 (s, 1H), 9.22 (s, 2H), 8.85 (d, J=2.3 Hz, 1H), 8.31 (dd, J=8.6, 2.5 Hz, 1H), 8.08 (s, 1H), 8.02-8.00 (m, 1H). LCMS $R_f$ (min)=3.805, MS m/z=333.1 $[M+H]^+$.

5-((5-(5-(Trifluoromethyl)pyrimidin-2-yl)oxazol-2-yl) amino)picolinonitrile (0.037 g, 0.11 mmol) was subjected to amidoxime formation in MeOH as per General Procedure 1 Method 2 to furnish N'-hydroxy-5-((5-(5-(trifluoromethyl) pyrimidin-2-yl)oxazol-2-yl)amino)picolinimidamide (71.3%, 29 mg) after isolation via filtering with water, and washing with water and $Et_2O$. $^1H$ NMR (401 MHz, DMSO-$d_6$) δ 11.69 (s, 1H), 10.91 (br s, 1H), 9.22 (d, J=0.8 Hz, 2H), 8.88 (d, J=2.5 Hz, 1H), 8.29 (dd, J=8.8, 2.6 Hz, 1H), 8.08 (s, 1H), 8.03 (d, J=8.8 Hz, 1H). $^{13}C$ NMR (101 MHz, DMSO-$d_6$) δ 158.50, 155.81, 154.53, 143.26, 138.88, 138.54, 134.27, 124.96, 124.23, 123.15, 122.26, 120.84, 120.51. LCMS $R_f$ (min)=3.037, MS m/z=366.1 $[M+H]^+$. HRMS (ESI) calcd for $C_{14}H_{11}F_3N_7O_2^+$ $[M+H]^+$ 366.0921, found 366.0918.

66. N'-Hydroxy-5-((5-(5-(trifluoromethyl)pyrazin-2-yl)oxazol-2-yl)amino)picolinimidamide (Scheme 63)

Scheme 63

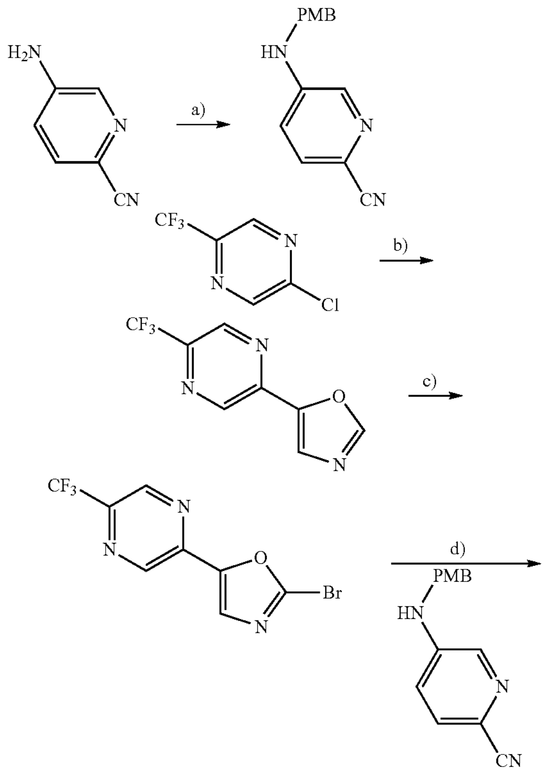

-continued

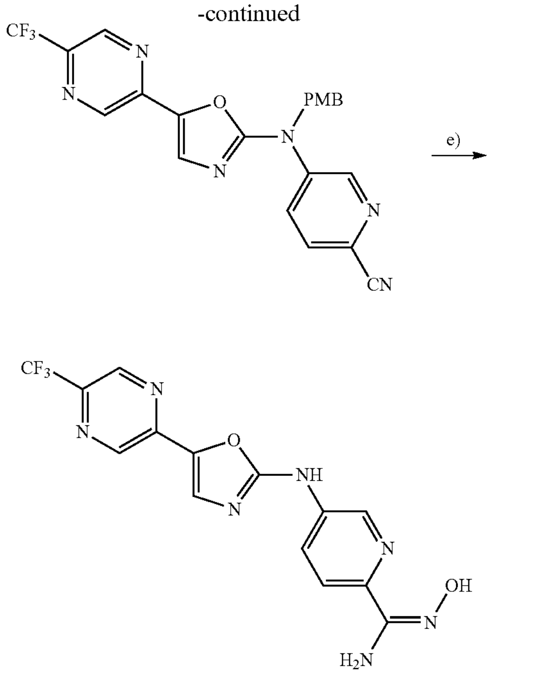

a) Anisaldehyde, AcOH, $Na(AcO)_3BH$, DCE, rt; b) $PdCl_2(PPh_3)_2$, THF:1M $Na_2CO_3$ (3.5:1.5), reflux 16 h; c) t-BuOLi, $BrCF_2CF_2Br$, DMF/m-xylene; d) $Pd_2(dba)_3$, Xantphos, $Cs_2CO_3$, 1,4-diozane, 110° C., 18 h; e) i. TFA, anisole, ii. $NH_2OH.HCl$, $Et_3N$, MeOH, reflux, 18 h.

5-Aminopicolinonitrile (5 g, 41.97 mmol) and anisaldehyde (5.45 g, 46.16 mmol) was dissolved in DCE (100 mL), AcOH (7.2 mL, 126 mmol) added, and the reaction mixture was stirred at rt overnight. $NaBH(AcO)_3$ (17.8 g, 83.9 mmol) was added in portions every hr, until most of the starting amine has been consumed as evidenced by TLC. The reaction mixture was diluted with DCM (100 mL), poured slowly into saturated $NaHCO_3$ solution (200 mL). The aqueous phase was made alkaline (pH~8) by addition of solid $NaHCO_3$. After separation, the aqueous phase was extracted with more DCM (3×). The combined organic phase was dried over $MgSO_4$, evaporated to dryness. The residue was purified on silica gel using mixtures of DCM and EtOAc (0 to 10%) as eluents to provide 5-((4-methoxybenzyl)amino)picolinonitrile in 51.8% yield (5.2 g). $^1H$ NMR (401 MHz, $CDCl_3$) δ 8.06 (d, J=2.8 Hz, 1H), 7.43 (d, J=8.6 Hz, 1H), 7.26-7.21 (m, 2H), 6.92-6.86 (m, 2H), 6.82 (dd, J=8.6, 2.9 Hz, 1H), 4.32 (s, 2H), 3.80 (s, 3H). LCMS $R_f$ (min)=2.772, MS m/z=240.1 $[M+H]^+$.

To a degassed biphasic solution of THF (3.5 mL) and 1 M $Na_2CO_3$ (1.5 mL), was added 2-chloro-5-(trifluoromethyl)pyrazine (150 mg, 0.822 mmol, 1.0 eq.), 5-(4,4,5,5-tetramethyl-1,3,2-dioxaborolan-2-yl)oxazole (1.0 M in THF, 904 0.904 mmol, 1.1 eq.) and $PdCl_2(PPh_3)_2$ (58 mg, 0.082 mmol, 0.1 eq.). The mixture was reacted according to General Procedure 12 Method 1 to afford 5-(5-(trifluoromethyl)pyrazin-2-yl)oxazole as a brown solid (53 mg, 30%). $^1H$ NMR (401 MHz, $CDCl_3$) δ 9.02 (s, 1H), 8.92 (s, 1H), 8.10 (s, 1H), 7.92 (s, 1H); $^{13}C$ NMR (101 MHz, $CDCl_3$) δ 152.8, 148.0, 145.5, 143.0, 142.6, 142.3, 141.9, 141.5, 141.5, 141.5, 141.4, 140.0, 129.1, 125.2, 122.5, 119.7, 117.0 ppm. LCMS $R_f$ (min)=3.223, MS m/z=216.0 $[M+H]^+$.

5-(5-(Trifluoromethyl)pyrazin-2-yl)oxazole (0.25 g, 1.16 mmol) was reacted with $BrCF_2CF_2Br$ (0.21 mL, 1.74 mmol) and t-BuOLi (0.121 g, 1.51 mmol) in DMF/m-xylene (3/3 mL) as per General Procedure 15 Method 2 to provide 2-bromo-5-(5-(trifluoromethyl)pyrazin-2-yl)oxazole (0.232 g, 67%) as a yellow solid. $^1H$ NMR (401 MHz, $CDCl_3$) δ 8.98 (d, J=1.1 Hz, 1H), 8.93 (d, J=1.0 Hz, 1H), 7.86 (s, 1H). LCMS $R_f$ (min)=2.939, MS m/z=294.0 $[M+H]^+$.

2-Bromo-5-(5-(trifluoromethyl)pyrazin-2-yl)oxazole) (0.22 g, 0.748 mmol) was reacted with 5-((4-methoxybenzyl)amino)picolinonitrile (0.42 g, 1.76 mmol) following General Procedure 4 Method 1. The crude product was purified on silica gel using mixtures of DCM and EtOAc (0 to 15%) as eluents to provide the 5-((4-methoxybenzyl)(5-(5-(trifluoromethyl)pyrazin-2-yl)oxazol-2-yl)amino)picolinonitrile in 54.9% yield (0.186 g). $^1H$ NMR (401 MHz, $CDCl_3$) δ 8.86 (d, J=2.3 Hz, 1H), 8.83 (d, J=1.0 Hz, 1H), 8.73 (d, J=1.1 Hz, 1H), 8.01 (dd, J=8.6, 2.8 Hz, 1H), 7.77 (s, 1H), 7.69 (dd, J=8.6, 0.5 Hz, 1H), 7.20 (d, J=8.7 Hz, 2H), 6.88-6.85 (m, 2H), 5.29 (s, 2H), 3.78 (s, 3H). LCMS $R_f$ (min)=3.579, MS m/z=453.1 $[M+H]^+$.

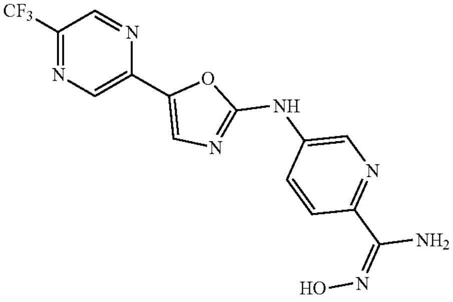 [SMILES: N/C(=N/O)c1ccc(Nc2ncc(-c3cnc(C(F)(F)F)cn3)o2)cn1]

5-((4-Methoxybenzyl)(5-(5-(trifluoromethyl)pyrazin-2-yl)oxazol-2-yl)amino)picolinonitrile (0.186 g, 0.408 mmol) was deprotected with TFA and anisole mixture as per General Procedure 11. The PMB-deprotected product, which was collected via trituration with $Et_2O$ (LCMS $R_f$ (min)=2.843, MS m/z=333.1 $[M+H]^+$ was subjected to amidoxime formation in MeOH as per General Procedure 1 Method 2 to furnish N'-hydroxy-5-((5-(5-(trifluoromethyl)pyrazin-2-yl)oxazol-2-yl)amino)picolinimidamide (63.6%, 95 mg) after purification with preparative HPLC. $^1H$ NMR (401 MHz, DMSO-$d_6$) δ 11.26 (s, 1H), 9.77 (s, 1H), 9.08 (s, 2H), 8.78 (d, J=2.1 Hz, 1H), 8.16-8.08 (m, 2H), 7.86 (d, J=8.8 Hz, 1H), 5.77 (s, 2H). $^{13}C$ NMR (101 MHz, DMSO-$d_6$) δ 158.77, 149.77, 146.10, 144.13, 141.77, 141.74, 140.11, 139.38, 139.03, 138.68, 138.34, 137.60, 136.14, 132.35, 124.83, 123.35, 120.63, 120.24. LCMS $R_f$ (min)=2.326, MS m/z=366.0 $[M+H]^+$. HRMS (ESI) calcd for $C_{14}H_{11}F_3N_7O_2^+$ $[M+H]^+$ 366.0921, found 366.0924.

67. 6-((5-(4-(Trifluoromethoxy)phenyl)-1,3,4-oxadiazol-2-yl)amino)pyridin-3-ol (Scheme 64)

Scheme 64

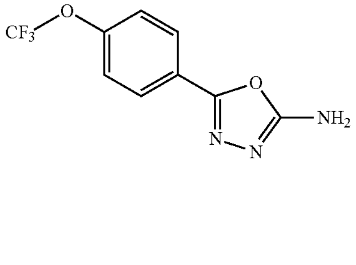

-continued

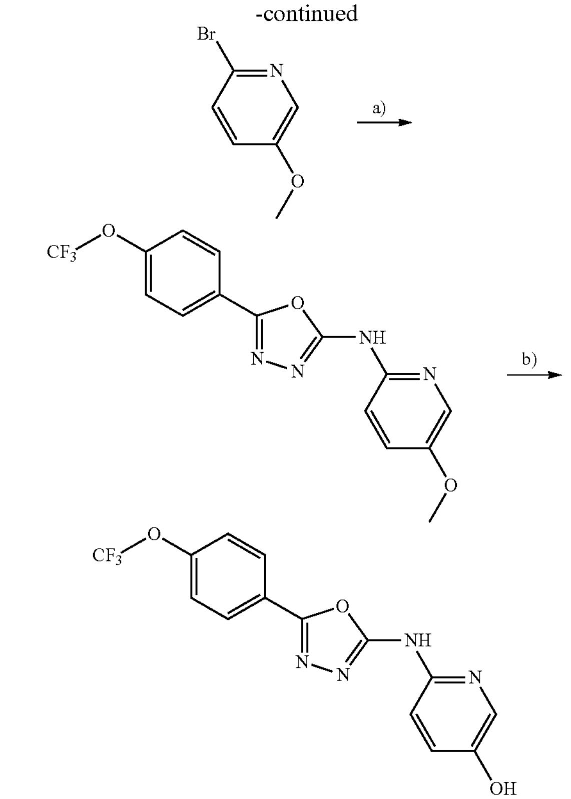

a) $Pd_2(dba)_3$, Xantphos, $Cs_2CO_3$, 1,4-dioxane, 110° C., 18 h; b) $BBr_3$, DCM rt, 18 h.

5-(4-(Trifluoromethoxy)phenyl)-1,3,4-oxadiazol-2-amine (0.58 g, 0.2.36 mmol) was reacted with 2-bromo-5-methoxypyridine (0.89 g, 4.73 mmol) following General Procedure 4 Method 1. The crude product was triturated, filtered, and washed well with water. Excess of catalyst and ligands were removed by washing with $Et_2O$ and DCM, providing the N-(5-methoxypyridin-2-yl)-5-(4-(trifluoromethoxy)phenyl)-1,3,4-oxadiazol-2-amine in 31.3% yield (0.261 g). $^1$H NMR (401 MHz, DMSO-$d_6$) δ 11.11 (s, 1H), 8.05 (s, 1H), 8.00 (d, J=8.3 Hz, 2H), 7.88 (d, J=8.9 Hz, 1H), 7.59 (d, J=7.9 Hz, 2H), 7.52 (d, J=6.9 Hz, 1H), 3.81 (s, 3H). LCMS $R_f$ (min)=3.227, MS m/z=353.1 $[M+H]^+$.

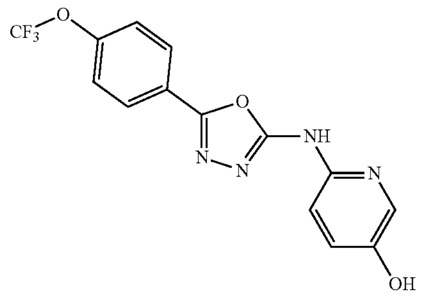 [SMILES: Oc1ccc(Nc2nnc(-c3ccc(OC(F)(F)F)cc3)o2)nc1]

N-(5-Methoxypyridin-2-yl)-5-(4-(trifluoromethoxy)phenyl)-1,3,4-oxadiazol-2-amine (0.26 g, 0.738 mmol) was deprotected with $BBr_3$ in DCM as per General Procedure 8. The crude product was purified on preparative HPLC to furnish 6-((5-(4-(trifluoromethoxy)phenyl)-1,3,4-oxadiazol-2-yl)amino)pyridin-3-ol (73.3%, 183 mg). $^1$H NMR (401 MHz, DMSO-$d_6$) δ 10.94 (s, 1H), 9.60 (s, 1H), 7.99 (d, J=8.6 Hz, 2H), 7.88 (d, J=2.2 Hz, 1H), 7.77 (d, J=8.8 Hz, 1H), 7.58 (d, J=8.2 Hz, 2H), 7.29 (dd, J=8.8, 2.6 Hz, 1H). $^{13}$C NMR (101 MHz, DMSO-$d_6$) δ 160.48, 157.54, 150.28, 149.90, 144.34, 135.51, 128.22, 125.66, 123.53, 122.29, 112.64. LCMS $R_f$ (min)=2.691, MS m/z=339.1 $[M+H]^+$. HRMS (ESI) calcd for $C_{14}H_{10}F_3N_4O_3^+$ $[M+H]^+$ 339.07, found 339.0704.

68. 1-Hydroxy-4-((5-(5-(trifluoromethyl)pyridin-2-yl)oxazol-2-yl)amino)pyridin-2(1H)-one (Scheme 65)

Scheme 65

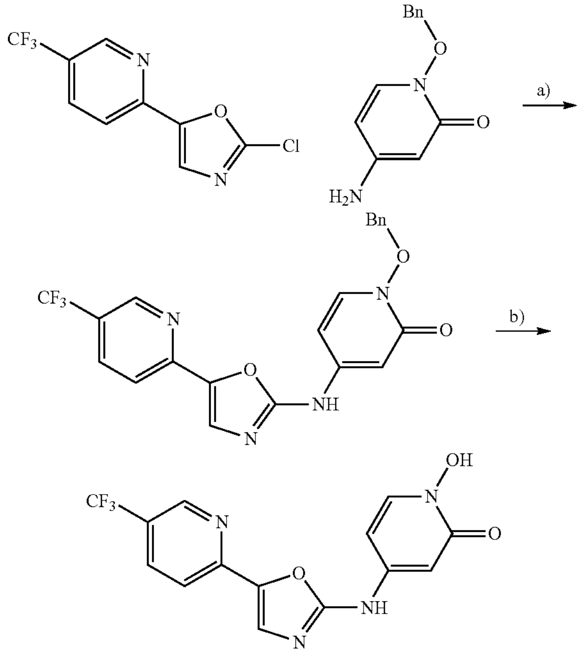

a) NaH (60% dispersion in mineral oil), DMF, rt, 110° C., 18 h; b) TFA, reflux, 16 h.

2-Chloro-5-(5-(trifluoromethyl)pyridin-2-yl)oxazole (Intermediate J, 0.741 g, 2.98 mmol) was reacted with 4-amino-1-(benzyloxy)pyridin-2(1H)-one (0.645 g, 2.98 mmol) following General Procedure 2 Method 2. The crude product was triturated with water and DCM to provide the 1-(benzyloxy)-4-((5-(5-(trifluoromethyl)pyridin-2-yl)oxazol-2-yl)amino)pyridin-2(1H)-one in 50% yield (0.624 g). $^1$H NMR (401 MHz, DMSO-$d_6$) δ 11.09 (s, 1H), 8.96-8.92 (m, 1H), 8.28 (dd, J=8.5, 1.8 Hz, 1H), 7.92 (s, 1H), 7.81 (d, J=8.4 Hz, 1H), 7.68 (d, J=7.8 Hz, 1H), 7.48 (m, 2H), 7.41 (m, 3H), 6.99 (d, J=2.8 Hz, 1H), 6.22 (dd, J=7.8, 2.9 Hz, 1H), 5.18 (s, 2H). LCMS $R_f$ (min)=3.653, MS m/z=429.1 $[M+H]^+$.

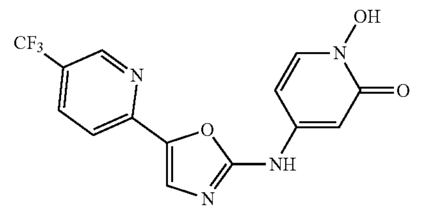 [SMILES: O=c1cc(Nc2ncc(-c3ccc(C(F)(F)F)cn3)o2)ccn1O]

1-(Benzyloxy)-4-((5-(5-(trifluoromethyl)pyridin-2-yl) oxazol-2-yl)amino)pyridin-2(1H)-one (0.2 g, 0.47 mmol) was stirred in TFA (10 mL) at reflux for 16 h. The volatile solvents were removed in vacuo, and the residual crude product was purified on preparative HPLC to furnish 1-hydroxy-4-((5-(5-(trifluoromethyl)pyridin-2-yl)oxazol-2-yl) amino)pyridin-2(1H)-one (48%, 76 mg). $^{1}$H NMR (401 MHz, DMSO-$d_6$) δ 11.05 (s, 1H), 8.94 (d, J=0.9 Hz, 1H), 8.27 (dd, J=8.5, 1.9 Hz, 1H), 7.92 (s, 1H), 7.82 (d, J=2.5 Hz, 1H), 7.80 (d, J=3.3 Hz, 1H), 6.95 (d, J=2.8 Hz, 1H), 6.33 (dd, J=7.7, 2.8 Hz, 1H). LCMS $R_f$ (min)=3.204, MS m/z=339.1 [M+H]$^+$. HRMS (ESI) calcd for $C_{14}H_{10}F_3N_4O_3^+$ [M+H]$^+$ 339.07, found 339.0706.

69. N'-Hydroxy-5-((5-(5-(trifluoromethyl)pyridin-2-yl)-1,3,4-oxadiazol-2-yl)amino)picolinimidamide (Scheme 66)

Scheme 66

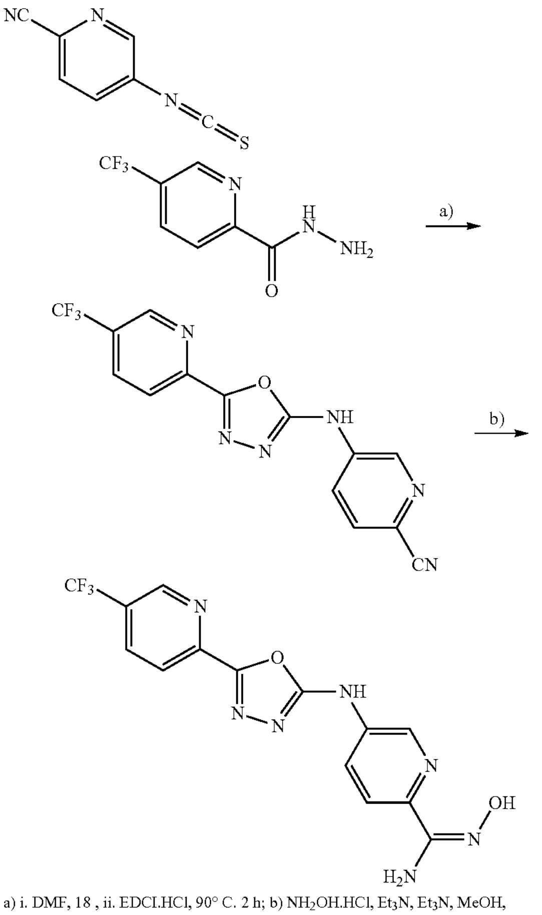

a) i. DMF, 18 , ii. EDCI.HCl, 90° C. 2 h; b) $NH_2OH.HCl$, $Et_3N$, $Et_3N$, MeOH, reflux, 18 h.

5-Isothiocyanatopicolinonitrile (0.161 g, 1.01 mmol) was reacted with 5-(trifluoromethyl)picolinohydrazide (0.173 g, 0.843 mmol) following General Procedure 7. The crude product was purified on silica gel using mixtures of DCM and EtOAc (0 to 30%) as eluents to provide 5-((5-(5-(trifluoromethyl)pyridin-2-yl)-1,3,4-oxadiazol-2-yl)amino) picolinonitrile in 81% yield (0.227 g). $^{1}$H NMR (401 MHz, DMSO-$d_6$) δ 11.93 (br s, 1H), 9.18-9.15 (m, 1H), 8.85-8.83 (m, 1H), 8.45 (dd, J=8.4, 1.8 Hz, 1H), 8.34-8.26 (m, 2H), 8.08 (dd, J=8.6, 0.5 Hz, 1H). LCMS $R_f$ (min)=3.450, MS m/z=333.1 [M+H]$^+$.

5-((5-(5-(Trifluoromethyl)pyridin-2-yl)-1,3,4-oxadiazol-2-yl)amino)picolinonitrile (0.212 g, 0.638 mmol) was subjected to amidoxime formation in MeOH as per General Procedure 1 Method 2 to furnish N'-hydroxy-5-((5-(5-(trifluoromethyl)pyridin-2-yl)-1,3,4-oxadiazol-

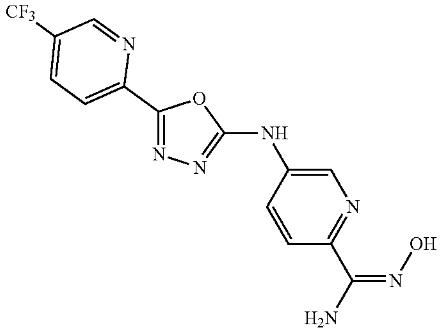

2-yl)amino)picolinimidamide hydrochloride (38.2%, 98 mg) after filtering and washing with water, then washing with MeOH, $Et_2O$, and finally freeze-drying from dioxane with 1.5 equivalents of HCl as 4 M dioxane solution. $^{1}$H NMR (401 MHz, DMSO-$d_6$) δ 11.95 (s, 1H), 11.04 (br s, 1H), 9.17 (s, 1H), 8.95 (d, J=2.5 Hz, 1H), 8.97-8.69 (br s, 2H), 8.46 (dd, J=8.5, 1.9 Hz, 1H), 8.35-8.24 (m, 3H), 8.17 (d, J=8.8 Hz, 1H). LCMS $R_f$ (min)=3.019, MS m/z=366.1 [M+H]$^+$. HRMS (ESI) calcd for $C_{14}H_{11}F_3N_7O_2^+$ [M+H]$^+$ 366.0921, found 366.092.

70. N'-Hydroxy-5-((5-(4-(trifluoromethoxy)phenyl) oxazol-2-yl)amino)pyrazine-2-carboximidamide (Scheme 67)

Scheme 67

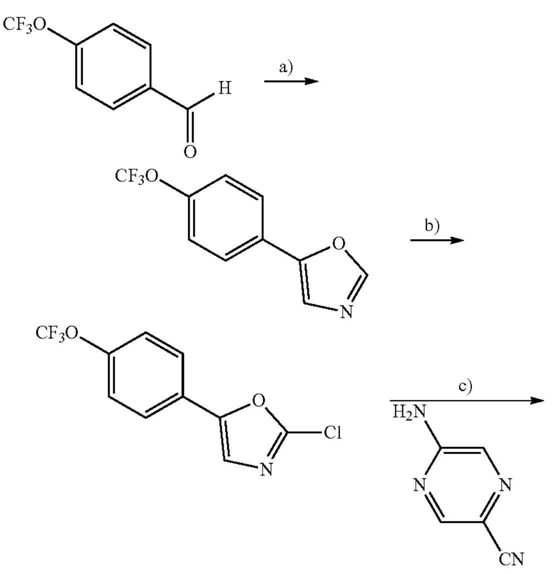

-continued

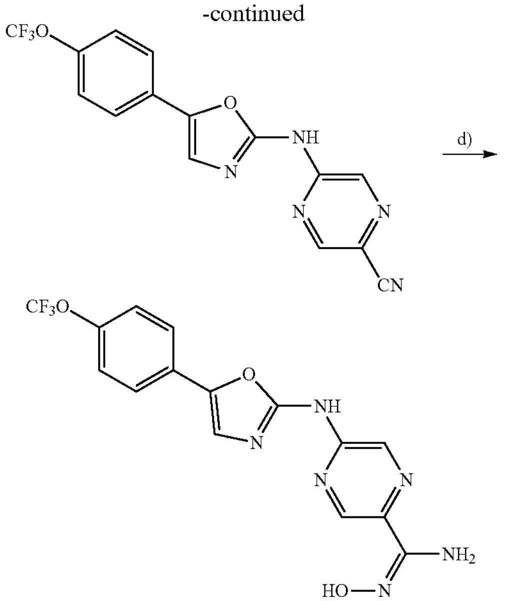

a) TosMIC, $K_2CO_3$, MeOH, reflux, 5 h; b) i. LiHMDS, THF, -78° C., o.5 h, ii. $C_2Cl_6$, -78° C.~rt, 5 h; c) $Pd_2(Dba)_3$, Xantphos, $Cs_2CO_3$, 1,4-dioxane, 110° C., 18 h; b) $NH_2OH.HCl$, $Et_3N$, EtOH, reflux, 18 h.

4-(Trifluoromethoxy)benzaldehyde (5.0 g, 26.3 mmol) was reacted TosMIC (5.65 g, 18.93 mmol) and $K_2CO_3$ (4.36 g, 31.56 mmol) in MeOH (60 mL) as per General Procedure 14 to provide 5-(4-(trifluoromethoxy)phenyl)oxazole (5.18 g, 86%) as a white solid. $^1H$ NMR (401 MHz, $CDCl_3$) δ 7.93 (s, 1H), 7.73-7.62 (m, 2H), 7.36 (s, 1H), 7.32-7.24 (m, 2H). LCMS $R_f$ (min)=3.046, MS m/z=230.0 $[M+H]^+$.

5-(4-(Trifluoromethoxy)phenyl)oxazole (2.0 g, 8.72 mmol) was reacted with LiHMDS (9.6 mL, 9.6 mmol, 1 M in hexane) and $C_2Cl_6$ (3.11 g, 13.13 mmol) in THF (20 mL) as per General Procedure 15 Method 1 to provide 2-chloro-5-(4-(trifluoromethoxy)phenyl)oxazole (1.85 g, 80%) as a white solid. $^1H$ NMR (401 MHz, $CDCl_3$) δ 7.61-7.58 (m, 2H), 7.59-7.56 (m, 2H), 7.24 (s, 1H). LCMS $R_f$(min)=3.328, MS m/z=264.0 $[M+H]^+$.

2-Chloro-5-(4-(trifluoromethoxy)phenyl)oxazole) (1.2 g, 4.55 mmol) was reacted with 5-aminopyrazine-2-carbonitrile (0.656 g, 5.46 mmol) following General Procedure 4 Method 1. The crude product was purified on silica gel with mixtures of EtOAc (0 to 60%) in DCM as eluents, then on preparative HPLC to provide the 5-((5-(4-(trifluoromethoxy)phenyl)oxazol-2-yl)amino)pyrazine-2-carbonitrile in 12.5% yield (0.197 g). $^1H$ NMR (401 MHz, DMSO-$d_6$) δ 8.41 (br s, 1H), 7.84 (s, 1H), 6.95 (d, J=8.7 Hz, 2H), 6.67 (s, 1H), 6.54 (d, J=8.3 Hz, 2H). LCMS $R_f$(min)=3.859, MS m/z=348.1 $[M+H]^+$.

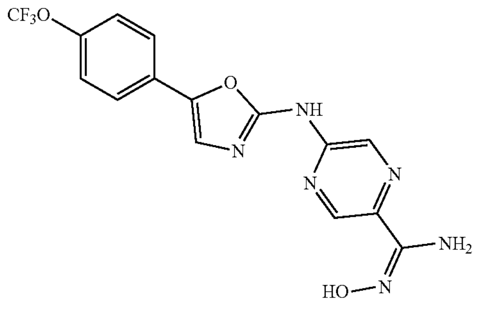

5-((5-(4-(Trifluoromethoxy)phenyl)oxazol-2-yl)amino)pyrazine-2-carbonitrile (0.1 g, 0.287 mmol) was subjected to amidoxime formation in MeOH as per General Procedure 1 Method 2 to furnish N'-hydroxy-5-((5-(4-(trifluoromethoxy)phenyl)oxazol-2-yl)amino)pyrazine-2-carboximidamide (44.7%, 49 mg) after isolation via filtering with water, and washing with water, MeOH, and $Et_2O$. $^1H$ NMR (401 MHz, DMSO-$d_6$) δ 11.52 (s, 1H), 9.95 (s, 1H), 9.24 (s, 1H), 8.74 (d, J=1.1 Hz, 1H), 7.74 (d, J=8.7 Hz, 2H), 7.65 (s, 1H), 7.47 (d, J=8.2 Hz, 2H), 5.88 (s, 2H). LCMS $R_f$ (min)=3.425, MS m/z=381.1 $[M+H]^+$. HRMS (ESI) calcd for $C_{15}H_{12}F_3N_6O_3^+$ $[M+H]^+$ 381.0917, found 381.0925.

71. 5-((5-(5-Chloropyridin-2-yl)-1,3,4-oxadiazol-2-yl)amino)-N'-hydroxypicolinimidamide (Scheme 68)

Scheme 68

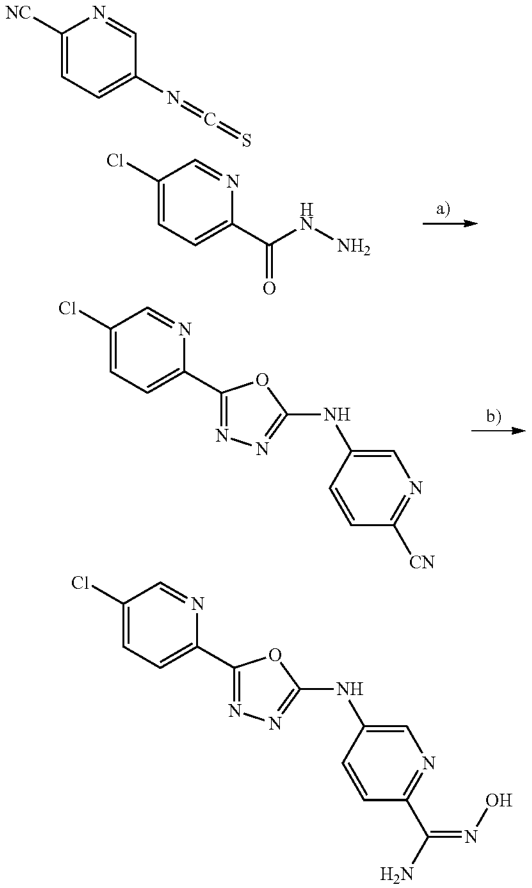

a) i. DMF, 18 , ii. EDCI.HCl, 90° C. 2 h; b) $NH_2OH.HCl$, $Et_3N$, $Et_3N$, MeOH, reflux, 18 h.

5-Isothiocyanatopicolinonitrile (0.163 g, 1.01 mmol) was reacted with 5-chloropicolinohydrazide (0.173 g, 1.01 mmol) following General Procedure 7. The crude product was filtered with water, and washing with water, MeOH, and to provide the desired 5-((5-(5-chloropyridin-2-yl)-1,3,4-oxadiazol-2-yl)amino)picolinonitrile in 90.9% yield (0.274 g). $^1H$ NMR (401 MHz, DMSO) δ 11.84 (br s, 1H), 8.83 (m, 2H), 8.28 (dd, J=8.6, 2.6 Hz, 1H), 8.18 (dd, J=8.5, 2.3 Hz, 1H), 8.13 (d, J=8.5 Hz, 1H), 8.07 (d, J=8.6 Hz, 1H). LCMS $R_f$ (min)=3.428, MS m/z=299.0 $[M+H]^+$.

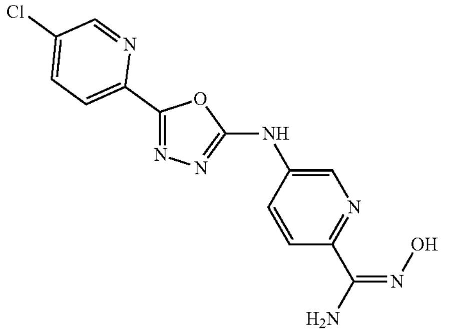 [SMILES: N/C(=N/O)c1ccc(Nc2nnc(-c3ccc(Cl)cn3)o2)cn1]

5-((5-(5-Chloropyridin-2-yl)-1,3,4-oxadiazol-2-yl)amino)picolinonitrile (0.25 g, 0.836 mmol) was subjected to amidoxime formation in MeOH as per General Procedure 1 Method 2 to furnish 5-((5-(5-chloropyridin-2-yl)-1,3,4-oxadiazol-2-yl)amino)-N'-hydroxypicolinimidamide hydrochloride (83.4%, 257 mg) after filtering and washing with water, then washing with MeOH, $Et_2O$, and finally freeze-drying from dioxane with 1.5 equivalents of HCl as 4 M dioxane solution. $^1H$ NMR (401 MHz, DMSO-$d_6$) δ 11.65 (s, 1H), 10.52 (br s, 1H), 8.84 (m, 2H), 8.31-7.90 (m, 4H), 7.52 (br s, 2H). $^{13}C$ NMR (101 MHz, DMSO-$d_6$) δ 160.55, 158.01, 149.30, 141.82, 138.41, 138.07, 133.31, 124.73, 123.58, 122.20. LCMS $R_f$ (min)=2.943, MS m/z=332.0 $[M+H]^+$. HRMS (ESI) calcd for $C_{13}H_{11}ClN_7O_2^+$ $[M+H]^+$ 332.0657, found 332.0669.

72. N'-Hydroxy-5-((1-(5-(trifluoromethyl)pyridin-2-yl)-1H-pyrazol-4-yl)amino)picolinimidamide (Scheme 69)

Scheme 69

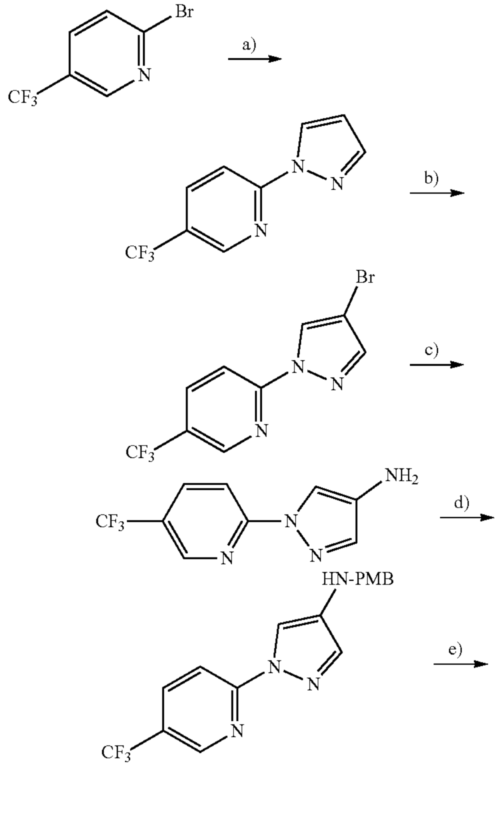

-continued

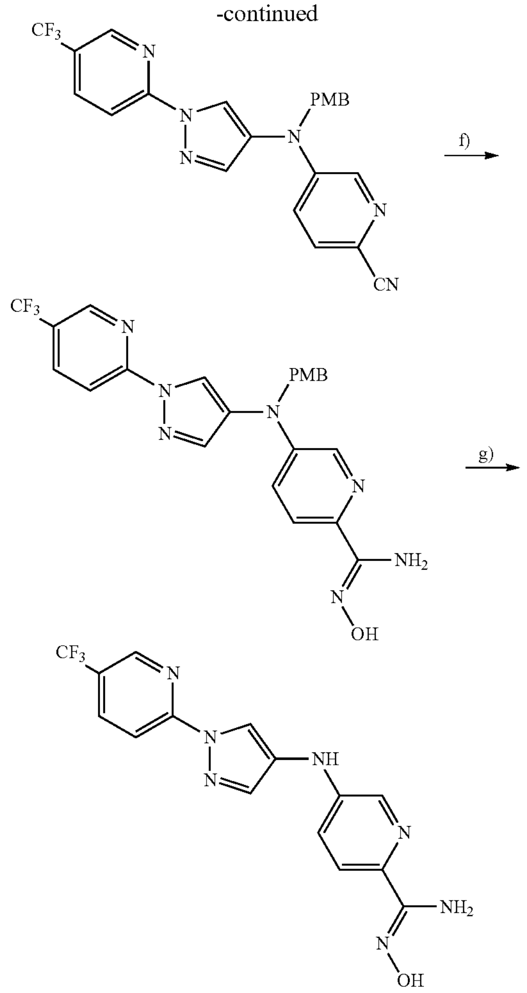

a) pyrazole, $Cu_2O$, $K_3PO_4$, DMSO, water, Mw 100° C., 1 h; b) NBS, $CH_3CN$, rt, 48 h; c) i. $Pd_2(dba)_3$, Xantphos, $Cs_2CO_3$, 1,4-dioxane, 110° C., 18 h, ii. $NH_2OH.HCl$, NaOAc, MeOH, r 18 h; d) Anisaldehyde, AcOH, $Na(AcO)_3BH$, DCE, rt; e) $Pd_2(dba)_3$, Xantphos, $Cs_2CO_3$, 1,4-dioxane, 110° C., 18 h; g) $NH_2OH.HCl$, $Et_3N$, MeOH, reflux, 18 h; f) TFA, anisole, rt, on.

An oven-dried tube was charged with 2-bromo-5-(trifluoromethyl)pyridine (2.5 g, 11.06 mmol), pyrazole (0.98 g, 14.38 mmol), $Cu_2O$ (0.158 g, 1.106 mmol) and $K_3PO_4$ (4.69 g, 22.12 mmol). DMSO (11 mL) and water (0. 5 mL) were added, and the tube was sealed under nitrogen, then irradiated with microwave at 100° C. for 1 h. The reaction mixture was cooled to room temperature, diluted with $Et_2O$ and half-brine. After separation the aqueous phase was extracted with $Et_2O$ (4×), the combined organic phases were dried over ($MgSO_4$), evaporated to dryness. The residue was purified on silica gel using mixtures of petroleum spirits and DCM as eluents to provide 2-(1H-pyrazol-1-yl)-5-(trifluoromethyl)pyridine in 53.9% yield (1.8 g). $^1H$ NMR (401 MHz, $CDCl_3$) δ 8.68-8.65 (m, 1H), 8.59 (dd, J=2.7, 0.7 Hz, 1H), 8.10 (d, J=8.7 Hz, 1H), 8.03 (ddd, J=8.7, 2.3, 0.5 Hz, 1H), 7.77 (d, J=1.0 Hz, 1H), 6.50 (dd, J=2.7, 1.7 Hz, 1H). LCMS $R_f$(min)=3.879, MS m/z=214.1 $[M+H]^+$.

Intermediate M: 2-(4-bromo-1H-pyrazol-1-yl)-5-(trifluoromethyl)pyridine 2-(1H-Pyrazol-1-yl)-5-(trifluoromethyl)pyridine (1.7 g, 7.98 mmol) was stirred with NBS (3.12 g, 17.54 mmol) in $CH_3CN$ (16 mL) at rt for 48 h. The volatile solvents were removed and the residue was taken up in DCM and saturated aq. $NaHCO_3$ solutions. After separation the aqueous phase was extracted with DCM (4×), the combined organic phases were dried over ($MgSO_4$), evaporated to dryness. The residue was purified on silica gel using mixtures of petroleum spirits and DCM as eluents to provide 2-(4-bromo-1H-pyrazol-1-yl)-5-(trifluoromethyl)pyridine in 85.9% yield (2 g). $^1$H NMR (401 MHz, $CDCl_3$) δ 8.67-8.64 (m, 1H), 8.61 (d, J=0.7 Hz, 1H), 8.07-8.02 (m, 2H), 7.70 (s, 1H). LCMS $R_f$(min)=4.319, MS m/z=292.0/294.0 $[M+H]^+$.

Intermediate M (2-(4-bromo-1H-pyrazol-1-yl)-5-(trifluoromethyl)pyridine) (1.5 g, 5.136 mmol) was reacted with diphenylmethanimine (1.4 g, 7.71 mmol) following General Procedure 4 Method 1. Upon completion, the reaction mixture was concentrated to dryness. The crude product was re-suspended in MeOH, and stirred with $NH_2OH·HCl$ (1.074 g, 15.41 mmol) and NaOAc (1.264 g, 15.41 mmol) at rt for 18 h. The volatile solvents were removed and the residue taken up in DCM and saturated aq. $NaHCO_3$ solutions. After separation the aqueous phase was extracted with DCM (4×), the combined organic phases were dried over ($MgSO_4$), evaporated to dryness. The residue was purified on silica gel using mixture of DCM and EtOAc, then DCM and MeOH as eluents to provide 1-(5-(trifluoromethyl)pyridin-2-yl)-1H-pyrazol-4-amine in 34.5% yield (0.405 g). $^1$H NMR (401 MHz, $CDCl_3$) δ 8.59-8.55 (m, 1H), 8.05 (d, J=0.9 Hz, 1H), 7.95 (d, J=8.7 Hz, 1H), 7.91 (dd, J=8.8, 2.1 Hz, 1H), 7.43 (d, J=0.8 Hz, 1H), 3.16 (br s, 2H). LCMS $R_f$ (min)=2.303, MS m/z=229.1 $[M+H]^+$.

AcOH (0.23 mL, 4.08 mmol) was added to a solution of 1-(5-(Trifluoromethyl)pyridin-2-yl)-1H-pyrazol-4-amine (0.31 g, 1.358 mmol) and anisaldehyde (0.176 g, 1.49 mmol) was in DCE (7 mL), and the reaction mixture was stirred at rt for 18 h. $NaBH(AcO)_3$ (0.575 g, 2.72 mmol) was added in portions every hr, until most of the starting amine has been consumed as evidenced by TLC. The reaction mixture was diluted with DCM (10 mL), poured slowly into saturated aq. $NaHCO_3$ solution (20 mL). The aqueous phase was made alkaline (pH~8) by addition of solid $NaHCO_3$. After separation, the aqueous phase was extracted with more DCM (3×). The combined organic phase was dried over $MgSO_4$, evaporated to dryness. The residue was purified on silica gel using mixtures of DCM and EtOAc as eluents to provide N-(4-methoxybenzyl)-1-(5-(trifluoromethyl)pyridin-2-yl)-1H-pyrazol-4-amine in 72.9% yield (0.345 g). $^1$H NMR (401 MHz, $CDCl_3$) δ 8.58-8.56 (m, 1H), 7.97-7.92 (m, 2H), 7.89 (dd, J=8.8, 2.2 Hz, 1H), 7.43 (d, J=0.8 Hz, 1H), 7.32-7.26 (m, 2H), 6.90-6.83 (m, 2H), 4.15 (s, 2H), 3.78 (s, 3H), 3.34 (br s, 1H). $^{13}$C NMR (101 MHz, $CDCl_3$) δ 158.99, 153.70, 145.52, 145.48, 145.43, 145.39, 136.40, 135.46, 135.42, 134.64, 130.96, 128.98, 127.76, 125.07, 123.30, 122.97, 122.64, 122.37, 122.31, 119.67, 114.02, 111.14, 110.68, 55.24, 50.70. LCMS $R_f$(min)=3.218, MS m/z=349.1 $[M+H]^+$.

N-(4-Methoxybenzyl)-1-(5-(trifluoromethyl)pyridin-2-yl)-1H-pyrazol-4-amine (0.345 g, 0.99 mmol) was reacted with 5-bromopicolinonitrile (0.272 g, 1.485 mmol) following General Procedure 4 Method 1. The crude product was purified on silica gel with mixtures of DCM and EtOAc as eluents to provide 5-((4-methoxybenzyl)(1-(5-(trifluoromethyl)pyridin-2-yl)-1H-pyrazol-4-yl)amino)picolinonitrile in 91.23% yield (0.407 g). $^1$H NMR (401 MHz, $CDCl_3$) δ 8.63-8.61 (m, 1H), 8.59 (d, J=0.8 Hz, 1H), 8.28 (d, J=2.6 Hz, 1H), 8.08 (d, J=8.7 Hz, 1H), 8.03 (dd, J=8.7, 2.0 Hz, 1H), 7.73 (d, J=0.8 Hz, 1H), 7.43-7.40 (m, 1H), 7.19-7.16 (m, 2H), 7.12 (dd, J=8.8, 3.0 Hz, 1H), 6.87-6.84 (m, 2H), 4.88 (s, 2H), 3.75 (s, 3H). $^{13}$C NMR (101 MHz, $CDCl_3$) δ 159.25, 153.08, 146.03, 145.70, 145.66, 145.62, 145.57, 140.04, 137.70, 136.24, 136.21, 130.15, 128.97, 127.76, 127.54, 125.06, 124.73, 124.39, 124.06, 123.50, 122.03, 121.83, 119.40, 118.27, 114.53, 111.80, 56.25, 55.30. LCMS $R_f$ (min)=4.121, MS m/z=451.2 $[M+H]^+$.

5-((4-Methoxybenzyl)(1-(5-(trifluoromethyl)pyridin-2-yl)-1H-pyrazol-4-yl)amino)picolinonitrile (0.4 g, 0.888 mmol) was subjected to amidoxime formation in MeOH as per General Procedure 1 Method 2 to provide the desired N'-hydroxy-5-((4-methoxybenzyl)(1-(5-(trifluoromethyl)pyridin-2-yl)-1H-pyrazol-4-yl)amino)picolinimidamide after filtering and washing with $H_2O$, MeOH, and $Et_2O$ (94.3% yield, 0.405 g). $^1$H NMR (401 MHz, DMSO-$d_6$) δ 9.64 (s, 1H), 8.85 (m, 1H), 8.62 (d, J=0.8 Hz, 1H), 8.37 (dd, J=8.8, 2.0 Hz, 1H), 8.23 (d, J=2.5 Hz, 1H), 8.08 (d, J=8.7 Hz, 1H), 8.05 (d, J=0.8 Hz, 1H), 7.68 (d, J=8.8 Hz, 1H), 7.39 (dd, J=8.9, 2.9 Hz, 1H), 7.26 (m, 2H), 6.89 (m, 2H), 5.68 (s, 2H), 4.97 (s, 2H), 3.71 (s, 3H). LCMS $R_f$ (min)=3.577, MS m/z=484.2 $[M+H]^+$.

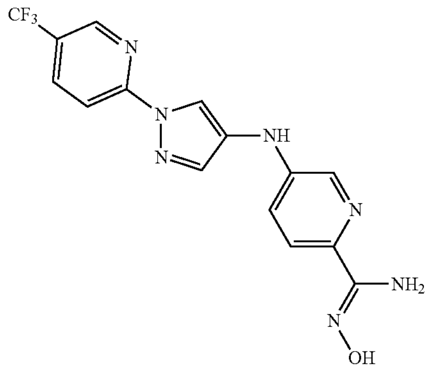 [SMILES: N/C(=N\O)c1ccc(Nc2cnn(-c3ccc(C(F)(F)F)cn3)c2)cn1]

N'-Hydroxy-5-((4-methoxybenzyl)(1-(5-(trifluoromethyl)pyridin-2-yl)-1H-pyrazol-4-yl)amino)picolinimidamide (0.4 g, 0.827 mmol) was subjected to PMB deprotection in TFA and anisole as per General Procedure 11 to furnish N'-hydroxy-5-((1-(5-(trifluoromethyl)pyridin-2-yl)-1H-pyrazol-4-yl)amino)picolinimidamide (81.5%, 243 mg) after purification with preparative HPLC. $^1$H NMR (401 MHz, DMSO-$d_6$) δ 9.60 (s, 1H), 8.86 (s, 1H), 8.62 (s, 1H), 8.55 (s, 1H), 8.35 (dd, J=8.8, 2.2 Hz, 1H), 8.22 (d, J=2.6 Hz, 1H), 8.07 (d, J=8.7 Hz, 1H), 7.95 (s, 1H), 7.72 (d, J=8.7 Hz, 1H), 7.37 (dd, J=8.8, 2.8 Hz, 1H), 5.68 (s, 2H). $^{13}$C NMR (101 MHz, DMSO-$d_6$) δ 153.68, 150.05, 146.34, 141.79, 140.43, 138.03, 137.31, 134.95, 128.28, 125.56, 122.92, 122.60, 120.66, 120.58, 115.67, 111.98. LCMS $R_f$ (min)=3.140, MS m/z=364.1 $[M+H]^+$. HRMS (ESI) calcd for $C_{15}H_{13}F_3N_7O^+$ $[M+H]^+$ 364.1128, found 364.1145.

73. N'-Hydroxy-5-((1-(5-(trifluoromethyl)pyridin-2-yl)-1H-pyrazol-3-yl)amino)picolinimidamide (Scheme 70)

Scheme 70

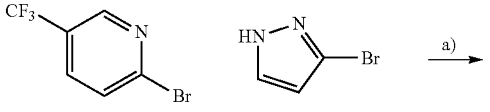

-continued

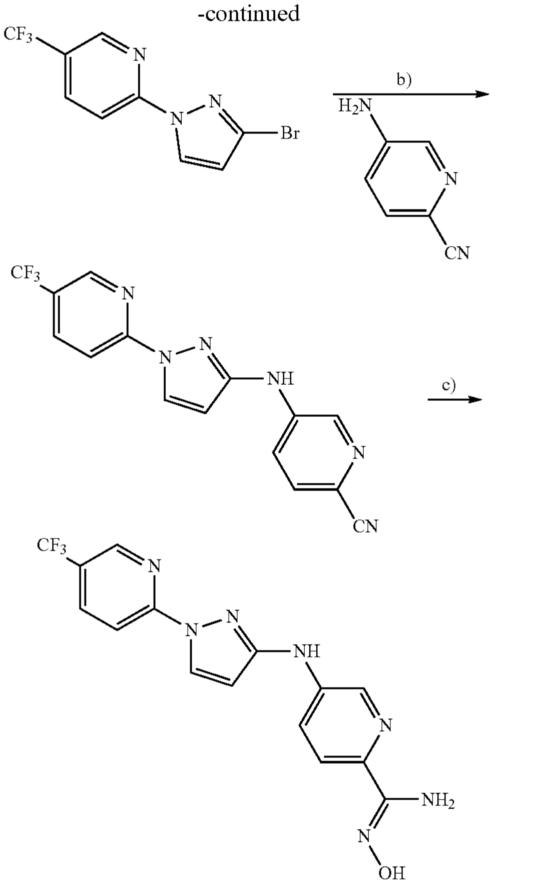

a) $K_2CO_3$, DMF, 110° C., 18 h; b) $^t$Bu-Brettphos Pd G3, $Cs_2CO_3$, $^t$BuOH, 100° C., 18 h: c) $NH_2OH.HCl$, $Et_3N$, MeOH, reflux, 18 h.

Intermediate N: 2-(3-bromo-1H-pyrazol-1-yl)-5-(trifluoromethyl)pyridine

2-Bromo-5-(trifluoromethyl)pyridine (0.92 g, 4.08 mmol) was stirred with 3-bromo-1H-pyrazole (0.5 g, 3.4 mmol) in DMF (14 mL) at 110° C. for 18 h. The reaction mixture was cooled to rt, diluted with EtOAc and water. After separation the aqueous phase was extracted with EtOAc (4×), the combined organic phases were dried over ($MgSO_4$), evaporated to dryness. The residue was purified on silica gel using mixtures of petroleum spirits and DCM as eluents to provide 2-(3-bromo-1H-pyrazol-1-yl)-5-(trifluoromethyl)pyridine in 92.6% yield (0.92 g). $^1$H NMR (401 MHz, $CDCl_3$) δ 8.67-8.65 (m, 1H), 8.50 (d, J=2.7 Hz, 1H), 8.07 (d, J=8.4 Hz, 1H), 8.04 (dd, J=8.9, 2.1 Hz, 1H), 6.52 (d, J=2.7 Hz, 1H). LCMS $R_f$ (min)=4.168, MS m/z=292.0/294.0 [M+H]$^+$.

Intermediate N (2-(3-bromo-1H-pyrazol-1-yl)-5-(trifluoromethyl)pyridine) (0.336 g, 1.15 mmol) was reacted with 5-aminopicolinonitrile (0.274 g, 2.3 mmol) following General Procedure 4 Method 2. Upon completion, the volatile solvents were removed and the residue taken up in EtOAc and water. After separation the aqueous phase was extracted with EtOAc (4×), the combined organic phases were dried over ($MgSO_4$), evaporated to dryness. The residue was purified on normal silica gel using mixture of DCM and EtOAc, then on reversed phase C18 silica gel using mixtures of $CH_3CN$ and water as eluents to provide 5-((1-(5-(trifluoromethyl)pyridin-2-yl)-1H-pyrazol-3-yl)amino)picolinonitrile in 84.2% yield (0.32 g). $^1$H NMR (401 MHz, $CDCl_3$) δ 8.70 (d, J=2.4 Hz, 1H), 8.67-8.63 (m, 1H), 8.55 (d, J=2.7 Hz, 1H), 8.12 (dd, J=8.6, 2.4 Hz, 1H), 8.04 (dd, J=8.7, 2.0 Hz, 1H), 7.96 (d, J=8.6 Hz, 1H), 7.66 (d, J=8.6 Hz, 1H), 6.69 (s, 1H), 6.21 (d, J=2.8 Hz, 1H). LCMS $R_f$ (min)=3.079, MS m/z=331.1 [M+H]$^+$.

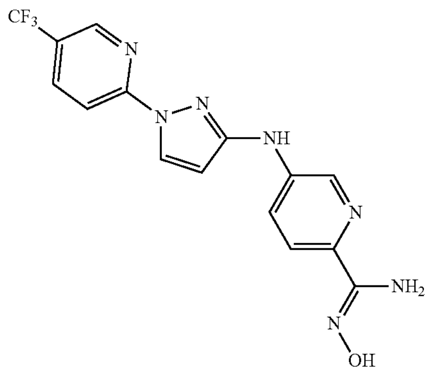 [SMILES: N/C(=N\O)c1ccc(Nc2ccn(-c3ccc(C(F)(F)F)cn3)n2)cn1]

5-((1-(5-(Trifluoromethyl)pyridin-2-yl)-1H-pyrazol-3-yl)amino)picolinonitrile (0.32 g, 0.968 mmol) was subjected to amidoxime formation in MeOH as per General Procedure 1 Method 2 to provide the desired N'-hydroxy-5-((1-(5-(trifluoromethyl)pyridin-2-yl)-1H-pyrazol-3-yl)amino)picolinimidamide after filtering and washing with $H_2O$, MeOH, and $Et_2O$ (86.64% yield, 0.305 g). $^1$H NMR NMR (401 MHz, DMSO) δ 9.68 (s, 1H), 9.57 (s, 1H), 8.82 (s, 1H), 8.79 (s, 1H), 8.57 (s, 1H), 8.33 (d, J=8.0 Hz, 1H), 8.08-7.94 (m, 2H), 7.80 (d, J=8.4 Hz, 1H), 6.28 (s, 1H), 5.75 (s, 2H). $^{13}$C NMR (101 MHz, DMSO) δ 154.24, 153.42, 150.11, 146.24, 141.55, 139.38, 137.41, 136.43, 128.96, 125.70, 123.36, 123.00, 121.93, 121.61, 120.19, 111.39, 100.70. LCMS $R_f$ (min)=2.449, MS m/z=364.1 [M+H]$^+$. HRMS (ESI) calcd for $C_{15}H_{13}F_3N_7O^+$ [M+H]$^+$ 364.1128, found 364.1136.

74. N'-Hydroxy-5-((1-(4-(trifluoromethyl)phenyl)-1H-pyrazol-3-yl)amino)picolinimidamide (Scheme 71)

Scheme 71

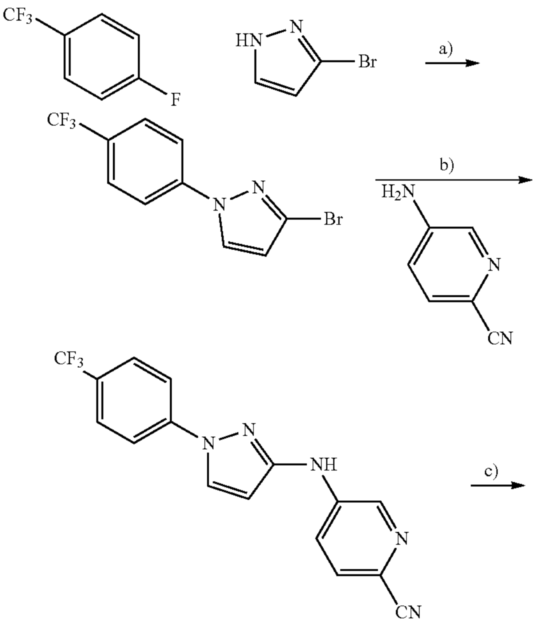

-continued

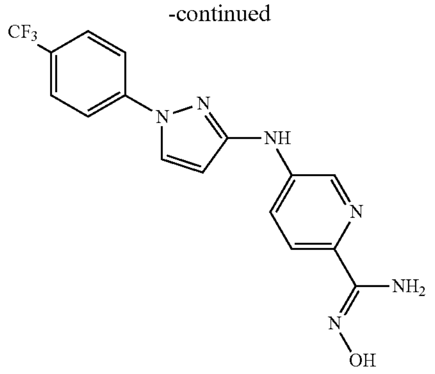

a) $K_2CO_3$, DMF, 110° C., 18 h; b) tBu-Brettphos Pd G3, $Cs_2CO_3$, tBuOH, 100° C., 18 h: c) $NH_2OH.HCl$, $Et_3N$, MeOH, reflux, 18 h.

Intermediate O: 3-bromo-1-(4-(trifluoromethyl)phenyl)-1H-pyrazole 1-Fluoro-4-(trifluoromethyl)benzene (1 g, 6.1 mmol) was reacted with 3-bromo-1H-pyrazole (0.895 g, 6.1 mmol) as per step a), Scheme 70 to provide 3-bromo-1-(4-(trifluoromethyl)phenyl)-1H-pyrazole in 84.56% yield (1.5 g). $^1H$ NMR (401 MHz, $CDCl_3$) δ 7.87 (d, J=2.6 Hz, 1H), 7.79 (d, J=8.5 Hz, 2H), 7.71 (d, J=8.6 Hz, 2H), 6.53 (d, J=2.6 Hz, 1H). LCMS $R_f$ (min)=4.193, MS m/z=290.9/292.9 $[M+H]^+$.

Intermediate 0 (3-bromo-1-(4-(trifluoromethyl)phenyl)-1H-pyrazole) (0.48 g, 1.65 mmol) was reacted with 5-aminopicolinonitrile (0.393 g, 3.3 mmol) as per step b), Scheme 70 to provide to provide 5-((1-(4-(trifluoromethyl)phenyl)-1H-pyrazol-3-yl)amino)picolinonitrile in 63.9% yield (0.347 g). $^1H$ NMR (401 MHz, MeOH-$d_4$) δ 8.71 (dd, J=2.7, 0.5 Hz, 1H), 8.34 (dd, J=8.7, 2.7 Hz, 1H), 8.31 (d, J=2.7 Hz, 1H), 7.97 (d, J=8.5 Hz, 2H), 7.79-7.75 (m, 3H), 6.25 (d, J=2.7 Hz, 1H). LCMS $R_f$ (min)=3.062, MS m/z=330.0 $[M+H]^+$.

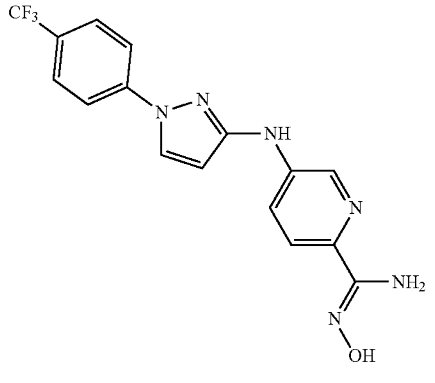

5-((1-(4-(Trifluoromethyl)phenyl)-1H-pyrazol-3-yl)amino)picolinonitrile (0.345 g, 1.047 mmol) was subjected to amidoxime formation in MeOH as per General Procedure 1 Method 2 to provide the desired N'-hydroxy-5-((1-(4-(trifluoromethyl)phenyl)-1H-pyrazol-3-yl)amino)picolinimidamide after filtering and washing with $H_2O$, MeOH, and $Et_2O$ (82.45% yield, 0.313 g). $^1H$ NMR (401 MHz, DMSO-$d_6$) δ 9.69 (s, 1H), 9.44 (s, 1H), 8.80 (s, 1H), 8.56 (d, J=2.1 Hz, 1H), 8.05-7.97 (m, 3H), 7.88-7.75 (m, 3H), 6.23 (d, J=2.1 Hz, 1H), 5.81 (s, 2H). $^{13}C$ NMR (101 MHz, DMSO-$d_6$) δ 153.27, 150.28, 142.83, 140.98, 139.80, 136.21, 129.38, 127.26, 126.14, 125.26, 124.94, 123.44, 122.95, 120.27, 117.43, 99.42. LCMS $R_f$ (min)=3.311, MS m/z=363.1 $[M+H]^+$. HRMS (ESI) calcd for $C_{16}H_{14}F_3N_6O^+$ $[M+H]^+$ 363.1176, found 363.1168.

75. N'-Hydroxy-5-((3-(5-(trifluoromethyl)pyridin-2-yl)isoxazol-5-yl)amino)picolinimidamide (Scheme 72)

Scheme 72

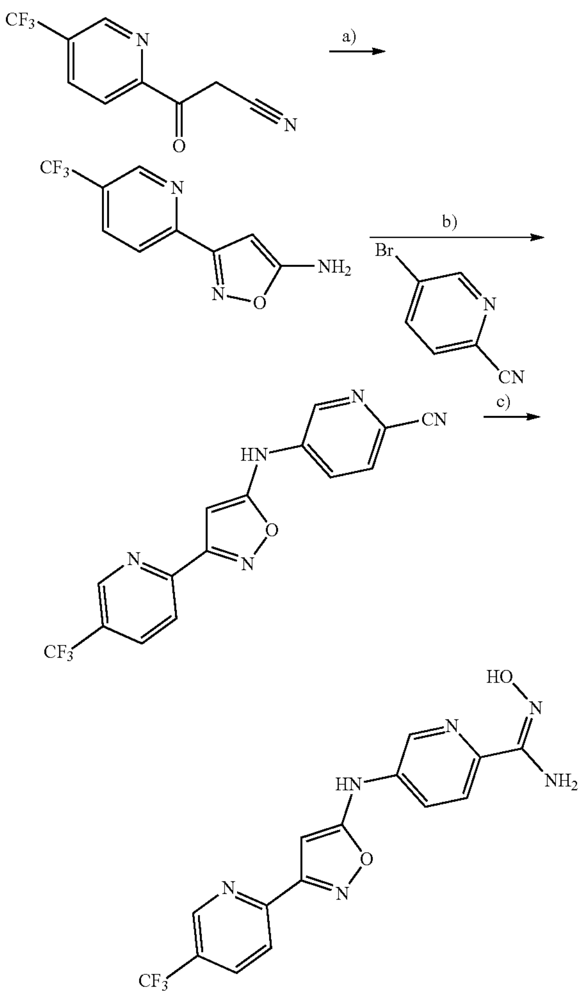

a) $NH_2OH•HCl$, NaOAc, MeOH 18 h; b) $Pd_2(dba)_3$, Xantphos, $Cs_2CO_3$, 1,4-dioxane, 110° C., 18 h; c) $NH_2OH•HCl$, $Et_3N$, MeOH, reflux, 18 h.

$NH_2OH·HCl$ (0.37 g, 5.3 mmol) and NaOAc (0.346 g, 5.3 mmol) were stirred in MeOH (9.0 mL) at room temperature for 1 h, and then 3-oxo-3-(5-(trifluoromethyl)pyridin-2-yl)propanenitrile (0.38 g, 1.77 mmol) was added to the mixture. The reaction mixture was stirred at rt for 18 h. Upon completion, the volatile solvents were removed and the residue taken up in EtOAc and saturated aq. $NaHCO_3$ solution. After separation the aqueous phase was extracted with EtOAc (4×), the combined organic phases were dried over ($MgSO_4$), evaporated to dryness. The residue was purified on silica gel using mixtures of EtOAc in DCM to provide 3-(5-(trifluoromethyl)pyridin-2-yl)isoxazol-5-amine in 92.95% yield (0.378 g). $^1H$ NMR (401 MHz, $CDCl_3$) δ 8.92-8.88 (m, 1H), 8.11 (d, J=8.3 Hz, 1H), 8.01-7.97 (m, 1H), 5.81 (s, 1H), 4.65 (br s, 2H). LCMS $R_f$ (min)=3.434, MS m/z=230.0 $[M+H]^+$.

3-(5-(Trifluoromethyl)pyridin-2-yl)isoxazol-5-amine (0.25 g, 1.09 mmol) was reacted with 5-bromopicolinonitrile (0.2 g, 1.09 mmol) following General Procedure 4 Method 1. The crude product was purified on silica gel with mixtures of DCM and EtOAc (0 to 40%) as eluents to provide 5-((3-(5-(trifluoromethyl)pyridin-2-yl)isoxazol-5-yl)amino)picolinonitrile in 23.8% yield (0.086 g). $^1$H NMR (401 MHz, MeOH-$d_4$) δ 9.02-8.97 (m, 1H), 8.56 (m, 1H), 8.26 (m, 1H), 8.22 (m, 1H), 7.87-7.83 (m, 2H), 6.48 (s, 1H). LCMS $R_f$ (min)=3.678, MS m/z=332.1 [M+H]$^+$.

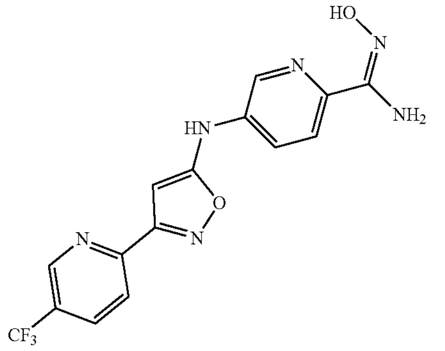 [SMILES: N/C(=N/O)c1ccc(Nc2cc(-c3ccc(C(F)(F)F)cn3)no2)cn1]

5-((3-(5-(Trifluoromethyl)pyridin-2-yl)isoxazol-5-yl)amino)picolinonitrile (0.086 g, 0.259 mmol) was subjected to amidoxime formation in MeOH as per General Procedure 1 Method 2 to provide the desired N'-hydroxy-5-((3-(5-(trifluoromethyl)pyridin-2-yl)isoxazol-5-yl)amino)picolinimidamide after filtering and washing with water and MeOH, then purified with preparative HPLC. (72.95% yield, 0.069 g). $^1$H NMR (401 MHz, DMSO-$d_6$) δ 11.08 (s, 1H), 11.07-10.73 (br, 1H), 9.11 (d, J=2.2 Hz, 1H), 8.61 (d, J=2.6 Hz, 1H), 8.8-8.3 (br, 1H), 8.39 (dd, J=8.3, 2.3 Hz, 1H), 8.22 (d, J=8.3 Hz, 1H), 8.05 (d, J=8.8 Hz, 1H), 7.91 (dd, J=8.8, 2.7 Hz, 1H), 6.52 (s, 1H). LCMS $R_f$ (min)=2.463, MS m/z=365.1 [M+H]$^+$. HRMS (ESI) calcd for $C_{15}H_{12}F_3N_6O_2^+$ [M+H]$^+$ 365.0968, found 365.0979.

76. N'-Hydroxy-5-((1-methyl-3-(5-(trifluoromethyl)pyridin-2-yl)-1H-pyrazol-5-yl)amino)picolinimidamide (Scheme 73)

Scheme 73

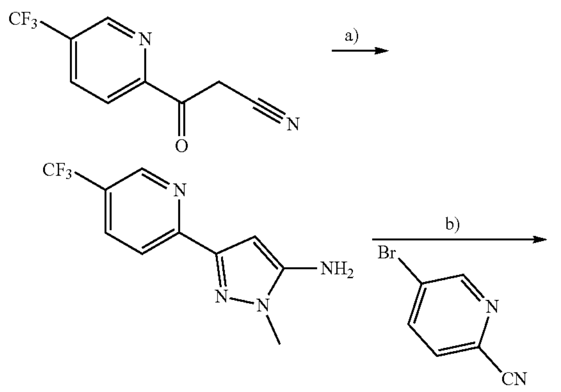

-continued

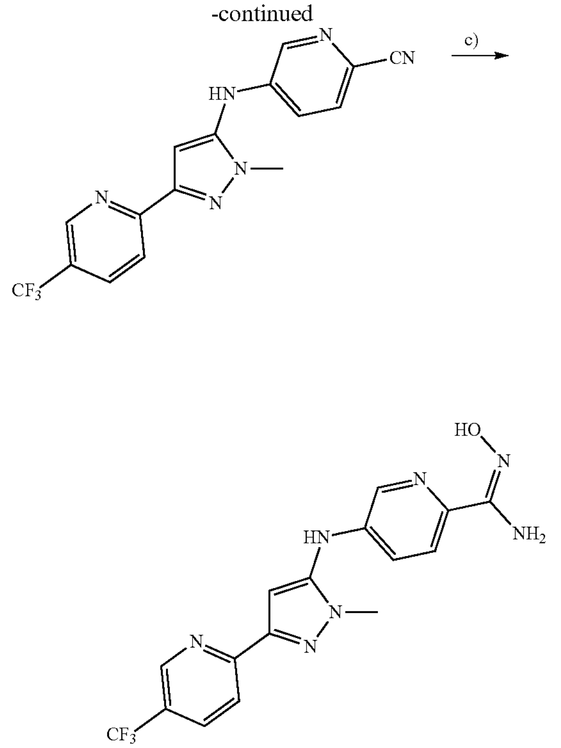

a) $MeNHNH_2$•HCl, $Et_3N$, EtOH, reflux, 18 h; b) $Pd_2(dba)_3$, Xantphos, $Cs_2CO_3$, 1,4-dioxane, 110° C., 18 h; c) $NH_2OH$•HCl, $Et_3N$, MeOH, reflux, 18 h.

3-Oxo-3-(5-(trifluoromethyl)pyridin-2-yl)propanenitrile (0.3 g, 1.4 mmol), $MeNHNH_2$·HCl (0.145 g, 1.75 mmol), and $Et_3N$ (0.177 g, 1.75 mmol) were stirred in EtOH (7.0 mL) at room temperature for 0.5 h, then at reflux for 10 h. Upon completion, the volatile solvents were removed and the residue taken up in DCM and saturated aq. $NaHCO_3$. After separation the aqueous phase was extracted with DCM (4×), the combined organic phases were dried over ($MgSO_4$), evaporated to dryness. The residue was purified on silica gel using mixtures of petroleum spirit and EtOAc to provide 1-methyl-3-(5-(trifluoromethyl)pyridin-2-yl)-1H-pyrazol-5-amine in 31.7% yield (0.107 g). $^1$H NMR (401 MHz, DMSO-$d_6$) δ 8.86 (s, 1H), 8.10 (dd, J=8.4, 2.0 Hz, 1H), 7.99 (d, J=8.5 Hz, 1H), 5.95 (s, 1H), 5.41 (s, 2H), 3.63 (s, 3H). LCMS $R_f$ (min)=2.567, MS m/z=243.1 [M+H]$^+$.

1-Methyl-3-(5-(trifluoromethyl)pyridin-2-yl)-1H-pyrazol-5-amine (0.098 g, 0.404 mmol) was reacted with 5-bromopicolinonitrile (0.074 g, 0.404 mmol) following General Procedure 4 Method 1. The crude product was purified on silica gel with mixtures of DCM and EtOAc (0 to 40%) as eluents to provide 5-((1-methyl-3-(5-(trifluoromethyl)pyridin-2-yl)-1H-pyrazol-5-yl)amino)picolinonitrile in 18.7% yield (0.026 g). $^1$H NMR (401 MHz, MeOH-$d_4$) δ 8.86 (s, 1H), 8.33 (dd, J=2.8, 0.5 Hz, 1H), 8.19-8.14 (m, 2H), 7.71 (dd, J=8.6, 0.5 Hz, 1H), 7.35 (dd, J=8.6, 2.8 Hz, 1H), 6.90 (s, 1H), 3.87 (s, 3H). LCMS $R_f$ (min)=2.848, MS m/z=345.1 [M+H]$^+$.

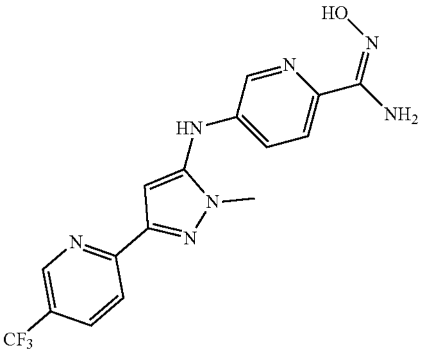 [SMILES: Cn1nc(-c2ccc(C(F)(F)F)cn2)cc1Nc1ccc(/C(N)=N\O)nc1]

-continued

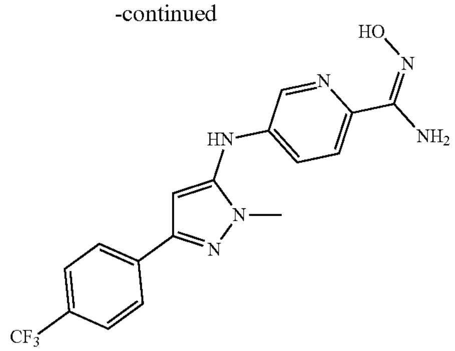

a) $MeNHNH_2$•HCl, $Et_3N$, EtOH, reflux, 18 h; b) $Pd_2(dba)_3$, Xantphos, $Cs_2CO_3$, 1,4-dioxane, 110° C., 18 h; c) $NH_2OH$•HCl, $Et_3N$, MeOH, reflux, 18 h.

5-((1-Methyl-3-(5-(trifluoromethyl)pyridin-2-yl)-1H-pyrazol-5-yl)amino)picolinonitrile (0.026 g, 0.075 mmol) was subjected to amidoxime formation in MeOH as per General Procedure 1 Method 2 to provide the desired N'-hydroxy-5-((1-methyl-3-(5-(trifluoromethyl)pyridin-2-yl)-1H-pyrazol-5-yl)amino)picolinimidamide after filtering and washing with water and MeOH. (49.13% yield, 0.014 g). $^1$H NMR (401 MHz, DMSO-$d_6$) δ 10.95 (br s, 1H), 9.23 (s, 1H), 8.96-8.92 (m, 1H), 8.89-8.4 (br s, 2H), 8.40 (d, J=2.7 Hz, 1H), 8.23 (dd, J=8.4, 2.0 Hz, 1H), 8.13 (d, J=8.4 Hz, 1H), 7.94 (d, J=8.8 Hz, 1H), 7.42 (dd, J=8.8, 2.8 Hz, 1H), 6.82 (s, 1H), 3.82 (s, 3H). $^{13}$C NMR (101 MHz, DMSO-$d_6$) δ 155.72, 148.63, 146.62, 144.33, 140.79, 137.42, 134.80, 125.71, 124.19, 124.09, 123.87, 123.01, 120.44, 119.29, 96.77, 36.24. LCMS $R_f$ (min)=2.367, MS m/z=378.1 [M+H]$^+$. HRMS (ESI) calcd for $C_{16}H_{15}F_3N_7O^+$ [M+H]$^+$ 378.1285, found 378.1295.

77. N'-Hydroxy-5-((1-methyl-3-(4-(trifluoromethyl)phenyl)-1H-pyrazol-5-yl)amino)picolinimidamide (Scheme 74)

Scheme 74

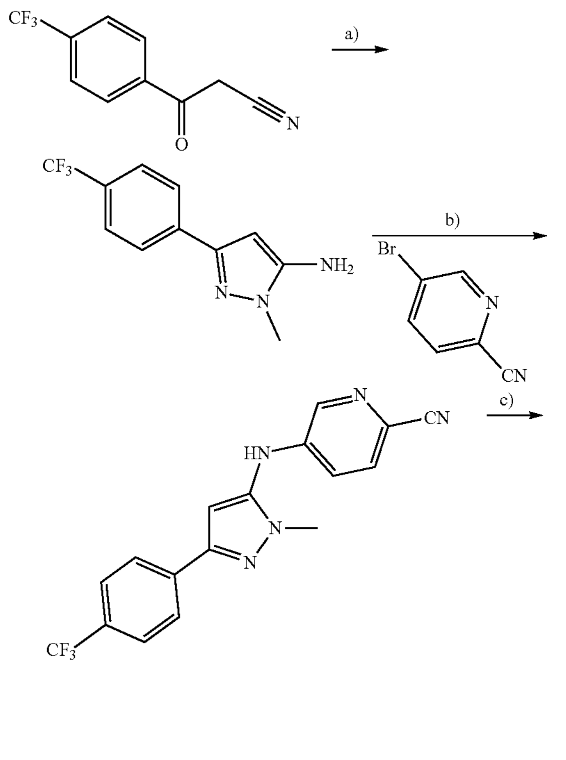

3-Oxo-3-(4-(trifluoromethyl)phenyl)propanenitrile (0.48 g, 2.25 mmol) was converted to 1-methyl-3-(4-(trifluoromethyl)phenyl)-1H-pyrazol-5-amine as per step a), Scheme 73 (37% yield (0.201 g). $^1$H NMR (401 MHz, $CDCl_3$) δ 7.81 (d, J=8.0 Hz, 2H), 7.60 (d, J=8.1 Hz, 2H), 5.89 (s, 1H), 3.72 (s, 3H), 3.59 (br s, 2H). LCMS $R_f$ (min)=2.671, MS m/z=242.1 [M+H]$^+$.

1-Methyl-3-(4-(trifluoromethyl)phenyl)-1H-pyrazol-5-amine (0.2 g, 0.83 mmol) was reacted with 5-bromopicolinonitrile (0.152 g, 0.83 mmol) following General Procedure 4 Method 1. The crude product was purified on silica gel with mixtures of DCM and EtOAc (0 to 40%) as eluents to provide 5-((1-methyl-3-(4-(trifluoromethyl)phenyl)-1H-pyrazol-5-yl)amino)picolinonitrile in 63.6% yield (0.181 g). $^1$H NMR (401 MHz, DMSO-$d_6$) δ 9.21 (s, 1H), 8.37 (d, J=2.4 Hz, 1H), 8.03 (d, J=8.1 Hz, 2H), 7.82 (d, J=8.6 Hz, 1H), 7.75 (d, J=8.2 Hz, 2H), 7.35 (dd, J=8.7, 2.8 Hz, 1H), 6.87 (s, 1H), 3.77 (s, 3H). LCMS $R_f$ (min)=2.888, MS m/z=344.1 [M+H]$^+$.

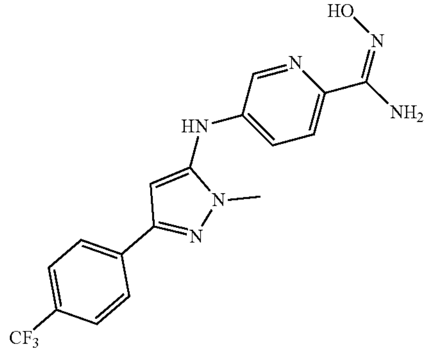 [SMILES: Cn1nc(-c2ccc(C(F)(F)F)cc2)cc1Nc1ccc(/C(N)=N\O)nc1]

5-((1-methyl-3-(4-(trifluoromethyl)phenyl)-1H-pyrazol-5-yl)amino)picolinonitrile (0.171 g, 0.498 mmol) was subjected to amidoxime formation in MeOH as per General Procedure 1 Method 2 to provide the desired N'-hydroxy-5-((1-methyl-3-(4-(trifluoromethyl)phenyl)-1H-pyrazol-5-yl)amino)picolinimidamide after filtering and washing with water and MeOH, then purified in preparative HPLC (72% yield (corrected for presence of 1 molar equivalent of DMSO), 0.163 g). $^1$H NMR (401 MHz, DMSO-$d_6$) δ 9.64 (s, 1H), 8.59 (s, 1H), 8.26 (dd, J=2.7, 0.5 Hz, 1H), 8.02 (d, J=8.1 Hz, 2H), 7.76-7.70 (m, 3H), 7.35 (dd, J=8.8, 2.8 Hz, 1H), 6.74 (s, 1H), 5.70 (s, 2H), 3.77 (s, 3H). $^{13}$C NMR (101 MHz, DMSO-$d_6$) δ 149.96, 147.51, 142.00, 141.65, 141.39, 137.88, 135.58, 128.12, 127.81, 126.22, 126.03, 126.00, 125.96, 125.92, 125.78, 123.53, 122.00, 120.52, 94.21, 35.87. LCMS $R_f$ (min)=2.450, MS m/z=377.1 $[M+H]^+$. HRMS (ESI) calcd for $C_{17}H_{16}F_3N_6O^+$ $[M+H]^+$ 377.1332, found 377.1334.

78. 5-((3-(4-chlorophenyl)-1,2,4-oxadiazol-5-yl)amino)-N'-hydroxypicolinimidamide (Scheme 75)

Scheme 75

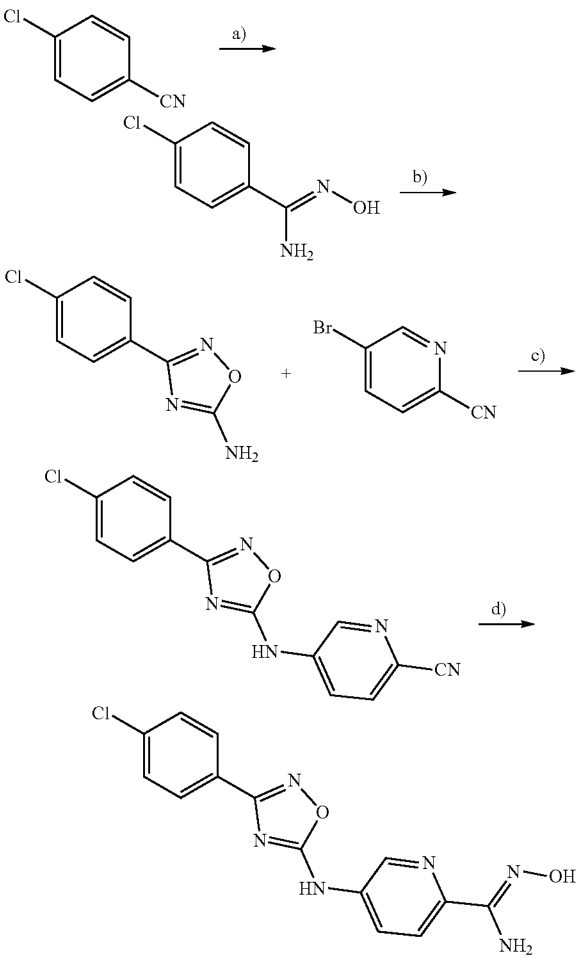

a) aq. $NH_2OH$ (50%), EtOH, reflux, 8 h; b) i) trichloroacetic anhydride, toluene, reflux, 5 h; ii) aq. $NH_3$ (28~30%), rt, overnight; c) $Pd_2(dba)_3$, Xantphos, $Cs_2CO_3$, 1,4-dioxane, 95° C., 5 h; d) $NH_2OH$•HCl, $Et_3N$, dry MeOH, reflux, 1 h.

4-Chlorobenzonitrile (2.0 g, 14.60 mmol) was reacted with $NH_2OH$ (0.95 mL, 15.33 mmoL, aq. 50%) in EtOH (12 mL) for 8 h as per General Procedure 1 Method 1 to provide 4-chloro-N'-hydroxybenzimidamide in 100% yield (2.48 g).

4-Chloro-N'-hydroxybenzimidamide (2.46 g, 14.5 mmol) was reacted with trichloroacetic anhydride (2.91 mL, 15.92 mmol) in toluene (10 mL) for 8 h, followed by the treatment with $NH_3$ (50 mL, aq. 28-30%) as per General Procedure 3 to provide 3-(4-chlorophenyl)-1,2,4-oxadiazol-5-amine in 83% (2.34 g). $^1H$ NMR (401 MHz, DMSO-$d_6$) δ 8.00 (s, 2H), 7.87 (d, J=7.8 Hz, 2H), 7.57 (d, J=7.7 Hz, 2H). LCMS $R_f$ (min)=2.626, MS m/z=196.0 $[M+H]^+$.

3-(4-Chlorophenyl)-1,2,4-oxadiazol-5-amine (0.2 g, 1.03 mmol) was reacted with 5-bromopicolinonitrile (0.144 g, 0.79 mmol), $Pd_2(dba)_3$ (0.0434 g, 0.047 mmol), Xantphos (0.0366 g, 0.063 mmol) and $Cs_2CO_3$ (0.515 g, 1.58 mmol) in 1,4-dioxane (8 mL) per General Procedure 4 Method 1 to provide 5-((3-(4-chlorophenyl)-1,2,4-oxadiazol-5-yl)amino)picolinonitrile in 91% yield (0. 215 g). $^1H$ NMR (401 MHz, DMSO-$d_6$) δ 8.83 (s, 1H), 8.36 (d, J=8.4 Hz, 1H), 8.03-8.02 (m, 3H), 7.63 (d, J=7.6 Hz, 2H). LCMS $R_f$ (min)=3.959, MS m/z=298.0 $[M+H]^+$.

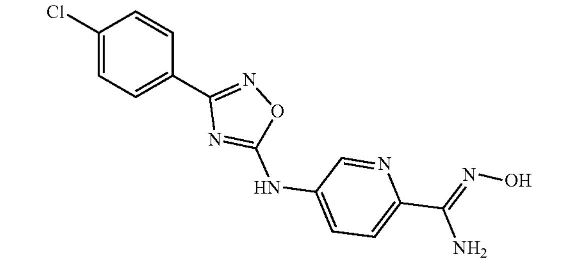 [SMILES: N/C(=N\O)c1ccc(Nc2nc(-c3ccc(Cl)cc3)no2)cn1]

5-((3-(4-Chlorophenyl)-1,2,4-oxadiazol-5-yl)amino)picolinonitrile (0.2 g, 0.67 mmol) was reacted with $NH_2OH$·HCl (0.14 g, 2.01 mmol) and $Et_3N$ (0.28 mL, 2.01 mmol) in MeOH (8 mL) for 1 h as per General Procedure 1 Method 2 to provide 5-((3-(4-chlorophenyl)-1,2,4-oxadiazol-5-yl)amino)-N'-hydroxypicolinimidamide in 87% yield (0.196 g). $^1H$ NMR (401 MHz, DMSO-$d_6$) δ 11.53 (s, 1H), 9.87 (s, 1H), 8.82 (d, J=1.8 Hz, 1H), 8.13 (dd, J=8.7, 2.1 Hz, 1H), 8.01 (d, J=8.4 Hz, 2H), 7.90 (d, J=8.7 Hz, 1H), 7.62 (d, J=8.4 Hz, 2H), 5.84 (br s, 2H). $^{13}C$ NMR (101 MHz, DMSO-$d_6$) δ 168.0, 166.7, 149.3, 144.5, 137.8, 136.1, 135.1, 129.3, 128.7, 125.6, 125.3, 119.9. LCMS $R_f$ (min)=3.400, HRMS (ESI) calcd for $C_{14}H_{12}ClN_6O_2^+$ $[M+H]^+$ 331.0710, found 331.0715.

79. 5-((3-(4-chlorophenyl)-1,2,4-oxadiazol-5-yl)amino)-N'-hydroxypyrazine-2-carboximidamide (Scheme 76)

Scheme 76

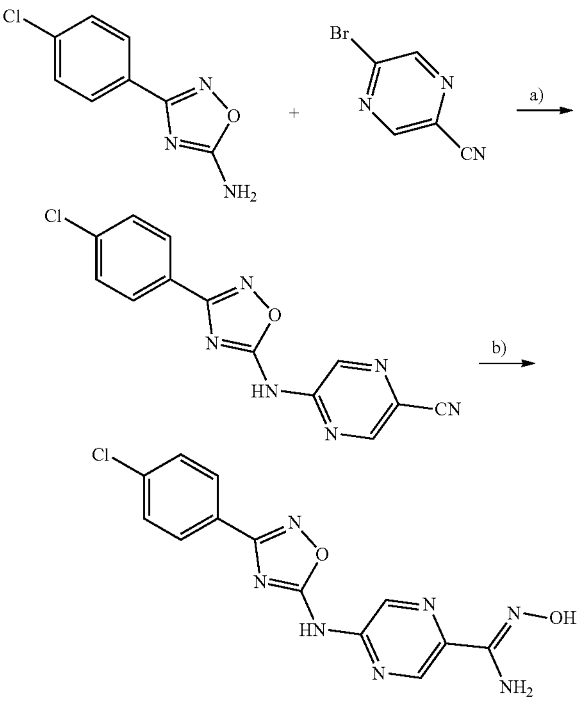

a) $Pd_2(dba)_3$, Xantphos, $Cs_2CO_3$, 1,4-dioxane, 95° C., 5 h; b) $NH_2OH$•HCl, $Et_3N$, dry MeOH, reflux, 1 h.

3-(4-Chlorophenyl)-1,2,4-oxadiazol-5-amine (0.2 g, 1.03 mmol) was reacted with 5-bromopyrazine-2-carbonitrile (0.144 g, 0.79 mmol), $Pd_2(dba)_3$ (0.0434 g, 0.047 mmol), Xantphos (0.0366 g, 0.063 mmol) and $Cs_2CO_3$ (0.515 g, 1.58 mmol) in 1,4-dioxane (8 mL) as per General Procedure 4 Method 1 to provide 5-((3-(4-chlorophenyl)-1,2,4-oxadiazol-5-yl)amino)pyrazine-2-carbonitrile in 93% yield (0.218 g). $^1$H NMR (401 MHz, DMSO-$d_6$) δ 9.34 (s, 1H), 8.98 (s, 1H), 8.03 (d, J=8.0 Hz, 2H), 7.63 (d, J=8.0 Hz, 2H). LCMS $R_f$ (min)=3.042, MS m/z=297.0 $[M-H]^-$.

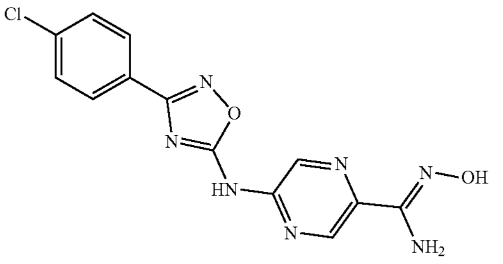 [SMILES: N/C(=N\O)c1cnc(Nc2nc(-c3ccc(Cl)cc3)no2)cn1]

(5-((3-(4-Chlorophenyl)-1,2,4-oxadiazol-5-yl)amino) pyrazine-2-carbonitrile (0.2 g, 0.67 mmol) was reacted with $NH_2OH\cdot HCl$ (0.14 g, 2.01 mmol) and $Et_3N$ (0.28 mL, 2.01 mmol) in MeOH (8 mL) as per General Procedure 1 Method 2 to provide 5-((3-(4-chlorophenyl)-1,2,4-oxadiazol-5-yl) amino)-N'-hydroxypyrazine-2-carboximidamide in 82% yield (0.182 g). $^1$H NMR (401 MHz, DMSO-$d_6$) δ 12.27 (br s, 1H), 10.05 (s, 1H), 9.27 (s, 1H), 8.82 (s, 1H), 8.03 (d, J=8.0 Hz, 2H), 7.64 (d, J=7.6 Hz, 2H), 5.91 (br s, 2H). $^{13}$C NMR (101 MHz, DMSO-$d_6$) δ 167.5, 166.6, 148.2, 147.4, 140.3, 139.4, 136.2, 132.4, 129.3, 128.7, 125.5. LCMS $R_f$ (min)=2.682, HRMS (ESI) calcd for $C_{13}H_{11}ClN_7O_2^+$ $[M+H]^+$ 332.0663, found 332.0663.

80. 5-((3-(5-Chloropyridin-2-yl)-1,2,4-oxadiazol-5-yl)amino)-N'-hydroxypicolinimidamide (Scheme 77)

Scheme 77

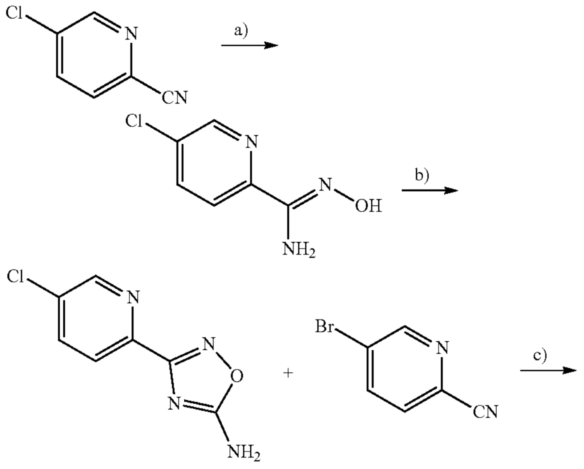

-continued

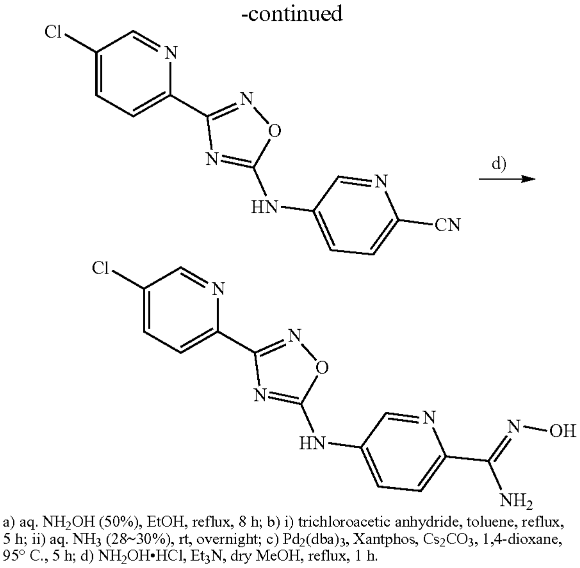

a) aq. $NH_2OH$ (50%), EtOH, reflux, 8 h; b) i) trichloroacetic anhydride, toluene, reflux, 5 h; ii) aq. $NH_3$ (28~30%), rt, overnight; c) $Pd_2(dba)_3$, Xantphos, $Cs_2CO_3$, 1,4-dioxane, 95° C., 5 h; d) $NH_2OH\cdot HCl$, $Et_3N$, dry MeOH, reflux, 1 h.

5-Chloropicolinonitrile (2.0 g, 14.49 mmol) was reacted with $NH_2OH$ (0.93 mL, 15.22 mmoL, aq. 50%) in EtOH (12 mL) for 8 h as per General Procedure 1 Method 1 to provide 5-chloro-N'-hydroxypicolinimidamide in 100% yield (2.48 g).

5-Chloro-N'-hydroxypicolinimidamide (2.48 g, 14.49 mmol) was reacted with trichloroacetic anhydride (2.91 mL, 15.94 mmol) in toluene (10 mL) for 5 h, followed by the treatment with $NH_3$ (50 mL, aq. 28-30%) as per General Procedure 3 to provide 3-(5-chloropyridin-2-yl)-1,2,4-oxadiazol-5-amine in 75% yield (2.13 g). $^1$H NMR (401 MHz, DMSO-$d_6$) δ 8.74 (s, 1H), 8.09 (m, 1H), 8.02 (s, 2H), 7.92 (d, J=8.4 Hz, 1H). LCMS $R_f$ (min)=2.250, MS m/z=197.1 $[M+H]^+$.

3-(5-Chloropyridin-2-yl)-1,2,4-oxadiazol-5-amine (0.3 g, 1.53 mmol) was reacted with 5-bromopicolinonitrile (0.215 g, 1.17 mmol), $Pd_2(dba)_3$ (0.0643 g, 0.070 mmol), Xantphos (0.0542 g, 0.094 mmol) and $Cs_2CO_3$ (0.762 g, 2.34 mmol) in 1,4-dioxane (12 mL) as per General Procedure 4 Method 1 to provide 5-((3-(5-chloropyridin-2-yl)-1,2,4-oxadiazol-5-yl)amino)picolinonitrile in 95% yield (0.33 g). $^1$H NMR (401 MHz, DMSO-$d_6$) δ 8.76 (s, 1H), 8.62 (s, 1H), 8.28 (s, 1H), 8.09 (s, 2H), 7.86 (s, 1H), 7.40 (m, 1H). LCMS $R_f$ (min)=2.685, MS m/z=299.0 $[M+H]^+$.

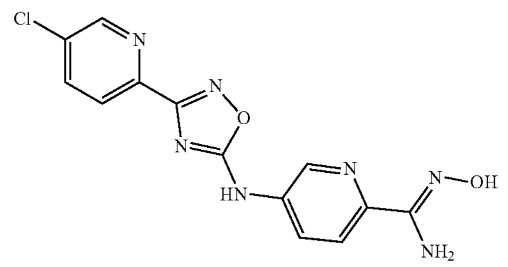 [SMILES: N/C(=N\O)c1ccc(Nc2nc(-c3ccc(Cl)cn3)no2)cn1]

5-((3-(5-Chloropyridin-2-yl)-1,2,4-oxadiazol-5-yl) amino)picolinonitrile (0.25 g, 0.84 mmol) was reacted with $NH_2OH\cdot HCl$ (0.174 g, 2.51 mmol) and $Et_3N$ (0.35 mL, 2.51 mmol) in MeOH (8 mL) for 1 h as per General Procedure 1 Method 2 to provide 5-((3-(5-chloropyridin-2-yl)-1,2,4-oxadiazol-5-yl)amino)-N'-hydroxypicolinimidamide in 96% yield (0.268 g). $^{1}H$ NMR (401 MHz, DMSO-$d_6$) δ 11.56 (br s, 1H), 9.85 (s, 1H), 8.81 (s, 2H), 8.15-8.13 (m, 3H), 5.81 (br s, 2H). $^{13}C$ NMR (101 MHz, DMSO-$d_6$) δ 168.2, 166.8, 149.2, 148.9, 144.7, 137.9, 137.4, 135.0, 133.2, 125.4, 124.5, 119.9. LCMS $R_f$(min)=3.015, HRMS (ESI) calcd for $C_{13}H_{11}ClN_7O_2^+$ [M+H]$^+$ 332.0663, found 332.0667.

81. 5-((3-(5-Chloropyridin-2-yl)-1,2,4-oxadiazol-5-yl)amino)-N'-hydroxypyrazine-2-carboximidamide (Scheme 78)

Scheme 78

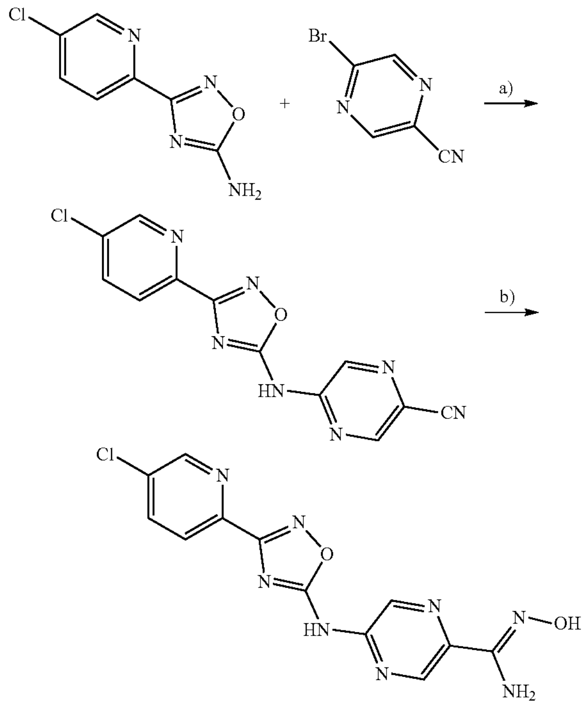

a) $Pd_2(dba)_3$, Xantphos, $Cs_2CO_3$, 1,4-dioxane, 95° C., 5 h; b) $NH_2OH$•HCl, $Et_3N$, dry MeOH, reflux, 1 h.

3-(5-Chloropyridin-2-yl)-1,2,4-oxadiazol-5-amine (0.3 g, 1.53 mmol) was reacted with 5-bromopyrazine-2-carbonitrile (0.216 g, 1.17 mmol), $Pd_2(dba)_3$ (0.0643 g, 0.07 mmol), Xantphos (0.0542 g, 0.094 mmol) and $Cs_2CO_3$ (0.762 g, 2.34 mmol) in 1,4-dioxane (12 mL) as per General Procedure 4 Method 1 to provide 5-((3-(5-chloropyridin-2-yl)-1,2,4-oxadiazol-5-yl)amino)pyrazine-2-carbonitrile 93% yield (0.326 g). $^{1}H$ NMR (401 MHz, DMSO-$d_6$) δ 8.76-8.67 (m, 2H), 8.50 (s, 1H), 8.06-8.03 (m, 3H). LCMS $R_f$(min)=2.649, MS m/z=300.0 [M−H]$^-$.

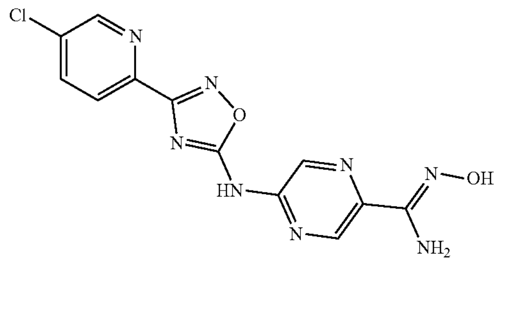 [SMILES: N/C(=N\O)c1cnc(Nc2nc(-c3ccc(Cl)cn3)no2)cn1]

5-((3-(5-Chloropyridin-2-yl)-1,2,4-oxadiazol-5-yl)amino)pyrazine-2-carbonitrile (0.25 g, 0.83 mmol) was reacted with $NH_2OH{\cdot}HCl$ (0.174 g, 2.50 mmol) and $Et_3N$ (0.35 mL, 2.50 mmol) in MeOH (8 mL) for 1 h as per General Procedure 1 Method 2 to provide 5-((3-(5-chloropyridin-2-yl)-1,2,4-oxadiazol-5-yl)amino)-N'-hydroxypyrazine-2-carboximidamide in 70% yield (0.196 g). $^{1}H$ NMR (401 MHz, DMSO-$d_6$) δ 11.97 (br s, 1H), 10.05 (s, 1H), 9.27 (d, J=1.5 Hz, 1H), 8.83-8.82 (m, 2H), 8.13-8.18 (m, 2H), 5.91 (br s, 2H). $^{13}C$ NMR (101 MHz, DMSO-$d_6$) δ 167.8, 166.8, 148.9, 148.2, 147.4, 144.5, 140.3, 139.4, 137.5, 133.3, 132.3, 124.5. LCMS $R_f$(min)=3.088, HRMS (ESI) calcd for $C_{12}H_{10}ClN_8O_2^+$ [M+H]$^+$ 333.0615, found 333.0614.

82. N'-hydroxy-5-((3-(4-(trifluoromethyl)phenyl)-1,2,4-oxadiazol-5-yl)amino)picolinimidamide (Scheme 79)

Scheme 79

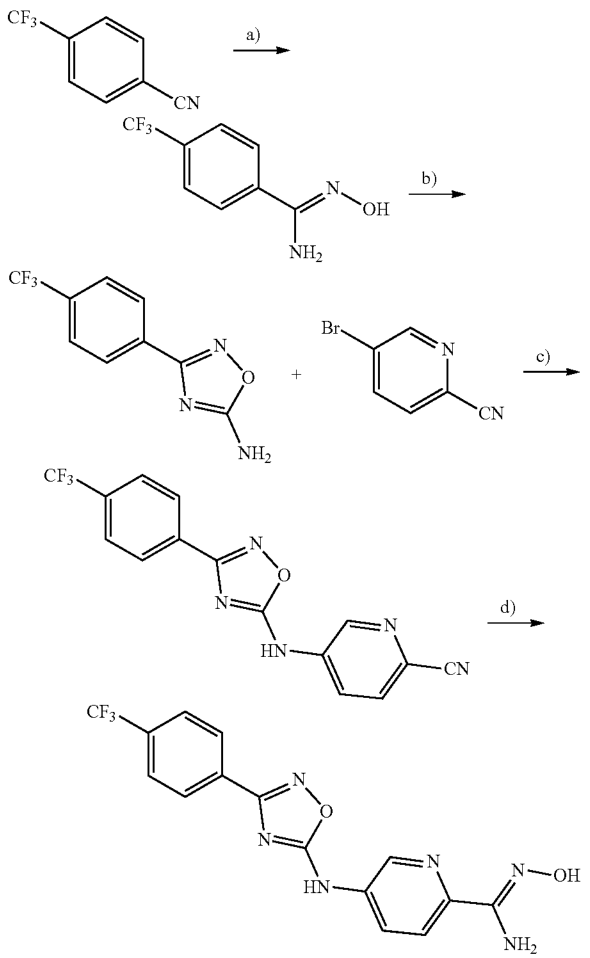

a) aq. $NH_2OH$ (50%), EtOH, reflux, 8 h; b) i) trichloroacetic anhydride, toluene, reflux, 5 h; ii) aq. $NH_3$ (28~30%), rt, overnight; c) $Pd_2(dba)_3$, Xantphos, $Cs_2CO_3$, 1,4-dioxane, 95° C., 16 h; d) $NH_2OH$•HCl, $Et_3N$, dry MeOH, reflux, 1 h.

4-(Trifluoromethyl)benzonitrile (1.0 g, 5.84 mmol) was reacted with $NH_2OH$ (0.37 mL, 6.13 mmol, aq. 50%) in EtOH (6 mL) for 8 h as per General Procedure 1 Method 1 to provide N'-hydroxy-4-(trifluoromethyl)benzimidamide in 100% yield (1.19 g).

N'-Hydroxy-4-(trifluoromethyl)benzimidamide (1.19 g, 5.84 mmol) was reacted with trichloroacetic anhydride (1.17 mL, 6.42 mmol) in toluene (6 mL) for 5 h, followed by the treatment with $NH_3$ (25 mL, aq. 28-30%) as per General Procedure 3 to provide 3-(4-(trifluoromethyl)phenyl)-1,2,4-oxadiazol-5-amine in 72% yield (0.96 g).

3-(4-(Trifluoromethyl)phenyl)-1,2,4-oxadiazol-5-amine (0.1 g, 0.44 mmol) was reacted with 5-bromopicolinonitrile (0.089 g, 0.48 mmol), $Pd_2(dba)_3$ (0.020 g, 0.022 mmol), Xantphos (0.025 g, 0.044 mmol) and $Cs_2CO_3$ (0.286 g, 0.88 mmol) in 1,4-dioxane (6 mL) as per General Procedure 4 Method 1 to provide 5-((3-(4-(trifluoromethyl)phenyl)-1,2,4-oxadiazol-5-yl)amino)picolinonitrile in 88% yield (0.128 g). $^1H$ NMR (401 MHz, MeOH-$d_4$) δ 8.92 (d, J=2.3 Hz, 1H), 8.51 (dd, J=8.6, 2.7 Hz, 1H), 8.30 (d, J=8.1 Hz, 2H), 7.94 (d, J=8.6 Hz, 1H), 8.30 (d, J=8.2 Hz, 2H). LCMS $R_f$ (min)=3.946. MS m/z=330.0 $[M-H]^-$.

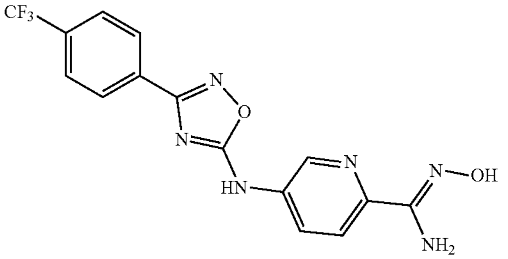 [SMILES: N/C(=N\O)c1ccc(Nc2nc(-c3ccc(C(F)(F)F)cc3)no2)cn1]

5-((3-(4-(Trifluoromethyl)phenyl)-1,2,4-oxadiazol-5-yl)amino)picolinonitrile (0.11 g, 0.33 mmol) was reacted with $NH_2OH{\cdot}HCl$ (0.184 g, 2.66 mmol) and $Et_3N$ (0.37 mL, 2.66 mmol) in MeOH (5 mL) as per General Procedure 1 Method 2 to provide N'-hydroxy-5-((3-(4-(trifluoromethyl)phenyl)-1,2,4-oxadiazol-5-yl)amino)picolinimidamide in 38% yield (0.046 g). $^1H$ NMR (401 MHz, DMSO-$d_6$) δ 11.61 (s, 1H), 9.88 (s, 1H), 8.85 (d, J=2.2 Hz, 1H), 8.23 (d, J=8.1 Hz, 2H), 8.14 (dd, J=8.7, 2.5 Hz, 1H), 7.96-7.91 (m, 3H), 5.86 (br s, 2H). $^{13}C$ NMR (101 MHz, DMSO-$d_6$) δ 168.3, 166.6, 149.3, 144.6, 137.9, 135.1, 131.4, 130.7, 127.8, 126.20, 126.17, 125.5, 125.3, 119.9. LCMS $R_f$ (min)=2.630, HRMS (ESI) calcd for $C_{15}H_{12}F_3N_6O_2^+$ $[M+H]^+$ 365.0974, found 365.0979.

83. N'-Hydroxy-5-((3-(4-(trifluoromethyl)phenyl)-1,2,4-oxadiazol-5-yl)amino)pyrazine-2-carboximidamide (Scheme 80)

Scheme 80

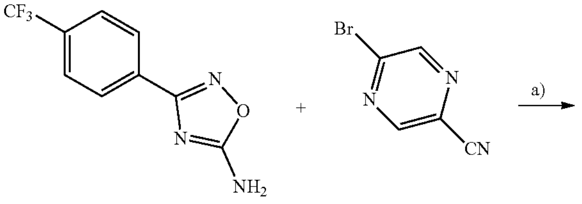

-continued

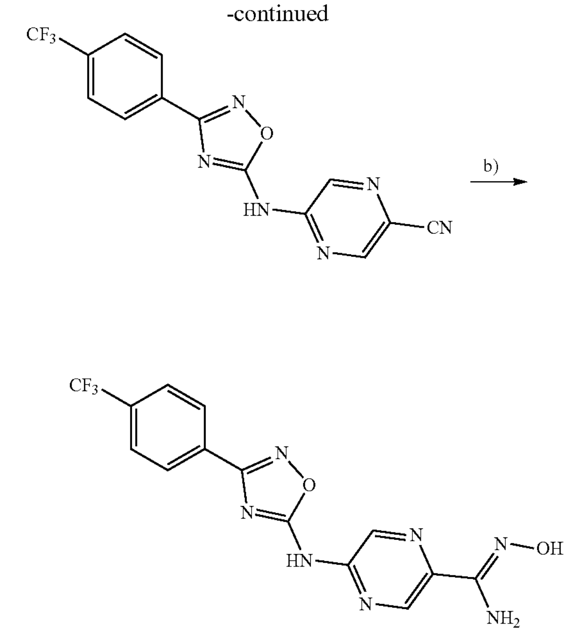

a) $Pd_2(dba)_3$, Xantphos, $Cs_2CO_3$, 1,4-dioxane, 95° C., 5 h; b) $NH_2OH{\cdot}HCl$, $Et_3N$, dry MeOH, reflux, 1 h.

3-(4-(Trifluoromethyl)phenyl)-1,2,4-oxadiazol-5-amine (0.3 g, 1.31 mmol) was reacted with 5-bromopyrazine-2-carbonitrile (0.20 g, 1.09 mmol), $Pd_2(dba)_3$ (0.060 g, 0.065 mmol), Xantphos (0.050 g, 0.087 mmol) and $Cs_2CO_3$ (0.710 g, 2.18 mmol) in 1,4-dioxane (12 mL) as per General Procedure 4 Method 1 to provide 5-((3-(4-(trifluoromethyl)phenyl)-1,2,4-oxadiazol-5-yl)amino)pyrazine-2-carbonitrile in 98% yield (0.355 g). $^1H$ NMR (401 MHz, DMSO-$d_6$) δ 8.66 (d, J=1.4 Hz, 1H),), 8.46 (d, J=1.4 Hz, 1H),), 8.15 (d, J=8.0 Hz, 2H),), 7.86 (d, J=8.2 Hz, 2H). LCMS $R_f$ (min)=3.082. MS m/z=331.0 $[M-H]^-$.

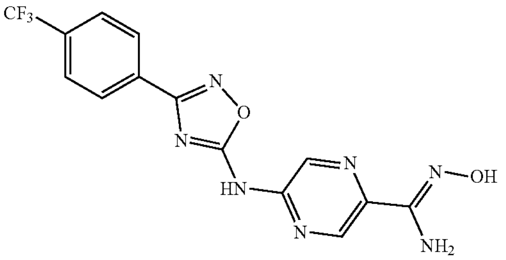 [SMILES: N/C(=N\O)c1cnc(Nc2nc(-c3ccc(C(F)(F)F)cc3)no2)cn1]

5-((3-(4-(Trifluoromethyl)phenyl)-1,2,4-oxadiazol-5-yl)amino)pyrazine-2-carbonitrile (0.30 g, 0.90 mmol) was reacted with $NH_2OH{\cdot}HCl$ (0.188 g, 2.71 mmol) and $Et_3N$ (0.38 mL, 2.71 mmol) in MeOH (8 mL) for 1 h as per General Procedure 1 Method 2 to provide N'-hydroxy-5-((3-(4-(trifluoromethyl)phenyl)-1,2,4-oxadiazol-5-yl)amino)pyrazine-2-carboximidamide in 74% yield (0.242 g). $^1H$ NMR (401 MHz, DMSO-$d_6$) δ 12.29 (br s, 1H), 10.07 (s, 1H), 9.29 (d, J=1.4 Hz, 1H), 8.83 (d, J=1.4 Hz, 1H), 8.25 (d, J=8.1 Hz, 2H), 7.96 (d, J=8.3 Hz, 2H), 5.91 (br s, 2H). $^{13}C$ NMR (101 MHz, DMSO-$d_6$) δ 168.2, 167.0, 148.7, 147.8, 140.9, 139.9, 132.8, 131.9, 131.5, 130.9, 128.3, 126.6, 125.7, 123.0. LCMS $R_f$(min)=2.761, HRMS (ESI) calcd for $C_{14}H_{11}F_3N_7O_2^+$ $[M+H]^+$ 366.0926, found 366.0939.

84. N'-Hydroxy-5-((3-(5-(trifluoromethyl)pyridin-2-yl)-1,2,4-oxadiazol-5-yl)amino)picolinimidamide (Scheme 81)

Scheme 81

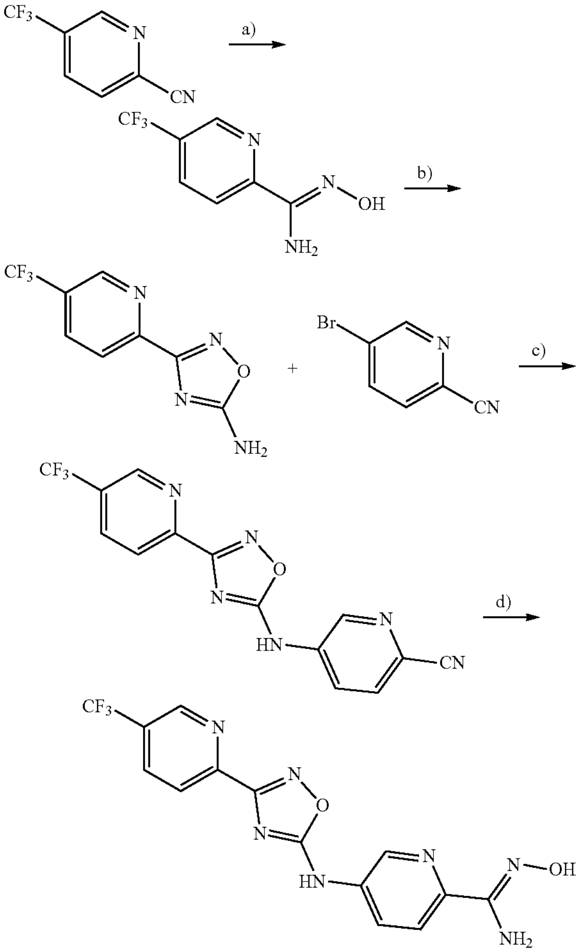

a) aq. $NH_2OH$ (50%), EtOH, reflux, 8 h; b) i) trichloroacetic anhydride, toluene, reflux, 5 h; ii) aq. $NH_3$ (28~30%), rt, overnight; c) $Pd_2(dba)_3$, Xantphos, $Cs_2CO_3$, 1,4-dioxane, 95° C., 16 h; d) $NH_2OH$•HCl, $Et_3N$, dry MeOH, reflux, 1 h.

5-(Trifluoromethyl)picolinonitrile (2.0 g, 11.62 mmol) was reacted with $NH_2OH$ (0.75 mL, 12.20 mmoL, aq. 50%) in EtOH (12 mL) for 8 h as per General Procedure 1 Method 1 to provide N'-hydroxy-5-(trifluoromethyl)picolinimidamide in 100% yield (2.38 g).

N'-Hydroxy-5-(trifluoromethyl)picolinimidamide (2.38 g, 11.62 mmol) was reacted with trichloroacetic anhydride (2.34 mL, 12.78 mmol) in toluene (6 mL) for 5 h, followed by the treatment of $NH_3$ (50 mL, aq. 28-30%) as per General Procedure 3 to provide 3-(5-(trifluoromethyl)pyridin-2-yl)-1,2,4-oxadiazol-5-amine in 63% yield (1.67 g). $^1H$ NMR (401 MHz, DMSO-$d_6$) δ 9.07 (s, 1H), 8.36 (s, 1H), 8.12-8.08 (m, 3H). LCMS $R_f$ (min)=3.154, MS m/z=231.1 $[M+H]^+$.

3-(5-(Trifluoromethyl)pyridin-2-yl)-1,2,4-oxadiazol-5-amine (0.31 g, 1.35 mmol) was reacted with 5-bromopicolinonitrile (0.176 g, 0.96 mmol), $Pd_2(dba)_3$ (0.053 g, 0.058 mmol), Xantphos (0.044 g, 0.077 mmol) and $Cs_2CO_3$ (0.626 g, 1.92 mmol) in 1,4-dioxane (10 mL) as per General Procedure 4 Method 1 to provide 5-((3-(5-(trifluoromethyl)pyridin-2-yl)-1,2,4-oxadiazol-5-yl)amino)picolinonitrile in 96% yield (0.308 g). $^1H$ NMR (401 MHz, DMSO-$d_6$) δ 9.12 (s, 1H), 8.83 (s, 1H), 8.40-8.34 (m, 4H), 8.02 (s, 1H). LCMS $R_f$ (min)=3.676, MS m/z=333.1 $[M+H]^+$.

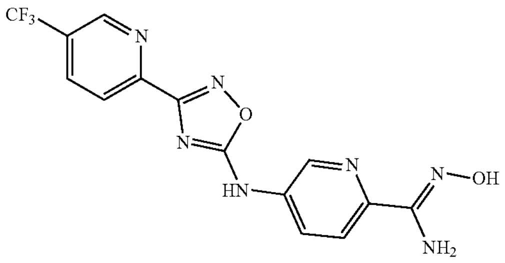

5-((3-(5-(Trifluoromethyl)pyridin-2-yl)-1,2,4-oxadiazol-5-yl)amino)picolinonitrile (0.10 g, 0.30 mmol) was reacted with $NH_2OH{\cdot}HCl$ (0.063 mg, 0.90 mmol) and $Et_3N$ (0.13 mL, 0.90 mmol) in MeOH (5 mL) for 1 h as per General Procedure 1 Method 2 to provide N'-hydroxy-5-((3-(5-(trifluoromethyl)pyridin-2-yl)-1,2,4-oxadiazol-5-yl)amino)picolinimidamide in 81% yield (0.088 g). $^1H$ NMR (401 MHz, DMSO-$d_6$) δ 9.87 (s, 1H), 9.15 (s, 1H), 8.82 (d, J=2.3 Hz, 1H), 8.44 (dd, J=8.3, 1.9 Hz, 1H), 8.31 (d, J=8.2 Hz, 1H), 8.14 (dd, J=8.8, 2.6 Hz, 1H), 7.91 (d, J=8.7 Hz, 1H), 5.81 (br s, 2H). $^{13}C$ NMR (101 MHz, DMSO-$d_6$) δ 168.6, 166.9, 149.9, 149.5, 147.1, 144.9, 138.2, 137.9, 135.5, 135.2, 127.0, 126.6, 125.7, 124.9, 123.5, 120.1. LCMS $R_f$ (min)=3.158, HRMS (ESI) calcd for $C_{14}H_{11}F_3N_7O_2^+$ $[M+H]^+$ 366.0926, found 366.0933.

85. N'-hydroxy-5-((3-(5-(trifluoromethyl)pyridin-2-yl)-1,2,4-oxadiazol-5-yl)amino)pyrazine-2-carboximidamide (Scheme 82)

Scheme 82

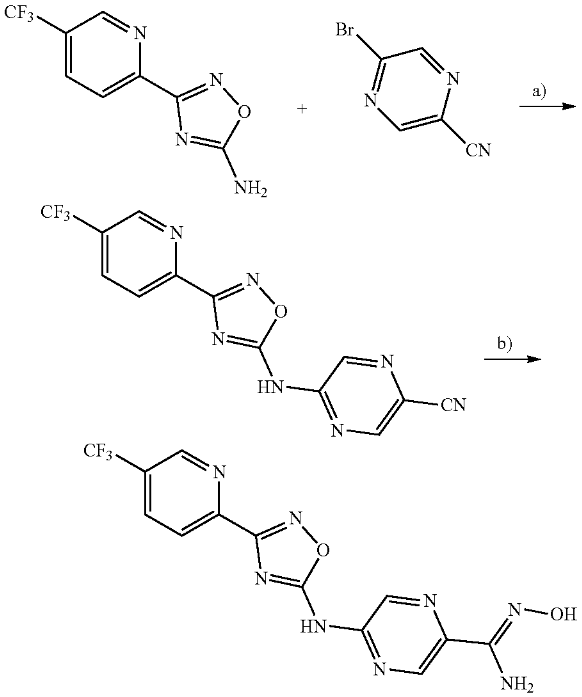

a) $Pd_2(dba)_3$, Xantphos, $Cs_2CO_3$, 1,4-dioxane, 95° C., 5 h; b) $NH_2OH$•HCl, $Et_3N$, dry MeOH, reflux, 1 h.

3-(5-(Trifluoromethyl)pyridin-2-yl)-1,2,4-oxadiazol-5-amine (0.3 g, 1.30 mmol) was reacted with 5-bromopyrazine-2-carbonitrile (0.171 g, 0.93 mmol), $Pd_2(dba)_3$ (0.051 g, 0.056 mmol), Xantphos (0.043 g, 0.074 mmol) and $Cs_2CO_3$ (0.606 g, 1.86 mmol) in 1,4-dioxane (12 mL) as per General Procedure 4 Method 1 to provide 5-((3-(5-(trifluoromethyl)pyridin-2-yl)-1,2,4-oxadiazol-5-yl)amino)pyrazine-2-carbonitrile in 98% yield (0.305 g). $^1H$ NMR (401 MHz, DMSO-$d_6$) δ 9.08 (s, 1H), 8.21-8.61 (m, 5H). LCMS $R_f$ (min)=3.649, MS m/z=334.1 $[M+H]^+$.

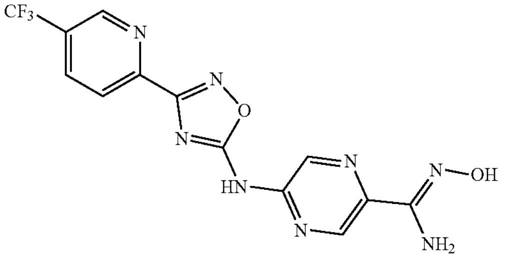 [SMILES: N/C(=N\O)c1cnc(Nc2nc(-c3ccc(C(F)(F)F)cn3)no2)cn1]

5-((3-(5-(Trifluoromethyl)pyridin-2-yl)-1,2,4-oxadiazol-5-yl)amino)pyrazine-2-carbonitrile (0.15 g, 0.45 mmol) was reacted with $NH_2OH{\cdot}HCl$ (0.094 g, 1.35 mmol) and $Et_3N$ (0.19 mL, 1.35 mmol) in MeOH (6 mL) for 1 h as per General procedure 1 Method 2 to provide N'-hydroxy-5-((3-(5-(trifluoromethyl)pyridin-2-yl)-1,2,4-oxadiazol-5-yl)amino)pyrazine-2-carboximidamide in 53% yield (0.088 g). $^1H$ NMR (401 MHz, DMSO-$d_6$) δ 12.33 (br s, 1H), 10.07 (s, 1H), 9.28 (d, J=1.5 Hz, 1H), 8.83 (d, J=1.5 Hz, 1H), 8.46 (dd, J=8.3, 1.9 Hz, 1H), 8.33 (d, J=8.2 Hz, 1H), 5.91 (br s, 2H). $^{13}C$ NMR (101 MHz, DMSO-$d_6$) δ 168.0, 166.7, 149.6, 148.2, 147.3, 147.0, 140.5, 139.4, 135.4, 132.4, 126.8, 126.5, 124.8, 123.4, 122.1. LCMS $R_f$ (min)=2.456, HRMS (ESI) calcd for $C_{13}H_{10}F_3N_8O_2^+$ $[M+H]^+$ 367.0879, found 367.0889.

86. N'-Hydroxy-5-((3-(4-(trifluoromethoxy)phenyl)-1,2,4-oxadiazol-5-yl)amino)picolinimidamide (Scheme 83)

Scheme 83

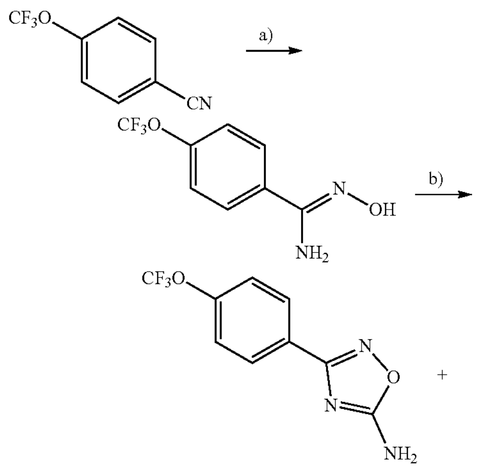

-continued

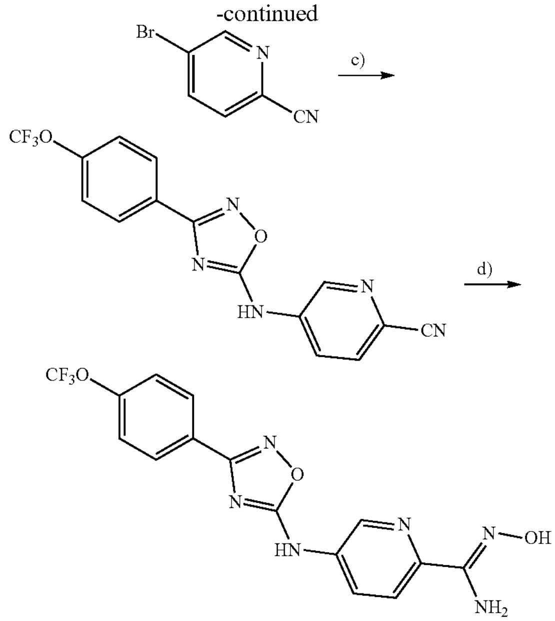

a) aq. $NH_2OH$ (50%), EtOH, reflux, 8 h; b) i) trichloroacetic anhydride, toluene, reflux, 5 h; ii) aq. $NH_3$ (28~30%), rt, overnight; c) $Pd_2(dba)_3$, Xantphos, $Cs_2CO_3$, 1,4-dioxane, 95° C., 5 h; d) $NH_2OH{\cdot}HCl$, $Et_3N$, dry MeOH, reflux, 1 h.

4-(Trifluoromethoxy)benzonitrile (2.0 g, 10.69 mmol) was reacted with $NH_2OH$ (0.69 mL, 11.23 mmoL, aq. 50%) in EtOH (12 mL) for 8 has per General Procedure 1 Method 1 to provide N'-hydroxy-4-(trifluoromethoxy)benzimidamide in 100% yield (2.35 g).

N'-Hydroxy-4-(trifluoromethoxy)benzimidamide (2.35 g, 10.69 mmol) was reacted with trichloroacetic anhydride (2.15 mL, 11.76 mmol) in toluene (10 mL) for 5 h, followed by the treatment with $NH_3$ (50 mL, aq. 28-30%) as per General Procedure 3 to provide 3-(4-(trifluoromethoxy)phenyl)-1,2,4-oxadiazol-5-amine in 78% yield (2.11 g). $^1H$ NMR (401 MHz, DMSO-$d_6$) δ 8.06-7.94 (m, 4H), 7.50 (d, J=8.0 Hz, 2H). LCMS $R_f$ (min)=2.774, MS m/z=246.1 $[M+H]^+$.

3-(4-(Trifluoromethoxy)phenyl)-1,2,4-oxadiazol-5-amine (0.30 g, 1.22 mmol) was reacted with 5-bromopicolinonitrile (0.171 g, 0.94 mmol), $Pd_2(dba)_3$ (0.052 g, 0.056 mmol), Xantphos (0.044 g, 0.075 mmol) and $Cs_2CO_3$ (0.612 g, 1.88 mmol) in 1,4-dioxane (12 mL) as per General Procedure 4 Method 1 to provide 5-((3-(4-(trifluoromethoxy)phenyl)-1,2,4-oxadiazol-5-yl)amino)picolinonitrile in 64% yield (0.21 g). $^1H$ NMR (401 MHz, DMSO-$d_6$) δ 8.75 (s, 1H), 8.32 (d, J=7.7 Hz, 1H), 8.12 (d, J=7.8 Hz, 2H), 7.95 (d, J=8.4 Hz, 1H), 7.54 (d, J=7.3 Hz, 2H). LCMS $R_f$ (min)=3.145, MS m/z=348.0 $[M+H]^+$.

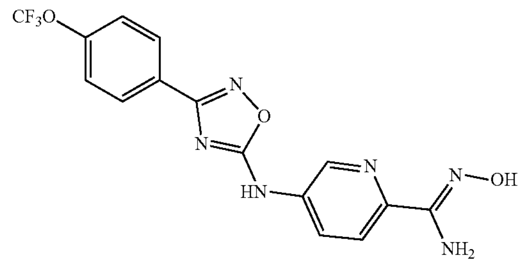

5-((3-(4-(Trifluoromethoxy)phenyl)-1,2,4-oxadiazol-5-yl)amino)picolinonitrile (0.15 g, 0.43 mmol) was reacted with $NH_2OH{\cdot}HCl$ (0.09 g, 1.30 mmol) and $Et_3N$ (0.18 mL, 1.30 mmol) in MeOH (5 mL) for 1 h as per General Procedure 1 Method 2 to provide N'-hydroxy-5-((3-(4-(trifluoromethoxy)phenyl)-1,2,4-oxadiazol-5-yl)amino)picolinimidamide in 95% yield (0.155 g). $^1H$ NMR (401 MHz, DMSO-$d_6$) δ 11.53 (br s, 1H), 9.85 (s, 1H), 8.84 (s, 1H), 8.15-8.13 (m, 3H), 7.91 (d, J=8.7, 1H), 7.56 (d, J=8.2 Hz, 2H), 5.81 (br s, 2H). $^{13}C$ NMR (101 MHz, DMSO-$d_6$) δ 168.1, 166.5, 150.3, 149.2, 144.6, 137.9, 135.1, 129.1, 126.0, 125.4, 121.6, 119.8. LCMS $R_f$ (min)=3.535, HRMS (ESI) calcd for $C_{15}H_{12}F_3N_6O_3^+$ [M+H]$^+$ 381.0917, found 381.0930.

87. N'-Hydroxy-5-((3-(4-(trifluoromethoxy)phenyl)-1,2,4-oxadiazol-5-yl)amino)pyrazine-2-carboximidamide (Scheme 84)

Scheme 84

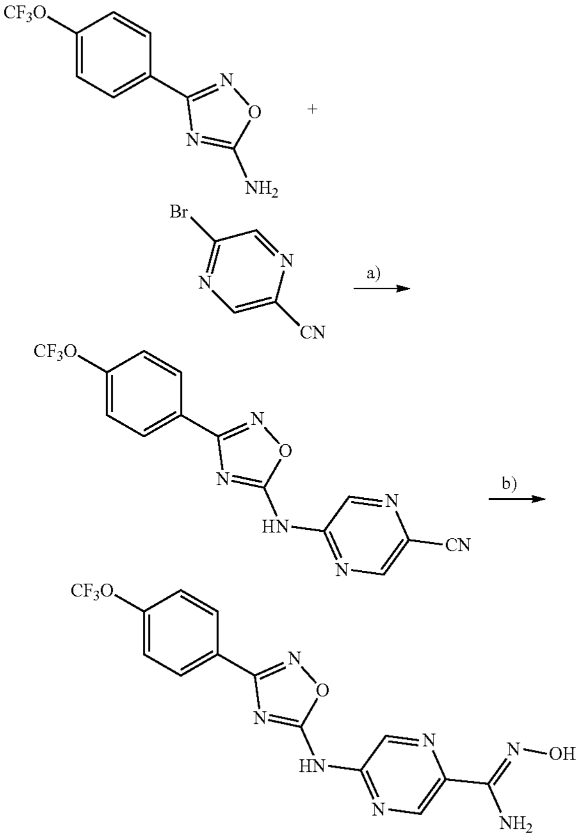

a) $Pd_2(dba)_3$, Xantphos, $Cs_2CO_3$, 1,4-dioxane, 95° C., 5 h; b) $NH_2OH{\cdot}HCl$, $Et_3N$, dry MeOH, reflux, 1 h.

3-(4-(Trifluoromethoxy)phenyl)-1,2,4-oxadiazol-5-amine (0.3 g, 1.22 mmol) was reacted with 5-bromopyrazine-2-carbonitrile (0.187 g, 1.02 mmol), $Pd_2(dba)_3$ (0.056 g, 0.061 mmol), Xantphos (0.047 g, 0.082 mmol) and $Cs_2CO_3$ (0.665 g, 2.04 mmol) in 1,4-dioxane (12 mL) as per General Procedure 4 Method 1 to provide 5-((3-(4-(trifluoromethoxy)phenyl)-1,2,4-oxadiazol-5-yl)amino)pyrazine-2-carbonitrile in 79% yield (0.283 g). $^1H$ NMR (401 MHz, DMSO-$d_6$) δ 9.26 (s, 1H), 8.91 (s, 1H), 8.15 (d, J=6.7 Hz, 2H), 7.57 (d, J=7.3 Hz, 2H), LCMS $R_f$ (min)=3.129, MS m/z=347.0 [M−H]$^-$.

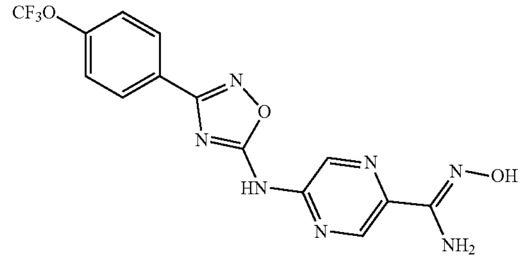

5-((3-(4-(Trifluoromethoxy)phenyl)-1,2,4-oxadiazol-5-yl)amino)pyrazine-2-carbonitrile (0.21 g, 0.60 mmol) was reacted with $NH_2OH{\cdot}HCl$ (0.126 g, 1.81 mmol) and $Et_3N$ (0.25 mL, 1.81 mmol) in MeOH (7 mL) for 1 h As per General Procedure 1 Method 2 to provide N'-hydroxy-5-((3-(4-(trifluoromethoxy)phenyl)-1,2,4-oxadiazol-5-yl)amino) pyrazine-2-carboximidamide in 90% yield (0.206 g). $^1H$ NMR (401 MHz, DMSO-$d_6$) δ 12.27 (br s, 1H), 10.06 (s, 1H), 9.27 (d, J=1.1 Hz, 1H), 8.82 (d, J=1.1 Hz, 1H), 8.15 (d, J=8.8, 2H), 7.57 (d, J=8.2 Hz, 2H), 5.90 (br s, 2H). $^{13}C$ NMR (101 MHz, DMSO-$d_6$) δ 167.6, 166.5, 150.4, 148.2, 147.5, 140.4, 139.4, 132.3, 129.2, 125.8, 121.6, 121.3, 118.7. LCMS $R_f$ (min)=3.684, HRMS (ESI)calcd for $C_{14}H_{11}F_3N_7O_3^+$ [M+H]$^+$ 382.0875, found 382.0882.

88. N'-hydroxy-5-((3-(5-(trifluoromethoxy)pyridin-2-yl)-1,2,4-oxadiazol-5-yl)amino)picolinimidamide (Scheme 85)

Scheme 85

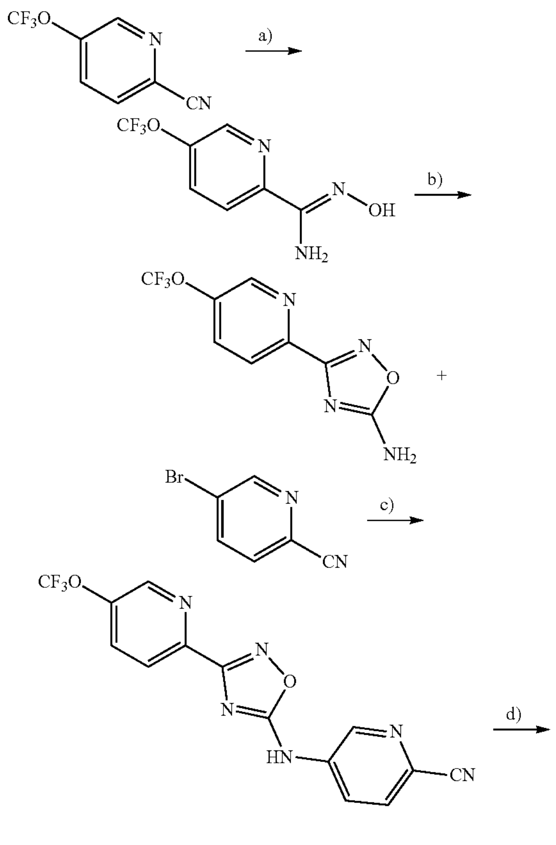

-continued

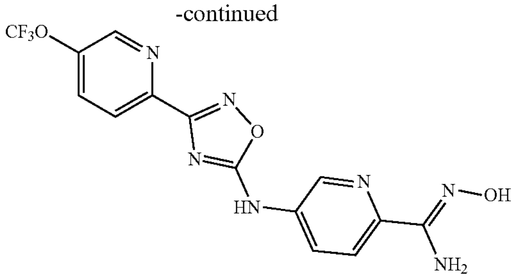

a) aq. $NH_2OH$ (50%), EtOH, rt, 1 h; b) i) trichloroacetic anhydride, toluene, reflux, 5 h; ii) aq. $NH_3$ (28~30%), rt, overnight; c) $Pd_2(dba)_3$, Xantphos, $Cs_2CO_3$, 1,4-dioxane, 95° C., 5 h; d) $NH_2OH$•HCl, $Et_3N$, dry MeOH, reflux, 1 h.

5-(Trifluoromethoxy)picolinonitrile (1.0 g, 5.32 mmol) was reacted with $NH_2OH$ (0.36 mL, 5.85 mmoL, aq. 50%) in EtOH (6 mL) for 1 h as per General Procedure 1 Method 1 to provide N'-hydroxy-5-(trifluoromethoxy)picolinimidamide in 100% yield (1.18 g). $^1H$ NMR (401 MHz, DMSO-$d_6$) δ 10.08 (s, 1H), 8.64 (d, J=2.7 Hz, 1H), 7.99 (dd, J=8.9, 0.6 Hz, 1H), 7.93-7.89 (m, 1H), 5.89 (br s, 2H). LCMS $R_f$ (min)=2.528, MS m/z=222.1 $[M+H]^+$.

N'-Hydroxy-5-(trifluoromethoxy)picolinimidamide (1.16 g, 5.32 mmol) was reacted with trichloroacetic anhydride (1.05 mL, 5.77 mmol) in toluene (5 mL) for 5 h, followed by the treatment with $NH_3$ (45 mL, aq. 28-30%) as per General Procedure 3 to provide 3-(5-(trifluoromethoxy)pyridin-2-yl)-1,2,4-oxadiazol-5-amine in 93% yield (1.16 g). $^1H$ NMR (401 MHz, DMSO-$d_6$) δ 8.78 (s, 1H), 8.06-8.05 (m, 4H). LCMS $R_f$ (min)=3.204, MS m/z=247.1 $[M+H]^+$.

3-(5-(Trifluoromethoxy)pyridin-2-yl)-1,2,4-oxadiazol-5-amine (0.20 g, 0.81 mmol) was reacted with 5-bromopicolinonitrile (0.124 g, 0.68 mmol), $Pd_2(dba)_3$ (0.038 g, 0.041 mmol), Xantphos (0.032 g, 0.054 mmol) and $Cs_2CO_3$ (0.443 g, 1.36 mmol) in 1,4-dioxane (8 mL) as per General Procedure 4 Method 1 to provide 5-((3-(5-(trifluoromethoxy)pyridin-2-yl)-1,2,4-oxadiazol-5-yl)amino)picolinonitrile in 95% yield (0.268 g). $^1H$ NMR (401 MHz, DMSO-$d_6$) δ 8.89 (s, 1H), 8.86 (s, 1H), 8.38 (d, J=7.6 Hz, 1H), 8.26 (d, J=8.3 Hz, 1H), 8.08-8.13 (m, 2H). LCMS $R_f$ (min)=2.841, MS m/z=349.0 $[M+H]^+$.

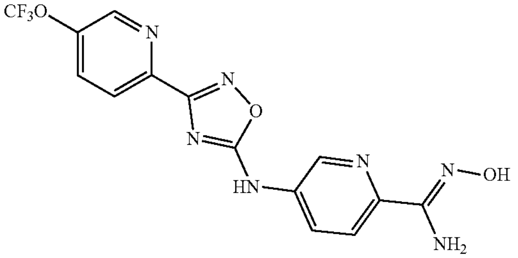

5-((3-(5-(Trifluoromethoxy)pyridin-2-yl)-1,2,4-oxadiazol-5-yl)amino)picolinonitrile (0.20 g, 0.574 mmol) was reacted with $NH_2OH$·HCl (0.12 g, 1.72 mmol), $Et_3N$ (0.24 mL, 1.72 mmol) in MeOH (6 mL), reflux for 1 as per General Procedure 1 Method 2 to provide N'-hydroxy-5-((3-(5-(trifluoromethoxy)pyridin-2-yl)-1,2,4-oxadiazol-5-yl)amino)picolinimidamide in 71% yield (0.156 g). $^1H$ NMR (401 MHz, DMSO-$d_6$) δ 11.42 (s, 1H), 9.85 (s, 1H), 8.85 (s, 1H), 8.82 (s, 1H), 8.25 (d, J=8.6 Hz, 1H), 8.15-8.10 (m, 2H), 7.91 (d, J=8.7 Hz, 1H), 5.81 (br s, 2H). $^{13}C$ NMR (101 MHz, DMSO-$d_6$) δ 168.3, 166.6, 149.2, 146.4, 145.2, 144.7, 143.2, 137.9, 135.0, 130.0, 125.4, 124.7, 121.3, 119.9, 118.7. LCMS $R_f$ (min)=3.165, HRMS (ESI) calcd for $C_{14}H_{11}F_3N_7O_3^+$ $[M+H]^+$ 382.0875, found 382.0885.

89. N'-hydroxy-5-((3-(4-(trifluoromethyl)phenyl)isoxazol-5-yl)amino)picolinimidamide (Scheme 86)

Scheme 86

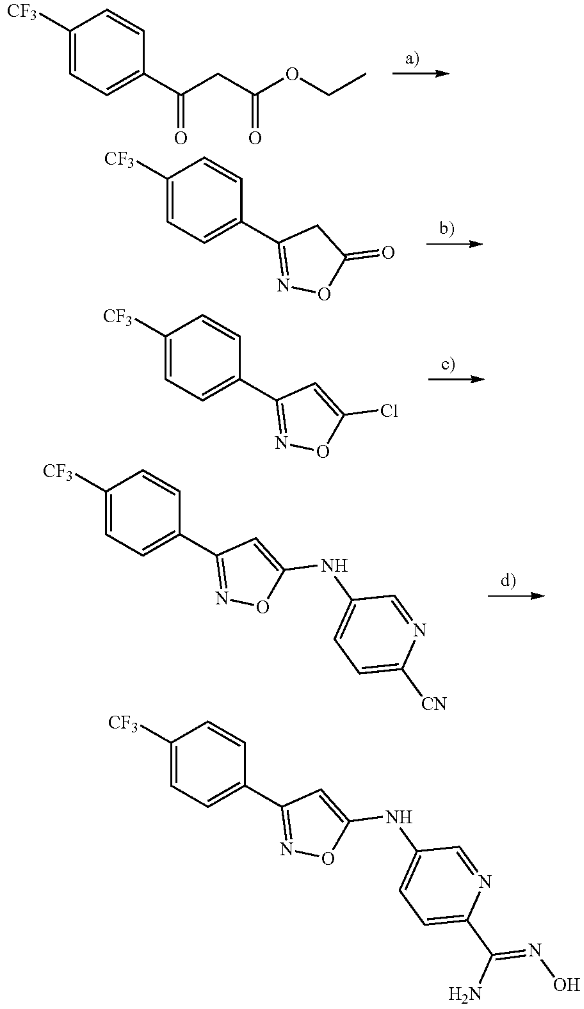

a) $NH_2OH$•HCl, NaOAc, MeOH, rt, overnight; b) $POCl_3$, $Et_3N$, 0~60° C., 50 h; c) 5-aminopicolinonitrile, NaH (60% dispersion in mineral oil), dry DMF, 0° C.~rt, 16 h; d) $NH_2OH$•HCl, $Et_3N$, dry MeOH, reflux, 2 h.

Ethyl 3-oxo-3-(4-(trifluoromethyl)phenyl)propanoate (1.0 g, 3.84 mmol) was reacted with $NH_2OH$·HCl (0.801 g, 11.53 mmol) and NaOAc (0.946 g, 11.53 mmol) in MeOH (10 mL) as per General Procedure 9 to provide 3-(4-(trifluoromethyl)phenyl)isoxazol-5(4H)-one in 100% yield (0.88 g).

Ethyl 3-(4-(trifluoromethyl)phenyl)isoxazol-5(4H)-one (0.88 g, 3.84 mmol) was reacted with $POCl_3$ (3.6 mL) and $Et_3N$ (0.32 mL, 2.30 mmol) as per General Procedure 10 to provide 5-chloro-3-(4-(trifluoromethyl)phenyl)isoxazole in 96% yield (0.91 g).

5-Chloro-3-(4-(trifluoromethyl)phenyl)isoxazole (0.15 g, 0.61 mmol) was reacted with 5-aminopicolinonitrile (0.108 g, 0.91 mmol) and NaH (60%, 0.049 g, 1.22 mmol) in DMF (4 mL) as per General Procedure 2 Method 2 to provide 5-((3-(4-(trifluoromethyl)phenyl)isoxazol-5-yl)amino)picolinonitrile in 88% yield (0.176 g). $^{1}$H NMR (401 MHz, DMSO-$d_6$) δ 11.06 (s, 1H), 8.62 (s, 1H), 8.14 (d, J=7.6 Hz, 2H), 8.00 (d, J=8.6 Hz, 1H), 7.90 (d, J=8.1 Hz, 2H), 7.83 (d, J=8.0 Hz, 1H), 6.76 (s, 1H). LCMS $R_f$ (min)=3.858, MS m/z=329.1 [M−H]$^-$.

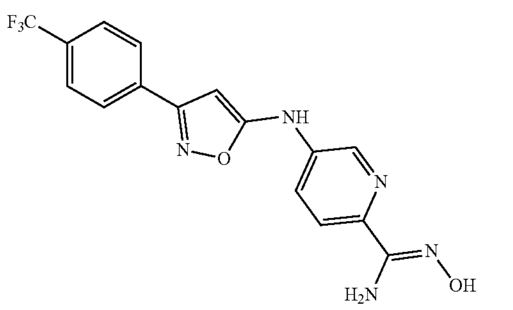 [SMILES: N/C(=N\O)c1ccc(Nc2cc(-c3ccc(C(F)(F)F)cc3)no2)cn1]

5-((3-(4-(Trifluoromethyl)phenyl)isoxazol-5-yl)amino)picolinonitrile (0.18 g, 0.545 mmol) was reacted with $NH_2OH$·HCl (0.114 g, 1.64 mmol) and $Et_3N$ (0.23 mL, 1.64 mmol) in MeOH (6 mL) for 2 h as per General Procedure 1 Method 2 to provide N'-hydroxy-5-((3-(4-(trifluoromethyl)phenyl)isoxazol-5-yl)amino)picolinimidamide in 67% yield (0.132 g). $^{1}$H NMR (401 MHz, DMSO-$d_6$) δ 10.54 (s, 1H), 9.78 (s, 1H), 8.50 (s, 1H), 8.12 (d, J=7.3 Hz, 2H), 7.89-7.83 (m, 3H), 7.72 (d, J=7.5 Hz, 1H), 6.55 (s, 1H), 5.76 (br s, 2H). $^{13}$C NMR (101 MHz, DMSO-$d_6$) δ 165.5, 161.8, 149.3, 143.2, 136.7, 136.6, 133.1, 130.6, 130.3, 130.0, 129.7, 127.3, 125.9, 125.4, 123.7, 120.0, 80.4. LCMS $R_f$ (min)=3.393, HRMS (ESI) calcd for $C_{16}H_{13}F_3N_5O_2^+$ [M+H]$^+$ 364.1021, found 364.1025.

90. 5-((5-(5-Chloropyridin-2-yl)oxazol-2-yl)amino)-N'-hydroxypicolinimidamide (Scheme 87)

Scheme 87

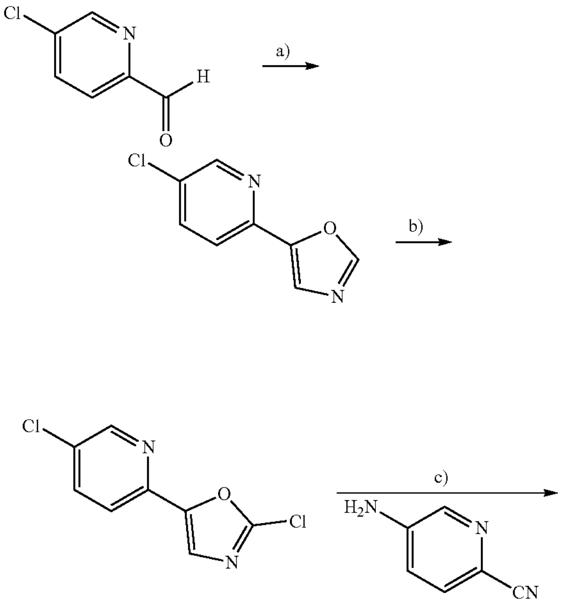

-continued

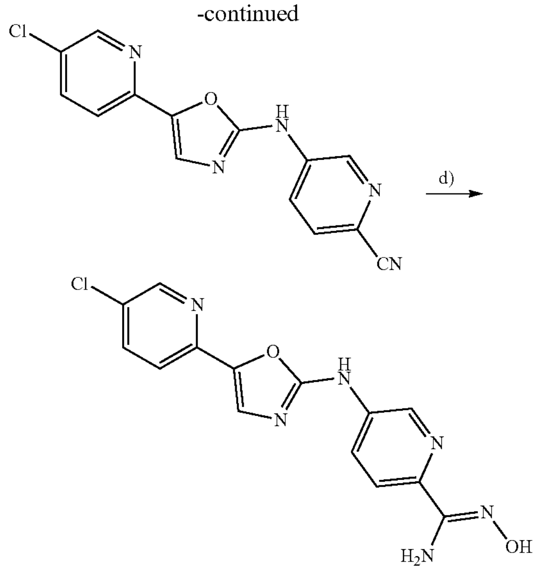

a) TosMIC, $K_2CO_3$, MeOH, reflx, 5 h; b) i. LiHMDS, THF, -78° C., 0.5 h, ii. $C_2Cl_6$, -78° C.~rt, 5 h; c) iso-propanol, reflux, 16 h; d) $NH_2OH$•HCl, $Et_3N$, dry MeOH, reflux, 8 h.

5-Chloropicolinaldehyde (3.09 g, 21.83 mmol) and TosMIC (5.11 g, 26.20 mmol) were reacted as per General Procedure 14, giving 5-(5-chloropyridin-2-yl)oxazole (4.0 g, 100%) as a white solid. $^{1}$H NMR (401 MHz, DMSO-$d_6$) δ 8.69 (dd, J=2.5, 0.7 Hz, 1H), 8.57 (s, 1H), 8.07 (dd, J=8.5, 2.5 Hz, 1H), 7.84 (s, 1H), 7.81 (dd, J=8.5, 0.7 Hz, 1H); LCMS $R_f$ (min)=2.55. MS m/z=181.1 [M+H]$^+$.

5-(5-Chloropyridin-2-yl)oxazole (3.20 g, 17.7 mmol) was reacted with LiHMDS (21.3 mL, 21.3 mmol) then $C_2Cl_6$ (6.3 g, 26.6 mmol) in dry THF as per General Procedure 15 Method 1 to give 2-chloro-5-(5-chloropyridin-2-yl)oxazole (3.01 g, 79% yield) as a white solid. $^{1}$H NMR (401 MHz, DMSO-$d_6$) δ 8.69 (dd, J=2.5, 0.6 Hz, 1H), 8.07 (dd, J=8.5, 2.5 Hz, 1H), 7.92 (s, 1H), 7.79 (dd, J=8.5, 0.5 Hz, 1H). LCMS $R_f$ (min)=2.943, MS m/z=215.0 [M+H]$^+$.

2-Chloro-5-(5-chloropyridin-2-yl)oxazole (0.5 g, 2.33 mmol) was reacted with 5-aminopicolinonitrile (0.416 g, 3.49 mmol) in iso-propanol (10 mL) as per General Procedure 2 Method 1 to provide 5-((5-(5-chloropyridin-2-yl)oxazol-2-yl)amino)picolinonitrile in 71% yield (0.492 g). $^{1}$H NMR (401 MHz, DMSO-$d_6$) δ 8.83 (s, 1H), 8.62 (s, 1H), 8.32 (d, J=7.7 Hz, 1H), 7.00-7.98 (m, 2H), 7.76 (s, 1H), 7.66 (d, J=8.0 Hz, 1H). LCMS $R_f$ (min)=2.794, MS m/z=298.1 [M+H]$^+$.

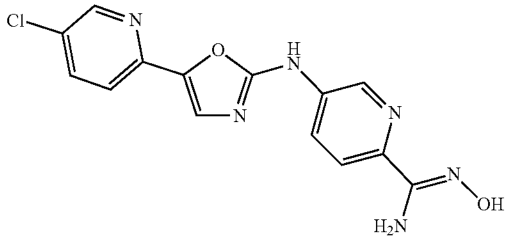 [SMILES: N/C(=N\O)c1ccc(Nc2ncc(-c3ccc(Cl)cn3)o2)cn1]

5-((5-(5-Chloropyridin-2-yl)oxazol-2-yl)amino)picolinonitrile (0.30 g, 1.01 mmol) was reacted with $NH_2OH$·HCl (0.561 g, 8.08 mmol) and $Et_3N$ (1.13 mL, 8.08 mmol) in MeOH (10 mL) for 8 h as per General Procedure 1 Method 2 to provide 5-((5-(5-chloropyridin-2-yl)oxazol-2-yl)

amino)-N'-hydroxypicolinimidamide in 92% yield (0.306 g). $^{1}$H NMR (401 MHz, DMSO-$d_6$) δ 10.98 (s, 1H), 9.75 (s, 1H), 8.77 (s, 1H), 8.61 (s, 1H), 8.12-7.62 (m, 5H), 5.77 (br s, 2H). $^{13}$C NMR (101 MHz, DMSO-$d_6$) δ 156.8, 149.4, 148.2, 145.2, 143.5, 143.2, 137.0, 136.8, 136.1, 128.7, 126.9, 124.0, 119.7, 119.0. LCMS $R_f$ (min)=2.241, HRMS (ESI) calcd for $C_{14}H_{12}ClN_6O_2^+$ [M+H]$^+$ 331.0705, found 331.0715.

91. rac-N-(2,3-dihydroxypropyl)-5-((5-(4-(trifluoromethyl)phenyl)oxazol-2-yl)amino)picolinimidamide (Scheme 88)

Scheme 88

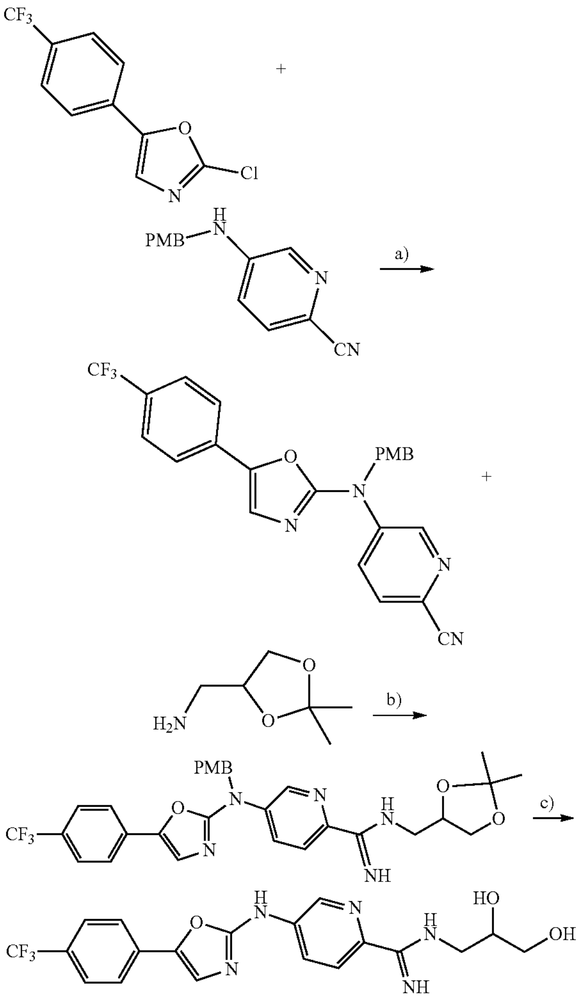

a) NaH (60% dispersion in mineral oil), dry DMF, 0° C., 1 h;
b) Na, MeOH, rt~reflux, 16 h;
c) TFA, 70° C., 24 h.

2-Chloro-5-(4-(trifluoromethyl)phenyl)oxazole (Intermediate I, 0.50 g, 2.02 mmol) was reacted with 5-((4-methoxybenzyl)amino)picolinonitrile (0.483 g, 2.02 mmol) and NaH (60%, 0.121 g, 3.03 mmol) in DMF (9 mL) as per General Procedure 2 Method 2 to provide 5-((4-methoxybenzyl)(5-(4-(trifluoromethyl)phenyl)oxazol-2-yl)amino)picolinonitrile in 98% yield (0.89 g). $^{1}$H NMR (401 MHz, DMSO-$d_6$) δ 8.85 (d, J=2.3 Hz, 1H), 7.97 (dd, J=8.7, 2.8 Hz, 1H), 7.66-7.57 (m, 5H), 7.32 (s, 1H), 7.21 (d, J=8.7 Hz, 2H), 6.87 (d, J=8.7 Hz, 2H), 5.27 (s, 2H). 3.78 (s, 3H). LCMS $R_f$ (min)=3.336, MS m/z=451.2 [M+H]$^+$.

Sodium metal (0.044 g, 1.9 mmol) was dissolved in anhydrous MeOH (2 mL) and then added to a suspension of 5-((4-methoxybenzyl)(5-(4-(trifluoromethyl)phenyl)oxazol-2-yl)amino)picolinonitrile (0.172 g, 0.38 mmol) in anhydrous MeOH (2 mL). The reaction mixture was stirred at rt for 0.5 h then refluxed for a further 1 h. rac-(2,2-Dimethyl-1,3-dioxolan-4-yl)methanamine·HCl (0.255 g, 1.52 mmol) was added to the mixture. The reaction mixture was refluxed for 16 h to provide rac-N-((2,2-dimethyl-1,3-dioxolan-4-yl)methyl)-5-((4-methoxybenzyl)(5-(4-(trifluoromethyl)phenyl)oxazol-2-yl)amino)picolinimidamide in yield 84% (0.186 g). $^{1}$H NMR (401 MHz, MeOH-$d_4$) δ 9.03 (s, 1H), 8.24 (d, J=7.3 Hz, 1H), 8.16 (d, J=8.2 Hz, 1H), 7.78 (d, J=8.0 Hz, 2H), 7.72 (d, J=7.8 Hz, 2H), 7.60 (s, 1H), 7.32 (d, J=8.0, 2H), 6.91 (d, J=8.2 Hz, 2H), 5.41 (s, 2H), 4.50 (m, 1H), 4.19 (m, 1H), 3.87-3.72 (m, 6H), 1.43 (s, 3H), 1.37 (s, 3H). LCMS $R_f$ (min)=3.642, MS m/z=582.3 [M+H]$^+$.

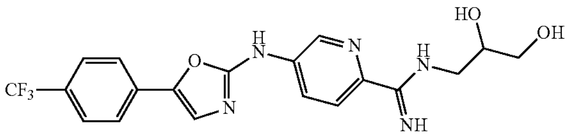 [SMILES: N=C(NCC(O)CO)c1ccc(Nc2ncc(-c3ccc(C(F)(F)F)cc3)o2)cn1]

rac-N-((2,2-Dimethyl-1,3-dioxolan-4-yl)methyl)-5-((4-methoxybenzyl)(5-(4-(trifluoromethyl)phenyl)oxazol-2-yl)amino)picolinimidamide (0.05 g, 0.086 mmol) was reacted with TFA (5 mL) at 70° C. for 24 h as per General Procedure 11, except without addition of $Et_3SiH$ or anisole, to provide rac-N-(2,3-dihydroxypropyl)-5-((5-(4-(trifluoromethyl)phenyl)oxazol-2-yl)amino)picolinimidamide in 72% yield (0.026 g). $^{1}$H NMR (401 MHz, MeOH-$d_4$) δ 8.94 (dd, J=2.6, 0.5 Hz, 1H), 8.51 (dd, J=8.8, 2.6 Hz, 1H), 8.17 (dd, J=8.8, 0.5 Hz, 1H), 7.84 (d, J=8.2 Hz, 2H), 7.74 (d, J=8.4 Hz, 2H), 7.59 (s, 1H), 4.00 (m, 1H), 3.73-3.61 (m, 4H). $^{13}$C NMR (101 MHz, MeOH-$d_4$) δ 146.1, 141.6, 140.2, 137.1, 132.8, 127.1, 126.9, 125.3, 124.5, 124.40, 124.36, 124.3, 71.1, 68.1, 64.8. LCMS $R_f$ (min)=3.128, HRMS (ESI) calcd for $C_{19}H_{19}F_3N_5O_3^+$ [M+H]$^+$ 422.1440, found 422.1449.

92. 5-((5-(4-(Trifluoromethyl)phenyl)oxazol-2-yl)amino)picolinohydrazide (Scheme 89)

Scheme 89

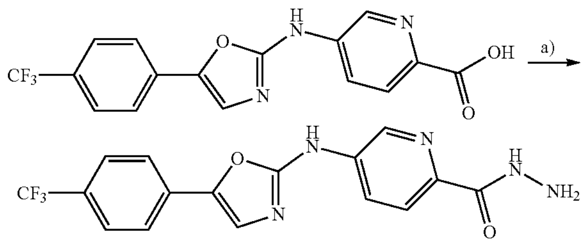

a) EDAC•HCl, HOBt, hydrazine monohydride, DMF, rt, overnight.

EDAC·HCl (0.071 g, 0.371 mmol) and HOBt (0.054 g, 0.4 mmol) were added to a suspension of 5-((5-(4-(trifluoromethyl)phenyl)oxazol-2-yl)amino)picolinic acid (Intermediate B, 0.10 g, 0.286 mmol) in DMF (5.0 mL). The resulting mixture was stirred at rt for 3 h. Hydrazine monohydrate (0.022 g, 0.43 mmol) was then added to the reaction mixture and stirring was continued overnight. The reaction mixture was concentrated under reduced pressure to obtain a gummy solid, which was purified using preparative HPLC in a 95% A:5% B to 100% B solvent system. The TFA and acetonitrile were removed through rotary evaporation and $H_2O$ through freeze-drying, providing 5-((5-(4-(trifluoromethyl)phenyl)oxazol-2-yl)amino)picolinohydrazide as a beige solid (0.066 g, 63% yield). $^1H$ NMR (400 MHz, DMSO-$d_6$) δ 11.23 (m, 1H), 8.83 (m, 1H), 8.34 (m, 1H), 8.09 (m, 1H), 7.82-7.79 (m, 5H). $^{13}C$ NMR (101 MHz, DMSO-$d_6$) δ 163.3, 159.0, 156.1, 143.5, 139.0, 138.5, 137.6, 137.3, 131.4, 126.1, 125.6, 125.3, 123.7, 123.5, 123.2. LCMS $R_f$ (min)=3.931. HRMS (ESI) calcd for $C_{16}H_{13}F_3N_5O_2^+$ $[M+H]^+$ 364.1021, found 364.1021.

93. N'-formyl-5-((5-(4-(trifluoromethyl)phenyl)oxazol-2-yl)amino)picolinohydrazide (Scheme 90)

Scheme 90

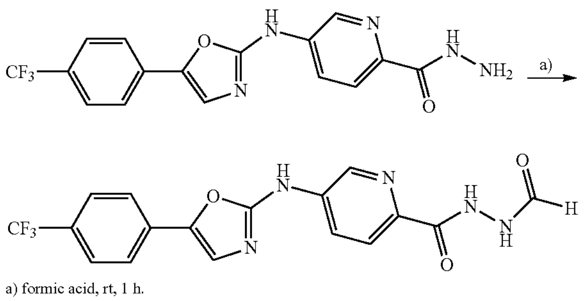

5-((5-(4-(Trifluoromethyl)phenyl)oxazol-2-yl)amino)picolinohydrazide (0.05 g, 13.7 mmol) was added to formic acid (5 mL) at rt. The mixture was stirred for 1 h. The volatiles were removed under reduced pressure to give a residue that was purified using preparative HPLC in a 95% A:5% B to 100% B solvent system. The TFA and acetonitrile were removed through rotary evaporation and $H_2O$ through freeze-drying, providing 5-((5-(4-(trifluoromethyl)phenyl)oxazol-2-yl)amino)picolinohydrazide as a beige solid (0.032 g, 60% yield). $^1H$ NMR (401 MHz, DMSO-$d_6$) δ 11.18 (s, 1H), 10.33 (s, 1H), 10.07 (s, 1H), 8.83 (J=2.3, 1H), 8.32 (d, J=8.7 Hz, 1H), 8.09 (s, 1H), 8.04 (d, J=8.7 Hz, 1H), 7.82 (br s, 4H), 7.79 (s, 1H). $^{13}C$ NMR (101 MHz, DMSO-$d_6$) δ 162.5, 159.7, 156.2, 141.7, 138.6, 137.4, 131.5, 126.2, 125.3, 123.5, 123.4, 123.2. LCMS $R_f$(min)=3.492, HRMS (ESI) calcd for $C_{17}H_{13}F_3N_5O_3^+$ $[M+H]^+$ 392.0970, found 392.0974.

94. N'-Methyl-5-((5-(4-(trifluoromethyl)phenyl)oxazol-2-yl)amino)picolinohydrazide (Scheme 91)

Scheme 91

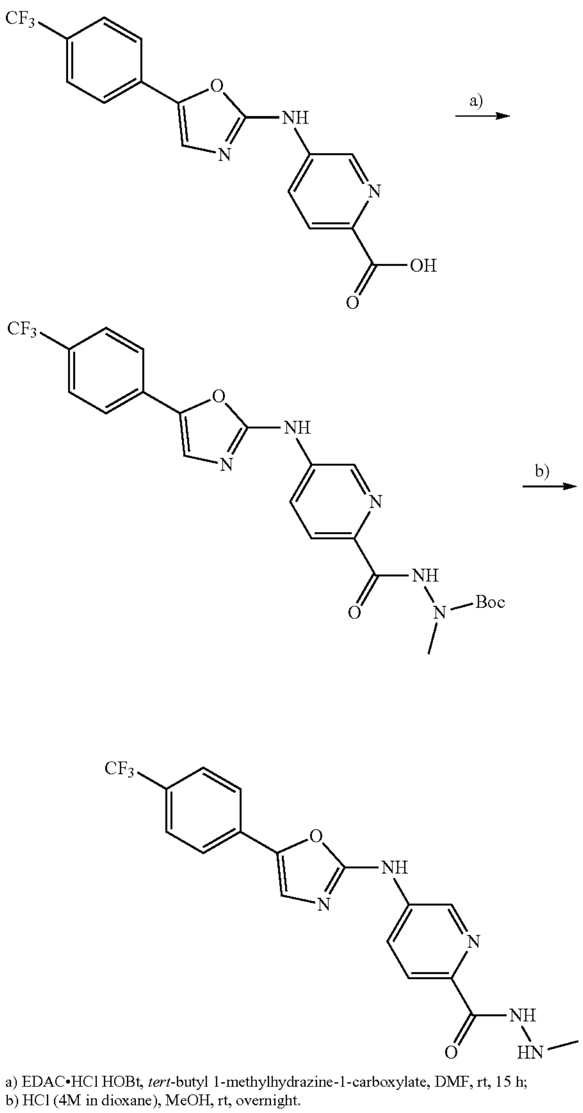

EDAC·HCl (0.071 g, 0.371 mmol) and HOBt (0.054 g, 0.4 mmol) were added to a suspension of 5-((5-(4-(trifluoromethyl)phenyl)oxazol-2-yl)amino)picolinic acid (Intermediate B, 0.10 g, 0.286 mmol) in DMF (5.0 mL). The resulting mixture was stirred at rt for 3 h. tert-Butyl 1-methylhydrazine-1-carboxylate (0.084 g, 0.572 mmol) was then added to the reaction mixture and stirring was continued overnight. The reaction mixture was concentrated under reduced pressure to obtain a gummy solid, which was purified using flash chromatography to give tert-butyl 1-methyl-2-(5-((5-(4-(trifluoromethyl)phenyl)oxazol-2-yl)amino)picolinoyl)hydrazine-1-carboxylate as a white solid (0.117 g, 86% yield). $^1H$ NMR (400 MHz, DMSO-$d_6$) δ 7.99 (s, 1H), 7.97 (s, 1H), 7.73 (s, 1H), 7.71 (s, 1H), 7.56-7.52 (m, 2H), 7.43-7.39 (m, 2H), 2.54 (s, 9H). LCMS $R_f$(min)=3.116, MS m/z=476.1 $[M-H]^-$.

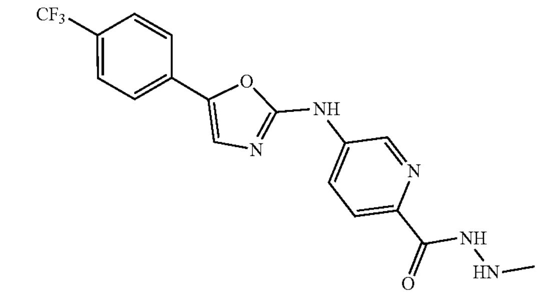 [SMILES: CNNC(=O)c1ccc(Nc2ncc(-c3ccc(C(F)(F)F)cc3)o2)cn1]

HCl (0.5 mL, 2.0 mmol, 4M in dioxane) was added to a solution of tert-butyl 1-methyl-2-(5-((5-(4-(trifluoromethyl)phenyl)oxazol-2-yl)amino)picolinoyl)hydrazine-1-carboxylate (0.06, 0.126 mmol) in MeOH (5 mL) at rt. The mixture was stirred overnight. The volatiles were removed under reduced pressure to give a residue that was purified using preparative HPLC in a 95% A: 5% B to 100% B solvent system. The TFA and acetonitrile were removed through rotary evaporation and $H_2O$ through freeze-drying, providing N'-methyl-5-((5-(4-(trifluoromethyl)phenyl)oxazol-2-yl)amino)picolinohydrazide (0.038 g, 80% yield). $^1H$ NMR (401 MHz, DMSO-$d_6$) δ 11.27 (s, 1H), 8.86 (d, J=2.4, 1H), 8.36 (dd, J=8.7, 2.5 Hz, 1H), 8.10 (d, J=8.7 Hz, 1H), 7.83 (br s, 4H), 7.81 (s, 1H), 2.80 (s, 3H). $^{13}C$ NMR (101 MHz, DMSO-$d_6$) δ 162.7, 156.1, 143.5, 140.4, 139.1, 137.6, 131.4, 126.1, 125.3, 123.8, 123.5, 123.2, 122.9, 66.4. LCMS $R_f$ (min)=3.893, HRMS (ESI) calcd for $C_{17}H_{15}F_3N_5O_2^+$ $[M+H]^+$ 378.1178, found 378.1190.

95. (R)—N-(2,3-dihydroxypropyl)-5-((5-(5-(trifluoromethyl)pyridin-2-yl)oxazol-2-yl)amino)picolinamide (Scheme 92)

Scheme 92

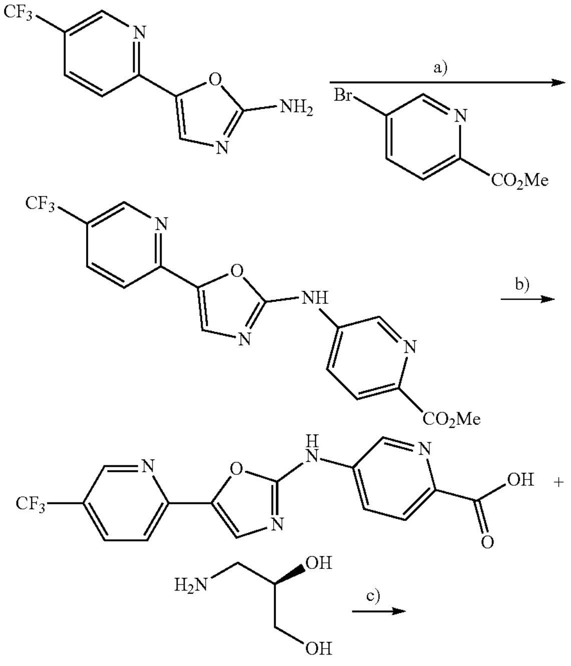

-continued

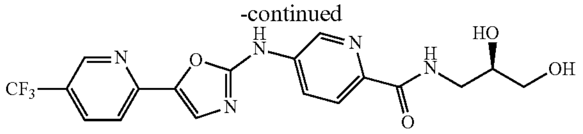

a) $Pd_2(dba)_3$, Xantphos, $Cs_2CO_3$, 1,4-dioxane, 90° C., 16 h;
b) $LiOH•H_2O$, 1,4-dioxane/MeOH/$H_2O$, rt, 18 h;
c) EDAC•HCl, HOBt, DMF, rt, overnight.

5-(5-(trifluoromethyl)pyridin-2-yl)oxazol-2-amine (0.6 g, 2.62 mmol) and methyl 5-bromopicolinate (0.68 g, 3.14 mmol) were reacted as per General Procedure 4 Method 1, using 5 mol % $Pd_2(dba)_3$, 10 mol % Xantphos, 1.5 eq $Cs_2CO_3$ in 1,4-dioxane at 90° C. for 16 h to give methyl 5-((5-(5-(trifluoromethyl)pyridin-2-yl)oxazol-2-yl)amino)picolinate (0.63 g, 63%). $^1H$ NMR (401 MHz, DMSO-$d_6$) δ 11.45 (br s, 1H), 8.94 (s, 1H), 8.84 (d, J=2.4 Hz, 1H), 8.32 (dd, J=8.7, 2.6 Hz, 1H), 8.27 (dd, J=8.4, 1.8 Hz, 1H), 8.09 (d, J=8.7 Hz, 1H), 7.94 (s, 1H), 7.81 (d, J=8.4 Hz, 1H), 3.85 (s, 3H). LCMS $R_f$ (min)=2.748, MS m/z=365.1 $[M+H]^+$.

$LiOH·H_2O$ (0.07 g, 1.65 mmol) was added to a suspension of methyl 5-((5-(5-(trifluoromethyl)pyridin-2-yl)oxazol-2-yl)amino)picolinate (0.20 g, 0.55 mmol) in 1,4-dioxane (2 mL), MeOH (2 mL) and $H_2O$ (2 mL). The reaction mixture was stirred at rt for 18 h. The volatiles were removed in vacuo and brine was added (2 mL). This residue was then acidified with 6M HCl aq. (2 mL) at 0° C. then filtered, washed with $H_2O$ (4 mL) and $Et_2O$ (4 mL) to give 5-((5-(5-(trifluoromethyl)pyridin-2-yl)oxazol-2-yl)amino)picolinic acid (0.18 g, 94% yield). $^1H$ NMR (401 MHz, DMSO-$d_6$) δ 11.42 (s, 1H), 8.94 (s, 1H), 8.84 (d, J=2.4 Hz, 1H), 8.33-8.23 (m, 2H), 8.08 (d, J=8.7 Hz, 1H), 7.93 (s, 1H), 7.81 (d, J=8.4 Hz, 1H). LCMS $R_f$ (min)=2.511, MS m/z=351.0 $[M+H]^+$.

EDAC·HCl (0.089 g, 0.46 mmol) and HOBt (0.068 g, 0.50 mmol) were added to a suspension of 5-((5-(5-(trifluoromethyl)pyridin-2-yl)oxazol-2-yl)amino)picolinic acid (0.125 g, 0.36 mmol) in DMF (8.0 mL). The resulting mixture was stirred at rt for 3 h. (R)-3-Aminopropane-1,2-diol·HCl (0.066 g, 0.72 mmol) was then added to the reaction mixture and stirring was continued overnight. The reaction mixture was concentrated under reduced pressure to obtain a gummy solid, which was purified using preparative HPLC in a 95% A: 5% B to 100% B solvent system. The TFA and acetonitrile were removed through rotary evaporation and $H_2O$ through freeze-drying, providing (R)—N-(2,3-dihydroxypropyl)-5-((5-(5-(trifluoromethyl)pyridin-2-yl)oxazol-2-yl)amino)picolinamide as a beige solid (0.07 g, 46% yield). $^1H$ NMR (400 MHz, DMSO-$d_6$) δ 11.32 (br s, 1H), 8.93 (m, 1H), 8.80 (d, J=2.2 Hz, 1H), 8.46 (t, J=5.9 Hz, 1H), 8.30 (dd, J=8.6, 2.0 Hz, 1H), 8.26 (dd, J=8.5, 1.9 Hz, 1H), 8.04 (d, J=8.6, 1H), 7.92 (s, 1H), 7.80 (d, J=8.4 Hz, 1H), 4.95 (d, J=4.9 Hz, 1H), 4.67 (t, J=5.6 Hz, 1H), 3.61 (m, 1H), 3.52-3.46 (m, 2H), 3.29-3.19 (m, 2H). $^{13}C$ NMR (101 MHz, DMSO-$d_6$) δ 163.7, 157.2, 149.9, 146.6, 143.6, 143.0, 138.0, 137.4, 134.8, 129.1, 125.2, 123.9, 122.6, 122.5, 119.78, 117.8, 70.2, 64.0, 42.4. LCMS $R_f$ (min)=3.218. HRMS (ESI) calcd for $C_{18}H_{17}F_3N_5O_4^+$ $[M+H]^+$ 424.1233, found 424.1232.

96. (R)—N-(2,3-dihydroxypropyl)-5-((4-methyl-5-(4-(trifluoromethyl)phenyl)oxazol-2-yl)amino)picolinamide (Scheme 93)

Scheme 93

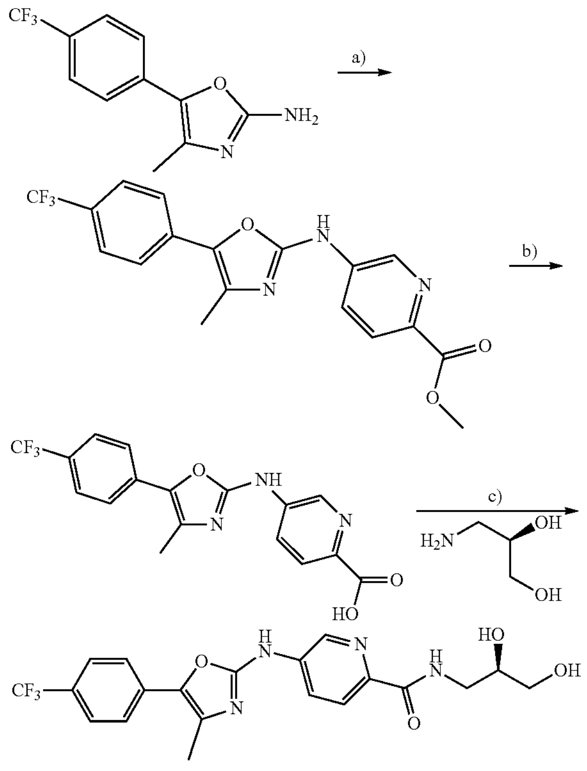

a) methyl 5-bromopicolinate, $Pd_2(dba)_3$, Xantphos, $Cs_2CO_3$, 1,4-dioxane, 100° C., 5 h;
b) $LiOH{\bullet}H_2O$, 1,4-dioxane: MeOH: $H_2O$ (1:1:1), rt, 3 h;
c) EDAC•HCl, HOBt, DMF, rt, overnight.

4-Methyl-5-(4-(trifluoromethyl)phenyl)oxazol-2-amine (0.23 g, 0.95 mmol) was reacted with methyl 5-bromopicolinate (0.246 g, 1.14 mmol), $Pd_2(dba)_3$ (0.043 g, 0.048 mmol), Xantphos (0.055 g, 0.095 mmol) and $Cs_2CO_3$ (0.464 g, 1.43 mmol) in 1,4-dioxane (8 mL) at 100° C. for 5 h as per General Procedure 4 Method 1 to provide methyl 5-((4-methyl-5-(4-(trifluoromethyl)phenyl)oxazol-2-yl)amino)picolinate in 89% yield (0.32 g). $^1$H NMR (401 MHz, DMSO-$d_6$) δ 8.07 (d, J=8.4 Hz, 2H), 7.85 (d, J=8.3 Hz, 2H), 7.85 (m, 1H), 7.40 (m, 1H), 7.10 (s, 1H), 3.84 (s, 3H), 2.40 (s, 3H). LCMS $R_f$ (min)=3.951, MS m/z=377.9 $[M+H]^+$.

$LiOH{\cdot}H_2O$ (0.40 g, 1.60 mmol) in $H_2O$ (1 mL) was added to a solution of methyl 5-((4-methyl-5-(4-(trifluoromethyl)phenyl)oxazol-2-yl)amino)picolinate (0.15 g, 0.40 mmol) in 1,4-dioxane (1 mL) and MeOH (1 mL). The reaction mixture was stirred at rt for 3 h. Volatile solvents were removed in vacuo and to the obtained suspension was added brine (2 mL), followed by HCl (2 mL, 6M) dropwise at 0° C. The resulting precipitate was filtered and washed with $H_2O$ (2×1 mL), providing 5-((4-methyl-5-(4-(trifluoromethyl)phenyl)oxazol-2-yl)amino)picolinic acid in 84% yield (0.122 g). $^1$H NMR (400 MHz, DMSO-$d_6$) δ 8.05 (d, J=8.2 Hz, 2H), 7.94 (d, J=8.3 Hz, 2H), 7.83 (d, J=3.0 Hz, 1H), 7.40 (dd, J=9.0, 3.1 Hz, 1H), 7.10 (d, J=8.9 Hz, 1H), 3.72 (s, 3H). LCMS $R_f$ (min)=3.379, MS m/z=364.0 $[M+H]^+$.

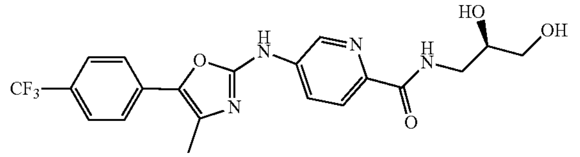 [SMILES: Cc1nc(Nc2ccc(C(=O)NC[C@@H](O)CO)nc2)oc1-c1ccc(C(F)(F)F)cc1]

EDAC·HCl (0.027 g, 0.14 mmol) and HOBt (0.021 g, 0.154 mmol) were added to a suspension of 5-((4-methyl-5-(4-(trifluoromethyl)phenyl)oxazol-2-yl)amino)picolinic acid (0.04 g, 0.11 mmol) in DMF (2 mL). The resulting mixture was stirred at rt for 3 h. (R)-3-Aminopropane-1,2-diol·HCl (0.02 g, 0.22 mmol) was then added to the reaction mixture and stirring was continued overnight. The reaction mixture was concentrated under reduced pressure to obtain a gummy solid, which was purified using preparative HPLC in a 95% A:5% B to 100% B solvent system. The TFA and acetonitrile were removed through rotary evaporation and $H_2O$ through freeze-drying, providing (R)—N-(2,3-dihydroxypropyl)-5-((4-methyl-5-(4-(trifluoromethyl)phenyl)oxazol-2-yl)amino)picolinamide as a beige solid (0.032 g, 67% yield). $^1$H NMR (400 MHz, DMSO-$d_6$) δ 11.02 (br s, 1H), 8.79 (d, J=2.4 Hz, 1H), 8.44 (t, J=5.8 Hz, 1H), 8.29 (dd, J=8.6, 2.6 Hz, 1H), 8.04 (d, J=8.6 Hz, 1H), 7.82 (d, J=8.5 Hz, 2H), 7.73 (d, J=8.3 Hz, 2H), 4.94 (d, J=4.9 Hz, 1H), 4.66 (t, J=5.5 Hz, 1H), 3.62 (m, 1H), 3.52-3.46 (m, 2H), 3.25-3.19 (m, 2H). $^{13}$C NMR (101 MHz, DMSO-$d_6$) δ 163.7, 154.7, 142.7, 138.2, 137.5, 137.2, 134.6, 132.4, 126.0, 124.2, 123.5, 122.6, 70.2, 63.9, 42.4, 13.7. LCMS $R_f$ (min)=2.740. HRMS (ESI) calcd for $C_{20}H_{20}F_3N_4O_4^+$ $[M+H]^+$ 437.1437, found 437.1442.

97. (R)-5-((5-(3,4-Difluorophenyl)oxazol-2-yl)amino)-N-(2,3-dihydroxypropyl)picolinamide (Scheme 94)

Scheme 94

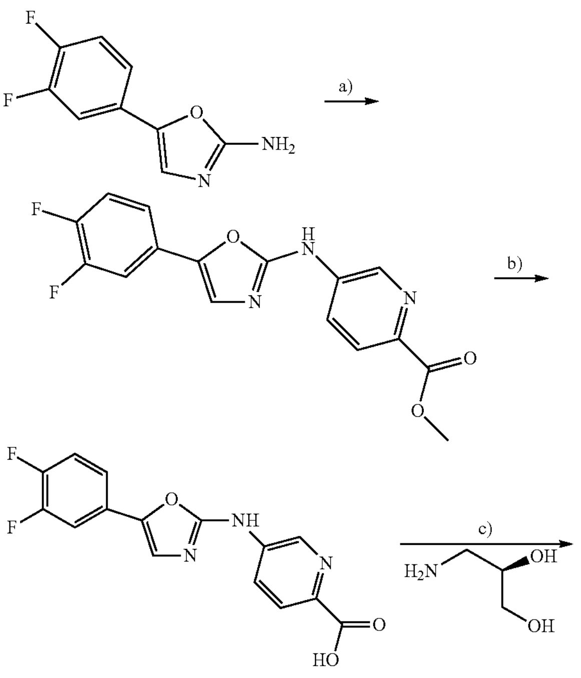

-continued

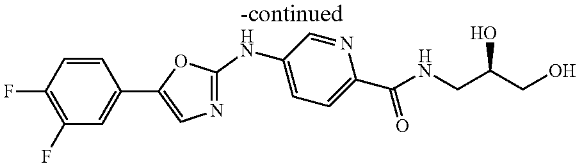

a) methyl 5-bromopicolinate, $Pd_2(dba)_3$, Xantphos, $Cs_2CO_3$, 1,4-dioxane, 100° C., 5 h;
b) $LiOH{\bullet}H_2O$, 1,4-dioxane: MeOH: $H_2O$ (1:1:1), rt, 3 h;
c) EDAC•HCl, HOBt, DMF, rt, overnight.

5-(3,4-Difluorophenyl)oxazol-2-amine (0.25 g, 1.27 mmol) was reacted with methyl 5-bromopicolinate (0.33 g, 1.53 mmol), $Pd_2(dba)_3$ (0.058 g, 0.064 mmol), Xantphos (0.044 g, 0.076 mmol) and $Cs_2CO_3$ (0.622 g, 1.91 mmol) in 1,4-dioxane (10 mL) at 100° C. for 5 h as per General Procedure 4 Method 1 to provide methyl 5-((5-(3,4-difluorophenyl)oxazol-2-yl)amino)picolinate in 88% yield (0.37 g). $^1$H NMR (401 MHz, DMSO-$d_6$) δ 8.54 (s, 1H), 8.21 (dd, J=8.8, 2.5 Hz, 1H), 7.92 (d, J=8.8 Hz, 1H), 7.79 (m, 1H), 7.60 (m, 1H), 7.51 (s, 1H), 7.46 (s, 1H), 7.36 (m, 1H), 3.80 (s, 3H). LCMS $R_f$ (min)=3.068, MS m/z=332.0 $[M+H]^+$.

$LiOH{\cdot}H_2O$ (0.101 g, 4.23 mmol) in $H_2O$ (2 mL) was added to a solution of methyl 5-((5-(3,4-difluorophenyl)oxazol-2-yl)amino)picolinate (0.35 g, 1.05 mmol) in 1,4-dioxane (2 mL) and MeOH (2 mL). The reaction mixture was stirred at rt for 3 h. Organic solvents were removed in vacuo and to the obtained suspension was added brine (2 mL), followed by HCl (2 mL, 6M) dropwise at 0° C. The resulting precipitate was filtered and washed with $H_2O$ (2×2 mL), providing 5-((5-(3,4-difluorophenyl)oxazol-2-yl)amino)picolinic acid in 80% yield (0.267 g). $^1$H NMR (401 MHz, DMSO-$d_6$) δ 11.30 (br s, 1H), 8.87 (d, J=2.4 Hz, 1H), 8.33 (dd, J=8.7, 2.5 Hz, 1H), 8.10 (d, J=8.7 Hz, 1H), 7.70 (m, 1H), 7.64 (s, 1H), 7.54 (m, 1H), 7.45 (m, 1H). LCMS $R_f$ (min)=3.003, MS m/z=318.0 $[M+H]^+$.

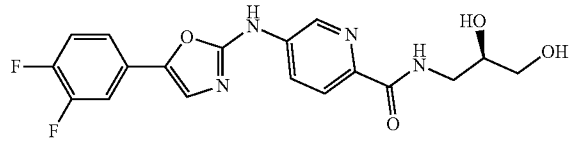 [SMILES: O=C(NC[C@@H](O)CO)c1ccc(Nc2ncc(-c3ccc(F)c(F)c3)o2)cn1]

5-((5-(3,4-Difluorophenyl)oxazol-2-yl)amino)picolinic acid (0.10 g, 0.315) was reacted with EDAC·HCl (0.079 g, 0.41 mmol), HOBt (0.059 g, 0.441 mmol) and (R)-3-aminopropane-1,2-diol (0.034 g, 0.378 mmol) as per step c, Scheme 92 to provide (R)-5-((5-(3,4-difluorophenyl)oxazol-2-yl)amino)-N-(2,3-dihydroxypropyl)picolinamide in 35% yield (0.043 g). $^1$H NMR (400 MHz, DMSO-$d_6$) δ 11.04 (s, 1H), 8.78 (d, J=2.3 Hz, 1H), 8.45 (t, J=5.9 Hz, 1H), 8.29 (dd, J=8.6, 2.6 Hz, 1H), 8.03 (d, J=8.7 Hz, 1H), 7.69 (ddd, J=11.7, 7.6, 2.1 Hz, 1H), 7.62 (s, 1H), 7.55 (dt, J=10.5, 8.5 Hz, 1H), 7.43 (m, 1H), 4.95 (d, J=5.0 Hz, 1H), 4.66 (t, J=5.8 Hz, 1H), 3.61 (dt, J=10.8, 5.3 Hz, 1H). *Resonances that overlapped with $H_2O$ residue were not assigned. $^{13}$C NMR (101 MHz, DMSO-$d_6$) δ 163.9, 155.8, 142.6, 138.2, 137.1, 123.8, 123.4, 122.6, 119.6, 118.6, 112.1, 111.9, 70.2, 63.9, 42.3. LCMS $R_f$ (min)=2.949. HRMS (ESI) calcd for $C_{18}H_{17}F_2N_4O_4^+$ $[M+H]^+$ 391.1218, found 391.1222.

98. (R)—N-(2,3-dihydroxypropyl)-5-((5-(4-fluorophenyl)oxazol-2-yl)amino)picolinamide (Scheme 95)

Scheme 95

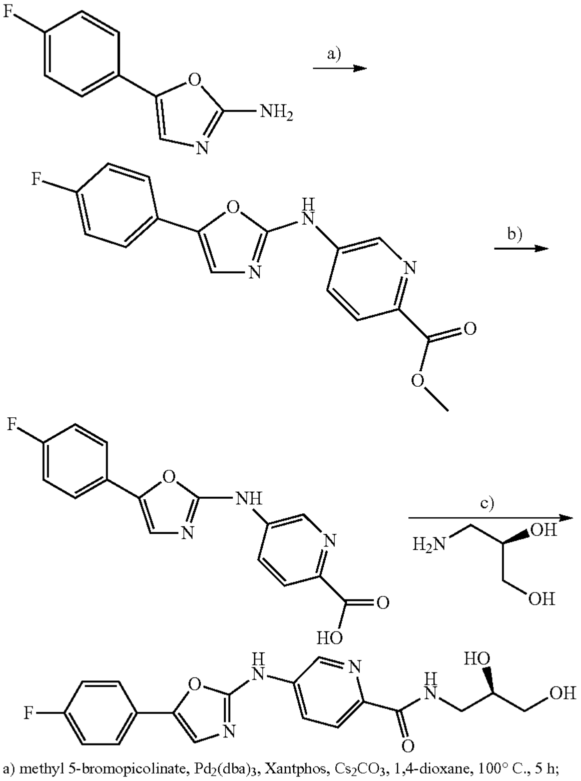

a) methyl 5-bromopicolinate, $Pd_2(dba)_3$, Xantphos, $Cs_2CO_3$, 1,4-dioxane, 100° C., 5 h;
b) $LiOH{\bullet}H_2O$, 1,4-dioxane: MeOH:$H_2O$ (1:1:1), rt, 3 h;
c) EDAC•HCl, HOBt, DMF, rt, overnight.

5-(4-Fluorophenyl)oxazol-2-amine (0.17 g, 0.95 mmol) was reacted with methyl 5-bromopicolinate (0.247 g, 1.15 mmol), $Pd_2(dba)_3$ (0.043 g, 0.048 mmol), Xantphos (0.033 g, 0.057 mmol) and $Cs_2CO_3$ (0.464 g, 1.43 mmol) in 1,4-dioxane (10 mL) at 100° C. for 5 h as per General Procedure 4 Method 1 to provide methyl 5-((5-(4-fluorophenyl)oxazol-2-yl)amino)picolinate in 82% yield (0.243 g). $^1$H NMR (401 MHz, DMSO-$d_6$) δ 8.56 (s, 1H), 8.22 (m, 1H), 7.92 (d, J=8.7 Hz, 1H), 7.58 (m, 2H), 7.42 (s, 1H), 7.25 (m, 2H), 3.80 (s, 3H). LCMS $R_f$ (min)=2.767, MS m/z=314.1 $[M+H]^+$.

$LiOH{\cdot}H_2O$ (0.058 g, 2.43 mmol) in $H_2O$ (3 mL) was added to a solution of methyl 5-((5-(4-fluorophenyl)oxazol-2-yl)amino)picolinate (0.19 g, 0.61 mmol) in 1,4-dioxane (3 mL) and MeOH (3 mL). The reaction mixture was stirred at rt for 3 h. Volatile solvents were removed in vacuo and to the obtained suspension was added brine (2 mL), followed by HCl (2 mL, 6M) dropwise at 0° C. The resulting precipitate was filtered and washed with $H_2O$ (2×2 mL), providing 5-((5-(4-fluorophenyl)oxazol-2-yl)amino)picolinic acid in 86% yield (0.158 g). $^1$H NMR (401 MHz, DMSO-$d_6$) δ 11.08 (s, 1H), 8.82 (d, J=2.3 Hz, 1H), 8.29 (dd, J=8.7, 2.6 Hz, 1H), 8.06 (d, J=8.6 Hz, 1H), 7.80-7.60 (m, 2H), 7.54 (s, 1H), 7.31 (dd, J=12.4, 5.5 Hz, 2H). LCMS $R_f$ (min)=2.966, MS m/z=300.1 $[M+H]^+$.

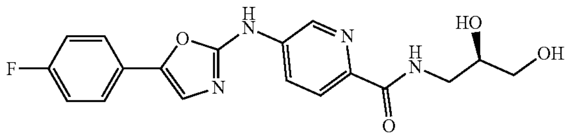 [SMILES: O=C(NC[C@@H](O)CO)c1ccc(Nc2ncc(-c3ccc(F)cc3)o2)cn1]

5-((5-(4-Fluorophenyl)oxazol-2-yl)amino)picolinic acid (0.10 g, 0.334) was reacted with EDAC·HCl (0.083 g, 0.434 mmol), HOBt (0.063 g, 0.468 mmol) and (R)-3-aminopropane-1,2-diol (0.036 g, 0.40 mmol) as per step c, Scheme 92 to provide (R)—N-(2,3-dihydroxypropyl)-5-((5-(4-fluorophenyl)oxazol-2-yl)amino)picolinamide in 44% yield (0.055 g). $^1$H NMR (400 MHz, DMSO-$d_6$) δ 10.97 (br s, 1H), 8.78 (d, J=2.6 Hz, 1H), 8.44 (t, J=5.9 Hz, 1H), 8.29 (dd, J=8.7, 2.6 Hz, 1H), 8.03 (d, J=8.6 Hz, 1H), 7.66 (dd, J=8.8, 5.3 Hz, 2H), 7.53 (s, 1H), 7.31 (t, J=8.9 Hz, 2H), 4.95 (d, J=5.0 Hz, 1H), 4.66 (t, J=5.7 Hz, 1H), 3.61 (m, 1H). *Resonance overlapping with $H_2O$ residue were not assigned. $^{13}$C NMR (101 MHz, DMSO-$d_6$) δ 160.8, 152.1, 144.3, 142.6, 139.3, 138.3, 137.1, 130.4, 129.6, 123.2, 122.2, 120.6, 118.5, 117.6, 115.3, 111.7, 110.2, 70.66, 65.1, 42.70. LCMS $R_f$ (min)=2.965. HRMS (ESI) calcd for $C_{18}H_{18}FN_4O_4^+$ [M+H]$^+$ 373.1312, found 373.1306.

99. N'-Hydroxy-5-((5-(5-(trifluoromethoxy)pyridin-2-yl)oxazol-2-yl)amino)picolinimidamide (Scheme 96)

Scheme 96

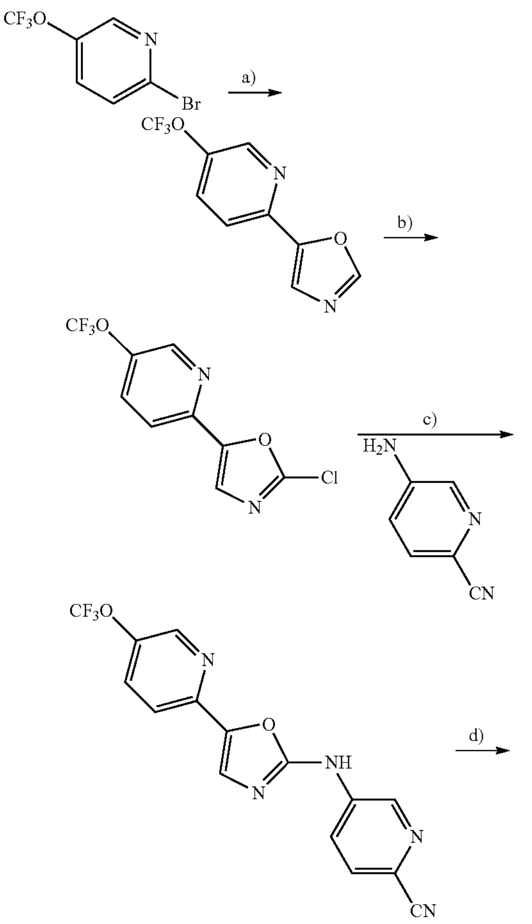

-continued

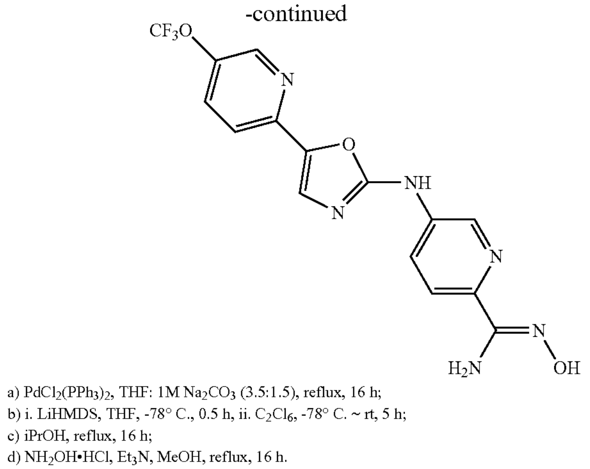

To a degassed biphasic solution of THF (3.5 mL) and 1 M $Na_2CO_3$ (aq.) (1.5 mL), was added 2-bromo-5-(trifluoromethoxy)pyridine (1.20 g, 4.96 mmol), 5-(4,4,5,5-tetramethyl-1,3,2-dioxaborolan-2-yl)oxazole (1.0 M in THF, 5.45 mL, 5.45 mmol) and $PdCl_2(PPh_3)_2$ (348 mg, 0.496 mmol). The mixture was reacted according to General Procedure 12 Method 1 to afford 5-(5-(trifluoromethoxy)pyridin-2-yl)oxazole as a brown solid (57.8 mg, 5.1%). $^1$H NMR (401 MHz, $CDCl_3$) δ 8.52 (d, J=2.6 Hz, 1H), 7.95 (s, 1H), 7.72-7.66 (m, 2H), 7.63-7.56 (m, 1H).

5-(5-(Trifluoromethoxy)pyridin-2-yl)oxazole (0.33 g, 1.43 mmol) was reacted with LiHMDS (1.57 mL, 1.57 mmol, 1 M in hexane) and $C_2Cl_6$ (0.51 g, 2.15 mmol) in THF (6 mL) as per General Procedure 15 Method 1 to provide 2-chloro-5-(5-(trifluoromethoxy)pyridin-2-yl)oxazole (0.322 g, 85%) as a white solid. $^1$H NMR (401 MHz, $CDCl_3$) δ 8.51 (s, 1H), 7.76-7.49 (m, 3H), LCMS $R_f$ (min)=3.065, MS m/z=265.0 [M+H]$^+$.

2-Chloro-5-(5-(trifluoromethoxy)pyridin-2-yl)oxazole (185 mg, 0.699 mmol, 1.0 eq.) and 5-aminopicolinonitrile (125 mg, 1.05 mmol, 1.5 eq.) in 2-propanol (5 mL) was reacted according to General Procedure 2 Method 1 to afford 5-((5-(5-(trifluoromethoxy)pyridin-2-yl)oxazol-2-yl)amino)picolinonitrile as a beige solid (205.1 mg, 85%) $^1$H NMR (401 MHz, DMSO-$d_6$) δ 8.85 (d, J=2.6 Hz, 1H), 8.67 (d, J=2.8 Hz, 1H), 8.33 (dd, J=8.7, 2.6 Hz, 1H), 8.00 (m, 2H), 7.83-7.71 (m, 2H). LCMS $R_f$ (min)=2.905, MS m/z=348.1 [M+H]$^+$.

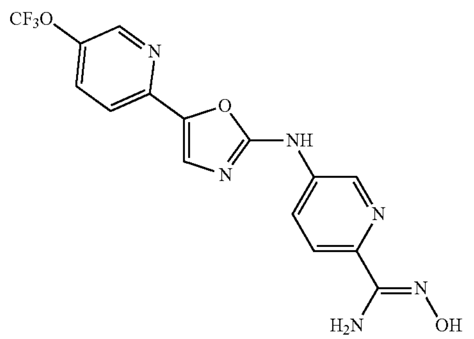

5-((5-(5-(Trifluoromethoxy)pyridin-2-yl)oxazol-2-yl)amino)picolinonitrile (285 mg, 0.821 mmol, 1.0 eq.), $NH_2OH$·HCl (456 mg, 6.57 mmol, 8.0 eq.) and $Et_3N$ (0.916 mL, 6.57 mmol 8.0 eq.) in anhydrous MeOH (10 mL) was reacted according to General Procedure 1 Method 2 to afford N'-hydroxy-5-((5-(5-(trifluoromethoxy)pyridin-2-yl)oxazol-2-yl)amino)picolinimidamide as a beige solid (0.027 g, 22%). $^1$H NMR (401 MHz, DMSO-$d_6$) δ 9.75 (s, 1H), 8.79 (d, J=2.4 Hz, 1H), 8.66 (d, J=2.6 Hz, 1H), 8.13 (dd, J=8.8, 2.6 Hz, 1H), 8.02-7.94 (m, 1H), 7.84 (d, J=8.8 Hz, 1H), 7.74 (m, 2H), 5.76 (s, 2H); $^{13}$C NMR (101 MHz, DMSO) δ 157.0, 149.4, 145.9, 143.5, 143.4, 143.2, 143.0, 136.9, 136.1, 130.4, 130.4, 127.2, 124.0, 119.7, 119.0. LCMS $R_f$ (min)=2.385, MS m/z=381.1 [M+H]$^+$. HRMS (ESI) calcd for $C_{15}H_{12}F_3N_6O_3^+$ ([M+H]$^+$ 381.0917, found 381.0935.

100. 5-((5-(4-Chlorophenyl)oxazol-2-yl)amino)-N'-hydroxypicolinimidamide (Scheme 97)

Scheme 97

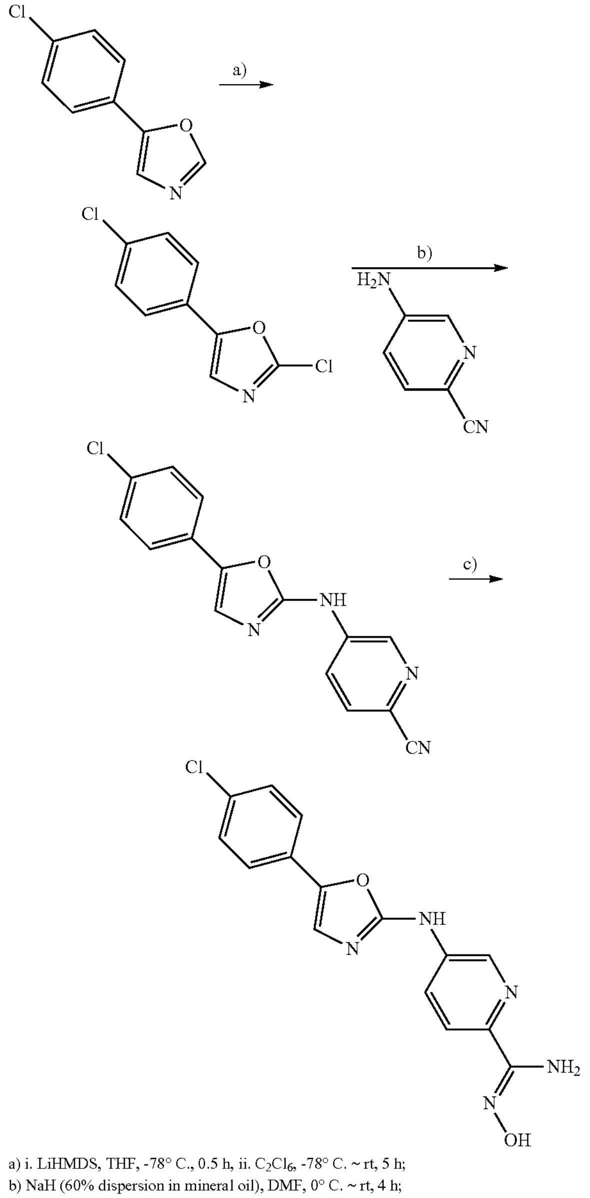

a) i. LiHMDS, THF, -78° C., 0.5 h, ii. $C_2Cl_6$, -78° C. ~ rt, 5 h;
b) NaH (60% dispersion in mineral oil), DMF, 0° C. ~ rt, 4 h;
d) $NH_2OH$•HCl, $Et_3N$, MeOH, reflux, 16 h.

5-(4-Chlorophenyl)oxazole (5.0 g, 27.8 mmol) was reacted with LiHMDS (33.4 mL, 33.4 mmol) then $C_2Cl_6$ (9.9 g, 41.8 mmol) in dry THF as per General Procedure 15 Method 1 to give 2-chloro-5-(4-chlorophenyl)oxazole (5.1 g, 86% yield) as a white solid. $^1$H NMR (401 MHz, $CDCl_3$) δ 7.57-7.50 (m, 2H), 7.44-7.38 (m, 2H), 7.28 (s, 1H). LCMS $R_f$ (min)=3.265, MS m/z=214.0 [M+H]$^+$.

5-Aminopicolinonitrile (200 mg, 1.68 mmol, 1.0 eq.), NaH (60%, 60 mg, 2.52 mmol, 1.5 eq.) and 2-chloro-5-(4-chlorophenyl)oxazole (431 mg, 2.01 mmol, 1.2 eq.) in anhydrous DMF (4 mL) was reacted according to General Procedure 2 Method 2 to afford 5-((5-(4-chlorophenyl)oxazol-2-yl)amino)picolinonitrile as a beige solid (186 mg, 37%). $^1$H NMR (401 MHz, DMSO-$d_6$) δ 8.82 (d, J=2.4 Hz, 1H), 8.31 (dd, J=8.7, 2.6 Hz, 1H), 7.98 (d, J=8.8 Hz, 1H), 7.66-7.60 (m, 3H), 7.54-7.48 (m, 2H), $^{13}$C NMR (101 MHz, DMSO-$d_6$) δ 155.21, 144.11, 140.19, 139.20, 131.99, 129.94, 129.27, 126.51, 124.69, 123.72, 123.37, 122.68, 118.15. LCMS $R_f$ (min)=3.039, MS m/z=297.0 [M+H]$^+$.

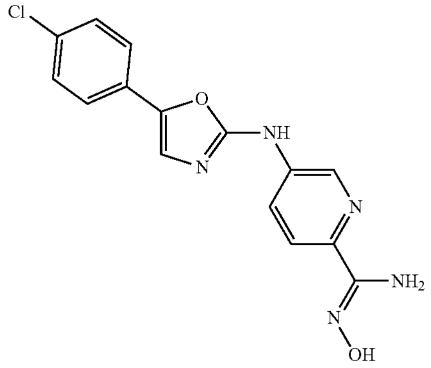 [SMILES: N/C(=N\O)c1ccc(Nc2ncc(-c3ccc(Cl)cc3)o2)cn1]

5-((5-(4-Chlorophenyl)oxazol-2-yl)amino)picolinonitrile (50 mg, 0.169 mmol, 1.0 eq.), $NH_2OH$·HCl (47 mg, 0.674 mmol, 4.0 eq.) and $Et_3N$ (94 μL, 0.674 mmol, 4.0 eq.) in anhydrous MeOH (2 mL) was reacted according to General Procedure 1 Method 2 to afford 5-((5-(4-chlorophenyl)oxazol-2-yl)amino)-N'-hydroxypicolinimidamide as a beige solid (48 mg, 86%). $^1$H NMR (401 MHz, DMSO-$d_6$) δ 10.80 (s, 1H), 9.75 (s, 1H), 8.76 (d, J=2.5 Hz, 1H), 8.11 (dd, J=8.8, 2.6 Hz, 1H), 7.82 (d, J=8.8 Hz, 1H), 7.62 (d, J=8.6 Hz, 2H), 7.56 (s, 1H), 7.50 (d, J=8.6 Hz, 2H), 5.76 (s, 2H), $^{13}$C NMR (101 MHz, DMSO-$d_6$) δ 156.06, 149.48, 143.43, 142.98, 136.76, 136.34, 131.57, 129.14, 126.73, 124.41, 123.82, 123.37, 119.74. LCMS $R_f$ (min)=2.446, MS m/z=330.1 [M+H]$^+$. HRMS (ESI) calcd for $C_{15}H_{13}ClN_5O_2^+$ ([M+H]$^+$ 330.0752, found 330.0764.

101. 5-((5-(4-Chlorophenyl)oxazol-2-yl)amino)-N'-hydroxypyrazine-2-carboximidamide (Scheme 98)

Scheme 98

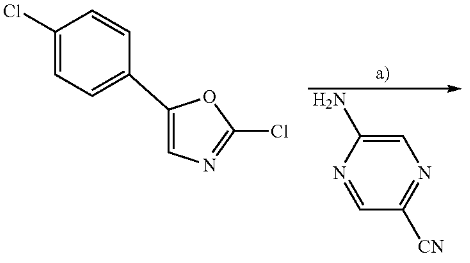

-continued

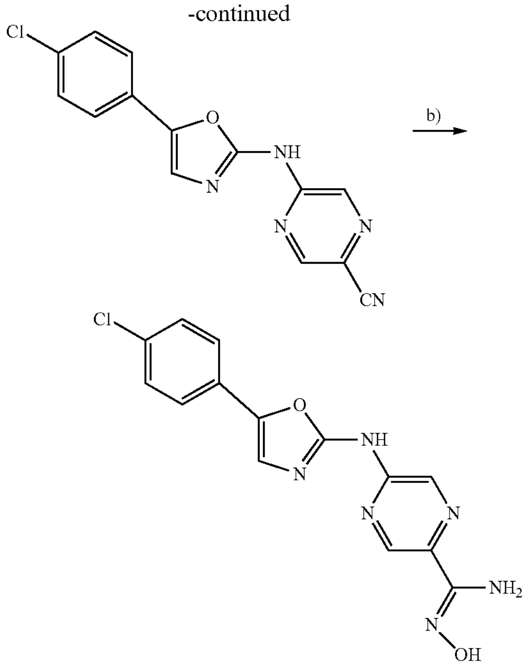

a) NaH (60% dispersion in mineral oil), DMF, 0° C. ~ rt, 4 h;
b) $NH_2OH$•HCl, $Et_3N$, MeOH, reflux, 16 h.

5-Aminopyrazine-2-carbonitrile (200 mg, 1.67 mmol, 1.0 eq.), NaH (60%, 60 mg, 2.50 mmol, 1.5 eq.) and 2-chloro-5-(4-chlorophenyl)oxazole (428 mg, 2.00 mmol, 1.2 eq.) in anhydrous DMF (4 mL) was reacted according to General Procedure 2 Method 2 to afford 5-((5-(4-chlorophenyl) oxazol-2-yl)amino)pyrazine-2-carbonitrile as a yellow solid (355 mg, 72%). $^1$H NMR (401 MHz, DMSO-$d_6$) δ 9.21 (s, 1H), 8.85 (d, J=1.3 Hz, 1H), 7.69 (s, 1H), 7.68-7.63 (m, 2H), 7.56-7.51 (m, 2H); $^{13}$C NMR (101 MHz, DMSO-$d_6$) δ 154.23, 147.62, 132.33, 129.28, 126.31, 124.91, 120.39, 117.00, 113.95 ppm. LCMS $R_f$ (min)=3.010, MS m/z=298.0 $[M+H]^+$.

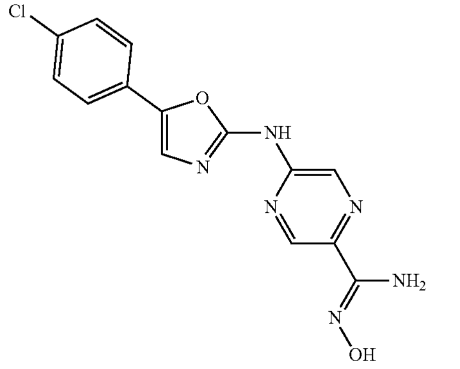

5-((5-(4-Chlorophenyl)oxazol-2-yl)amino)pyrazine-2-carbonitrile (50 mg, 0.168 mmol, 1.0 eq.), $NH_2OH$·HCl (47 mg, 0.672 mmol, 4.0 eq.) and $Et_3N$ (94 μL, 0.672 mmol, 4.0 eq.) in anhydrous MeOH (2 mL) was reacted according to General Procedure 1 Method 2 to afford 5-((5-(4-chlorophenyl)oxazol-2-yl)amino)-N'-hydroxypyrazine-2-carboximidamide as a white solid (43 mg, 77%). $^1$H NMR (401 MHz, DMSO-$d_6$) δ 9.09 (s, 1H), 8.38 (s, 1H), 7.89 (s, 1H), 6.92-6.73 (m, 3H), 6.68 (d, J=8.3 Hz, 2H), 5.01 (s, 2H); $^{13}$C NMR (101 MHz, DMSO-$d_6$) δ 154.92, 148.36, 139.30, 138.91, 131.82, 129.17, 126.55, 124.57, 123.35. LCMS $R_f$ (min)=2.537, MS m/z=331.0 $[M+H]^+$. HRMS (ESI) calcd for $C_{14}H_{12}ClN_6O_2^+$ ($[M+H]^+$ 331.0705, found 331.0704.

102. 5-((5-(5-Chloropyridin-2-yl)oxazol-2-yl)amino)-N'-hydroxypyrazine-2-carboximidamide (Scheme 99)

Scheme 99

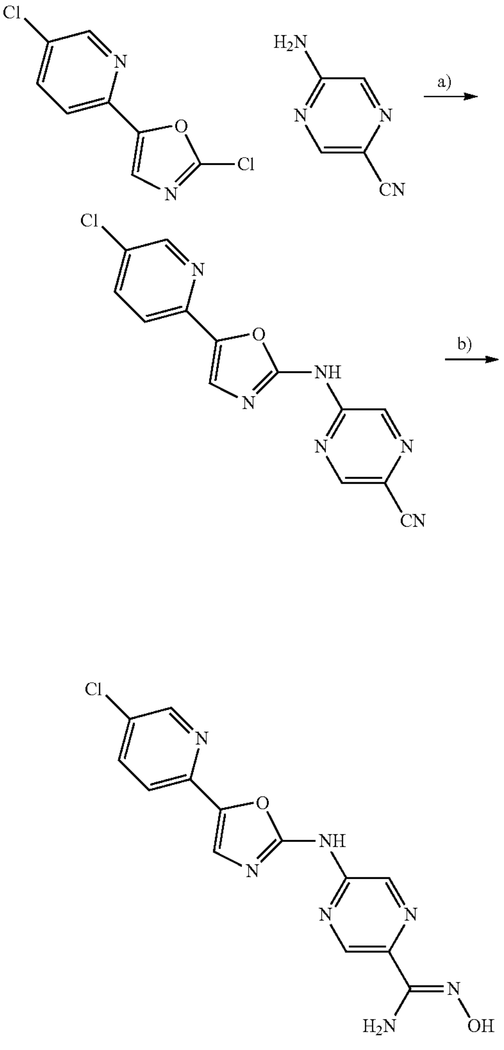

a) NaH (60% dispersion in mineral oil), DMF, 0° C. ~ rt, 4 h;
b) $NH_2OH$•HCl, $Et_3N$, MeOH, reflux, 16 h.

5-Aminopyrazine-2-carbonitrile (279 mg, 2.33 mmol, 1.2 eq.), NaH (60%, 84 mg, 3.49 mmol, 3.0 eq.) and 2-chloro-5-(5-chloropyridin-2-yl)oxazole (250 mg, 1.16 mmol, 1.0 eq.) in anhydrous DMF (5 mL) was reacted according to General Procedure 2 Method 2 to afford 5-((5-(5-chloropyridin-2-yl)oxazol-2-yl)amino)pyrazine-2-carbonitrile as a yellow solid (232 mg, 67%). $^1$H NMR (401 MHz, DMSO-$d_6$) δ 9.23 (s, 1H), 8.83 (s, 1H), 8.64 (d, J=2.3 Hz, 1H), 8.07-7.97 (m, 1H), 7.79 (s, 1H), 7.67 (d, J=8.6 Hz, 1H). LCMS $R_f$ (min)=2.717, MS m/z=299.1 $[M+H]^+$.

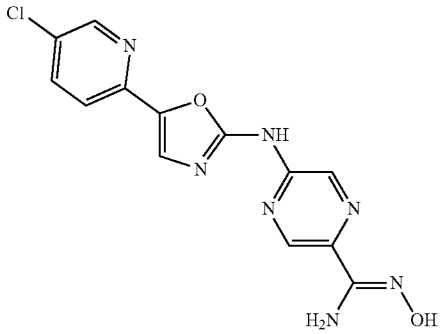 [SMILES: N/C(=N\O)c1cnc(Nc2ncc(-c3ccc(Cl)cn3)o2)cn1]

5-((5-(5-Chloropyridin-2-yl)oxazol-2-yl)amino)pyrazine-2-carbonitrile (100 mg, 0.336 mmol, 1.0 eq.), $NH_2OH{\cdot}HCl$ (93 mg, 1.34 mmol, 4.0 eq.) and $Et_3N$ (187 μL, 1.34 mmol, 4.0 eq.) in anhydrous MeOH (5 mL) was reacted according to General Procedure 1 Method 2 to afford 5-((5-(5-chloropyridin-2-yl)oxazol-2-yl)amino)-N'-hydroxypyrazine-2-carboximidamide as a beige solid (91 mg, 81%). $^1H$ NMR (401 MHz, DMSO-$d_6$) δ 9.96 (s, 1H), 9.25 (s, 1H), 8.75 (m, 1H), 8.63 (d, J=2.4 Hz, 1H), 8.02 (dd, J=8.5, 2.5 Hz, 1H), 7.77 (s, 1H), 7.66 (d, J=8.5 Hz, 1H), 5.86 (s, 2H). LCMS $R_f$ (min)=2.423, MS m/z=332.1 $[M+H]^+$. HRMS (ESI) calcd for $C_{13}H_{11}ClN_7O_2^+$ ($[M+H]^+$ 332.0657, found 332.0666.

103. 5-((1-(5-Chloropyridin-2-yl)-1H-pyrazol-4-yl)amino)-N'-hydroxypicolinimidamide (Scheme 100)

Scheme 100

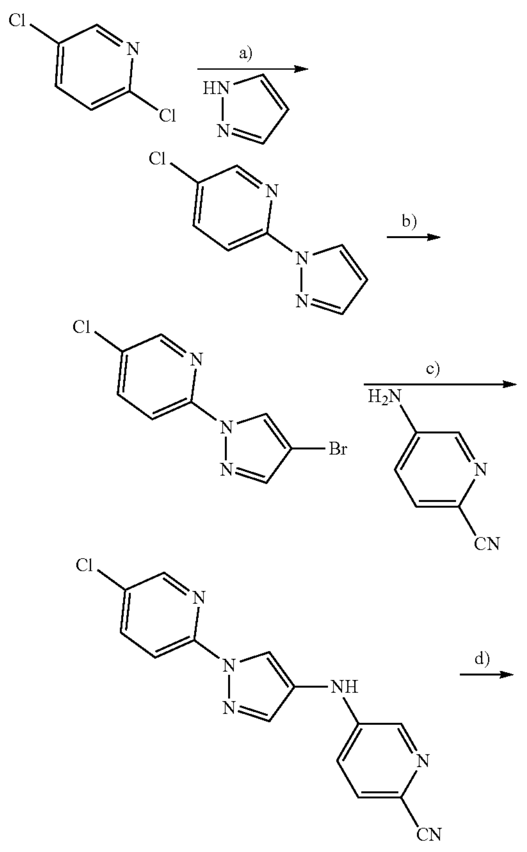

-continued

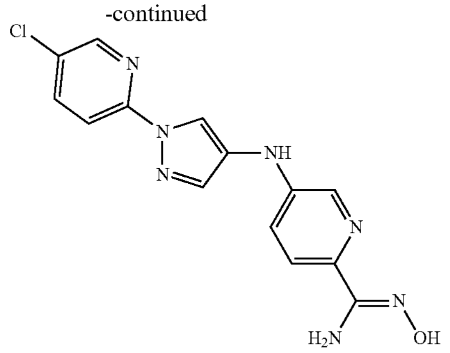

a) $K_2CO_3$, DMF, 100° C., 16 h; b) NBS, MeCN, 25° C., 16 h; c) tBuBrettPhos Pd G3, $Cs_2CO_3$, tBuOH, reflux, 16 h; d) $NH_2OH{\cdot}HCl$, $Et_3N$, MeOH, reflux, 16 h.

To a solution of 2,5-dichloropyridine (3.0 g, 20.3 mmol, 1.0 eq.) in DMF (25 mL), was added $K_2CO_3$ (7.0 g, 50.7 mmol, 2.5. eq.) and 1H-pyrazole (2.76 g, 40.5 mmol, 2.0 eq.), and the mixture was allowed to stir at 100° C. for 16 h. Upon cooling, the reaction mixture was concentrated in vacuo and purified via column chromatography (petroleum spirits, 0-20% EtOAc) to give 5-chloro-2-(1H-pyrazol-1-yl)pyridine as a white solid (3.21 g, 88%). $^1H$ NMR (401 MHz, DMSO-$d_6$) δ 8.56 (dd, J=2.6, 0.6 Hz, 1H), 8.51-8.47 (m, 1H), 8.07 (dd, J=8.8, 2.6 Hz, 1H), 7.92 (dd, J=8.8, 0.5 Hz, 1H), 7.83 (dd, J=1.5, 0.5 Hz, 1H), 6.58 (dd, J=2.6, 1.7 Hz, 1H). LCMS $R_f$ (min)=2.992, MS m/z=180.1 $[M+H]^+$.

To a solution of 5-chloro-2-(1H-pyrazol-1-yl)pyridine (3.0 g, 16.7 mmol, 1.0 eq.) in MeCN (25 mL) was added N-bromosuccinimide (4.46 g, 25.1 mmol, 1.5 eq.), and the mixture was allowed to stir at 25° C. for 16 h. Upon completion, the reaction mixture was concentrated in vacuo and purified via reverse-phase column chromatography ($H_2O$, MeCN 10-100%) to give 2-(4-bromo-1H-pyrazol-1-yl)-5-chloropyridine as a white solid (499 mg, 12%). $^1H$ NMR (401 MHz, DMSO-$d_6$) δ 8.82-8.75 (m, 1H), 8.55 (d, J=2.3 Hz, 1H), 8.13 (dd, J=8.8, 2.6 Hz, 1H), 7.99 (s, 1H), 7.92 (d, J=8.8 Hz, 1H). $^{13}C$ NMR (101 MHz, DMSO-$d_6$) δ 148.80, 146.82, 142.96, 139.59, 129.02, 127.62, 113.26, 96.42. LCMS $R_f$ (min)=3.396, MS m/z=258.0 $[M+H]^+$.

2-(4-Bromo-1H-pyrazol-1-yl)-5-chloropyridine (150 mg, 0.58 mmol, 1.0 eq.), 5-aminopicolinonitrile (104 mg, 0.87 mmol, 1.5 eq.), $Cs_2CO_3$ (567 mg, 1.74 mmol, 3.0 eq.) in tBuOH was charged with tBuBrettPhos Pd G3 (25 mg, 0.029 mmol, 0.05 eq.) and was reacted according to General Procedure 4 Method 2 to afford 5-((1-(5-chloropyridin-2-yl)-1H-pyrazol-4-yl)amino)picolinonitrile as a brown solid (105 mg, 61%). $^1H$ NMR (401 MHz, DMSO-$d_6$) δ 9.14 (s, 1H), 8.65-8.48 (m, 2H), 8.28 (d, J=2.3 Hz, 1H), 8.10 (dd, J=8.8, 2.2 Hz, 1H), 7.93 (m, 2H), 7.76 (d, J=8.7 Hz, 1H), 7.34 (dd, J=8.6, 2.5 Hz, 1H). LCMS $R_f$ (min)=2.898, MS m/z=297.0 $[M+H]^+$.

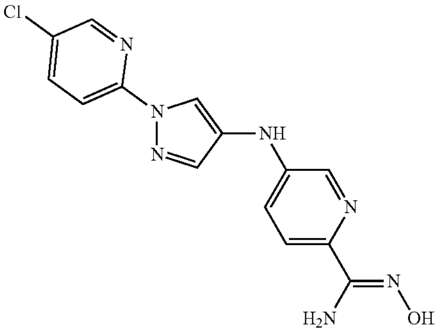 [SMILES: N/C(=N\O)c1ccc(Nc2cnn(-c3ccc(Cl)cn3)c2)cn1]

5-((1-(5-Chloropyridin-2-yl)-1H-pyrazol-4-yl)amino)picolinonitrile (105 mg, 0.353 mmol, 1.0 eq.), $NH_2OH{\cdot}HCl$ (98 mg, 1.41 mmol, 4.0 eq.) and $Et_3N$ (197 μL, 1.41 mmol, 4.0 eq.) in anhydrous MeOH (5 mL) was reacted according to General Procedure 1 Method 2 to afford 5-((1-(5-chloropyridin-2-yl)-1H-pyrazol-4-yl)amino)-N'-hydroxypicolinimidamide as a beige solid (70 mg, 60%). $^1H$ NMR (401 MHz, DMSO-$d_6$) δ 9.57 (s, 1H), 8.57-8.51 (m, 2H), 8.47 (s, 1H), 8.19 (d, J=2.6 Hz, 1H), 8.09 (dd, J=8.8, 2.5 Hz, 1H), 7.92 (d, J=8.9 Hz, 1H), 7.87 (s, 1H), 7.71 (d, J=8.7 Hz, 1H), 7.34 (dd, J=8.7, 2.7 Hz, 1H), 5.67 (s, 2H). $^{13}C$ NMR (101 MHz, DMSO-$d_6$) δ 149.33, 149.17, 146.31, 141.34, 139.50, 138.85, 136.35, 134.07, 127.48, 126.98, 119.82, 119.70, 115.27, 112.51. LCMS $R_f$ (min)=2.271, MS m/z=330.1 $[M+H]^+$. HRMS (ESI) calcd for $C_{14}H_{13}ClN_7O^+$ ($[M+H]^+$ 330.0865, found 330.0872.

104. rac-N-(2,3-Dihydroxypropyl)-5-((1-(5-(trifluoromethyl)pyridin-2-yl)-1H-pyrazol-4-yl)amino)picolinamide (Scheme 101)

Scheme 101

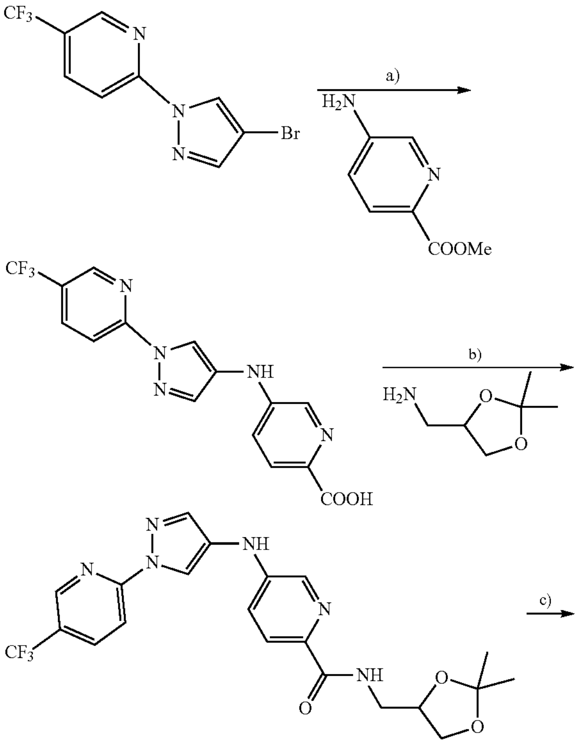

-continued

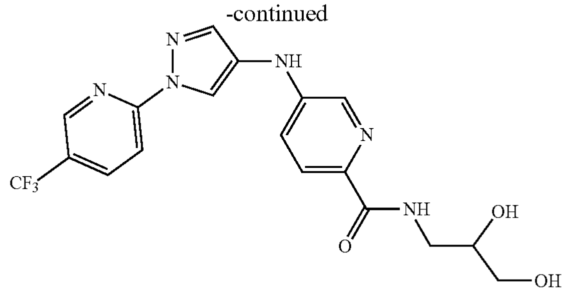

*a*) i. tBuBrettPhos Pd G3, $Cs_2CO_3$, tBuOH, reflux, 16 h, ii. $LiOH{\cdot}H_2O$, 80° C., 1 h;
*b*) EDCI•HCl, HOBt, DIPEA, anhydrous DMF, 25° C., 16 h;
*c*) TFA, 25° C., 2 h.

A solution of 2-(4-bromo-1H-pyrazol-1-yl)-5-(trifluoromethyl)pyridine (Intermediate M, 250 mg, 0.856 mmol, 1.0 eq.), methyl 5-aminopicolinate (153 mg, 1.28 mmol, 1.5 eq.), $Cs_2CO_3$ (837 mg, 2.57 mmol, 3.0 eq.) in tBuOH (5 mL) was charged with tBuBrettPhos Pd G3 (37 mg, 0.043 mmol, 0.05 eq.) and the mixture was subjected to three cycles of evacuation and backfilling with $N_2$. The reaction mixture was heated to refluxed and stirred for 16 h. Upon cooling, $LiOH{\cdot}H_2O$ (108 mg, 2.57 mmol, 3 eq.) in $H_2O$ (1.5 mL) was added and the mixture was stirred at 80° C. for 1 h. The suspension was acidified with concentrated HCl to pH 1, at which precipitation was observed. The precipitate was filtered and washed with $H_2O$ (15 mL) to yield the crude material, which was purified via reverse-phase column chromatography ($H_2O$, MeCN 10-100%) to afford 5-((1-(5-(trifluoromethyl)pyridin-2-yl)-1H-pyrazol-4-yl)amino)picolinic acid as a yellow solid (108 mg, 38%). $^1H$ NMR (401 MHz, DMSO-$d_6$) δ 9.00 (s, 1H), 8.88 (d, J=0.8 Hz, 1H), 8.63 (s, 1H), 8.37 (dd, J=8.8, 2.3 Hz, 1H), 8.30 (d, J=2.6 Hz, 1H), 8.09 (d, J=8.7 Hz, 1H), 8.00 (s, 1H), 7.93 (d, J=8.7 Hz, 1H), 7.39 (dd, J=8.7, 2.8 Hz, 1H). LCMS $R_f$ (min)=2.541, MS m/z=350.1 $[M+H]^+$ To a solution of 5-((1-(5-(trifluoromethyl)pyridin-2-yl)-1H-pyrazol-4-yl)amino)picolinic acid (80 mg, 0.229 mmol, 1.0 eq.), EDCI·HCl (57 mg, 0.298 mmol, 1.3 eq.), HOBt (43 mg, 0.321 mmol, 1.4 eq.), DIPEA (79 μL, 0.458 mmol, 2.0 eq.) in anhydrous DMF (5 mL) was added (2,2-dimethyl-1,3-dioxolan-4-yl)methanamine hydrochloride (60 mg, 0.458 mmol, 2.0 eq.). The reaction was allowed to stir at 25° C. for 16 h. Upon completion, the reaction was added to a mixture of ice-water (25 mL), at which precipitation was observed. The precipitate was filtered to afford rac-N-((2,2-dimethyl-1,3-dioxolan-4-yl)methyl)-5-((1-(5-(trifluoromethyl)pyridin-2-yl)-1H-pyrazol-4-yl)amino)picolinamide as orange solid (89 mg, 84%). $^1H$ NMR (401 MHz, DMSO-$d_6$) δ 8.88 (dd, J=6.6, 5.3 Hz, 2H), 8.61 (d, J=0.6 Hz, 1H), 8.43 (t, J=6.1 Hz, 1H), 8.36 (dd, J=8.8, 2.3 Hz, 1H), 8.24 (d, J=2.7 Hz, 1H), 8.09 (d, J=8.7 Hz, 1H), 7.98 (d, J=0.7 Hz, 1H), 7.90 (d, J=8.6 Hz, 1H), 7.43 (dd, J=8.6, 2.8 Hz, 1H), 4.30-4.16 (m, 1H), 3.97 (dd, J=8.3, 6.4 Hz, 1H), 3.70 (dd, J=8.3, 5.7 Hz, 1H), 3.41 (d, J=6.0 Hz, 2H), 1.35 (s, 3H), 1.26 (s, 3H); $^{13}C$ NMR (101 MHz, DMSO-$d_6$) δ 164.19, 153.20, 145.91, 143.41, 139.45, 137.84, 136.98, 135.16, 127.01, 123.23, 122.66, 122.34, 119.02, 116.34, 111.64, 108.43, 74.25, 66.67, 41.49, 26.82, 25.28. LCMS $R_f$ (min)=2.978, MS m/z=463.2 $[M+H]^+$

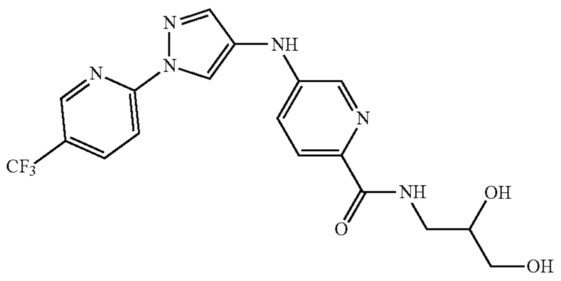 [SMILES: O=C(NCC(O)CO)c1ccc(Nc2cnn(-c3ccc(C(F)(F)F)cn3)c2)cn1]

rac-N-((2,2-Dimethyl-1,3-dioxolan-4-yl)methyl)-5-((1-(5-(trifluoromethyl)pyridin-2-yl)-1H-pyrazol-4-yl)amino) picolinamide (70 mg, 0.151 mmol, 1.0 eq.) was stirred in TFA (2 mL) at 25° C. for 2 h. Upon completion, the reaction was concentrated in vacuo and subjected to purification via reverse-phase column chromatography ($H_2O$, MeCN 10-100%) to afford rac-N-(2,3-dihydroxypropyl)-5-((1-(5-(trifluoromethyl)pyridin-2-yl)-1H-pyrazol-4-yl)amino)picolinamide as a beige solid (18 mg, 28%). $^1H$ NMR (401 MHz, DMSO-$d_6$) δ 8.94-8.84 (m, 2H), 8.61 (s, 1H), 8.36 (dd, J=8.7, 2.1 Hz, 1H), 8.31 (t, J=5.9 Hz, 1H), 8.25 (d, J=2.7 Hz, 1H), 8.09 (d, J=8.7 Hz, 1H), 7.98 (s, 1H), 7.90 (d, J=8.6 Hz, 1H), 7.44 (dd, J=8.6, 2.7 Hz, 1H), 4.93 (d, J=4.9 Hz, 1H), 4.65 (t, J=5.7 Hz, 1H), 3.65-3.54 (m, 1H), 3.54-3.43 (m, 1H), 3.24-3.12 (m, 1H) *Resonances that overlapped with $H_2O$ were not assigned; $^{13}C$ NMR (101 MHz, DMSO-$d_6$) δ 164.06, 153.20, 145.92, 143.33, 139.93, 139.62, 137.81, 136.98, 135.18, 127.06, 123.10, 122.66, 119.07, 116.27, 111.65, 70.32, 63.93, 42.23. LCMS $R_f$(min)=2.566, MS m/z=423.1 [M+H]$^+$. HRMS (ESI) calcd for $C_{18}H_{18}F_3N_6O_3^+$ ([M+H]$^+$ 423.1387, found 423.1399.

105. 6-((5-(4-(Trifluoromethoxy)phenyl)oxazol-2-yl)amino)pyridin-3-ol (Scheme 102)

Scheme 102

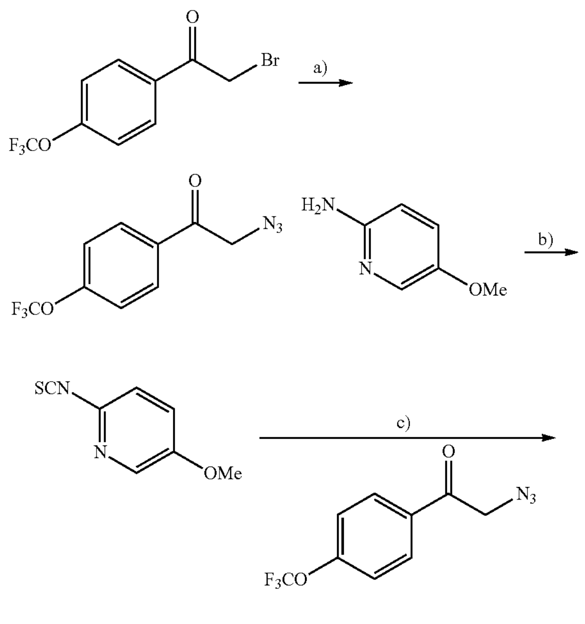

-continued

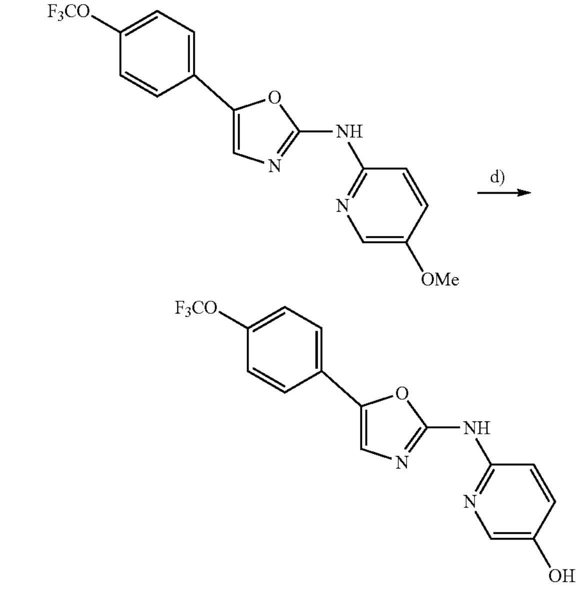

a) $NaN_3$, acetone, rt, on;
b) Thiophosgene, 25% $NaHCO_3$ (aq.), acetone, rt, 1 h;
c) $PPh_3$, 1,4-dioxane, 90° C., 2 h;
d) $BBr_3$, DCM, rt, 48 h.

A solution of 2-bromo-1-(4-(trifluoromethoxy)phenyl) ethan-1-one (0.51 g, 1.80 mmol) and $NaN_3$ (0.23 g, 3.59 mmol) in acetone (9 mL) was stirred for 18 h at rt. The reaction mixture was then concentrated in vacuo and the residue was redissolved in EtOAc (30 mL), washed with $H_2O$ (15 mL) and brine (15 mL). The organic layer was dried over $MgSO_4$ and concentrated under reduced pressure to give 2-azido-1-(4-(trifluoromethoxy)phenyl)ethan-1-one as a yellow solid (0.41 g, 92%). $^1H$ NMR (401 MHz, $CDCl_3$) δ 7.98 (d, J=9.0 Hz, 2H), 7.33 (m, 2H), 4.54 (s, 2H).

5-Methoxypyridin-2-amine (0.33 g, 2.63 mmol) was reacted with thiophosgene (0.24 mL, 3.15 mmol) as per General Procedure 6. The suspension was allowed to stir for 1 h at rt to give 2-isothiocyanato-5-methoxypyridine as an orange wax (0.24 g, 54% yield). $^1H$ NMR (401 MHz, $CDCl_3$) δ 8.09 (d, J=2.8 Hz, 1H), 7.21 (dd, J=8.7, 3.1 Hz, 1H), 7.07 (m, 1H), 3.87 (s, 3H).

2-Azido-1-(4-(trifluoromethoxy)phenyl)ethan-1-one (0.20 g, 0.83 mmol) and 2-isothiocyanato-5-methoxypyridine (0.15 g, 0.92 mmol) were reacted as per General Procedure 5 for 2.5 h. The reaction mixture was then concentrated to a solid and triturated with DCM to give N-(5-methoxypyridin-2-yl)-5-(4-(trifluoromethoxy)phenyl) oxazol-2-amine (0.15 g, 51% yield) as a white solid. $^1H$ NMR (401 MHz, DMSO-$d_6$) δ 10.73 (s, 1H), 8.01 (m, 1H), 7.98 (d, J=9.1 Hz, 1H), 7.69 (d, J=8.9 Hz, 2H), 7.54 (s, 1H), 7.49-7.41 (m, 3H), 3.80 (s, 3H). LCMS $R_f$(min)=2.97, MS m/z=352.1 [M+H]$^+$.

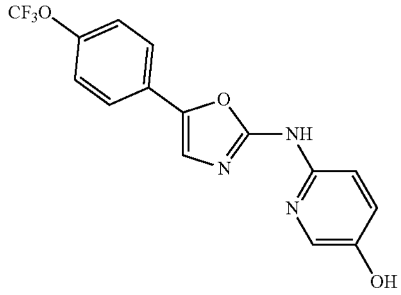

N-(5-Methoxypyridin-2-yl)-5-(4-(trifluoromethoxy)phenyl)oxazol-2-amine (0.10 g, 0.29 mmol) was demethylated as per General Procedure 8 using $BBr_3$ (1.0 M in DCM, 0.9 mL, 0.88 mmol) in dry DCM (1.5 mL) and the reaction mixture was allowed to stir for 48 h at rt. The crude residue was purified through C18 reverse phase column chromatography to give 6-((5-(4-(trifluoromethoxy)phenyl)oxazol-2-yl)amino)pyridin-3-ol (0.04 g, 38%) as an off-white solid. $^1$H NMR (401 MHz, DMSO-$d_6$) δ 10.56 (s, 1H), 9.48 (s, 1H), 7.87 (d, J=8.9 Hz, 1H), 7.84 (d, J=2.9 Hz, 1H), 7.68 (d, J=8.9 Hz, 2H), 7.51 (s, 1H), 7.43 (d, J=8.1 Hz, 2H), 7.23 (dd, J=8.9, 3.0 Hz, 1H). $^{13}$C NMR (101 MHz, DMSO-$d_6$) δ 156.6, 149.0, 146.9, 144.5, 142.7, 135.0, 127.4, 125.0, 124.3, 123.5, 121.80, 111.6. LCMS $R_f$ (min)=2.65, MS m/z=338.1 [M+H]$^+$ HRMS (ESI) calcd for $C_{15}H_{11}F_3N_3O_3^+$ [M+H]$^+$ 338.0747, found 338.0757.

106. N'-Hydroxy-5-((1-(4-(trifluoromethyl)phenyl)-1H-1,2,4-triazol-3-yl)amino)pyrazine-2-carboximidamide (Scheme 103)

Scheme 103

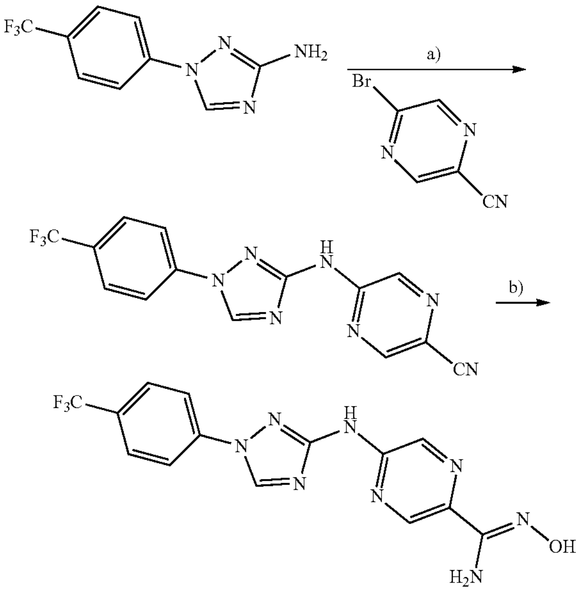

a) $Pd_2(dba)_3$, Xantphos, $Cs_2CO_3$, 1,4-Dioxane, 90° C., 16 h; $NH_2OH$•HCl, $NEt_3$, MeOH, 80° C., 18 h.

Intermediate F (0.07 g, 0.33 mmol) and 5-bromopyrazine-2-carbonitrile (0.05 g, 0.27 mmol) were reacted as per General Procedure 4 Method 1, using 5 mol % $Pd_2(dba)_3$, 10 mol % Xantphos, 1.5 eq $Cs_2CO_3$ and heated at 90° C. for 16 h. The crude residue was purified as described in General Procedure 4 Method 1 to give 5-((1-(4-(trifluoromethyl)phenyl)-1H-1,2,4-triazol-3-yl)amino)pyrazine-2-carbonitrile (0.07 g, 80% yield) as an orange solid. $^1$H NMR (401 MHz, DMSO-$d_6$) δ 11.39 (s, 1H), 9.41 (s, 1H), 9.24 (d, J=1.1 Hz, 1H), 8.80 (d, J=1.4 Hz, 1H), 8.12 (d, J=8.5 Hz, 2H), 7.96 (d, J=8.6 Hz, 2H). LCMS $R_f$ (min)=2.90, MS m/z=332.0 [M+H]$^+$.

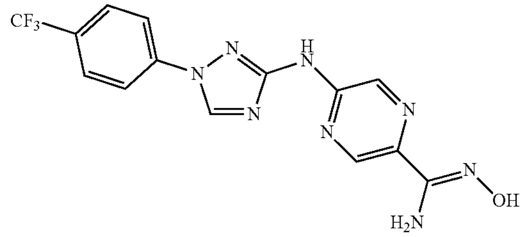 [SMILES: N/C(=N\O)c1cnc(Nc2ncn(-c3ccc(C(F)(F)F)cc3)n2)cn1]

5-((1-(4-(Trifluoromethyl)phenyl)-1H-1,2,4-triazol-3-yl)amino)pyrazine-2-carbonitrile (0.06 g, 0.18 mmol) was reacted as per General Procedure 1 Method 2 using $NH_2OH$·HCl (0.05 g, 0.70 mmol) and $NEt_3$ (0.1 mL, 0.70 mmol) in dry MeOH (1 mL) to give N'-hydroxy-5-((1-(4-(trifluoromethyl)phenyl)-1H-1,2,4-triazol-3-yl)amino)pyrazine-2-carboximidamide (0.04 g, 67% yield) as a pink solid. $^1$H NMR (401 MHz, DMSO-$d_6$) δ 10.70 (s, 1H), 9.89 (s, 1H), 9.36 (s, 1H), 9.25 (d, J=1.1 Hz, 1H), 8.70 (d, J=1.2 Hz, 1H), 8.11 (d, J=8.4 Hz, 2H), 7.96 (d, J=8.6 Hz, 2H), 5.84 (s, 2H). $^{13}$C NMR (101 MHz, DMSO-$d_6$) δ 159.2, 149.88, 148.5, 139.5, 139.3, 137.7, 130.7, 127.1, 118.8. LCMS $R_f$ (min)=2.44. MS m/z=365.1 [M+H]$^+$. HRMS (ESI) calcd for $C_{14}H_{12}F_3N_8O^+$ [M+H]$^+$ 365.1081, found 365.1100.

107. N'-Hydroxy-5-((1-(5-(trifluoromethyl)pyridin-2-yl)-1H-1,2,4-triazol-3-yl)amino)picolinimidamide (Scheme 104)

Scheme 104

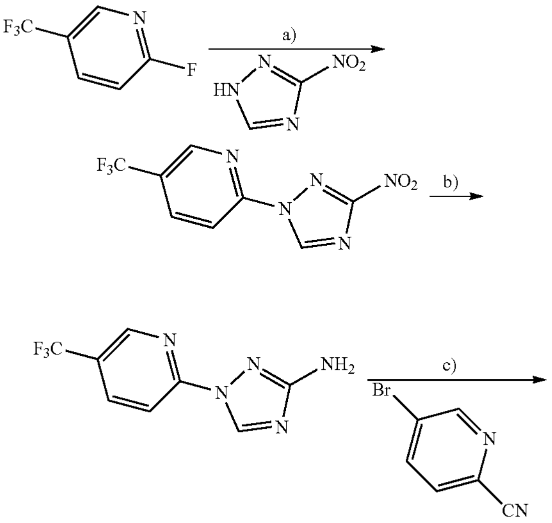

-continued

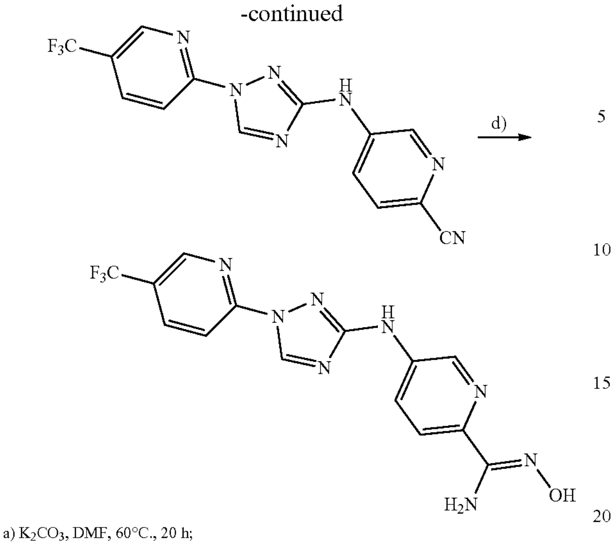

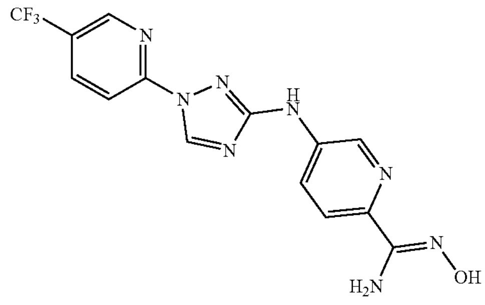 [SMILES: N/C(=N\O)c1ccc(Nc2ncn(-c3ccc(C(F)(F)F)cn3)n2)cn1]

a) $K_2CO_3$, DMF, 60°C., 20 h;
b) Pd/C, $H_2$, MeOH, rt, 2 h;
c) $Pd_2(dba)_3$, Xantphos, $Cs_2CO_3$, 1,4-Dioxane, 90° C., 16 h;
d) $NH_2OH$•HCl, $NEt_3$, MeOH, reflux, 2 h.

A suspension of 2-fluoro-5-(trifluoromethyl)pyridine (3.0 g, 18.17 mmol), 3-nitro-1H-1,2,4-triazole (3.11 g, 27.26 mmol) and $K_2CO_3$ (6.28 g, 45.43 mmol) in DMF (90 mL) was heated to 60° C. and allowed to stir for 20 h. The reaction mixture was diluted with EtOAc (2×100 mL), washed with $H_2O$ (100 mL) and brine (100 mL). The organic layer was dried over $MgSO_4$ and concentrated under reduced pressure. The resultant crude residue was purified by flash chromatography, eluting with 20-30% EtOAc in petroleum spirit to give 2-(3-nitro-1H-1,2,4-triazol-1-yl)-5-(trifluoromethyl)pyridine (2.50 g, 53% yield) as a white solid. $^1$H NMR (401 MHz, DMSO-$d_6$) δ 9.79 (s, 1H), 9.08 (dd, J=1.5, 0.8 Hz, 1H), 8.58 (ddd, J=8.7, 2.4, 0.5 Hz, 1H), 8.17 (d, J=8.6 Hz, 1H). LCMS $R_f$ (min)=2.85, MS m/z=260.1 $[M+H]^+$.

A solution of 2-(3-nitro-1H-1,2,4-triazol-1-yl)-5-(trifluoromethyl)pyridine (1.50 g, 5.79 mmol) in MeOH (50 mL) was evacuated and backfilled with $N_2$×3, then 10% Pd/C (0.75 g) was added. The suspension was evacuated and flushed with $H_2$×3 and stirred under a hydrogen atmosphere (balloon) for 2 h. The reaction mixture was then filtered through a pad of celite and the filtrate was concentrated under reduced pressure to give 1-(5-(trifluoromethyl)pyridin-2-yl)-1H-1,2,4-triazol-3-amine (0.78 g, 59% yield) as a black solid. $^1$H NMR (401 MHz, DMSO-$d_6$) δ 8.99 (s, 1H), 8.84 (dd, J=1.5, 0.8 Hz, 1H), 8.37 (dd, J=8.7, 2.0 Hz, 1H), 7.74 (d, J=8.6 Hz, 1H), 6.05 (s, 2H). LCMS $R_f$ (min)=2.60. MS m/z=230.1 $[M+H]^+$.

1-(5-(Trifluoromethyl)pyridin-2-yl)-1H-1,2,4-triazol-3-amine (0.05 g, 0.22 mmol) and 5-bromopicolinonitrile (0.04 g, 0.20 mmol) were reacted as per General Procedure 4 Method 1, using 5 mol % $Pd_2(dba)_3$, 10 mol % Xantphos, 1.5 eq $Cs_2CO_3$ and heated at 90° C. for 16 h. The crude residue was purified as per General Procedure 4 Method 1 to give 5-((1-(5-(trifluoromethyl)pyridin-2-yl)-1H-1,2,4-triazol-3-yl)amino)picolinonitrile (0.04 g, 65% yield) as a grey solid. $^1$H NMR (401 MHz, DMSO-$d_6$) δ 10.70 (s, 1H), 9.39 (s, 1H), 8.94 (s, 1H), 8.89 (d, J=2.6 Hz, 1H), 8.48 (dd, J=8.7, 2.3 Hz, 1H), 8.32 (dd, J=8.7, 2.6 Hz, 1H), 8.07 (d, J=8.5 Hz, 1H), 7.97 (d, J=8.7 Hz, 1H); LCMS $R_f$ (min)=2.91. MS m/z=332.1 $[M+H]^+$.

5-((1-(5-(Trifluoromethyl)pyridin-2-yl)-1H-1,2,4-triazol-3-yl)amino)picolinonitrile (0.05 g, 0.16 mmol) was reacted as per General Procedure 1 Method 3 using $NH_2OH \cdot HCl$ (0.04 g, 0.63 mmol) and $NEt_3$ (0.09 mL, 0.63 mmol) in dry MeOH (1.0 mL). The resultant crude residue was then purified by C18 reverse phase column chromatography to give N'-hydroxy-5-((1-(5-(trifluoromethyl)pyridin-2-yl)-1H-1,2,4-triazol-3-yl)amino)picolinimidamide (0.02 g, 40%) as a white solid. $^1$H NMR (401 MHz, DMSO-$d_6$) δ 10.14 (s, 1H), 9.69 (s, 1H), 9.32 (s, 1H), 8.92 (s, 1H), 8.87 (d, J=2.4 Hz, 1H), 8.46 (dd, J=8.7, 2.1 Hz, 1H), 8.10 (dd, J=8.8, 2.6 Hz, 1H), 8.04 (d, J=8.6 Hz, 1H), 7.82 (d, J=8.8 Hz, 1H), 5.74 (s, 2H). $^{13}$C NMR (101 MHz, DMSO-$d_6$) δ 160.8, 149.5, 141.9, 137.9, 136.8, 123.4, 119.6, 112.2; LCMS $R_f$ (min)=3.13, MS m/z=365.1 $[M+H]^+$. HRMS (ESI) calcd for $C_{14}H_{12}F_3N_8O$ $[M+H]^+$ 365.1081, found 365.1093.

108. N'-Hydroxy-5-((1-(5-(trifluoromethyl)pyridin-2-yl)-1H-1,2,4-triazol-3-yl)amino)pyrazine-2-carboximidamide (Scheme 105)

Scheme 105

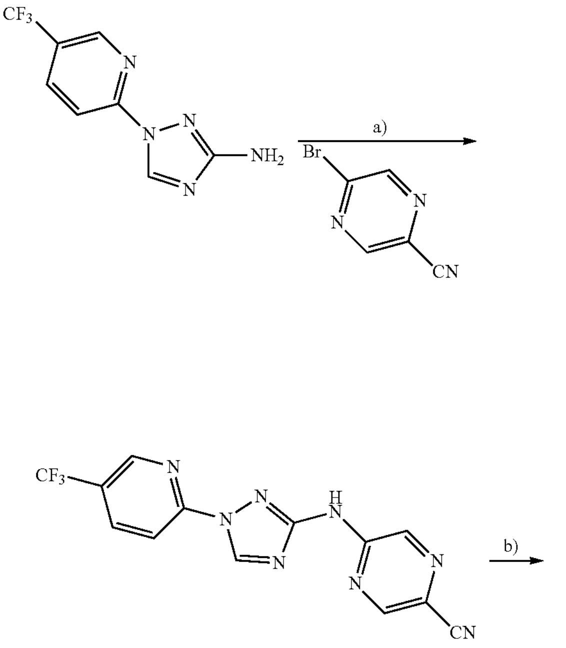

-continued

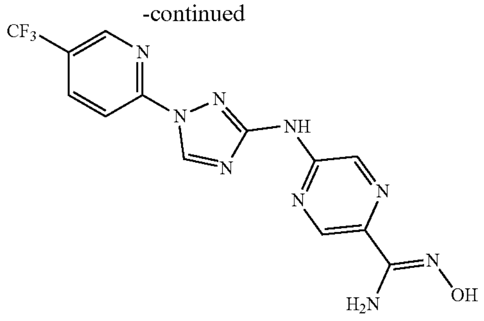

a) $Pd_2(dba)_3$, Xantphos, $Cs_2CO_3$, 1,4-Dioxane, 90° C., 16 h;
b) $NH_2OH{\bullet}HCl$, $NEt_3$, MeOH, reflux, 3 h.

1-(5-(Trifluoromethyl)pyridin-2-yl)-1H-1,2,4-triazol-3-amine (0.05 g, 0.22 mmol) and 5-Bromopyrazine-2-carbonitrile (0.04 g, 0.20 mmol) were reacted as per General Procedure 4 Method 1, using 5 mol % $Pd_2(dba)_3$, 10 mol % Xantphos, 1.5 eq $Cs_2CO_3$ and heated at 90° C. for 16 h. The crude residue was purified as per General Procedure 4 Method 1 to give 5-((1-(5-(trifluoromethyl)pyridin-2-yl)-1H-1,2,4-triazol-3-yl)amino)pyrazine-2-carbonitrile (0.02 g, 25% yield) as a grey solid. $^1H$ NMR (401 MHz, DMSO-$d_6$) δ 11.13 (s, 1H), 9.44 (s, 1H), 9.27 (s, 1H), 8.96 (s, 1H), 8.83 (s, 1H), 8.49 (dd, J=8.6, 2.3 Hz, 1H), 8.07 (d, J=8.6 Hz, 1H); LCMS $R_f$ (min)=2.88. MS m/z=333.1 $[M+H]^+$.

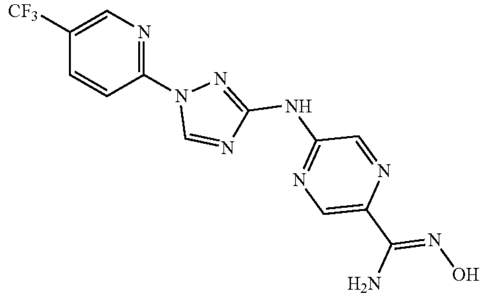 [SMILES: N/C(=N\O)c1cnc(Nc2ncn(-c3ccc(C(F)(F)F)cn3)n2)cn1]

5-((1-(5-(Trifluoromethyl)pyridin-2-yl)-1H-1,2,4-triazol-3-yl)amino)pyrazine-2-carbonitrile (0.02 g, 0.06 mmol) was reacted as per General Procedure 1 Method 3 using $NH_2OH{\cdot}HCl$ (0.02 g, 0.22 mmol) and $NEt_3$ (0.03 mL, 0.22 mmol) in dry MeOH (0.3 mL) to give N'-hydroxy-5-((1-(5-(trifluoromethyl)pyridin-2-yl)-1H-1,2,4-triazol-3-yl)amino)pyrazine-2-carboximidamide (0.02 g, 74%) as white solid. $^1H$ NMR (401 MHz, DMSO-$d_6$) δ 10.81 (s, 1H), 9.89 (s, 1H), 9.38 (s, 1H), 9.26 (s, 1H), 8.95 (s, 1H), 8.72 (d, J=0.7 Hz, 1H), 8.49 (dd, J=8.6, 0.9 Hz, 1H), 8.04 (d, J=8.3 Hz, 1H), 5.82 (s, 2H); LCMS $R_f$ (min)=2.51, MS m/z=366.1 $[M+H]^+$. HRMS (ESI) calcd for $C_{13}H_{11}F_3N_9O$ $[M+H]^+$ 366.1033, found 366.1021.

109. N'-Hydroxy-5-((1-methyl-5-(5-(trifluoromethyl)pyridin-2-yl)-1H-pyrazol-3-yl)amino)picolinimidamide (Scheme 106)

Scheme 106

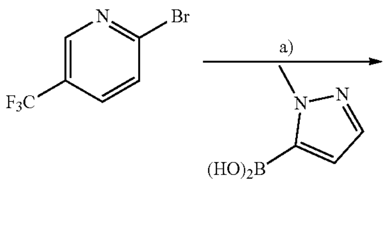

-continued

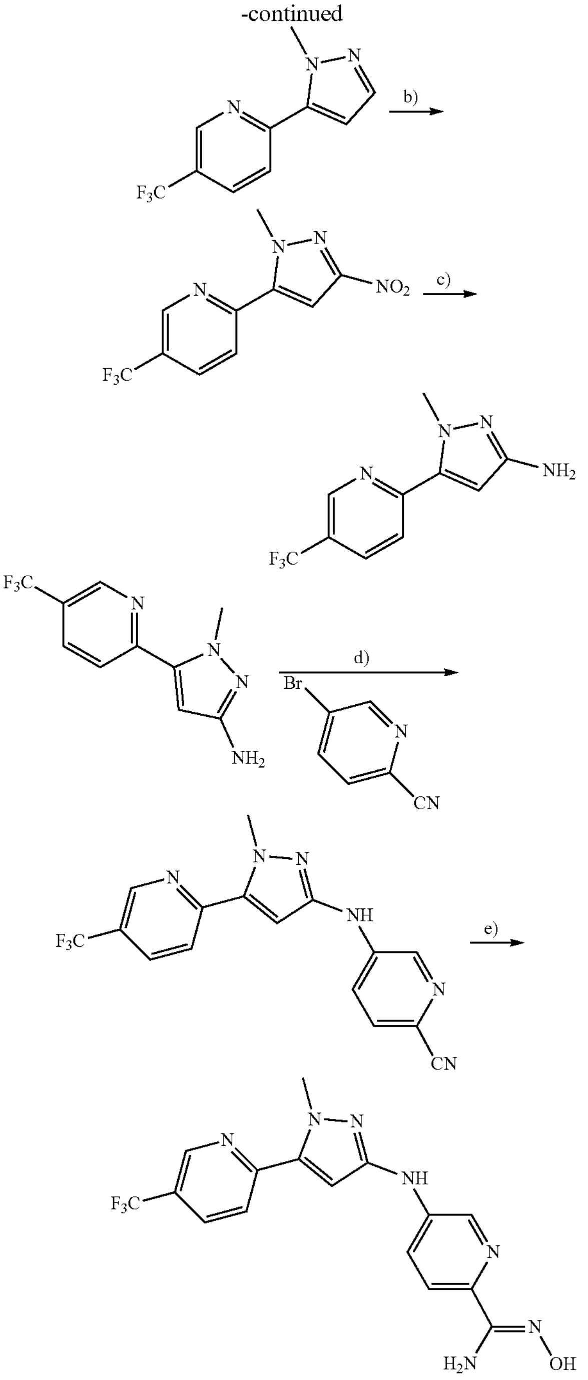

a) $K_2CO_3$, $Pd(PPh_3)_2Cl_2$, DME, $H_2O$, reflux, 48 h;
b) $HNO_3$, $Ac_2O$, 0° C.-rt, 16 h;
c) Pd/C, $H_2$, MeOH, rt, 0.5 h:
d) $Pd_2(dba)_3$, Xantphos, $Cs_2CO_3$, 1,4-Dioxane, 90° C.,16 h;
e) $NH_2OH{\bullet}HCl$, $NEt_3$, MeOH, reflux, 3 h.

A suspension of 2-bromo-5-(trifluoromethyl)pyridine (5.38 g, 23.83 mmol), (1-methyl-1H-pyrazol-5-yl)boronic acid (3.0 g, 23.83 mmol), $K_2CO_3$ (13.17 g, 95.30 mmol), $Pd(PPh_3)_2Cl_2$ (0.84 g, 1.19 mmol) in DME (95 mL) and $H_2O$ (10 mL) was heated to reflux for 48 h. The volatiles were removed in vacuo then $H_2O$ (100 mL) was added, extracted with EtOAc (2×100 mL) and washed with brine (100 mL). The combined organic layer was dried over $MgSO_4$ and concentrated under reduced pressure. The resultant crude residue was purified by flash chromatography, eluting with 20-30% EtOAc in petroleum spirits to give 2-(1-methyl-1H-pyrazol-5-yl)-5-(trifluoromethyl)pyridine (1.85 g, 34% yield) as a yellow solid. $^1$H NMR (401 MHz, DMSO-$d_6$) δ 9.06 (dd, J=1.5, 0.9 Hz, 1H), 8.31 (ddd, J=8.4, 2.4, 0.6 Hz, 1H), 8.04 (d, J=8.4 Hz, 1H), 7.55 (d, J=2.0 Hz, 1H), 6.98 (d, J=2.0 Hz, 1H), 4.18 (s, 3H). LCMS $R_f$ (min)=2.88, MS m/z=228.1 $[M+H]^+$.

$HNO_3$ (37% aq., 1.7 mL) was slowly added into a solution of 2-(1-methyl-1H-pyrazol-5-yl)-5-(trifluoromethyl)pyridine in $Ac_2O$ (10 mL) at 0° C. The reaction mixture was slowly warmed up to rt and allowed to stir for 16 h. The reaction mixture was poured into ice water. To this cold aqueous mixture was added sat. aq. $NaHCO_3$ (aq.) (25 mL), followed by extraction with EtOAc (2×25 mL). The combined organic layer was washed with $H_2O$ (25 mL) and brine (25 mL), then dried over $MgSO_4$ and concentrated under reduced pressure. The resultant crude residue was purified by flash chromatography, eluting with 15-20% EtOAc in petroleum spirits to give 2-(1-methyl-3-nitro-1H-pyrazol-5-yl)-5-(trifluoromethyl)pyridine (0.67 g, 59% yield) as a white solid. $^1$H NMR (401 MHz, DMSO-$d_6$) δ 9.14 (dd, J=1.4, 0.8 Hz, 1H), 8.44 (dd, J=8.4, 1.9 Hz, 1H), 8.24 (d, J=8.4 Hz, 1H), 7.87 (s, 1H), 4.30 (s, 3H). LCMS $R_f$ (min)=3.01, MS m/z=273.0 $[M+H]^+$.

A solution of 2-(1-methyl-3-nitro-1H-pyrazol-5-yl)-5-(trifluoromethyl)pyridine (0.67 g, 2.46 mmol) in MeOH (25 mL) was evacuated and backfilled with $N_2$×3, then 10% Pd/C (0.33 g) was added. The resultant suspension was evacuated and flushed with $H_2$×3 and stirred under a hydrogen atmosphere (balloon) for 0.5 h. The reaction mixture was filtered through a pad of celite and the filtrate was concentrated under reduced pressure to give 1-methyl-5-(5-(trifluoromethyl)pyridin-2-yl)-1H-pyrazol-3-amine (0.50 g, 83% yield) as an off-white solid. $^1$H NMR (401 MHz, DMSO-$d_6$) δ 9.00 (s, 1H), 8.23 (dd, J=8.4, 2.3 Hz, 1H), 7.89 (d, J=8.4 Hz, 1H), 6.05 (s, 1H), 4.74 (s, 2H), 3.93 (s, 3H). LCMS $R_f$ (min)=3.22, MS m/z=243.1 $[M+H]^+$.

1-Methyl-5-(5-(trifluoromethyl)pyridin-2-yl)-1H-pyrazol-3-amine (0.1 g, 0.41 mmol) and 5-bromopicolinonitrile (0.069 g, 0.38 mmol) were reacted as per General Procedure 4 Method 1, using 5 mol % $Pd_2(dba)_3$, 10 mol % Xantphos, 1.5 eq $Cs_2CO_3$ and heated at 90° C. for 16 h. The crude residue was purified by flash chromatography, eluting with 50-70% EtOAc in petroleum spirits to give 5-((1-methyl-5-(5-(trifluoromethyl)pyridin-2-yl)-1H-pyrazol-3-yl)amino)picolinonitrile (0.09 g, 70% yield) as a yellow solid. $^1$H NMR (401 MHz, DMSO-$d_6$) δ 9.71 (s, 1H), 9.09 (s, 1H), 8.62 (d, J=2.5 Hz, 1H), 8.34 (dd, J=8.6, 2.2 Hz, 1H), 8.09 (d, J=8.2 Hz, 1H), 8.01 (dd, J=8.7, 2.7 Hz, 1H), 7.83 (d, J=8.5 Hz, 1H), 6.64 (s, 1H), 4.13 (s, 3H); LCMS $R_f$ (min)=2.89, MS m/z=345.1 $[M+H]^+$.

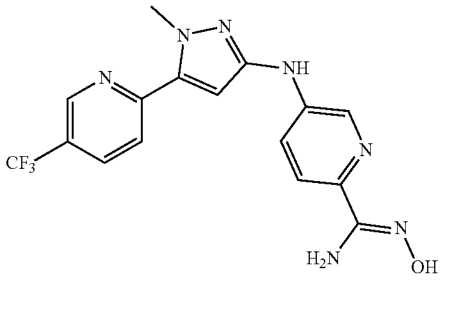 [SMILES: Cn1nc(Nc2ccc(/C(N)=N/O)nc2)cc1-c1ccc(C(F)(F)F)cn1]

5-((1-Methyl-5-(5-(trifluoromethyl)pyridin-2-yl)-1H-pyrazol-3-yl)amino)picolinonitrile (0.09 g, 0.26 mmol) was reacted as per General Procedure 1 Method 3 using $NH_2OH·HCl$ (0.07 g, 1.06 mmol) and $NEt_3$ (0.1 mL, 0.70 mmol) in dry MeOH (1.3 mL) to give N'-hydroxy-5-((1-methyl-5-(5-(trifluoromethyl)pyridin-2-yl)-1H-pyrazol-3-yl)amino)picolinimidamide (0.09 g, 93% yield) as a yellow solid. $^1$H NMR (401 MHz, DMSO-$d_6$) δ 9.58 (s, 1H), 9.07 (m, 2H), 8.59 (d, J=2.3 Hz, 1H), 8.32 (d, J=8.3 Hz, 1H), 8.07 (d, J=8.4 Hz, 1H), 7.84 (dd, J=8.8, 2.5 Hz, 1H), 7.71 (d, J=8.8 Hz, 1H), 6.55 (s, 1H), 5.68 (s, 2H), 4.11 (s, 3H); $^{13}$C NMR (101 MHz, DMSO-$d_6$) δ 152.4, 149.7, 149.3, 140.2, 140.0, 139.9, 135.2, 134.8, 125.1, 123.5, 123.0, 122.4, 121.5, 119.6, 96.1, 39.2. LCMS $R_f$ (min)=2.42, MS m/z=378.1 $[M+H]^+$. HRMS (ESI) calcd for $C_{16}H_{15}F_3N_7O$ $[M+H]^+$ 378.1285, found 378.1294.

110. N'-Hydroxy-5-((1-methyl-5-(5-(trifluoromethyl)pyridin-2-yl)-1H-pyrazol-3-yl)amino)pyrazine-2-carboximidamide (Scheme 107)

Scheme 107

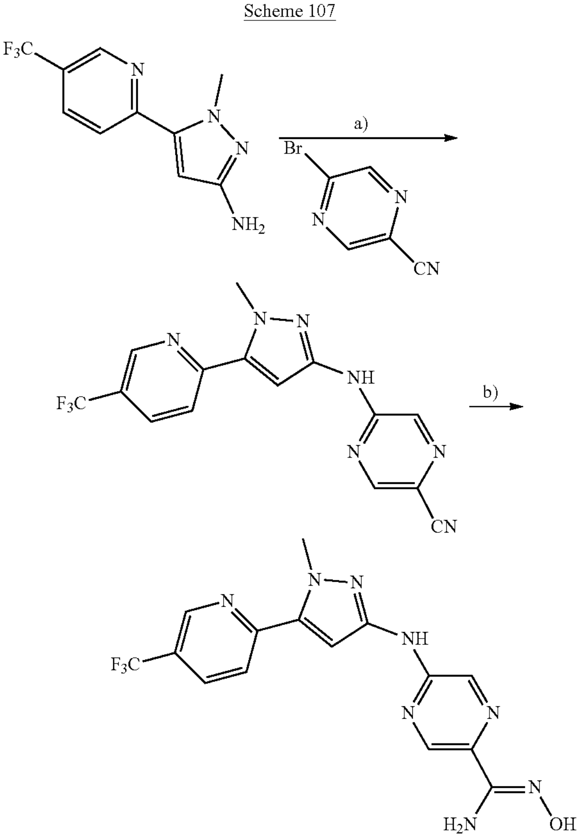

a) $Pd_2(dba)_3$, Xantphos, $Cs_2CO_3$, 1,4-dioxane, 90°C., 16 h;
b) $NH_2OH•HCl$, $NEt_3$, MeOH, reflux, 2 h 1-Methyl-5-(5-(trifluoromethyl)pyridin-2-yl)-1H-pyrazol-3-amine (0.1 g, 0.41 mmol) and 5-bromopyrazine-2-carbonitrile (0.069 g, 0.38 mmol) were reacted as per General Procedure 4 Method 1, using 5 mol % $Pd_2(dba)_3$, 10 mol % Xantphos, 1.5 eq $Cs_2CO_3$ and heated at 90° C. for 16 h. The reaction mixture was diluted with EtOAc (10 mL), washed with $H_2O$ (10 mL) and brine (10 mL). The combined organic layer was dried over $MgSO_4$ and concentrated under reduced pressure. The crude residue was purified by flash chromatography, eluting with 25-30% EtOAc in petroleum spirit to give 5-((1-methyl-5-(5-(trifluoromethyl)pyridin-2-yl)-1H-pyrazol-3-yl)amino)pyrazine-2-carbonitrile (0.04 g, 34% yield) as a pale-yellow solid. $^1$H NMR (401 MHz, DMSO-$d_6$) δ 10.93 (s, 1H), 9.09 (s, 1H), 8.68 (d, J=1.3 Hz, 1H), 8.44 (s, 1H), 8.32 (d, J=8.1 Hz, 1H), 8.05 (d, J=8.2 Hz, 1H), 7.22 (s, 1H), 4.14 (s, 3H); LCMS $R_f$ (min)=2.98, MS m/z=346.0 [M+H]$^+$.

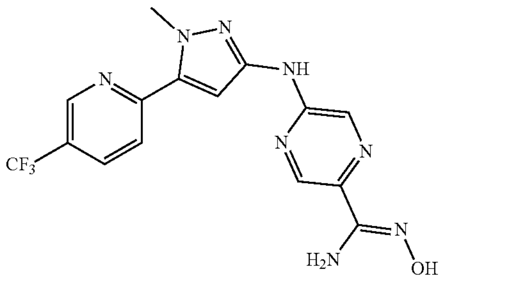 [SMILES: Cn1nc(Nc2cnc(/C(N)=N/O)cn2)cc1-c1ccc(C(F)(F)F)cn1]

5-((1-Methyl-5-(5-(trifluoromethyl)pyridin-2-yl)-1H-pyrazol-3-yl)amino)pyrazine-2-carbonitrile (0.03 g, 0.08 mmol) was reacted as per General Procedure 1 Method 3 using $NH_2OH{\cdot}HCl$ (0.02 g, 0.3 mmol) and $NEt_3$ (0.04 mL, 0.3 mmol) in dry MeOH (0.5 mL) to give N'-hydroxy-5-((1-methyl-5-(5-(trifluoromethyl)pyridin-2-yl)-1H-pyrazol-3-yl)amino)pyrazine-2-carboximidamide (0.02 g, 76% yield) as a white solid. $^1$H NMR (401 MHz, DMSO-$d_6$) δ 10.11 (s, 1H), 9.72 (s, 1H), 9.07 (dd, J=1.3, 0.8 Hz, 1H), 8.60 (d, J=1.4 Hz, 1H), 8.47 (d, J=1.4 Hz, 1H), 8.30 (dd, J=8.5, 2.0 Hz, 1H), 8.05 (d, J=8.4 Hz, 1H), 7.11 (s, 1H), 5.73 (s, 2H), 4.12 (s, 3H); $^{13}$C NMR (101 MHz, DMSO-$d_6$) δ 152.4, 151.1, 148.7, 147.2, 139.6, 138.6, 135.4, 131.1, 122.8, 97.8, 39.3; LCMS $R_f$(min)=2.39, MS m/z=379.1 [M+H]$^+$. HRMS (ESI) calcd for $C_{15}H_{14}F_3N_8O$ [M+H]$^+$ 379.1237, found 379.1253.

111. N'-Hydroxy-5-((1-(4-(trifluoromethyl)phenyl)-1H-pyrazol-3-yl)amino)pyrazine-2-carboximidamide (Scheme 108)

Scheme 108

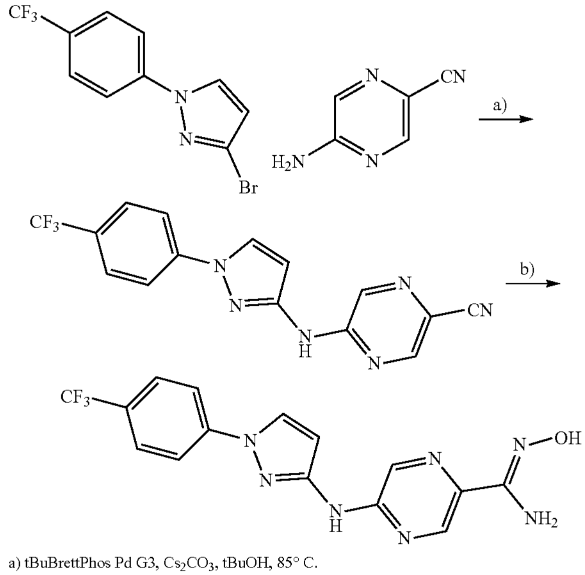

a) tBuBrettPhos Pd G3, $Cs_2CO_3$, tBuOH, 85° C.
b)$NH_2OH{\bullet}HCl$, $Et_3N$, dry MeOH, reflux, 3h 3-Bromo-1-(4-(trifluoromethyl)phenyl)-1H-pyrazole (Intermediate 0, 1 eq.) and 5-aminopyrazine-2-carbonitrile (1.4 eq) were reacted as per General Procedure 4 Method 2 using 5 mol % Pd precatalyst, 4 eq. $Cs_2CO_3$ and heated at 85° C. for 20 h. The crude product was purified using 25-35% EtOAc in petroleum spirits gradient to give 5-((1-(4-(trifluoromethyl)phenyl)-1H-pyrazol-3-yl)amino)pyrazine-2-carbonitrile (98.5 mg, 84% yield). $^1$H NMR (401 MHz, DMSO-$d_6$) δ 8.72 (d, J=1.3 Hz, 1H), 8.66 (d, J=2.7 Hz, 1H), 8.62 (s, 1H), 8.04 (d, J=8.5 Hz, 2H), 7.87 (d, J=8.6 Hz, 2H), 6.91 (d, J=2.0 Hz, 1H). LCMS $R_f$(min)=3.96, MS m/z 331.1 [M+H]$^+$.

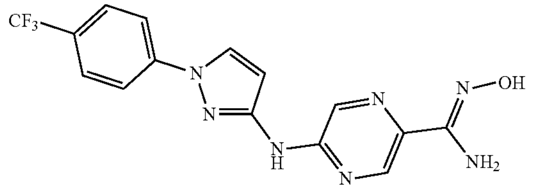 [SMILES: N/C(=N\O)c1cnc(Nc2ccn(-c3ccc(C(F)(F)F)cc3)n2)cn1]

5-((1-(4-(Trifluoromethyl)phenyl)-1H-pyrazol-3-yl)amino)pyrazine-2-carbonitrile was reacted as per General Procedure 1 Method 3 using 4 eq. $NH_2OH{\cdot}HCl$ and 4 eq. $Et_3N$ for 3 h to give N'-hydroxy-5-((1-(4-(trifluoromethyl)phenyl)-1H-pyrazol-3-yl)amino)pyrazine-2-carboximidamide as a white solid (84.2 mg, 83%) $^1$H NMR (401 MHz, DMSO-$d_6$) δ 10.34 (s, 1H), 9.79 (s, 1H), 8.77 (d, J=1.5 Hz, 1H), 8.64 (d, J=1.5 Hz, 1H), 8.61 (d, J=2.7 Hz, 1H), 8.02 (d, J=8.5 Hz, 2H), 7.86 (d, J=8.6 Hz, 2H), 6.74 (d, J=2.7 Hz, 1H), 5.78 (s, 2H). $^{13}$C NMR (101 MHz, DMSO-$d_6$) δ 151.0, 150.7, 148.7, 142.3, 138.9, 136.3, 131.1, 128.9, 126.9, 126.9, 125.6, 125.3, 125.0, 122.9, 117.3, 100.2. LCMS $R_f$ (min)=2.52, MS m/z 364.1 [M+H]$^+$. HRMS (ESI) calcd for $C_{15}H_{13}F_3N_7O^+$ [M+H]$^+$ 364.1128, found 364.1133.

112. N'-Hydroxy-5-((1-(5-(trifluoromethyl)pyridin-2-yl)-1H-pyrazol-3-yl)amino)pyrazine-2-carboximidamide (Scheme 109)

Scheme 109

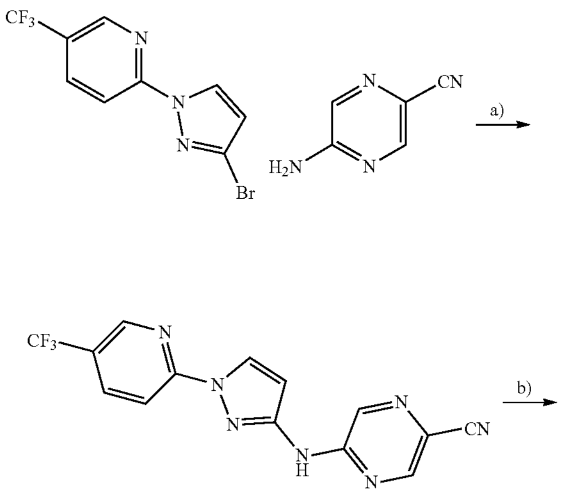

-continued

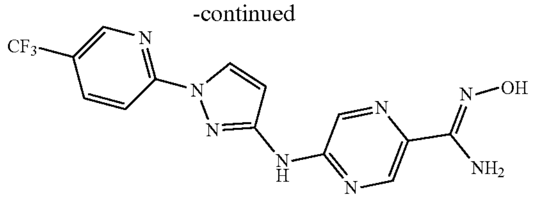

a) tBuBrettPhos Pd G3, $Cs_2CO_3$, tBuOH, 85° C., 20 h;
b)$NH_2OH$•HCl, $Et_3N$, MeOH, reflux, 3h.

2-(3-Bromo-1H-pyrazol-1-yl)-5-(trifluoromethyl)pyridine (Intermediate N, 1 eq.) and 5-aminopyrazine-2-carbonitrile (1.4 eq) were reacted as per General Procedure 4 Method 2 using 6 mol % Pd precatalyst, 3.8 eq. $Cs_2CO_3$ and heated at 85° C. for 20 h. The crude product was purified using 25-35% EtOAc in petroleum spirits gradient to give 5-((1-(5-(trifluoromethyl)pyridin-2-yl)-1H-pyrazol-3-yl)amino)pyrazine-2-carbonitrile (97.3 mg, 82% yield). LCMS $R_f$ (min)=4.00, MS m/z 332.1 $[M+H]^+$.

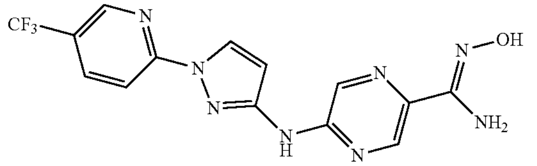 [SMILES: N/C(=N\O)c1cnc(Nc2ccn(-c3ccc(C(F)(F)F)cn3)n2)cn1]

5-((1-(5-(Trifluoromethyl)pyridin-2-yl)-1H-pyrazol-3-yl)amino)pyrazine-2-carbonitrile was reacted as per General Procedure 1 Method 3 using 4 eq. $NH_2OH{\cdot}HCl$ and 4 eq. $Et_3N$ for 3 h to give N'-hydroxy-5-((1-(5-(trifluoromethyl)pyridin-2-yl)-1H-pyrazol-3-yl)amino)pyrazine-2-carboximidamide as a white solid (63.8 mg, 67%) $^1$H NMR (401 MHz, DMSO-$d_6$) δ 10.45 (s, 1H), 9.83 (s, 1H), 8.87-8.84 (m, 2H), 8.67 (d, J=1.5 Hz, 1H), 8.62 (d, J=2.8 Hz, 1H), 8.39 (dd, J=9.0, 2.2 Hz, 1H), 7.97 (d, J=8.7 Hz, 1H), 6.78 (d, J=2.8 Hz, 1H), 5.80 (s, 2H). $^{13}$C NMR (101 MHz, DMSO-$d_6$) δ 152.9, 152.1, 150.4, 148.6, 145.8, 138.9, 137.1, 137.1, 136.7, 131.2, 128.5, 125.2, 122.5, 121.9, 121.6, 111.1, 101.2. LCMS $R_f$(min)=2.52, MS m/z 365.1 $[M+H]^+$. HRMS (ESI) calcd for $C_{14}H_{12}F_3N_8O^+$ $[M+H]^+$ 365.1081, found 365.1085.

113. N'-Hydroxy-5-((1-(4-(trifluoromethyl)phenyl)-1H-pyrazol-4-yl)amino)picolinimidamide (Scheme 110)

Scheme 110

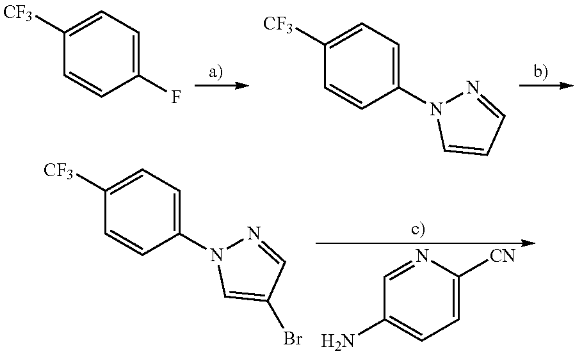

-continued

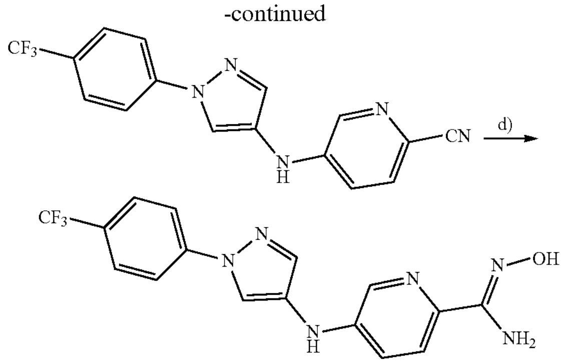

a) pyrazole, $K_2CO_3$, DMF, 110° C., 18 h;
b) NBS, $CH_3CN$, rt, 48 h;
c) tBuBrettPhos Pd G3, $Cs_2CO_3$, tBuOH, 85° C.;
d) $NH_2OH$•HCl, $Et_3N$, MeOH, reflux, 3 h.

1-Fluoro-4-(trifluoromethyl)benzene (5 g, 30.46 mmol) was stirred with pyrazole (2.5 g, 36.6 mmol) in DMF (60 mL) at 110° C. for 18 h. The reaction mixture was cooled to room temperature, diluted with $Et_2O$ and water. After separation the aqueous phase was extracted with $Et_2O$ (4×), the combined organic phases were dried over ($MgSO_4$), evaporated to dryness. The residue was purified on silica gel using mixtures of petroleum spirits and DCM as eluents to provide 1-(4-(trifluoromethyl)phenyl)-1H-pyrazole in 37.1% yield (2.4 g). $^1$H NMR (401 MHz, $CDCl_3$) δ 7.98 (dd, J=2.6, 0.4 Hz, 1H), 7.82 (d, J=8.4 Hz, 2H), 7.75 (d, J=1.6 Hz, 1H), 7.70 (d, J=8.5 Hz, 2H), 6.51 (dd, J=2.5, 1.8 Hz, 1H). LCMS $R_f$ (min)=3.062, MS m/z=213.0 $[M+H]^+$.

1-(4-(Trifluoromethyl)phenyl)-1H-pyrazole (2.4 g, 11.31 mmol) was stirred with NBS (3 g, 17 mmol) in $CH_3CN$ (16 mL) at rt for 48 h. The volatile solvents were removed and the residue taken up in DCM and saturated $NaHCO_3$ solutions. After separation the aqueous phase was extracted with DCM (4×), the combined organic phases were dried over ($MgSO_4$), evaporated to dryness. The residue was purified on silica gel using mixtures of petroleum spirits and DCM as eluents to provide 4-bromo-1-(4-(trifluoromethyl)phenyl)-1H-pyrazole in 36.5% yield (1.2 g). $^1$H NMR (401 MHz, $CDCl_3$) δ 8.00 (s, 1H), 7.78 (d, J=8.7 Hz, 2H), 7.73 (m, 3H). LCMS $R_f$ (min)=4.197, MS m/z=291.0/293.0 $[M+H]^+$.

4-Bromo-1-(4-(trifluoromethyl)phenyl)-1H-pyrazole (1 eq.) and 5-aminopicolinonitrile (1.4 eq) were reacted as per General Procedure 4 Method 2 using 5 mol % Pd precatalyst, 2.8 eq. $Cs_2CO_3$ and heated at 85° C. for 20 h. The crude product was purified using 10-100% EtOAc in petroleum spirits gradient to give 5-((1-(4-(trifluoromethyl)phenyl)-1H-pyrazol-4-yl)amino)picolinonitrile (58.5 mg, 50% yield). $^1$H NMR (401 MHz, DMSO-$d_6$) δ 9.16 (s, 1H), 8.78 (s, 1H), 8.33 (d, J=2.6 Hz, 1H), 8.11 (d, J=8.5 Hz, 2H), 7.90-7.85 (m, 3H), 7.78 (d, J=8.7 Hz, 1H), 7.39 (dd, J=8.7, 2.9 Hz, 1H). LCMS $R_f$(min)=3.87, MS m/z 330.1 $[M+H]^+$.

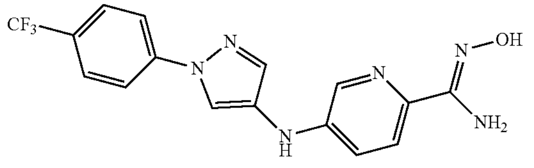 [SMILES: N/C(=N\O)c1ccc(Nc2cnn(-c3ccc(C(F)(F)F)cc3)c2)cn1]

5-((1-(4-(Trifluoromethyl)phenyl)-1H-pyrazol-4-yl)amino)picolinonitrile was reacted as per General Procedure 1 Method 3 using 4 eq. $NH_2OH{\cdot}HCl$ and 4 eq. $Et_3N$ for 3 h to give N'-hydroxy-5-((1-(4-(trifluoromethyl)phenyl)-1H-pyrazol-4-yl)amino)picolinimidamide as a white solid (34.9 mg, 54%) $^1H$ NMR (401 MHz, DMSO-$d_6$) δ 9.59 (s, 1H), 8.68 (s, 1H), 8.53 (s, 1H), 8.24 (d, J=2.3 Hz, 1H), 8.11 (d, J=8.5 Hz, 2H), 7.86 (d, J=8.6 Hz, 2H), 7.79 (s, 1H), 7.70 (d, J=8.8 Hz, 1H), 7.38 (dd, J=8.8, 2.8 Hz, 1H), 5.67 (s, 2H). $^{13}C$ NMR (101 MHz, DMSO-$d_6$) δ 149.6, 142.5, 141.7, 139.6, 136.0, 134.2, 127.3, 126.8, 126.8, 125.8, 125.6, 125.5, 125.2, 122.9, 120.0, 120.0 117.9, 117.1. LCMS $R_f$ (min)=3.28, MS m/z 363.1 $[M+H]^+$. HRMS (ESI) calcd for $C_{16}H_{14}F_3N_6O^+$ $[M+H]^+$ 363.1176, found 363.1187.

114. N'-Hydroxy-5-((1-(4-(trifluoromethyl)phenyl)-1H-pyrazol-4-yl)amino)pyrazine-2-carboximidamide (Scheme 111)

Scheme 111

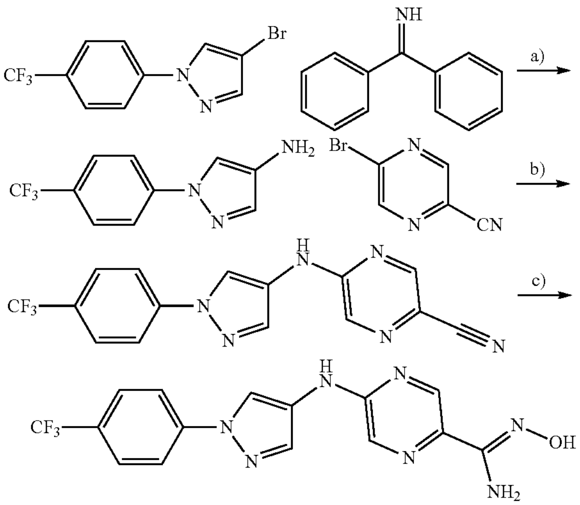

a) tBuBrettPhos Pd G3, $Cs_2CO_3$, 1,4-dioxane, 90° C. then $NH_2OH{\bullet}HCl$ and NaOH(aq.), 148 h;
b) DIPEA, 1,4-dioxane, 80° C.;
c) $NH_2OH{\bullet}HCl$, $Et_3N$, MeOH, reflux, 1 h.

4-Bromo-1-(4-(trifluoromethyl)phenyl)-1H-pyrazole (0.314 g, 1.08 mmol), $Cs_2CO_3$ (1.01 g, 3.1 mmol) and tBuBrettPhos Pd G3 precatalyst (0.044 g, 0.052 mmol) and diphenylmethanimine (0.35 ml, 2.1 mmol) were placed in round bottom flask under $N_2$. Anhydrous dioxane (4 mL) was added and the reaction was heated to 90° C. for 20 h, cooled then $NH_2OH{\cdot}HCl$ (0.285 g, 4.1 mmol) and 2M aq. NaOH were added (2 mL, 4 mmol) and the mixture was stirred at room temperature. After 24 h, the mixture was diluted with 4 mL dioxane, 4 mL MeOH and 2 mL water and $NH_2OH{\cdot}HCl$ (0.285 g, 4.1 mmol) was added. After stirring for 24 h the mixture was added to 400 mL water and the resulting solid was collected by filtration, dried, dissolved in EtOAc and concentrated onto silica. The crude product was purified by flash chromatography (25-100% EtOAc in DCM) to give 1-(4-(trifluoromethyl)phenyl)-1H-pyrazol-4-amine (0.0525 g, 0.231 mmol, 21%) $^1H$ NMR (401 MHz, $CDCl_3$) δ 7.87-7.86 (m, 1H), 7.77 (d, J=8.9 Hz, 2H), 7.72 (d, J=8.8 Hz, 2H), 7.64 (s, 1H). LCMS $R_f$ (min)=3.13, MS m/z 228.1 $[M+H]^+$.

1-(4-(Trifluoromethyl)phenyl)-1H-pyrazol-4-amine (0.0525 g, 0.231 mmol) and 5-bromopyrazine-2-carbonitrile (0.127 g, 0.693 mmol) were placed under $N_2$ in a screw cap vial, anhydrous dioxane (2 mL) and diisopropylethylamine (0.12 mL, 0.69 mmol) were added and the vial was capped then heated to 80° C. for 22 h. The reaction was cooled, diluted with EtOAc, concentrated onto silica and purified by flash chromatography (25-50% EtOAc in petroleum spirits) to give 5-((1-(4-(trifluoromethyl)phenyl)-1H-pyrazol-4-yl)amino)pyrazine-2-carbonitrile (0.0525 g, 0.159 mmol, 69%) $^1H$ NMR (401 MHz, DMSO-$d_6$) δ 8.84 (s, 1H), 8.66 (s, 1H), 8.23 (s, 1H), 8.06 (d, J=8.5 Hz, 2H), 8.01 (s, 1H), 7.87 (d, J=8.7 Hz, 2H). LCMS $R_f$ (min)=3.89, MS m/z 331.1 $[M+H]^+$.

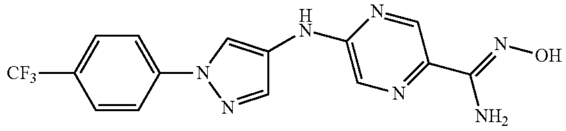 [SMILES: N/C(=N\O)c1cnc(Nc2cnn(-c3ccc(C(F)(F)F)cc3)c2)cn1]

5-((1-(4-(Trifluoromethyl)phenyl)-1H-pyrazol-4-yl)amino)pyrazine-2-carbonitrile was reacted as per General Procedure 1 Method 3 using 4 eq. $NH_2OH{\cdot}HCl$ and 4 eq. $Et_3N$ for 1 h with addition of water to induce precipitation and washing with DCM prior to drying to give N'-hydroxy-5-((1-(4-(trifluoromethyl)phenyl)-1H-pyrazol-4-yl)amino)pyrazine-2-carboximidamide as a cream solid (36.5 mg, 0.100 mmol, 63%) $^1H$ NMR (401 MHz, DMSO-$d_6$) δ 9.86 (s, 1H), 9.71 (s, 1H), 8.82 (s, 1H), 8.64 (d, J=1.4 Hz, 1H), 8.16 (d, J=1.4 Hz, 1H), 8.06 (d, J=8.5 Hz, 2H), 7.93 (s, 1H), 7.85 (d, J=8.6 Hz, 2H), 5.72 (s, 2H). LCMS $R_f$ (min)=3.25. MS m/z 364.1 $[M+H]^+$. HRMS (ESI) calcd for $C_{15}H_{12}F_3N_6O_2^+$ $[M+H]^+$ 364.1128, found 364.1133.

115. N'-Hydroxy-5-((1-(5-(trifluoromethyl)pyridin-2-yl)-1H-1,2,3-triazol-4-yl)amino)picolinimidamide (Scheme 112)

Scheme 112

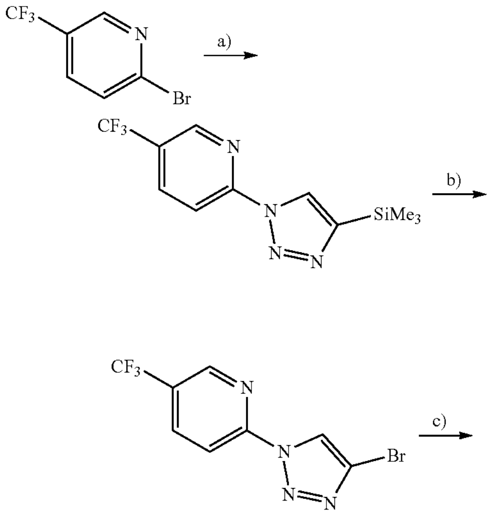

-continued

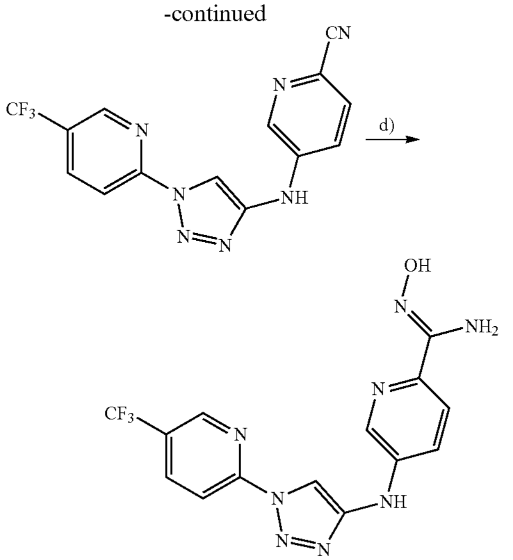

a) $NaN_3$, DMSO, 70° C., overnight, then $CuSO_4•5H_2O$, Na-ascorbate, $HCCSiMe_3$, $H_2O$, MeOH, rt, 2 days;
b) NBS, $SiO_2$, MeCN 80° C., 1 h;
c) tBuBrettPhos Pd G3, $Cs_2CO_3$, tBuOH, 85° C., 20 h;
d) $NH_2OH•HCl$, $Et_3N$, MeOH, reflux, 1 h.

To a solution of 2-bromo-5-(trifluoromethyl)pyridine (1.5 g, 6.64 mmol) in DMSO (33 ml) was added sodium azide (0.86 g, 13.3 mmol) at room temperature, and the mixture stirred at 70° C. overnight. The reaction solution was diluted with $Et_2O$, and the mixture was washed with water and brine. The organic layer was dried over anhydrous $MgSO_4$ to give an $Et_2O$ solution of 2-azido-5-(trifluoromethyl) pyridine which then used directly in the following step after analysis by LCMS. LCMS $R_f$ (min)=3.15, MS m/z 189.1 $[M+H]^+$, 163.0 $[M-N_2+3H]^+$. A separate 500 mL round-bottom flask was charged with $CuSO_4·5H_2O$ (0.83 g, 3.30 mmol) and Na-ascorbate (1.31 g, 6.63 mmol). With stirring, $H_2O$ (70 mL) and MeOH (70 mL) were added. To this mixture was added ethynyltrimethylsilane (1.30 g, 13.3 mmol) followed by the above prepared solution of 2-azido-5-(trifluoromethyl)pyridine (6.64 mmol) in $Et_2O$. After stirring the reaction mixture at ambient temperature overnight, $CuSO_4·5H_2O$ (0.83 g, 3.30 mmol) and Na-ascorbate (1.31 g, 6.63 mmol) were added, and the stirring continued overnight. The volatile solvents were removed in vacuo, and the residue stirred with a mixtures of 15% aq. $NH_4OH$ and DCM (100 mL each). The mixture was filtered through a pad of celite, which was washed with DCM (3×). These washing DCM solutions were used to extract the aqueous phase. The combined organic solvents were dried over $MgSO_4$, filtered and evaporated to dryness. The residue was dissolved in EtOAc, concentrated onto silica gel and purified by flash chromatography (10-35% EtOAc in petroleum spirits) to give 5-(trifluoromethyl)-2-(4-(trimethylsilyl)-1H-1,2,3-triazol-1-yl)pyridine (10.6%, 0.201 g, 0.701 mmol). $^1H$ NMR (401 MHz, $CDCl_3$) δ 8.78-8.76 (m, 1H), 8.59 (s, 1H), 8.38-8.34 (m, 1H), 8.17-8.13 (m, 1H), 0.39 (s, 9H). LCMS $R_f$ (min)=4.24, MS m/z 287.1 $[M+H]^+$ To a solution of 5-(trifluoromethyl)-2-(4-(trimethylsilyl)-1H-1,2,3-triazol-1-yl)pyridine (0.131 g, 0.46 mmol) in MeCN (3 mL) was added silica gel (0.712 g, 11.9 mmol) and N-bromosuccinimide (0.285 g, 1.6 mmol), the reaction was heated to 80° C. for 1 h, cooled, filtered, the silica gel was washed with EtOAc. The filtrate was washed with mixture of water and brine, then 5% aq. $Na_2S_2O_3$ then brine, dried with $MgSO_4$, filtered and concentrated. The residue was dissolved in minimal petroleum spirits and DCM and purified by silica gel flash chromatography (5-10% EtOAc in petroleum spirits) to give 2-(4-bromo-1H-1,2,3-triazol-1-yl)-5-(trifluoromethyl)pyridine (0.0360 g, 0.123 mmol, 27%). $^1H$ NMR (401 MHz, $CDCl_3$) δ 8.80-8.77 (m, 1H), 8.63 (s, 1H), 8.36-8.32 (m, 1H), 8.21-8.17 (m, 1H).

2-(4-Bromo-1H-1,2,3-triazol-1-yl)-5-(trifluoromethyl) pyridine (1 eq.) and 5-aminopicolinonitrile (1.5 eq.) were reacted as per General Procedure 4 Method 2 using 10 mol % Pd precatalyst and 3 eq. $Cs_2CO_3$ and heated at 85° C. for 20 h with the following alteration to the work up, the reaction was diluted with EtOAc and water, the phases were separated and the aq. layer extracted twice with EtOAc, the combined organic layers were washed sequentially with 5% aq. citric acid, water and brine, dried with $MgSO_4$, filtered and concentrated. The residue was dissolved in MeOH, EtOAc and 0.1 mL $Et_3N$ then concentrated onto silica gel and purified using silica gel flash chromatography (25-100% EtOAc in petroleum spirits). Fractions containing product were combined, washed with water then brine, dried with $MgSO_4$, filtered, concentrated and triturated with warm MeOH to remove residual 5-aminopicolinonitrile to give 5-((1-(5-(trifluoromethyl)pyridin-2-yl)-1H-1,2,3-triazol-4-yl)amino)picolinonitrile (0.0122 g, 0.0368 mmol, 50%) $^1H$ NMR (401 MHz, DMSO-$d_6$) δ 9.97 (s, 1H), 9.05 (s, 1H), 8.71 (s, 1H), 8.57-8.53 (m, 2H), 8.36 (d, J=8.6 Hz, 1H), 7.87 (d, J=8.6 Hz, 1H), 7.80 (dd, J=8.7, 2.6 Hz, 1H). LCMS $R_f$ (min)=3.66, MS m/z 332.1 $[M+H]^+$.

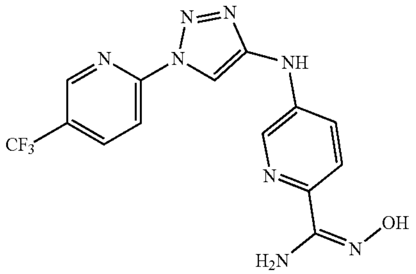 [SMILES: N/C(=N/O)c1ccc(Nc2cn(-c3ccc(C(F)(F)F)cn3)nn2)cn1]

5-((1-(5-(Trifluoromethyl)pyridin-2-yl)-1H-1,2,3-triazol-4-yl)amino)picolinonitrile was reacted as per General procedure 1 Method 3 using 4 eq. $NH_2OH·HCl$ and 4 eq. $Et_3N$ to give N'-hydroxy-5-((1-(5-(trifluoromethyl)pyridin-2-yl)-1H-1,2,3-triazol-4-yl)amino)picolinimidamide as a white solid (0.002 g, 15%) $^1H$ NMR (401 MHz, DMSO-$d_6$) δ 9.63 (s, 1H), 9.39 (s, 1H), 9.05-9.03 (m, 1H), 8.56-8.51 (m, 2H), 8.49-8.46 (m, 1H), 8.37-8.33 (m, 1H), 7.76 (d, J=8.8 Hz, 1H), 7.69 (dd, J=8.8, 2.7 Hz, 1H), 5.70 (s, 2H). LCMS $R_f$ (min)=3.14, MS m/z 365.2 $[M+H]^+$. HRMS (ESI) calcd for $C_{14}H_{12}F_3N_8O$ $[M+H]^+$ 365.1081, found 365.1088.

116. rac-5-((5-(5-Chloropyridin-2-yl)oxazol-2-yl)amino)-N-(2,3-dihydroxypropyl)picolinamide hydrochloride (Scheme 113)

Scheme 113

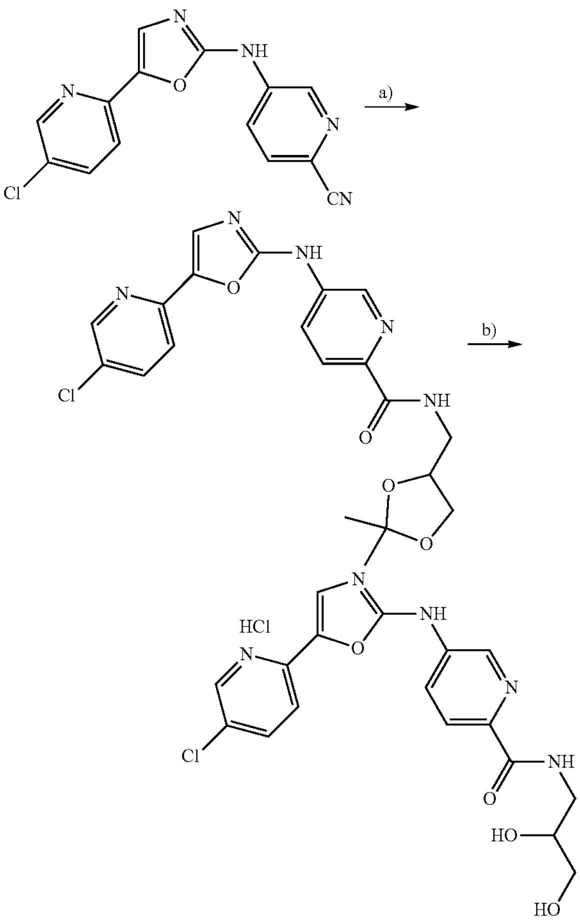

a) NaOMe, MeOH, reflux, 22 h then (2,2-dimethyl-1,3-dioxolan-4-yl)methanamine hydrochloride, T3P (50% w/w in DMF), pyridine, DMF, 65° C., 3 days
b) HCl in MeOH, DCM, rt, 4 h.

5-((5-(5-Chloropyridin-2-yl)oxazol-2-yl)amino)picolinonitrile (0.3084 g, 1.04 mmol) was added to 4 mL of a 1.9 M solution of NaOMe (7.6 mmol) (prepared from addition of Na metal to anhydrous MeOH) and heated in a bath set to 110° C. for 22 h under a $N_2$ atmosphere. After this time the solvent had evaporated. The cooled residue was dissolved in a mixture of 2M NaOH (5 mL) and water (200 mL) and then washed with EtOAc (2×50 mL), the aq. layer was acidified with 0.5 M aq. HCl to pH=4 giving a precipitate which was collected by filtration and washed with $Et_2O$, giving 119 mg of a solid which was determined by LCMS to consist of a mixture of 5-((5-(5-chloropyridin-2-yl)oxazol-2-yl)amino)picolinic acid and 5-((5-(5-chloropyridin-2-yl)oxazol-2-yl)amino)picolinamide in an approximately 2:1 ratio in favour of the carboxylic acid. LCMS of 5-((5-(5-chloropyridin-2-yl)oxazol-2-yl)amino)picolinic acid: $R_f$(min)=3.15, MS m/z 317.1 $[M+H]^+$. This mixture was used without further purification, and was dissolved in 3 mL anhydrous DMF, rac-(2,2-dimethyl-1,3-dioxolan-4-yl)methanamine hydrochloride (0.103 g, 0.614 mmol) was added followed by propylphosphonic anhydride solution (50% w/w in DMF, 1.1 mL, 1.88 mmol) and pyridine (0.3 mL, 3.72 mmol) then heated to 65° C. for 3 days, then cooled, poured into water and filtered. The resulting solid was dissolved in a mixture of EtOAc, MeOH and acetone then concentrated onto silica gel and purified by flash chromatography (25-100% EtOAc in petroleum spirits), fractions containing the desired product were concentrated, dissolved in minimal DCM and purified by flash chromatography (50-75% EtOAc in DCM) to give rac-5-((5-(5-chloropyridin-2-yl)oxazol-2-yl)amino)-N-((2,2-dimethyl-1,3-dioxolan-4-yl)methyl)picolinamide (0.0248 g, 0.058 mmol, 6% yield from nitrile). $^1H$ NMR (401 MHz, MeOH-d4: $CDCl_3$ approx. 1:1 v/v) δ 8.66 (d, J=2.4 Hz, 1H), 8.43 (dd, J=2.4, 0.6 Hz, 1H), 8.20 (dd, J=8.6, 2.6 Hz, 1H), 8.06 (d, J=8.6 Hz, 1H), 7.72 (dd, J=8.6, 2.4 Hz, 1H), 7.53-7.47 (m, 2H), 4.35-4.28 (m, 1H), 4.06 (dd, J=8.5, 6.5 Hz, 1H), 3.69 (dd, J=8.5, 6.3 Hz, 1H), 3.62 (dd, J=14.0, 4.2 Hz, 1H), 3.52 (dd, J=14.0, 5.6 Hz, 1H), 1.43 (s, 3H), 1.32 (s, 3H). LCMS $R_f$ (min)=3.55, MS m/z 430.1 $[M+H]^+$.

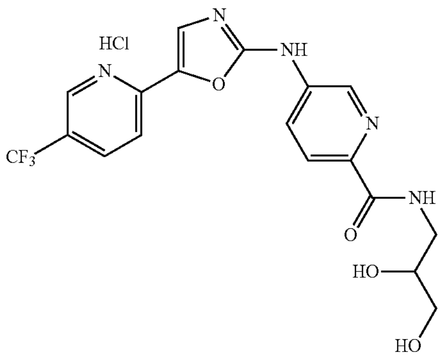 [SMILES: O=C(NCC(O)CO)c1ccc(Nc2ncc(-c3ccc(C(F)(F)F)cn3)o2)cn1 ; Cl]

rac-5-((5-(5-Chloropyridin-2-yl)oxazol-2-yl)amino)-N-((2,2-dimethyl-1,3-dioxolan-4-yl)methyl)picolinamide (0.0248 g, 0.058 mmol) was dissolved in 3 mL of a 1:1 v/v mixture of MeOH and DCM, HCl (1.25 M in MeOH, 0.2 mL, 0.25 mmol) was added and the mixture stirred at room temperature, after 1 h 1.5 mL of a 1.25 M HCl in MeOH solution (1.9 mmol) was added, after a further 3 h the reaction was concentrated, the residue suspended in 5 mL water, diluted with 5 mL MeOH and filtered and the solid was then washed with $Et_2O$ and DCM to give rac-5-((5-(5-chloropyridin-2-yl)oxazol-2-yl)amino)-N-(2,3-dihydroxypropyl)picolinamide hydrochloride as a yellow solid (14.9 mg, 0.0350 mmol, 61%) in 90% purity as determined by HPLC (254 nm). The filtrate was left stand overnight after which time a precipitate formed which was collected by filtration and washed with water and let dry to give the title compound (1.6 mg, 0.004 mmol, 7%) in 98% purity as determined by HPLC (254 nm). $^1H$ NMR (401 MHz, DMSO-$d_6$) δ 11.20 (s, 1H), 8.79 (d, J=2.5 Hz, 1H), 8.64-8.61 (m, 1H), 8.45 (t, J=5.9 Hz, 1H), 8.30 (dd, J=8.6, 2.6 Hz, 1H), 8.06-7.99 (m, 2H), 7.75 (s, 1H), 7.65 (d, J=8.6 Hz, 1H), 4.93 (d, J=5.0 Hz, 1H), 4.64 (t, J=5.7 Hz, 1H), 3.66-3.56 (m, 1H), 3.54-3.45 (m, 1H), 3.42-3.35 (m, 2H)*, 3.26-3.17 (m, 1H). *overlapped with $H_2O$ signal. LCMS $R_f$ (min)=3.12, MS m/z 390.1 $[M+H]^+$. HRMS (ESI) calcd for $C_{34}H_{32}N_{10}O_8K$ $[2M+K]^+$ 747.2036, found 747.2034.

117. 5-((5-(5-Fluoropyridin-2-yl)oxazol-2-yl)amino)-N'-hydroxypicolinimidamide (Scheme 114)

Scheme 114

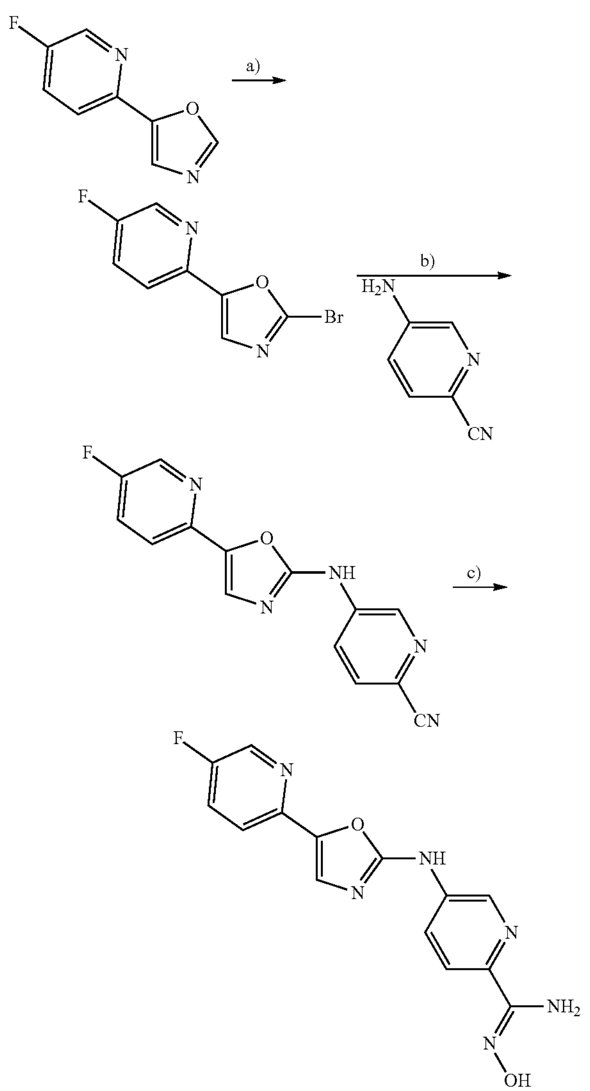

a) t-BuOLi, $BrCF_2CF_2Br$, DMF/m-xylene, 60° C., 3 h;
b) $Pd_2(dba)_3$, Xantphos, $Cs_2CO_3$, 1,4-dioxane, 100° C., 16 h;
c) $NH_2OH$•HCl, $Et_3N$, MeOH, reflux, 16 h.

5-(5-Fluoropyridin-2-yl)oxazole (0.40 g, 2.45 mmol) was reacted with $BrCF_2CF_2Br$ (0.58 mL, 4.90 mmol) and t-BuOLi (0.392 g, 4.90 mmol) in DMF/m-xylene (4/4 mL) at 60° C. for 3 h as per General Procedure 15 Method 2 to provide 2-bromo-5-(5-fluoropyridin-2-yl)oxazole (0.28 g, 46%) as a yellow solid. $^1$H NMR (401 MHz, $CDCl_3$) δ 8.46 (d, J=2.8 Hz, 1H), 7.62 (dd, J=8.7, 4.3 Hz, 1H), 7.56 (s, 1H), 7.47 (ddd, J=8.7, 8.0, 2.9 Hz, 1H). LCMS $R_f$ (min)=3.446, MS m/z=245.0 [M+H]$^+$.

5-Aminopicolinonitrile (280 mg, 2.35 mmol, 3.0 eq.), $Cs_2CO_3$ (764 mg, 2.35 mmol, 3.0 eq.) and 2-bromo-5-(5-fluoropyridin-2-yl)oxazole (190 mg, 0.782 mmol, 1.0 eq.) in 1,4-dioxane (8 mL) was charged with $Pd_2(dba)_3$ (36 mg, 0.039 mmol, 0.05 eq.), Xantphos (45 mg, 0.078 mmol, 0.1 eq.) and reacted according to General Procedure 4 Method 1 to afford 5-((5-(5-fluoropyridin-2-yl)oxazol-2-yl)amino)picolinonitrile as yellow solid (190 mg, 83%). LCMS $R_f$ (min)=3.215, MS m/z=282.1 [M+H]$^+$.

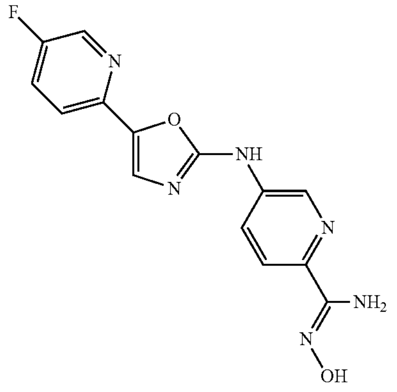 [SMILES: N/C(=N\O)c1ccc(Nc2ncc(-c3ccc(F)cn3)o2)cn1]

5-((5-(5-Fluoropyridin-2-yl)oxazol-2-yl)amino)picolinonitrile (180 mg, 0.64 mmol, 1.0 eq.) was suspended in EtOH (15 mL) followed by the addition of $NH_2OH$·HCl (356 mg, 5.12 mmol, 8.0 eq.) and $Et_3N$ (714 μL, 5.12 mmol, 8.0 eq.) and reacted according to General Procedure 1 Method 2 to afford 5-((5-(5-fluoropyridin-2-yl)oxazol-2-yl)amino)-N'-hydroxypicolinimidamide as beige solid (40 mg, 20%). $^1$H NMR (401 MHz, DMSO-$d_6$) δ 10.92 (br s, 1H), 9.75 (br s, 1H), 8.77 (br s, 1H), 8.58 (s, 1H), 8.12 (br s, 1H), 7.83 (br s, 2H), 7.63 (br s, 2H), 5.76 (br s, 2H). LCMS $R_f$ (min)=2.999, MS m/z=315.1 [M+H]$^+$. HRMS (ESI) calcd for $C_{14}H_{12}FN_6O_2^+$ ([M+H]$^+$ 315.1000, found 315.1004.

118. N'-Hydroxy-5-((5-(4-(trifluoromethoxy)phenyl)oxazol-2-yl)amino)picolinimidamide (Scheme 115)

Scheme 115

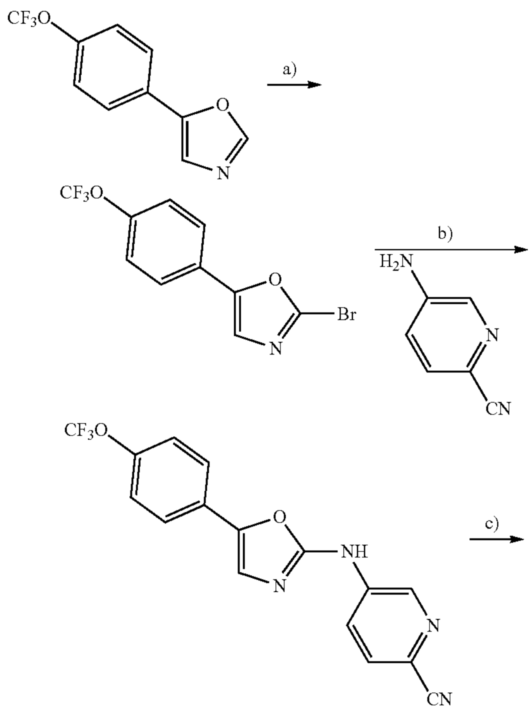

-continued

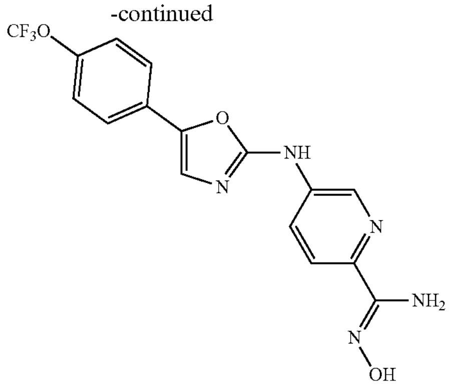

a) $BrCF_2CF_2Br$, t-BuOLi, DMF/m-xylene, 60° C., 3 h; b) $Pd_2(dba)_3$, Xantphos, $Cs_2CO_3$, 1,4-Dioxane, 100° C., 16 h; c) $NH_2OH$•HCl, $Et_3N$, MeOH, reflux, 16 h.

5-(4-(Trifluoromethoxy)phenyl)oxazole (0.9 g, 3.93 mmol) was reacted with $BrCF_2CF_2Br$ (0.70 mL, 5.90 mmol) and t-BuOLi (0.409 g, 5.11 mmol) in DMF/m-xylene (5/5 mL) as per General Procedure 15 Method 2 to provide 2-bromo-5-(4-(trifluoromethoxy)phenyl)oxazole (0.676 g, 56%) as an orange solid. $^1H$ NMR (401 MHz, $CDCl_3$) δ 7.62-7.54 (m, 2H), 7.26 (s, 1H, overlapping with $CHCl_3$ residue), 7.25-7.23 (m, 2H). LCMS $R_f$ (min)=3.752, MS m/z=309.9 $[M+H]^+$.

5-Aminopicolinonitrile (232 mg, 1.95 mmol, 3.0 eq.), $Cs_2CO_3$ (634 mg, 1.95 mmol, 3.0 eq.) and 2-bromo-5-(4-(trifluoromethoxy)phenyl)oxazole (200 mg, 0.649 mmol, 1.0 eq.) in 1,4-dioxane (8 mL) was charged with $Pd_2(dba)_3$ (30 mg, 0.033 mmol, 0.05 eq.) and Xantphos (37 mg, 0.064 mmol, 0.1 eq.) and reacted according to General Procedure 4 Method 1 to afford 5-((5-(4-(trifluoromethoxy)phenyl)oxazol-2-yl)amino)picolinonitrile as yellow solid (160 mg, 71%). $^1H$ NMR (401 MHz, DMSO-$d_6$) δ 11.37 (s, 1H), 8.87 (d, J=2.5 Hz, 1H), 8.36 (dd, J=8.7, 2.7 Hz, 1H), 8.02 (d, J=8.7 Hz, 1H), 7.84-7.73 (m, 2H), 7.69 (s, 1H), 7.50 (d, J=8.1 Hz, 2H). LCMS $R_f$ (min)=3.935, MS m/z=347.0 $[M+H]^+$.

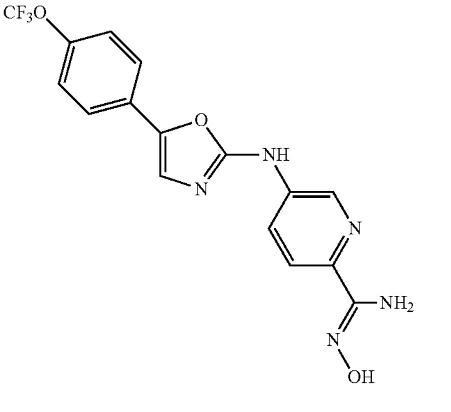

5-((5-(4-(Trifluoromethoxy)phenyl)oxazol-2-yl)amino)picolinonitrile (70 mg, 0.202 mmol, 1.0 eq.) was suspended in absolute MeOH (8 mL) followed by the addition of $NH_2OH$·HCl (112 mg, 1.61 mmol, 8.0 eq.) and $Et_3N$ (226 1.61 mmol, 8.0 eq.) and reacted according to General Procedure 1 Method 2 to afford N'-hydroxy-5-((5-(4-(trifluoromethoxy)phenyl)oxazol-2-yl)amino)picolinimidamide as beige solid (30 mg, 39%). $^1H$ NMR (401 MHz, DMSO-$d_6$) δ 10.80 (s, 1H), 9.73 (s, 1H), 8.77 (d, J=2.3 Hz, 1H), 8.12

(dd, J=8.8, 2.5 Hz, 1H), 7.83 (d, J=8.8 Hz, 1H), 7.72 (d, J=8.7 Hz, 2H), 7.60 (s, 1H), 7.46 (d, J=8.3 Hz, 2H), 5.75 (s, 2H); $^{13}C$ NMR (101 MHz, DMSO-$d_6$) δ 156.1, 149.4, 147.1, 143.2, 143.0, 136.7, 136.3, 127.2, 124.4, 123.8, 123.6, 121.9, 121.4, 119.7, 118.8. LCMS $R_f$ (min)=3.294, MS m/z=380.1 $[M+H]^+$. HRMS (ESI) calcd for $C_{16}H_{13}F_3N_5O_3^+$ ($[M+H]^+$ 380.0965, found 380.0975.

119. N'-Hydroxy-5-((5-(6-(trifluoromethyl)pyridazin-3-yl)oxazol-2-yl)amino)picolinimidamide (Scheme 116)

Scheme 116

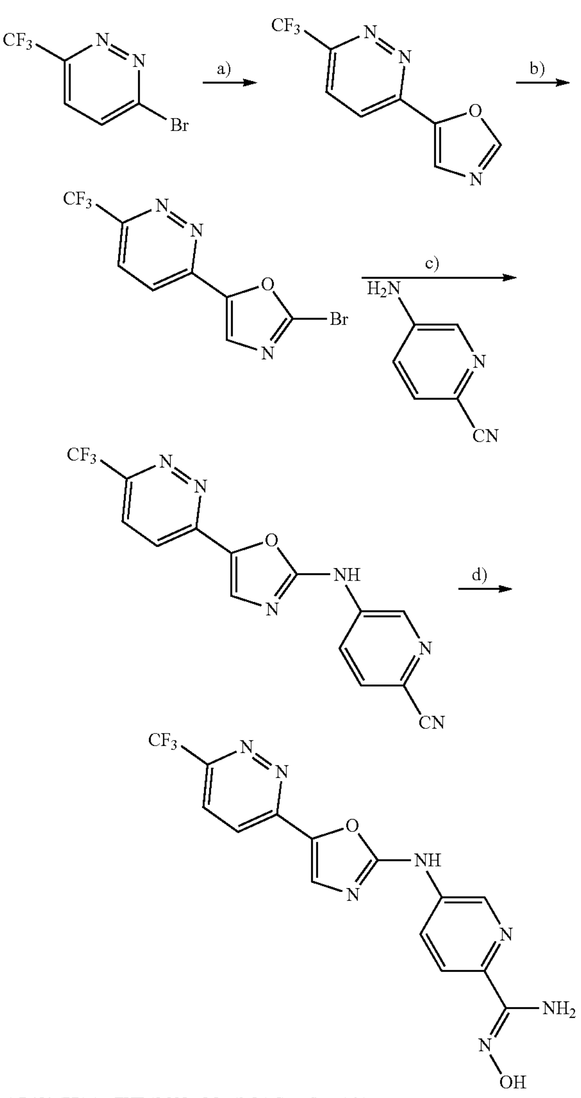

a) $PdCl_2(PPh_3)_2$, THF:1M $Na_2CO_3$ (3.5:1.5), reflux, 16 h;
b) $BrCF_2CF_2Br$, t-BuOLi, DMF/m-xylene, 50° C., 3 h;
b) $Pd_2(dba)_3$, Xantphos, $Cs_2CO_3$, 1,4-Dioxane, 100° C., 16 h;
c) $NH_2OH$•HCl, $Et_3N$, MeOH, reflux, 16 h.

To a degassed biphasic solution of THF (3.5 mL) and 1 M $Na_2CO_3$ (1.5 mL), was added 3-chloro-6-(trifluoromethyl)pyridazine (150 mg, 0.822 mmol, 1.0 eq.), 5-(4,4,5,5-tetramethyl-1,3,2-dioxaborolan-2-yl)oxazole (1.0 M in THF, 904 μL, 0.904 mmol, 1.1 eq.) and $PdCl_2(PPh_3)_2$ (58 mg, 0.082 mmol, 0.1 eq.). The mixture was reacted according to General Procedure 12 Method 1 to afford 5-(6-(trifluoromethyl)pyridazin-3-yl)oxazole as a brown solid (99 mg, 55%). $^{1}H$ NMR (401 MHz, $CDCl_3$) δ 8.12 (m, 2H), 7.98 (d, J=8.9 Hz, 1H), 7.90 (d, J=8.8 Hz, 1H); $^{13}C$ NMR (101 MHz, $CDCl_3$) δ 152.9, 152.4, 150.7, 150.4, 147.7, 125.4, 124.6, 124.6, 124.5, 124.5, 122.9, 122.9, 122.7, 120.0. LCMS $R_f$ (min)=3.223, MS m/z=216.0 $[M+H]^+$.

5-(6-(Trifluoromethyl)pyridazin-3-yl)oxazole (0.322 g, 1.50 mmol) was reacted with $BrCF_2CF_2Br$ (0.27 mL, 2.25 mmol) and t-BuOLi (0.156 g, 1.94 mmol) in DMF/m-xylene (3/3 mL) at 50° C. for 3 h as per General Procedure 15 Method 2 to provide 2-bromo-5-(6-(trifluoromethyl)pyridazin-3-yl)oxazole (0.221 g, 50%) as an orange solid. $^{1}H$ NMR (401 MHz, $CDCl_3$) δ 8.04 (s, 1H), 7.96-7.90 (m, 2H). LCMS $R_f$ (min)=3.033, MS m/z=295.9 $[M+H]^+$.

5-Aminopicolinonitrile (110 mg, 0.923 mmol, 3.0 eq.), $Cs_2CO_3$ (301 mg, 0.924 mmol, 3.0 eq.) and 2-bromo-5-(6-(trifluoromethyl)pyridazin-3-yl)oxazole (90 mg, 0.307 mmol, 1.0 eq.) in 1,4-dioxane (5 mL) was charged with $Pd_2(dba)_3$ (14 mg, 0.015 mmol, 0.05 eq.), Xantphos (18 mg, 0.031 mmol, 0.1 eq.) and reacted according to General Procedure 4 Method 1 to afford 5-((5-(6-(trifluoromethyl)pyridazin-3-yl)oxazol-2-yl)amino)picolinonitrile as yellow solid (50 mg, 49%). $^{1}H$ NMR (401 MHz, DMSO) δ 11.77 (s, 1H), 8.87 (s, 1H), 8.39-8.32 (m, 1H), 8.30 (dd, J=9.1, 4.6 Hz, 1H), 8.23 (dd, J=8.9, 4.3 Hz, 2H), 8.02 (dd, J=8.6, 4.4 Hz, 1H) ppm. LCMS $R_f$ (min)=3.359, MS m/z=333.0 $[M+H]^+$.

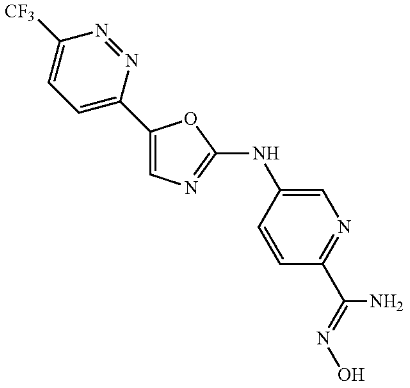 [SMILES: N/C(=N\O)c1ccc(Nc2ncc(-c3ccc(C(F)(F)F)nn3)o2)cn1]

5-((5-(6-(Trifluoromethyl)pyridazin-3-yl)oxazol-2-yl)amino)picolinonitrile (40 mg, 0.12 mmol, 1.0 eq.) was suspended in absolute MeOH (4 mL) followed by the addition of $NH_2OH{\cdot}HCl$ (67 mg, 0.964 mmol, 8.0 eq.) and $Et_3N$ (134 0.964 mmol, 8.0 eq.) according to General Procedure 1 Method 2 to afford N'-hydroxy-5-((5-(6-(trifluoromethyl)pyridazin-3-yl)oxazol-2-yl)amino)picolinimidamide as beige solid (30 mg, 68%). $^{1}H$ NMR (401 MHz, DMSO-$d_6$) δ 11.27 (s, 1H), 9.77 (s, 1H), 8.81 (s, 1H), 8.28 (d, J=9.2 Hz, 1H), 8.21-8.14 (m, 3H), 7.86 (d, J=8.8 Hz, 1H), 5.78 (s, 2H); $^{13}C$ NMR (101 MHz, DMSO) δ 158.4, 151.7, 149.3, 148.3, 148.0, 143.6, 140.7, 137.1, 135.8, 131.7, 125.1, 124.3, 123.1, 119.8 ppm. LCMS $R_f$ (min)=2.283, MS m/z=366.1 $[M+H]^+$. HRMS (ESI) calcd for $C_{14}H_{11}F_3N_7O_2^+$ $([M+H]^+$ 366.0921, found 366.0935.

120. 5-((5-(4-Cyclopropylphenyl)oxazol-2-yl)amino)-N'-hydroxypicolinimidamide (Scheme 117)

Scheme 117

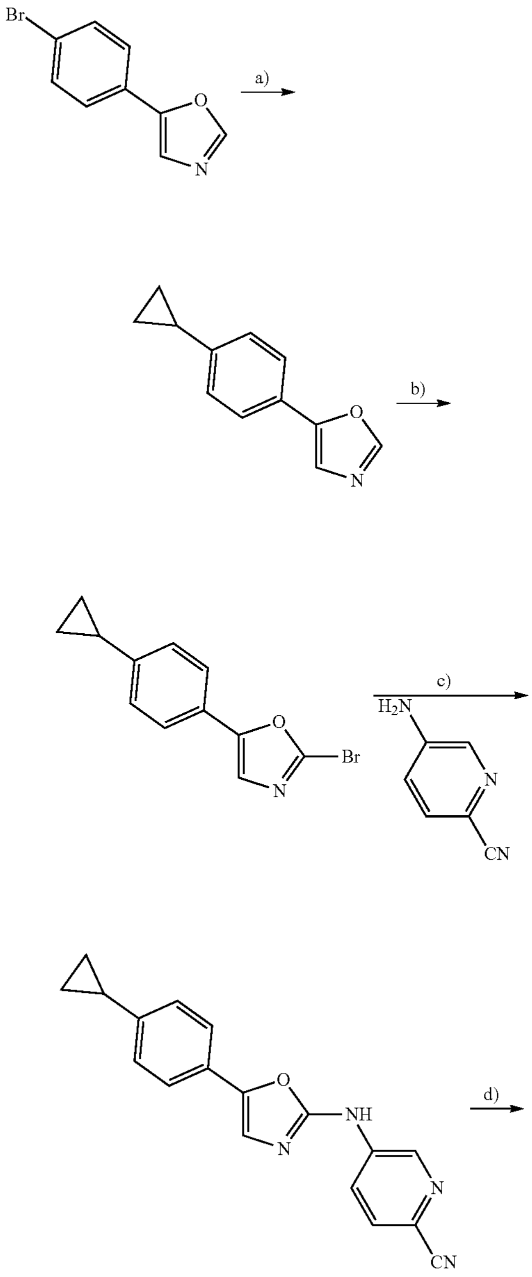

-continued

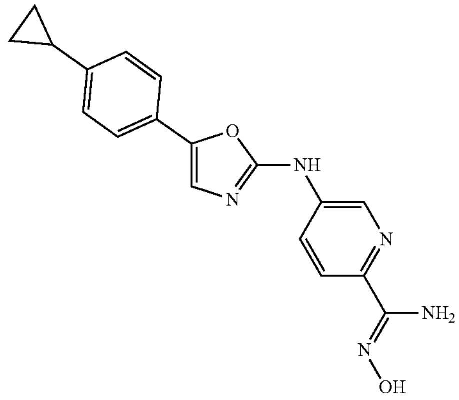

a) cyclopropylboronic acid, $Pd(OAc)_2$, $K_3PO_4$, toluene/$H_2O$, 100° C., 16 h;
b) $BrCF_2CF_2Br$, t-BuOLi, DMF/m-xylene, 60° C., 3 h;
b) $Pd_2(dba)_3$, Xantphos, $Cs_2CO_3$, 1,4-Dioxane, 100° C., 16 h;
c) $NH_2OH$•HCl, $Et_3N$, MeOH, reflux, 16 h.

5-(4-Bromophenyl)oxazole (1.53 g, 6.83 mmol) was reacted with cyclopropylboronic acid (0.76, 8.88 mmol), potassium phosphate (4.35 g, 20.49 mmol), $Pd(OAc)_2$ (0.077 g, 0.34 mmol) and tricyclohexylphosphine (0.192 g, 0.68 mmol) in toluene/$H_2O$ (40/4 mL) as per General Procedure 12 Method 2 to provide 5-(4-cyclopropylphenyl) oxazole (1.26 g, 89%) as a white solid. $^1H$ NMR (401 MHz, $CDCl_3$) δ 7.88 (s, 1H), 7.53 (d, J=8.3 Hz, 2H), 7.28 (s, 1H), 7.11 (d, J=8.3 Hz, 2H), 1.91 (m, 1H), 1.19-0.92 (m, 2H), 0.84-0.58 (m, 2H). LCMS $R_f$ (min)=3.461, MS m/z=186.1 $[M+H]^+$.

5-(4-Cyclopropylphenyl)oxazole (0.60 g, 3.24 mmol) was reacted with $BrCF_2CF_2Br$ (0.58 mL, 4.86 mmol) and t-BuOLi (0.337 g, 4.21 mmol) in DMF/m-xylene (8/8 mL) at 60° C. for h as per General Procedure 15 Method 2 to provide 2-bromo-5-(4-cyclopropylphenyl)oxazole (0.419 g, 49%) as a yellow solid. $^1H$ NMR (401 MHz, $CDCl_3$) δ 7.48 (d, J=8.4 Hz, 2H), 7.22 (s, 1H), 7.11 (d, J=8.3 Hz, 2H), 1.92 (m, 1H), 1.02 (ddd, J=8.4, 6.5, 4.6 Hz, 2H), 0.73 (dt, J=6.6, 4.7 Hz, 2H). LCMS $R_f$ (min)=3.703, MS m/z=264.0 $[M+H]^+$.

5-Aminopicolinonitrile (271 mg, 2.27 mmol, 3.0 eq.), $Cs_2CO_3$ (741 mg, 2.27 mmol, 3.0 eq.) and 2-bromo-5-(5-(trifluoromethyl)pyrazin-2-yl)oxazole (200 mg, 0.757 mmol, 1.0 eq.) in 1,4-dioxane (8 mL) was charged with $Pd_2(dba)_3$ (35 mg, 0.038 mmol, 0.05 eq.) and Xantphos (44 mg, 0.076 mmol, 0.1 eq.) and reacted according to General Procedure 4 Method 1 to afford 5-((5-(4-cyclopropylphenyl) oxazol-2-yl)amino)picolinonitrile as yellow solid (150 mg, 66%). $^1H$ NMR (401 MHz, DMSO-$d_6$) δ 11.25 (s, 1H), 8.82 (s, 1H), 8.32 (d, J=6.6 Hz, 1H), 7.98 (d, J=8.7 Hz, 1H), 7.51 (s, 1H), 7.49 (s, 2H), 7.16 (d, J=8.0 Hz, 2H), 1.94 (m, 1H), 0.97 (m, 2H), 0.71 (m, 2H). LCMS $R_f$ (min)=3.256, MS m/z=303.1 $[M+H]^+$.

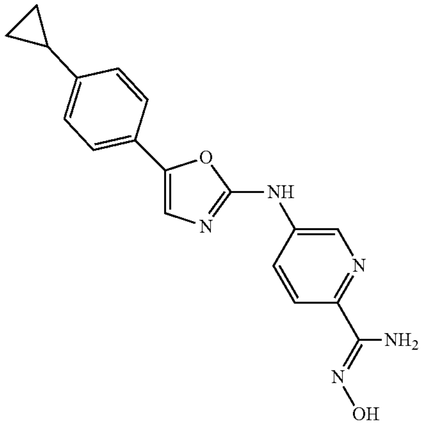 [SMILES: N/C(=N\O)c1ccc(Nc2ncc(-c3ccc(C4CC4)cc3)o2)cn1]

5-((5-(4-Cyclopropylphenyl)oxazol-2-yl)amino) picolinonitrile (75 mg, 0.248 mmol, 1.0 eq.) was suspended in absolute MeOH (6 mL) followed by the addition of $NH_2OH$·HCl (138 mg, 1.99 mmol, 8.0 eq.) and $Et_3N$ (201 mg, 1.99 mmol, 8.0 eq.) and reacted according to General Procedure 1 Method 2 to afford 5-((5-(4-cyclopropylphenyl) oxazol-2-yl)amino)-N'-hydroxypicolinimidamide as beige solid (40 mg, 48%). $^1H$ NMR (401 MHz, DMSO-$d_6$) δ 10.71 (s, 1H), 9.72 (s, 1H), 8.76 (s, 1H), 8.10 (m, 1H), 7.83 (m, 1H), 7.50-7.23 (m, 3H), 7.15 (m, 2H), 5.75 (s, 2H), 1.94 (m, 1H), 0.97 (m, 2H), 0.70 (m, 2H); $^{13}C$ NMR (101 MHz, DMSO) δ 155.5, 149.4, 144.5, 143.2, 142.7, 136.5, 136.4, 125.9, 124.9, 123.5, 122.7, 121.6, 119.7, 15.0, 9.6 ppm. LCMS $R_f$ (min)=2.519, MS m/z=336.1 $[M+H]^+$. HRMS (ESI) calcd for $C_{18}H_{18}N_5O_2^+$ ($[M+H]^+$ 336.1455, found 336.1464.

Example 2

Measurement of Dihydroceramide Desaturase-1 (Des-1) Activity

Compounds were assessed for Des-1 inhibitory activity. Measurement of Des1 activity was performed by HPLC using intact Jurkat cells labeled with DhCer-C6-NBD as described previously (Munoz-Olaya, J. M. et al. *ChemMedChem* 2008, 3, 946-953) with modifications to enhance sensitivity and reproducibility. These modifications included the use of parental Jurkat cells, 0.5% serum in the culture media, and cell harvesting via centrifugation at 500×g to maximise ceramide extraction. Extracted samples (50 ul) were analysed on a Waters HPLC coupled to a fluorescence detector using a 30 cm C18 reverse-phase column eluted with 1 ml/min 20% $H_2O$ and 80% acetonitrile, both with a 0.1% of trifluoroacetic acid. NBD-labelled substrate and product were quantitated with an excitation and emission wavelengths of 465 nm and 530 nm, respectively.

The results are presented in Table 2-1.
TABLE 2-1
| Compound | Structure | Des1 (h) Jurkat $IC_{50}$ [a] μM |
|---|---|---|
| 1 | 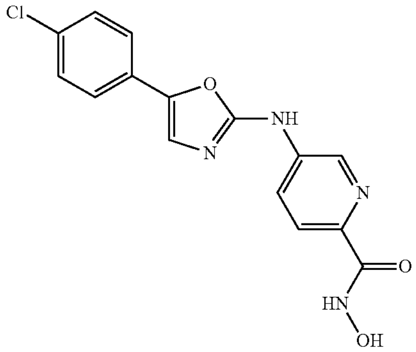 [SMILES: O=C(NO)c1ccc(Nc2ncc(-c3ccc(Cl)cc3)o2)cn1] | 0.1-1.0 |
| 2 | 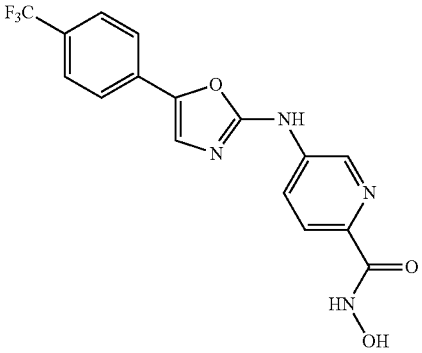 [SMILES: O=C(NO)c1ccc(Nc2ncc(-c3ccc(C(F)(F)F)cc3)o2)cn1] | 0.1-1.0 |
| 3 | 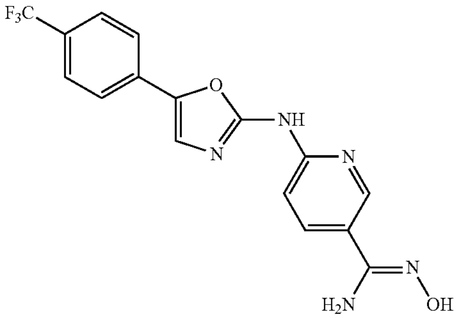 [SMILES: N/C(=N\O)c1ccc(Nc2ncc(-c3ccc(C(F)(F)F)cc3)o2)nc1] | 0.1-1.0 |
| 4 | 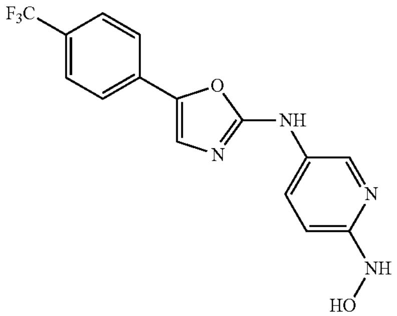 [SMILES: ONc1ccc(Nc2ncc(-c3ccc(C(F)(F)F)cc3)o2)cn1] | 1.0-10 |

TABLE 2-1-continued
| Compound | Structure | Des1 (h) Jurkat $IC_{50}$ [a] μM |
|---|---|---|
| 5 | 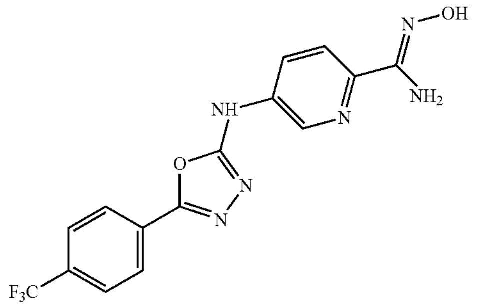 [SMILES: N/C(=N\O)c1ccc(Nc2nnc(-c3ccc(C(F)(F)F)cc3)o2)cn1] | 0.1-1.0 |
| 6 | 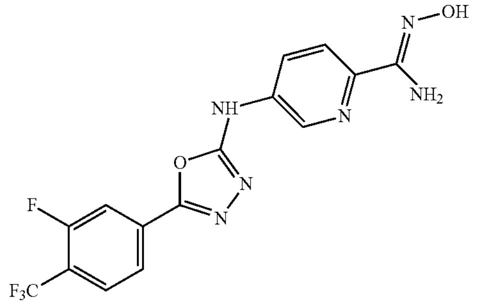 [SMILES: N/C(=N\O)c1ccc(Nc2nnc(-c3ccc(C(F)(F)F)c(F)c3)o2)cn1] | 0.1-1.0 |
| 7 | 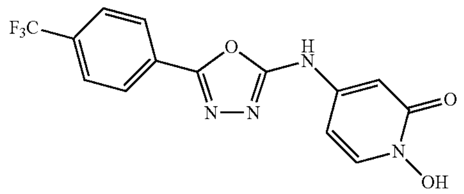 [SMILES: O=c1cc(Nc2nnc(-c3ccc(C(F)(F)F)cc3)o2)ccn1O] | <1 |
| 8 | 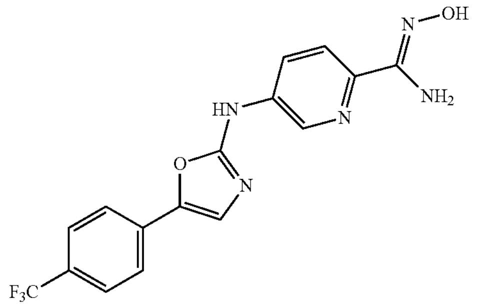 [SMILES: N/C(=N\O)c1ccc(Nc2ncc(-c3ccc(C(F)(F)F)cc3)o2)cn1] | 0.1-1.0 |
| 9 | 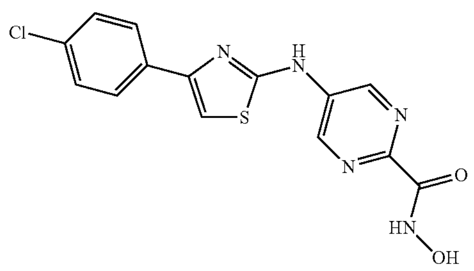 [SMILES: O=C(NO)c1ncc(Nc2nc(-c3ccc(Cl)cc3)cs2)cn1] | >10 (26% inhibition at 10 μM) |
| 10 | 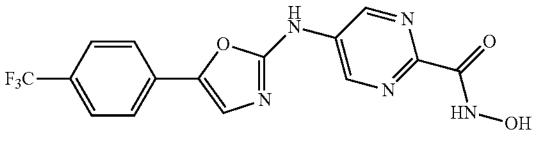 [SMILES: O=C(NO)c1ncc(Nc2ncc(-c3ccc(C(F)(F)F)cc3)o2)cn1] | 1.0-10 |

TABLE 2-1-continued
| Compound | Structure | Des1 (h) Jurkat $IC_{50}$ [a] μM |
|---|---|---|
| 11 | 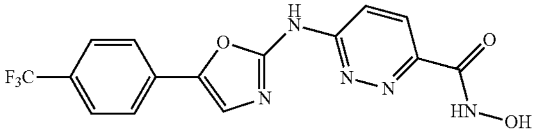 [SMILES: O=C(NO)c1ccc(Nc2ncc(-c3ccc(C(F)(F)F)cc3)o2)nn1] | 0.1-1.0 |
| 12 | 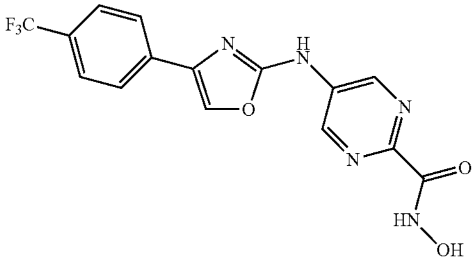 [SMILES: O=C(NO)c1ncc(Nc2nc(-c3ccc(C(F)(F)F)cc3)co2)cn1] | 1.0-10 |
| 13 | 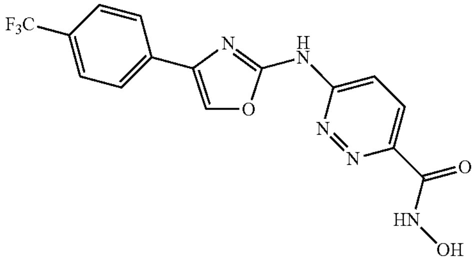 [SMILES: O=C(NO)c1ccc(Nc2nc(-c3ccc(C(F)(F)F)cc3)co2)nn1] | 1.0-10 |
| 14 | 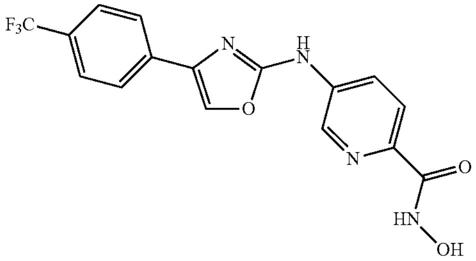 [SMILES: O=C(NO)c1ccc(Nc2nc(-c3ccc(C(F)(F)F)cc3)co2)cn1] | 0.1-1.0 |
| 15 | 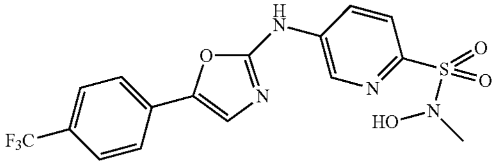 [SMILES: CN(O)S(=O)(=O)c1ccc(Nc2ncc(-c3ccc(C(F)(F)F)cc3)o2)cn1] | >1 (46% inhibition at 1 μM) |
| 16 | 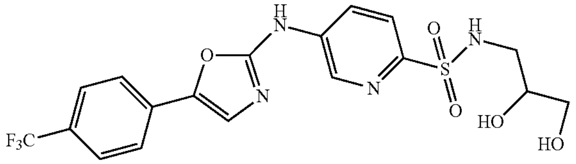 [SMILES: O=S(=O)(NCC(O)CO)c1ccc(Nc2ncc(-c3ccc(C(F)(F)F)cc3)o2)cn1] | >1 (42% inhibition at 1 μM) |
| 17 | 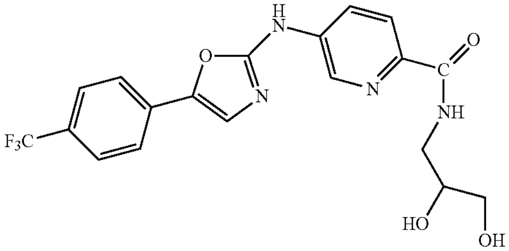 (racemic) | 0.001-0.01 |

TABLE 2-1-continued
| Compound | Structure | Des1 (h) Jurkat $IC_{50}$ [a] μM |
|---|---|---|
| 18 | 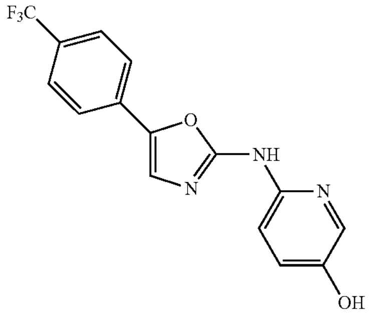 [SMILES: Oc1ccc(Nc2ncc(-c3ccc(C(F)(F)F)cc3)o2)nc1] | <1 |
| 19 | 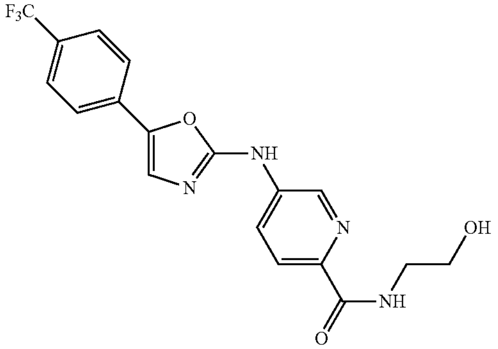 [SMILES: O=C(NCCO)c1ccc(Nc2ncc(-c3ccc(C(F)(F)F)cc3)o2)cn1] | 1.0-10 |
| 20 | 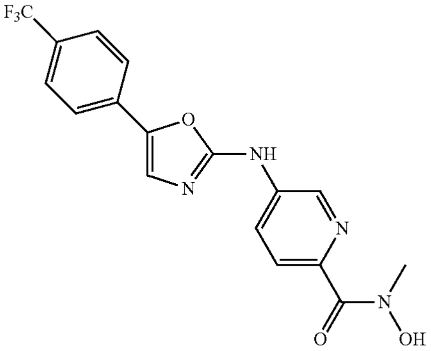 [SMILES: CN(O)C(=O)c1ccc(Nc2ncc(-c3ccc(C(F)(F)F)cc3)o2)cn1] | <0.1 |
| 21 | 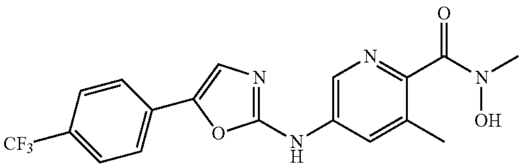 [SMILES: Cc1cc(Nc2ncc(-c3ccc(C(F)(F)F)cc3)o2)cnc1C(=O)N(C)O] | >1 (38% inhibition at 1 μM) |
| 22 | 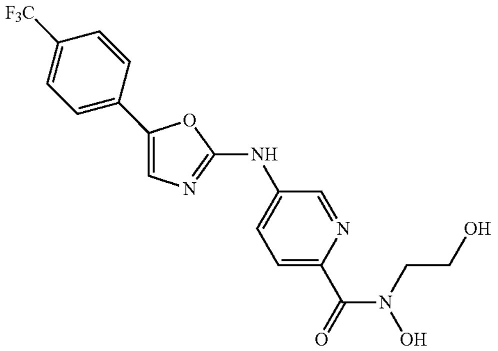 [SMILES: O=C(c1ccc(Nc2ncc(-c3ccc(C(F)(F)F)cc3)o2)cn1)N(O)CCO] | >10 (81% inhibition at 10 μM) |

TABLE 2-1-continued
| Compound | Structure | Des1 (h) Jurkat $IC_{50}$ [a] μM |
| --- | --- | --- |
| 23 | 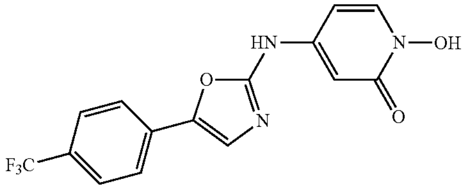 [SMILES: O=c1cc(Nc2ncc(-c3ccc(C(F)(F)F)cc3)o2)ccn1O] | 0.001-0.01 |
| 24 | 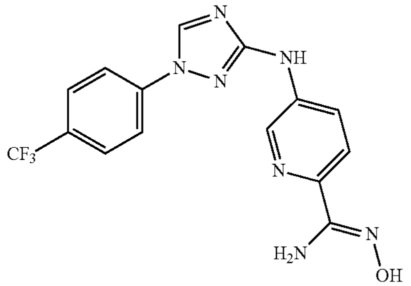 [SMILES: N/C(=N\O)c1ccc(Nc2ncn(-c3ccc(C(F)(F)F)cc3)n2)cn1] | 0.01-0.1 |
| 25 | 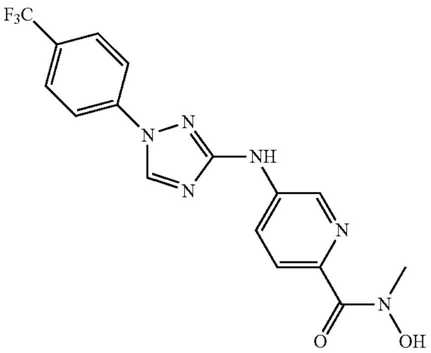 [SMILES: CN(O)C(=O)c1ccc(Nc2ncn(-c3ccc(C(F)(F)F)cc3)n2)cn1] | <1 |
| 26 | 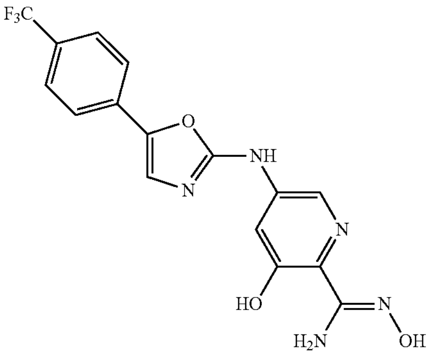 [SMILES: N/C(=N\O)c1ncc(Nc2ncc(-c3ccc(C(F)(F)F)cc3)o2)cc1O] | 0.001-0.01 |
| 27 | 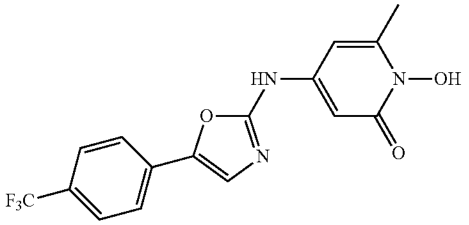 [SMILES: Cc1cc(Nc2ncc(-c3ccc(C(F)(F)F)cc3)o2)cc(=O)n1O] | 0.0001-0.001 |

TABLE 2-1-continued
| Compound | Structure | Des1 (h) Jurkat $IC_{50}$ [a] μM |
|---|---|---|
| 28 | 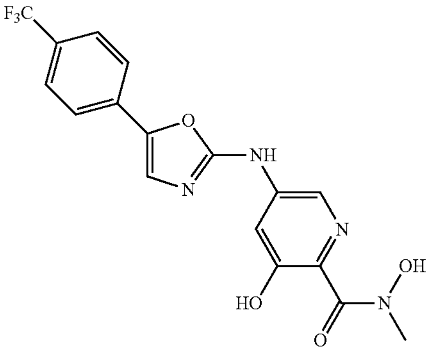 [SMILES: CN(O)C(=O)c1ncc(Nc2ncc(-c3ccc(C(F)(F)F)cc3)o2)cc1O] | <1 |
| 29 | 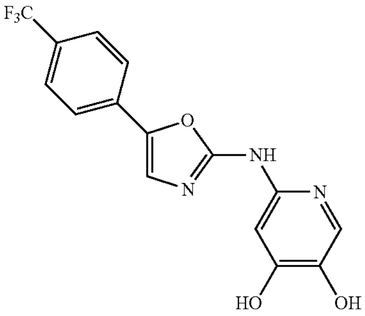 [SMILES: Oc1cnc(Nc2ncc(-c3ccc(C(F)(F)F)cc3)o2)cc1O] | <1 |
| 30 | 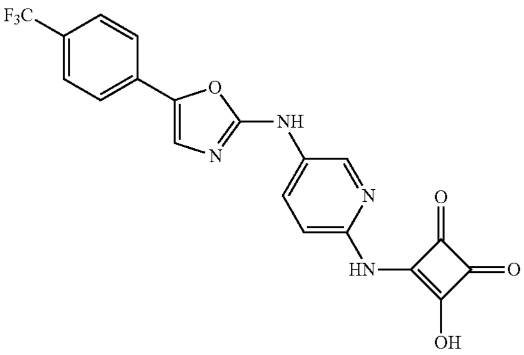 [SMILES: O=c1c(O)c(Nc2ccc(Nc3ncc(-c4ccc(C(F)(F)F)cc4)o3)cn2)c1=O] | <1 |
| 31 | 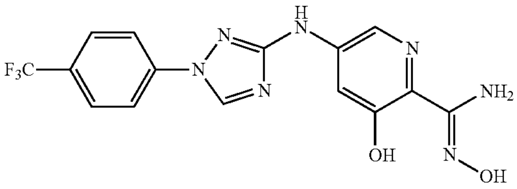 [SMILES: N/C(=N\O)c1ncc(Nc2ncn(-c3ccc(C(F)(F)F)cc3)n2)cc1O] | <1 |
| 32 | 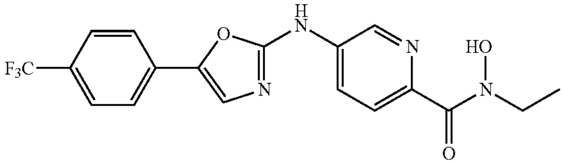 [SMILES: CCN(O)C(=O)c1ccc(Nc2ncc(-c3ccc(C(F)(F)F)cc3)o2)cn1] | <1 |
| 33 | 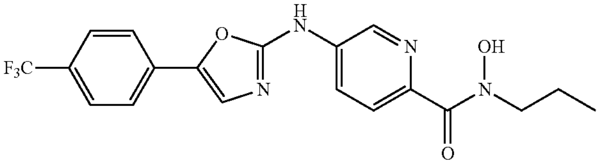 [SMILES: CCCN(O)C(=O)c1ccc(Nc2ncc(-c3ccc(C(F)(F)F)cc3)o2)cn1] | 1 |

TABLE 2-1-continued
| Compound | Structure | Des1 (h) Jurkat $IC_{50}$ [a] μM |
|---|---|---|
| 34 | 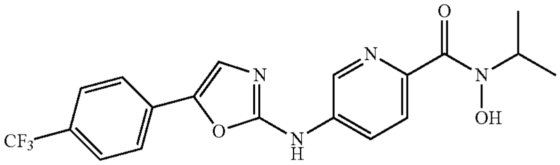 [SMILES: CC(C)N(O)C(=O)c1ccc(Nc2ncc(-c3ccc(C(F)(F)F)cc3)o2)cn1] | >1 (23% inhibition at 1 μM) |
| 35 | 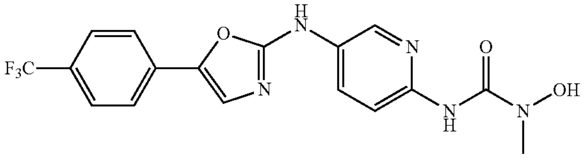 [SMILES: CN(O)C(=O)Nc1ccc(Nc2ncc(-c3ccc(C(F)(F)F)cc3)o2)cn1] | 0.01-0.1 |
| 36 | 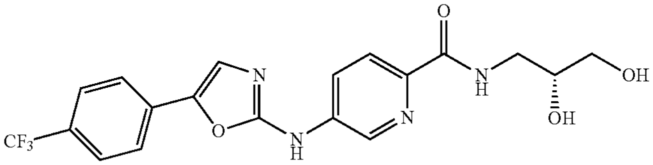 [SMILES: O=C(NC[C@@H](O)CO)c1ccc(Nc2ncc(-c3ccc(C(F)(F)F)cc3)o2)cn1] | 0.001-0.01 |
| 37 | 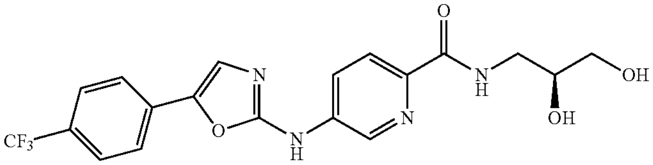 [SMILES: O=C(NC[C@H](O)CO)c1ccc(Nc2ncc(-c3ccc(C(F)(F)F)cc3)o2)cn1] | >1 (no inhibition at 1 μM) |
| 38 | 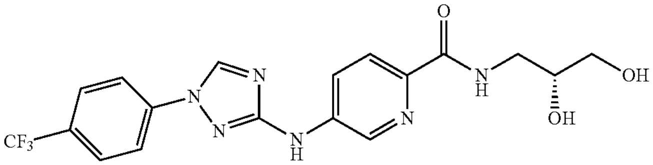 [SMILES: O=C(NC[C@@H](O)CO)c1ccc(Nc2ncn(-c3ccc(C(F)(F)F)cc3)n2)cn1] | >1 (30% inhibition at 1 μM) |
| 39 | 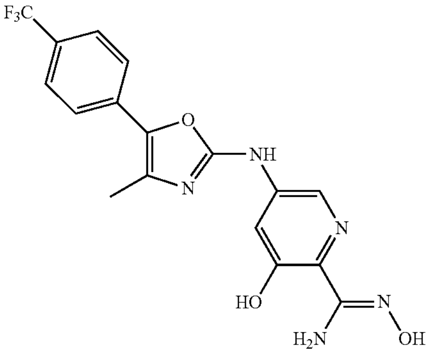 [SMILES: Cc1nc(Nc2cnc(/C(N)=N/O)c(O)c2)oc1-c1ccc(C(F)(F)F)cc1] | <1 |

TABLE 2-1-continued
| Compound | Structure | Des1 (h) Jurkat $IC_{50}$ [a] μM |
| --- | --- | --- |
| 40 | 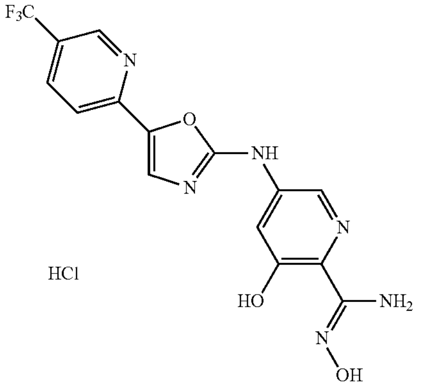 [SMILES: N/C(=N\O)c1ncc(Nc2ncc(-c3ccc(C(F)(F)F)cn3)o2)cc1O ; Cl] HCl | 0.01-0.1 |
| 41 | 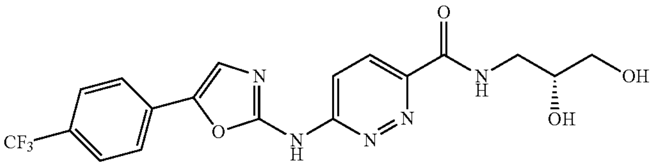 [SMILES: O=C(NC[C@@H](O)CO)c1ccc(Nc2ncc(-c3ccc(C(F)(F)F)cc3)o2)nn1] | <0.1 |
| 42 | 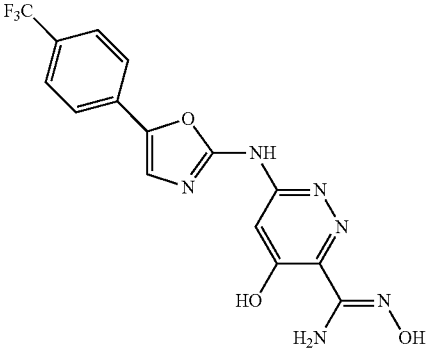 | 0.001-0.01 |
| 43 | 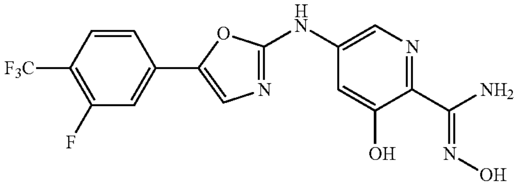 [SMILES: N/C(=N\O)c1ncc(Nc2ncc(-c3ccc(C(F)(F)F)c(F)c3)o2)cc1O] | 0.001-0.01 |
| 44 | 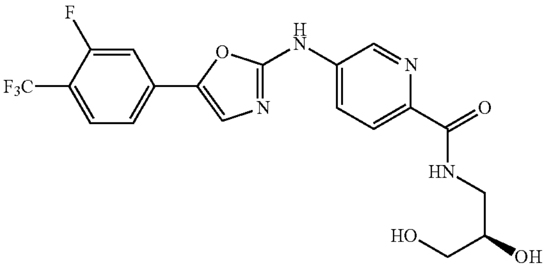 [SMILES: O=C(NC[C@@H](O)CO)c1ccc(Nc2ncc(-c3ccc(C(F)(F)F)c(F)c3)o2)cn1] | 0.001-0.01 |

TABLE 2-1-continued
| Compound | Structure | Des1 (h) Jurkat $IC_{50}$ [a] μM |
|---|---|---|
| 45 | 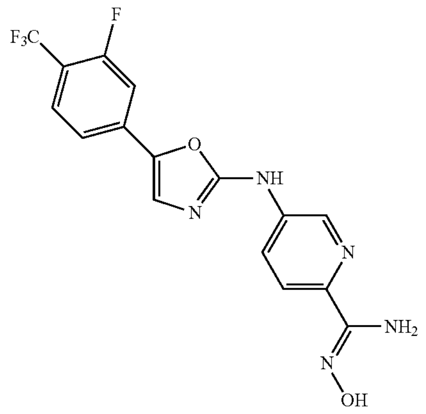 [SMILES: N/C(=N\O)c1ccc(Nc2ncc(-c3ccc(C(F)(F)F)c(F)c3)o2)cn1] | <0.1 |
| 46 | 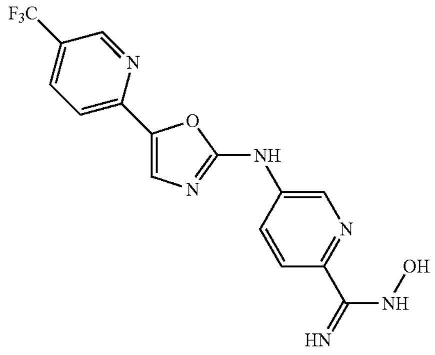 [SMILES: N=C(NO)c1ccc(Nc2ncc(-c3ccc(C(F)(F)F)cn3)o2)cn1] | 0.1-1.0 |
| 47 | 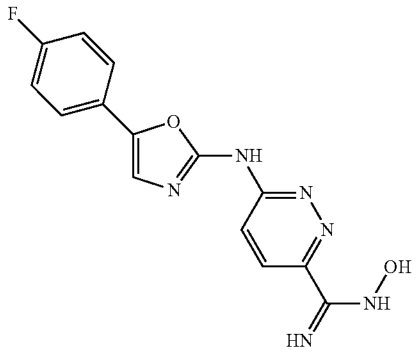 [SMILES: N=C(NO)c1ccc(Nc2ncc(-c3ccc(F)cc3)o2)nn1] | <0.1 |
| 48 | 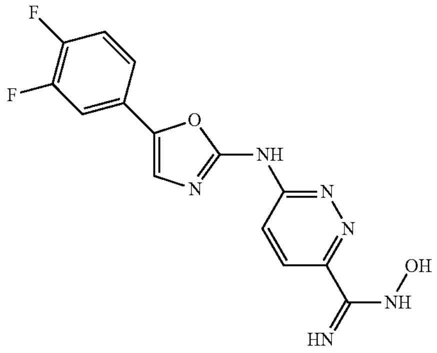 [SMILES: N=C(NO)c1ccc(Nc2ncc(-c3ccc(F)c(F)c3)o2)nn1] | 0.001-0.01 |

TABLE 2-1-continued
| Compound | Structure | Des1 (h) Jurkat $IC_{50}$ [a] μM |
|---|---|---|
| 49 | 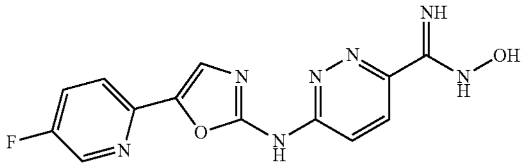 [SMILES: N=C(NO)c1ccc(Nc2ncc(-c3ccc(F)cn3)o2)nn1] | <0.1 |
| 50 | 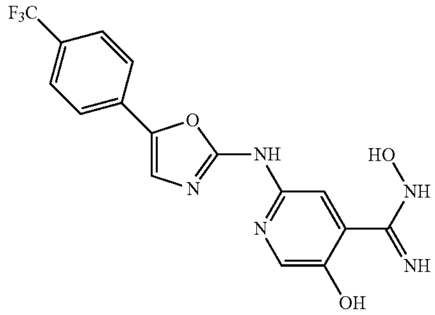 [SMILES: N=C(NO)c1cc(Nc2ncc(-c3ccc(C(F)(F)F)cc3)o2)ncc1O] | <1 |
| 51 | 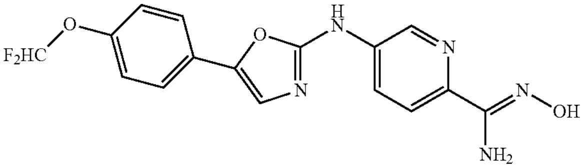 [SMILES: N/C(=N\O)c1ccc(Nc2ncc(-c3ccc(OC(F)F)cc3)o2)cn1] | 0.1-1.0 |
| 52 | 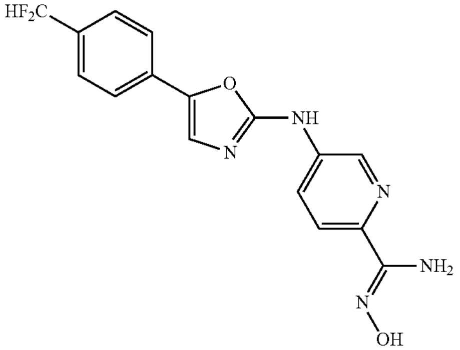 | 0.1-1.0 |
| 53 | 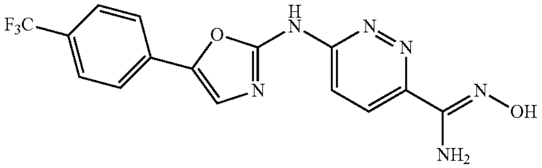 | 0.001-0.01 |
| 54 | 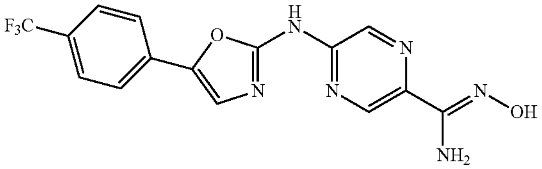 [SMILES: N/C(=N\O)c1cnc(Nc2ncc(-c3ccc(C(F)(F)F)cc3)o2)cn1] | 0.1-1.0 |
| 55 | 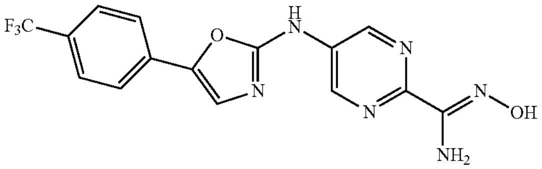 | <1 |

TABLE 2-1-continued
| Compound | Structure | Des1 (h) Jurkat $IC_{50}$ [a] μM |
|---|---|---|
| 56 | 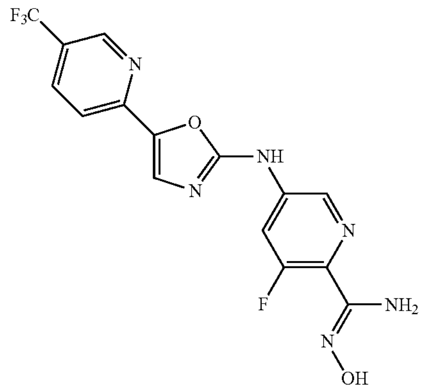 [SMILES: N/C(=N\O)c1ncc(Nc2ncc(-c3ccc(C(F)(F)F)cn3)o2)cc1F] | >0.1 (86% inhibition at 0.1 μM) |
| 57 | 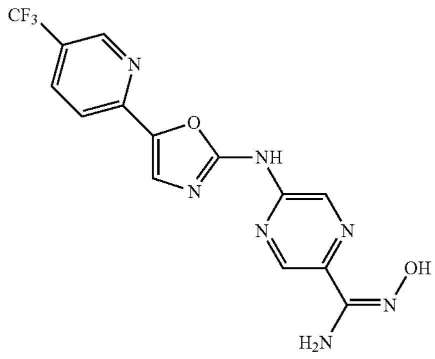 [SMILES: N/C(=N/O)c1cnc(Nc2ncc(-c3ccc(C(F)(F)F)cn3)o2)cn1] | <1 |
| 58 | 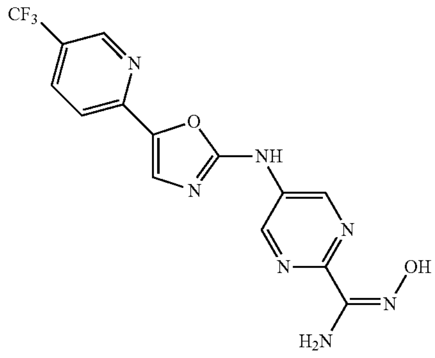 [SMILES: N/C(=N/O)c1ncc(Nc2ncc(-c3ccc(C(F)(F)F)cn3)o2)cn1] | >1 (40% inhibition at 1 μM) |
| 59 | 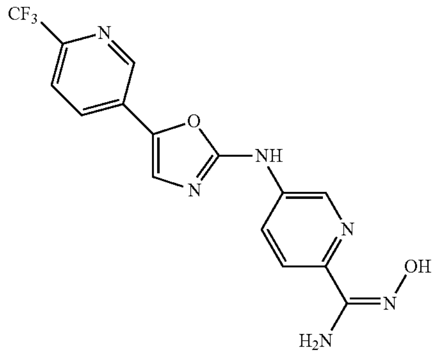 [SMILES: N/C(=N/O)c1ccc(Nc2ncc(-c3ccc(C(F)(F)F)nc3)o2)cn1] | <1 |

TABLE 2-1-continued
| Compound | Structure | Des1 (h) Jurkat $IC_{50}$ [a] μM |
|---|---|---|
| 60 | 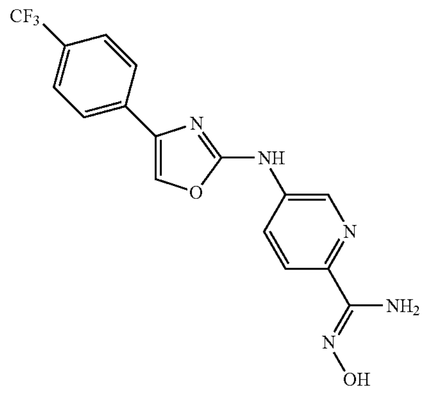 [SMILES: N/C(=N\O)c1ccc(Nc2nc(-c3ccc(C(F)(F)F)cc3)co2)cn1] | <1 |
| 61 | 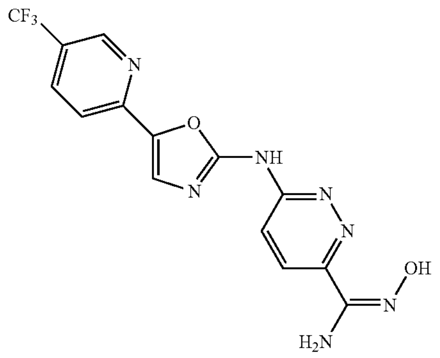 [SMILES: N/C(=N/O)c1ccc(Nc2ncc(-c3ccc(C(F)(F)F)cn3)o2)nn1] | <0.1 |
| 62 | 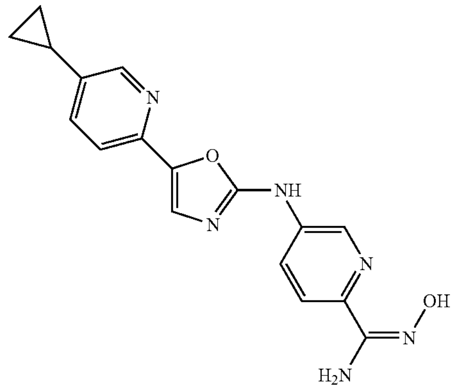 [SMILES: N/C(=N/O)c1ccc(Nc2ncc(-c3ccc(C4CC4)cn3)o2)cn1] | >1 (42% inhibition at 1 μM) |
| 63 | 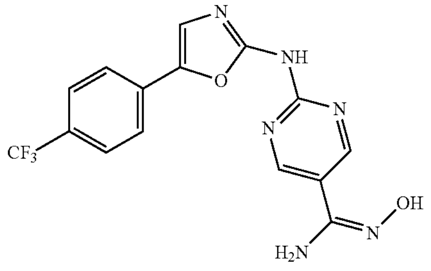 [SMILES: N/C(=N/O)c1cnc(Nc2ncc(-c3ccc(C(F)(F)F)cc3)o2)nc1] | >1 (23% inhibition at 1 μM) |

TABLE 2-1-continued
| Compound | Structure | Des1 (h) Jurkat $IC_{50}$ [a] μM |
|---|---|---|
| 64 | 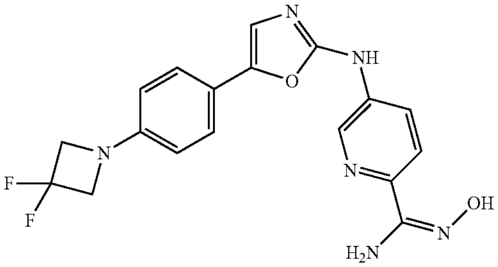 [SMILES: N/C(=N/O)c1ccc(Nc2ncc(-c3ccc(N4CC(F)(F)C4)cc3)o2)cn1] | >1 (23% inhibition at 1 μM) |
| 65 | 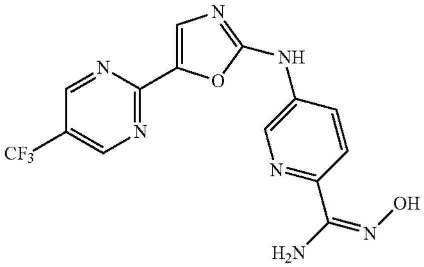 [SMILES: N/C(=N/O)c1ccc(Nc2ncc(-c3ncc(C(F)(F)F)cn3)o2)cn1] | >1 (26% inhibition at 1 μM) |
| 66 | 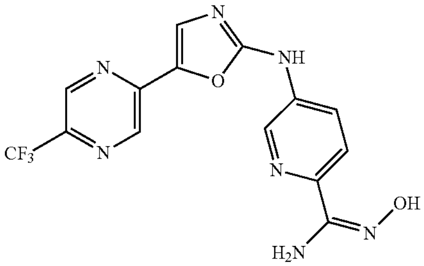 [SMILES: N/C(=N/O)c1ccc(Nc2ncc(-c3cnc(C(F)(F)F)cn3)o2)cn1] | >1 (47% inhibition at 1 μM) |
| 67 | 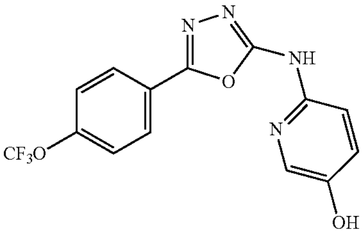 | <1 |
| 68 | 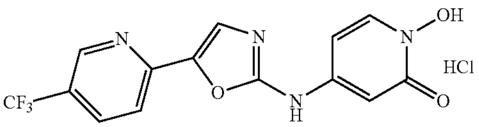 [SMILES: O=c1cc(Nc2ncc(-c3ccc(C(F)(F)F)cn3)o2)ccn1O ; Cl] | <1 |
| 69 | 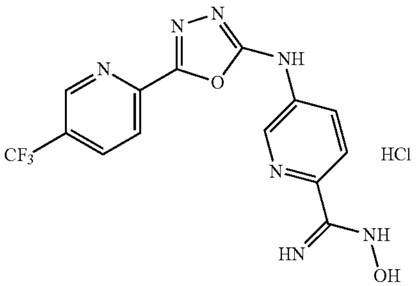 [SMILES: N=C(NO)c1ccc(Nc2nnc(-c3ccc(C(F)(F)F)cn3)o2)cn1 ; Cl] | >1 (no inhibition at 1 μM) |

TABLE 2-1-continued
| Compound | Structure | Des1 (h) Jurkat $IC_{50}$ [a] μM |
|---|---|---|
| 70 | 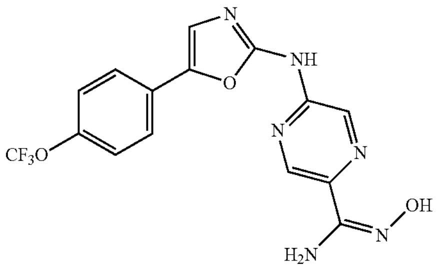 | <1 |
| 71 | 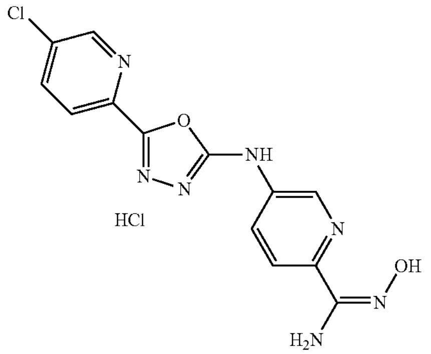 [SMILES: N/C(=N/O)c1ccc(Nc2nnc(-c3ccc(Cl)cn3)o2)cn1 ; Cl] | >1 (13% inhibition at 1 μM) |
| 72 | 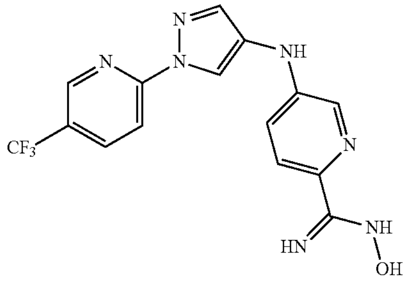 [SMILES: N=C(NO)c1ccc(Nc2cnn(-c3ccc(C(F)(F)F)cn3)c2)cn1] | <1 |
| 73 | 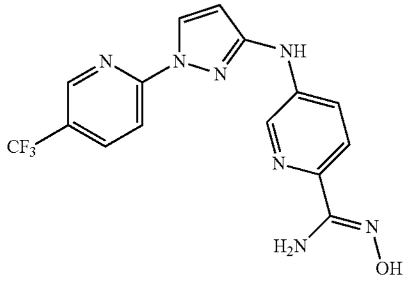 [SMILES: N/C(=N\O)c1ccc(Nc2ccn(-c3ccc(C(F)(F)F)cn3)n2)cn1] | <1 |
| 74 | 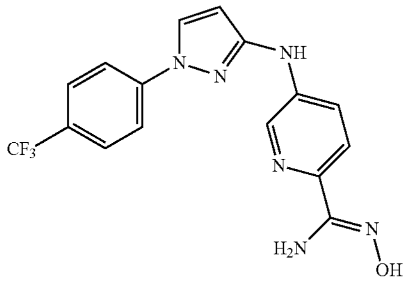 [SMILES: N/C(=N\O)c1ccc(Nc2ccn(-c3ccc(C(F)(F)F)cc3)n2)cn1] | <1 |

TABLE 2-1-continued
| Compound | Structure | Des1 (h) Jurkat $IC_{50}$ [a] μM |
|---|---|---|
| 75 | 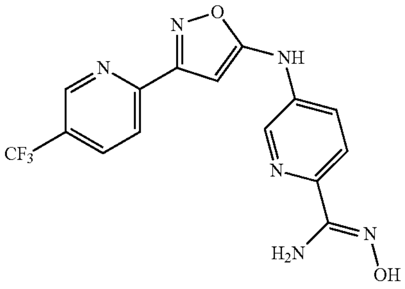 [SMILES: N/C(=N\O)c1ccc(Nc2cc(-c3ccc(C(F)(F)F)cn3)no2)cn1] | <1 |
| 76 | 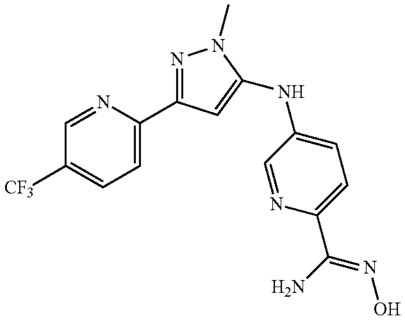 [SMILES: Cn1nc(-c2ccc(C(F)(F)F)cn2)cc1Nc1ccc(/C(N)=N/O)nc1] | >1 (8% inhibition at 1 μM) |
| 77 | 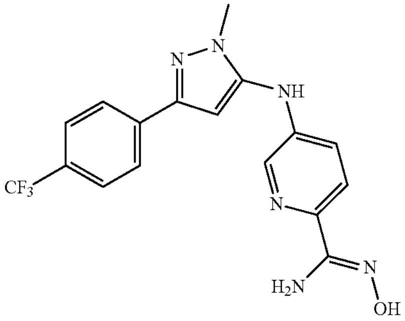 [SMILES: Cn1nc(-c2ccc(C(F)(F)F)cc2)cc1Nc1ccc(/C(N)=N/O)nc1] | >1 (47% inhibition at 1 μM) |
| 78 | 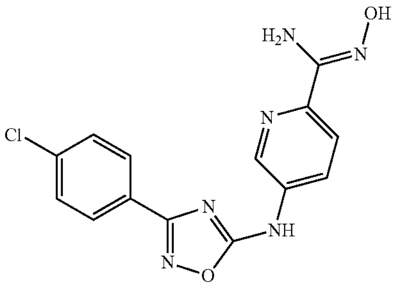 [SMILES: N/C(=N\O)c1ccc(Nc2nc(-c3ccc(Cl)cc3)no2)cn1] | <1 |
| 79 | 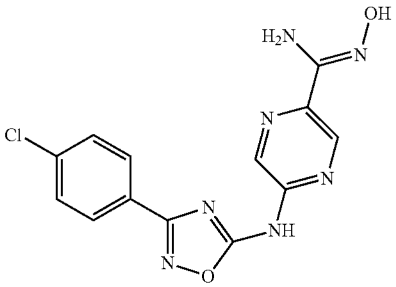 [SMILES: N/C(=N\O)c1cnc(Nc2nc(-c3ccc(Cl)cc3)no2)cn1] | <1 |

TABLE 2-1-continued
| Compound | Structure | Des1 (h) Jurkat $IC_{50}$ [a] μM |
| --- | --- | --- |
| 80 | 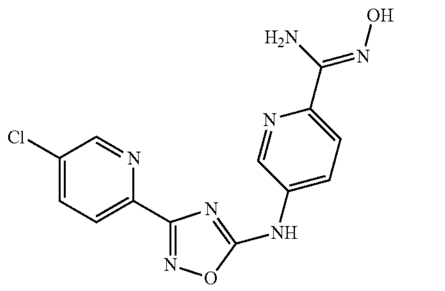 [SMILES: N/C(=N\O)c1ccc(Nc2nc(-c3ccc(Cl)cn3)no2)cn1] | >1 (24% inhibition at 1 μM) |
| 81 | 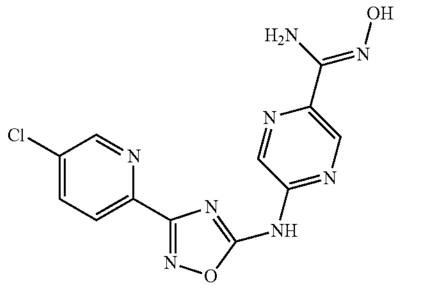 [SMILES: N/C(=N\O)c1cnc(Nc2nc(-c3ccc(Cl)cn3)no2)cn1] | >1 (7% inhibition at 1 μM) |
| 82 | 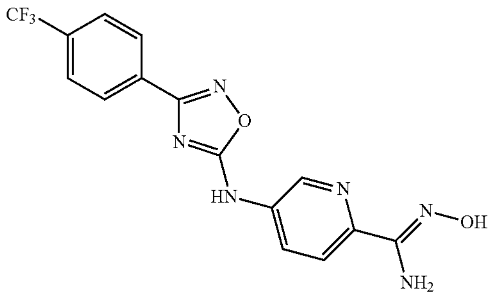 [SMILES: N/C(=N\O)c1ccc(Nc2nc(-c3ccc(C(F)(F)F)cc3)no2)cn1] | <1 |
| 83 | 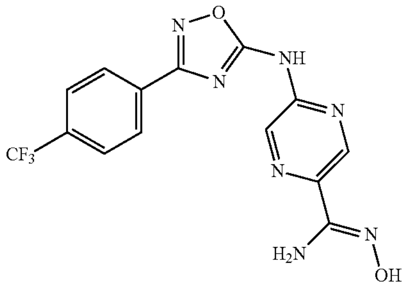 [SMILES: N/C(=N\O)c1cnc(Nc2nc(-c3ccc(C(F)(F)F)cc3)no2)cn1] | <1 |
| 84 | 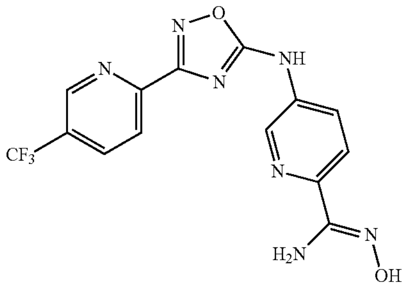 [SMILES: N/C(=N\O)c1ccc(Nc2nc(-c3ccc(C(F)(F)F)cn3)no2)cn1] | >1 (45% inhibition at 1 μM) |

TABLE 2-1-continued
| Compound | Structure | Des1 (h) Jurkat $IC_{50}$ [a] μM |
|---|---|---|
| 85 | 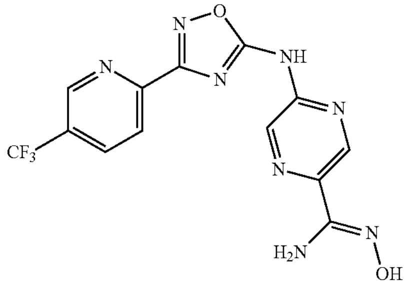 [SMILES: N/C(=N\O)c1cnc(Nc2nc(-c3ccc(C(F)(F)F)cn3)no2)cn1] | >1 (15% inhibition at 1 μM) |
| 86 | 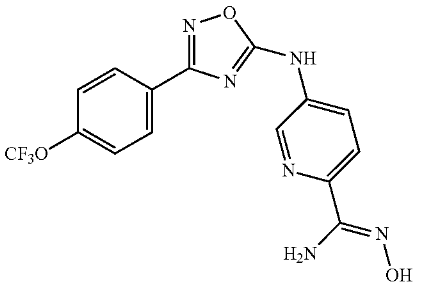 | <1 |
| 87 | 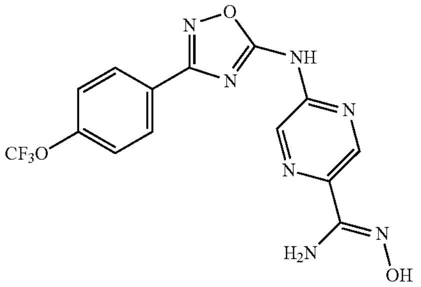 | 1 |
| 88 | 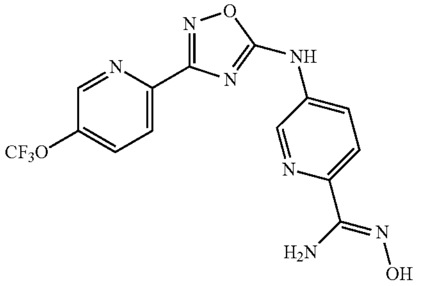 | >1 (29% inhibition at 1 μM) |
| 89 | 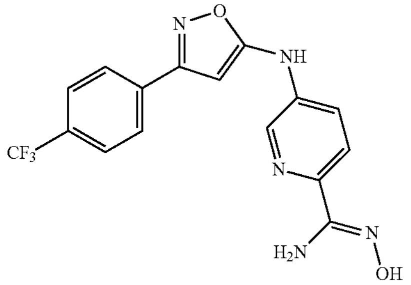 [SMILES: N/C(=N\O)c1ccc(Nc2cc(-c3ccc(C(F)(F)F)cc3)no2)cn1] | <1 |

TABLE 2-1-continued
| Compound | Structure | Des1 (h) Jurkat $IC_{50}$ [a] μM |
| --- | --- | --- |
| 90 | 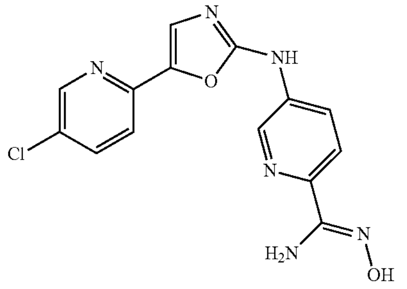 [SMILES: N/C(=N\O)c1ccc(Nc2ncc(-c3ccc(Cl)cn3)o2)cn1] | <1 |
| 91 | 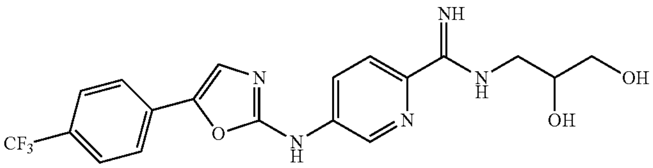 [SMILES: N=C(NCC(O)CO)c1ccc(Nc2ncc(-c3ccc(C(F)(F)F)cc3)o2)cn1] | >1 (44% inhibition at 1 μM) |
| 92 | 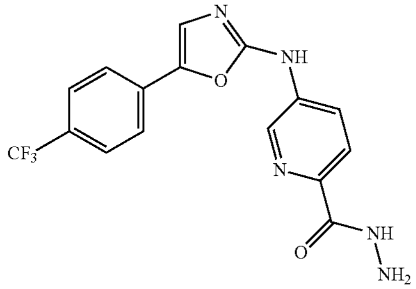 [SMILES: NNC(=O)c1ccc(Nc2ncc(-c3ccc(C(F)(F)F)cc3)o2)cn1] | 0.1-1.0 |
| 93 | 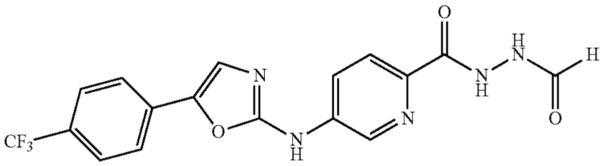 [SMILES: O=CNNC(=O)c1ccc(Nc2ncc(-c3ccc(C(F)(F)F)cc3)o2)cn1] | <1 |
| 94 | 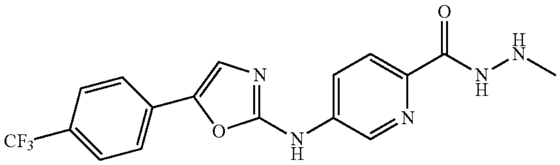 [SMILES: CNNC(=O)c1ccc(Nc2ncc(-c3ccc(C(F)(F)F)cc3)o2)cn1] | >1 (30% inhibition at 1 μM) |
| 95 | 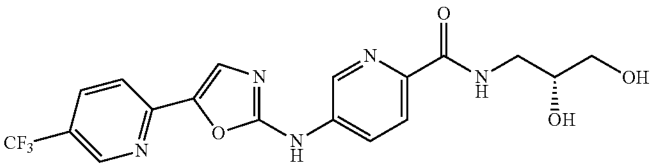 [SMILES: O=C(NC[C@@H](O)CO)c1ccc(Nc2ncc(-c3ccc(C(F)(F)F)cn3)o2)cn1] | 0.01-0.1 |
| 96 | 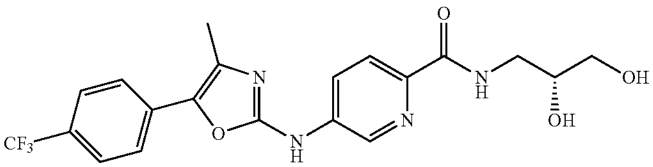 [SMILES: Cc1nc(Nc2ccc(C(=O)NC[C@@H](O)CO)nc2)oc1-c1ccc(C(F)(F)F)cc1] | <1 |

TABLE 2-1-continued
| Compound | Structure | Des1 (h) Jurkat $IC_{50}$ [a] μM |
|---|---|---|
| 97 | 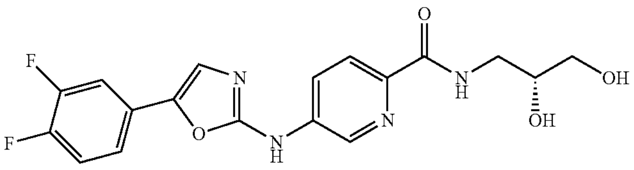 [SMILES: O=C(NC[C@@H](O)CO)c1ccc(Nc2ncc(-c3ccc(F)c(F)c3)o2)cn1] | >0.1 (55% inhibition at 0.1 μM) |
| 98 | 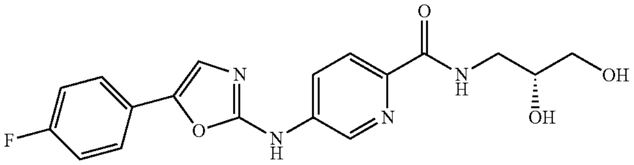 [SMILES: O=C(NC[C@@H](O)CO)c1ccc(Nc2ncc(-c3ccc(F)cc3)o2)cn1] | >0.1 (70% inhibition at 0.1 μM) |
| 99 | 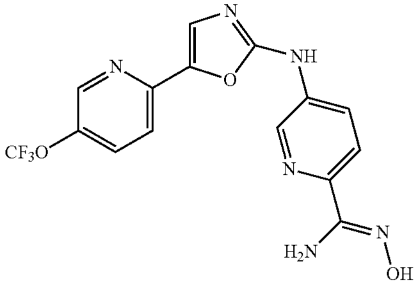 | >1 (47% inhibition at 1 μM) |
| 100 | 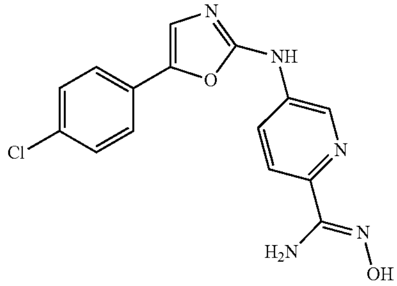 [SMILES: N/C(=N\O)c1ccc(Nc2ncc(-c3ccc(Cl)cc3)o2)cn1] | <1 |
| 101 | 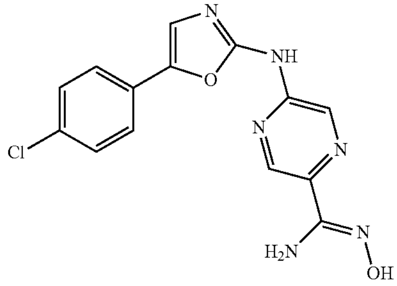 [SMILES: N/C(=N\O)c1cnc(Nc2ncc(-c3ccc(Cl)cc3)o2)cn1] | <1 |
| 102 | 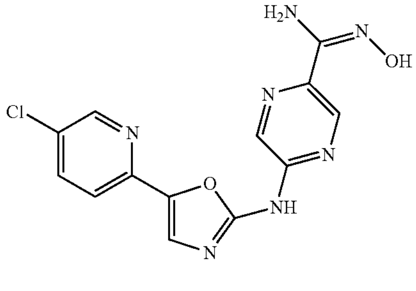 [SMILES: N/C(=N/O)c1cnc(Nc2ncc(-c3ccc(Cl)cn3)o2)cn1] | <1 |

TABLE 2-1-continued
| Compound | Structure | Des1 (h) Jurkat $IC_{50}$ [a] μM |
| --- | --- | --- |
| 103 | 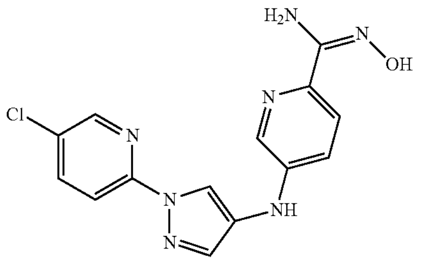 [SMILES: N/C(=N/O)c1ccc(Nc2cnn(-c3ccc(Cl)cn3)c2)cn1] | <1 |
| 104 | 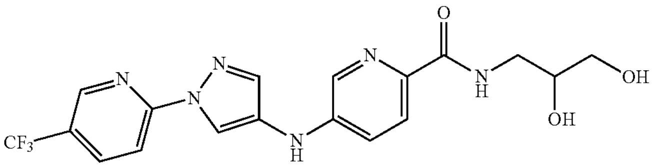 [SMILES: O=C(NCC(O)CO)c1ccc(Nc2cnn(-c3ccc(C(F)(F)F)cn3)c2)cn1] | >1 (26% inhibition at 1 μM) |
| 105 | 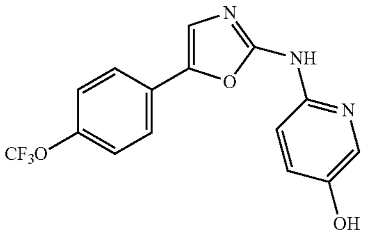 | <1 |
| 106 | 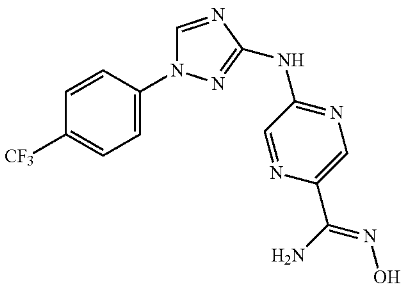 [SMILES: N/C(=N\O)c1cnc(Nc2ncn(-c3ccc(C(F)(F)F)cc3)n2)cn1] | <1 |
| 107 | 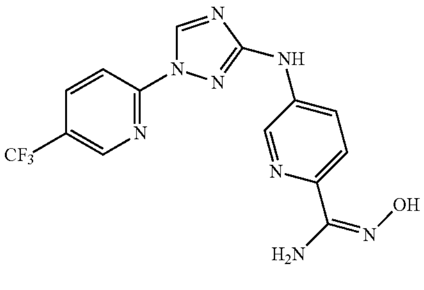 [SMILES: N/C(=N/O)c1ccc(Nc2ncn(-c3ccc(C(F)(F)F)cn3)n2)cn1] | <1 |
| 108 | 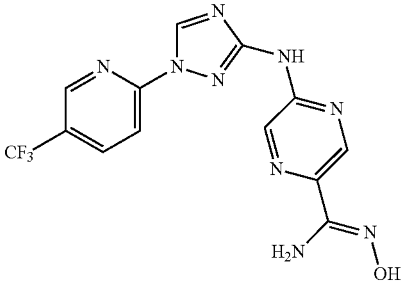 [SMILES: N/C(=N\O)c1cnc(Nc2ncn(-c3ccc(C(F)(F)F)cn3)n2)cn1] | <1 |

TABLE 2-1-continued
| Compound | Structure | Des1 (h) Jurkat $IC_{50}$ [a] μM |
|---|---|---|
| 109 | 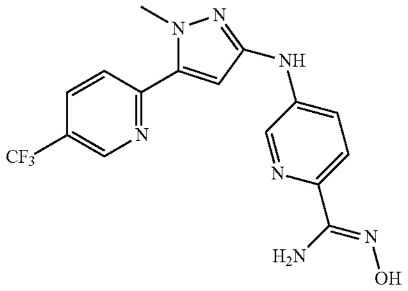 [SMILES: Cn1nc(Nc2ccc(/C(N)=N/O)nc2)cc1-c1ccc(C(F)(F)F)cn1] | <1 |
| 110 | 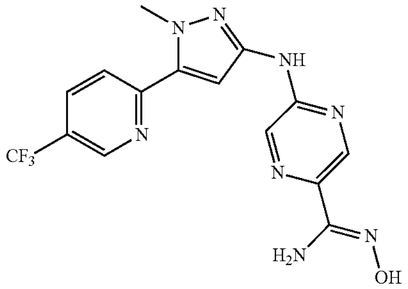 | >1 (31% inhibition at 1 μM) |
| 111 | 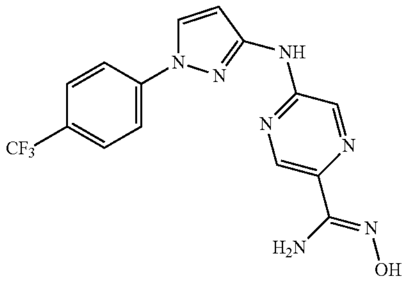 [SMILES: N/C(=N\O)c1cnc(Nc2ccn(-c3ccc(C(F)(F)F)cc3)n2)cn1] | <1 |
| 112 | 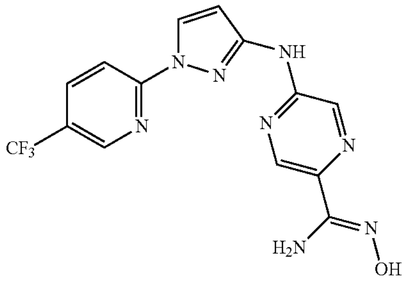 [SMILES: N/C(=N\O)c1cnc(Nc2ccn(-c3ccc(C(F)(F)F)cn3)n2)cn1] | <1 |
| 113 | 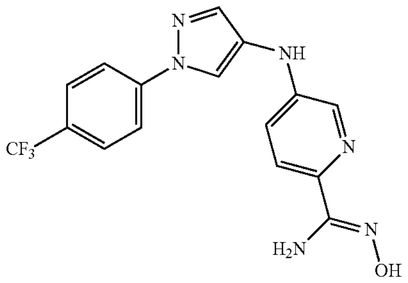 [SMILES: N/C(=N\O)c1ccc(Nc2cnn(-c3ccc(C(F)(F)F)cc3)c2)cn1] | <1 |

TABLE 2-1-continued
| Compound | Structure | Des1 (h) Jurkat $IC_{50}$ [a] μM |
|---|---|---|
| 114 | 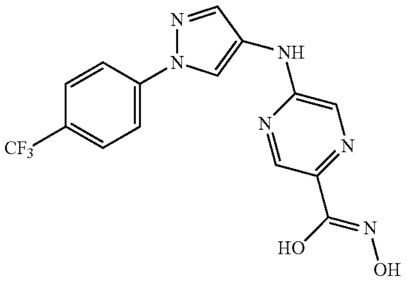 [SMILES: O/N=C(\O)c1cnc(Nc2cnn(-c3ccc(C(F)(F)F)cc3)c2)cn1] | <1 |
| 115 | 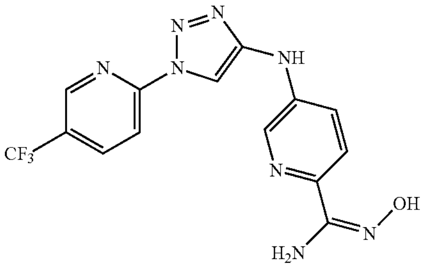 [SMILES: N/C(=N/O)c1ccc(Nc2cn(-c3ccc(C(F)(F)F)cn3)nn2)cn1] | <1 |
| 116 | 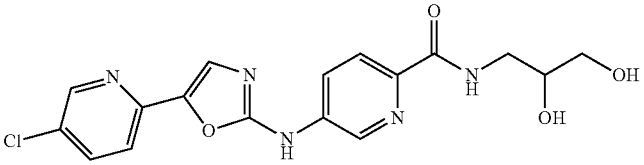 [SMILES: O=C(NCC(O)CO)c1ccc(Nc2ncc(-c3ccc(Cl)cn3)o2)cn1] | <1 |
| 117 | 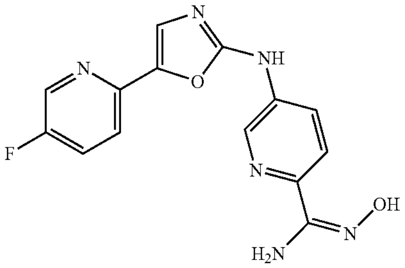 [SMILES: N/C(=N/O)c1ccc(Nc2ncc(-c3ccc(F)cn3)o2)cn1] | >1 (36% inhibition at 1 μM) |
| 118 | 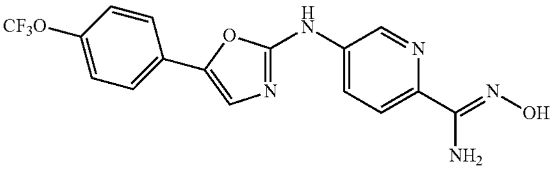 | <1 |
| 119 | 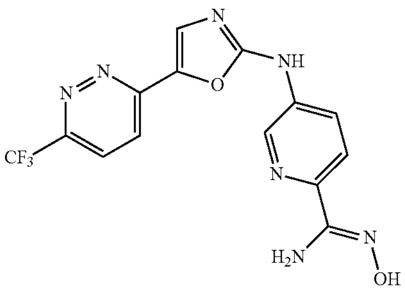 [SMILES: N/C(=N\O)c1ccc(Nc2ncc(-c3ccc(C(F)(F)F)nn3)o2)cn1] | >1 (44% inhibition at 1 μM) |

TABLE 2-1-continued

| Compound | Structure | Des1 (h) Jurkat $IC_{50}$ [a] μM |
|---|---|---|
| 120 | 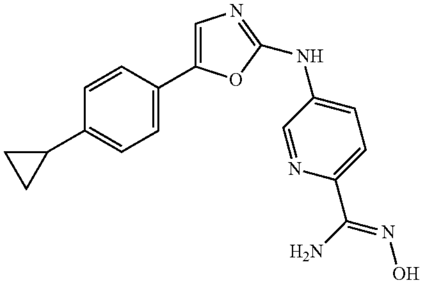 [SMILES: N/C(=N\O)c1ccc(Nc2ncc(-c3ccc(C4CC4)cc3)o2)cn1] | >1 (10% inhibition at 1 μM) |

[a] $IC_{50}$ = concentration of test compound required to reduce Des1 activity to 50% of the vehicle control. Unless otherwise stated, this given as the concentration range of test compound within which the activity of Des1 was shown reduce to or below 50% of the vehicle control. If only measured at one concentration X (X = 10, 1, or 0.1 μM) the value is given as either <X (indicating that the Des1 activty at X is <50% of the vehicle control) or as >X (and the %-inhibition of Des1 at X is given).

Example 3

In one or more embodiments, the presence of at least one ring nitrogen atom in W, e.g. in an ortho- and/or meta-position to the group $R^b$, may afford one or more surprising advantages, for example increased potency, improved selectivity, and/or one or more improved pharmacokinetic and/or physicochemical properties, e.g. absorption, distribution, metabolism and excretion, and solubility, compared to a W ring where nitrogen is absent, i.e. a phenyl group. Some non-limiting illustrative examples are presented below in Table 3-1.

TABLE 3-1

| Compound | Des1 $IC_{50}$ | $T_{1/2}$ Human Liver Microsomes |
|---|---|---|
| 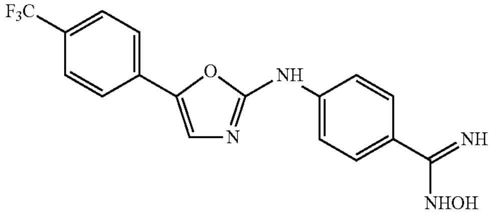 (Reference Compound) | 800-1000 nM | 30-40 min |
| 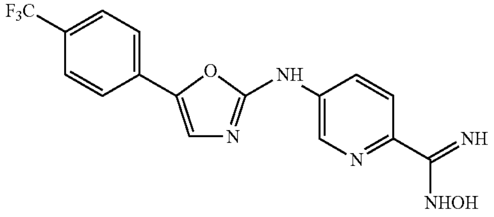 (Compound 8) | 100-200 nM | 90-100 min |
| 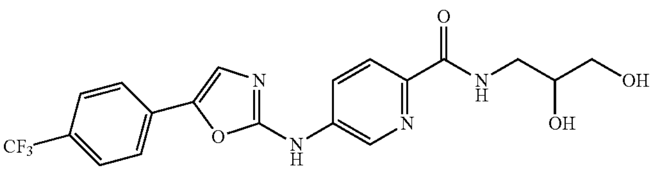 (Compound 17) | 1-10 nM | 210-220 min |

TABLE 3-1-continued

| Compound | Desl $IC_{50}$ | $T_{1/2}$ Human Liver Microsomes |
|---|---|---|
| 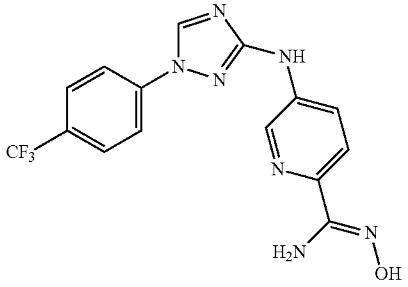 (Compound 24) | 70-80 nM | 170-180 min |
| 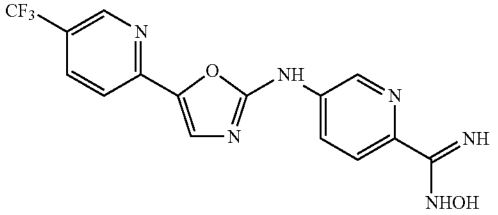 (Compound 46) | 400-500 nM | 190-200 min |
| 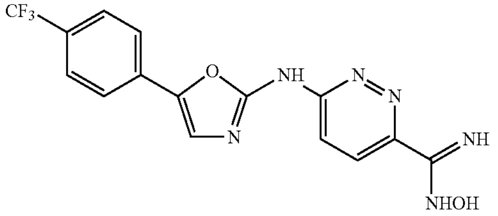 (Compound 53) | 1-10 nM | 150-170 min |

Example 4

Real Time Quantitative Polymerase Chain Reaction in Human Hepatic Stellate Cells (LX2) to Detect Connective Tissue Growth Factor (CTGF) Gene Expression The hepatic stellate cell line, LX2 was maintained in DMEM (LifeTechnologies) with 2% heat-inactivated FBS, 100U penicillin (LifeTechnologies), 0.1 mg/mL streptomycin (LifeTechnologies), and 2 mM L-glutamine (LifeTechnologies) at 37° C. with 5% $CO_2$. Cells were seeded into 6-well plates (200,000 cells per well, 2 mLs media) and grown overnight. The cells were changed to 2 mLs 0.5% FBS media for 24 hours prior to treatment. Treatments were added in 2 mLs fresh 0.5% FBS media (vehicle control, long/mL TGFβ alone (R&D Systems), 10 ng/mL TGFβ+ inhibitors) and incubated for 24 hours. Cells were washed once with cold PBS and lysed directly into RLT lysis buffer (Qiagen RNeasy kit, cat #74104, 350 μL) containing 1% β-Mercaptoethanol. RNA was extracted using Qiagen RNeasy kit (cat #74104), according to manufacturer's instructions. RNA (1 μg) was used to generate cDNA using the Qiagen Quantitect Reverse Transcription Kit (cat #205311), and stored at −20° C. cDNA was diluted (1:25 final) and combined with Sybr Green (Qiagen cat #204143), forward and reverse primers (50 ng each) and run on Real Time PCR Thermocycler machine (RG-6000, Corbett) with the following PCR conditions: Hold 1: 50° C. for 2 min; Hold 2: 95° C. for 15 min; Cycling: 45 cycles of: 95° C. for 30 sec, 58° C. for 21 sec, 72° C. for 15 sec, Hold 3: 72° C. for 30 sec, Melt: 72° C. to 99° C. GAPDH primers (Forward: ACC CAG AGG ACT GTG GAT GG; Reverse: CAG TGA GCT TCC CGT TCA G) CTGF primers (Forward: CTT GCG AAG CTG ACC TGG AAG A; Reverse: CCG TCG GTA CAT ACT CCA CAG A) [CTGF primers available from Origene, cat #HP205671)].

TABLE 4-1
| Compound | Structure | CTGF, LX2 % inhibition[a] 10 μM | 5 μM | 1 μM |
|---|---|---|---|---|
| 8 | 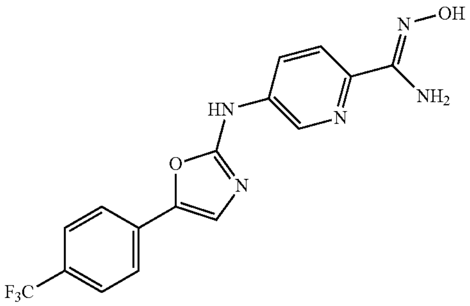 [SMILES: N/C(=N\O)c1ccc(Nc2ncc(-c3ccc(C(F)(F)F)cc3)o2)cn1] | — | >90 | — |
| 20 | 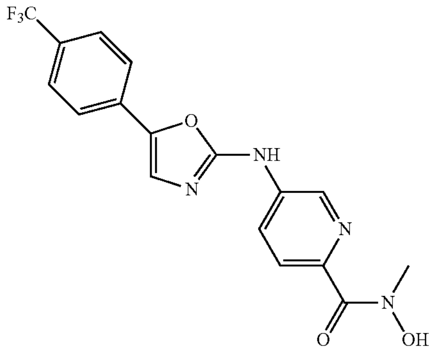 [SMILES: CN(O)C(=O)c1ccc(Nc2ncc(-c3ccc(C(F)(F)F)cc3)o2)cn1] | 70-80 | — | 10-20 |
| 23 | 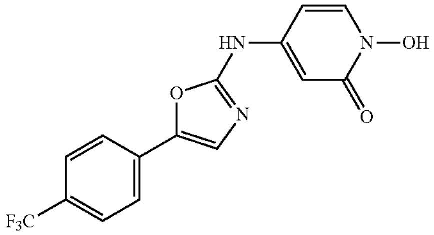 [SMILES: O=c1cc(Nc2ncc(-c3ccc(C(F)(F)F)cc3)o2)ccn1O] | >90 | — | 30-40 |
| 24 | 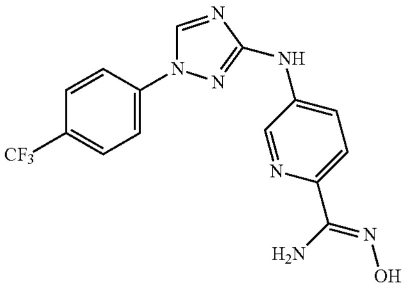 [SMILES: N/C(=N\O)c1ccc(Nc2ncn(-c3ccc(C(F)(F)F)cc3)n2)cn1] | — | 50-60 | — |
| 29 | 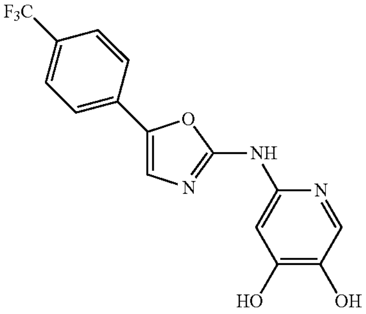 [SMILES: Oc1cnc(Nc2ncc(-c3ccc(C(F)(F)F)cc3)o2)cc1O] | >90 | — | >90 |

TABLE 4-1-continued
| Compound | Structure | CTGF, LX2 % inhibition[a] 10 μM | 5 μM | 1 μM |
|---|---|---|---|---|
| 42 | 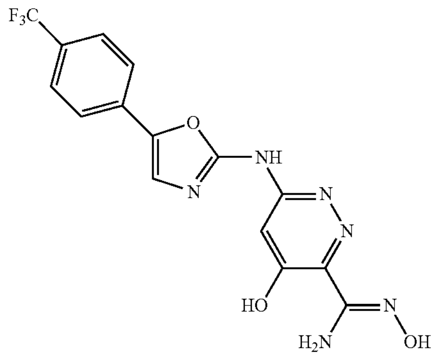 | 40-50 | — | 10-20 |
| 46 | 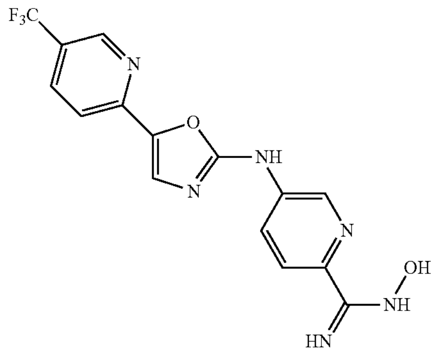 [SMILES: N=C(NO)c1ccc(Nc2ncc(-c3ccc(C(F)(F)F)cn3)o2)cn1] | — | >90 | — |
| 54 | 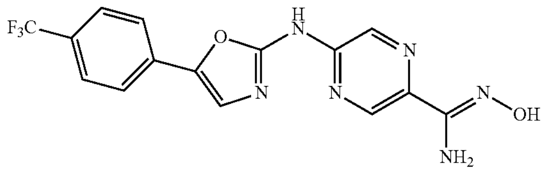 [SMILES: N/C(=N\O)c1cnc(Nc2ncc(-c3ccc(C(F)(F)F)cc3)o2)cn1] | 80-90 | — | 70-80 |
| 55 | 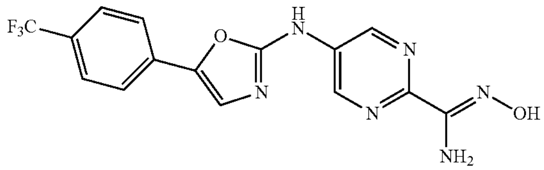 [SMILES: N/C(=N\O)c1ncc(Nc2ncc(-c3ccc(C(F)(F)F)cc3)o2)cn1] | 40-50 | — | 20-30 |
| 57 | 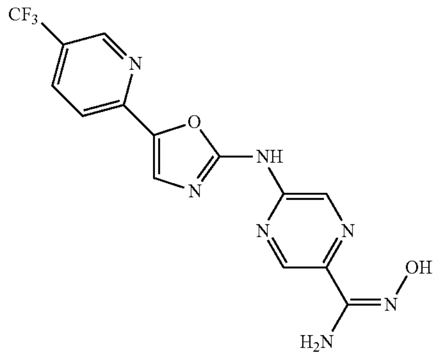 [SMILES: N/C(=N/O)c1cnc(Nc2ncc(-c3ccc(C(F)(F)F)cn3)o2)cn1] | 50-60 | — | 1-10 |

TABLE 4-1-continued
| | | CTGF, LX2 % inhibition[a] | | |
|---|---|---|---|---|
| Compound | Structure | 10 μM | 5 μM | 1 μM |
| 70 | 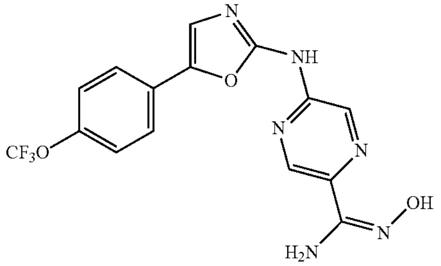 | — | >90 | — |
| 72 | 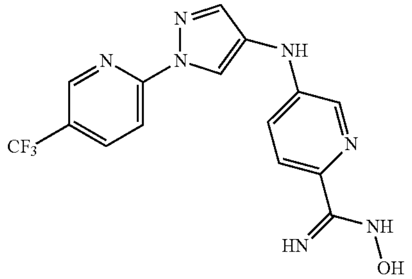 [SMILES: N=C(NO)c1ccc(Nc2cnn(-c3ccc(C(F)(F)F)cn3)c2)cn1] | — | 50-60 | 40-50 |
| 73 | 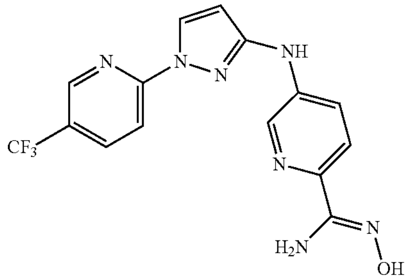 [SMILES: N/C(=N\O)c1ccc(Nc2ccn(-c3ccc(C(F)(F)F)cn3)n2)cn1] | — | >90 | — |
| 74 | 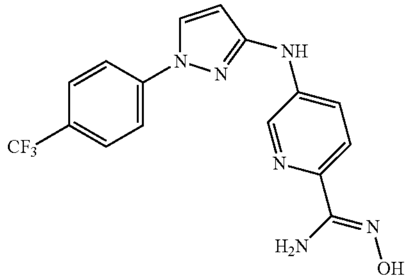 [SMILES: N/C(=N\O)c1ccc(Nc2ccn(-c3ccc(C(F)(F)F)cc3)n2)cn1] | — | 80-90 | — |
| 75 | 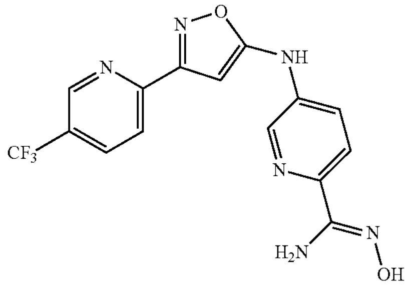 [SMILES: N/C(=N\O)c1ccc(Nc2cc(-c3ccc(C(F)(F)F)cn3)no2)cn1] | — | >90 | — |

TABLE 4-1-continued
| Compound | Structure | CTGF, LX2 % inhibition[a] 10 μM | 5 μM | 1 μM |
|---|---|---|---|---|
| 82 | 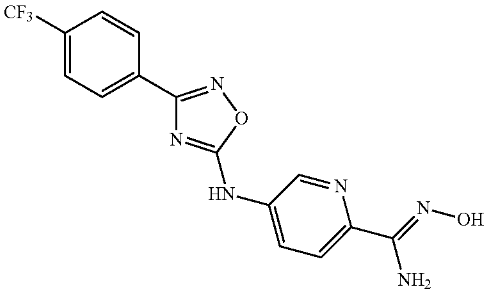 [SMILES: N/C(=N\O)c1ccc(Nc2nc(-c3ccc(C(F)(F)F)cc3)no2)cn1] | — | >90 | — |
| 84 | 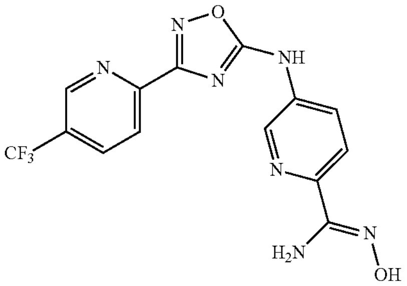 [SMILES: N/C(=N\O)c1ccc(Nc2nc(-c3ccc(C(F)(F)F)cn3)no2)cn1] | — | 80-90 | — |
| 86 | 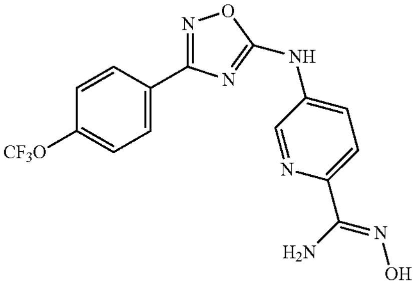 | — | >90 | — |
| 89 | 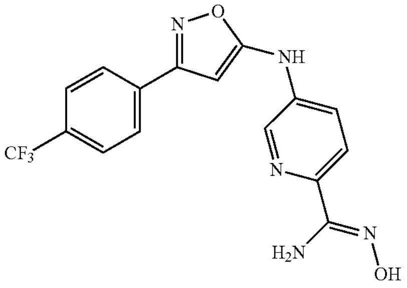 [SMILES: N/C(=N\O)c1ccc(Nc2cc(-c3ccc(C(F)(F)F)cc3)no2)cn1] | — | >90 | — |
| 90 | 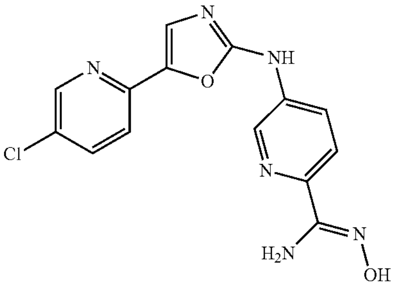 [SMILES: N/C(=N\O)c1ccc(Nc2ncc(-c3ccc(Cl)cn3)o2)cn1] | — | >90 | — |

TABLE 4-1-continued
| Compound | Structure | CTGF, LX2 % inhibition[a] 10 μM | 5 μM | 1 μM |
|---|---|---|---|---|
| 99 | 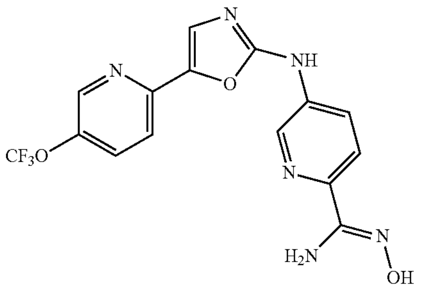 | 70-80 | — | 1-10 |
| 102 | 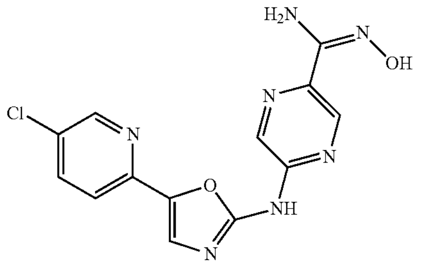 [SMILES: N/C(=N/O)c1cnc(Nc2ncc(-c3ccc(Cl)cn3)o2)cn1] | — | 70-80 | — |
| 103 | 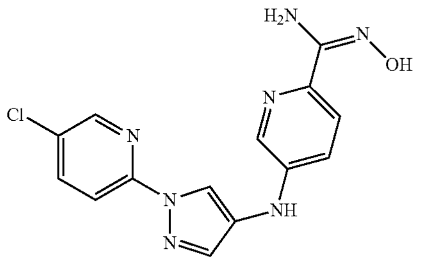 [SMILES: N/C(=N/O)c1ccc(Nc2cnn(-c3ccc(Cl)cn3)c2)cn1] | — | 70-80 | — |
| 106 | 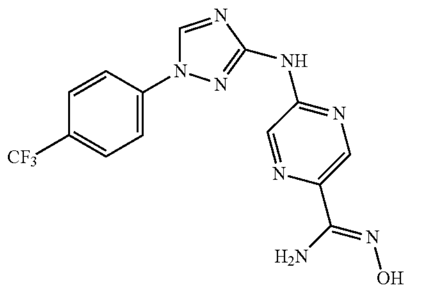 [SMILES: N/C(=N\O)c1cnc(Nc2ncn(-c3ccc(C(F)(F)F)cc3)n2)cn1] | — | — | 30-40 |
| 107 | 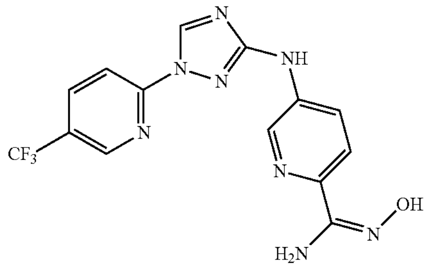 [SMILES: N/C(=N/O)c1ccc(Nc2ncn(-c3ccc(C(F)(F)F)cn3)n2)cn1] | — | >90 | — |

TABLE 4-1-continued
| | | CTGF, LX2 % inhibition[a] | | |
|---|---|---|---|---|
| Compound | Structure | 10 μM | 5 μM | 1 μM |
| 108 | 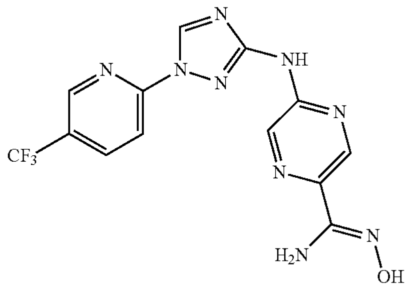 [SMILES: N/C(=N\O)c1cnc(Nc2ncn(-c3ccc(C(F)(F)F)cn3)n2)cn1] | — | 40-50 | — |
| 109 | 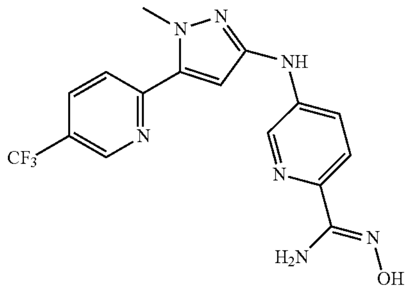 [SMILES: Cn1nc(Nc2ccc(/C(N)=N/O)nc2)cc1-c1ccc(C(F)(F)F)cn1] | — | >90 | — |
| 111 | 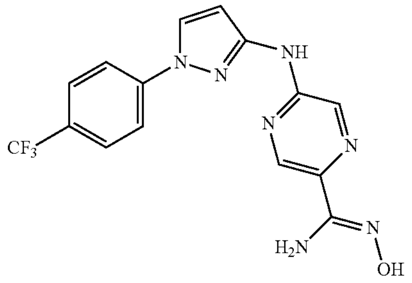 [SMILES: N/C(=N\O)c1cnc(Nc2ccn(-c3ccc(C(F)(F)F)cc3)n2)cn1] | — | >90 | — |
| 112 | 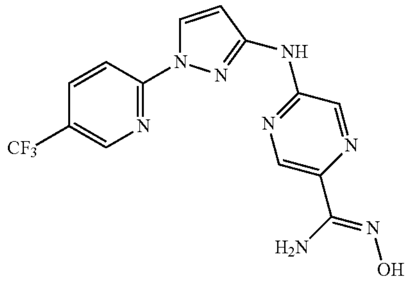 | — | — | >90 |
| 113 | 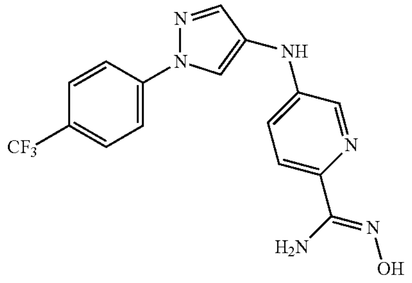 [SMILES: N/C(=N\O)c1ccc(Nc2cnn(-c3ccc(C(F)(F)F)cc3)c2)cn1] | — | >90 | — |

TABLE 4-1-continued

| | | CTGF, LX2 % inhibition[a] | | |
|---|---|---|---|---|
| Compound | Structure | 10 μM | 5 μM | 1 μM |
| 114 | 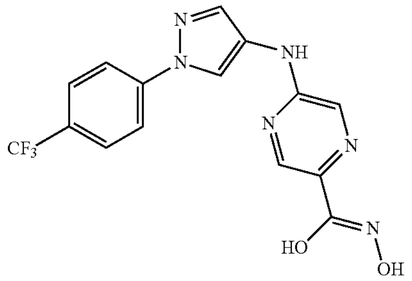 [SMILES: O/N=C(\O)c1cnc(Nc2cnn(-c3ccc(C(F)(F)F)cc3)c2)cn1] | — | >90 | — |
| 115 | 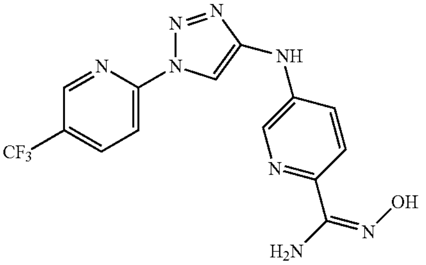 [SMILES: N/C(=N/O)c1ccc(Nc2cn(-c3ccc(C(F)(F)F)cn3)nn2)cn1] | — | >90 | — |
| 116 | 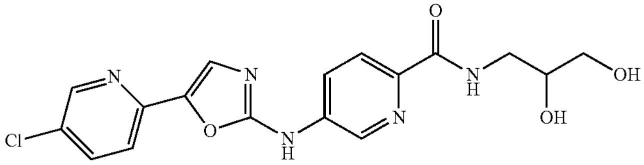 [SMILES: O=C(NCC(O)CO)c1ccc(Nc2ncc(-c3ccc(Cl)cn3)o2)cn1] | — | 70-80 | — |
| 118 | 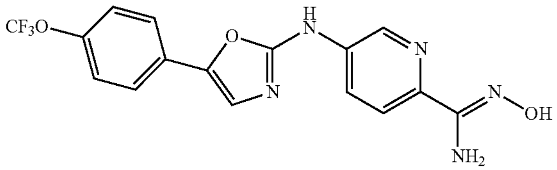 | 70-80 | — | 50-60 |
| 120 | 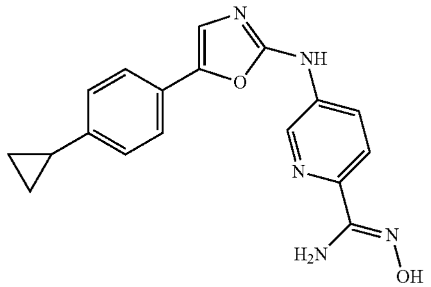 [SMILES: N/C(=N\O)c1ccc(Nc2ncc(-c3ccc(C4CC4)cc3)o2)cn1] | 40-50 | — | 40-50 |

[a]% inhibition = the percentage inhibition of CTGF mRNA levels in TGFβ-stimulated LX2 cells at 10, 5, 3 or 1 μM of test compounds was calculated with reference to the vehicle control (TBGβ-stimulated LX2 cells in the absence of test compounds).

Example 5

Inhibition of Collagen Synthesis in Rat Mesangial Cells (RMCs)

Mesangial cells at passage (P36, P39 and P39 for each run respectively) were be plated into 24 well dishes at ~15,000 cells/well. Cells were be allowed to adhere overnight, aiming for 60% confluence the next day. Actual reported confluence for each run was 90% by day 2. Cells were serum starved overnight in DMEM with 150 μM L-ascorbic acid, in the presence of 0.1% BSA. The following day the media was replaced with fresh starve medium containing Des1 inhibitor compounds at the doses of 0.01, 0.1, 1, 3, 10 μM each and incubated for 4 hrs before adding TGF-β (5 ng/ml, PeproTech) and 1 μCi/mL $^{3}$H-proline (Amersham L-(2,3,4, 5-3H)-proline, 75 Ci/mmol) for proline incorporation. Finally, cells were incubated for a further 44 hours. At the end of the incubation time, cells were be collected by aspirating the supernatant and washing cells 3 times with ice cold Phosphate Buffered Saline (PBS). Ice cold 10% of 1 ml Trichloroacetic acid (TCA)/well is added to each well and cells will be incubated on ice for 30 minutes. Cells were then washed with 1 ml ice cold 10% TCA and solubilised over night at 4° C. in 0.75 ml 1M Sodium Hydroxide (NaOH). 0.5 ml aliquots of solubilised cells were transferred to scintillation vials, neutralised with an equal volume of 1 M Hydrochloric Acid (HCl) and 10 ml of Instagel scintillant added. Counts were measured on a beta counter (PerkinElmer, Rowville, Australia). Proline incorporation is adjusted for protein content. An aliquot of the remaining lysate will be neutralised with 1M HCl and assayed in a BioRad (Bradford) Protein Assay. Results will be expressed as cpm $^3$H-proline/μg total protein. A standard curve of BSA containing an equivalent amount of NaOH and HCl as the samples is prepared Compounds 8 and 46 were tested at 5 doses in three independent experiments. Within each run, 3 technical replicates of each compound and dose were performed.

The results are depicted in FIGS. 1A and 1B.

Fibroblast-to-Myofibroblast Transition (FMT) in Human Lung Cells Derived from Idiopathic Pulmonary Fibrosis (IPF) Patient Donors Lung-derived primary human bronchial fibroblasts (from IPF donors) were seeded at 3,000 cells per well in 96-well plates, and were grown over 5 days prior to treatment with the desired compounds (cell medium was refreshed at 48 h). Cells were then treated with 8 different concentrations of Compound 8 or 46, in semi-log dilutions starting from the top dosage of 10 μM (vehicle control: 0.1% DMSO; positive control: SB525334 and nintendanib). 1-hour post compound addition, the cells were stimulated with the addition of 1.25 ng/mL TGF-β1, and incubated for 72 hours. Cells were then fixed with 4% formaldehyde, then stained using DAPI-labeled αSMA and imaged via high-content analysis. The assay was conducted in biological duplicates. This in vitro FMT assay results were provided by Charles River Laboratories through a service agreement.

The results are depicted in FIGS. 2A and 2B.

The invention claimed is:

1. A compound of formula (I'):

(I')

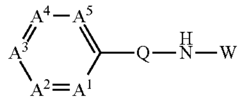

wherein:

$A^1$-$A^5$ are independently selected from C—$R^a$ and N, wherein any 0, 1, 2, 3 or 4 of $A^1$-$A^5$ may be N;

each $R^a$ is independently H or $R^{aa}$, wherein $R^{aa}$ is selected from halo, alkyl, haloalkyl, cycloalkyl, halocycloalkyl, alkoxy, haloalkoxy, cycloalkoxy, cycloamino, halocycloamino, alkoxylalkyl, and alkoxyalkoxy;

Q is a 5-membered heteroaromatic ring having 2, 3 or 4 ring heteroatoms, at least one of which must be N, and the remaining are independently selected from N, O and S, and wherein a ring carbon atom bearing a hydrogen atom, or a ring nitrogen atom bearing a hydrogen atom, if present, may be optionally substituted with $Q^a$, which is selected from halo, haloalkyl and alkyl;

W is a 6-membered N-containing heterocycle selected from:

(A)

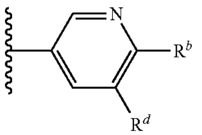

(B)

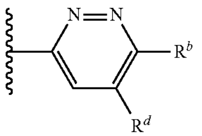

(C)

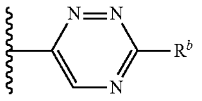

(D)

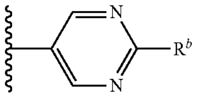

(E)

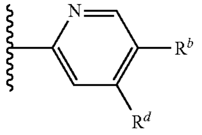

(F)

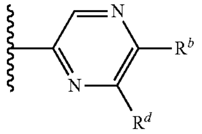

(G)

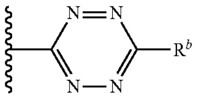

(H)

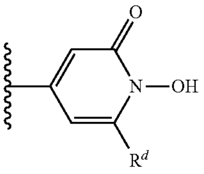

(I)

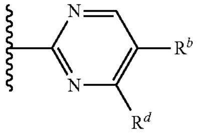

(J)

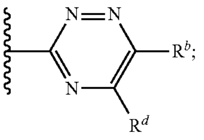

wherein $R^b$ is selected from:

—OH, provided that when $R^b$ is OH, W is (E) or (I);

—K—$NR^c$—Y, or a tautomer thereof,

—$(CH_2)_p$—NH—OH, and

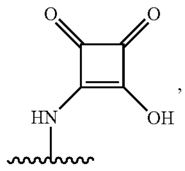

, wherein

K is SO, $SO_2$, C(=X') or NHC(=X'), where X' is O or NH;

$R^c$ is H, $C_{1-6}$alkyl; or hydroxy$C_{1-6}$alkyl;

Y is OH, $NHR^e$ (wherein $R^e$ is H, $C_{1-6}$alkyl, —(C=O)H or —(C=O)$C_{1-6}$alkyl), hydroxy$C_{1-6}$alkyl or ($SC_{1-6}$alkyl)$C_{1-6}$alkyl; and p is 0 or 1;

and $R^d$ is selected from H, OH, halo, $C_{1-6}$alkyl and $C_{1-6}$ alkoxy;

provided that the compound does not have the formula

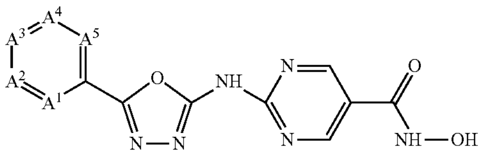

or

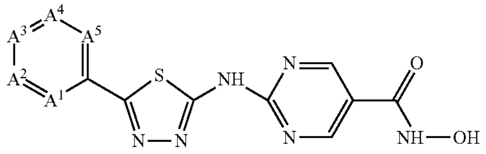

where any four of $A^1$-$A^5$ are C—H, and the other is C—$R^a$ where $R^a$ is H, halo, $CH_3$ or $OCH_3$;

or a pharmaceutically acceptable salt or solvate thereof.

2. The compound of formula (I') according to claim 1, or a pharmaceutically acceptable salt or solvate thereof, wherein Q is selected from heterocyclic formulas (a)-(kk), which may optionally substituted with a group $Q^a$ where permissible;

wherein the bonds labelled # are attached to NH and the bonds labelled * are attached to the aryl ring defined by $A^1$-$A^5$:

(a)

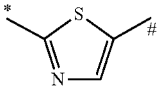

(b)

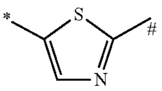

(c)

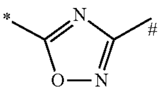

(d)

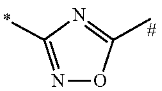

-continued (e)

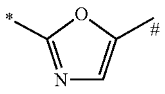

(f)

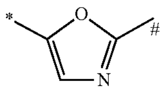

(g)

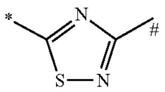

(h)

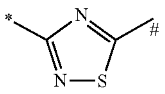

(i)

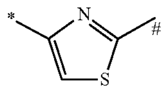

(j)

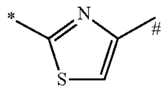

(k)

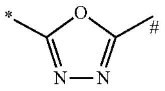

(l)

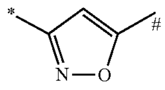

(m)

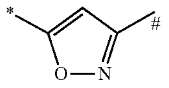

(n)

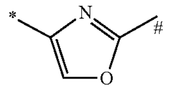

(o)

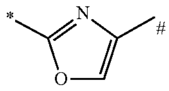

(p)

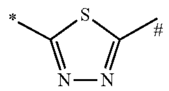

(q)

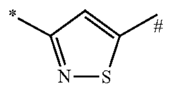

(r)

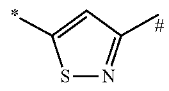

(s)

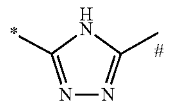

-continued (t)

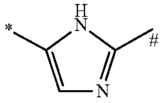

(u)

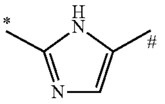

(v)

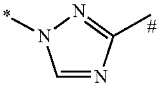

(w)

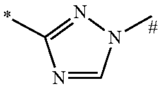

(x)

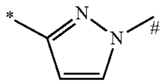

(y)

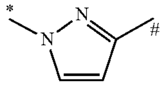

(z)

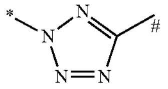

(aa)

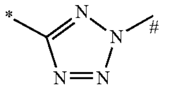

(bb)

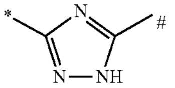

(cc)

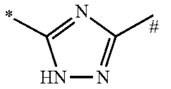

(dd)

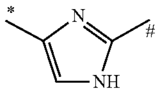

(ee)

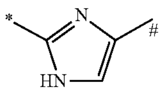

(ff)

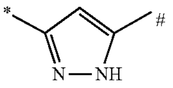

(gg)

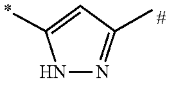

(hh)

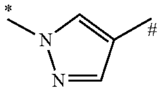

-continued (ii)

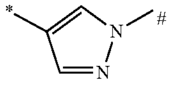

(jj)

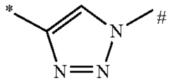

(kk)

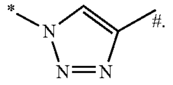

3. The compound of formula (I') according to claim 1, or a pharmaceutically acceptable salt or solvate thereof, wherein $Q^a$ is selected from halo, $C_{1-6}$alkyl, and halo $C_{1-6}$alkyl.

4. The compound of formula (I') according to claim 1, or a pharmaceutically acceptable salt or solvate thereof, wherein each of $A^1$-$A^5$ is C—$R^a$.

5. The compound of formula (I') according to claim 1, or a pharmaceutically acceptable salt or solvate thereof, wherein 1, 2, 3 or 4 of $A^1$, $A^2$, $A^4$ and $A^5$ are N.

6. The compound of formula (I') according to claim 5, or a pharmaceutically acceptable salt or solvate thereof, wherein $A^5$ or $A^1$ is N; or $A^2$ or $A^4$ is N; or $A^1$ and $A^5$ are both N; or $A^2$ and $A^4$ are both N $A^1$ and $A^4$, or $A^2$ and $A^5$ are both N; or $A^1$ and $A^2$ or $A^4$ and $A^5$ are both N.

7. The compound of formula (I') according to claim 1, or a pharmaceutically acceptable salt or solvate thereof, wherein $A^3$ is C—$R^{aa}$.

8. The compound of formula (I') according to claim 7, or a pharmaceutically acceptable salt or solvate thereof, where $R^{aa}$ is halo, haloalkyl or haloalkoxy.

9. The compound of Formula (I') according to claim 8, or a pharmaceutically acceptable salt or solvate thereof, wherein $R^{aa}$ is Cl, $CF_3$ or $OCF_3$.

10. The compound of formula (I') according to claim 1, or a pharmaceutically acceptable salt or solvate thereof, wherein W is selected from: (A), (B), (D), (E), (F), (H) and (I).

11. The compound of formula (I') according to claim 1, or a pharmaceutically acceptable salt or solvate thereof, where W is selected from (A), (B), (C), (D), (F), (G) (H) and (J).

12. The compound of formula (I') according to claim 2, or a pharmaceutically acceptable salt or solvate thereof, where Q is (f), optionally substituted with $Q^a$.

13. The compound according to claim 1 where W is (A).

14. The compound of formula (I') according to claim 1, or a pharmaceutically acceptable salt or solvate thereof, wherein $R^d$ is H, OH, CI, F, Br, I, $CH_3$ or $OCH_3$.

15. The compound of formula (I') according to claim 1, or a pharmaceutically acceptable salt or solvate thereof, wherein $R^b$ is K—$NR^c$—Y, or a tautomer thereof.

16. The compound of formula (I') according to claim 1, or a pharmaceutically acceptable salt or solvate thereof, wherein $R^b$ is —K—$NR^c$—Y, or a tautomer thereof, wherein:

K is $SO_2$, C(═O), C(═NH), or NHC(═O), $R^c$ is H, $C_{1-6}$alkyl; or hydroxy$C_{1-6}$alkyl; and Y is OH, $NH_2$, $NHC_{1-3}$alkyl, NHC(═O)H, NH(C═O) $C_{1-3}$alkyl, hydroxy$C_{1-6}$alkyl; or ($SC_{1-6}$alkyl) $C_{1-6}$alkyl.

17. The compound of formula (I') according to claim 1, or a pharmaceutically acceptable salt or solvate thereof, wherein $R^b$ is

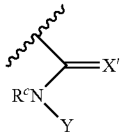

wherein

X' is O or NH, $R^c$ is H or $C_{1-6}$alkyl; or hydroxy$C_{1-6}$alkyl; and

Y is OH or $NHR^e$, or a tautomer thereof.

18. The compound of formula (I') according to claim 1, or a pharmaceutically acceptable salt or solvate thereof, wherein $R^b$ is selected from:

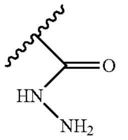
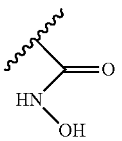
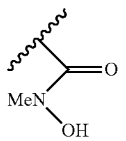
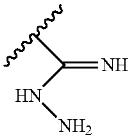
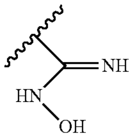
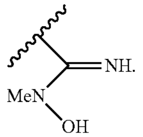

or a tautomer thereof.

19. The compound of formula (I') according to claim 1, or a pharmaceutically acceptable salt or solvate thereof, wherein Rb is:

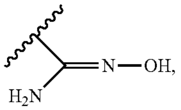
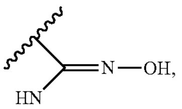
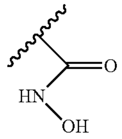
or
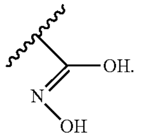

20. The compound of formula (I') according to claim 1, or a pharmaceutically acceptable salt or solvate thereof, wherein $R^b$ is OH and W is (E) or (I).

21. A compound of formula (I') according to claim 1 selected from:

5-((5-(4-Chlorophenyl)oxazol-2-yl)amino)-N-hydroxypicolinamide;

N-Hydroxy-5-((5-(4-(trifluoromethyl)phenyl)oxazol-2-yl)amino)picolinamide;

N'-Hydroxy-6-((5-(4-(trifluoromethyl)phenyl)oxazol-2-yl)amino) nicotinimidamide hydrochloride;

N-(6-(Hydroxyamino)pyridin-3-yl)-5-(4-(trifluoromethyl)phenyl)oxazol-2-amine;

5-((5-[4-(Trifluoromethyl)phenyl]-1,3,4-oxadiazol-2-yl) amino)-N-hydroxy-pyridine-2-carboximidamide;

5-((5-[3-Fluoro-4-(trifluoromethyl)phenyl]-1,3,4-oxadiazol-2-yl)amino)-N-hydroxypyridine-2-carboximidamide;

1-Hydroxy-4-((5-[4-(trifluoromethyl)phenyl]-1,3,4-oxadiazol-2-yl)amino)-1,2-dihydropyridin-2-one;

5-((5-[4-(Trifluoromethyl)phenyl]-1,3-oxazol-2-yl) amino)-N-hydroxy-pyridine-2-carboximidamide;

5-([4-(4-Chlorophenyl)-1,3-thiazol-2-yl] amino)-N-hydroxypyrimidine-2-carboxamide;

N-Hydroxy-6-((5-[4-(trifluoromethyl)phenyl]-1,3-oxazol-2-yl)amino)pyrimidine-3-carboxamide;

N-Hydroxy-6-((5-[4-(trifluoromethyl)phenyl]-1,3-oxazol-2-yl)amino)pyridazine-3-carboxamide;

N-Hydroxy-5-((4-[4-(trifluoromethyl)phenyl]-1,3-oxazol-2-yl)amino)pyrimidine-2-carboxamide;

N-Hydroxy-6-((4-(4-(trifluoromethyl)phenyl)oxazol-2-yl)amino)pyridazine-3-carboxamide;

N-Hydroxy-5-((4-[4-(trifluoromethyl)phenyl]-1,3-oxazol-2-yl)amino)picolinamide;

N-Hydroxy-N-methyl-5-((5-[4-(trifluoromethyl)phenyl]-1,3-oxazol-2-yl)amino)pyridine-2-sulfonamide;

rac-N-(2,3-Dihydroxypropyl)-5-((5-[4-(trifluoromethyl) phenyl]-1,3-oxazol-2-yl)amino) pyridine-2-sulfonamide;

rac-N-(2,3-Dihydroxypropyl)-5-((5-[4-(trifluoromethyl) phenyl]-1,3-oxazol-2-yl)amino) picolinamide;

6-((5-(4-(Trifluoromethyl)phenyl)oxazol-2-yl)amino) pyridin-3-ol;

N-(2-Hydroxyethyl)-5-((5-(4-(trifluoromethyl)phenyl) oxazol-2-yl)amino)picolinamide;

N-Nydroxy-N-methyl-5-((5-(4-(trifluoromethyl)phenyl) oxazol-2-yl)amino)picolinamide;

N-Hydroxy-N,3-dimethyl-5-((5-(4-(trifluoromethyl)phenyl)oxazol-2-yl)amino)picolinamide;

N-Hydroxy-N-(2-hydroxyethyl)-5-((5-(4-(trifluoromethyl)phenyl)oxazol-2-yl)amino)picolinamide;

1-(Hydroxy)-4-((5-(4-(trifluoromethyl)phenyl)oxazol-2-yl)amino)pyridin-2 (1H)-one;

N'-Hydroxy-5-((1-(4-(trifluoromethyl)phenyl)-1H-1,2,4-triazol-3yl)amino)picolinimidamide;

N-Hydroxy-N-methyl-5-((1-(4-(trifluoromethyl)phenyl)-1H-1,2,4-triazol-3-yl)amino)picolinamide;

N',3-Dihydroxy-5-((5-(4-(trifluoromethyl)phenyl)oxazol-2-yl)amino)picolinimidamide;

1-Hydroxy-6-methyl-4-((5-(4-(trifluoromethyl)phenyl) oxazol-2-yl)amino)pyridin-2 (1H)-one;

N,3-Dihydroxy-N-methyl-5-((5-(4-(trifluoromethyl)phenyl)oxazol-2-yl)amino)picolinamide;

6-((5-(4-(Trifluoromethyl)phenyl)oxazol-2-yl)amino) pyridine-3,4-diol;

3-Hydroxy-4-((5-((5-(4-(trifluoromethyl)phenyl)oxazol-2-yl)amino)pyridin-2-yl)amino) cyclobut-3-ene-1,2-dione;

N',3-Dihydroxy-5-((1-(4-(trifluoromethyl)phenyl)-1H-1,2,4-triazol-3-yl)amino)picolinimidamide;

N-Ethyl-N-hydroxy-5-((5-(4-(trifluoromethyl)phenyl) oxazol-2-yl)amino)picolinamide;

N-Hydroxy-N-propyl-5-((5-(4-(trifluoromethyl)phenyl) oxazol-2-yl)amino)picolinamide;

N-Hydroxy-N-isopropyl-5-((5-(4-(trifluoromethyl)phenyl)oxazol-2-yl)amino)picolinamide;

1-Hydroxy-1-methyl-3-(5-((5-(4-(trifluoromethyl)phenyl)oxazol-2-yl)amino)pyridin-2-yl) urea;

(R)—N-(2,3-Dihydroxypropyl)-5-((5-(4-(trifluoromethyl)phenyl)oxazol-2-yl)amino)picolinamide;

(S)—N-(2,3-Dihydroxypropyl)-5-((5-(4-(trifluoromethyl)phenyl)oxazol-2-yl)amino)picolinamide;

(R)—N-(2,3-Dihydroxypropyl)-5-((1-(4-(trifluoromethyl)phenyl)-1H-1,2,4-triazol-3-yl)amino)picolinamide;

N',3-Dihydroxy-5-((4-methyl-5-(4-(trifluoromethyl)phenyl)oxazol-2-yl)amino)picolinimidamide;

N',3-Dihydroxy-5-((5-(5-(trifluoromethyl)pyridin-2-yl)oxazol-2-yl)amino)picolinimidamide hydrochloride;

(R)—N-(2,3-Dihydroxypropyl)-6-((5-(4-(trifluoromethyl)phenyl)oxazol-2-yl)amino)-pyridazine-3-carboxamide;

N',4-Dihydroxy-6-((5-(4-(trifluoromethyl)phenyl)oxazol-2-yl)amino)pyridazine-3-carboximidamide;

5-((5-(3-Fluoro-4-(trifluoromethyl)phenyl)oxazol-2-yl)amino)-N',3-dihydroxypicolinimidamide;

(R)—N-(2,3-Dihydroxypropyl)-5-((5-(3-fluoro-4-(trifluoromethyl)phenyl)oxazol-2-yl)amino)picolinamide;

5-((5-(3-Fluoro-4-(trifluoromethyl)phenyl)oxazol-2-yl)amino)-N'-hydroxypicolinimidamide;

N'-hydroxy-5-((5-(5-(trifluoromethyl)pyridin-2-yl)oxazol-2-yl)amino)-picolinimidamide;

6-((5-(4-Fluorophenyl)oxazol-2-yl)amino)-N'-hydroxypyridazine-3-carboximidamide;

6-((5-(3,4-Difluorophenyl)oxazol-2-yl)amino)-N'-hydroxypyridazine-3-carboximidamide;

6-((5-(5-Fluoropyridin-2-yl)oxazol-2-yl)amino)-N'-hydroxypyridazine-3-carboximidamide;

N,5-Dihydroxy-2-((5-(4-(trifluoromethyl)phenyl)oxazol-2-yl)amino)isonicotinimid-amide;

5-((5-(4-(Difluoromethoxy) phenyl)oxazol-2-yl)amino)-N'-hydroxy picolinimidamide;

5-((5-(4-(Difluoromethyl)phenyl)oxazol-2-yl)amino)-N'-hydroxypicolinimidamide;

N'-Hydroxy-6-((5-(4-(trifluoromethyl)phenyl)oxazol-2-yl)amino)pyridazine-3-carboximidamide;

N'-Hydroxy-5-((5-(4-(trifluoromethyl)phenyl)oxazol-2-yl)amino)pyrazine-2-carboximidamide;

N'-Hydroxy-5-((5-(4-(trifluoromethyl)phenyl)oxazol-2-yl)amino)pyrimidine-2-carboximidamide;

3-Fluoro-N'-hydroxy-5-((5-(5-(trifluoromethyl)pyridin-2-yl)oxazol-2-yl)amino)picolinimidamide;

N'-Hydroxy-5-((5-(5-(trifluoromethyl)pyridin-2-yl)oxazol-2-yl)amino)pyrazine-2-carboximidamide;

N'-Hydroxy-5-((5-(5-(trifluoromethyl)pyridin-2-yl)oxazol-2-yl)amino)pyrimidine-2-carboximidamide;

N'-Hydroxy-5-((5-(6-(trifluoromethyl)pyridin-3-yl)oxazol-2-yl)amino)picolinimidamide;

N'-Hydroxy-5-((4-(4-(trifluoromethyl)phenyl)oxazol-2-yl)amino)picolinimidamide;

6-((5-(5-(Trifluoromethyl)pyridin-2-yl)oxazol-2-yl)amino)pyridazine-3-carbonitrile;

5-((5-(5-Cyclopropylpyridin-2-yl)oxazol-2-yl)amino)-N'-hydroxypicolinimidamide;

N'-Hydroxy-2-((5-(4-(trifluoromethyl)phenyl)oxazol-2-yl)amino)pyrimidine-5-carboximidamide;

5-((5-(4-(3,3-Difluoroazetidin-1-yl)phenyl)oxazol-2-yl)amino)-N'-hydroxypicolinimidamide;

N'-Hydroxy-5-((5-(5-(trifluoromethyl) pyrimidin-2-yl)oxazol-2-yl)amino)picolinimidamide;

N'-Hydroxy-5-((5-(5-(trifluoromethyl) pyrazin-2-yl)oxazol-2-yl)amino)picolinimidamide;

6-((5-(4-(Trifluoromethoxy) phenyl)-1,3,4-oxadiazol-2-yl)amino)pyridin-3-ol;

1-Hydroxy-4-((5-(5-(trifluoromethyl)pyridin-2-yl)oxazol-2-yl)amino)pyridin-2 (1H)-one;

N'-Hydroxy-5-((5-(5-(trifluoromethyl)pyridin-2-yl)-1,3,4-oxadiazol-2-yl)amino)picolinimidamide;

N'-Hydroxy-5-((5-(4-(trifluoromethoxy) phenyl)oxazol-2-yl)amino)pyrazine-2-carboximidamide;

5-((5-(5-Chloropyridin-2-yl)-1,3,4-oxadiazol-2-yl)amino)-N'-hydroxypicolinimidamide;

N'-Hydroxy-5-((1-(5-(trifluoromethyl)pyridin-2-yl)-1H-pyrazol-4-yl)amino)picolinimidamide;

N'-Hydroxy-5-((1-(5-(trifluoromethyl)pyridin-2-yl)-1H-pyrazol-3-yl)amino)picolinimidamide;

N'-Hydroxy-5-((1-(4-(trifluoromethyl)phenyl)-1H-pyrazol-3-yl)amino)picolinimidamide;

N'-Hydroxy-5-((3-(5-(trifluoromethyl)pyridin-2-yl)isoxazol-5-yl)amino)picolinimidamide;

N'-Hydroxy-5-((1-methyl-3-(5-(trifluoromethyl)pyridin-2-yl)-1H-pyrazol-5-yl)amino)picolinimidamide;

N'-Hydroxy-5-((1-methyl-3-(4-(trifluoromethyl)phenyl)-1H-pyrazol-5-yl)amino)picolinimidamide;

5-((3-(4-chlorophenyl)-1,2,4-oxadiazol-5-yl)amino)-N'-hydroxypicolinimidamide 5-((3-(4-chlorophenyl)-1,2,4-oxadiazol-5-yl)amino)-N'-hydroxypyrazine-2-carboximidamide;

5-((3-(5-Chloropyridin-2-yl)-1,2,4-oxadiazol-5-yl)amino)-N'-hydroxypicolinimidamide;

5-((3-(5-Chloropyridin-2-yl)-1,2,4-oxadiazol-5-yl)amino)-N'-hydroxypyrazine-2-carboximidamide;

N'-hydroxy-5-((3-(4-(trifluoromethyl)phenyl)-1,2,4-oxadiazol-5-yl)amino)picolinimidamide;

N'-Hydroxy-5-((3-(4-(trifluoromethyl)phenyl)-1,2,4-oxadiazol-5-yl)amino)pyrazine-2-carboximidamide;

N'-Hydroxy-5-((3-(5-(trifluoromethyl)pyridin-2-yl)-1,2,4-oxadiazol-5-yl)amino)picolinimidamide;

N'-hydroxy-5-((3-(5-(trifluoromethyl)pyridin-2-yl)-1,2,4-oxadiazol-5-yl)amino)pyrazine-2-carboximidamide;

N'-Hydroxy-5-((3-(4-(trifluoromethoxy) phenyl)-1,2,4-oxadiazol-5-yl)amino)picolinimidamide;

N'-Hydroxy-5-((3-(4-(trifluoromethoxy) phenyl)-1,2,4-oxadiazol-5-yl)amino)pyrazine-2-carboximidamide;

N'-hydroxy-5-((3-(5-(trifluoromethoxy)pyridin-2-yl)-1,2,4-oxadiazol-5-yl)amino)picolinimidamide;

N'-hydroxy-5-((3-(4-(trifluoromethyl)phenyl) isoxazol-5-yl)amino)picolinimidamide;

5-((5-(5-Chloropyridin-2-yl)oxazol-2-yl)amino)-N'-hydroxypicolinimidamide;

rac-N-(2,3-dihydroxypropyl)-5-((5-(4-(trifluoromethyl)phenyl)oxazol-2-yl)amino)picolinimidamide;

5-((5-(4-(Trifluoromethyl)phenyl)oxazol-2-yl)amino)picolinohydrazide;

N'-formyl-5-((5-(4-(trifluoromethyl)phenyl)oxazol-2-yl)amino)picolinohydrazide;

N'-Methyl-5-((5-(4-(trifluoromethyl)phenyl)oxazol-2-yl)amino)picolinohydrazide;

(R)—N-(2,3-dihydroxypropyl)-5-((5-(5-(trifluoromethyl)pyridin-2-yl)oxazol-2-yl)amino)picolinamide;

(R)—N-(2,3-dihydroxypropyl)-5-((4-methyl-5-(4-(trifluoromethyl)phenyl)oxazol-2-yl)amino)picolinamide;

(R)-5-((5-(3,4-Difluorophenyl)oxazol-2-yl)amino)-N-(2,3-dihydroxypropyl) picolinamide;

(R)—N-(2,3-dihydroxypropyl)-5-((5-(4-fluorophenyl)oxazol-2-yl)amino)picolinamide;

N'-Hydroxy-5-((5-(5-(trifluoromethoxy)pyridin-2-yl)oxazol-2-yl)amino)picolinimidamide;

5-((5-(4-Chlorophenyl)oxazol-2-yl)amino)-N'-hydroxypicolinimidamide;

5-((5-(4-Chlorophenyl)oxazol-2-yl)amino)-N-hydroxypyrazine-2-carboximidamide;

5-((5-(5-Chloropyridin-2-yl)oxazol-2-yl)amino)-N'-hydroxypyrazine-2-carboximidamide;

5-((1-(5-Chloropyridin-2-yl)-1H-pyrazol-4-yl)amino)-N'-hydroxypicolinimidamide;

rac-N-(2,3-Dihydroxypropyl)-5-((1-(5-(trifluoromethyl)pyridin-2-yl)-1H-pyrazol-4-yl)amino)picolinamide;

6-((5-(4-(Trifluoromethoxy) phenyl)oxazol-2-yl)amino)pyridin-3-ol;

N'-Hydroxy-5-((1-(4-(trifluoromethyl)phenyl)-1H-1,2,4-triazol-3-yl)amino)pyrazine-2-carboximidamide;

N'-Hydroxy-5-((1-(5-(trifluoromethyl)pyridin-2-yl)-1H-1,2,4-triazol-3-yl)amino)picolinimidamide;

N'-Hydroxy-5-((1-(5-(trifluoromethyl)pyridin-2-yl)-1H-1,2,4-triazol-3-yl)amino)pyrazine-2-carboximidamide;

N'-Hydroxy-5-((1-methyl-5-(5-(trifluoromethyl)pyridin-2-yl)-1H-pyrazol-3-yl)amino)picolinimidamide;

N'-Hydroxy-5-((1-methyl-5-(5-(trifluoromethyl)pyridin-2-yl)-1H-pyrazol-3-yl)amino)pyrazine-2-carboximidamide;

N'-Hydroxy-5-((1-(4-(trifluoromethyl)phenyl)-1H-pyrazol-3-yl)amino)pyrazine-2-carboximidamide;

N'-Hydroxy-5-((1-(5-(trifluoromethyl)pyridin-2-yl)-1H-pyrazol-3-yl)amino)pyrazine-2-carboximidamide;

N'-Hydroxy-5-((1-(4-(trifluoromethyl)phenyl)-1H-pyrazol-4-yl)amino)picolinimidamide;

N'-Hydroxy-5-((1-(4-(trifluoromethyl)phenyl)-1H-pyrazol-4-yl)amino)pyrazine-2-carboximidamide;

N'-Hydroxy-5-((1-(5-(trifluoromethyl)pyridin-2-yl)-1H-1,2,3-triazol-4-yl)amino)picolinimidamide;

rac-5-((5-(5-Chloropyridin-2-yl)oxazol-2-yl)amino)-N-(2,3-dihydroxypropyl) picolinamide hydrochloride;

5-((5-(5-Fluoropyridin-2-yl)oxazol-2-yl)amino)-N'-hydroxypicolinimidamide;

N'-Hydroxy-5-((5-(4-(trifluoromethoxy) phenyl)oxazol-2-yl)amino)picolinimidamide;

N'-Hydroxy-5-((5-(6-(trifluoromethyl) pyridazin-3-yl)oxazol-2-yl)amino)picolinimidamide;

and 5-((5-(4-Cyclopropylphenyl)oxazol-2-yl)amino)-N'-hydroxypicolinimidamide;

or a pharmaceutically acceptable salt or solvate thereof.

22. A composition comprising a compound of formula (I') according to claim 1, or a pharmaceutically acceptable salt or solvate thereof, and a pharmaceutically acceptable additive.

23. A method of treating a fibrosis or a fibrotic disease in a subject in need thereof, comprising administering to said subject, a compound of formula (I') according to claim 1, or a pharmaceutically acceptable salt or solvate thereof.

* * * * *